(12) United States Patent
Kozlowski et al.

(10) Patent No.: US 8,541,572 B2
(45) Date of Patent: *Sep. 24, 2013

(54) COMPOUNDS FOR THE TREATMENT OF INFLAMMATORY DISORDERS

(75) Inventors: Joseph A. Kozlowski, Princeton, NJ (US); Wensheng Yu, Edison, NJ (US); Michael K. C. Wong, Somerset, NJ (US); Seong Heon Kim, Livington, NJ (US); Ling Tong, Warren, NJ (US); Brian J. Lavey, New Providence, NJ (US); Bandarpalle B. Shankar, Branchburg, NJ (US); De-Yi Yang, Morris Plains, NJ (US); Robert Feltz, Washington, PA (US); Aneta Maria Kosinski, South Amboy, NJ (US); Guowei Zhou, Somerset, NJ (US); Razia K. Rizvi, Bloomfield, NJ (US); Chaoyang Dai, Acton, MA (US); Luke Fire, Cambridge, MA (US); Vinay Girijavallabhan, Denville, NJ (US); Dansu Li, Reading, MA (US); Janeta Popovici-Muller, Waltham, MA (US); Judson E. Richard, Kittery, ME (US); Kristin E. Rosner, Watertown, MA (US); M. Arshad Siddiqui, Newton, MA (US); Liping Yang, Arlington, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/127,952

(22) PCT Filed: Nov. 9, 2009

(86) PCT No.: PCT/US2009/063670
§ 371 (c)(1),
(2), (4) Date: Sep. 23, 2011

(87) PCT Pub. No.: WO2010/054279
PCT Pub. Date: May 14, 2010

(65) Prior Publication Data
US 2012/0010181 A1    Jan. 12, 2012

Related U.S. Application Data

(60) Provisional application No. 61/113,071, filed on Nov. 10, 2008.

(51) Int. Cl.
*C07D 295/03* (2006.01)
*C07D 241/20* (2006.01)
*C07D 211/30* (2006.01)
*C07D 213/46* (2006.01)
*C07D 403/06* (2006.01)
*C07D 203/16* (2006.01)

(52) U.S. Cl.
USPC ........... 544/59; 544/106; 544/386; 544/408; 546/225; 546/340; 548/312.1; 548/539; 548/966

(58) Field of Classification Search
None
See application file for complete search history.

(56) References Cited

U.S. PATENT DOCUMENTS

| | | | |
|---|---|---|---|
| 6,495,565 B2 | 12/2002 | Duan et al. | |
| 6,534,491 B2 | 3/2003 | Levin et al. | |
| 6,677,355 B1 | 1/2004 | Conrad et al. | |
| 7,041,693 B2 | 5/2006 | Sheppeck | |
| 7,482,370 B2 | 1/2009 | Yu et al. | |
| 7,488,745 B2 | 2/2009 | Yu et al. | |
| 7,504,424 B2 | 3/2009 | Yu et al. | |
| 7,524,842 B2* | 4/2009 | Lavey et al. | 514/227.8 |

(Continued)

FOREIGN PATENT DOCUMENTS

| | | |
|---|---|---|
| WO | WO02/074750 A1 | 9/2002 |
| WO | WO02/096426 A1 | 12/2002 |
| WO | WO03/053940 A1 | 7/2003 |
| WO | WO03/053941 A2 | 7/2003 |
| WO | WO2004/012663 A2 | 2/2004 |
| WO | WO2004/024698 A1 | 3/2004 |
| WO | WO2004/024715 A1 | 3/2004 |
| WO | WO2004/024721 A1 | 3/2004 |
| WO | WO2004/056766 A1 | 7/2004 |
| WO | WO2006/019768 A1 | 2/2006 |
| WO | WO2007/084451 A1 | 7/2007 |

OTHER PUBLICATIONS

Moss, M. L., Sklair-Tavron, L.,Nudelman, R. Drug Insight: tumor necrosis factor-converting enzyme as a pharmaceutical target for rheumatoid arthritis. Nature Clinical Practice Rheumatology. Apr. 4, 2008. 300-309.*

Shafer, S., Kolkhof, P. Failure is an option: learning from unsuccessful proof-of-concept trials. Drug Discovery Today. Nov. 13, 2008, 913-916.*

Horig, H., Pullman, W. From bench to clinic and back: Perspective on the 1st IQPC Translational Research conference. Journal of Translational Medicine. Dec. 2, 2004, 44.*

Girijavallabhan et al. Novel TNF-alpha converting enzyme (TACE) inhibitors as potential treatment for inflammatory diseases. Bioorganic & Medicinal Chemistry Letter. Oct. 20, 2010, 7283-7287.*

PCT International Search Report dated May 19, 2011 corresponding to PCT Application No. PCT/US2009/063670.

Knaggs, A., et al., "Biotransformation of Alosetron: Mechanism of Hydantoin Formation", Tetrahedron Letters, vol. 36, No. 3, pp. 477-480 (1995).

*Primary Examiner* — Jason M Nolan
*Assistant Examiner* — Po-Chih Chen
(74) *Attorney, Agent, or Firm* — Eric A. Meade; Valerie J. Camara

(57) ABSTRACT

This invention relates to compounds of the Formula (I): (Chemical formula should be inserted here as it appears on abstract in paper form) (I) or a pharmaceutically acceptable salt, solvate or isomer thereof, which can be useful for the treatment of diseases or conditions mediated by MMPs, ADAMs, TACE, aggrecanase, TNF—or combinations thereof.

(I)

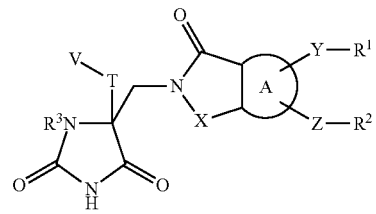

4 Claims, No Drawings

(56) References Cited

U.S. PATENT DOCUMENTS

| | | |
|---|---|---|
| 7,683,085 B2 | 3/2010 | Yu et al. |
| 7,683,088 B2 * | 3/2010 | Lavey et al. .................. 514/389 |
| 7,687,527 B2 | 3/2010 | Yu et al. |
| 7,772,263 B2 * | 8/2010 | Lavey et al. .................. 514/373 |
| 7,879,890 B2 | 2/2011 | Yu et al. |
| 7,998,961 B2 | 8/2011 | Mansoor et al. |
| 8,178,553 B2 * | 5/2012 | Lavey et al. .................. 514/300 |
| 2007/0219218 A1 * | 9/2007 | Yu et al. .................. 514/255.05 |
| 2011/0288054 A1 * | 11/2011 | Shankar et al. ................. 514/81 |
| 2011/0288077 A1 * | 11/2011 | Wong et al. .................. 514/218 |
| 2012/0015926 A1 | 1/2012 | Tong et al. |

\* cited by examiner

COMPOUNDS FOR THE TREATMENT OF INFLAMMATORY DISORDERS

CROSS-REFERENCE TO RELATED APPLICATIONS

This application is a 371 application filed Sep. 23, 2011, which is a national stage application of PCT/US09/63670 filed Nov. 9, 2009, which claims the priority of U.S. Provisional Application No. 61/113,071, filed Nov. 10, 2008, which is herein incorporated by reference in its entirety.

BACKGROUND OF THE INVENTION

1. Field of the Invention

This invention relates generally to novel hydantoin derivatives that can inhibit matrix metalloproteinases (MMPs), a disintegrin and metalloproteases (ADAMs) and/or tumor necrosis factor alpha-converting enzyme (TACE) and in so doing prevent the release of tumor necrosis factor alpha (TNF-$\alpha$), pharmaceutical compositions comprising such compounds, and methods of treatment using such compounds.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-$\alpha$) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-$\alpha$ has been shown to play a pivotal role in immune and inflammatory responses. Inappropriate or over-expression of TNF-$\alpha$0 is a hallmark of a number of diseases, including RA, Crohn's disease, multiple sclerosis, psoriasis and sepsis. Inhibition of TNF-$\alpha$ production has been shown to be beneficial in many preclinical models of inflammatory disease, making inhibition of TNF-$\alpha$ production or signaling an appealing target for the development of novel anti-inflammatory drugs.

TNF-$\alpha$ is a primary mediator in humans and animals of inflammation, fever and acute phase responses, similar to those observed during acute infection and shock. Excess TNF-$\alpha$ has been shown to be lethal. Blocking the effects of TNF-$\alpha$ with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-$\alpha$ are therefore of therapeutic importance for the treatment of inflammatory disorders. Recently it has been shown that metalloproteases, such as TACE, are capable of converting TNF-$\alpha$ from its inactive to active form (Gearing et al Nature, 1994, 370, 555). Since excessive TNF-$\alpha$ production has been noted in several disease conditions also characterized by MMP-mediated tissue degradation, compounds which inhibit both MMPs and TNF-$\alpha$ production may also have a particular advantage in diseases where both mechanisms are involved.

One approach to inhibiting the harmful effects of TNF-$\alpha$ is to inhibit the enzyme, TACE before it can process TNF-$\alpha$ to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-$\alpha$ from its "stalk" sequence and thus releasing the soluble form of the TNF-$\alpha$ protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. Nos. 6,677,355 and 6,534,491(B2) describe compounds that are hydroxamic acid derivatives and MMP inhibitors.

U.S. Pat. No. 6,495,565 discloses lactam derivatives that are potential inhibitors of MMPs and/or TNF-$\alpha$.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPs.

PCT Publications WO2006/019768 and WO2007/084451 refer to hydantoin derivatives that are TACE inhibitors.

There is a need in the art for inhibitors of MMPs, ADAMs, TACE, and TNF-$\alpha$, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

The present invention relates to compounds having the general structure shown in Formula (I):

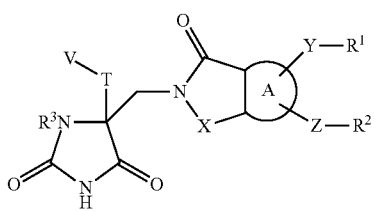

or a pharmaceutically acceptable salt, solvate, ester or isomer thereof, wherein:

ring A is selected from the group consisting of aryl and heteroaryl, each of which is substituted with —Y—$R^1$ and —Z—$R^2$ as shown;

X is selected from the group consisting of —S—, —O—, —S(O)$_2$—, S(O)—, —(C($R^3$)$_2$)$_m$— and —N($R^3$)—;

T is alkynyl;

V is selected from the group consisting H, alkyl, cycloalkyl, cycloalkenyl, aryl, heteroaryl, heterocyclyl, and N-oxides of said heteroaryl and heterocyclyl, wherein when each of said cycloalkyl, cycloalkenyl, aryl, heteroaryl, heterocyclyl, and N oxides of said heteroaryl and heterocyclyl contains two radicals on same or adjacent carbon atoms, said radicals may optionally be taken together with the carbon atom(s) to which they are attached to form a five- to eight-membered cycloalkyl, cycloalkenyl, aryl, heterocyclyl or heteroaryl ring, wherein each of the aforementioned cycloalkyl, cycloalkenyl, aryl, heteroaryl, and heterocyclyl, optionally with said five- to eight-membered cycloalkyl, cycloalkenyl, aryl, heterocyclyl, or heteroaryl is independently unsubstituted or substituted with one to four $R^{10}$ moieties which can be the same or different;

Y is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

Z is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

m is 1 to 3:

n is 1 to 3;

$R^1$ is selected from the group consisting of H, cyano, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^1$ is not halogen or cyano;

$R^2$ is selected from the group consisting of H, cyano, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^2$ alkyl, cycloalkyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^2$ is not halogen or cyano;

each $R^3$ is the same of different and is independently selected from the group consisting of H, alkyl, and aryl;

each $R^4$ is the same or different and is independently selected from the group consisting of H, alkyl, cycloalkyl, haloalkyl, hydroxy, -alkylcycloalkyl, -alkyl-N(alkyl)$_2$, heterocyclyl, aryl, and heteroaryl;

$R^{10}$ is selected from the group consisting of hydrogen, cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —C(O)N($R^4$)—S(O)$_2R^4$, —S(O)$_2$N($R_4$)—C(O)—$R^4$, —C(O)N($R^4$)C(O)$R^4$, —C(O)N($R^4$)C(O)N$R^4$—S(O)$_2$N($R^4$)$_2$, —N($R^4$)—C(O)O$R^4$, —OC(O)N($R^4$)$_2$, —N($R^4$)C(O)N($R^4$)$_2$, —S(O)$_2$N($R^4$)$_2$, —S(O)$_2$N($R_4$)—C(O)—$R^4$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl, wherein each of the $R^{10}$ alkyl, aryl, heteroaryl, heterocyclyl, and cycloalkyl is unsubstituted or optionally independently substituted with one to four $R^{30}$ moieties which can be the same or different;

or wherein two $R^{10}$ moieties, when attached to the same or adjacent carbon atoms may optionally be taken together with the carbon atom(s) to which they are attached to form a cycloalkyl, cycloalkenyl, heterocyclyl, aryl, or heteroaryl ring;

$R^{20}$ is selected from the group consisting of cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —C(O)N($R^4$)—S(O)$_2R^4$, —S(O)$_2$N($R_4$)—C(O)—$R^4$, —C(O)N($R^4$)C(O)$R^4$, —C(O)N($R^4$)C(O)N$R^4$—S(O)$_2$N($R^4$)$_2$, —N($R^4$)—C(O)O$R^4$, —OC(O)N($R^4$)$_2$, —N($R^4$)C(O)N($R^4$)$_2$, —S(O)$_2$N($R^4$)$_2$, —S(O)$_2$N($R_4$)—C(O)—$R^4$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl; wherein when each of said $R^{20}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said $R^{20}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH$_2$, —NH(alkyl), and —N(alkyl)$_2$;

or when two $R^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

$R^{30}$ is selected from the group consisting of cyano, nitro, —C($R^4$)=N—O$R^4$, —O$R^4$, —S$R^4$, —N($R^4$)$_2$, —S(O)$R^4$, —S(O)$_2$$R^4$, —N($R^4$)S(O)$_2$$R^4$, —N($R^4$)—C(O)—$R^4$, —C(O)N($R^4$)—S(O)$_2$$R^4$, —S(O)$_2$N($R_4$)—C(O)—$R^4$, —C(O)N($R^4$)C(O)$R^4$, —C(O)N($R^4$)C(O)N$R^4$—S(O)$_2$N($R^4$)$_2$, —N($R^4$)—C(O)O$R^4$, —OC(O)N($R^4$)$_2$, —N($R^4$)C(O)N($R^4$)$_2$, —S(O)$_2$N($R^4$)$_2$, —S(O)$_2$N($R_4$)—C(O)—$R^4$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl; wherein when each of said $R^{30}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said $R^{30}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, cyano, nitro, —NH$_2$, —NH(alkyl), and —N(alkyl)$_2$;

or when two $R^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring.

The present invention also relates to a compound selected from the group of compounds consisting of:

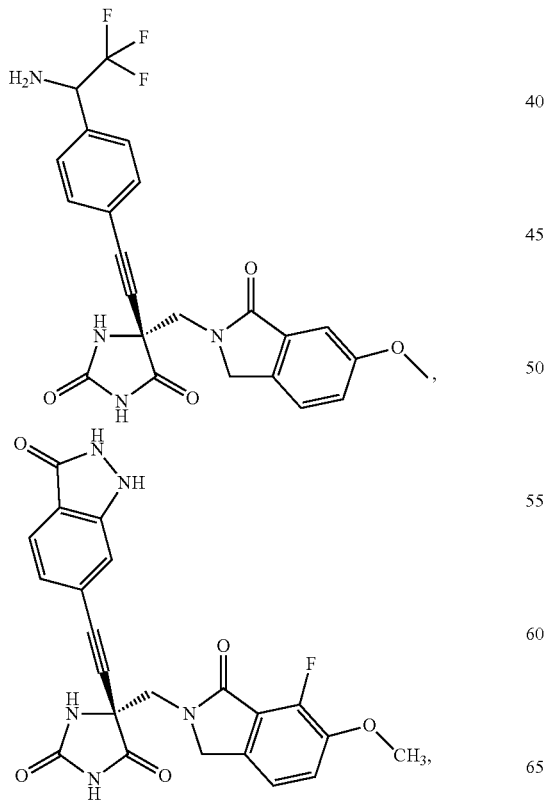

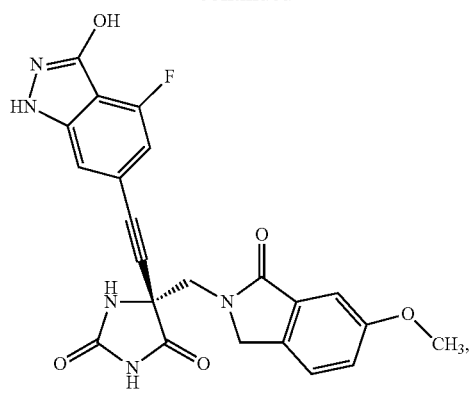

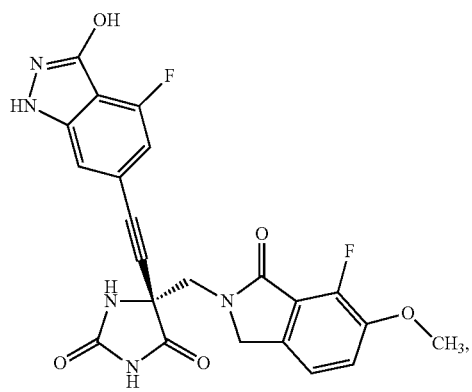

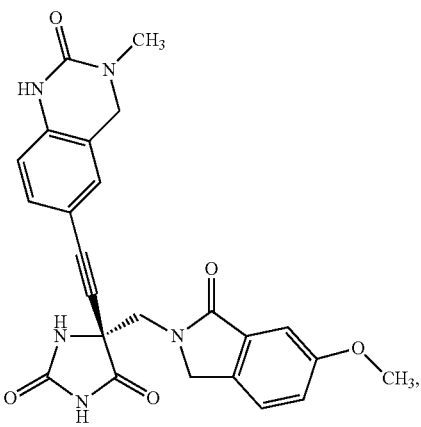

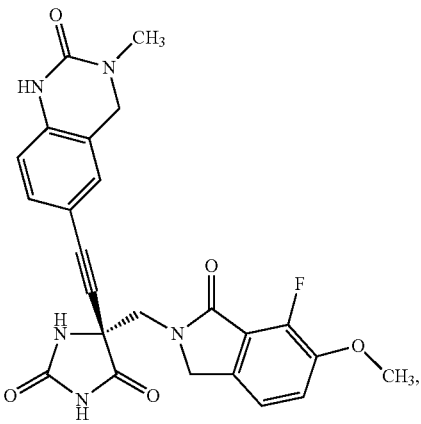

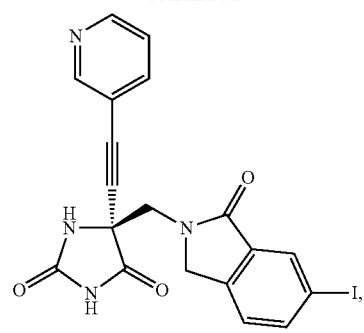
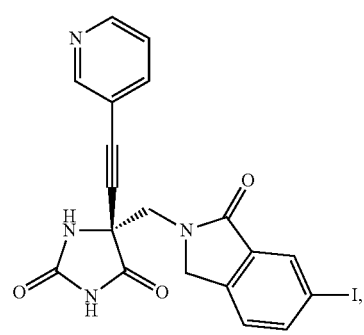
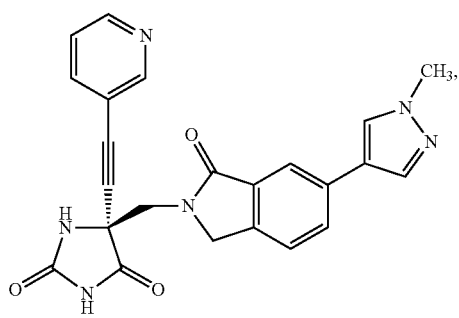
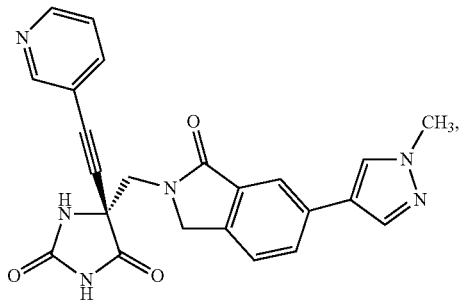
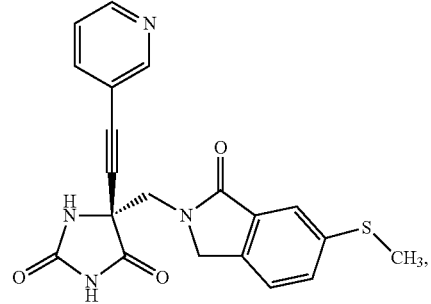
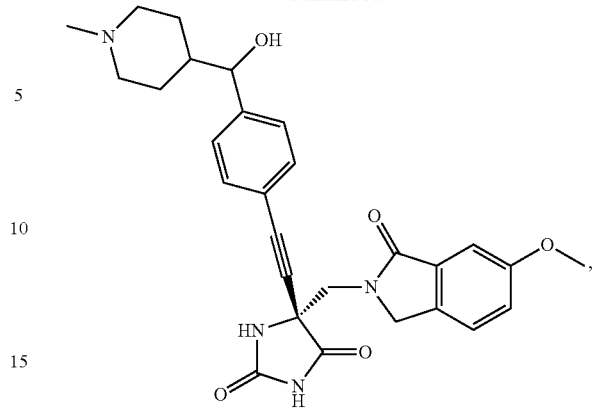
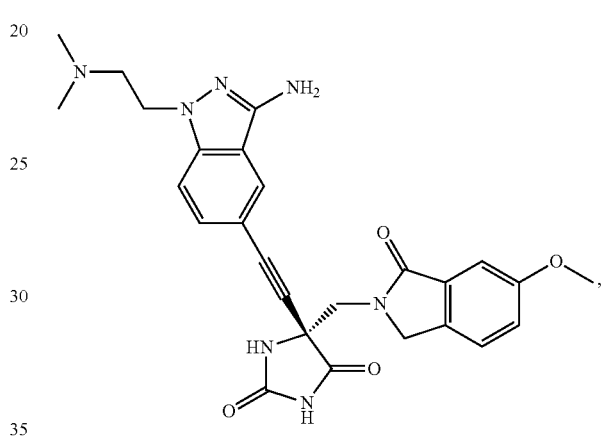
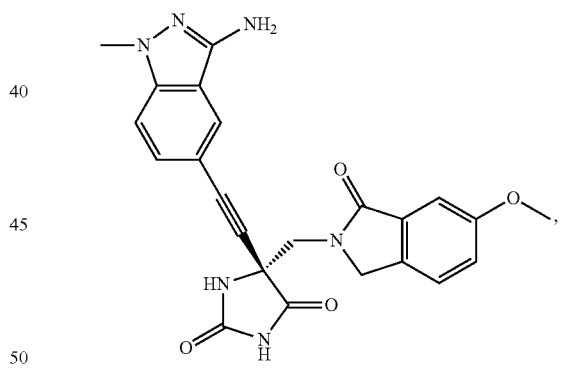
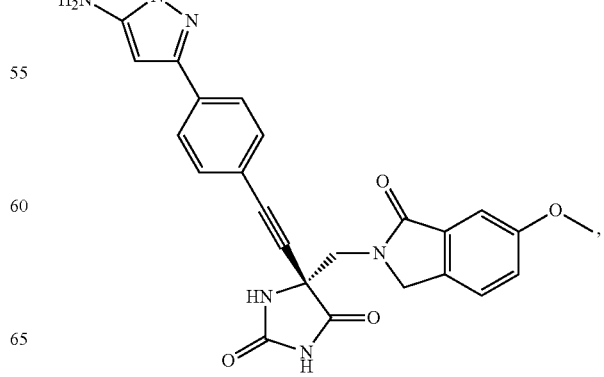

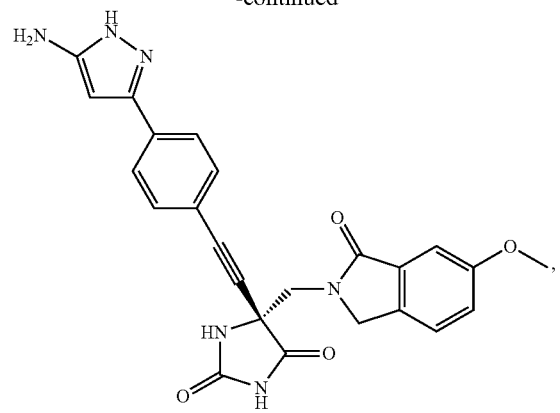
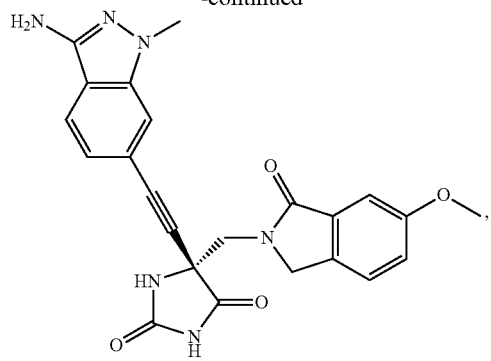
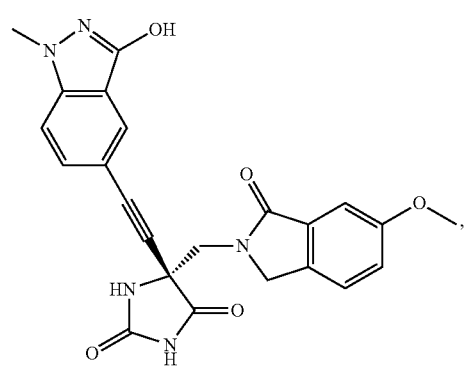
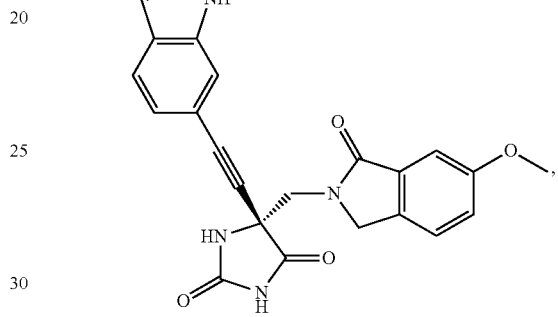
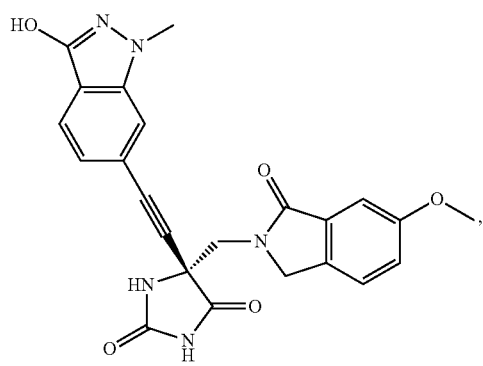
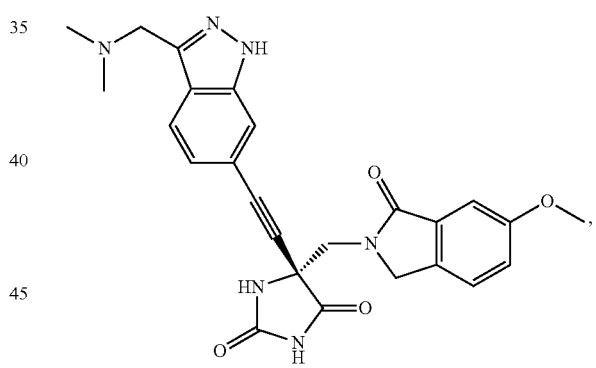
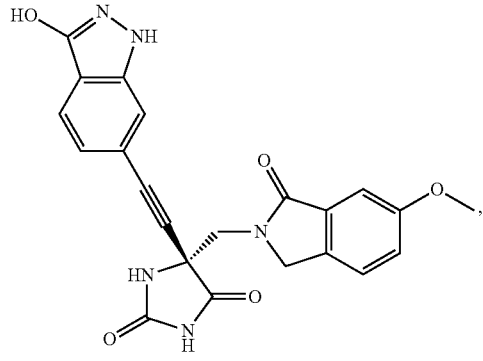
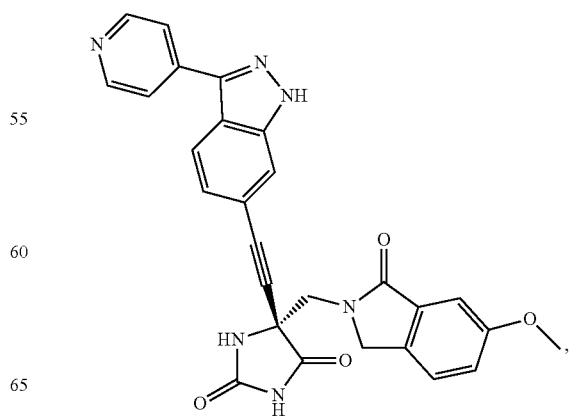

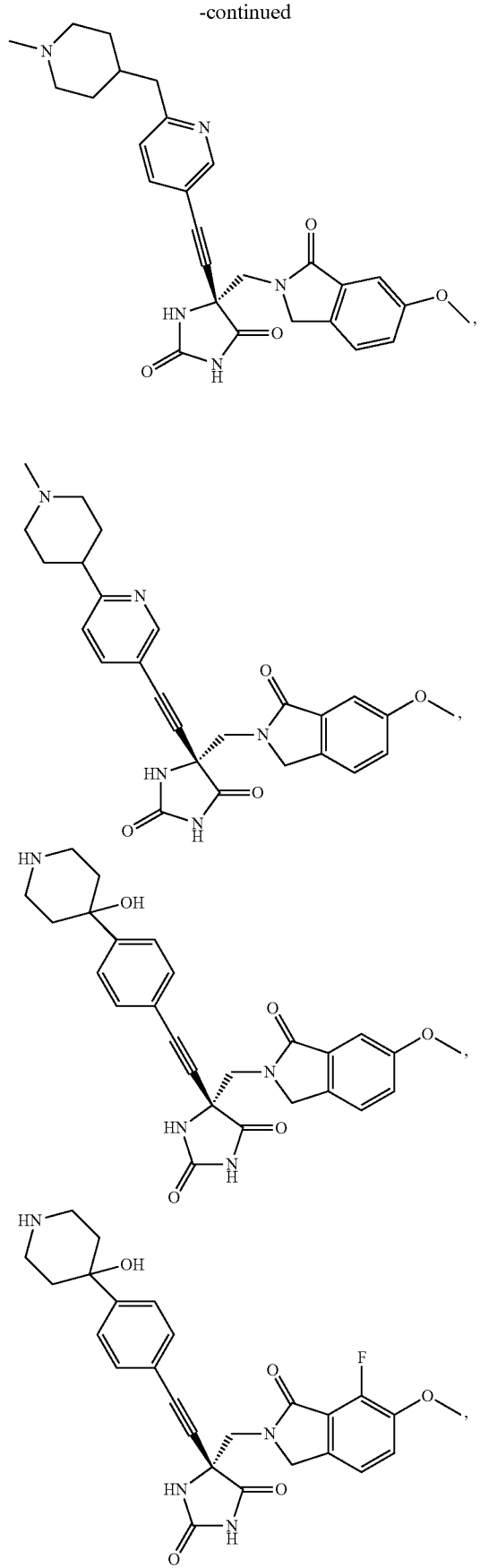
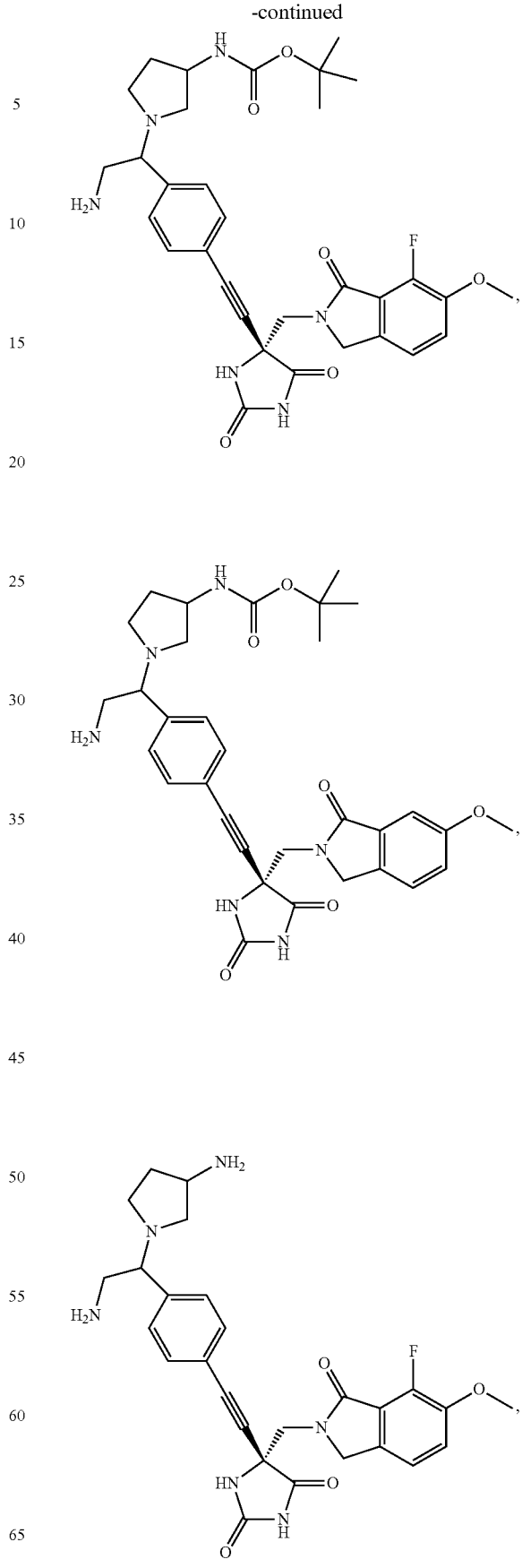

13
-continued
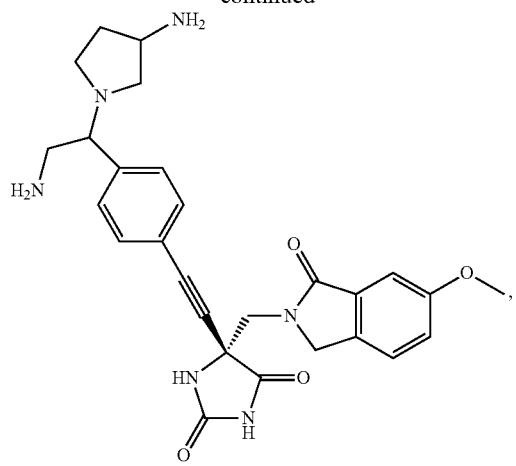
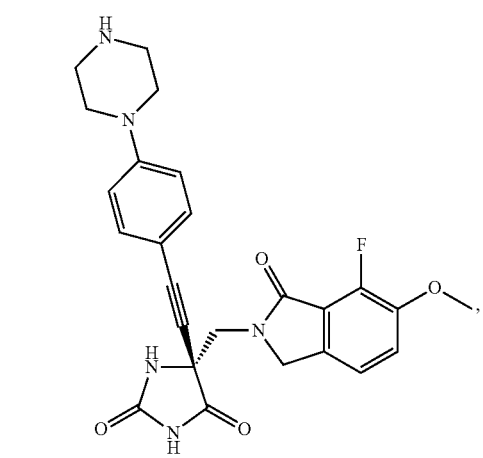
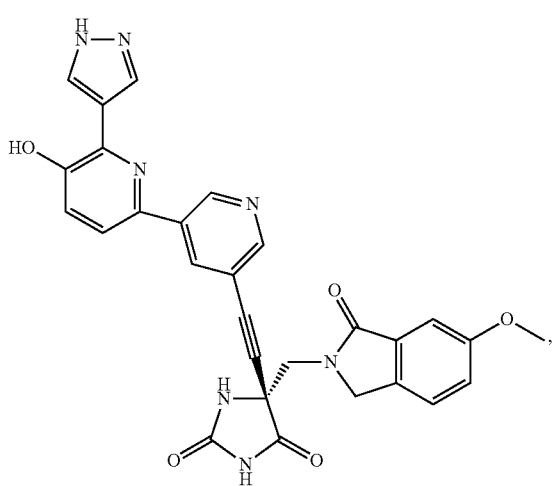
14
-continued
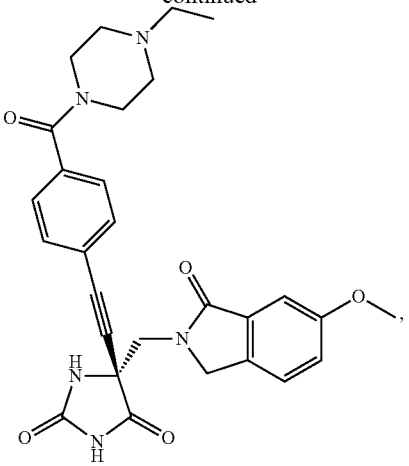
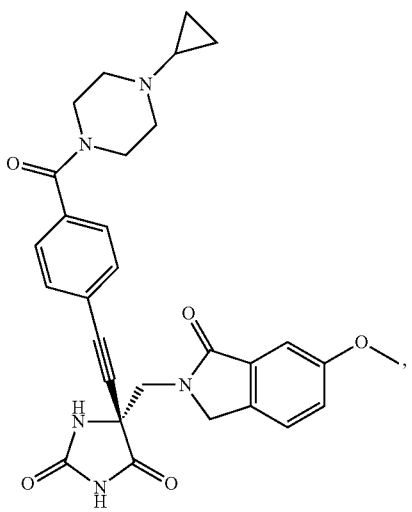
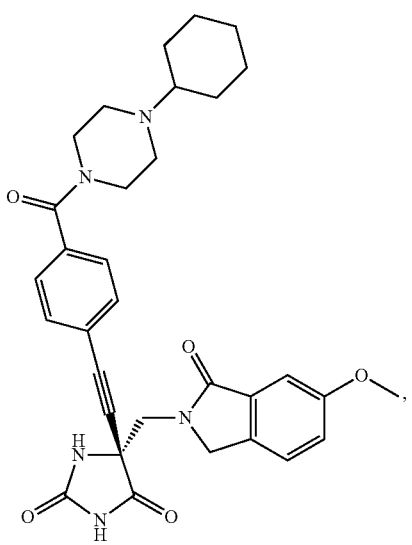

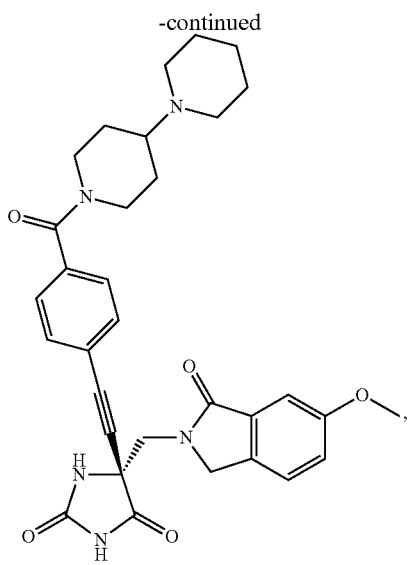
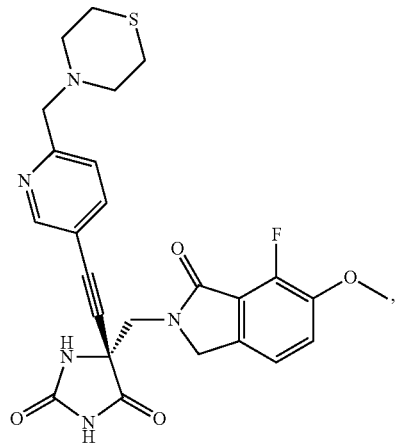
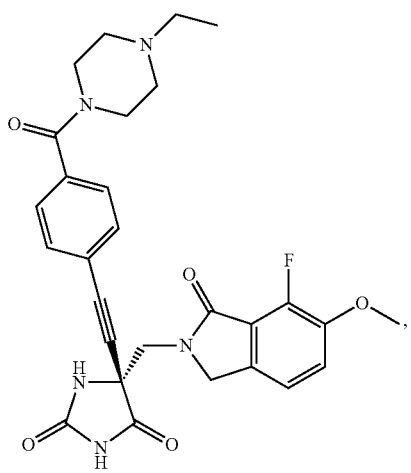
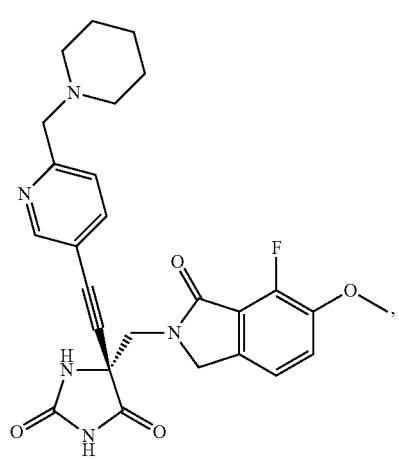
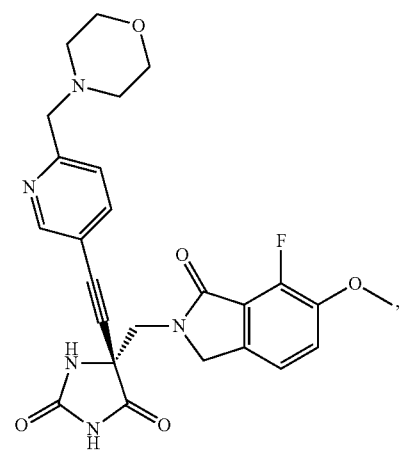
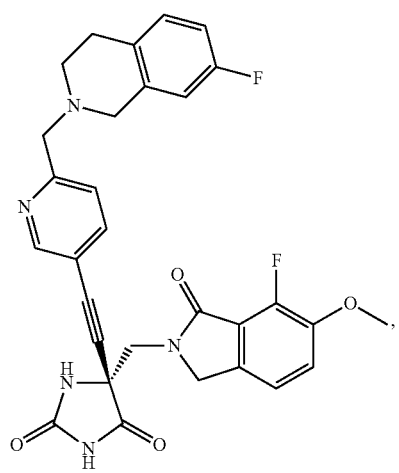

17
-continued
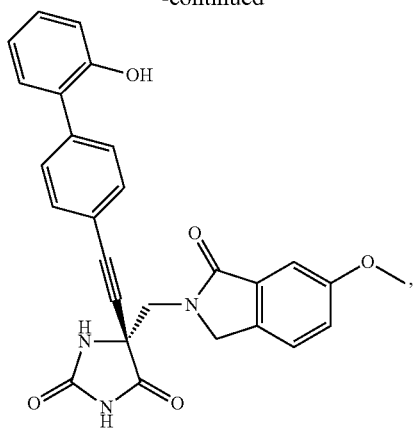
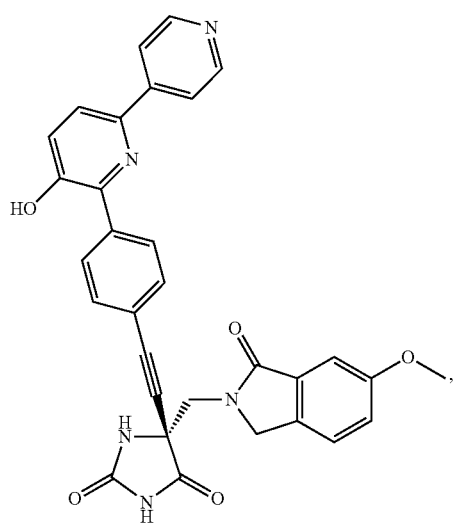
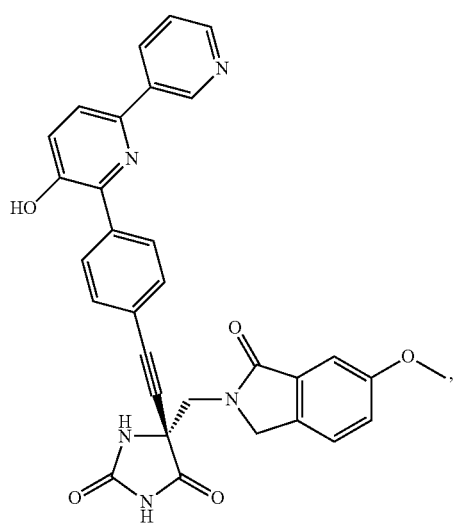
18
-continued
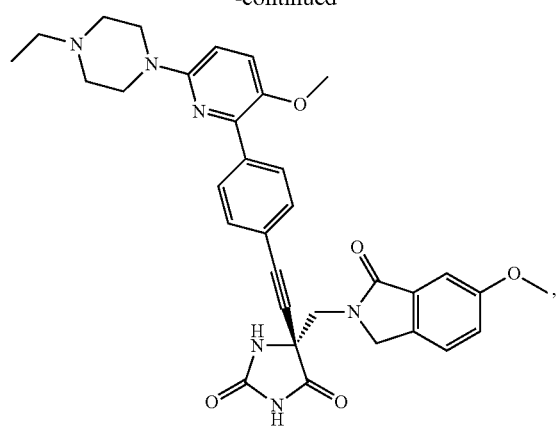
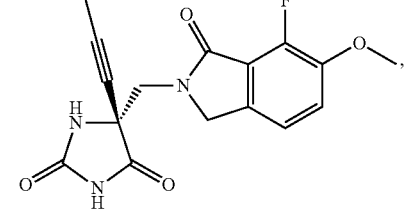

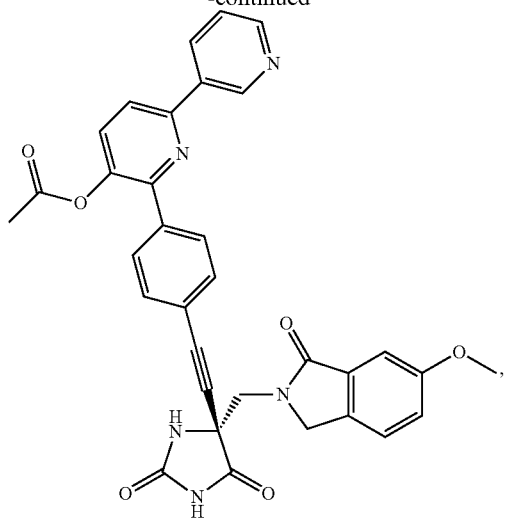
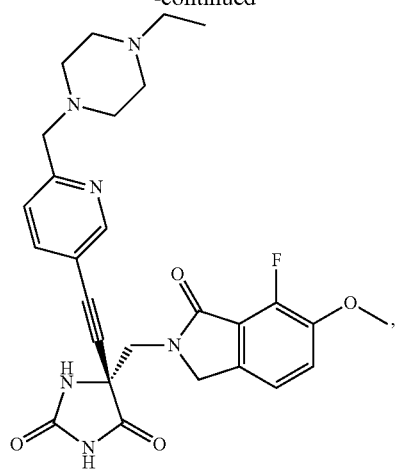
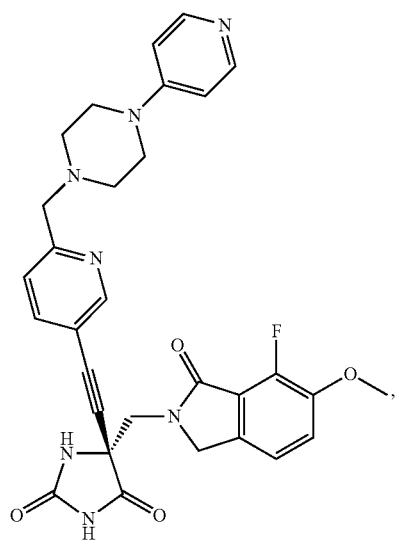
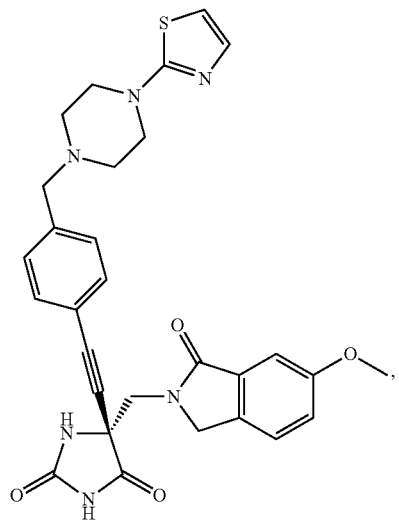

-continued
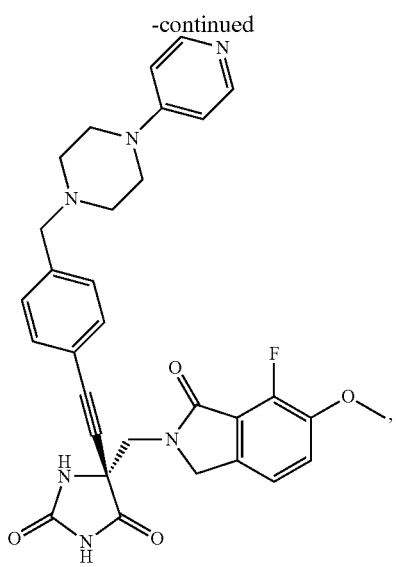
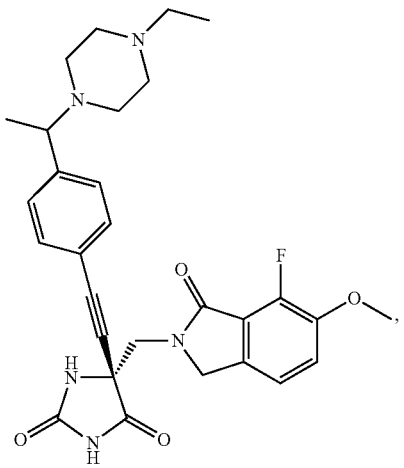
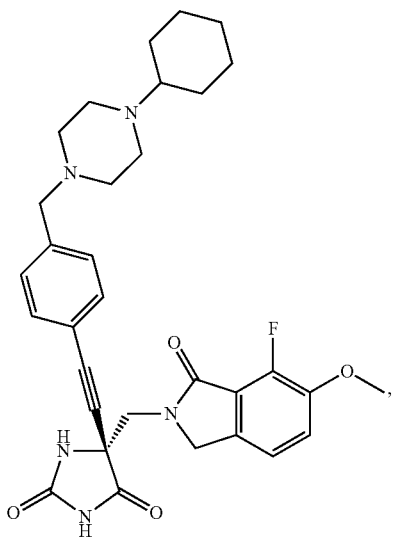
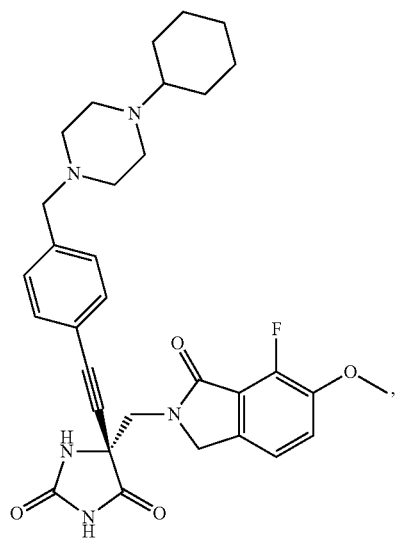
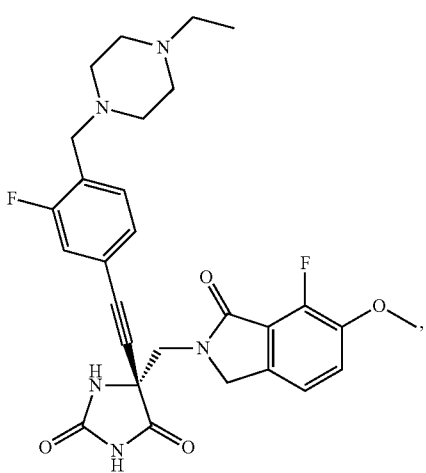
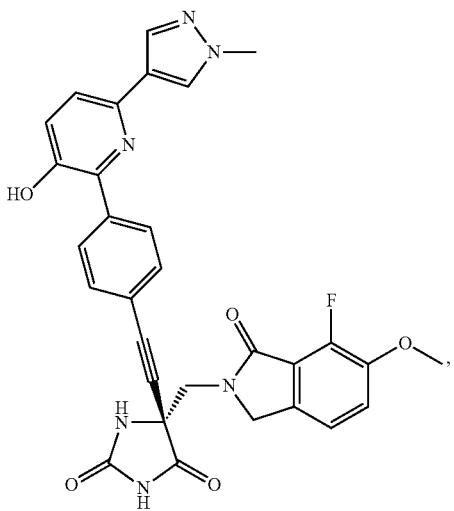

-continued
23
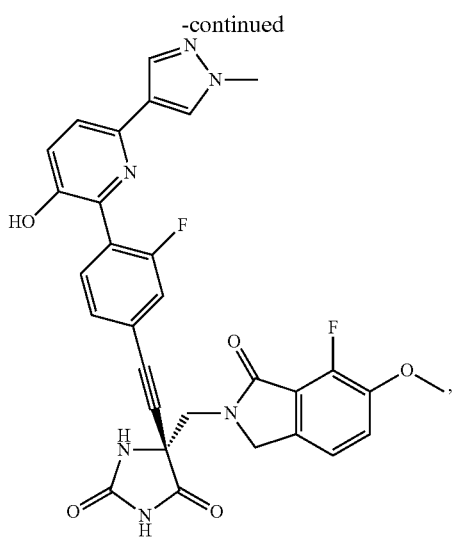
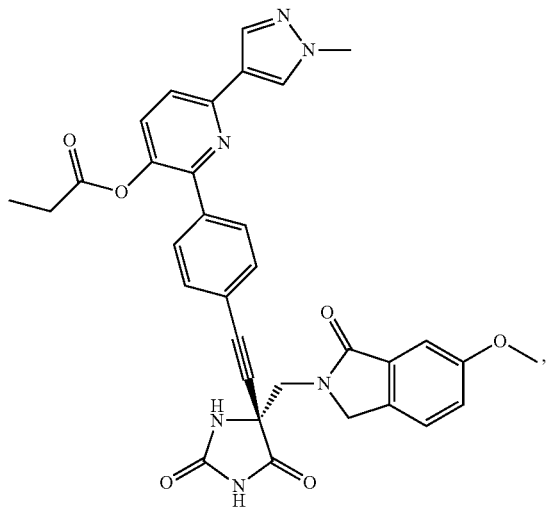
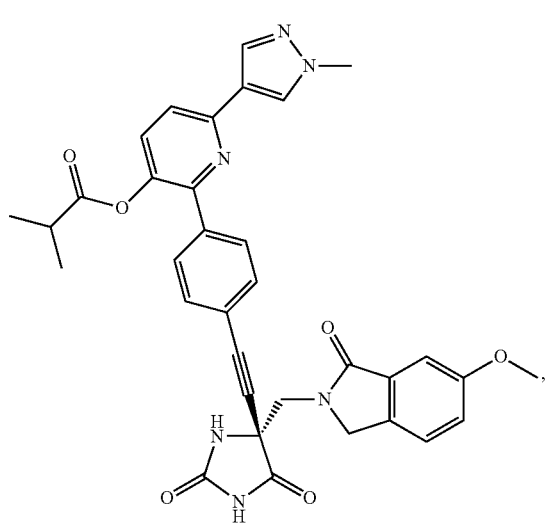
24
-continued
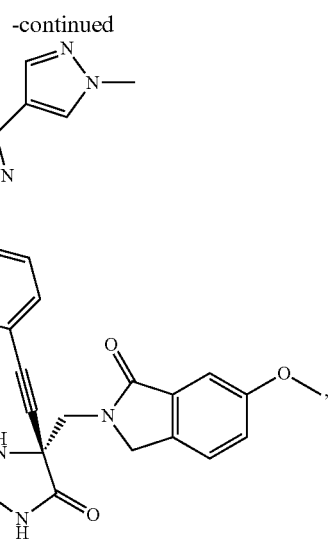
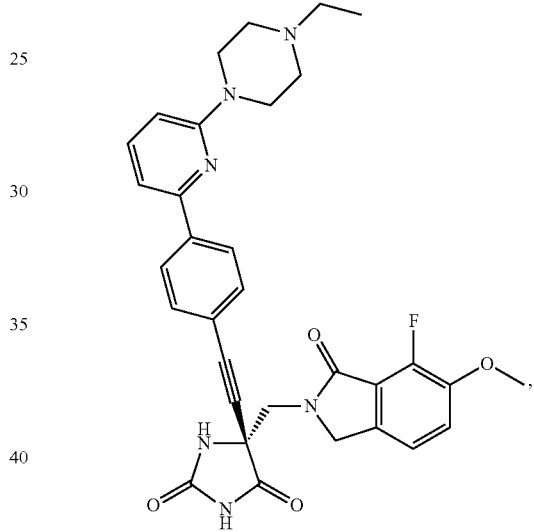
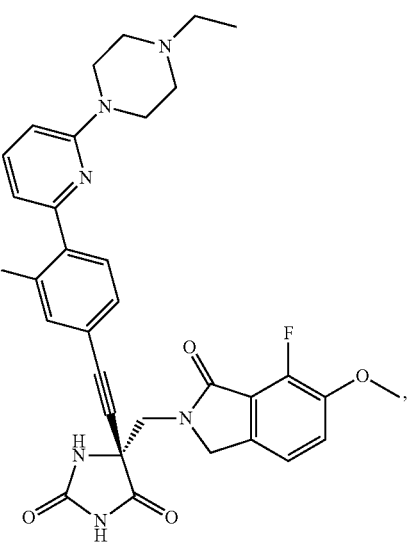

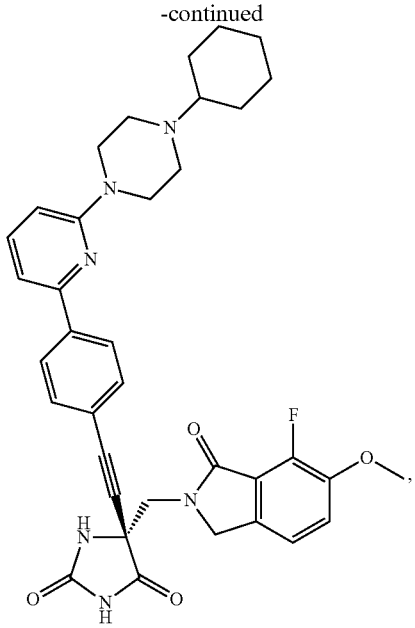
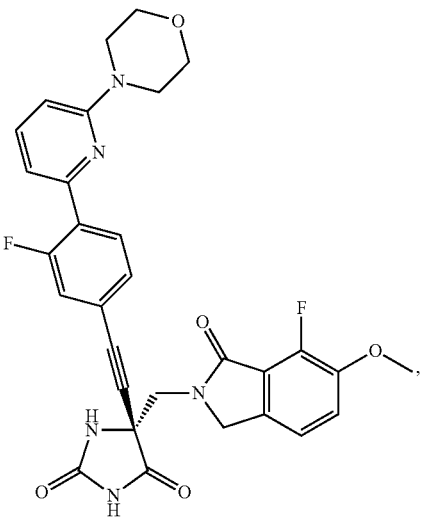
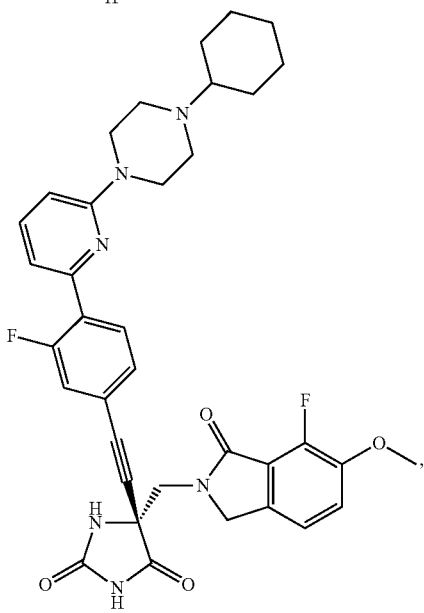
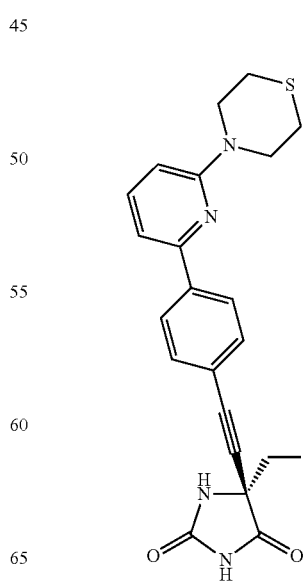
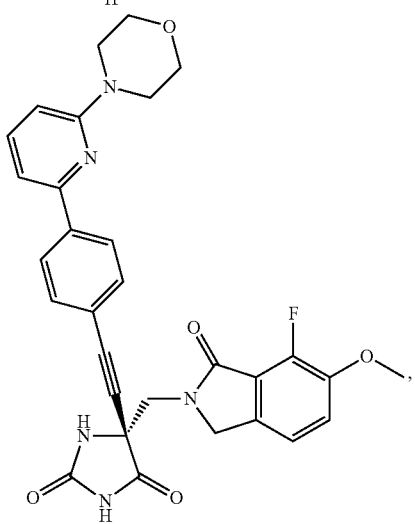

27
-continued
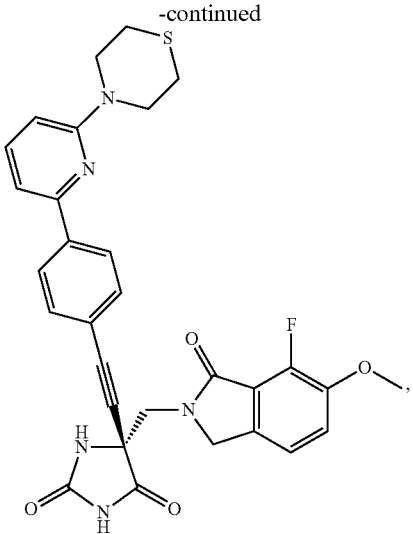
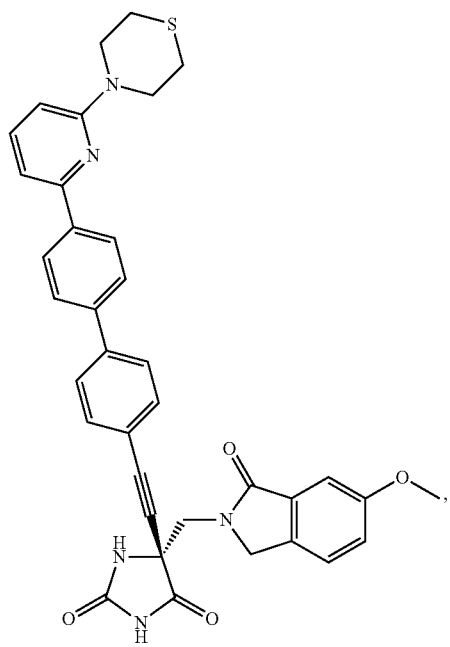
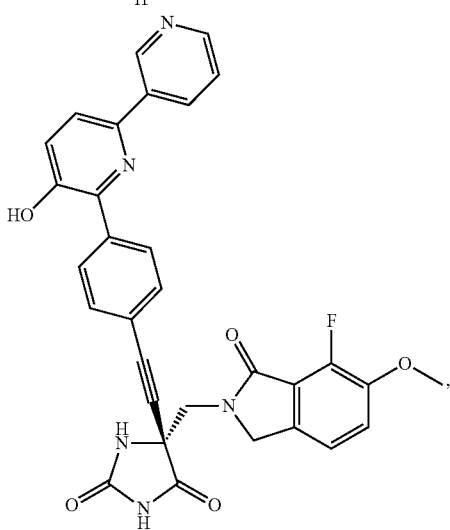
28
-continued
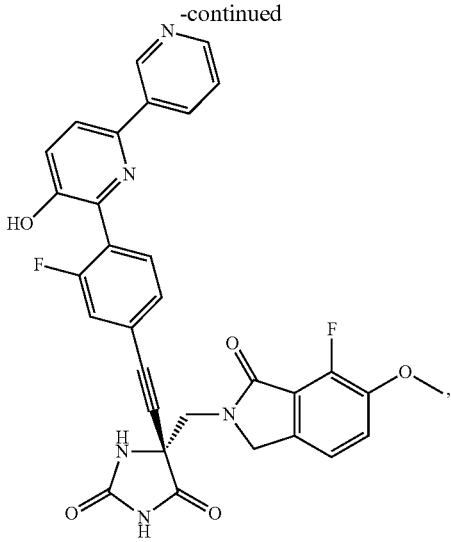
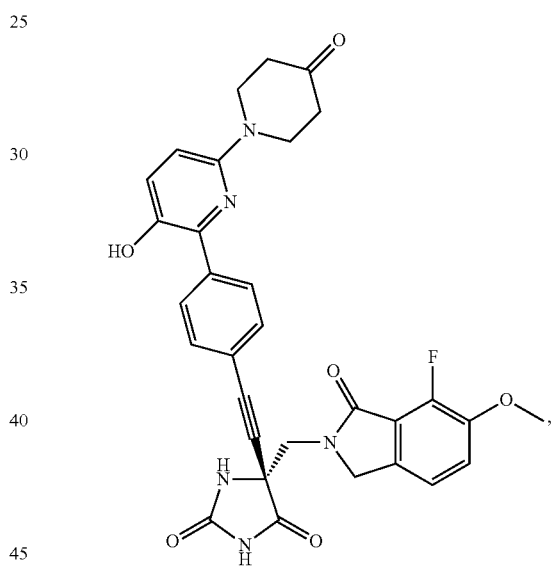
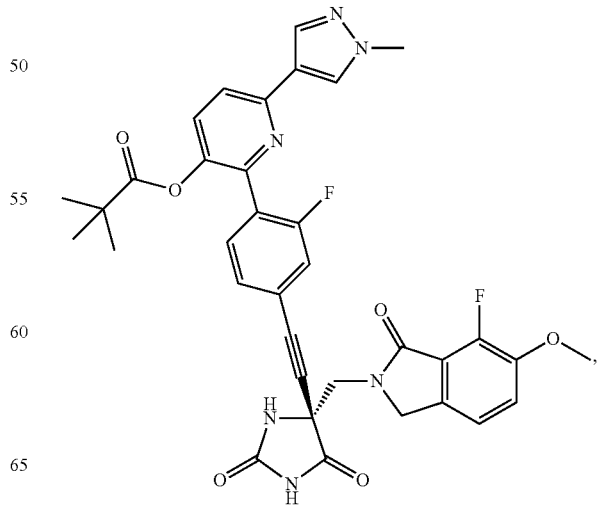

29
-continued
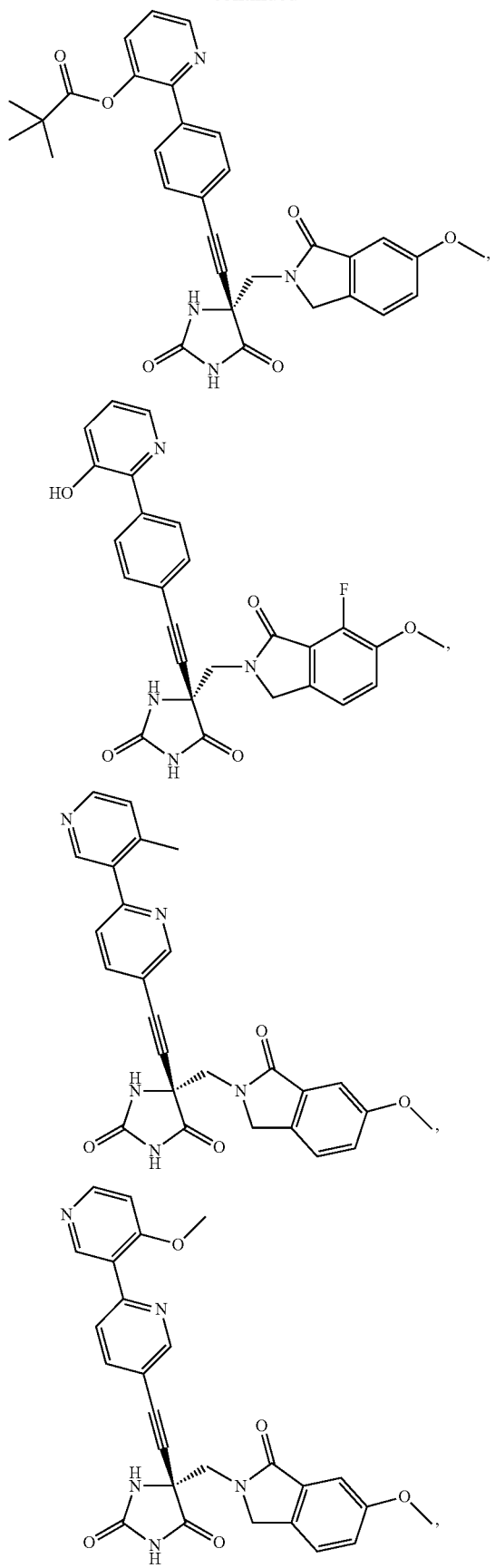
30
-continued
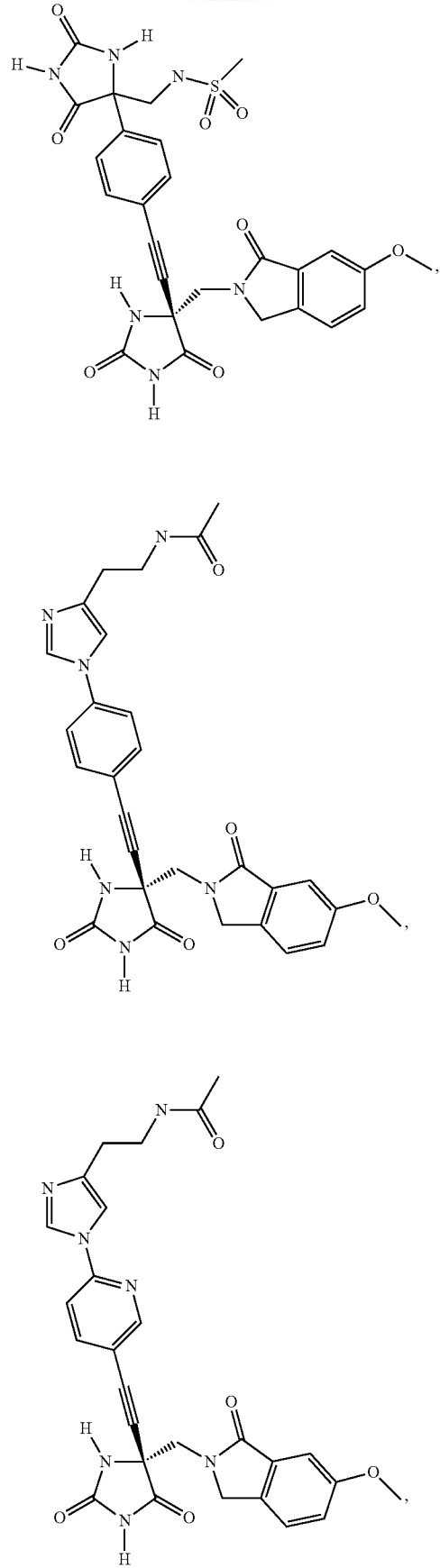

31
-continued
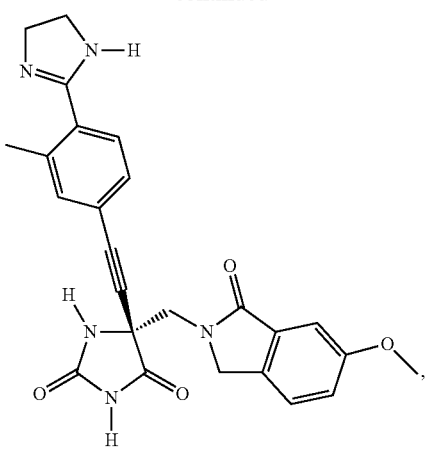
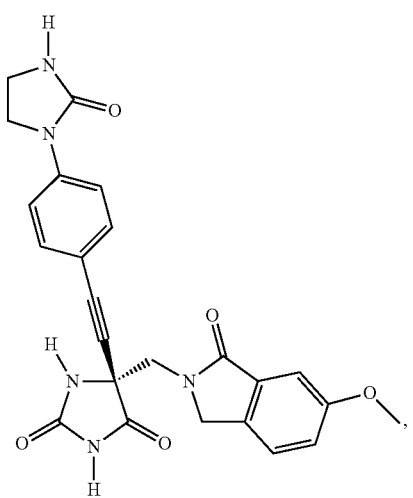
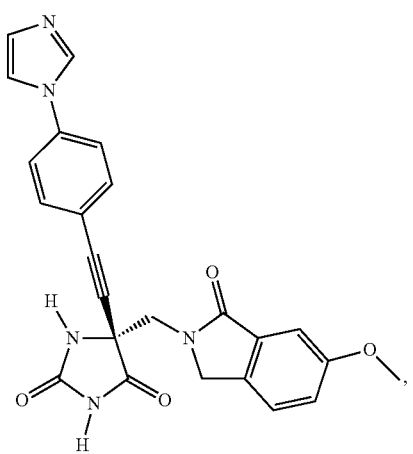
32
-continued
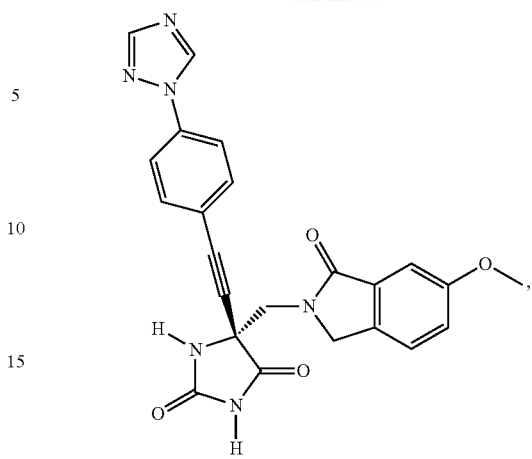
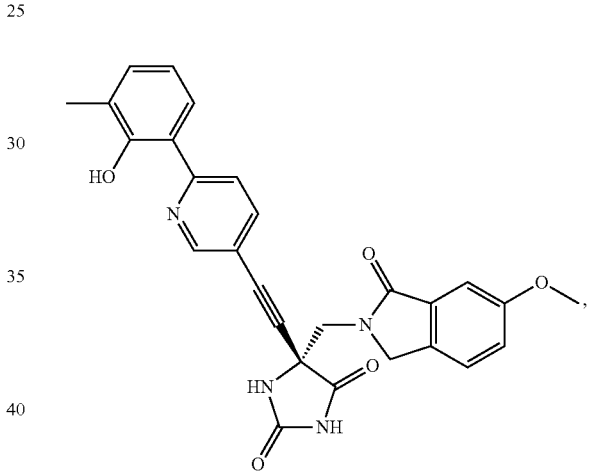
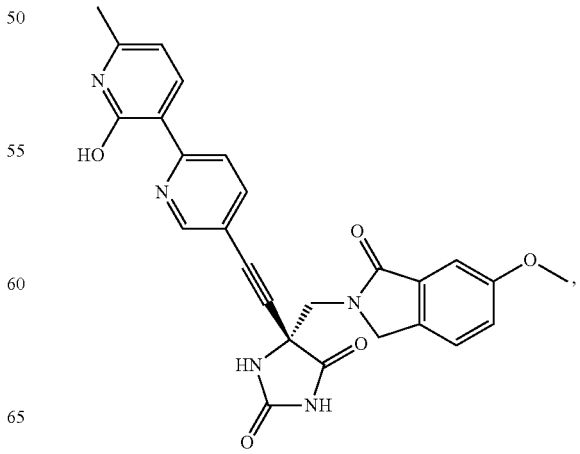

33
-continued
34
-continued
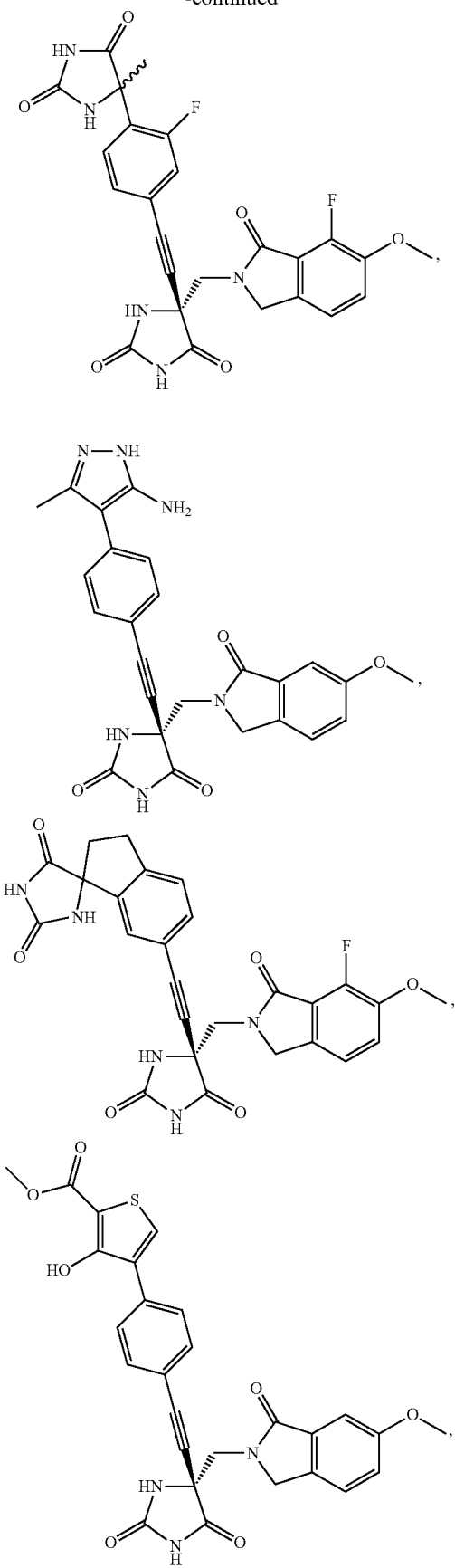
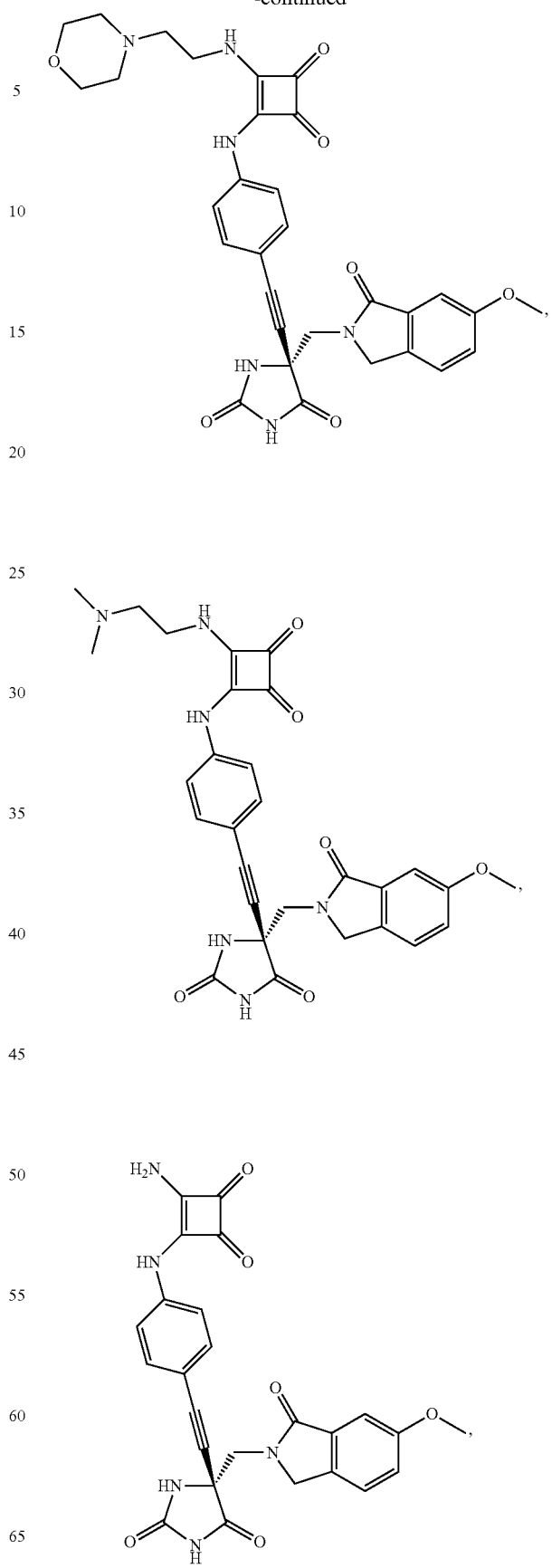

35
-continued
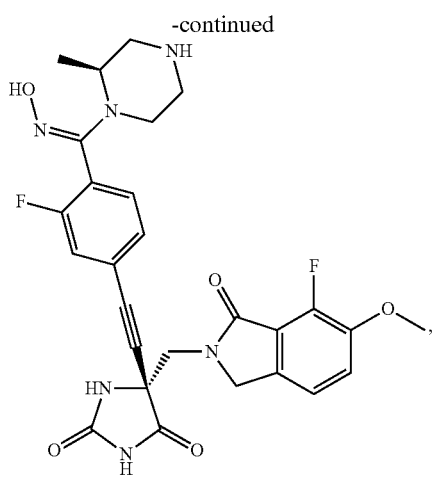
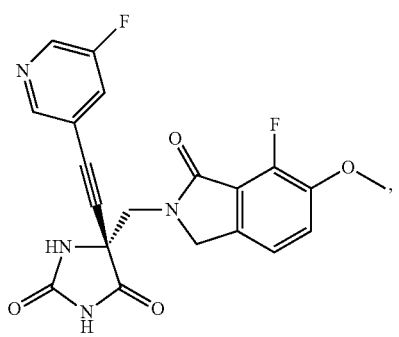
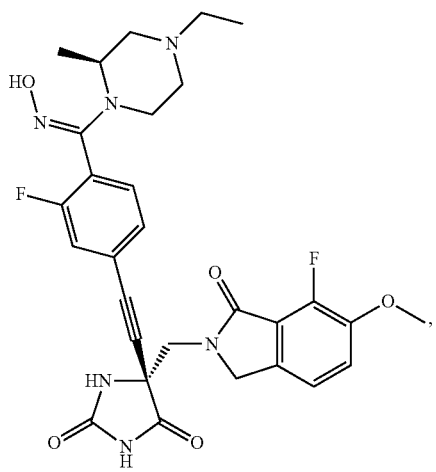
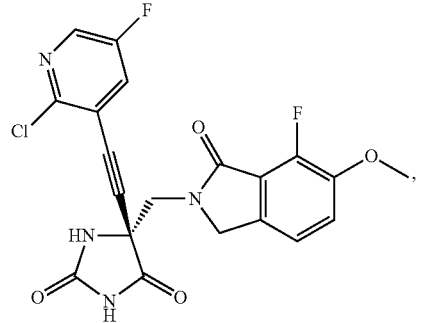
36
-continued
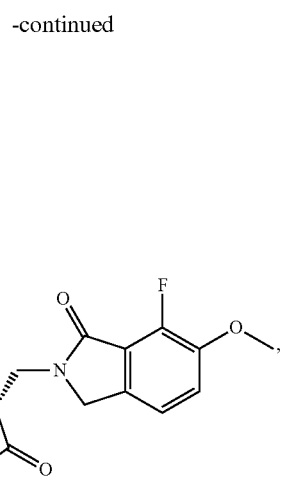
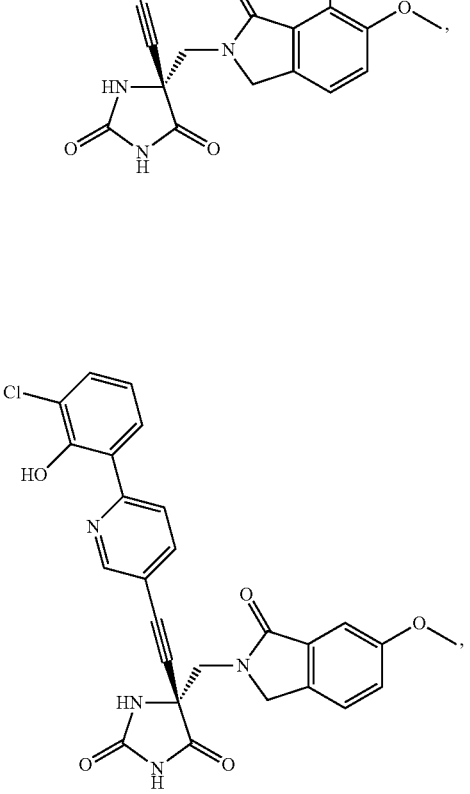

37
-continued
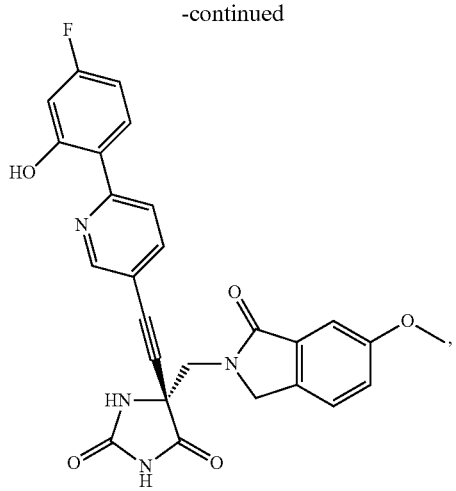
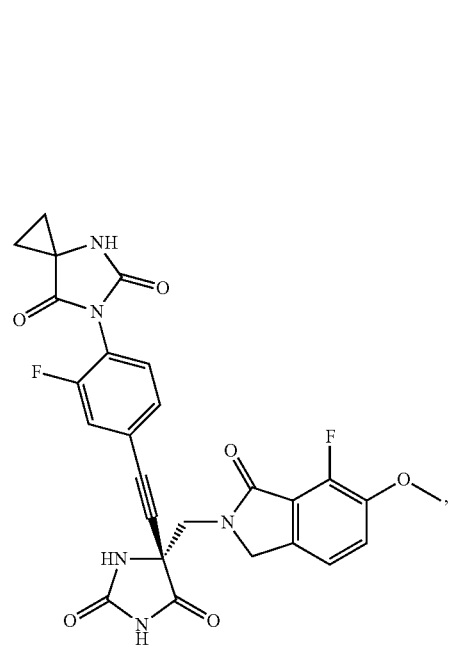
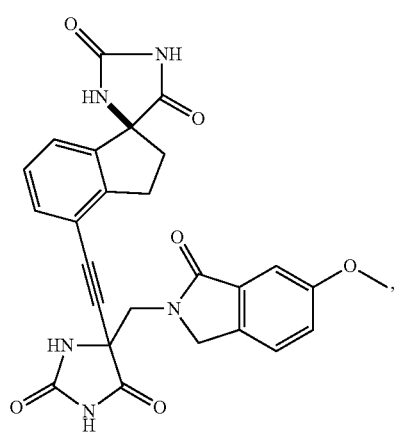
38
-continued
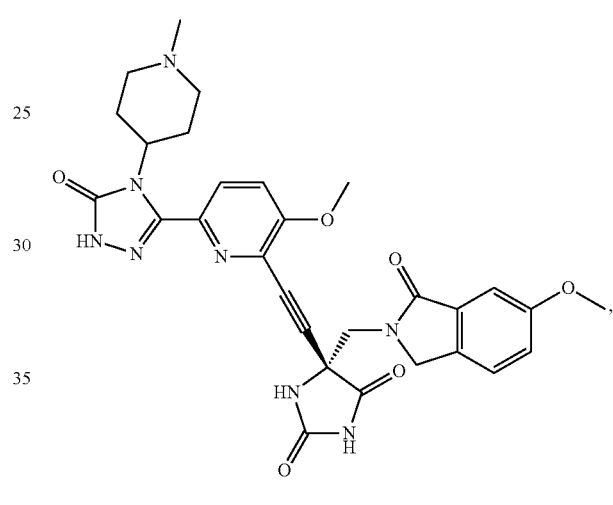
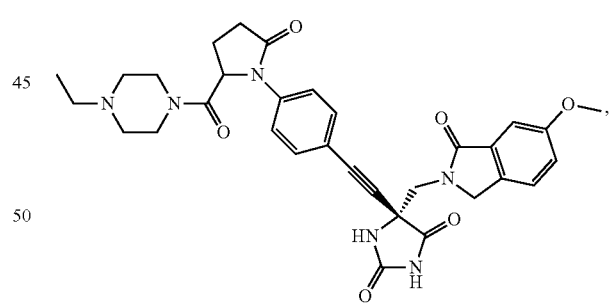
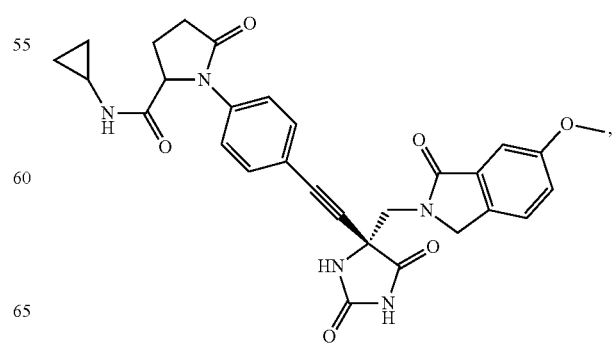

39
-continued
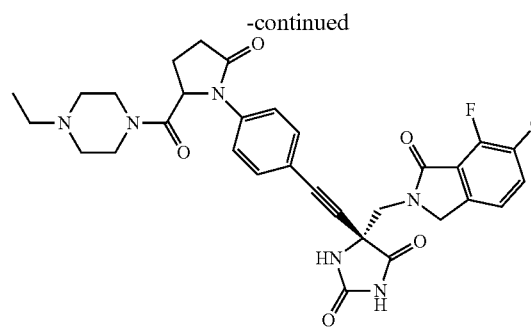
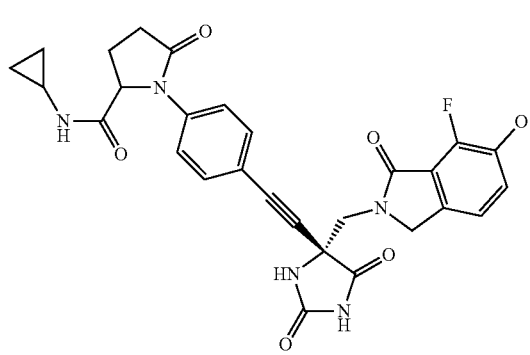
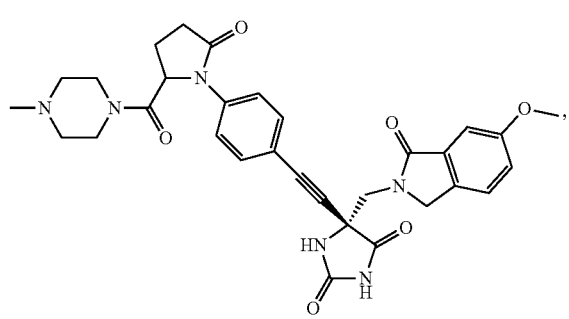
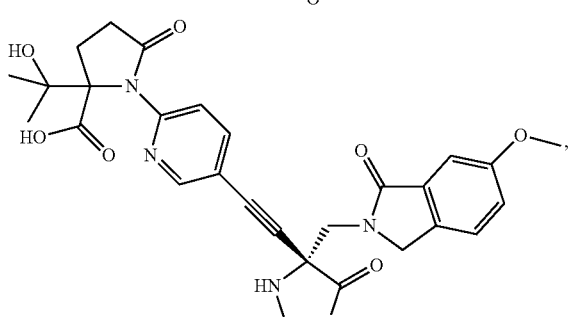
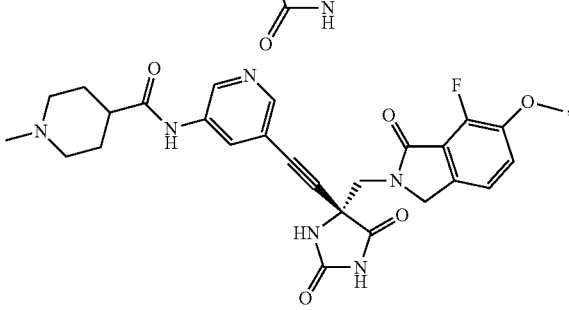
40
-continued
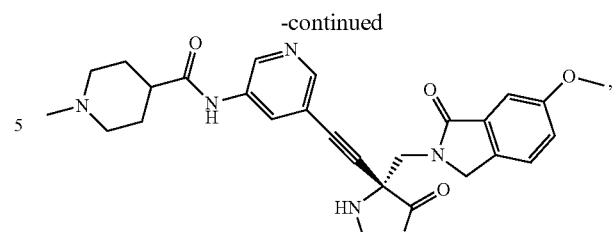
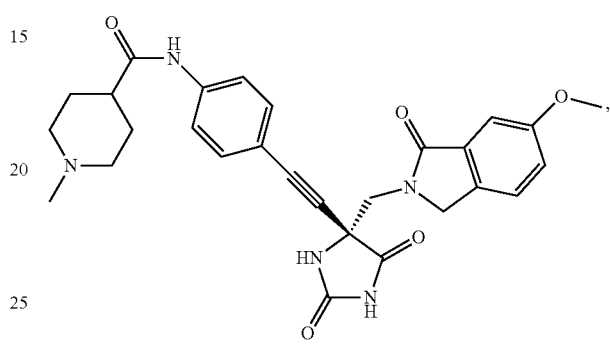
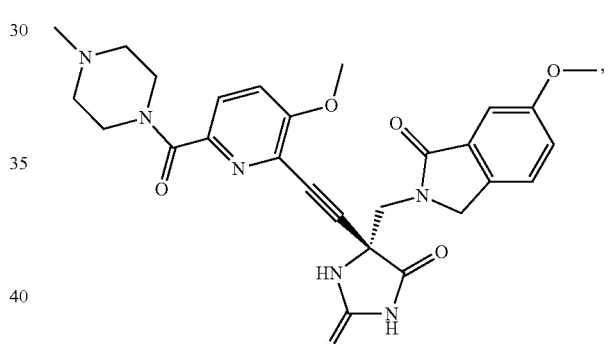
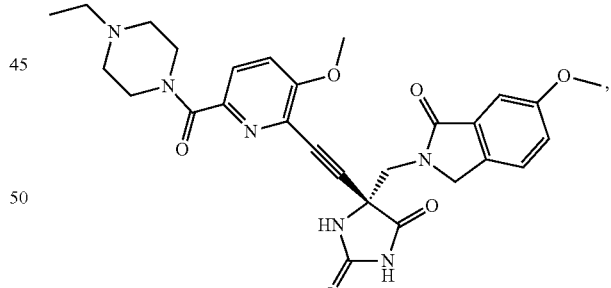
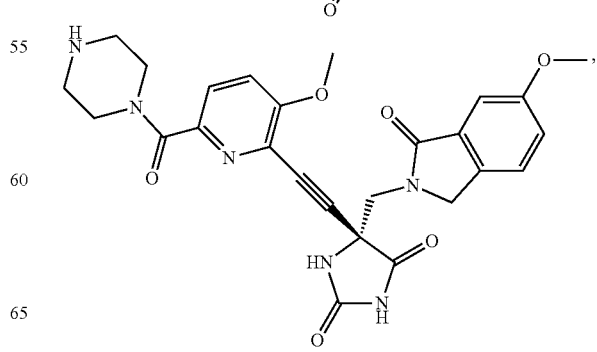

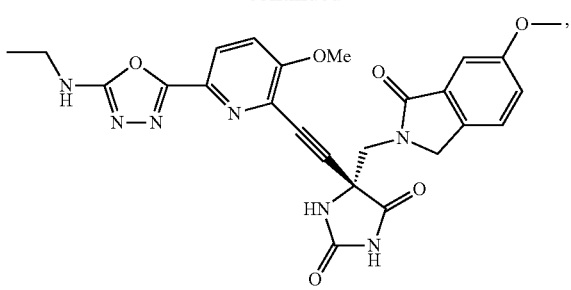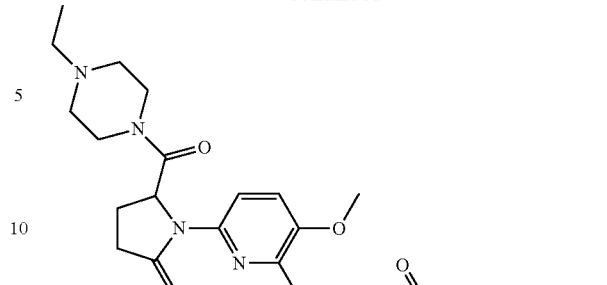

43
-continued
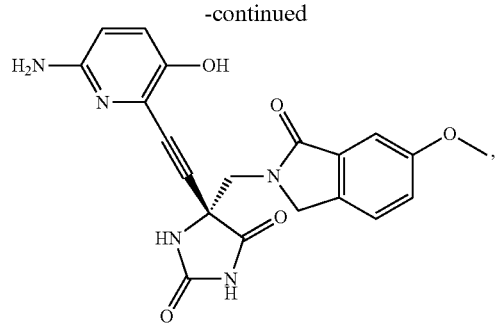
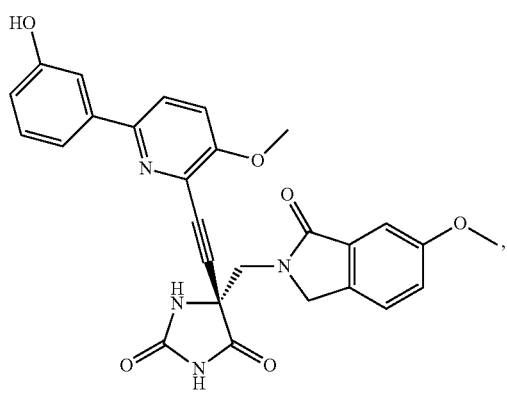
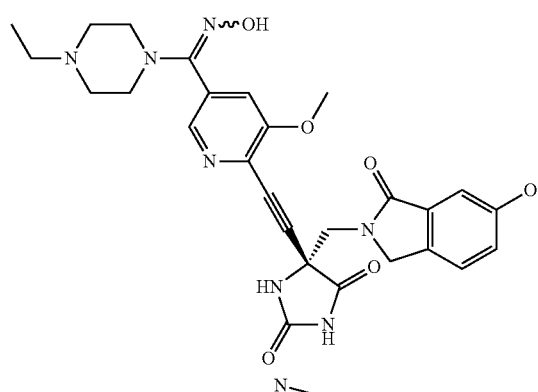
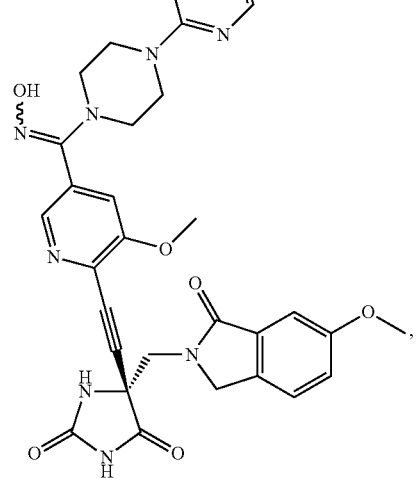
44
-continued
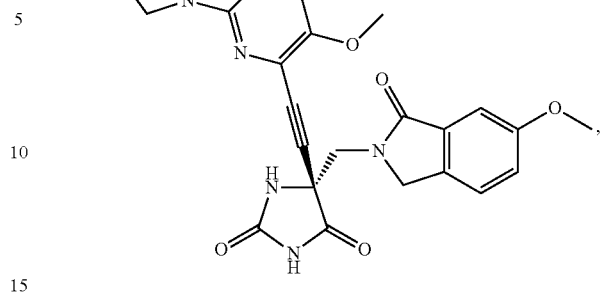
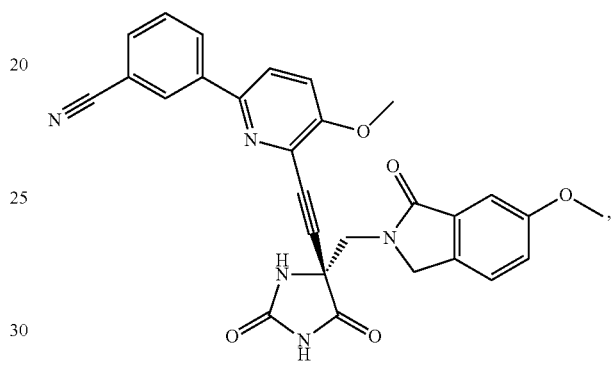
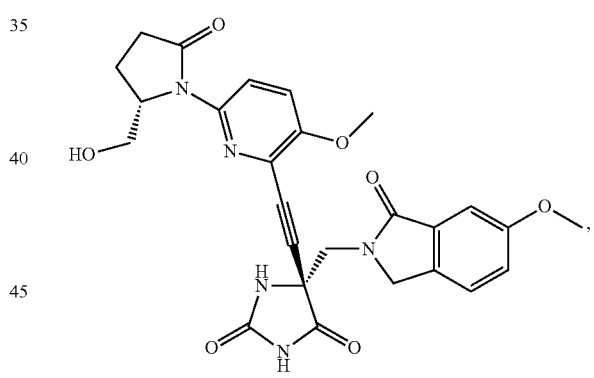
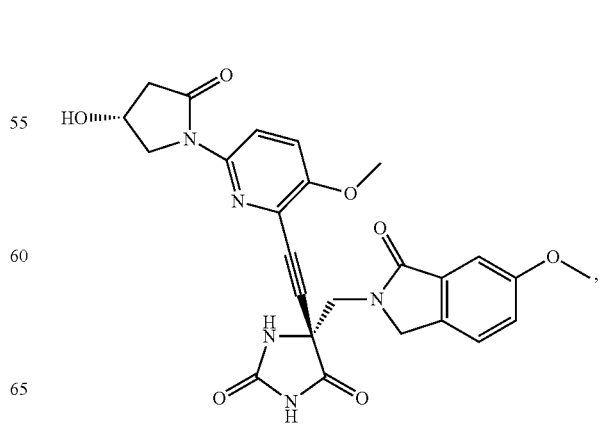

45
-continued
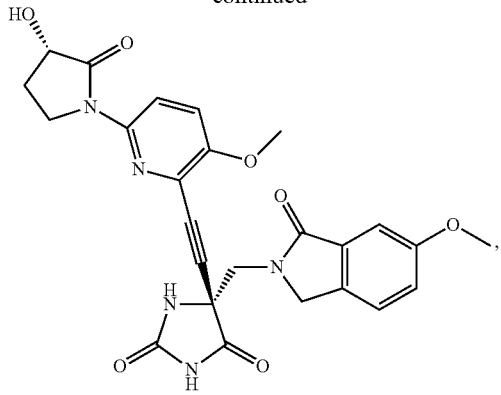
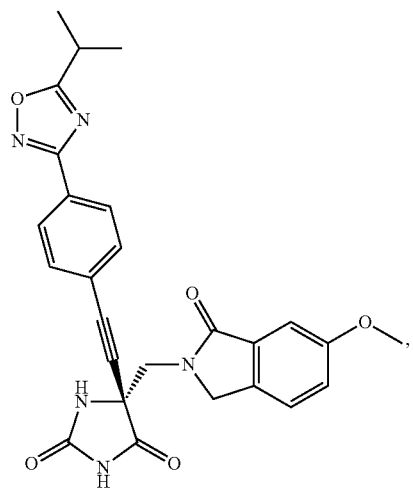
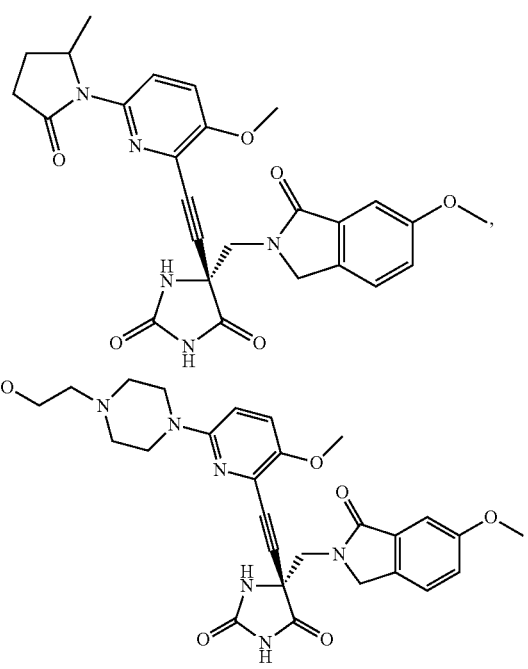
46
-continued
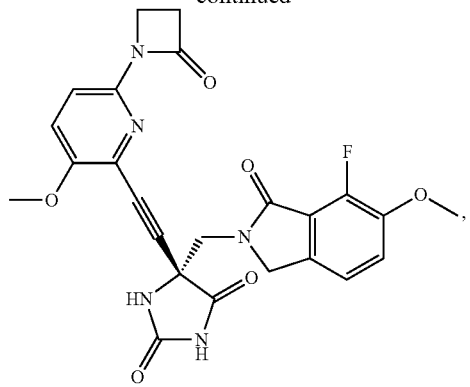
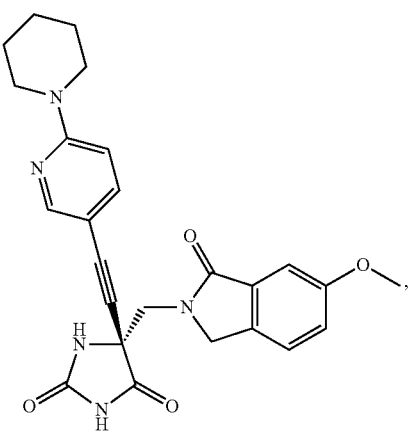
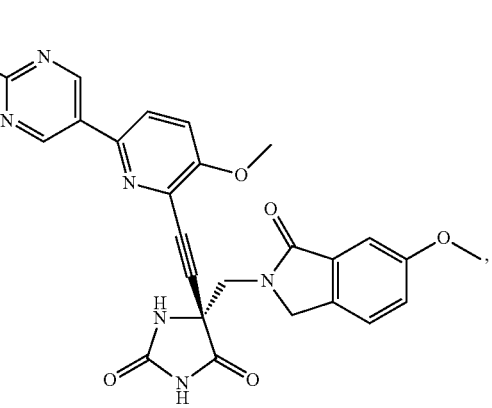
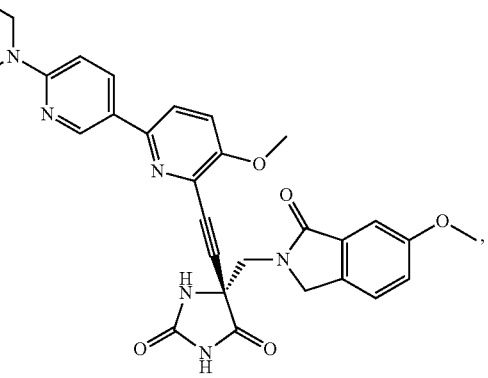

47
-continued
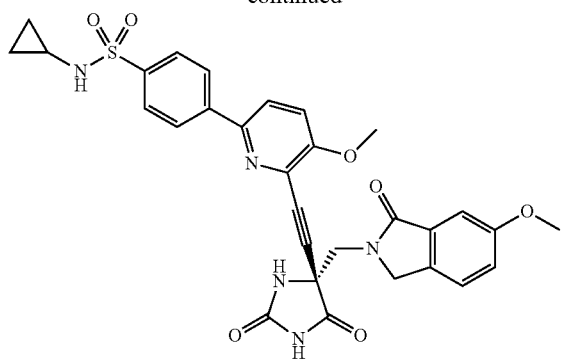
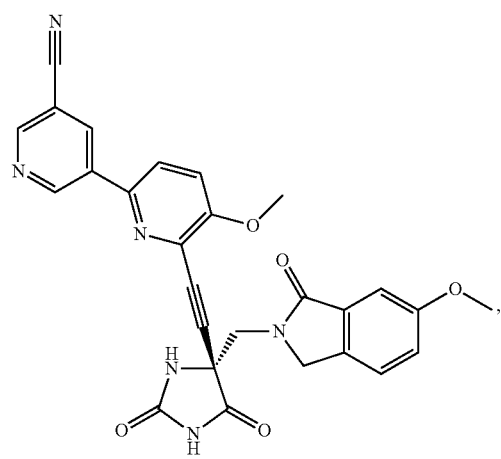
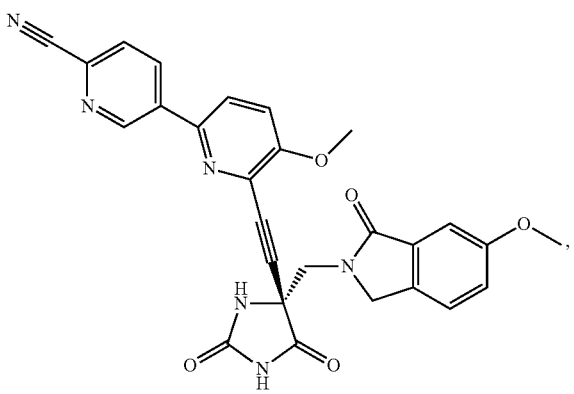
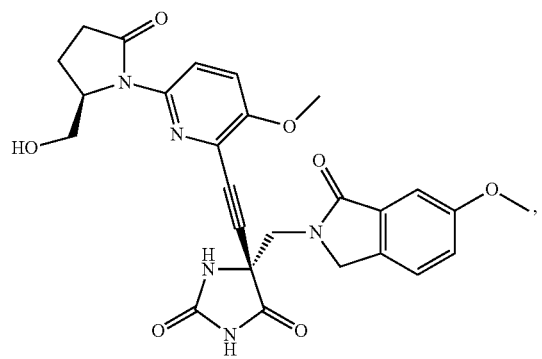
48
-continued
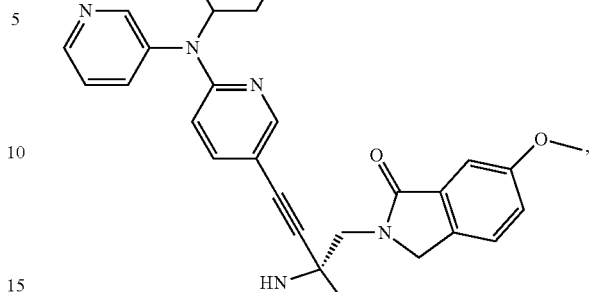
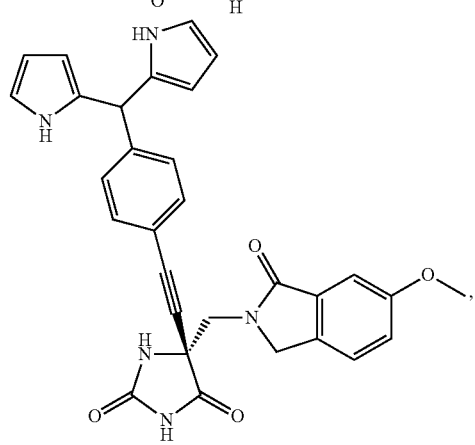
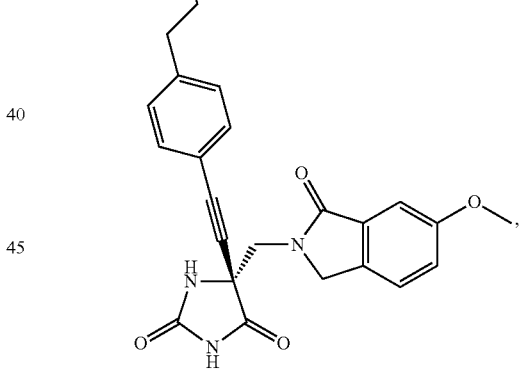
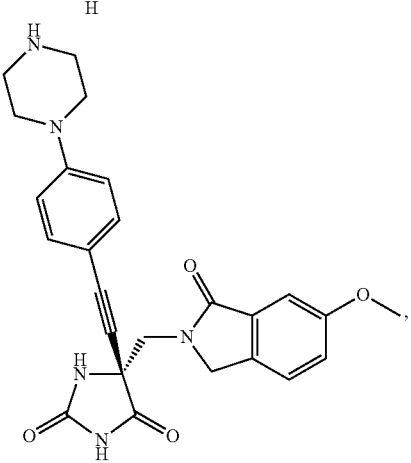

49
-continued
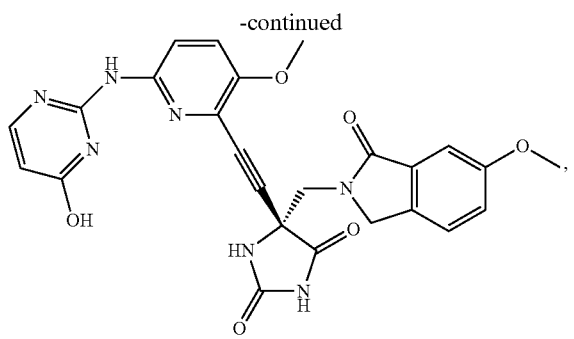
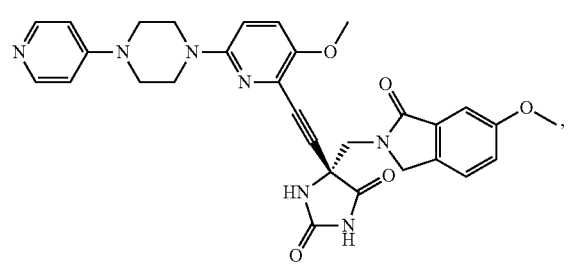
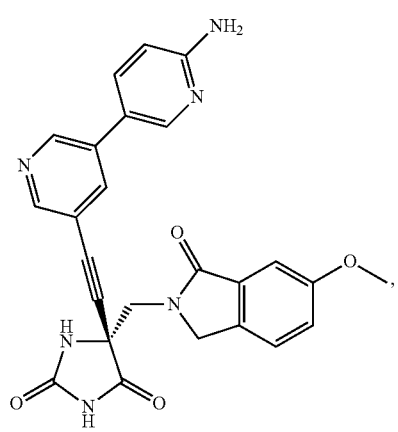
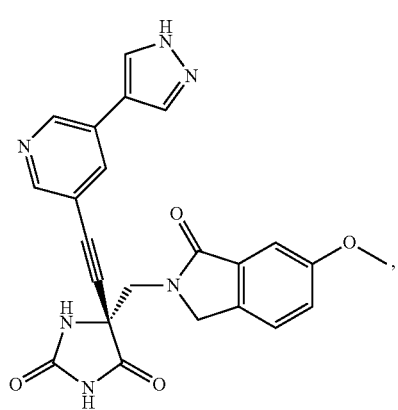
50
-continued
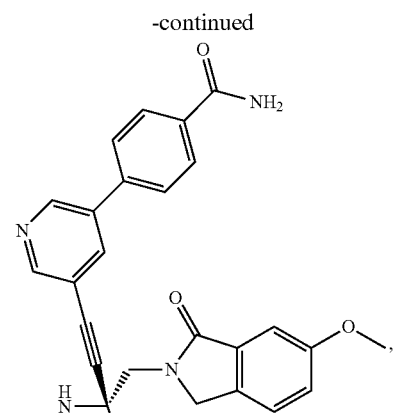
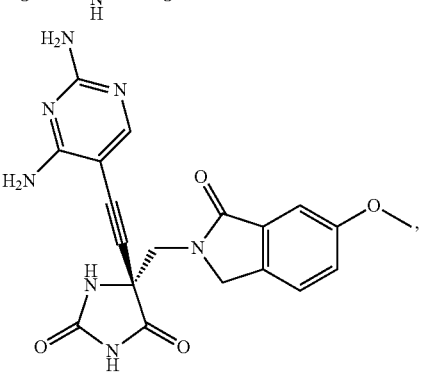
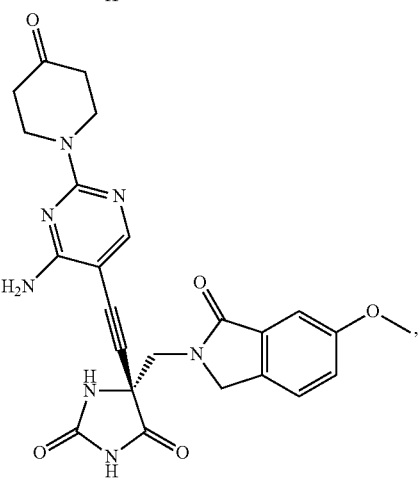
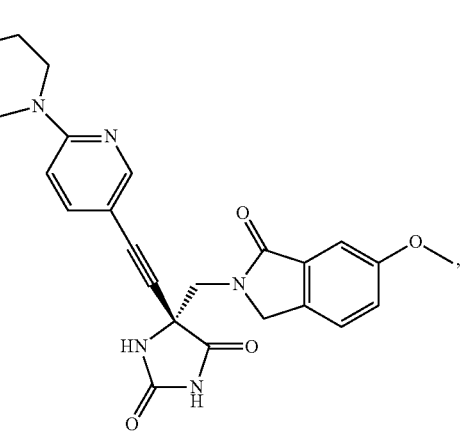

51
-continued
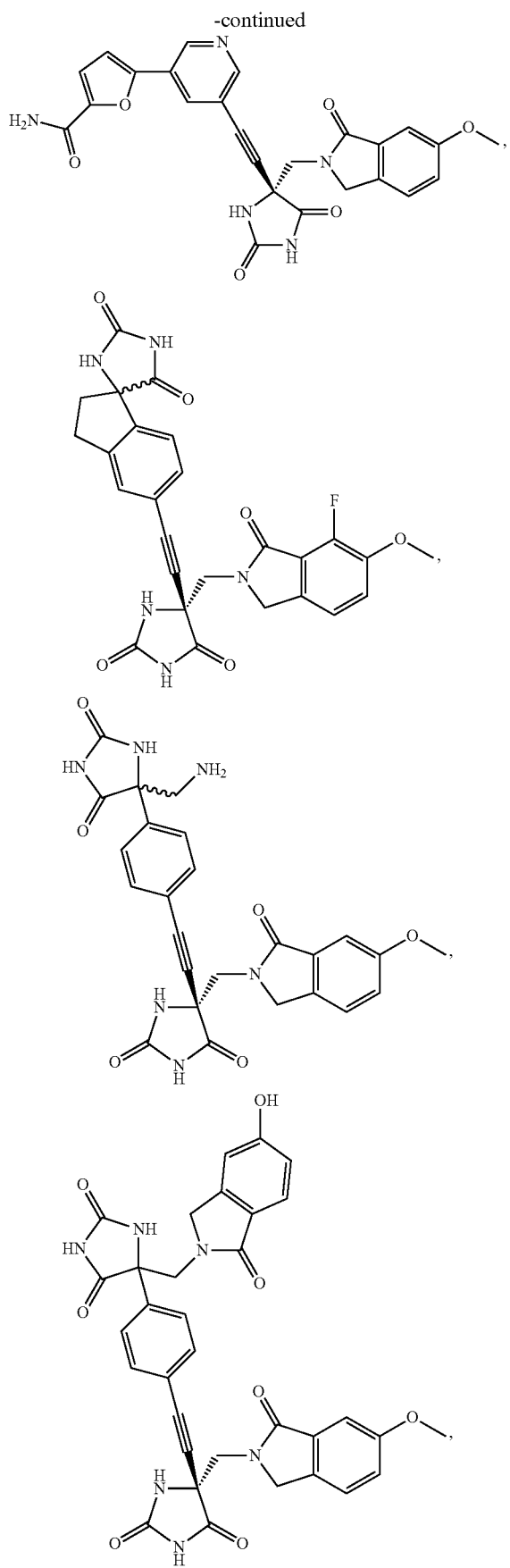
52
-continued
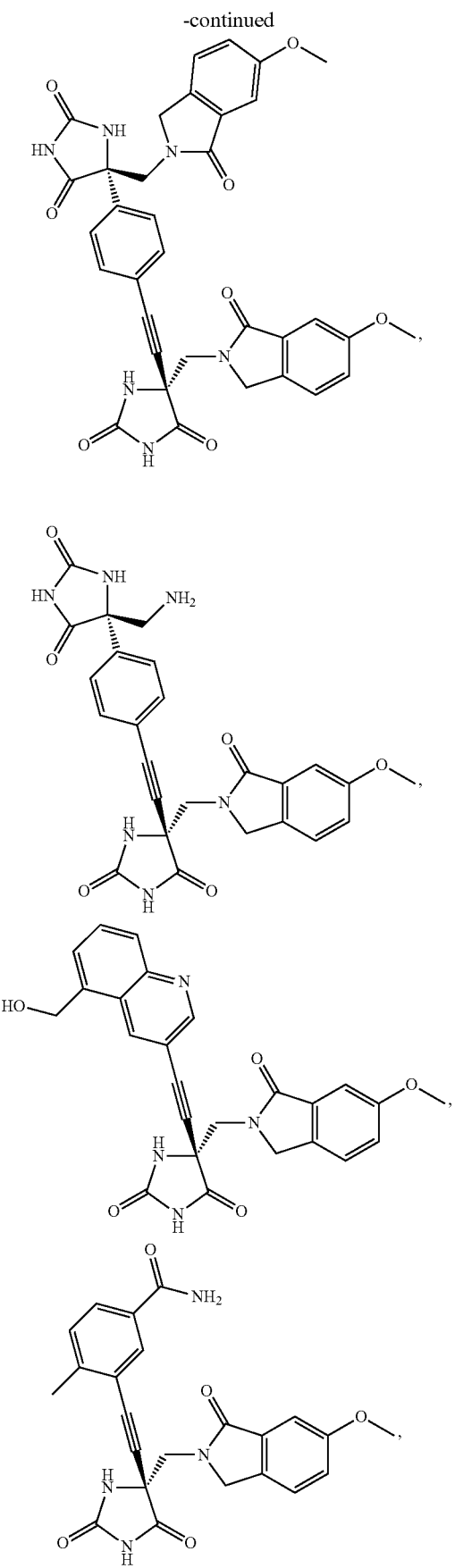

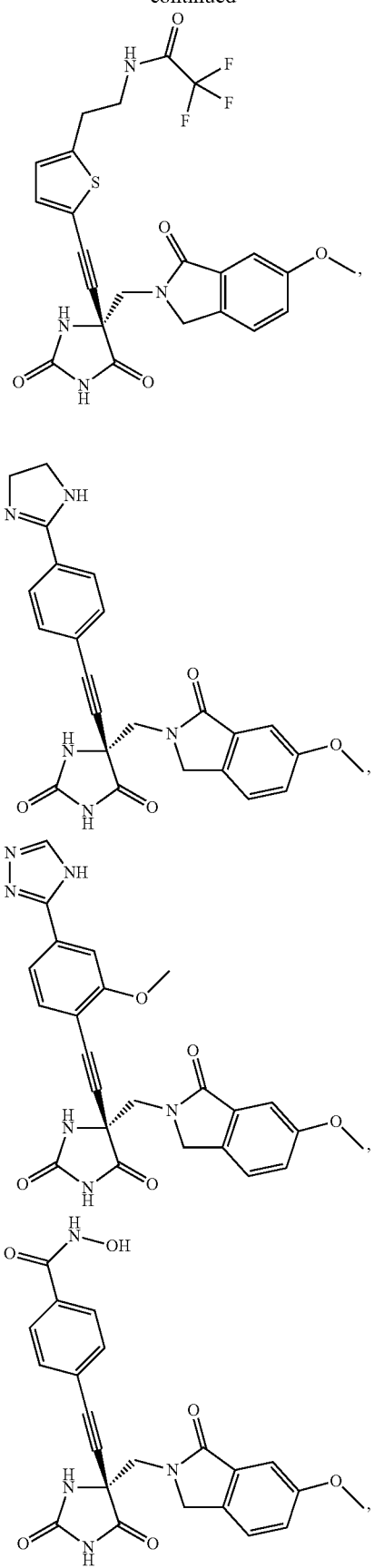
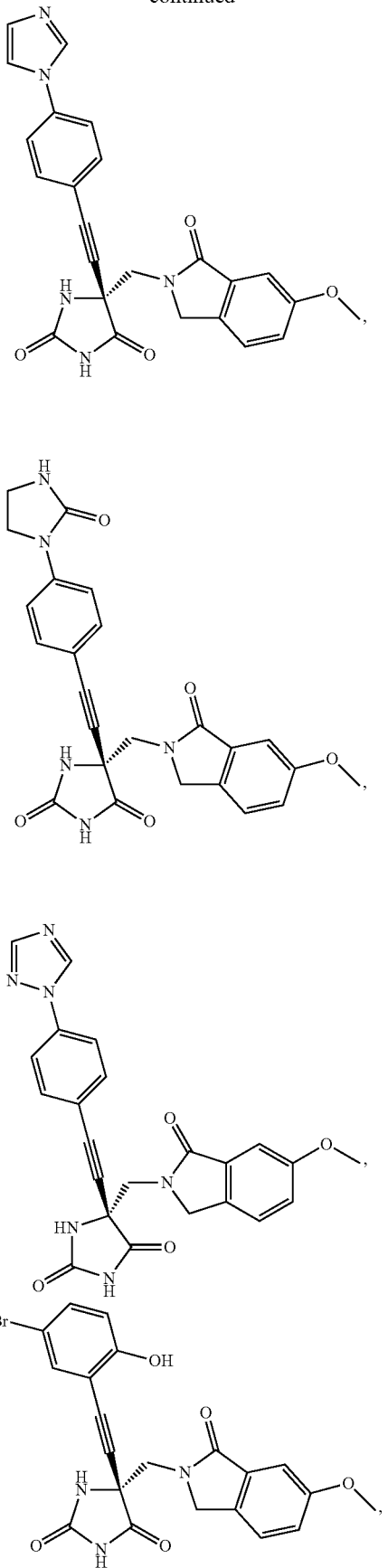

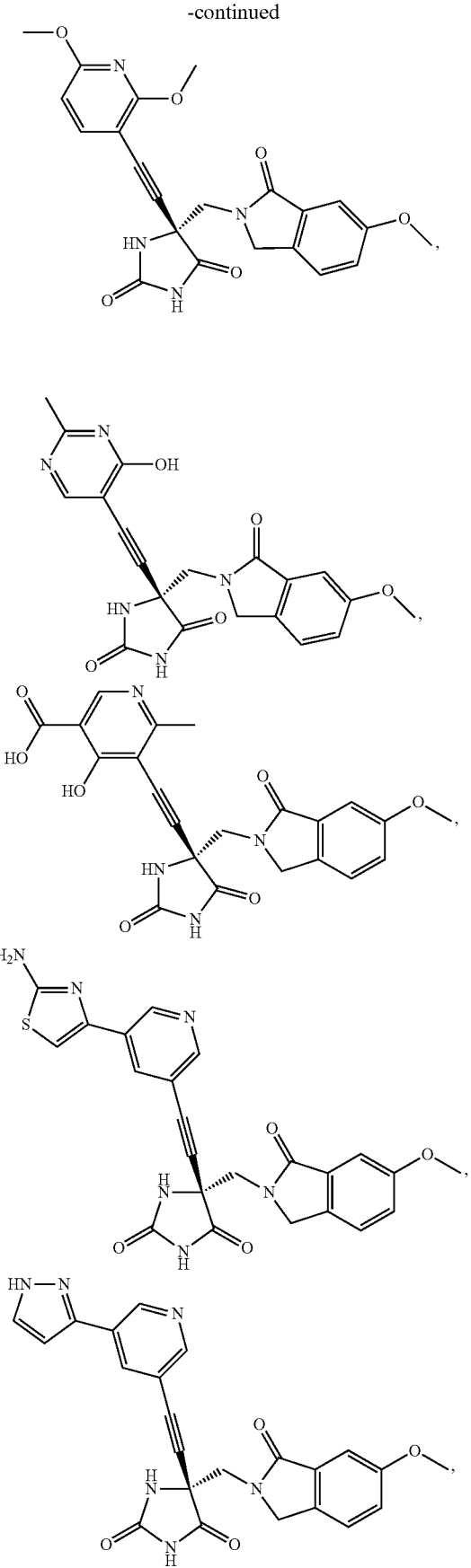
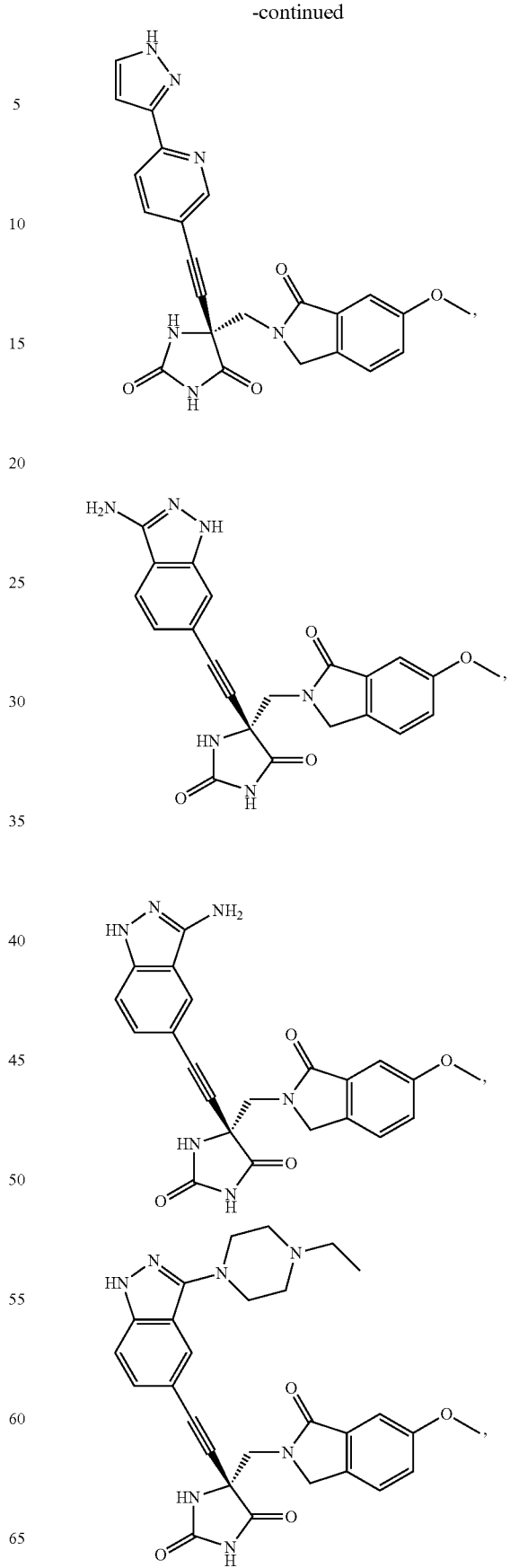

57
-continued
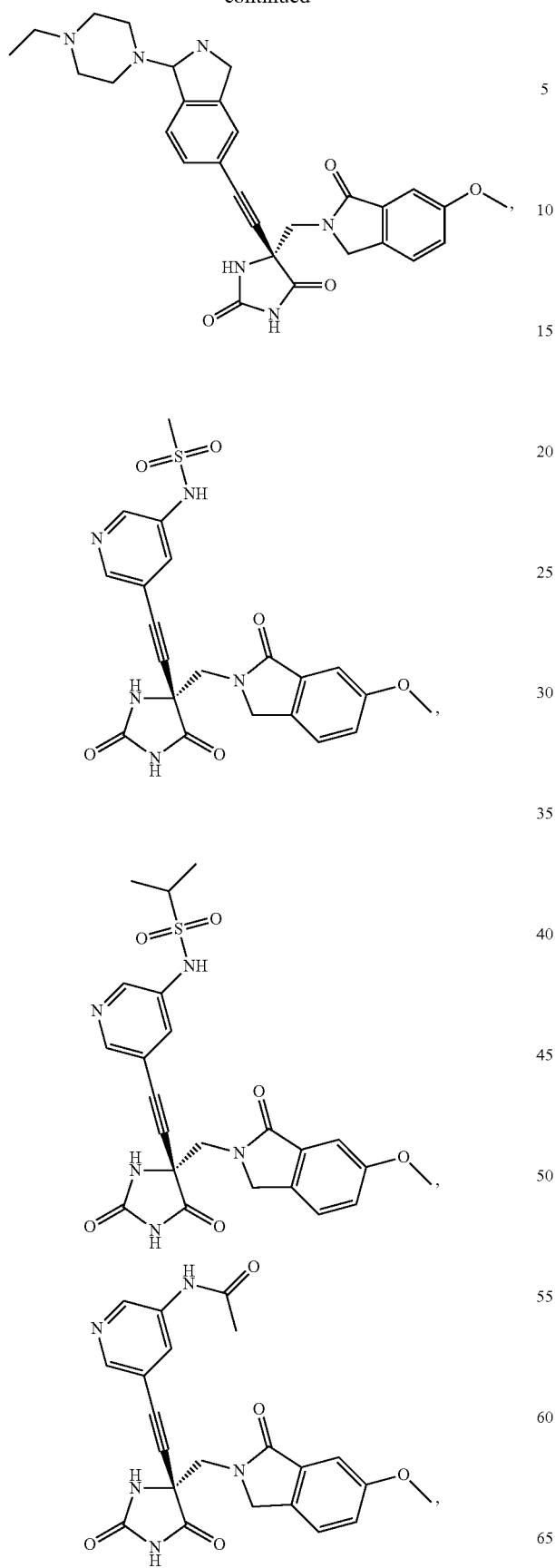
58
-continued
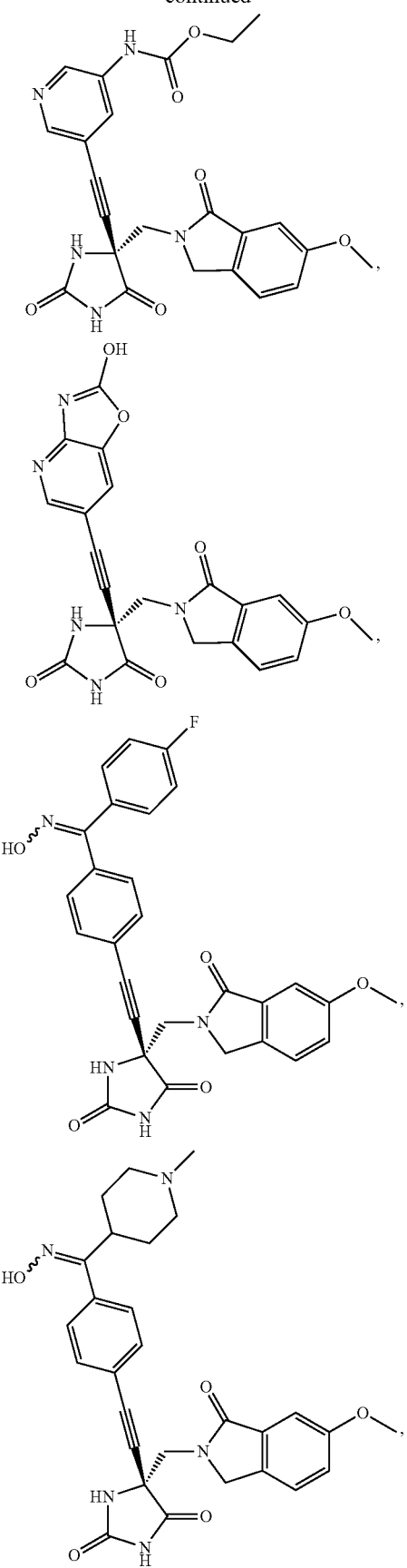

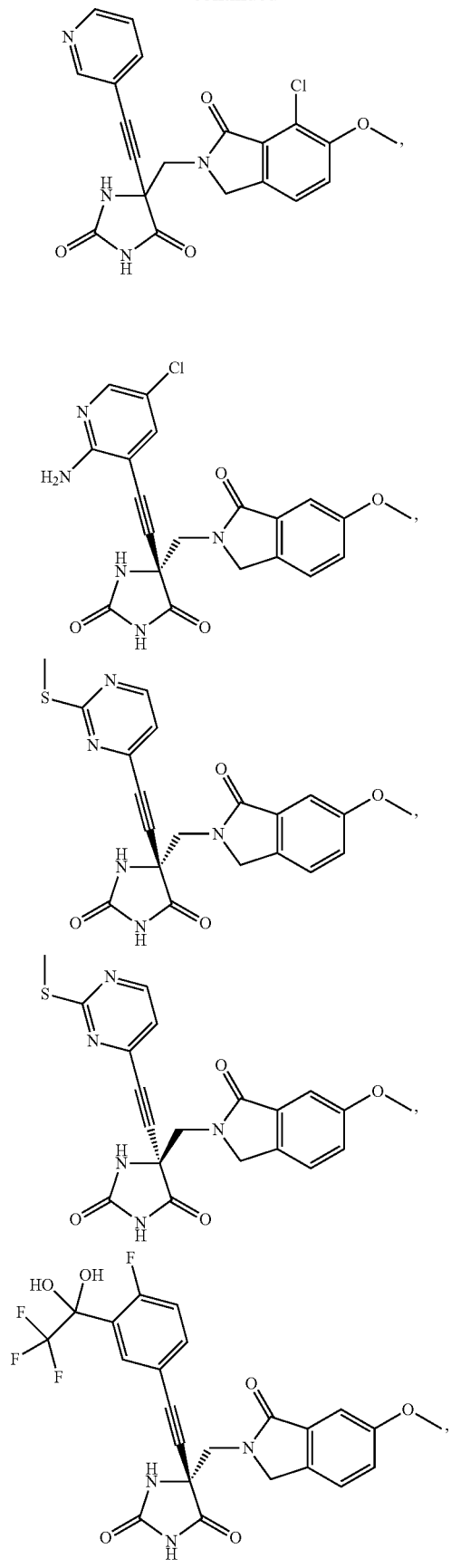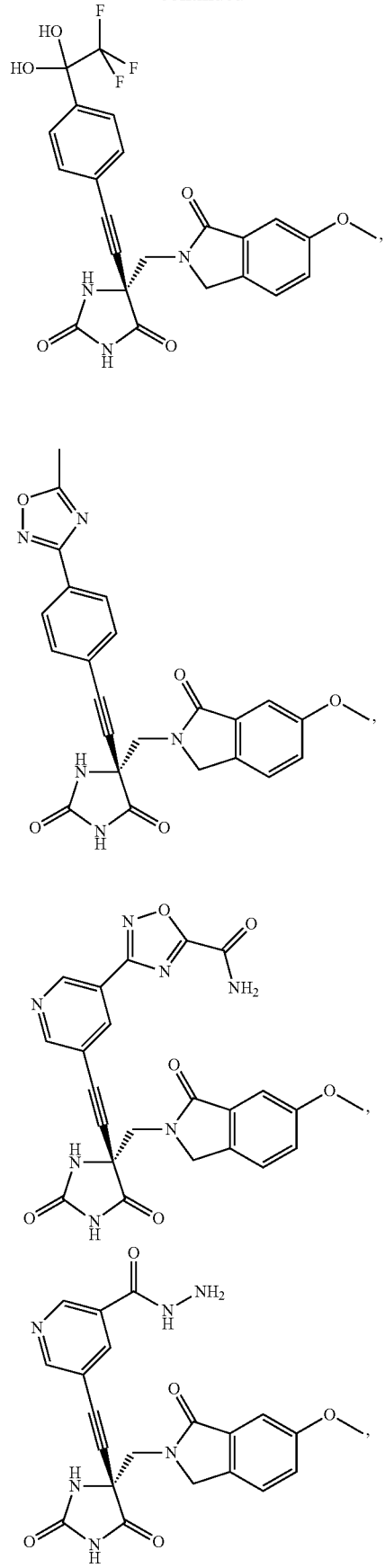

-continued
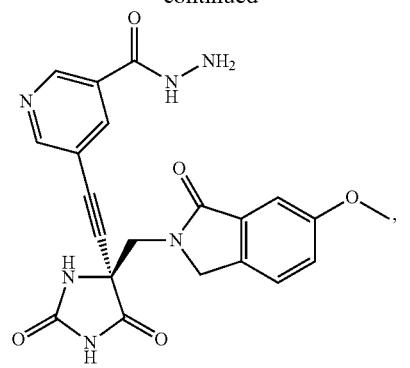
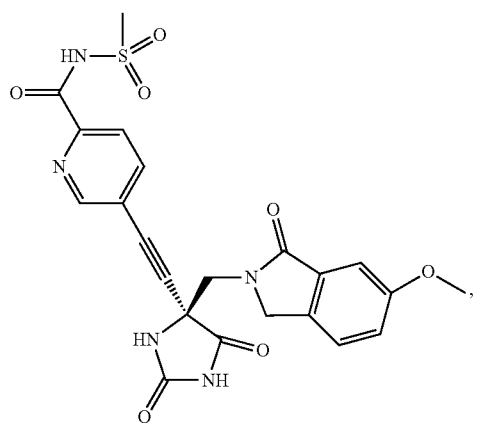
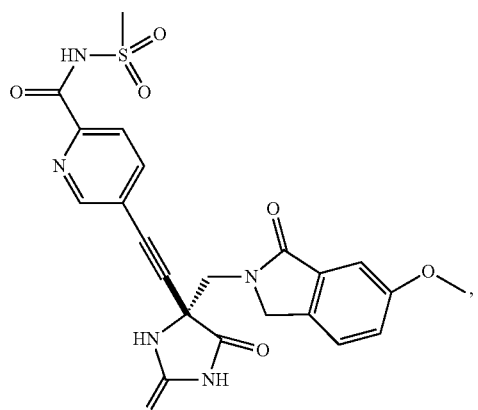
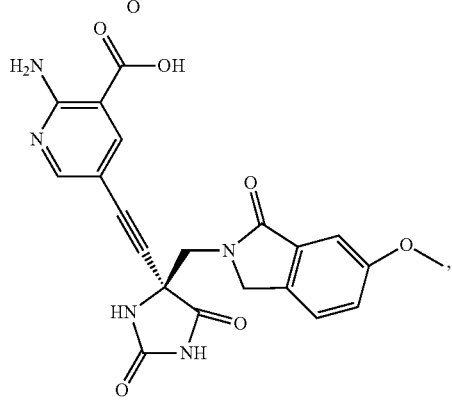
-continued
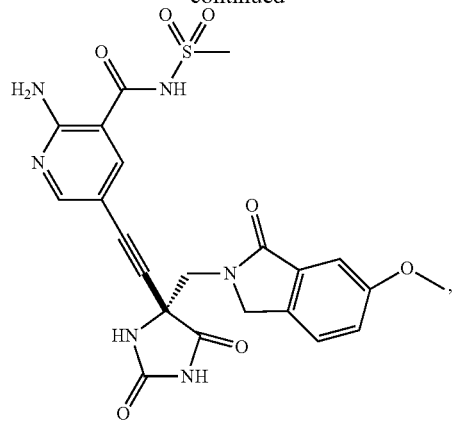
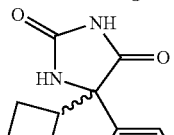
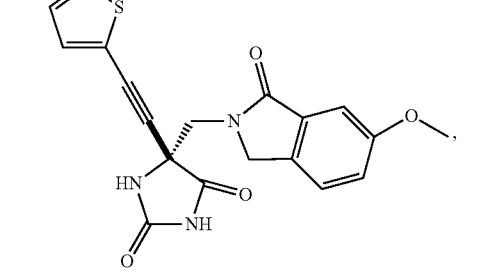

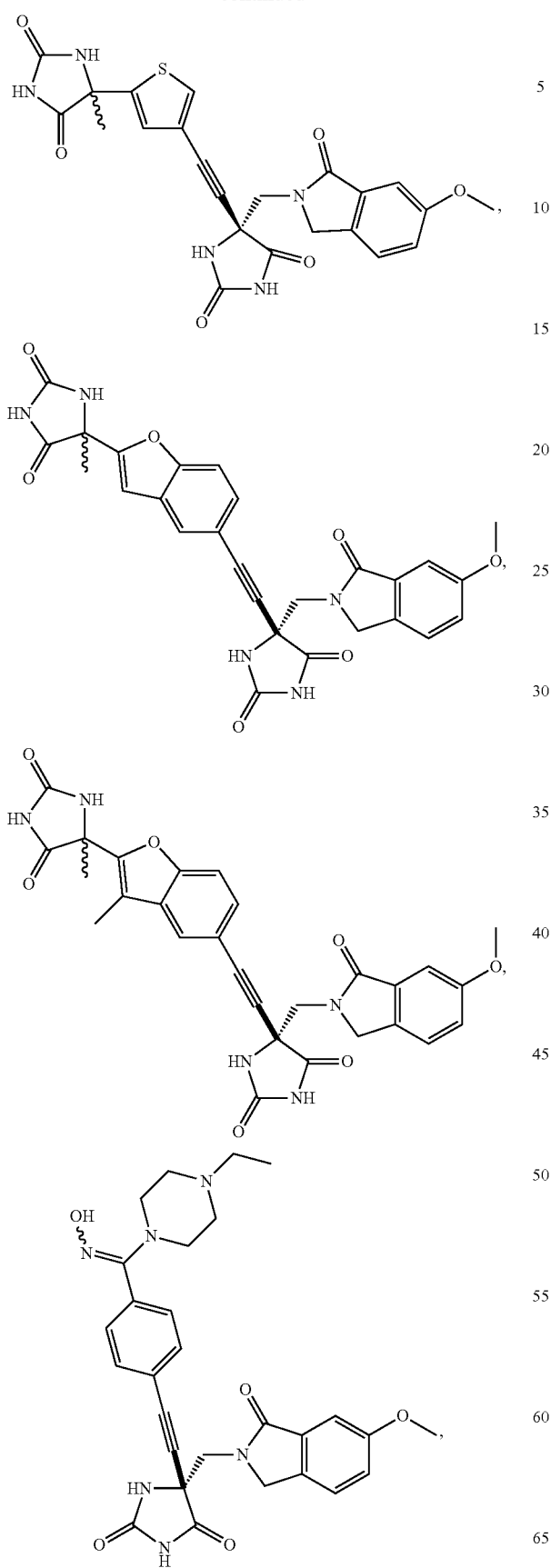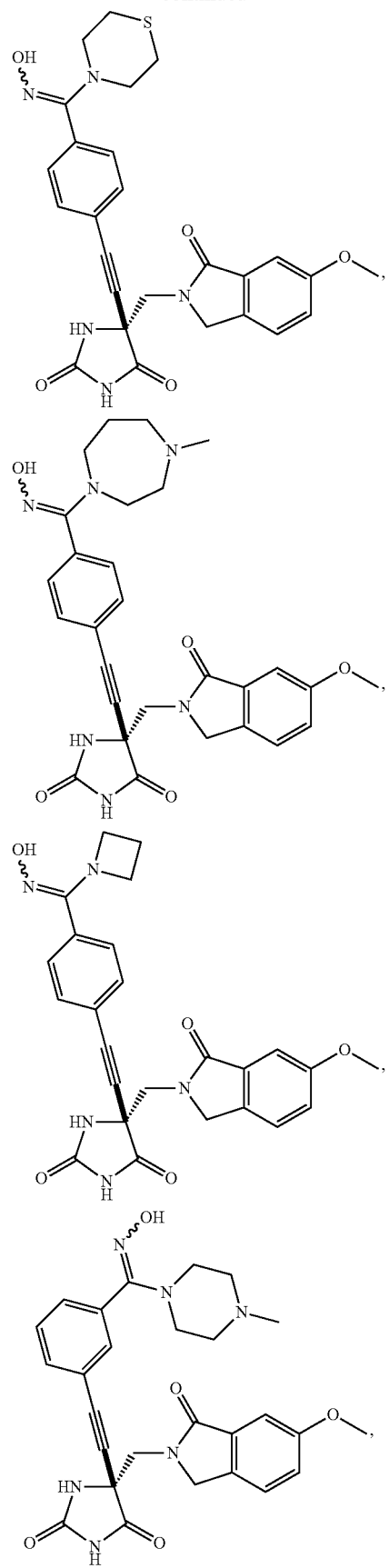

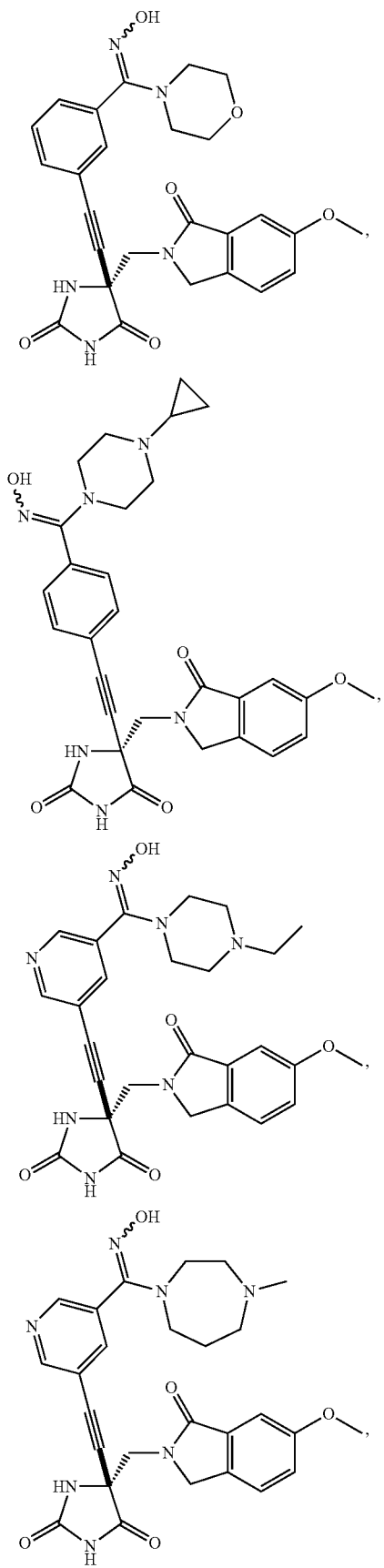
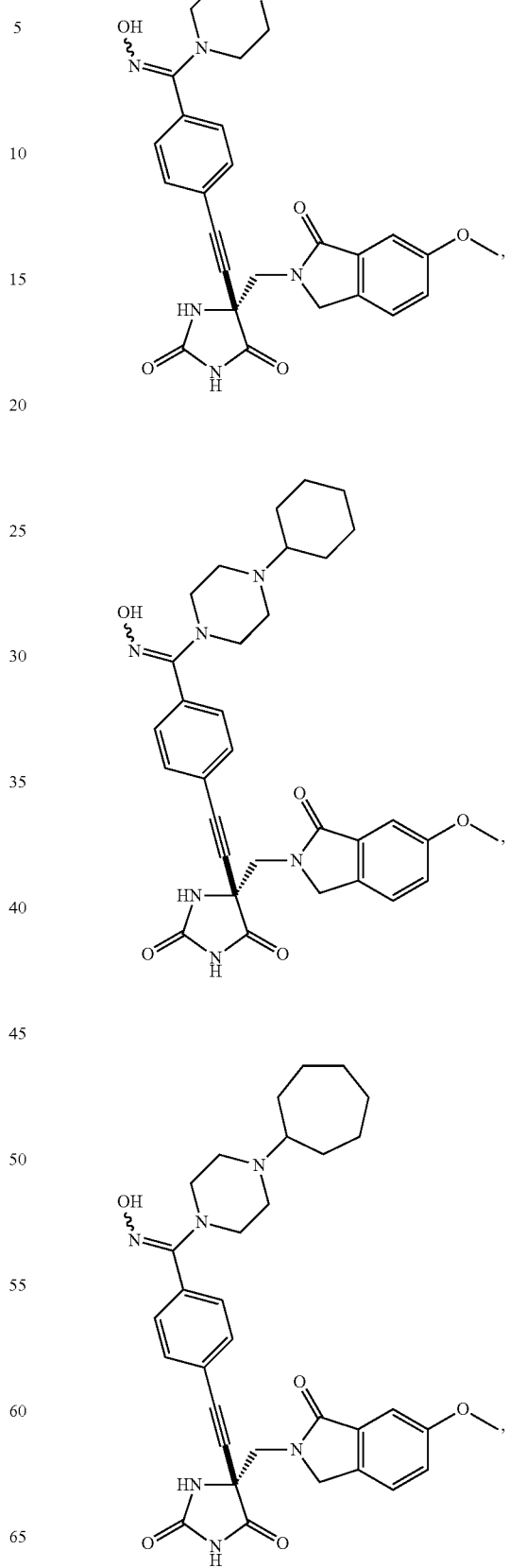

67
-continued
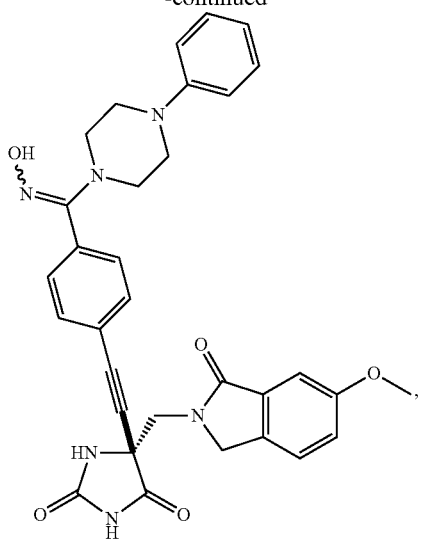
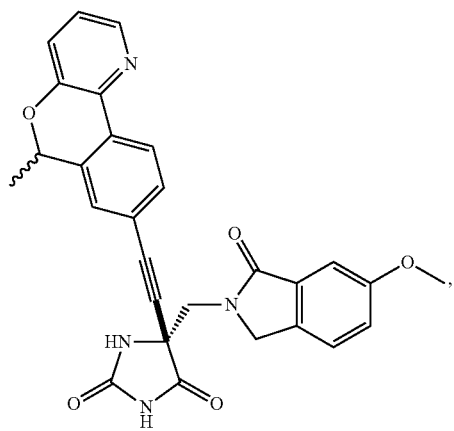
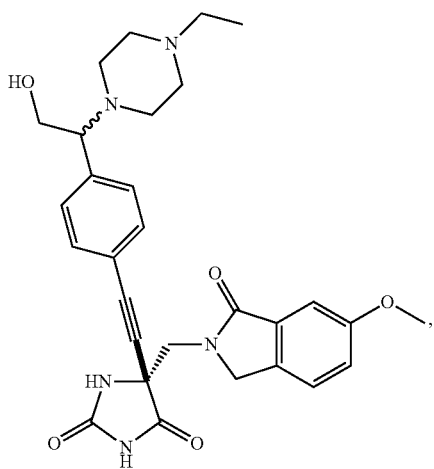
68
-continued
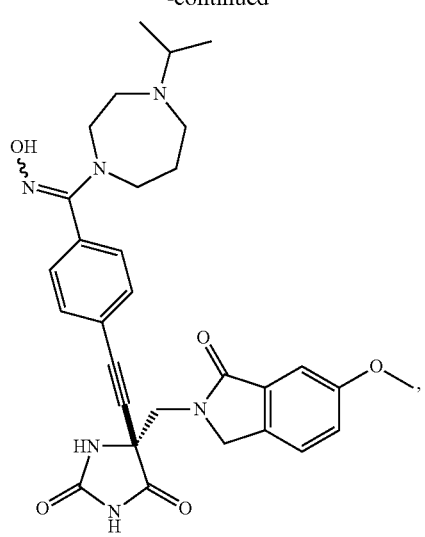
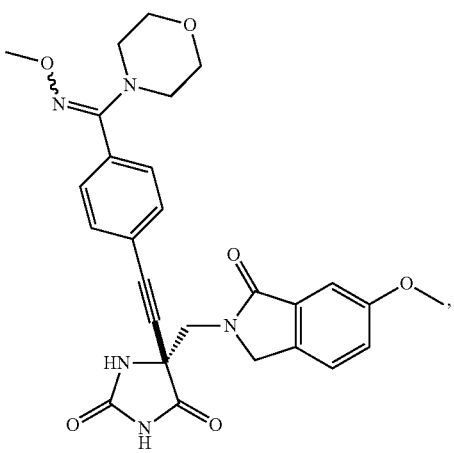
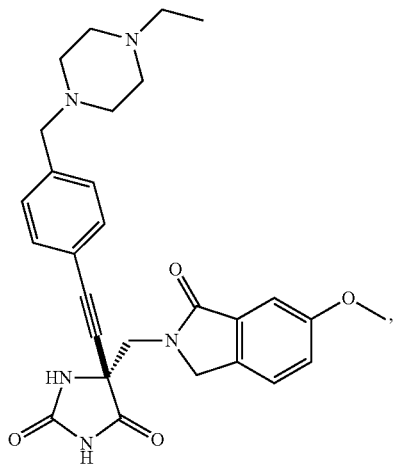

69
-continued
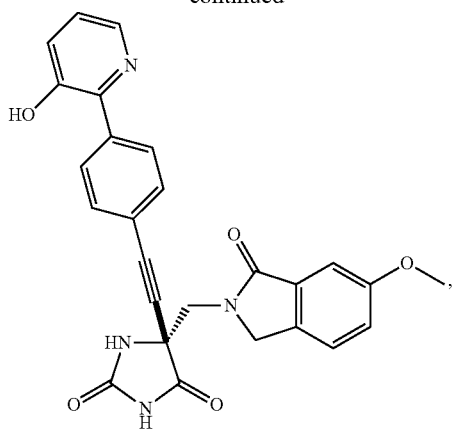
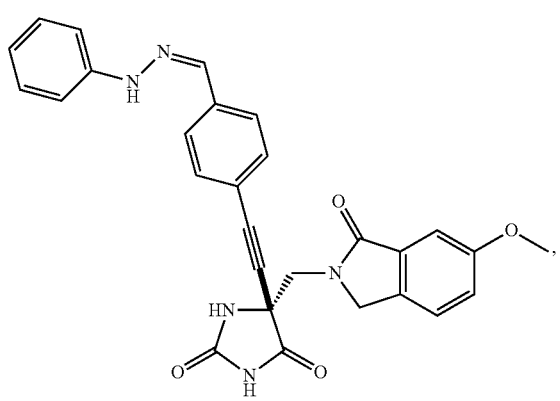
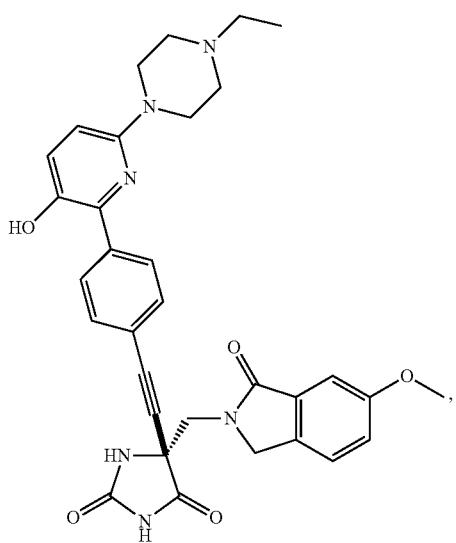
70
-continued
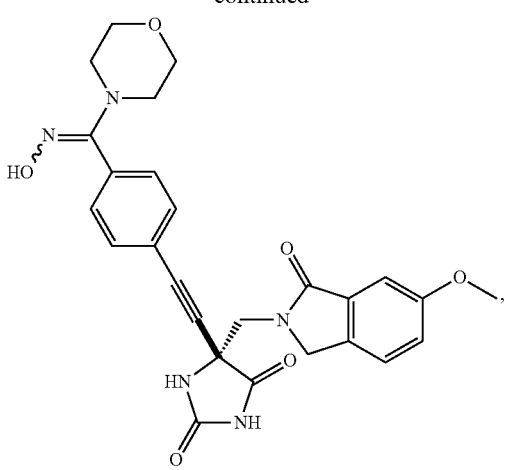
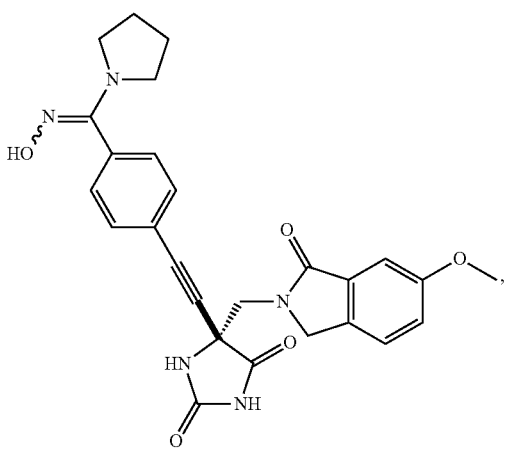
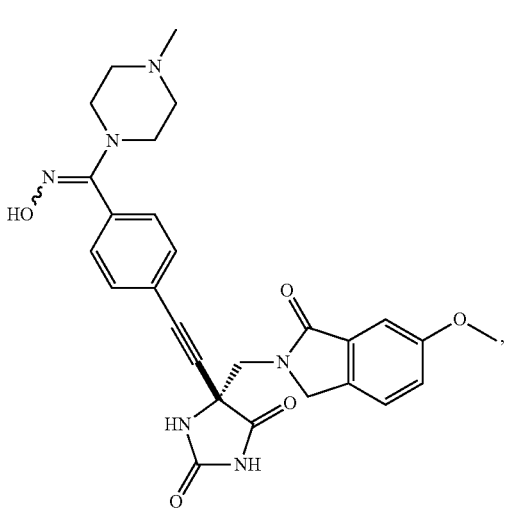

71
-continued
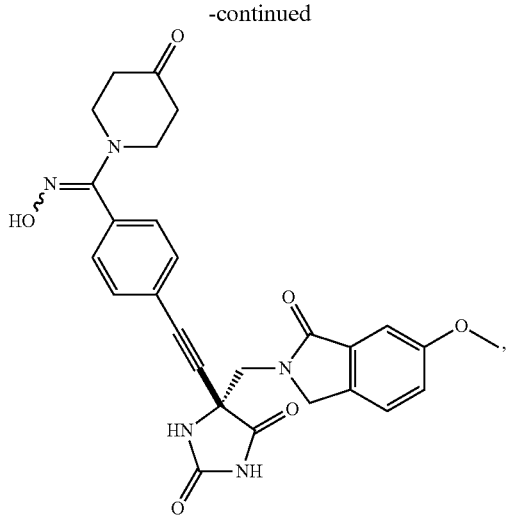
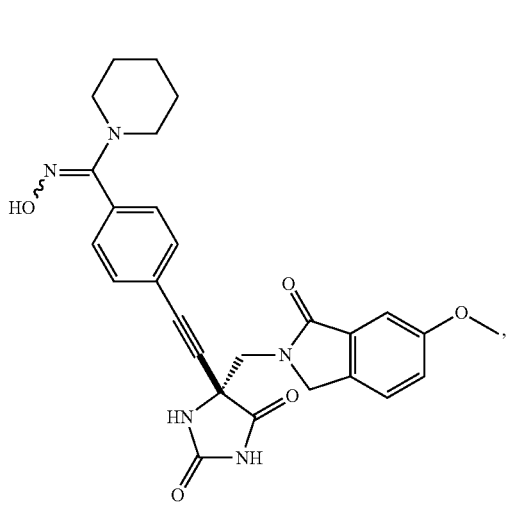
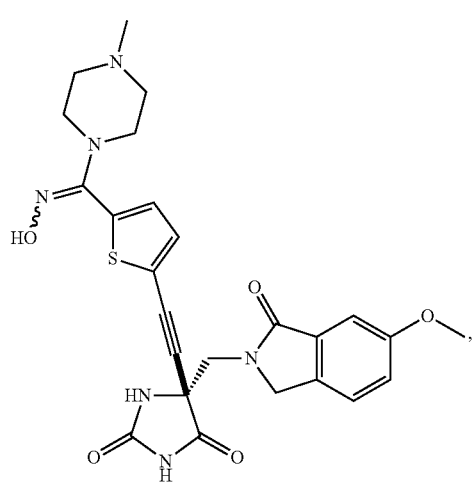
72
-continued
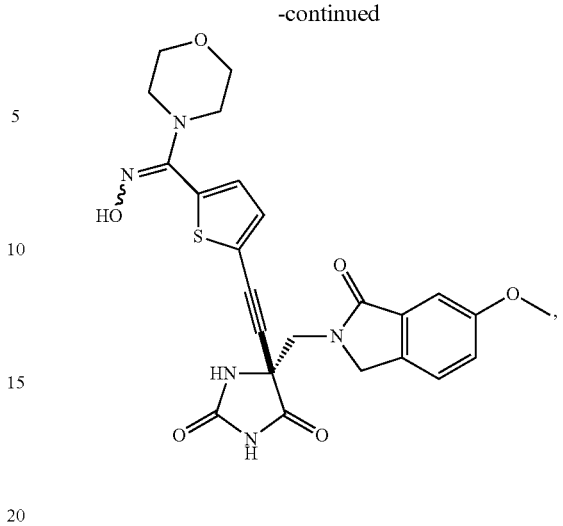
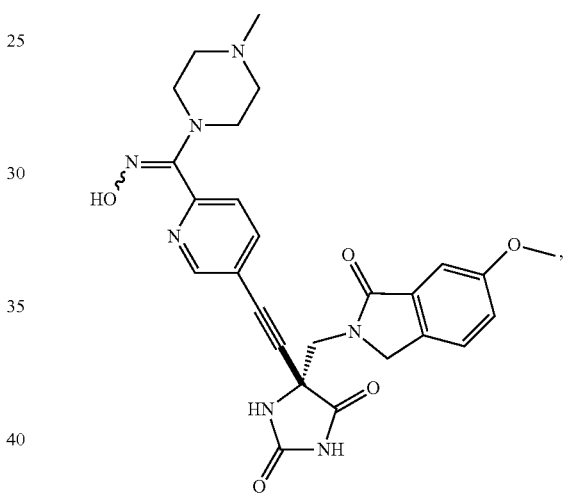
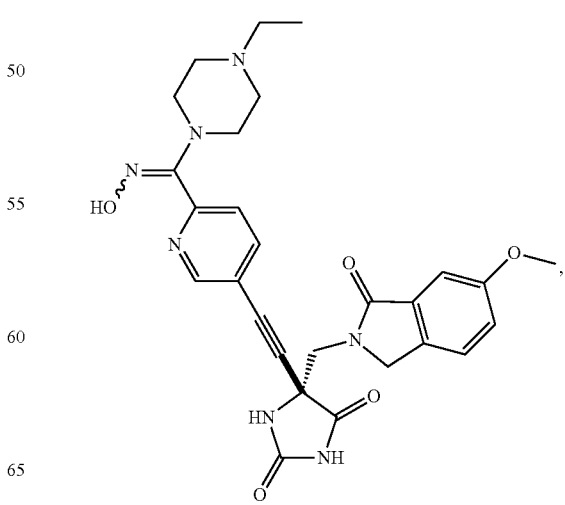

73
-continued
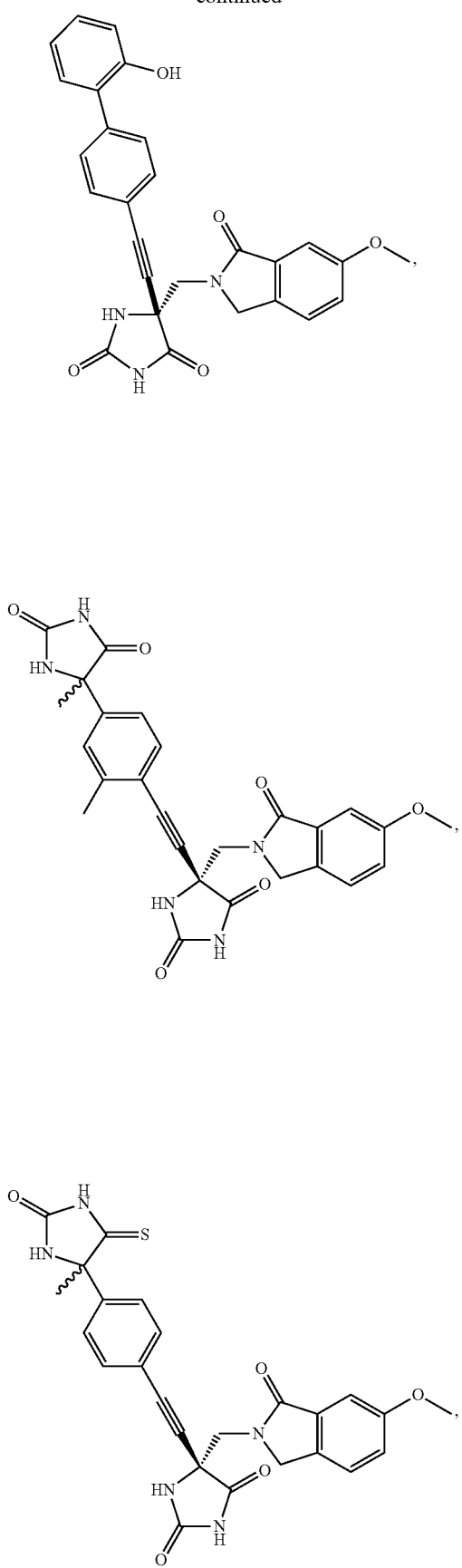
74
-continued
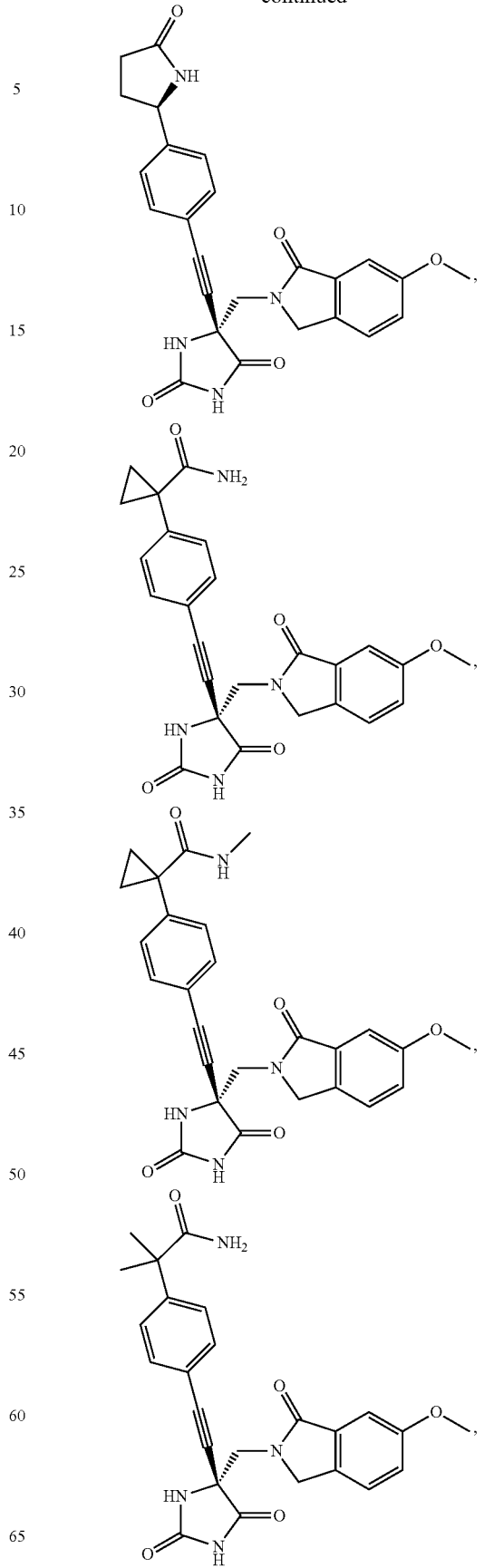

-continued
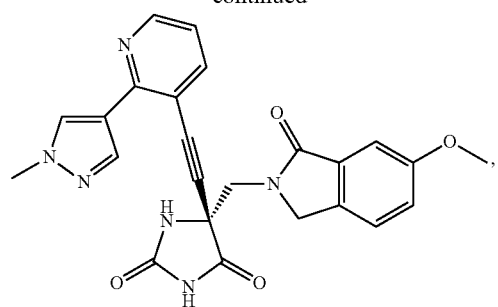
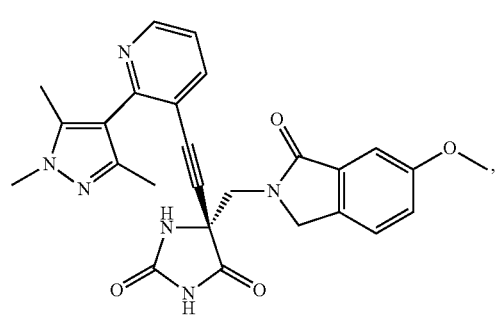
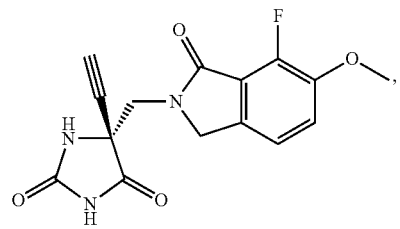
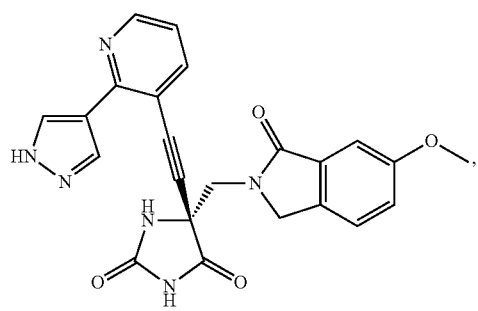
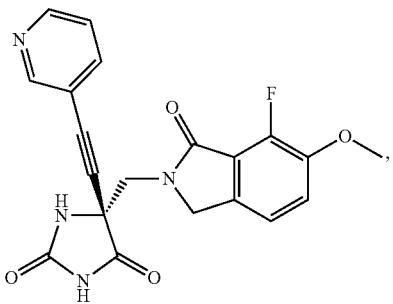
-continued
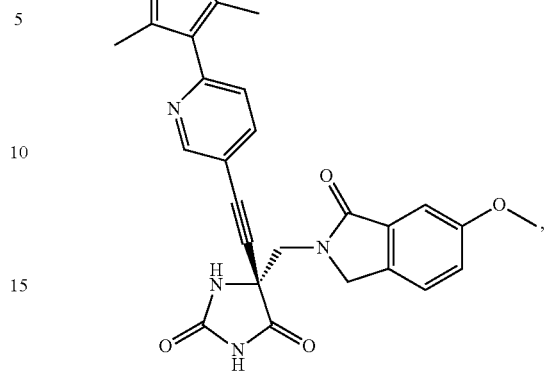
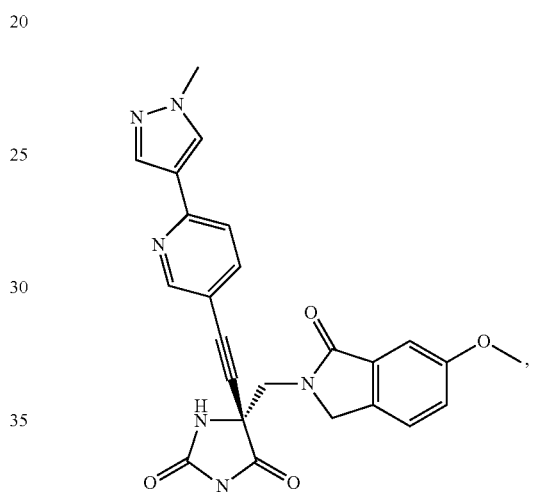

77
-continued
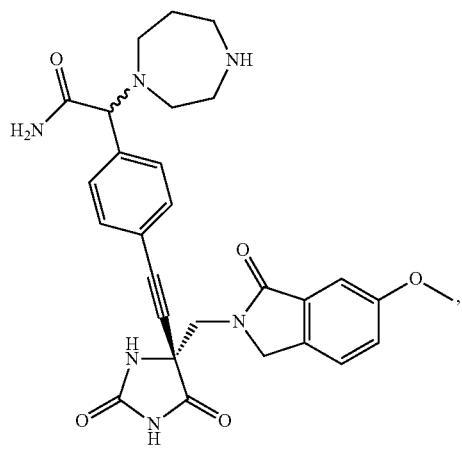
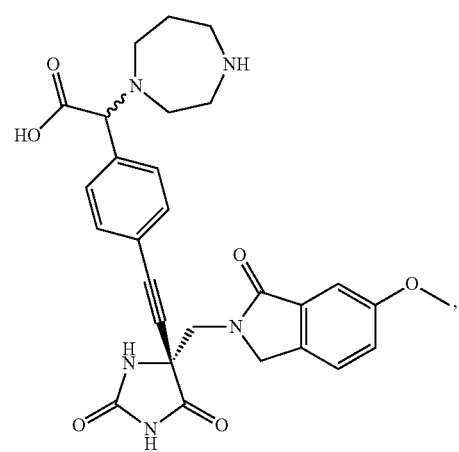
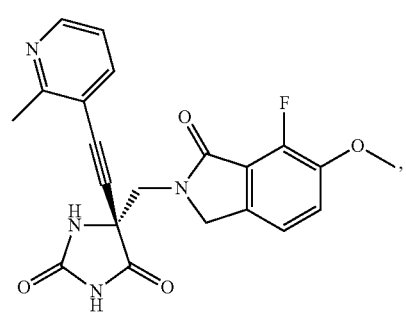
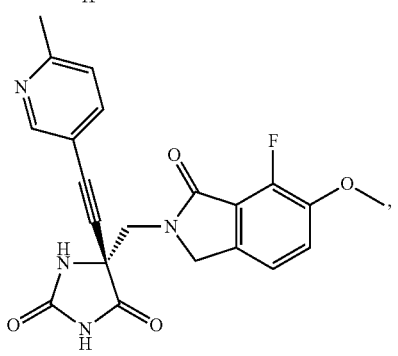
78
-continued
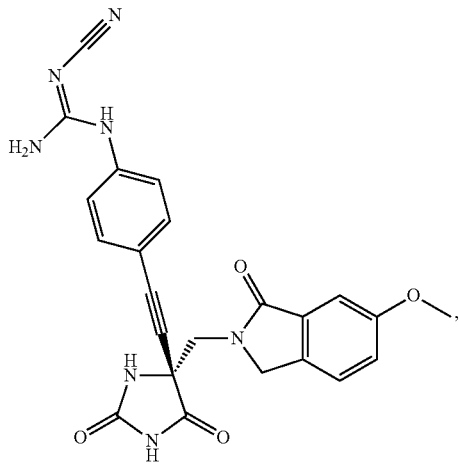
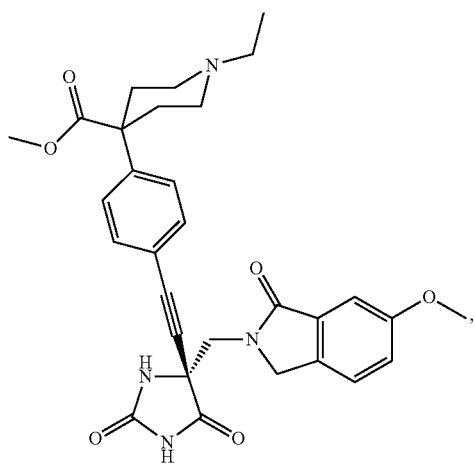
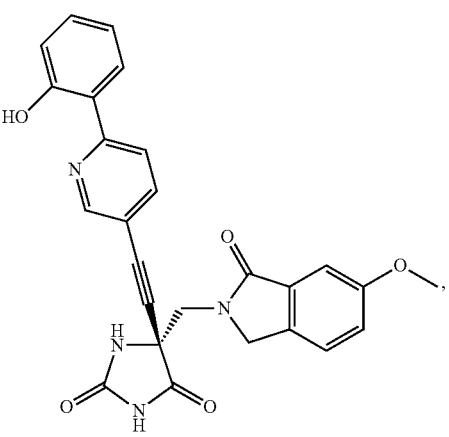

79
-continued
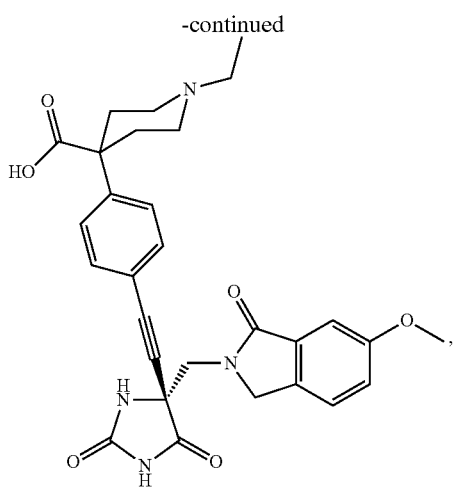
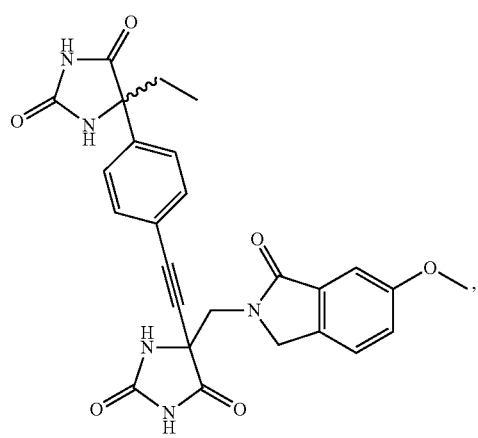
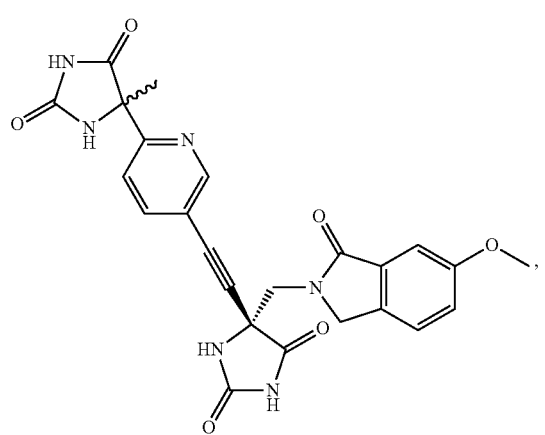
80
-continued
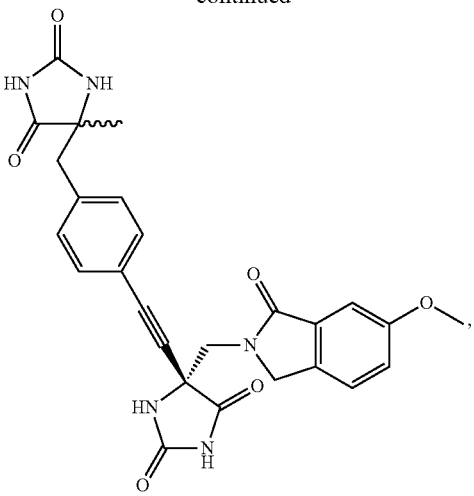
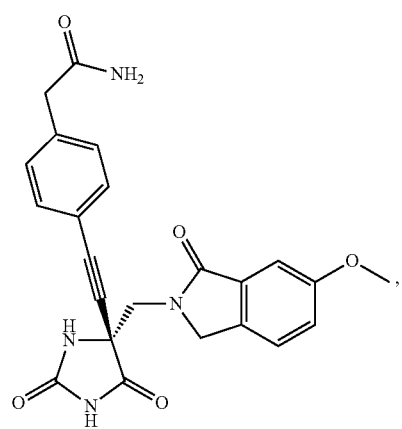

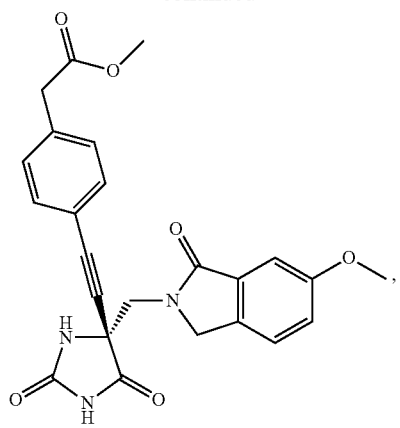
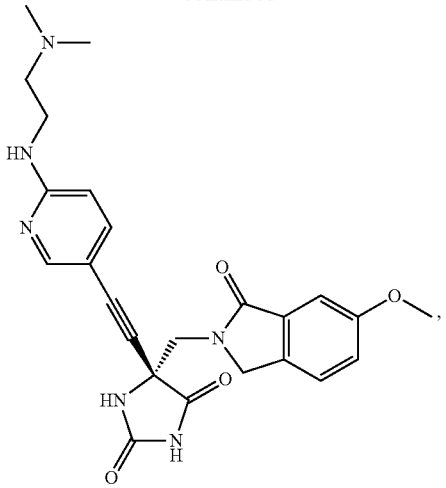
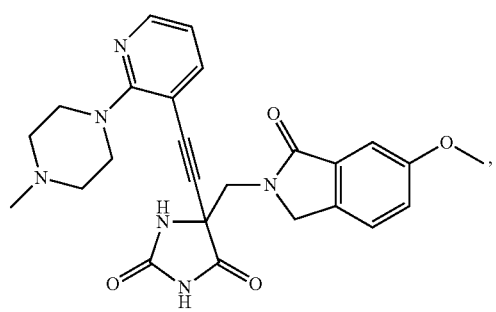
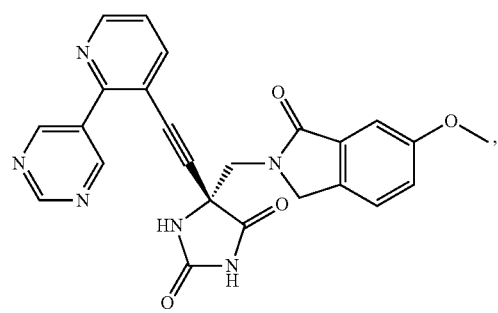
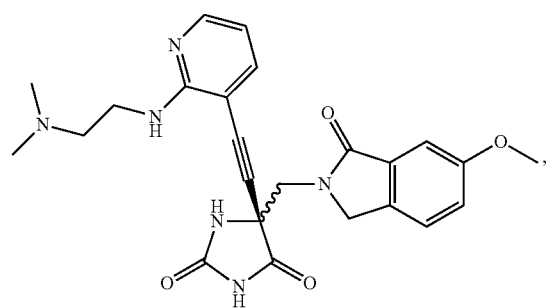
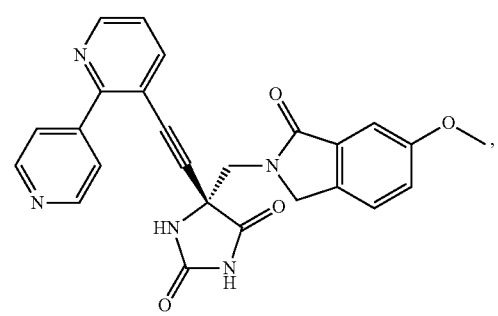
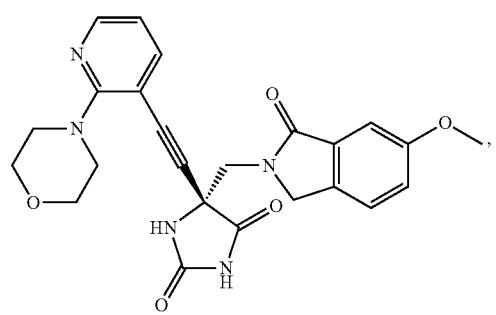
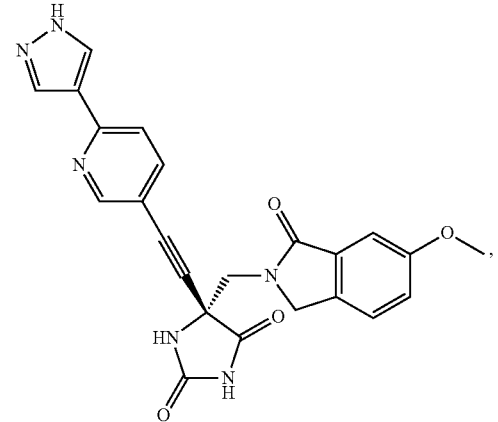

83
-continued
84
-continued
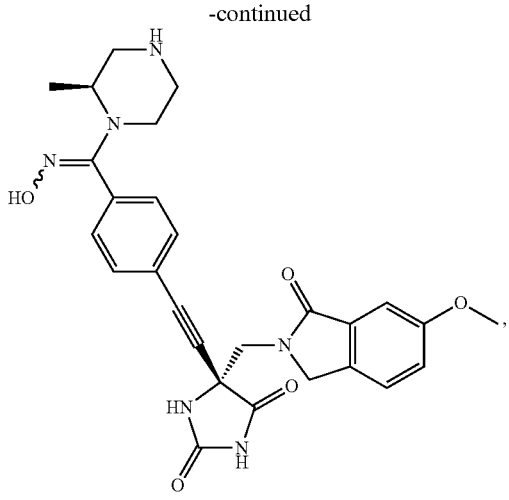
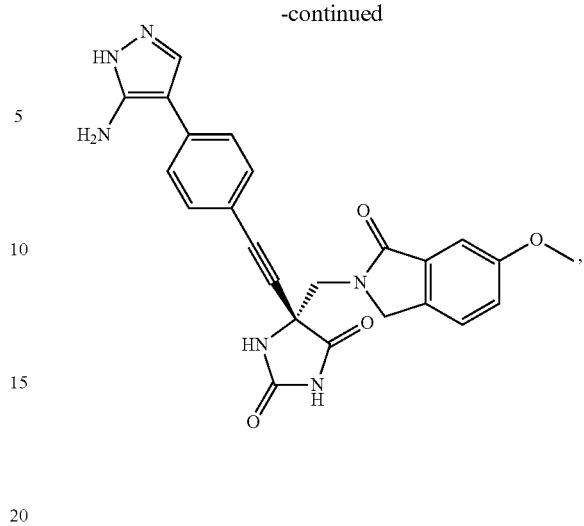

85
-continued
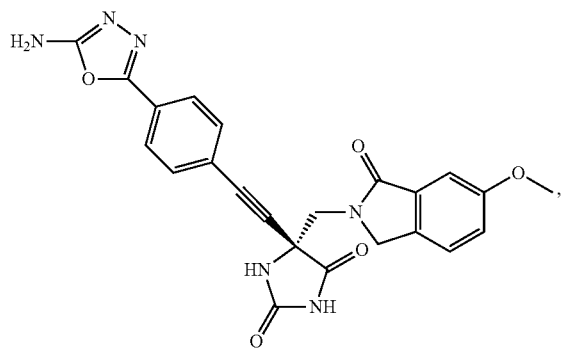
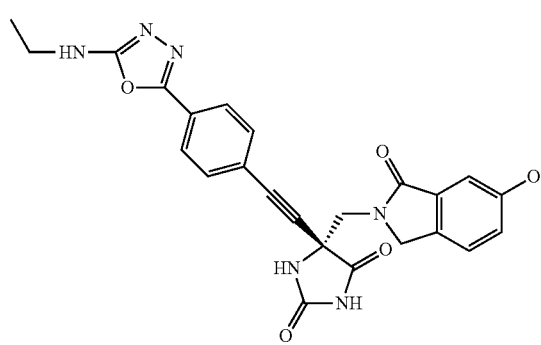
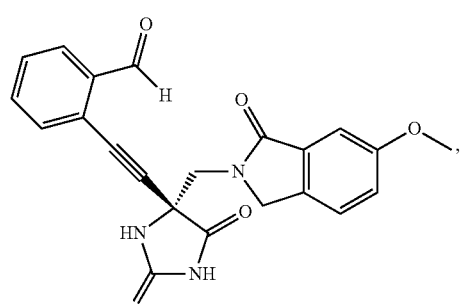
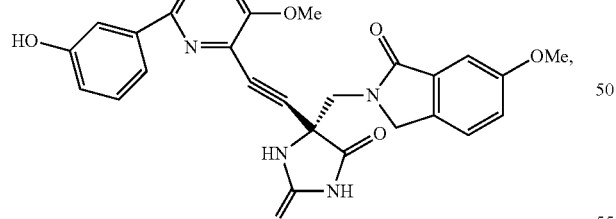
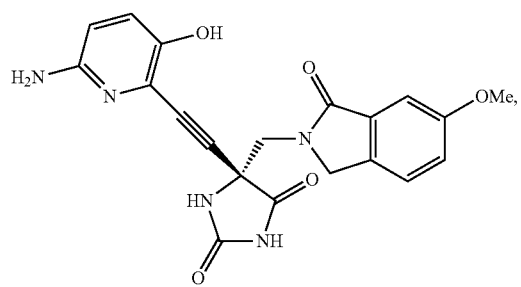
86
-continued
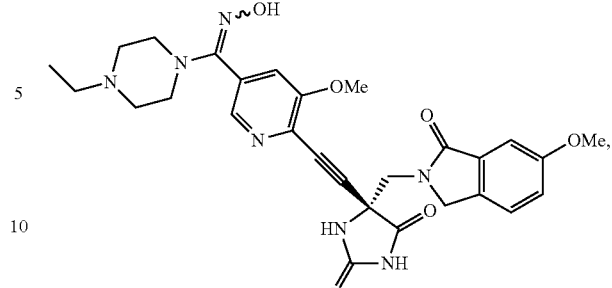
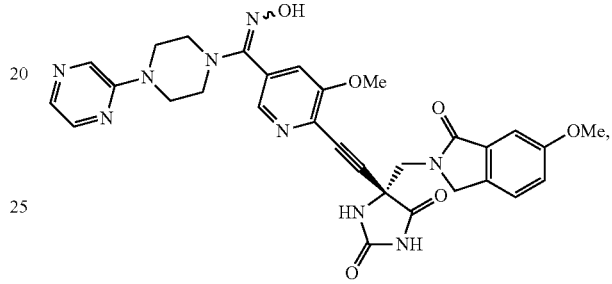
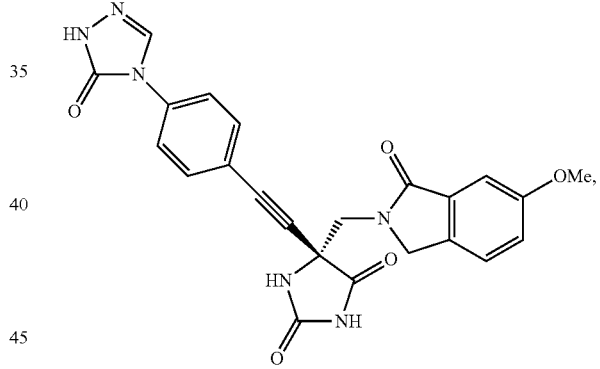
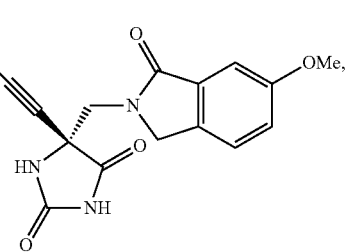

87
-continued
88
-continued
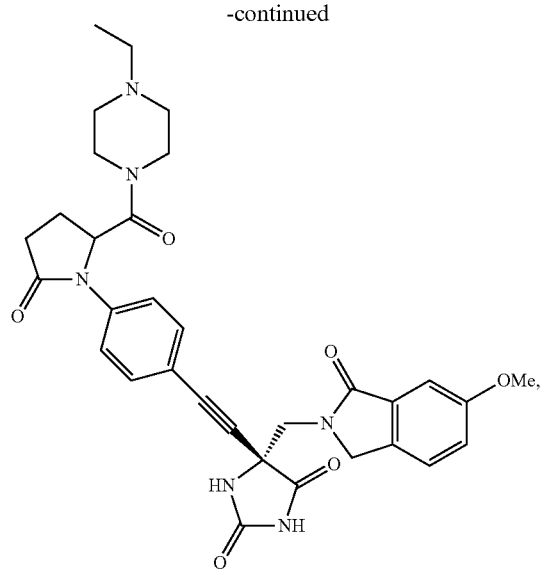
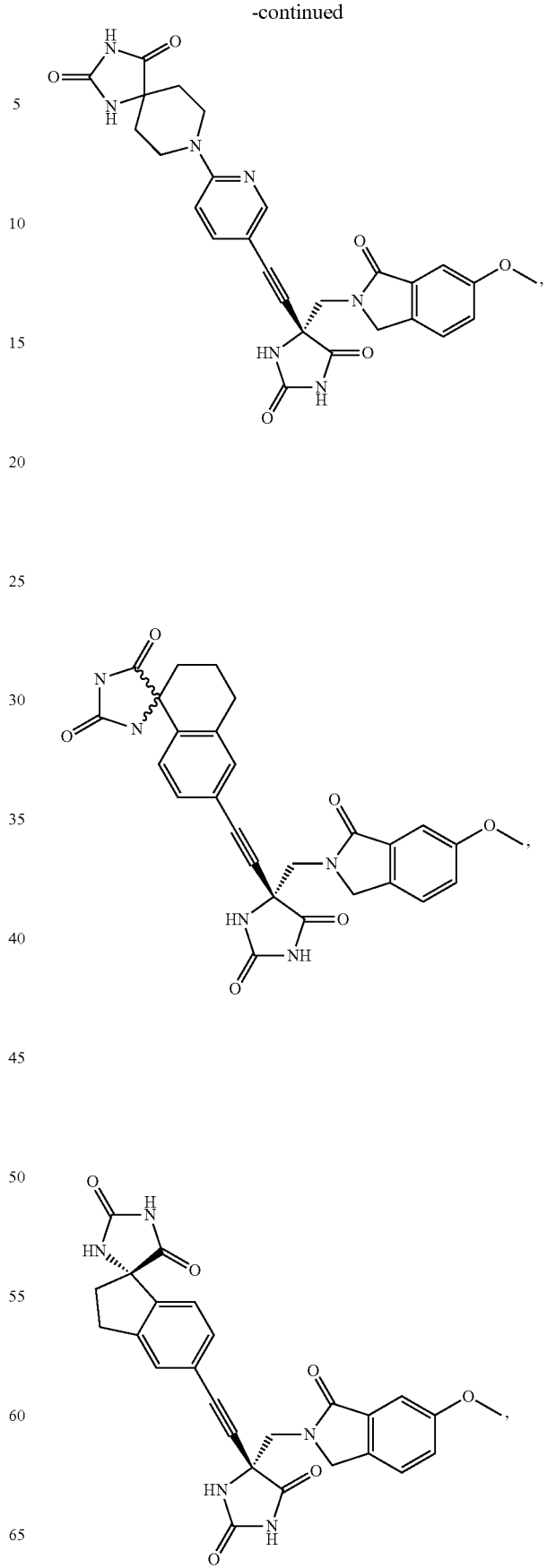

89
-continued
90
-continued
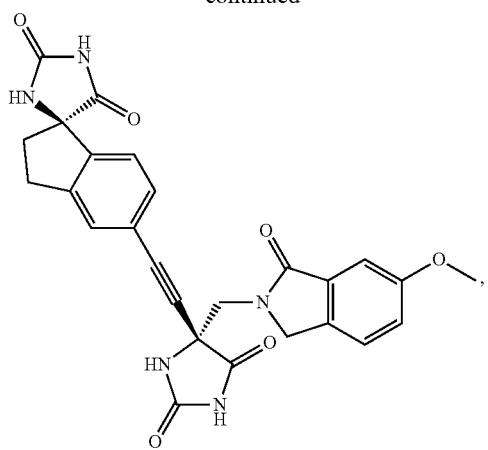
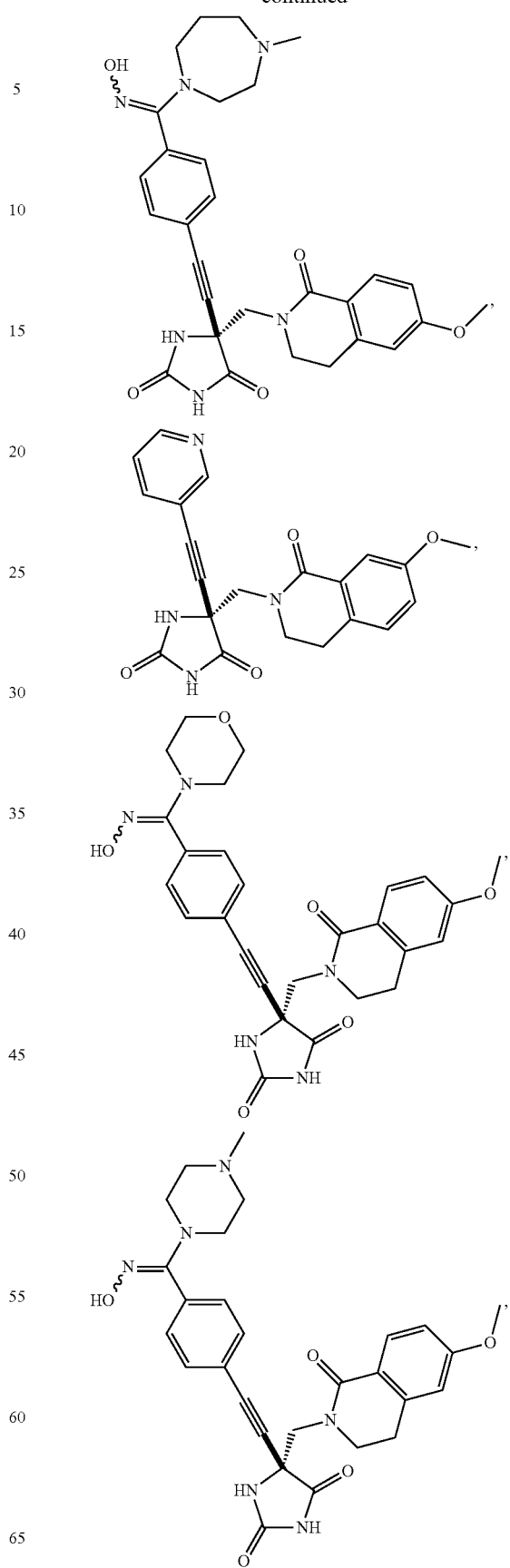

-continued

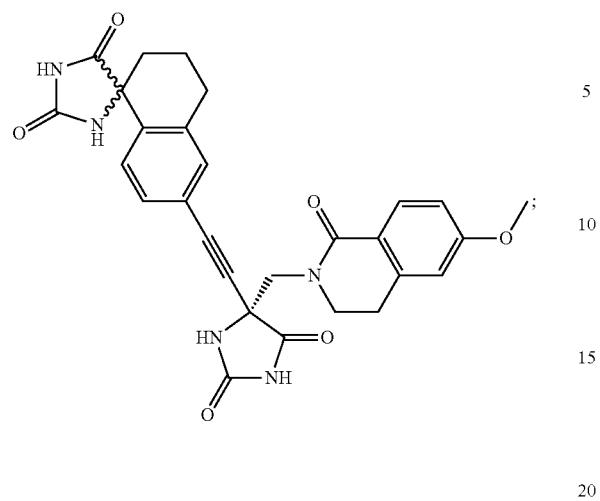

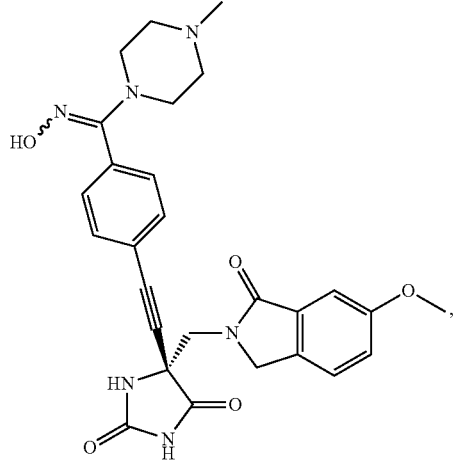

or a pharmaceutically acceptable salt thereof. The above-illustrated compounds are herein after referred to as "the above-identified compounds" or "the compounds of the invention."

The above identified compounds can be useful as inhibitors of TACE, TNF-α, MMPs, ADAMs and may be useful in the treatment and prevention of diseases associated with TACE, TNF-α, MMPs, ADAMs or any combination thereof.

DETAILED DESCRIPTION OF THE INVENTION

In its several embodiments, the present invention provides compounds as disclosed herein which are inhibitors of TACE, aggrecanase, the production of TNF-α, MMPs, ADAMs or any combination thereof, pharmaceutical compositions containing one or more of the compounds, methods of preparing pharmaceutical formulations comprising one or more such compounds as disclosed herein, and methods of treatment, prevention or amelioration of one or more of the symptoms of inflammation.

In one embodiment, the compounds of the present invention are selected from the group consisting of:

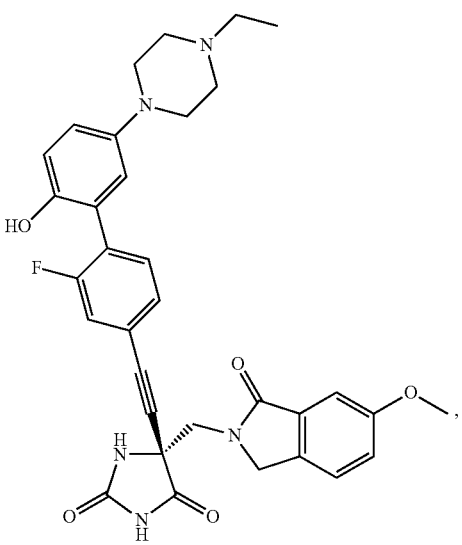

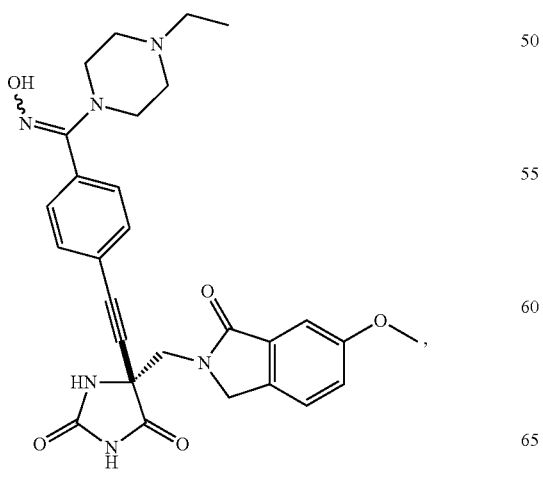

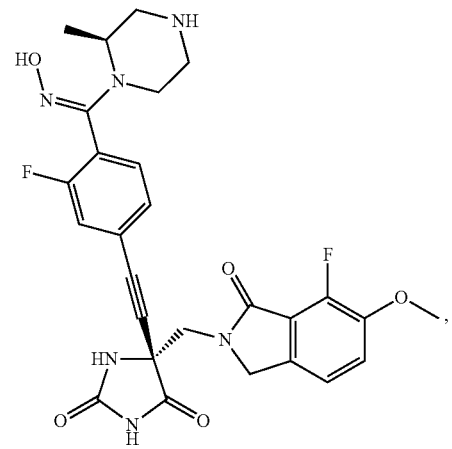

-continued
93
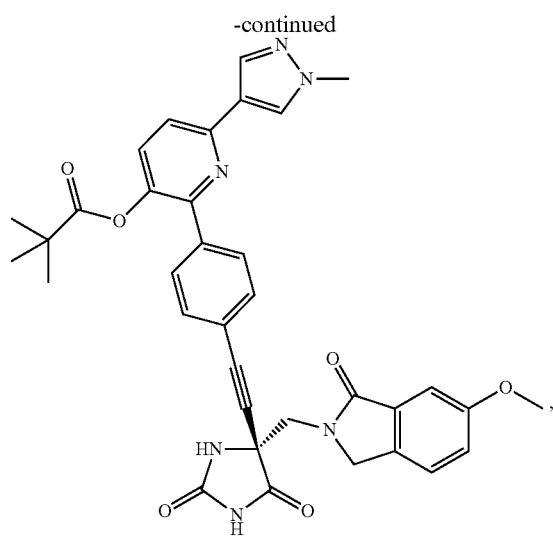
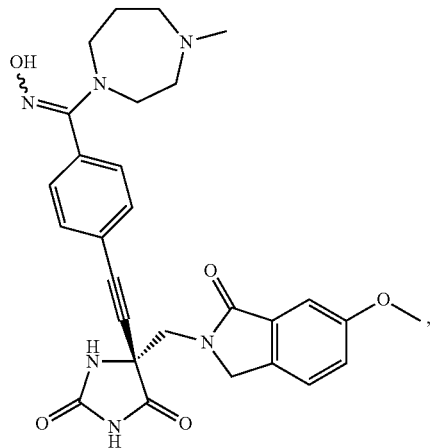
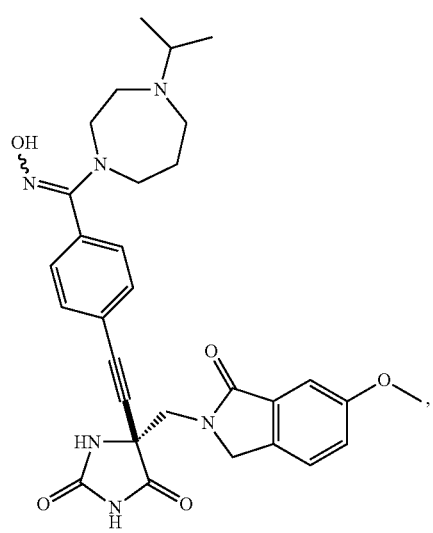
-continued
94
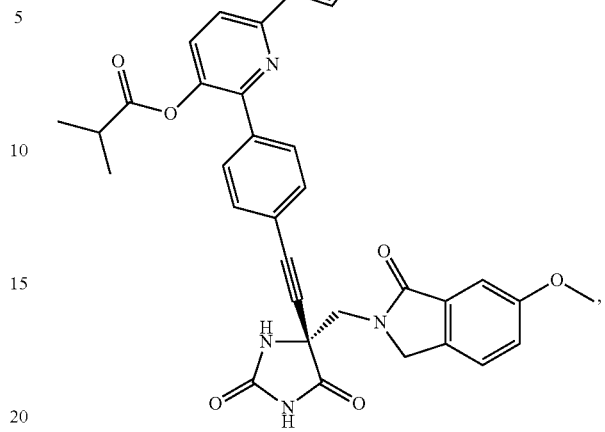
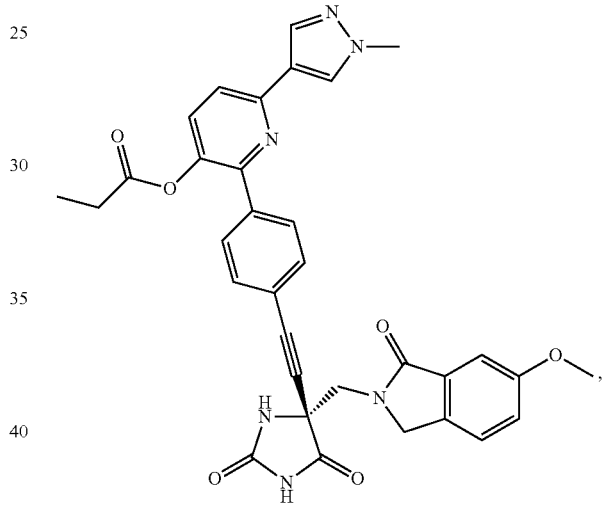
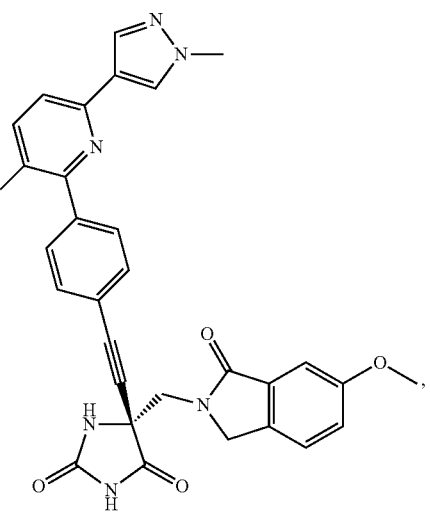

95
-continued
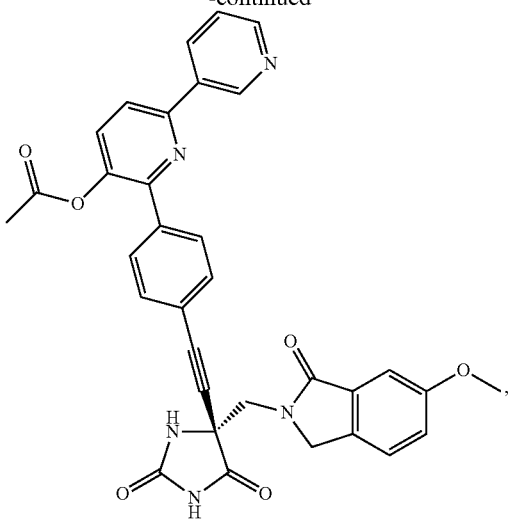
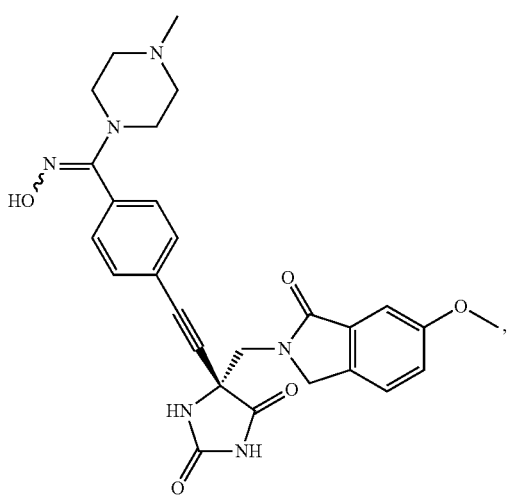
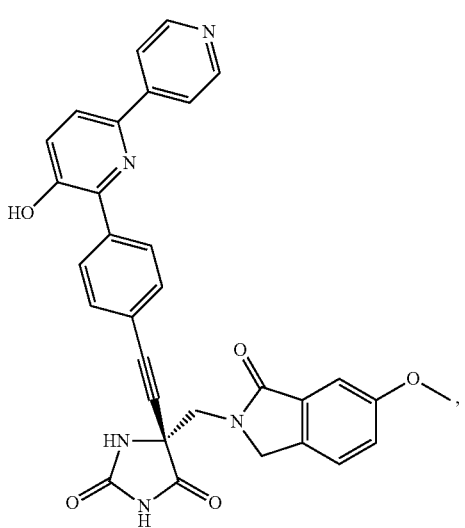
96
-continued
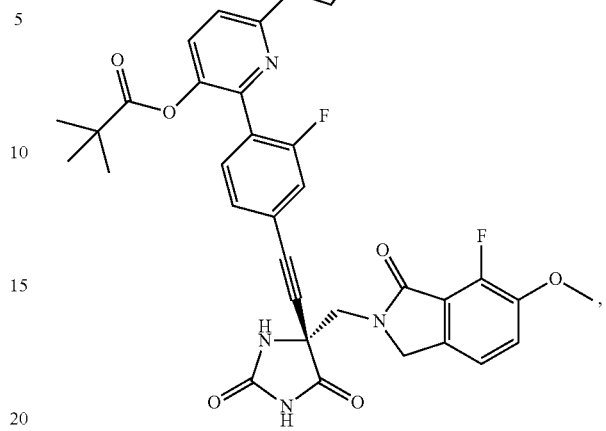
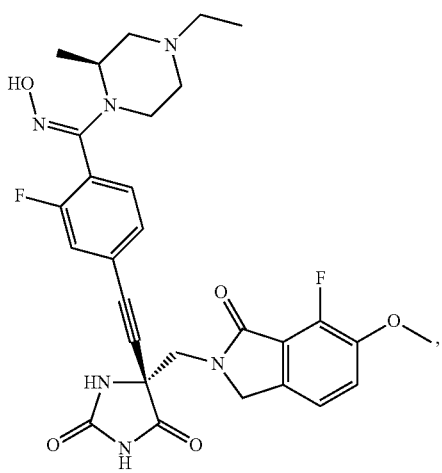
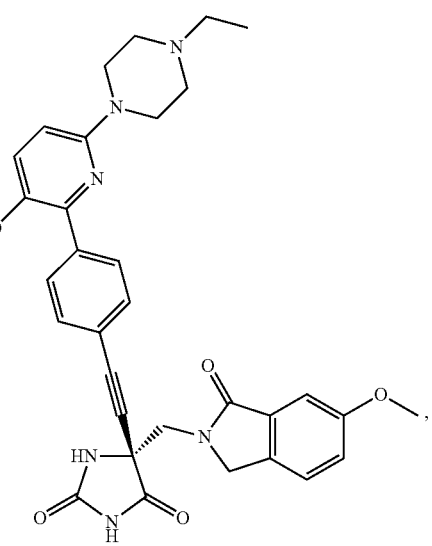

97
-continued
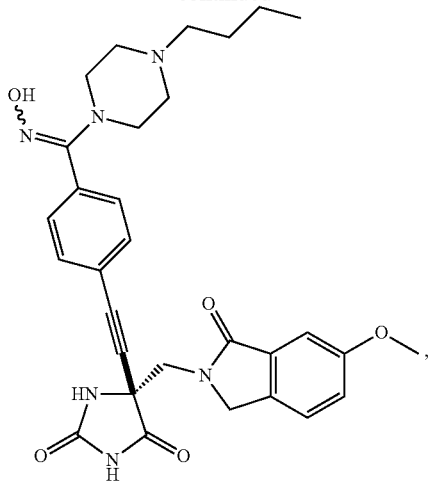
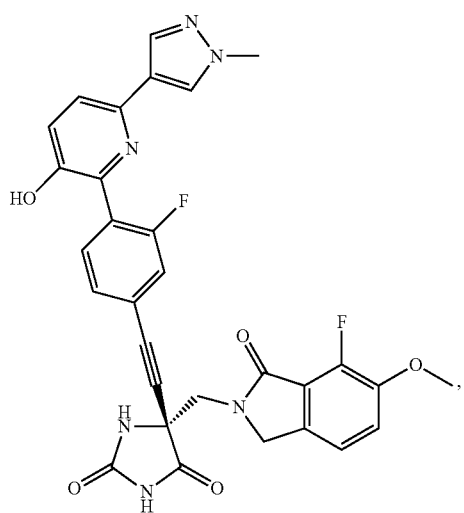
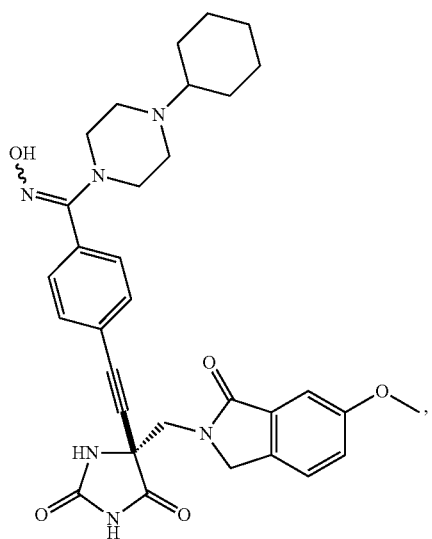
98
-continued
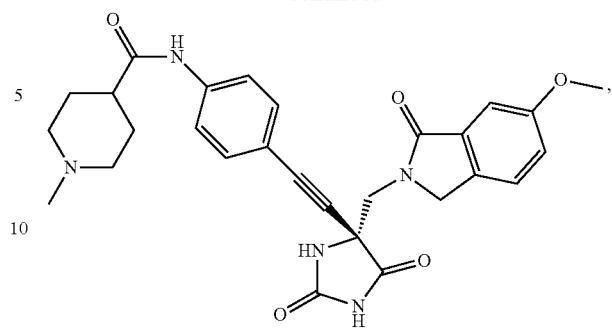
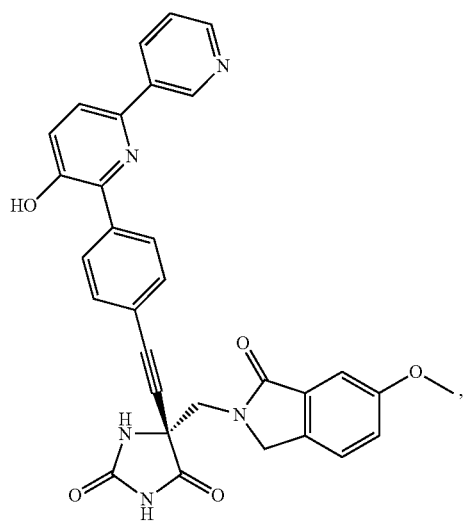
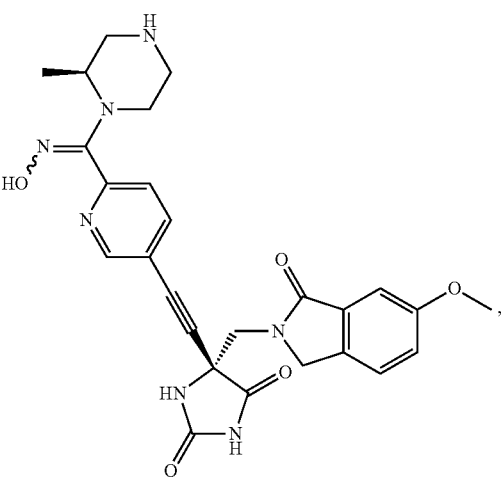

99
-continued
100
-continued
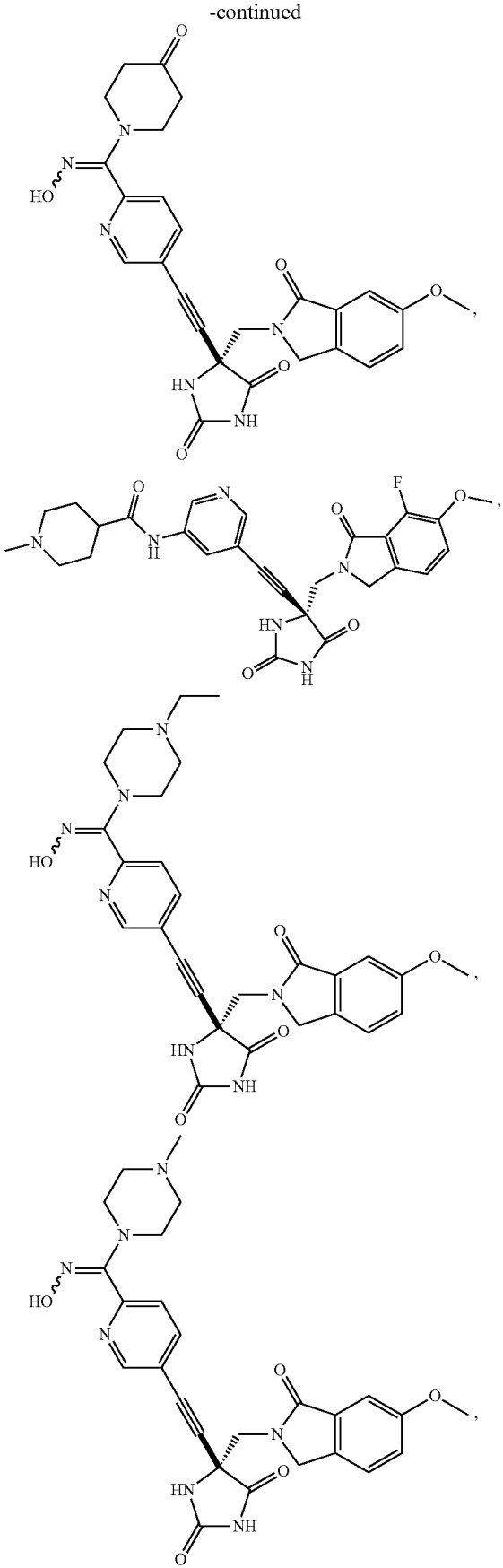
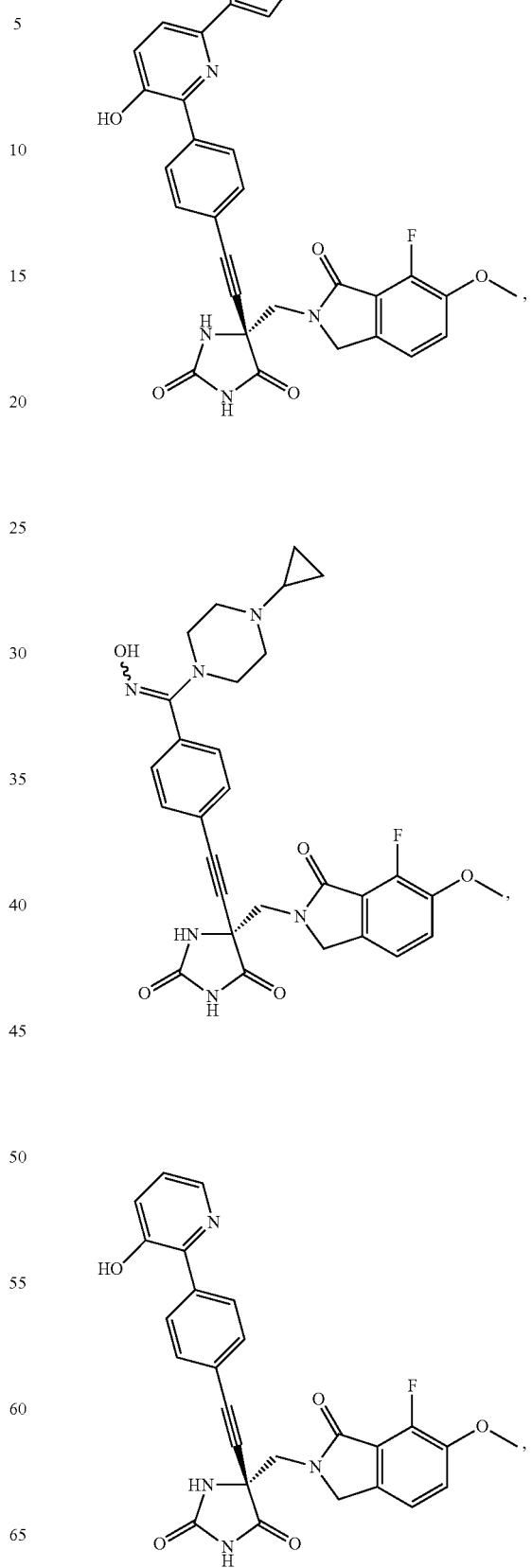

-continued
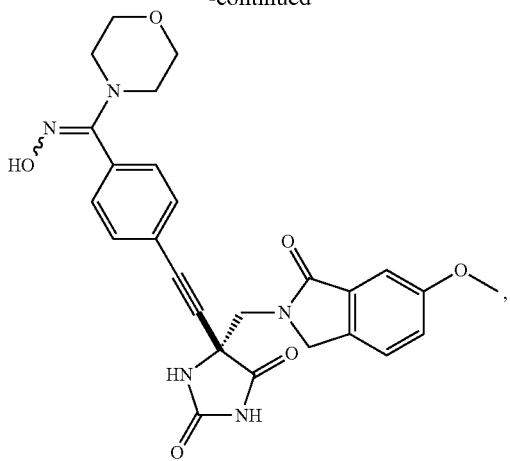
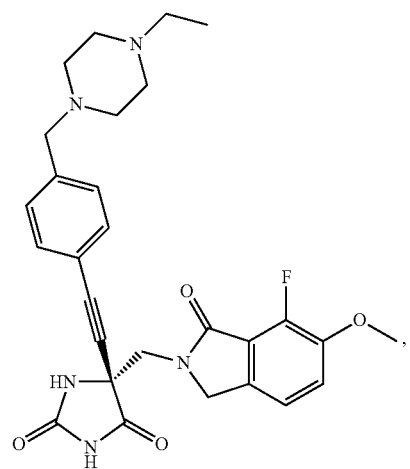
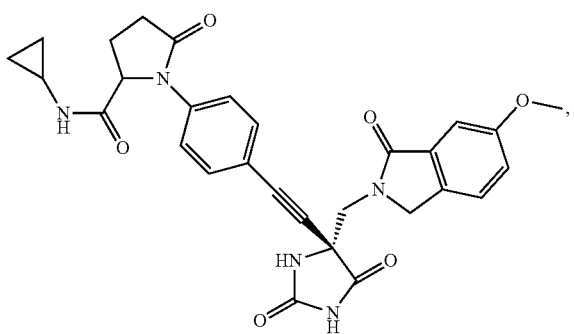
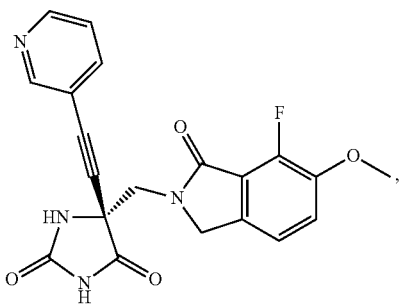
-continued
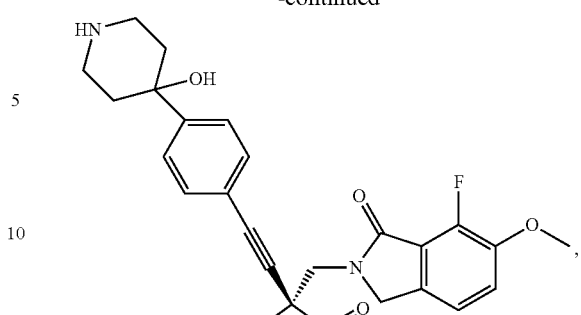
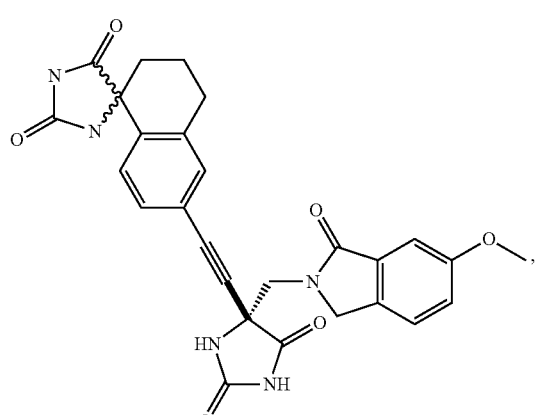
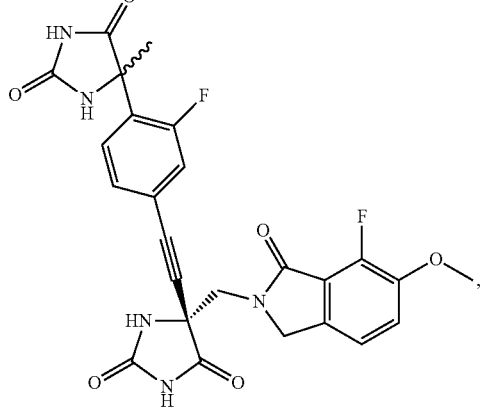
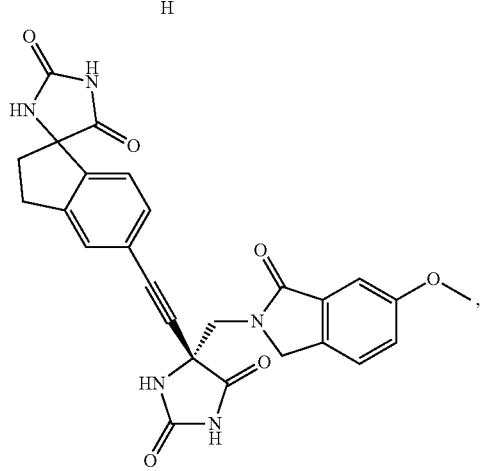

-continued
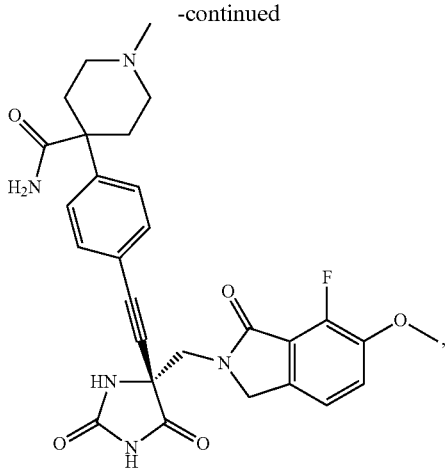
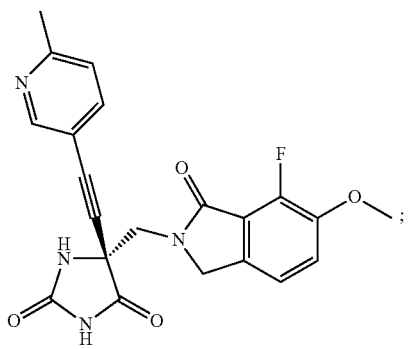
or a pharmaceutically acceptable salt thereof.
In another embodiment, the compounds of the present invention are selected from the group consisting of:
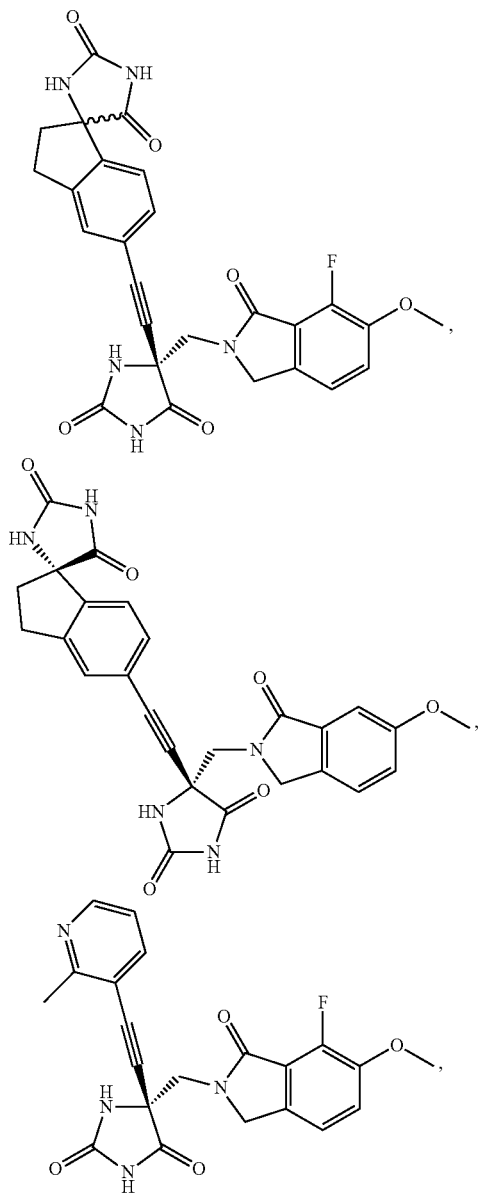
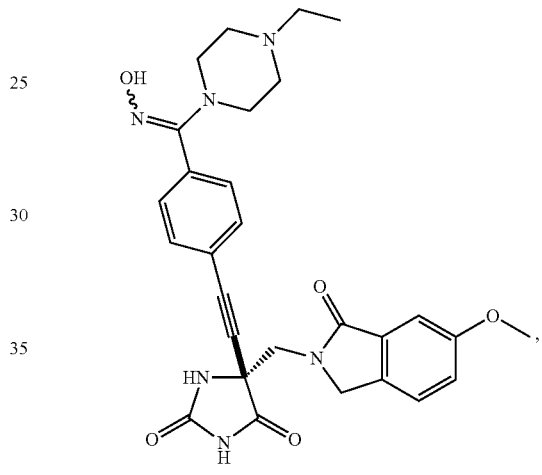
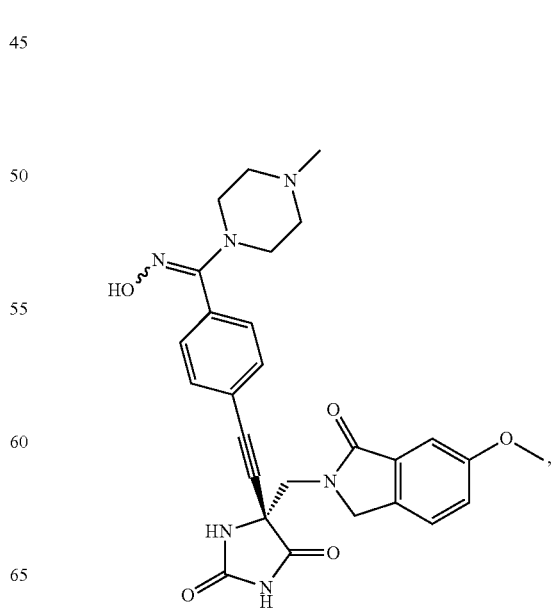

105
-continued
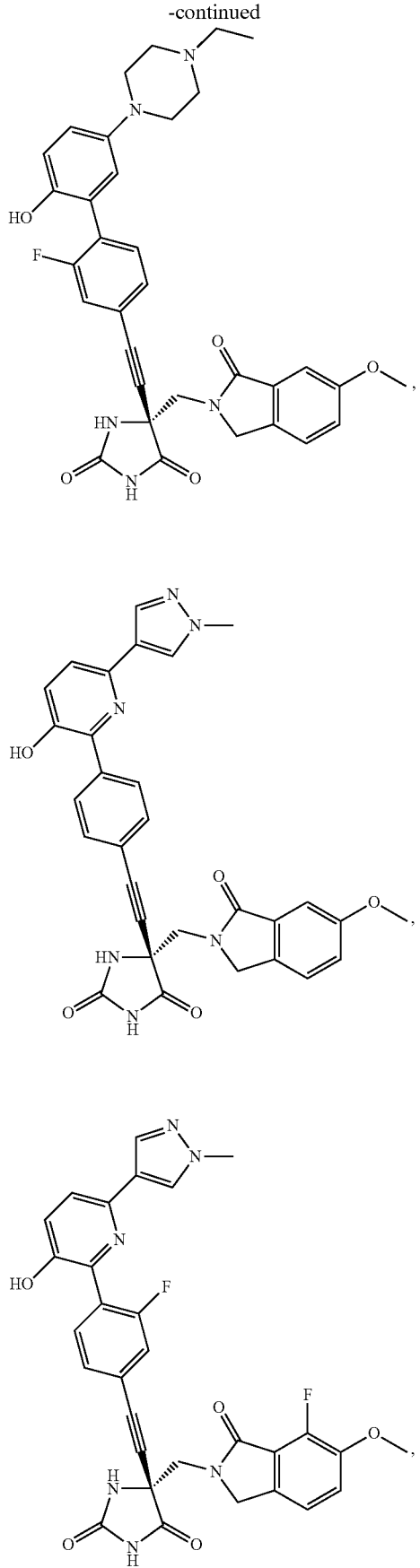
106
-continued
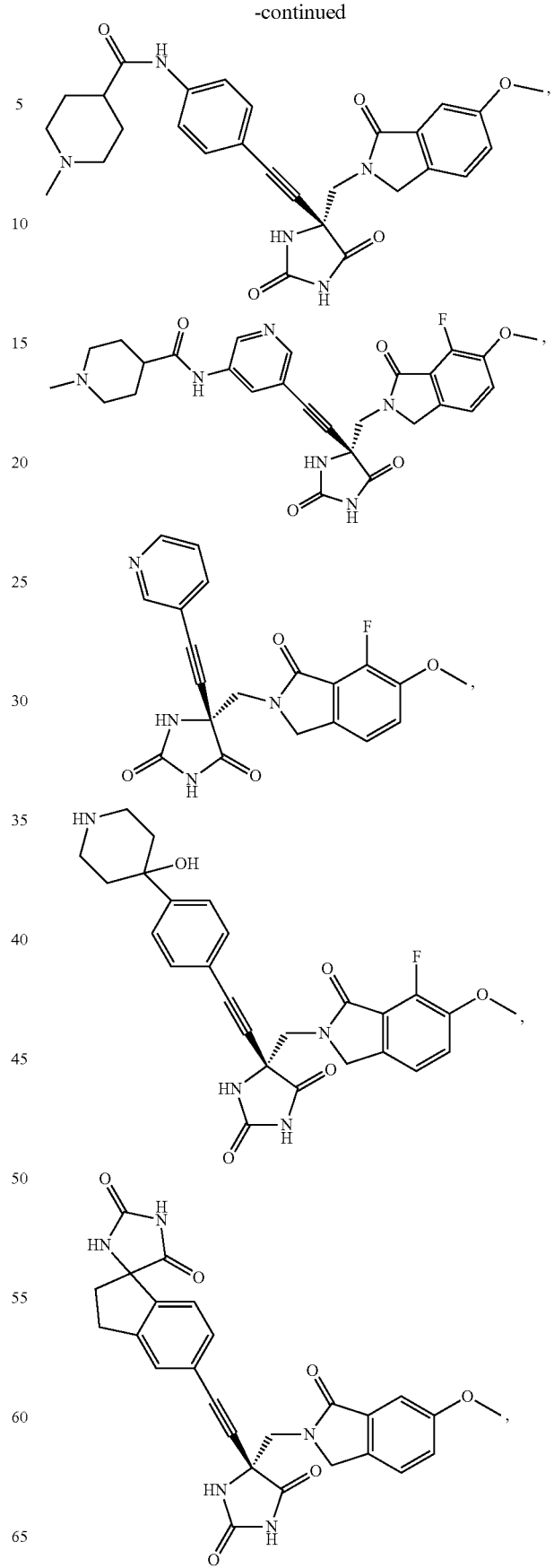

-continued

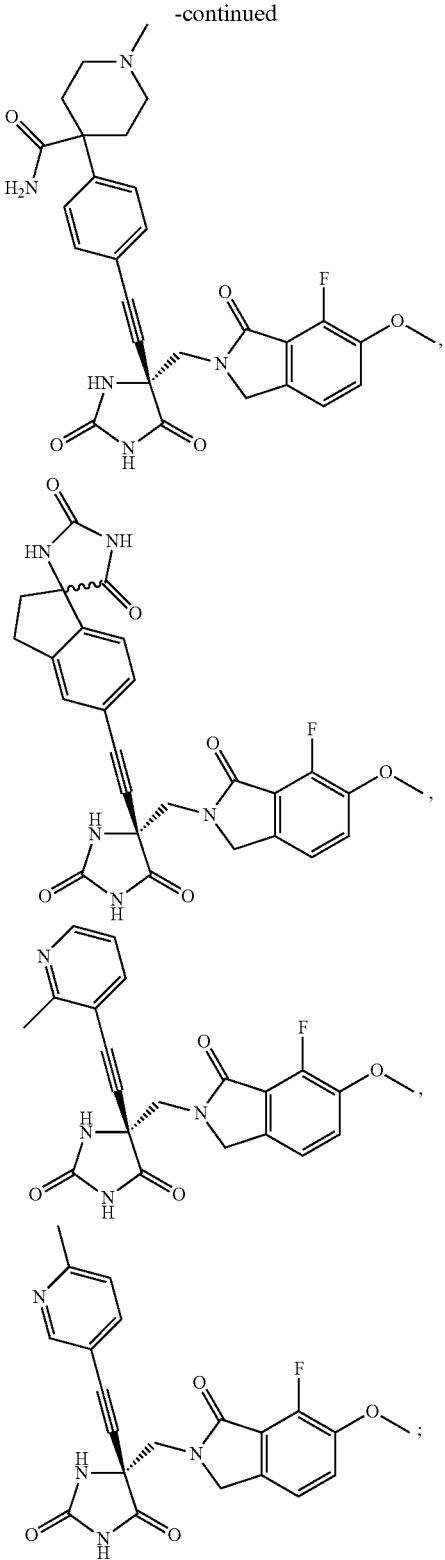

or a pharmaceutically acceptable salt thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above.

Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" (or "halo") means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), G$_1$G$_2$N—, G$_1$G$_2$N-alkyl-, G$_1$G$_2$NC(O)—, G$_1$G$_2$NSO$_2$— and —SO$_2$NG$_1$G$_2$, wherein G$_1$ and G$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such a moiety are methylene dioxy, ethylenedioxy, —C(CH$_3$)$_2$— and the like which form moieties such as, for example:

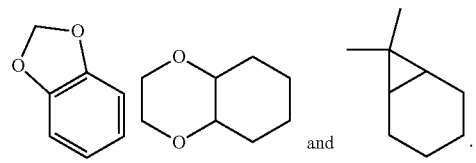

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. An example of such a moiety is pyrrolidone:

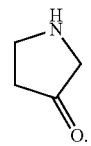

It should be noted that tautomeric forms such as, for example, the moieties:

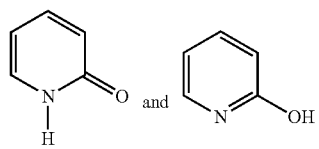 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. A non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. A non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well-known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in the above identified compounds, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prod rugs and solvates of the compounds of the invention are also contemplated herein. The term "prodrug", as employed herein, denotes a compound that is a drug precursor which, upon administration to a subject, undergoes chemical conversion by metabolic or chemical processes to yield the above identified compounds or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g., a drug precursor) that is transformed in vivo to yield the above identified compounds or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if the above identified compounds or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if the above identified compounds contains an alcohol functional group, a prodrug can be formed by the replacement of the hydrogen atom of the alcohol group with a group such as, for example, ($C_1$-$C_8$)alkanoyloxymethyl, 1-(($C_1$-$C_8$)alkanoyloxy)ethyl, 1-methyl-1-(($C_1$-$C_6$)alkanoyloxy)ethyl, ($C_1$-$C_8$)alkoxycarbonyloxymethyl, N—($C_1$-$C_8$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If the above identified compounds incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The above identified compounds can form salts which are also within the scope of this invention. Reference to the above identified compounds herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when the above identified compounds contain both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the above identified compounds may be formed, for example, by reacting the above identified compounds with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The above identified compounds, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of the above-identified compounds (e.g., those labeled with $^3H$ and $^{14}C$) are useful in compound and/or substrate tissue distribution assays. Tritiated (i.e., $^3H$) and carbon-14 (i.e., 140) isotopes are particularly preferred for their ease of preparation and detectability. Certain isotopically-labelled compounds of the above-identified compounds can be useful for medical imaging purposes. For example, those compounds labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of the above-identified compounds, in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the above identified compounds, and of the salts, solvates and prodrugs of the above identified compounds, are intended to be included in the present invention.

The present invention further includes the above-identified compounds in all their isolated forms. For example, the above-identified compounds are intended to encompass all forms of the compounds such as, any solvates, hydrates, stereoisomers, and tautomers thereof.

The compounds according to the invention have pharmacological properties; in particular, the above identified compounds can be inhibitors of TACE, aggrecanase, TNF-α, and/or MMP activity.

In one embodiment, the invention provides a pharmaceutical composition comprising as an active ingredient at least one of the above identified compounds.

In another embodiment, the invention provides pharmaceutical compositions of the above identified compounds additionally comprising at least one pharmaceutically acceptable carrier.

In another embodiment, the invention provides a method of treating disorders associated with TACE, aggrecanase, TNF-α, MMPs, ADAMs or any combination thereof, said method comprising administering to a patient in need of such treatment an effective amount of at least one of the above identified compounds.

In another embodiment, the invention provides a use of the above identified compounds for the manufacture of a medicament to treat disorders associated with TACE, aggrecanase, TNF-α, MMPs, ADAMs or any combination thereof.

The above identified compounds can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another embodiment, the invention provides a method of preparing a pharmaceutical composition for treating the disorders associated with TACE, aggrecanase, TNF-α, MMPs, ADAMs or any combination thereof, said method comprising bringing into intimate contact at least one of the above identified compounds and at least one pharmaceutically acceptable carrier.

In another embodiment, the invention provides at least one of the above identified compounds exhibiting TACE, TNF-α, MMPs, ADAMs or any combination thereof inhibitory activity, including pharmaceutically acceptable salts of said compound, said compound being selected from the compounds of structures set forth above.

In another embodiment, the invention provides a pharmaceutical composition for treating disorders associated with TACE, aggrecanase, TNF-α, MMP, ADAM or any combination thereof in a subject comprising, administering to the subject in need of such treatment a therapeutically effective amount of at least one of the above identified compounds or a pharmaceutically acceptable salt, solvate, ester, or isomer thereof.

In another embodiment, the invention provides the above identified compounds in purified form.

In another embodiment, the invention provides a method of treating a condition or disease mediated by TACE, MMPs, TNF-α, aggrecanase, or any combination thereof in a subject comprising: administering to the subject in need of such treatment a therapeutically effective amount of at least one of the above identified compounds or a pharmaceutically acceptable salt, solvate, ester or isomer thereof.

In another embodiment, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one of the above identified compounds or a pharmaceutically acceptable salt, solvate, ester or isomer thereof.

In another embodiment, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one of the above identified compounds or a pharmaceutically acceptable salt, solvate, ester, or isomer thereof.

In another embodiment, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least of the above identified compounds or a pharmaceutically acceptable salt, solvate, ester or isomer thereof.

In another embodiment, the invention provides a method of treating a condition or disease associated with COPD, comprising: administering to the subject in need of such treatment a therapeutically effective amount of at least one of the above identified compounds or a pharmaceutically acceptable salt, solvate, ester or isomer thereof.

In another embodiment, the invention provides a method of treating a condition or disease associated with rheumatoid arthritis, comprising: administering to the subject in need of such treatment a therapeutically effective amount of at least one of the above identified compounds or a pharmaceutically acceptable salt, solvate, ester, or isomer thereof.

In another embodiment, the invention provides a method of treating a condition or disease associated with Crohn's disease, comprising: administering to the subject in need of such treatment a therapeutically effective amount of at least one of the above identified compounds or a pharmaceutically acceptable salt, solvate, ester or isomer thereof.

In another embodiment, the invention provides a method of treating a condition or disease associated with psoriasis, comprising: administering to the subject in need of such treatment a therapeutically effective amount of at least one of the above identified compounds or a pharmaceutically acceptable salt, solvate, ester, or isomer thereof. In certain instances at least one of the above identified compounds or a pharmaceutically acceptable salt, solvate, ester, or isomer thereof is topically administered to the subject.

In another embodiment, the invention provides a method of treating a condition or disease associated with ankylosing spondylitis, comprising: administering to the subject in need of such treatment a therapeutically effective amount of at least one of the above identified compounds or a pharmaceutically acceptable salt, solvate, ester or isomer thereof.

In another embodiment, the invention provides a method of treating a condition or disease associated with sciatica, comprising: administering to the subject in need of such treatment a therapeutically effective amount of at least one of the above identified compounds or a pharmaceutically acceptable salt, solvate, ester or isomer thereof.

In another embodiment, the invention provides a method of treating a condition or disease associated with complex regional pain syndrome, comprising: administering to the subject in need of such treatment a therapeutically effective amount of at least one of the above identified compounds or a pharmaceutically acceptable salt, solvate, ester, or isomer thereof.

In another embodiment, the invention provides a method of treating a condition or disease associated with psoriatic arthritis, comprising: administering to the subject in need of such treatment a therapeutically effective amount of at least one of the above identified compounds, or a pharmaceutically acceptable salt, solvate, ester, or isomer thereof.

In another embodiment, the invention provides a method of treating a condition or disease associated with multiple sclerosis, comprising: administering to the subject in need of such treatment a therapeutically effective amount of at least one of the above identified compounds or a pharmaceutically acceptable salt, solvate, ester or isomer thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like; cycloxygenase-2 selective (COX-2) inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another embodiment, the invention provides a method of treating a condition or disease mediated by TACE, MMPs, TNF-α, aggrecanase, or any combination thereof in a subject comprising: administering to the subject in need of such treatment a therapeutically effective amount of at least one of the above identified compounds or a pharmaceutically acceptable salt, solvate or isomer thereof in combination with a therapeutically effective amount of at least one medicament selected from the group consisting of disease modifying antirheumatic drugs (DMARDS), NSAIDs, COX-2 inhibitors, COX-1 inhibitors, immunosuppressives, biological response modifiers (BRMs), anti-inflammatory agents and H1 antagonists.

In another embodiment, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one of the above identified compounds or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another embodiment, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection, comprising: administering to the subject in need of such treatment a therapeutically effective amount of at least one of the above identified compounds or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another embodiment, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one of the above identified compounds, or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another embodiment, the invention provides a method for treating RA comprising administering at least one the above identified compounds in combination with compound selected from the class consisting of a COX-2 inhibitor e.g., Celebrex® or Vioxx®; a COX-1 inhibitor e.g., Feldene®; an immunosuppressive e.g., methotrexate or cyclosporin; a steroid e.g., β-methasone; and anti-TNF-α compound, e.g., Enbrel® or Remicade®; a PDE IV inhibitor, or other classes of compounds indicated for the treatment of RA.

In another embodiment, the invention provides a method for treating multiple sclerosis comprising administering at least one the above identified compounds in combination with a compound selected from the group consisting of Avonex®, Betaseron, Copaxone or other compounds indicated for the treatment of multiple sclerosis.

TACE activity can be determined by a kinetic assay measuring the rate of increase in fluorescent intensity generated by TACE catalyzed cleavage of an internally quenched peptide substrate (TNF-FRET 2). The purified catalytic domain of recombinant human TACE (rhTACEc, Residue 215 to 477 with two mutation (S266A and N452Q) and a 6×His tail) is used in the assay. It is purified from the baculovirus/Hi5 cells expression system using affinity chromatography. The substrate TNF-FRET 2 is an internally quenched peptide (MCA-Pro-Leu-Ala-Gln-Ala-Val-Arg-Ser-Ser-Ser-Dpa-Arg-NH2. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 pM rhTACEc and a test compound. RhTACEc is pre-incubated with the test compound for 90 min at 25° C. in the absence of substrate. The reaction was started by addition of the substrate TNF-FRET 2. The fluorescent intensity (excitation at 320 nm, emission at 405 nm) was measured every 45 seconds for 30 min using a fluorospectrometer (GEMINI XS, Molecular Devices).

$K_i$ values were derived using non-linear regression fitting to the modified Morrison's equation. See $$v_i/v_o = 1 - \{(E_o + I_o + K_i^{app}) - [(E_o + I_o + K_i^{app})^2 4E_o I_o]^{1/2}\}/2E_o,$$

where $v_i$ is the measured initial velocity of substrate turnover at any given inhibitor concentration $I_o$, and $v_o$ is the initial velocity when $I_o = 0$. Apparent inhibitor dissociation constants $K_i^{app}$ were derived by curve fitting at different initial concentrations of TACE ($E_o$). The Ki values of representative compounds of the invention for this TACE assay are shown below in Table A.

The compounds' ability to inhibit TACE activity can also be determined in human whole blood using the assay conditions described in Example 15 below.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the above identified compounds useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations may be used in the procedures and schemes:

| | |
|---|---|
| ACN | Acetonitrile |
| AcOH | Acetic acid |
| Aq | Aqueous |
| BOC | tert-Butoxycarbonyl |
| BOC$_2$O | BOC Anhydride |
| C | degrees Celsius |
| CBZCl | Benzyl chloroformate |
| DBU | 1,8-Diazabicyclo[5.4.0]undec-7-ene |
| DCM | Dichloromethane |
| DEAD | Diethyl azodicarboxylate |
| (DHQ)2PHAL | Hydroquinine 1,4-phthalazinediyl diether |
| DIAD | Diisopropylazodicarboxylate |
| DIPEA | Diisopropylethylamine |
| DMA | N,N-Dimethylacetamide |
| DMAP | 4-Dimethylaminopyridine |
| DME | Dimethoxyethane |
| DMF | Dimethylformamide |
| DMPU | 1,3-Dimethyl-3,4,5,6-tetrahydro-2(1h)-pyrimidinone |
| DMSO | Dimethyl sulfoxide |
| EDCl | 1-(3-Dimethylaminopropyl)-3-ethylcarbodiimide hydrochloride |
| EI | Electron ionization |
| Eq | Equivalents |
| EtOAc | Ethyl acetate |
| EtOH | Ethanol |
| g | grams |
| h | hours |
| hr | hours |
| $^1$H | proton |
| HATU | N,N,N',N'-Tetramethyl-O-(7-Azabenzotriazol-1-yl) Uronium hexafluorophosphate |
| Hex | hexanes |
| HOBT | 1-Hydroxybenzotriazole |
| HPLC | High pressure liquid chromatography |
| LAH | Lithium aluminum hydride |
| LDA | Lithium diisopropylamide |
| M | Molar |
| mmol | milimolar |
| mCPBA | meta-Chloroperoxybenzoic acid |
| Me | Methyl |
| MeCN | Acetonitrile |
| MeOH | Methanol |
| min | Minutes |
| mg | Milligrams |
| MHZ | Megahertz |
| mL | Milliliter |
| MPLC | Medium Pressure Liquid Chromatography |
| NMR | Nuclear Magnetic Resonance |
| MS | Mass Spectroscopy |
| NBS | N-Bromosuccinimide |
| NMM | N-Methylmorpholine |
| NMP | 1-methyl-2-pyrrolidone |
| ON | Overnight |
| PCC | Pyridinium Chlorochromate |
| PTLC | Preparative thin layer chromatography |
| PyBrOP | Bromo-tris-pyrrolidino-phosphonium hexafluorophosphate |
| Pyr | Pyridine |
| RT | Room temperature |
| sgc | Silica gel 60 chromatography |
| tBOC | tert-Butoxycarbonyl |
| TACE | TNF-alpha converting enzyme |
| TEA | Triethylamine |
| TFA | Trifluoroacetic acid |
| THF | Tetrahydrofuran |
| TLC | Thin layer chromatography |

NMR spectra were acquired on the following instruments: 400 MHZ NMR (Bruker), 500 MHZ NMR (Bruker), 400 MHz NMR (Varian), 300 MHZ NMR (Varian) using CD$_3$OD, CDCl$_3$ or DMSO-d$_6$ as solvents. LC-MS data were obtained using a PESciex API 150EX quadropole mass spectrometer using electroscopy ionization.

Purification via reverse phase chromatography (Gilson) was accomplished using a C18 reverse phase column with a gradient of (0.1% formic acid) 5:95 to 90:10 acetonitrile:water, at a flow rate of 14 mL/min. Samples were collected using UV detection. Alternatively an ISCO Companion with (0.1% formic acid) 5:95 to 95:5 acetonitrile:water, at a flow rate=10-55 mL/min.

Normal phase silica gel chromatography was either accomplished on a Biotage instrument using a 60 Å 12/M, 25/M, or 40/M flash cartridges, or on a Jones Flash Master Personal instrument using Isolute flash SI 5 g, 10 g, 20 g, 50 g, or 70 g cartridges.

Scheme A:
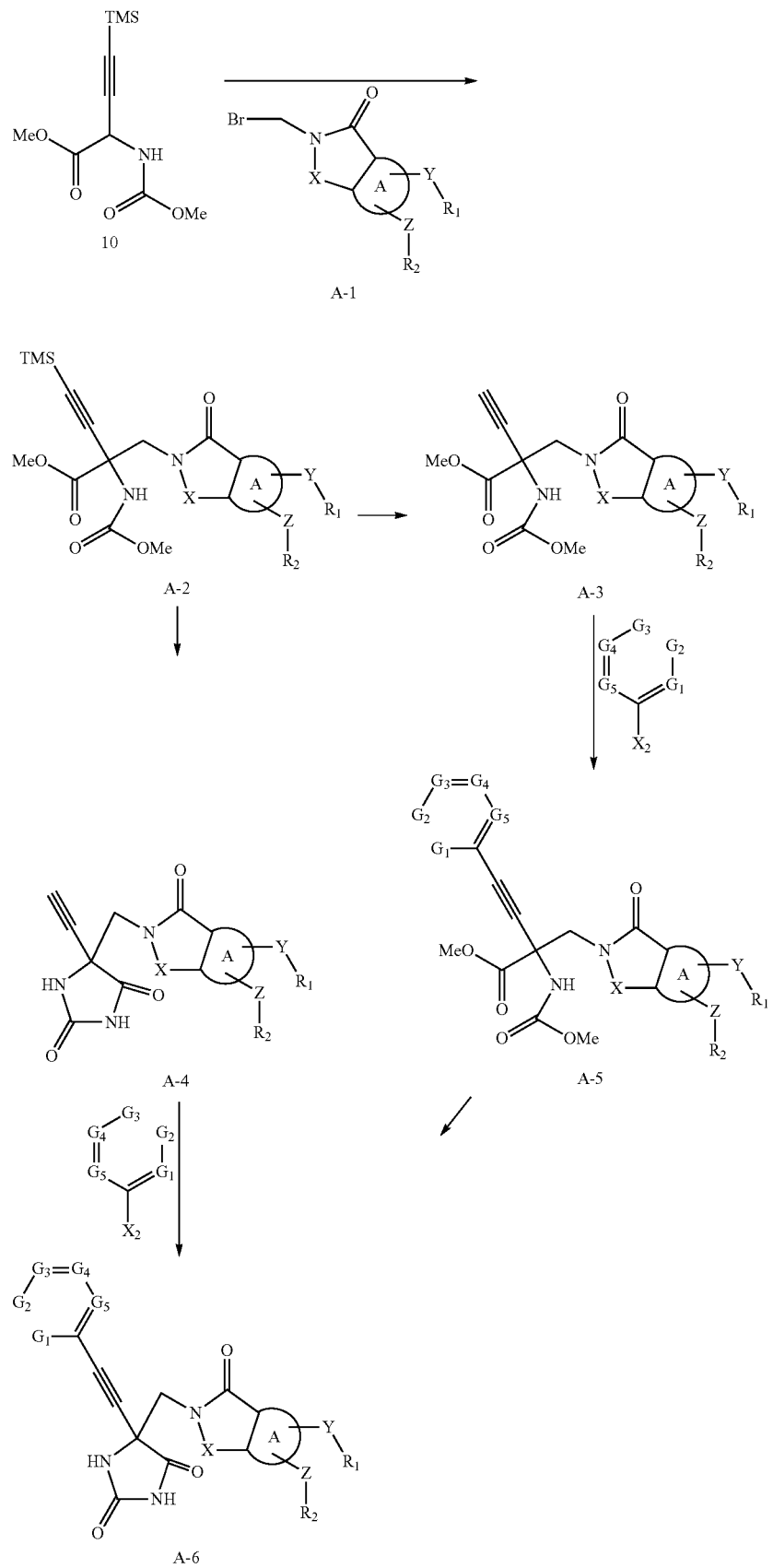

Alkylation of acetylene 10 with a suitable A-1 compound yields the quaternary protected amino acid derivative A-2. Compound A-2 may be either cyclized into hydantoin A-4 or deprotected to acetylene A-3. Introduction of the (hetero)aryl ring is readily accomplished via a Sonogashira reaction with a (hetero)arylhalide to afford intermediates A-5 or A-6. Compound A-5 is converted to A-6 by treatment with 7M ammonia in methanol solution at 80° C. in a sealed bottle.

Example 1

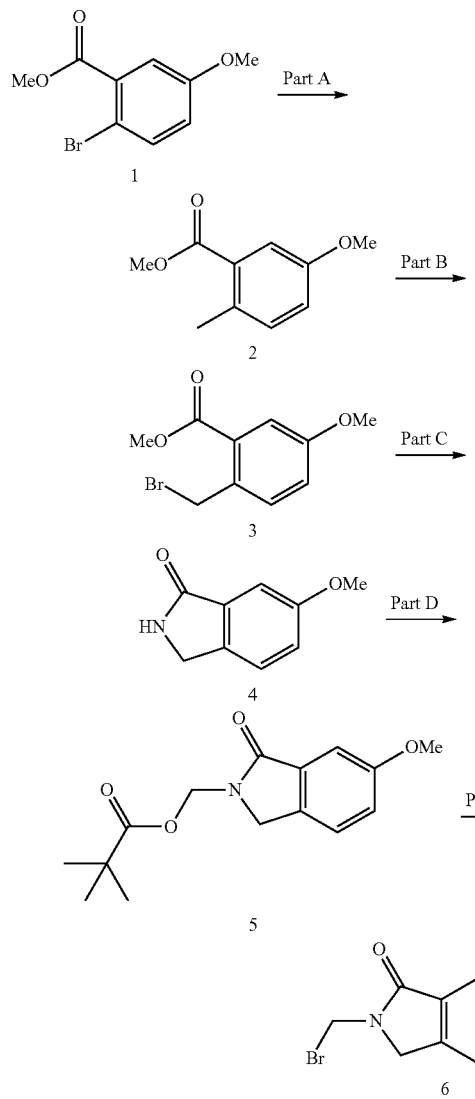

Part A:
Compound 1 (20.0 g, 81.61 mmol), trimethylboroxine (13.36 mL, 97.93 mmol), Pd(dppf)Cl$_2$ (1.0 g, 1.36 mmol), dioxane (350 mL), water (50 mL), and cesium carbonate (22.5 g, 163 mmol) were stirred at 110° C. (oil bath) under nitrogen for 16 hours. After cooling, the solid was removed by filtration. The solution was concentrated and purified by sgc (10:1 EtOAc/hexanes) to give 2 (12.1 g, 80%).

Part B:
Compound 2 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 3 (6.1 g, 98%).

Part C:
Compound 3 (32.0 g, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in methylene chloride. The methylene chloride solution was washed with water, dried over sodium sulfate, and concentrated to provide the desired product 4 (13.5 g, 67%).

Part D:
Compound 4 (2.2 g, 13.4 mmol) was dissolved in THF (250 mL) and DMPU (40 mL). Sodium t-butoxide (1.55 g, 16.13 mmol) was added and stirred for 5 hours. Chloromethylpivalate (3.0 mL, 20.1 mmol) was added dropwise and stirred overnight. The reaction was quenched with saturated ammonium chloride and extracted with ethyl acetate. The combined ethyl acetate layers were washed with water, brine, dried over sodium sulfate and concentrated. Purification by column chromatography (SiO$_2$, 25% ethyl acetate/hexanes) afforded the desired product 5 (2.5 g, 67%).

Part E:
Compound 5 (288 mg, 1.04 mmol) was dissolved in methylene chloride (5 mL) and cooled in an ice bath. Bromotrimethylsilane (0.3 mL, 2.08 mmol) was added dropwise and stirred in the ice bath for 30 minutes followed by 2 hours at room temperature. The reaction mixture was concentrated and re-dissolved in methylene chloride (2 mL). Hexanes (8 mL) was added and the solids were filtered to provide the desired product 6 (218 mg, 83%).

Example 2

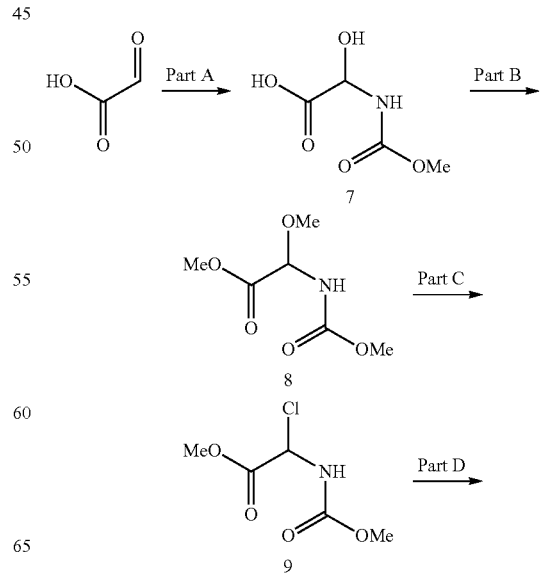

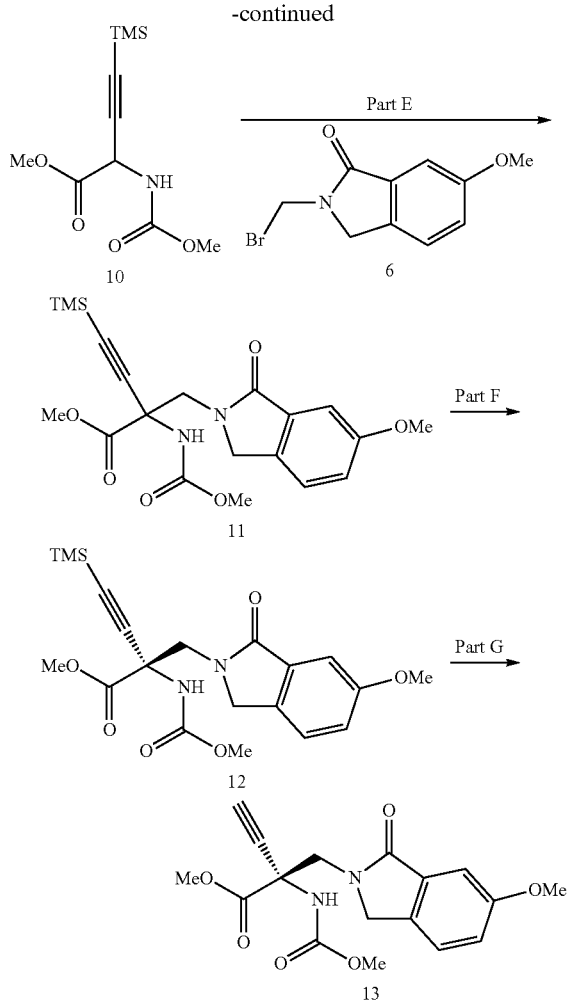

Part A:

Glyoxylic acid monohydrate (20.0 g, 218 mmol) and methyl carbamate (16.3 g, 218 mmol) were dissolved in diethyl ether (200 mL) and stirred overnight. The solids were filtered to provide the desired product 7 (32.0 g, 98%).

Part B:

Compound 7 (32.0 g, 214 mmol) was dissolved in MeOH (200 mL) and cooled in an ice bath. Concentrated sulfuric acid (8 mL) was added dropwise and the reaction was stirred overnight. The reaction mixture was diluted with ethyl acetate and water. The organic layer was washed with brine, dried over sodium sulfate, and concentrated to provide compound 8 that was used without purification (27.0 g, 71%).

Part C:

Compound 8 (27.0 g, 152 mmol) was dissolved in carbon tetrachloride (700 mL). Phosphorus pentachloride (50 g, 240 mmol) was added and the suspension was stirred for 18 hours (solution became clear over time). The solvent was removed under reduced pressure and the residue was stirred in petroleum ether (500 mL) overnight. The solids were filtered to provide compound 9 with no need for purification (26.5 g, 96%). The trituration step was repeated if mass yield was too high.

Part D:

Compound 9 (15.0 g, 82.7 mmol) was dissolved in methylene chloride (140 mL) and cooled in an ice bath. Bis(trimethylsilyl)acetylene (15.0 g, 88.2 mmol) was added in methylene chloride (20 mL). Freshly crushed aluminum chloride (11.0 g, 82.7 mmol) was added in portions over 20 minutes. The reaction mixture was allowed to slowly warm to room temperature and stirred overnight. The reaction was cooled in an ice bath and slowly quenched with water. The organic layer was washed several times with water, dried over sodium sulfate, and concentrated. The residue was triturated/recrystallized from hexanes to provide the desired product 10 (14.8 g, 69%). HPLC-MS $t_R$=1.84 min (ELSD); mass calculated for formula $C_{10}H_{17}NO_4Si$ 243.09, observed LCMS m/z 244.1 (M+H).

Part E:

Compound 10 (24.0 g, 98.7 mmol) and compound 6 (25.1 g, 99.0 mmol) were dissolved in THF (300 mL) and cooled to −78° C. A 1M solution of LiHMDS (198 mL, 198 mmol) was added dropwise over 30 minutes and the reaction mixture was stirred for 2 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography ($SiO_2$, 33% ethyl acetate/hexanes to 50% ethyl acetate/hexanes) afforded the desired product 11 (26.0 g, 63%). HPLC-MS $t_R$=1.90 min ($UV_{254\ nm}$); mass calculated for formula $C_{20}H_{26}N_2O_6Si$ 418.15, observed LCMS m/z 419.2 (M+H).

Part F:

The two isomers were separated using a chiral OD column. One gram of material was injected into the column and the two peaks were separated by using a solvent mixture of 85% hexanes/ethanol. The second isomer was the desired compound 12 (400 mg, 80%).

Part G:

Compound 12 (8.0 g, 19.1 mmol) was dissolved in THF (250 mL) and cooled to 0° C. Tetrabutylammonium fluoride (1 M in THF, 22.9 mL, 22.9 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 13 (5.8 g, 88%). The product was used without purification.

Example 3

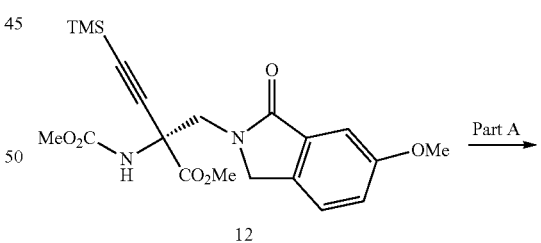

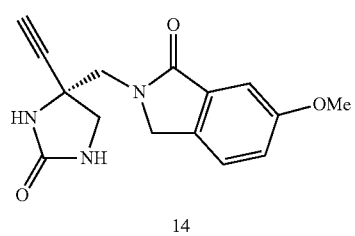

131

Part A:

Compound 12 (1.26 g, 3.0 mmol) in 7 M ammonia in methanol (20 mL) was heated to 85° C. in a pressure bottle overnight. The reaction mixture was concentrated to afford 14 (900 mg, 100%) which was used without further purification. HPLC-MS $t_R$=1.00 min (UV$_{254\ nm}$); mass calculated for formula $C_{15}H_{13}N_3O_4$ 299.09, observed LCMS m/z 300.1 (M+H).

Example 4

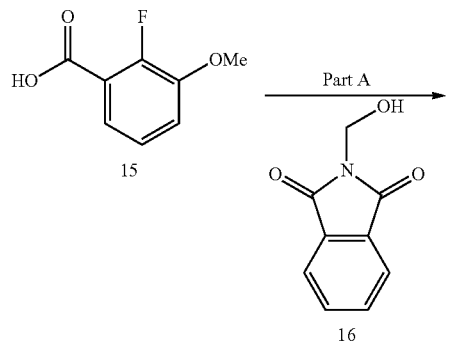

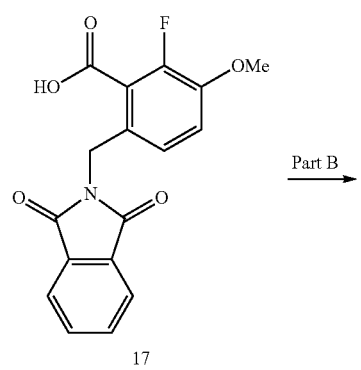

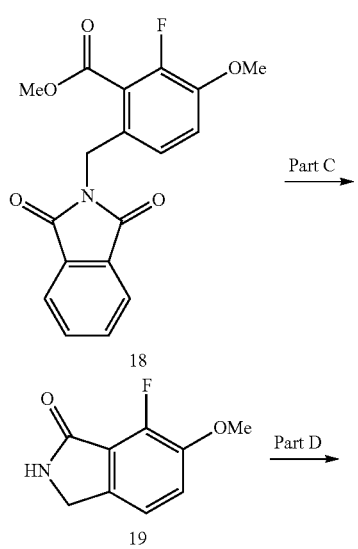

132

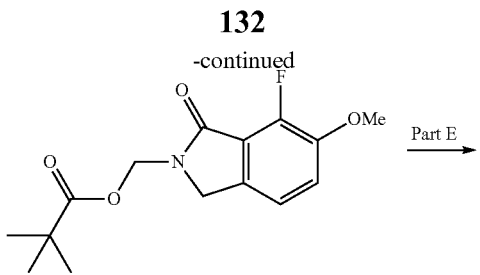

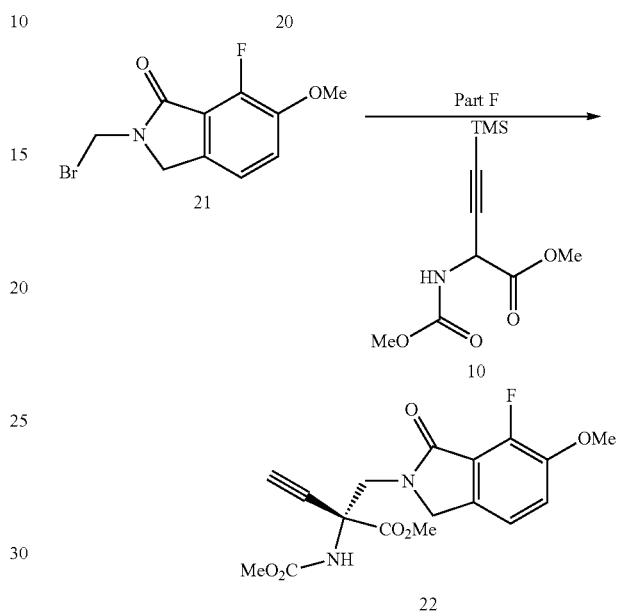

Part A:

Compound 15 (50.8 g, 298.65 mmol) and 16 (55.55 g, 313.58 mmol) were pre-mixed as solids and added to a concentrated sulfuric acid (150 mL) at 10° C. The reaction mixture was stirred at 10-15° C. for 2-3 hours. The reaction mixture was slowly added to ice water (800 mL) with good stirring. The reaction flask was rinsed with concentrated sulfuric acid and wash was added to the ice water. The solid was collected by filtration, washed with water (2×) and dried at 50° C. under vacuum to afford compound 17 (>100% by weight).

Part B:

To a solution of compound 17 (298.65 mmol) in DMF (1 L) was added sequentially cesium carbonate (127 g, 388.24 mmol) and methyl iodide (22.3 mL, 358.38 mmol). The reaction was stirred overnight at room temperature. The reaction mixture was diluted with water (800 ml) and ethyl acetate (800 mL) and the layers were separated. The aqueous layer was extracted with ethyl acetate (500 mL). The combined organic layers were washed with brine, dried over sodium sulfate and concentrated in vacuum. The crude reaction product was used without further purification.

Part C:

The crude product 18 was dissolved in methanol (1 L) and hydrazine hydrate (29 ml, 597.3 mmol) was added. The reaction mixture was stirred with a mechanical stirrer and heated to reflux for 3 hours. The reaction mixture was initially a suspension which cleared upon heating. As the reaction progressed a precipitate formed. The reaction mixture was cooled and the precipitate was collected by filtration. The solids were washed with methanol and the combined filtrate was reduced in volume to approximately 300 mL. The additional precipitate was collected by filtration and combined with the above solids. The solids were stirred with potassium carbonate solution (1 M, 200 mL) for 15 minutes and filtered. This washing process was repeated with another portion of potassium carbonate solution (1M, 150 ml). The solids were then washed with hydrochloric acid (2 M, 150 ml) for 15 minutes and filtered. This washing process was repeated with another portion of hydrochloric acid (1M, 150 ml) and the solid was rinsed with water. The potassium carbonate solution was extracted with ethyl acetate twice. The ethyl acetate washes were combined with the methanol filtrate, washed with brine, dried over sodium sulfate, and concentrated. The residue was washed with potassium carbonate solution (1 M, 20 mL) and hydrochloric acid (2 M, 20 mL). The additional solid was rinsed with water and combined with above solid. It was dried under vacuum at 50° C. for overnight to give compound 19 (47.87 g, 88.5% from compound 15).

Part D:

To a 3 L three neck flask was added compound 19 (61.07 g, 337.11 mmol) and DMPU (1500 mL). The suspension was stirred with a mechanic stirrer and gently warmed with a heat gun until a clear solution appeared. The solution was cooled to 0° C. and chloromethyl pivalate was added slowly with a syringe. The reaction mixture was stirred at 0° C. for three hours, diluted with $H_2O$ (1.5 L) and EtOAc (1.5 L), and the layers were separated. The organic layer was washed with $H_2O$ (500 mL×4), brine (500 mL), dried over sodium sulfate, and concentrated in vacuum. The product was purified by silica gel chromatography (Hexane/EtOAc: 2:1 to 1:1 to 0:1) to afford compound 20 (77.98 g, 78.3%)

Part E:

Compound 20 (70.97 g, 240.32 mmol) was dissolved in anhydrous $CH_2Cl_2$ (1 L). The solution was cooled to 0° C. and TMSBr (37.3 mL, 288.39 mmol) was added via syringe. The reaction mixture was stirred at 0° C. for two hours and concentrated in vacuum at 25° C. The residue was stirred with Hexane (500 mL) for 15 min, filtered, and rinsed with hexane (60 mL×2). The Hexane filtrate was concentrated in volume to approximately 100 mL and the additional solid was filtered, rinsed with hexane (10 mL×2), and combined with above solid. The solid was dried under vacuum for overnight to give compound 21 (64.81 g, 98.4%).

Part F:

To a flamed dried flask was added compound 21 (1.13 g, 4.11 mmol), compound 10 (1.0 g, 4.11 mmol), and anhydrous THF (25 mL). The solution was cooled to −78° C. and LiH-MDS (8.63 mL, 8.63 mmol) was added via syringe. The reaction mixture was stirred at −78° C. for two hours, diluted with saturated $NH_4Cl$ solution (30 mL) and EtOAc (50 mL). After warming up to room temperature, the aqueous layer was separated and extracted with EtOAc (20 mL) once. The organic layers were combined and TBAF (1 M in THF, 7 mL, 7 mmol) was added. The solution was stirred at 25° C. for 10 min, washed with water (50 mL), brine (50 mL), dried over sodium sulfate, and concentrated in vacuum. The product was purified by silica gel chromatography (Hexane/EtOAc: 2:1 to 1:1 to 0:1) to afford the racemate of compound 22 (891 mg, 59.5%)

The racemic mixture was separated using SFC conditions (20% $MeOH/CO_2$, 180 mL/min, back pressure of 225 bar, run time 9 minutes, OD-H chiral column). The racemate was dissolved in 1:1 acetonitrile/isopropyl alcohol (250 mg/mL).

Compound 22 was isolated as the first peak. HPLC-MS $t_R$=1.26 min (UV 254 nm); mass calculated for formula $C_{17}H_{17}FN_2O_6$ 364.11, observed LCMS m/z 365.0 (M+H).

Example 5

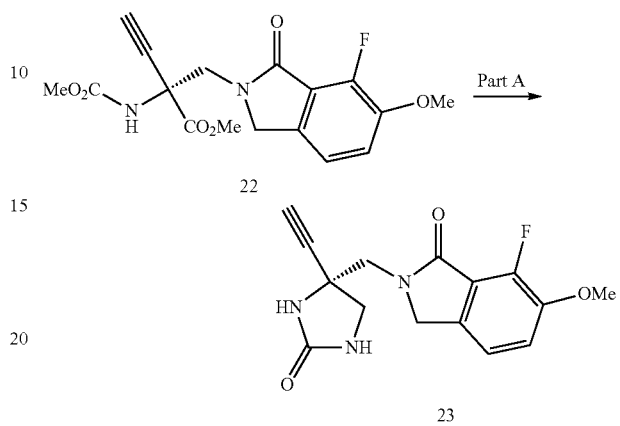

Part A:

Using the procedures described in Example 3, compound 22 (8.69 g, 23.8 mmol) was converted to 23 in quantitative yield. HPLC-MS $t_R$=0.93 min (UV 254 nm); mass calculated for formula $C_{15}H_{12}FN_3O_4$ 317.08, observed LCMS m/z 318.1 (M+H).

Example 6

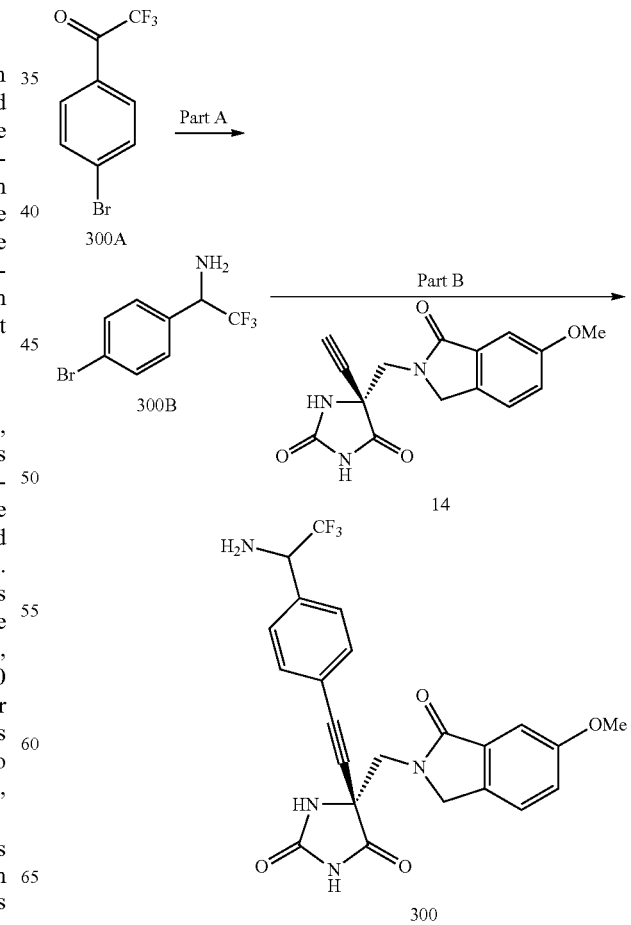

Part A

To 300A (252 mg, 1.00 mmol) in toluene (6 mL) was added LiHMDS (1.1 mL, 1.1 mmol) dropwise. After 15 min, borane-THF (2.0 mL, 2.0 mmol) was added. The resulting mixture was stirred for 20 min, cooled to 0° C., 2N NaOH solution (3 mL) was added. After 90 min at rt, the mixture was diluted with EtOAc, separated and the organic layer was washed with 2N NaOH, water, brine, dried and concentrated to give a crude oil which was purified by column chromatography (10% EtOAc in hexane) to give 300B (130 mg, 52%). HPLC-MS $t_R$=1.24 min (UV 254 nm); mass calculated for formula $C_8H_7BrF_3N$ 252.97, observed LCMS m/z 254.1 (M+H).

Part B

A mixture of 14 (129 mg, 0.43 mmol), 300B (120 mg, 0.47 mmol), copper iodide (8 mg, 0.043 mmol), $Pd(dba)_2$ (20 mg, 0.022 mmol), dppf (24 mg, 0.043 mmol) and triethylamine (0.120 mL, 0.86 mmol) in DMF (2 mL) was heated at 90° C. overnight. The reaction mixture was concentrated and purified by reserve phase chromatography using a 0.1% trifluoroacetic acid in the aqueous mobile phase. The isolated fractions were concentrated to afford 300 (42 mg) as a pale brown powder after lyophilization. HPLC-MS $t_R$=1.36 min ($UV_{254\ nm}$); mass calculated for formula $C_{23}H_{19}F_3N_4O_4$ 472.14, observed LCMS m/z 473.2 (M+H).

Additional compounds were prepared using methods similar to the one described in Example 6, Part B from the corresponding aryl- or heteroarylhalide intermediates. These compounds were compounds 306, 307, 2201-2203, 2209, 2219-2221, 2223, 2224, 2229-2231, 2240, 2242, 2243, 903, and 905. In addition, as identified in the examples below, additional compounds were prepared from the aryl- or heteroarylhalide using a coupling procedure similar to the one described in Example 6, Part B.

Example 7

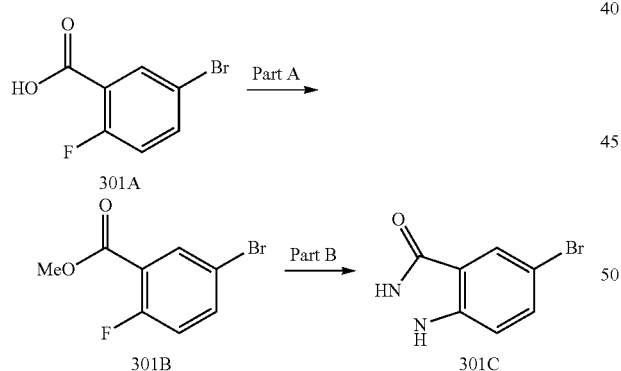

Part A

Compound 301A (1.15 g, 5.00 mmol) was dissolved in 10 mL of a 1:1 mixture of EtOH:MeCN followed by the dropwise addition of (trimethylsilyl)diazomethane (2.0M solution in THF, 3.30 mL, 6.50 mmol) The reaction was stirred for 15 minutes, then treated with 0.5 mL trifluoroacetic acid to quench any remaining diazomethane reagent. 50 mL EtOAc was added, and the mixture poured into a separating funnel containing 20 mL saturated sodium bicarbonate. The EtOAc layer was further washed with brine, dried over magnesium sulfate, then concentrated to provide desired product 301B (1.02 g, 83%).

Part B:

A solution of compound 301B (1.02 g, 4.2 mmol) in 8 mL EtOH was treated with hydrazine monohydrate (4.0 mL, 80 mmol) and the reaction mixture stirred at 100° C. for 30 minutes in a Biotage microwave. Conversion was incomplete as determined by LCMS; therefore, the mixture was concentrated, and fresh EtOH (6 mL) and hydrazine monohydrate (6 mL) were added. The reaction mixture was again stirred at 100° C. for 30 minutes in a microwave apparatus, then concentrated to dryness to provide desired product 301C (801 mg, 89%). HPLC-MS $t_R$=1.21 min (UV 254 nm); mass calculated for formula $C_7H_5BrN_2O$ 212.0/214.0, observed LCMS m/z 213.1/215.1 (M+H).

Compound 301 was prepared from compound 301C using the method described in Example 6, Part B. Compounds 302 and 303 were prepared using procedures similar to those described in Example 7 and Example 6, Part B.

Example 8

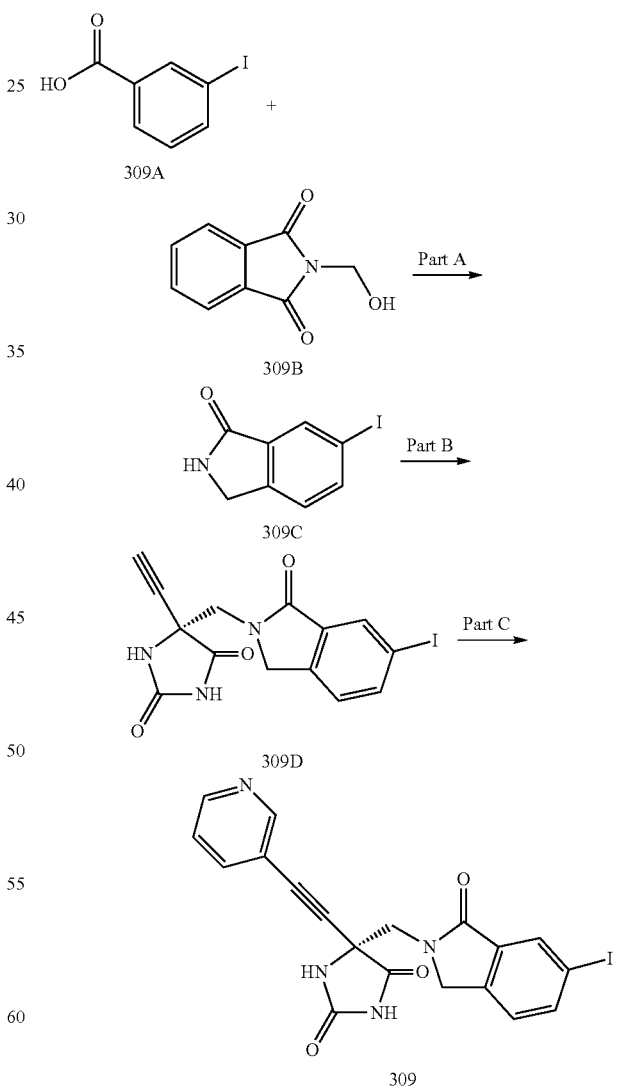

Part A

Compound 309A (4.96 g, 20 mmol) and compound 309B (3/2 g, 21 mmol) were suspended in concentrated sulfuric acid (20 mL) and heated at 55° C. for 3 hours, then at 90° C. for 3 hours. The reaction mixture was cooled to room temperature, poured into ice-water (150 mL), and filtered. The solid was washed with water, 3% ammonium hydroxide, dried, and heated in EtOH (30 mL) at 70° C. for 1 hour. The mixture was cooled to room temperature, filtered and a yellow solid (2.87 g, 55%) was obtained. HPLC-MS $t_R$=1.39 min (UV 254 nm); mass calculated for formula $C_8H_6INO$ 258.95, observed LCMS m/z 260.0 (M+H).

Part B

Compound 309D was prepared according to the procedures described in Example 1 part D and part E, and Example 2 part E, part F and part G. HPLC-MS $t_R$=1.39 min ($UV_{254\ nm}$); mass calculated for formula $C_{14}H_{10}IN_3O_3$ 394.98, observed LCMS m/z 396.0 (M+H).

Part C

A mixture of 309D (50 mg, 0.13 mmol), 3-iodopyridine (39 mg, 0.19 mmol), copper iodide (2.5 mg, 0.013 mmol), Pd(PPh$_3$)$_2$Cl$_2$ (4.4 mg, 0.006 mmol) and triethylamine (0.035 mL, 0.25 mmol) in DMF (1 mL) was heated at 100° C. in the microwave for 15 minutes. The reaction mixture was concentrated and purified by reverse phase chromatography using a 0.1% trifluoroacetic acid in the aqueous mobile phase. The isolated fractions were concentrated and converted to the HCl salt to afford 309 (7.8 mg) as a pale yellow powder after lyophilization.

HPLC-MS $t_R$=1.27 min ($UV_{254\ nm}$); mass calculated for formula $C_{19}H_{13}IN_4O_3$ 472.00, observed LCMS m/z 473.0 (M+H).

Compound 308 was prepared using procedures similar to Example 8 and Example 6, Part B.

Example 9

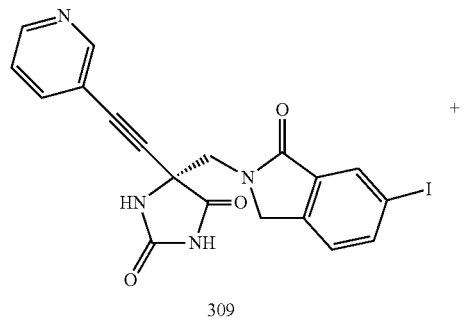

309

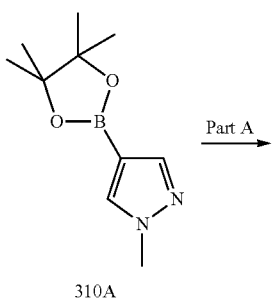

310A

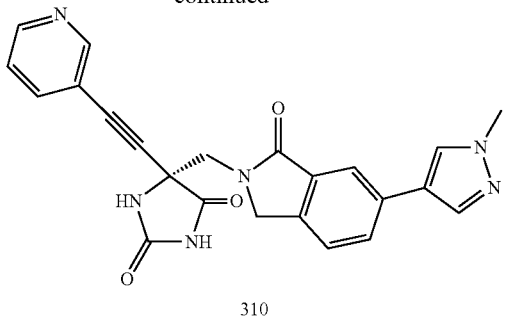

310

Part A

Compound 309 (20 mg, 0.048 mmol), 310A (13 mg, 0.063 mmol), Pd(dppf)$_2$Cl$_2$ (3 mg), and potassium phosphate (30 mg, 0.14 mmol) were dissolved in 1,4-dioxane (1 mL) water (0.2 mL) and stirred at 120° C. for 30 minutes in a microwave. The solvent was removed and the residue was purified by reverse phase chromatography to provide compound 310 (6.3 mg). HPLC-MS $t_R$=1.23 min ($UV_{254\ nm}$); mass calculated for formula $C_{23}H_{18}N_6O_3$ 426.14, observed LCMS m/z 427.1 (M+H).

Compound 311 was prepared using procedures similar to those described in Example 9 and Example 6, Part B.

Example 10

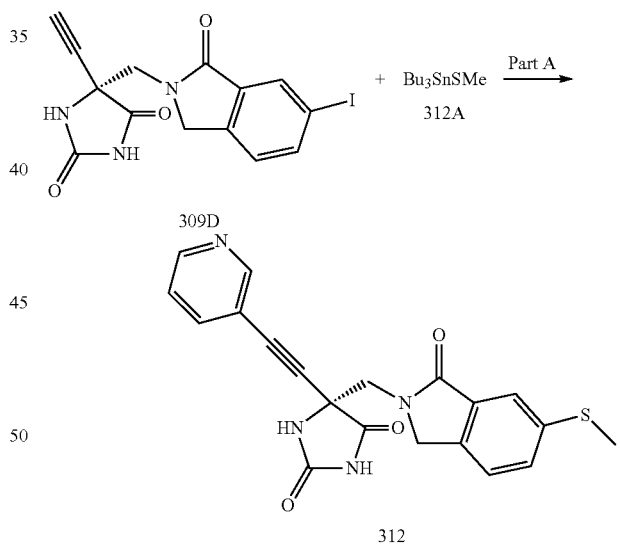

312A

309D

312

Part A

A mixture of 309D (20 mg, 0.051 mmol), 3-iodopyridine (31 mg, 0.15 mmol), copper iodide (0.4 mg, 0.002 mmol), Pd(PPh$_3$)$_2$Cl$_2$ (0.7 mg, 0.001 mmol) and triethylamine (0.014 mL, 0.10 mmol) in DMF (1 mL) was heated at 130° C. in the microwave for 15 minutes, cooled to room temperature, then 312A (51 mg, 0.15 mmol) and Pd(dppf)$_2$Cl$_2$ (4 mg) were added. The resulting mixture was heated at 130° C. in the microwave for 15 minutes. The solvent was removed and the residue was purified by reverse phase chromatography to provide compound 312 (4.5 mg). HPLC-MS $t_R$=1.22 min (UV$_{254\ nm}$); mass calculated for formula C$_{20}$H$_{16}$N$_4$O$_3$S 392.09, observed LCMS m/z 393.1 (M+H).

Example 11

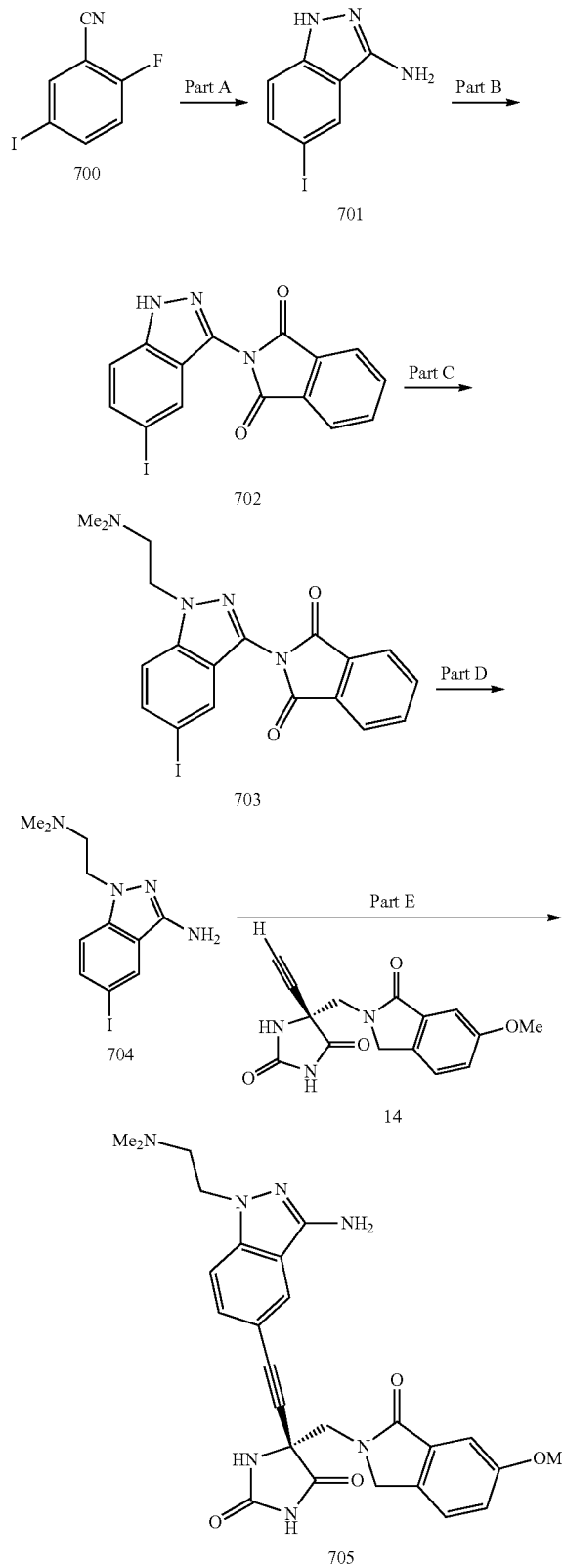

Part A:

Compound 700 (927 mg, 375 mmol) and hydrazine (0.5 mL) were dissolved in ethanol (10 mL) and stirred at 150° C. for 20 minutes in a microwave reactor. The reaction was diluted with water and ethyl acetate. The organic layer was dried over sodium sulfate and concentrated to provide compound 701 (920 mg).

Part B:

Compound 701 (706 mg, 27 mmol) and phthalic anhydride (436 mg, 2.97 mmol) were dissolved in dioxane (10 mL) and stirred at 150° C. for forty minutes in a microwave. The dioxane was removed under reduced pressure and the resulting solids were triturated with diethyl ether to provide compound 702 (720 mg). $^1$H NMR (400 MHz, DMSO) δ 12.5 (s, 1H), 8.2 (s, 1H), 8.0-7.8 (m, 4H), 7.6 (m, 1H), 7.45 (d, 1H).

Part C:

Compound 702 (350 mg, 0.89 mmol), 2-chloro-1-dimethylaminoethane hydrochloride (142 mg, 0.98 mmol), and potassium carbonate (0.5 g) were dissolved in DMF (10 mL) and stirred overnight at 90° C. The reaction was quenched with water and extracted with ethyl acetate. The combined organic layers were dried over sodium sulfate and concentrated to provide compound 703 that was used without purification (65 mg).

Part D:

Compound 703 (65 mg, 0.14 mmol) and hydrazine (0.1 mL) were dissolved in ethanol (5 mL) and stirred at 50° C. for 3 hours. The solids were filtered and the solvent was evaporated to provide compound 704 that was used without purification (46 mg).

HPLC-MS t$_R$=0.79 min (UV$_{254\ nm}$); mass calculated for formula C$_{11}$H$_{15}$N$_{41}$ 330.0, observed LCMS m/z 331.0 (M+H).

Part E:

The reaction was performed in a similar manner to Example 6, Part F. HPLC-MS t$_R$=1.02 min (UV$_{254\ nm}$); mass calculated for formula C26H27N7O4 501.2, observed LCMS m/z 502.3 (M+H). $^1$H NMR (400 MHz, DMSO): δ 11.2 (s, 1H), 10.0 (s, 1H), 8.9 (s, 1H), 7.8 (s, 1H), 7.5 (m, 2H), 7.4-7.3 (m, 2H), 4.5 (m, 4H), 4.05 (m, 2H), 3.8 (s, 3H), 2.8 (m, 6H).

Example 12

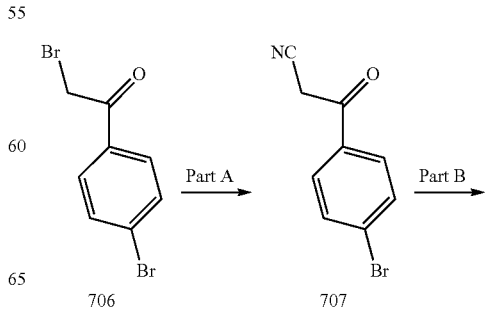

-continued

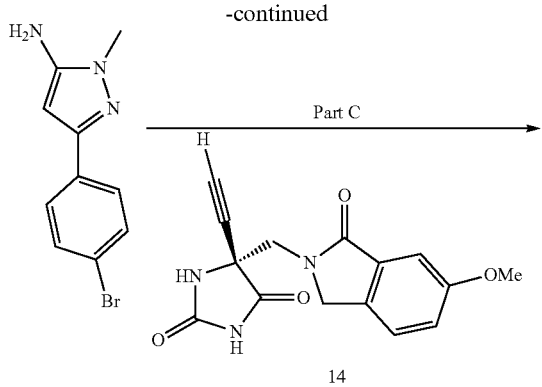

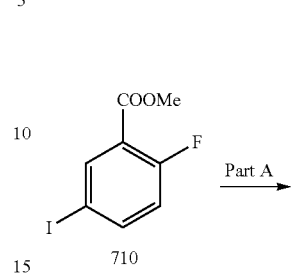

Compound 747 was prepared using procedures similar to those described in Example 12 and Example 6, Part B.

Example 13

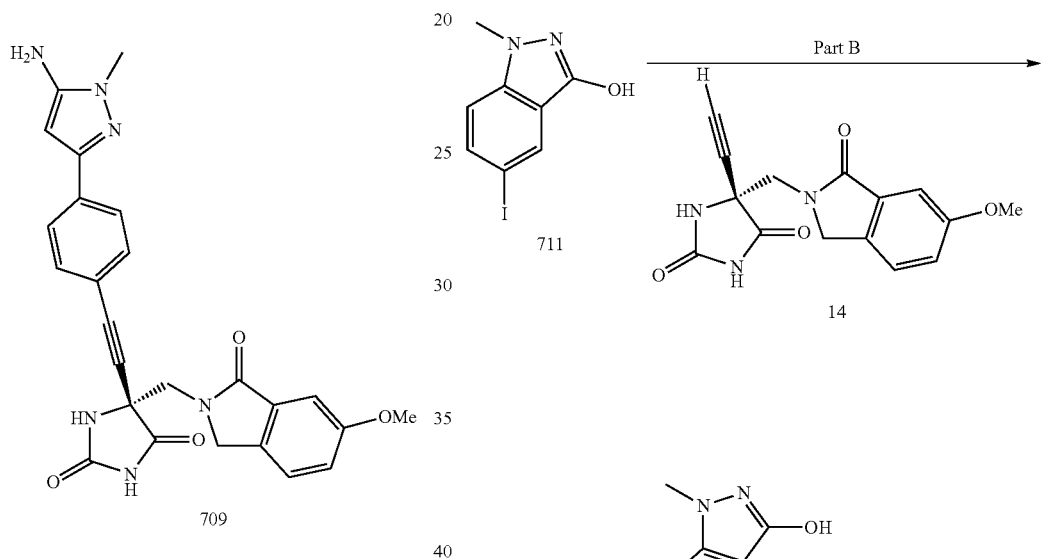

Part A:

Compound 706 (3.0 g, 10.9 mmol) and potassium cyanide (1.46 g, 21.8 mmol) were dissolved in ethanol (20 mL) and water (10 mL) and stirred for 30 minutes. The reaction was diluted with water (10 mL) and 1 N HCl (30 mL). The solids were filtered and washed with 5% ethyl acetate/hexanes to provide compound 707 (2.0 g).

Part B:

Compound 707 (478 mg, 2.14 mmol) was dissolved in ethanol (6 mL) and methylhydrazine (0.5 mL) and stirred at 70° C. overnight. The reaction was quenched with water and ethyl acetate. The organic layer was washed with brine, dried over sodium sulfate and concentrated under reduced pressure. The residue was recrystallized from ethyl acetate/hexanes to provide compound 708 (200 mg). HPLC-MS $t_R$=1.5 min (UV$_{254\ nm}$); mass calculated for formula C10H10BrN3 253.0, observed LCMS m/z 254.1 (M+H).

Part C:

The reaction was performed in a similar manner to Example 6, Part F. HPLC-MS $t_R$=1.32 min (UV$_{254\ nm}$); mass calculated for formula C25H22N6O4 470.1, observed LCMS m/z 471.1 (M+H). $^1$H NMR (400 MHz, DMSO): δ 11.2 (s, 1H), 8.9 (s, 1H), 7.8 (m, 2H), 7.5 (m, 3H), 7.4-7.3 (m, 3H), 6.1 (s, 1H), 4.5 (m, 2H), 4.05 (m, 2H), 3.8 (s, 3 H), 3.7 (s, 3H).

Part A:

Compound 710 (650 mg, 2.32 mmol) was dissolved in ethanol (6 mL) and methylhydrazine (0.7 ml) and stirred at 150° C. for 40 minutes in a microwave. The solids were filtered to provide compound 711 (550 mg).

Part B:

The reaction was performed in a similar manner to Example 6, Part F. HPLC-MS $t_R$=1.36 min (UV$_{254\ nm}$); mass calculated for formula C23H19N5O5 445.1, observed LCMS m/z 446.0 (M+H). $^1$H NMR (400 MHz, DMSO): δ 11.2 (s, 1H), 8.9 (s, 1H), 7.75 (m, 1H), 7.5 (m, 1H), 7.4 (m, 1H), 7.3 (m, 1H), 7.3-7.1 (m, 3H), 4.5 (m, 2H), 4.05 (m, 2H), 3.8 (s, 3 H), 3.75 (s, 3H).

Example 14

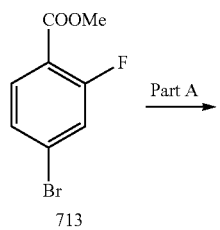

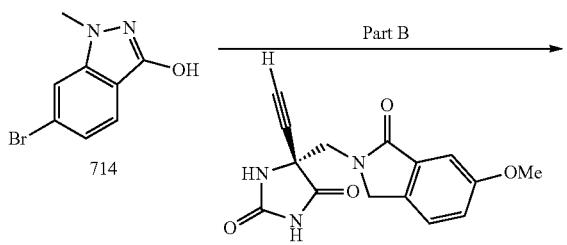

Compound 748 was prepared using procedures similar to those described in Example 14 and Example 6, Part B.

Example 15

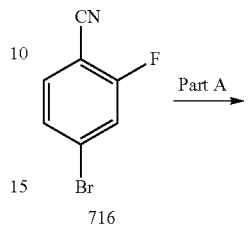

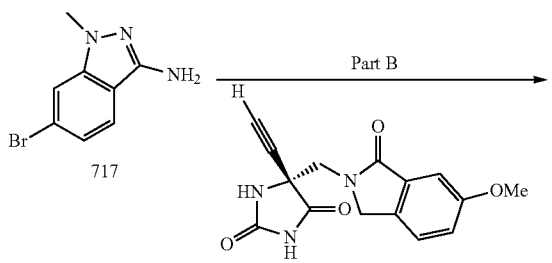

Part A:

Compound 713 (600 mg, 2.58 mmol) was dissolved in n-butanol (3 mL) and methylhydrazine (0.5 mL) and stirred at 170° C. for 40 minutes in a microwave. The reaction was quenched with water and ethyl acetate. The combined organic layers were dried over sodium sulfate and concentrated under reduced pressure. The residue was recrystallized from ethyl acetate/hexanes to provide compound 714 (500 mg).

Part B:

The reaction was performed in a similar manner to Example 6, Part F. HPLC-MS $t_R$=1.34 min (UV$_{254\,nm}$); mass calculated for formula C23H19N5O5 445.1, observed LCMS m/z 446.0 (M+H). $^1$H NMR (400 MHz, DMSO): δ 11.2 (s, 1H), 8.9 (s, 1H), 7.6-7.5 (m, 3H), 7.2 (m, 2H), 6.95 (m, 1H), 4.5 (m, 2H), 4.05 (m, 2H), 3.8 (s, 3 H), 3.75 (s, 3H).

Part A:

Compound 716 (661 mg, 3.28 mmol) was dissolved in ethanol (7 mL) and methylhydrazine (0.5 mL) and stirred at 120° C. for 25 minutes in a microwave. The reaction was quenched with water the product was extracted with ethyl acetate. The combined organic layers were dried over sodium sulfate and concentrated. The residue was recrystallized from ethyl acetate/hexanes to provide compound 717 (400 mg).

Part B:

The reaction was performed in a similar manner to Example 6, Part B. HPLC-MS $t_R$=1.13 min (UV$_{254\,nm}$); mass calculated for formula C23H20N6O4 444.1, observed LCMS m/z 445.1 (M+H). $^1$H NMR (400 MHz, DMSO): δ 11.2 (s, 1H), 8.9 (s, 1H), 7.75 (m, 1H), 7.5 (m, 2H), 7.2 (m, 3H), 6.95 (m, 1H), 4.5 (m, 2H), 4.05 (m, 2H), 3.8 (s, 3 H), 3.75 (s, 3H).

Compounds 746, 2236, and 2237 were prepared using procedures similar to Example 15 and Example 6, Part B.

Example 16

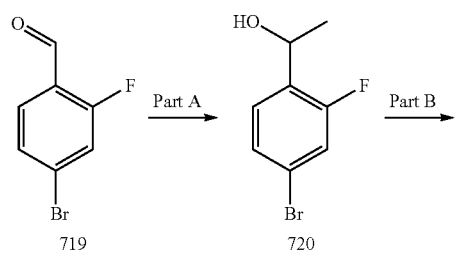

Part A:
Compound 719 (2.5 g, 12.3 mmol) was dissolved in THF (50 mL) and cooled in an ice bath. Methylmagnesium bromide (3M in THF, 4.9 mL, 14.8 mmol) was added dropwise and the reaction was stirred for 30 minutes. The reaction was quenched with 1N HCl and then extracted with ethyl acetate. The combined organic layers were dried over sodium sulfate and concentrated to provide compound 720 (2.5 g).

Part B:
Compound 720 (2.0 g, 9.17 mmol) and manganese dioxide (4.0 g, 45 mmol) were suspended in dioxane (50 mL) and refluxed for 2 hours. The reaction was filtered over celite and the solvent was removed to provide compound 721 (1.75 g).

Part C:
Compound 721 (1.1 g, 5.04 mmol) was dissolved in ethylene glycol (10 mL) and hydrazine monohydrate (277 mg, 5.5 mmol) and stirred at room temperature for 30 minutes followed by 1 hour at 200° C. in a microwave. The reaction was quenched with brine and extracted with methylene chloride. The organic layer was dried over sodium sulfate and concentrated to provide compound 722 (1.0 g). $^1$H NMR (400 MHz, CDCl3): δ 7.65 (m, 1H), 7.58 (m, 1H), 7.3 (m, 1H), 2.6 (s, 3H).

Part D:
The reaction was performed in a similar manner to Example 6, Part F. HPLC-MS $t_R$=1.325 min (UV$_{254nm}$); mass calculated for formula $C_{23}H_{19}N_5O_4$ 429.1, observed LCMS m/z 430.1 (M+H). $^1$H NMR (400 MHz, DMSO): δ 11.2 (s, 1H), 8.9 (s, 1H), 7.75 (m, 1H), 7.5 (m, 2H), 7.2 (m, 3H), 7.0 (m, 1H), 4.5 (m, 2H), 4.05 (m, 2H), 3.8 (s, 3H), 2.45 (s, 3H).

Example 17

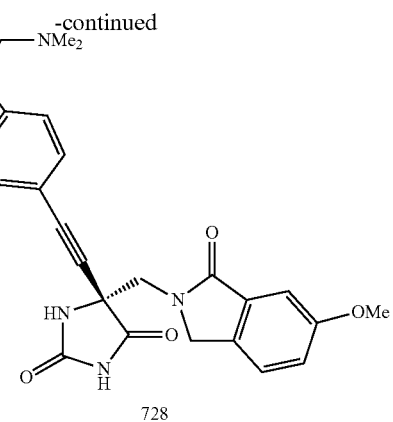

728

Part A:

Compound 722 (500 mg, 2.34 mmol) and acetyl chloride (278 mg, 3.52 mmol) were dissolved in acetonitrile (10 mL) and pyridine (1 mL) and stirred at room temperature for 2 hours. The reaction was quenched with 1 N HCl and extracted with ethyl acetate. The combined organic layers were dried over sodium sulfate and concentrated under reduced pressure to provide compound 725 (520 mg).

Part B:

Compound 725 (160 mg, 0.63 mmol), NBS (123 mg, 0.69 mmol), and benzoyl peroxide (20 mg) were dissolved in carbon tetrachloride (5 mL) and refluxed for 5 hours. The reaction was cooled to room temperature and filtered. The solvent was removed under reduced pressure to provide compound 726 that was used without purification (130 mg). HPLC-MS $t_R$=2.36 min ($UV_{254\,nm}$); mass calculated for formula $C_{10}H_8Br_2N_2O$ 331.99, observed LCMS m/z 333.0 (M+H).

Part C:

Compound 726 (130 mg) was dissolved in DMF (3 mL) and treated with 2 M dimethylamine in THF (3 mL). The reaction was stirred overnight and then quenched with water and extracted with ethyl acetate. The combined organic layers were dried over sodium sulfate and concentrated. The residue was dissolved in ether and washed with 1N HCl. The aqueous layer was treated with 1 N NaOH until the pH=10 and then extracted with ethyl acetate. The combined ethyl acetate layers were dried over sodium sulfate and concentrated to provide compound 727 (90 mg). HPLC-MS $t_R$=0.73 min ($UV_{254\,nm}$); mass calculated for formula $C_{10}H_{12}BrN_3$ 254.1, observed LCMS m/z 255.1 (M+H).

Part D:

The reaction was performed in a similar manner to Example 6, Part F. HPLC-MS $t_R$=0.86 min ($UV_{254\,nm}$); mass calculated for formula $C_{25}H_{24}N_6O_4$ 472.1, observed LCMS m/z 473.2 (M+H). $^1$H NMR (400 MHz, DMSO): δ 11.2 (s, 1H), 10.5 (bs, 1H), 8.9 (s, 1H), 8.0 (m, 1H), 7.75 (s, 1H), 7.5 (m, 1H), 7.2 (m, 3H), 4.5 (m, 2H), 4.05 (m, 2H), 3.8 (s, 3 H), 2.8 (s, 6H).

Example 18

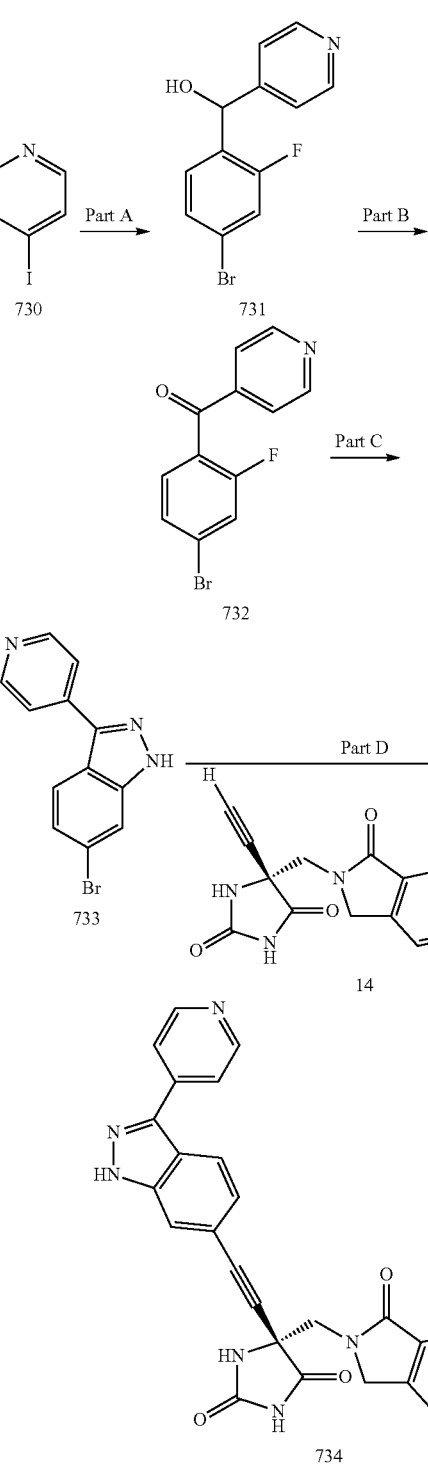

Part A:

Compound 730 (500 mg, 2.48 mmol) was dissolved in THF (15 mL) and treated with ethylmagnesium bromide (2M in THF, 1.5 mL, 3 mmol). After 30 minutes a solution of 4-bromo-2-fluorobenzaldehyde (648 mg, 3.22 mmol) in THF (5 mL) was added. The reaction was stirred for 3 hours and then quenched with saturated ammonium chloride. The aqueous layer was extracted with ethyl acetate. The combined organic layers were dried over sodium sulfate and concentrated. The residue was purified by column chromatography (1:1 Hexanes/ethyl acetate) to provide compound 731 (300 mg).

Part B:

Compound 731 (300 mg, 1.08 mmol) and manganese dioxide (1.0 g) were refluxed in dioxane for 2 hours. The reaction mixture was filtered over celite and the solvent was removed under reduced pressure to provide compound 732 (290 mg).

Part C:

Compound 732 (290 mg, 1.04 mmol) was dissolved in ethylene glycol (10 mL) and hydrazine (0.5 mL) and stirred at room temperature for 2 hours and 15 minutes at 200° C. in a microwave. The reaction was quenched with brine and ethyl acetate. The organic layer was washed with brine, dried over sodium sulfate, and concentrated under reduced pressure. The residue was triturated with ethyl acetate to provide compound 733 (200 mg). $^1$H NMR (400 MHz, DMSO): δ 8.7 (m, 2H), 8.25 (m, 1H), 7.95 (m, 2H), 7.78 (m, 1H), 7.4 (m, 1H).

Part D:

The reaction was performed in a similar manner to Example 6, Part F. HPLC-MS $t_R$=0.97 min (UV$_{254 nm}$); mass calculated for formula $C_{27}H_{20}N_6O_4$ 492.1, observed LCMS m/z 493.1 (M+H). $^1$H NMR (400 MHz, DMSO): δ 11.2 (s, 1H), 8.95-8.8 (m, 3H), 8.5 (m, 2H), 8.25 (m, 1H), 7.85 (s, 1H), 7.5 (m, 1H), 7.4 (m, 1H), 7.2 (s, 1H), 7.15 (m, 2H), 4.6 (m, 2H), 4.05 (m, 2H), 3.8 (s, 3 H).

Example 19

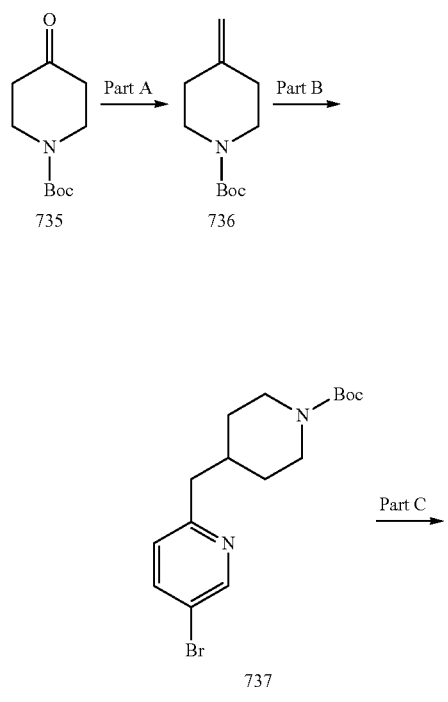

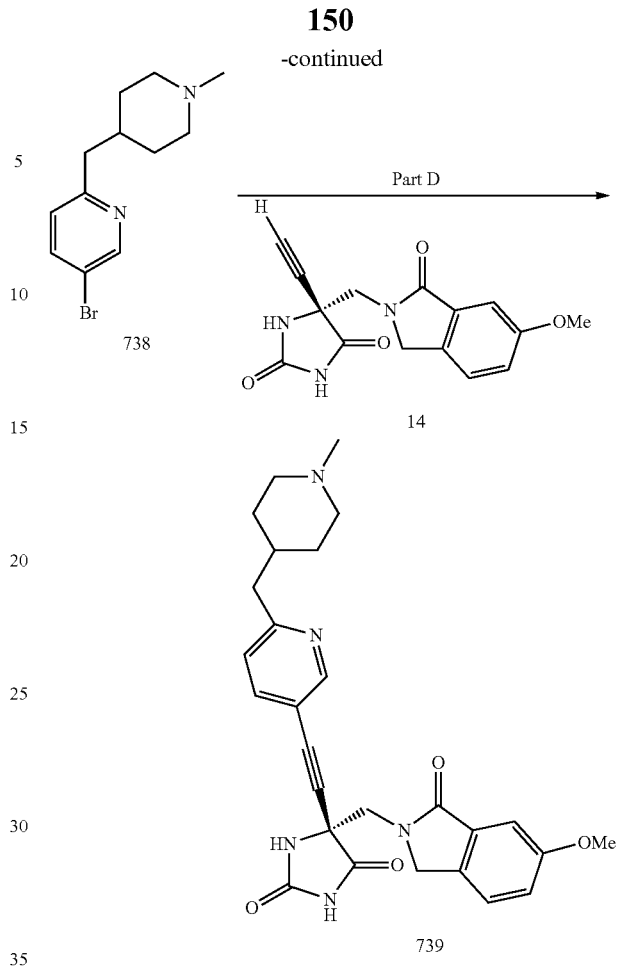

Part A:

Methyltriphenylphosphonium bromide (4.3 g, 12 mmol) was suspended in THF (13 mL) and 60% NaH (0.48 g, 12 mmol) was added followed by DMSO (15 mL). After 15 minutes compound 735 (2.0 g, 10 mmol) was added dropwise in THF (17 mL). The reaction was stirred for 45 minutes and then quenched with water and ethyl acetate. The organic layer was washed with saturated sodium bicarbonate, brine, dried over sodium sulfate and concentrated. The residue was treated with ether and the resulting solids were filtered and discarded. The solvent was removed under reduced pressure and the residue was purified by column chromatography (2:1 hexanes/ethyl acetate) to provide compound 736 (1.9 g).

Part B:

Compound 736 (930 mg, 4.7 mmol) was dissolved in 0.5 M 9-BBN solution (9.44 mL, 4.7 mmol) and refluxed for 1 hour. After cooling to room temperature, the solution was added to a solution of 2,5-dibromopyridine (994 mmol, 4.27 mmol), Pd(dppf)$_2$Cl$_2$ (95 mg), and potassium carbonate (760 mg) in DMF (10 mL) and water (2 mL). The reaction mixture was stirred at 60° C. overnight and then quenched with 1 N NaOH and ethyl acetate. The organic layer was dried over sodium sulfate and concentrated. The residue was purified by column chromatography (8:1 Hexanes/ethyl acetate→4:1 hexanes/ethyl acetate) to provide compound 737 (480 mg). HPLC-MS $t_R$=2.12 min (UV$_{254 nm}$); mass calculated for formula $C_{16}H_{23}BrN_2O_2$ 354.0, observed LCMS m/z 355.0 (M+H).

Part C:

Compound 737 (480 mg, 1.36 mmol) was dissolved in methylene chloride (5 mL) and TFA (1 mL) and stirred at room temperature for 1 hour. The reaction was then quenched with 1 N NaOH and ethyl acetate. The organic layer was dried over sodium sulfate and concentrated. The residue was suspended in methylene chloride (5 mL) and treated with 37% formaldehyde (0.11 mL, 0.39 mmol) and stirred for 1 hour. The reaction was treated with sodium triacetoxyborohydride (420 mg, 1.8 mmol) and stirred for another 3 hours. The reaction was quenched with saturated sodium bicarbonate and ethyl acetate. The organic layer was dried over sodium sulfate and concentrated to provide compound 738 (180 mg).

Part D:

The reaction was performed in a similar manner to Example 6, Part F. HPLC-MS $t_R$=1.002 min (UV$_{254\,nm}$); mass calculated for formula $C_{27}H_{29}N_5O_4$ 487.2, observed LCMS m/z 488.2 (M+H). $^1$H NMR (400 MHz, DMSO): δ 11.2 (s, 1H), 10.25 (bs, 1H), 8.95 (s, 1H), 8.6 (m, 1H), 7.95 (m, 1H), 7.5-7.4 (m, 2H), 7.2 (m, 2H), 4.6 (m, 2H), 4.05 (m, 2H), 3.8 (s, 3H), 3.25 (m, 2H), 3.0-2.75 (m, 5H), 2.6 (s, 3H), 2.0 (m, 1H), 1.8-1.4 (m, 4H).

Example 20

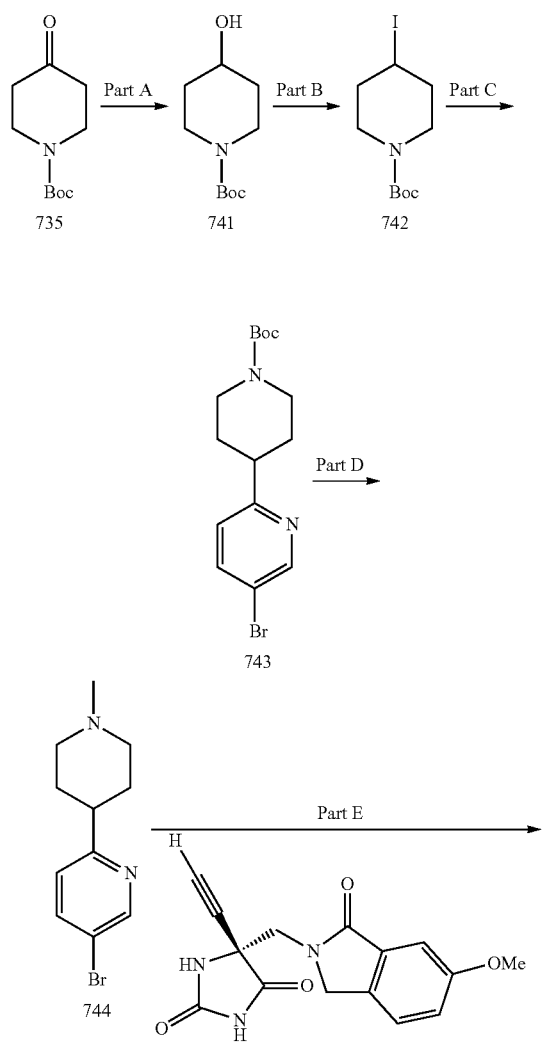

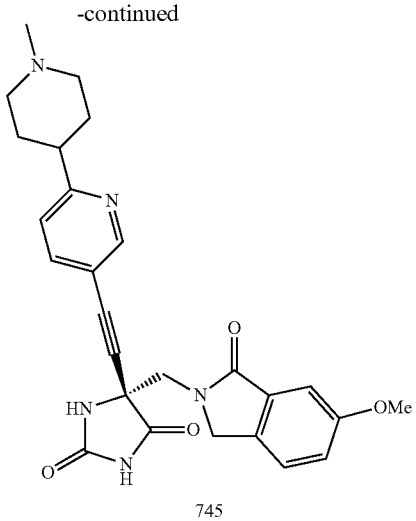

Part A:

Compound 735 (2.25 g, 11.25 mmol) was dissolved in ethanol (20 mL) and treated with sodium borohydride (400 mg). After 2 hours the reaction was quenched with water and ethyl acetate. The organic layer was dried over sodium sulfate and concentrated to provide compound 741 (2.25 g).

Part B:

Compound 741 (225 g, 11.25 mmol), triphenylphosphine (3.84 g, 17.6 mmol), imidazole (1.15 g, 16.8 mmol) and iodine (3.4 g, 12.3 mmol) were dissolved in methylene chloride (15 mL) and stirred for 3 hours. The reaction was quenched with water and ether. The ether layer was dried over sodium sulfate and concentrated. The residue was triturated with hexanes to provide compound 742 (3.1 g).

Part C:

Zinc (0.34 g, 5.17 mmol) was suspended in THF (4 mL) and 1,2-dibromoethane (0.029 mL, 0.34 mmol) and trimethylsilylchloride (0.041 mL, 0.032 mmol) were added and resulting mixture was stirred at 60° C. for 10 minutes. Compound 742 (1.1 g, 3.5 mmol) was added in DMA (5 mL) and the resulting mixture was stirred at 60° C. for 5 minutes and then 20 minutes at room temperature. 2,5-Dibromopyridine (906 mg, 3.83 mmol), Pd(dppf)Cl$_2$ (130 mg), and CuI (30 mg) were added to the reaction and stirred for 2 hours at 80° C. The reaction was quenched with water and ethyl acetate. The combined organic layers were dried over sodium sulfate and concentrated. The residue was purified using column chromatography (3:1 Hexanes/ethyl acetate) to provide compound 743 (300 mg). $^1$H NMR (400 MHz, CDCl$_3$): δ 8.6 (m, 1H), 7.8 (m, 1H), 7.1 (m, 1H), 4.25 (m, 2H), 3.0-2.9 (m, 2H), 1.9 (m, 2H), 1.7 (m, 3H), 1.5 (s, 9H).

Part D:

Compound 743 (280 mg, 0.79 mmol) was dissolved in methylene chloride (5 mL) and TFA (1 mL) and stirred at room temperature for 1 hour. The reaction was then quenched with 1 N NaOH and ethyl acetate. The organic layer was dried over sodium sulfate and concentrated. The residue was suspended in methylene chloride (5 mL) and treated with 37% formaldehyde (0.33 mL, 1.2 mmol) and stirred for 1 hour. The reaction was treated with sodium triacetoxyborohydride (420 mg, 1.8 mmol) and stirred for another 3 hours. The reaction was quenched with saturated sodium bicarbonate and ethyl acetate. The organic layer was dried over sodium sulfate and concentrated to provide compound 744 (150 mg).

Part E:

The reaction was performed in a similar manner to Example 6, Part F. HPLC-MS $t_R$=0.84 min (UV$_{254\ nm}$); mass calculated for formula $C_{26}H_{27}N_5O_4$ 473.2, observed LCMS m/z 474.1 (M+H). $^1$H NMR (400 MHz, DMSO): δ 11.2 (s, 1H), 10.5 (bs, 1H), 8.95 (s, 1H), 8.6 (m, 1H), 7.8 (m, 1H), 7.5 (m, 1H), 7.28 (m, 1H), 7.2 (m, 2H), 4.6 (m, 2H), 4.05 (m, 2H), 3.8 (s, 3 H), 3.45 (m, 2H), 3.0-2.9 (m, 3H), 2.7 (s, 3H), 2.0 (m, 4H).

Example 21

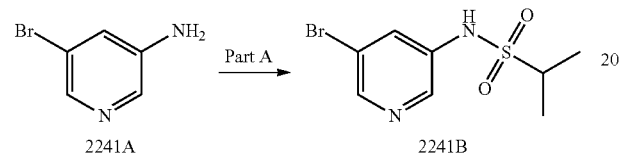

Part A:

In a round bottom flask was added 5-bromopyridine-3-amine (2241A) (780 mg, 4.5 mmol), pyridine (0.4 mL, 4.9 mmol) and DCM (10 mL) and the mixture was cooled at 0° C. Then isopropylsulfonyl chloride (0.55 mL, 4.9 mmol) was added and the mixture was allowed to warm up to rt and was monitored by LC-MS. The mixture was diluted and washed with water, dried and concentrated to a residue which was purified by column chromatography (SiO$_2$, 50% ethyl acetate/hexanes) to afford 2241B (0.46 g; 37%); HPLC-MS $t_R$=1.32 min (UV$_{254\ nm}$); mass calculated for formula $C_8H_{11}BrN_2O_2S$ 277.97, observed LCMS m/z 279.0 (M+H).

Compound 2241 was prepared from 2241B using a procedure similar to the one described in Example 6, part B.

Example 22

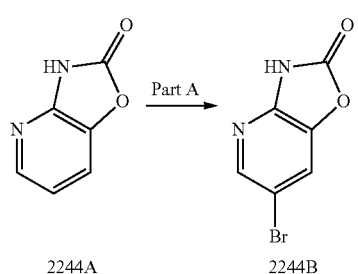 [SMILES: O=c1[nH]c2ncccc2o1 ; O=c1[nH]c2ncc(Br)cc2o1]

Part A:

Compound 2244B was prepared from commercially available 2244A as described in *Heterocycles* 1995, 41, 2799; HPLC-MS $t_R$=1.29 min (UV$_{254\ nm}$); mass calculated for formula $C_6H_3BrN_2O_2$ 213.94, observed LCMS m/z 214.9 (M+H).

Compound 2244 was prepared from 2244B using a procedure similar to the one described in Example 6, Part B.

Example 23

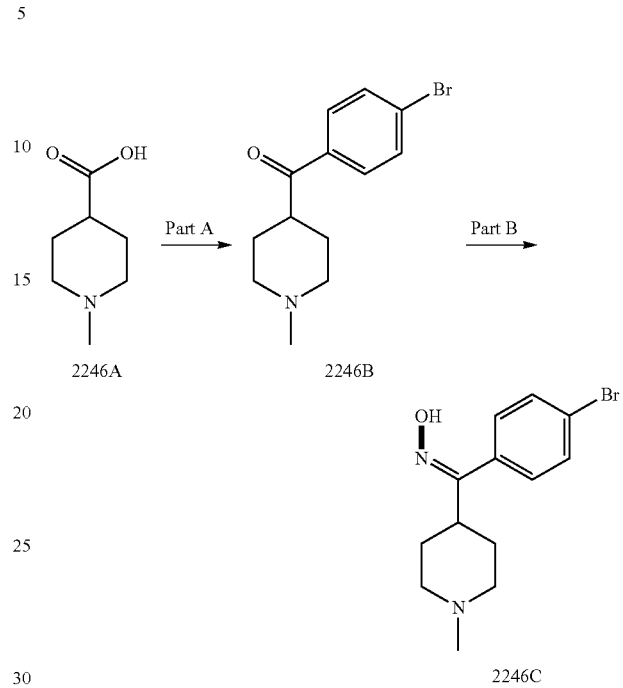

Part A:

Compound 2246B was prepared from commercially available 2246A as described by Pajouhesh, H. et al in WO2006024160; HPLC-MS $t_R$=0.90 min (UV$_{254\ nm}$); mass calculated for formula $C_{13}H_{16}BrNO$ 281.04, observed LCMS m/z 282.1 (M+H).

Part B:

Compound 2246C was prepared following procedures described in Example 27, Part A. HPLC-MS $t_R$=0.83 min (UV$_{254\ nm}$); mass calculated for formula $C_{13}H_{17}BrN_2O$ 296.05, observed LCMS m/z 297.1 (M+H).

Compound 2246 was prepared from 2246C using a procedure similar to the one described in Example 6, Part B.

Example 23A

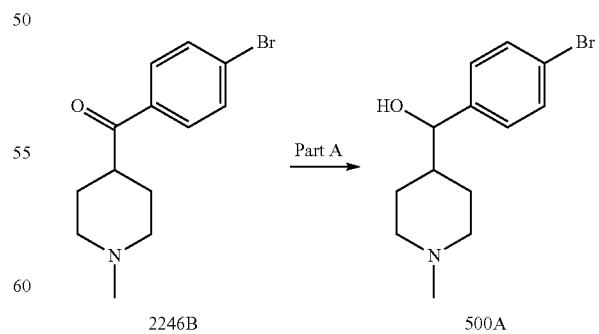

Part A:

In a round bottom flask was added 2246 B (0.83 g, 2.9 mmol), methanol (20 mL) and sodium borohydride (0.23 g, 6.18 mmol) and after the bubbling ceased the solution was stirred at rt for 2 h. The mixture was concentrated, diluted with water, and extracted with DCM. The combined DCM extracts were concentrated to give 0.7 g of 500A as a brown residue, which was used in the next step without further purification. HPLC-MS $t_R$=0.77 min (UV$_{254\,nm}$); mass calculated for formula $C_{13}H_{18}BrNO$ 283.05, observed LCMS m/z 284.0 (M+H).

Compound 500 was prepared from 500A using procedures similar to those described in Example 6.

Example 24

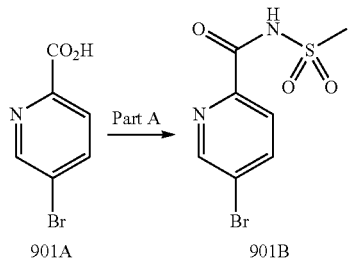

Part A:

Solid CDI (802 mg, 4.95 mmol) was added in a single portion to a suspension of carboxylic acid 901A (500 mg, 2.48 mmol) in dry THF (5 mL) in a pressure tube. The tube was sealed and heated at 70° C. for 2 h. The reaction mixture was allowed to cool to rt. Solid methanesulfonamide (471 mg, 4.95 mmol) and DBU (1.1 mL, 1.1 g, 7.4 mmol) were added and the resulting mixture was stirred at rt for 18 h. The volatile components were removed under reduced pressure. The residue was taken up in $CH_2Cl_2$ and washed sequentially with water and brine. The organic layer was dried over anhydrous $MgSO_4$, filtered, and concentrated. The crude product was purified by sgc (0-10% MeOH/$CH_2Cl_2$+1% $NH_4OH$ gradient) to afford 254 mg of Compound 901B from which DBU was not completely separated. This material was used without further purification.

Mass calcd for formula $C_7H_7BrN_2O_3S$ 279.1, observed m/z 280.9 [M+H]$^+$.

Compounds 901 and 902 were prepared from 901C using a procedure similar to the one described in Example 6, Part B.

Example 25

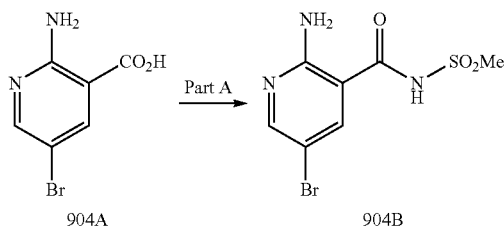 [SMILES: Nc1ncc(Br)cc1C(=O)O ; CS(=O)(=O)NC(=O)c1cc(Br)cnc1N]

Part A:

The commercially available Compound 904A was converted to Compound 904B using the procedure described in Example 901. Mass calcd for formula $C_7H_8BrN_3O_3S$ 279.1, observed m/z 294.0 [M+H]$^+$.

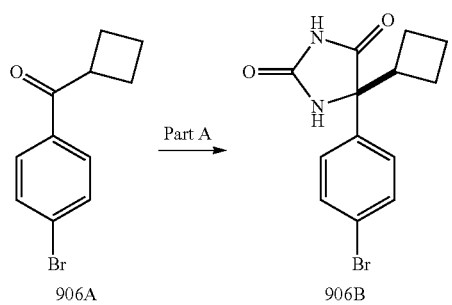 [SMILES: O=C(c1ccc(Br)cc1)C1CCC1 ; O=C1NC(=O)[C@@](c2ccc(Br)cc2)(C2CCC2)N1]

Example 26

In a pressure vessel, a mixture of Compound 906A (250 mg, 1.05 mmol), potassium cyanide (102 mg, 1.57 mmol), ammonium carbonate (303 mg, 3.15 mmol) was suspended in ammonia solution (3.5 mL, 7 N in methanol) and water (1.2 mL). The vessel was sealed and the reaction mixture was heated with stirring at 80° C. for 18 h. The reaction mixture was allowed to cool to rt. The solvents were evaporated under reduced pressure. The residue was taken up in $CH_2Cl_2$ (~10 mL) and the insoluble components were removed by filtration. The filtrate was applied directly to sgc (0-10% MeOH/ $CH_2Cl_2$+1% $NH_4OH$ gradient), and 277 mg of the desired Compound 906B was isolated (86% yield). Mass calcd for formula $C_{13}H_{13}^{79}BrN_2O_2$ 308.0, observed m/z 309.0 [M+H]$^+$.

Compounds 901B, 904B and 906B were converted to Compounds 901, 904, and 906, respectively, via the procedure given in Example 6.

Likewise, Compounds 907, 908, 909, 910, 1318, and 2312 were prepared using procedures described above.

Example 27

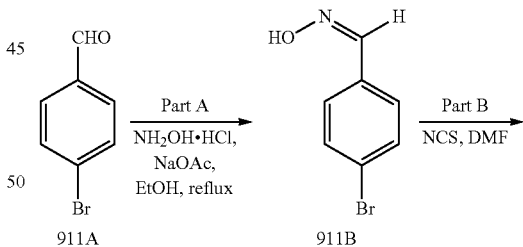

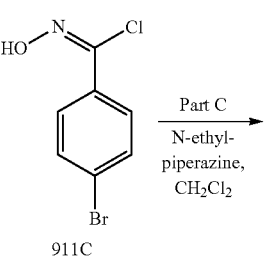

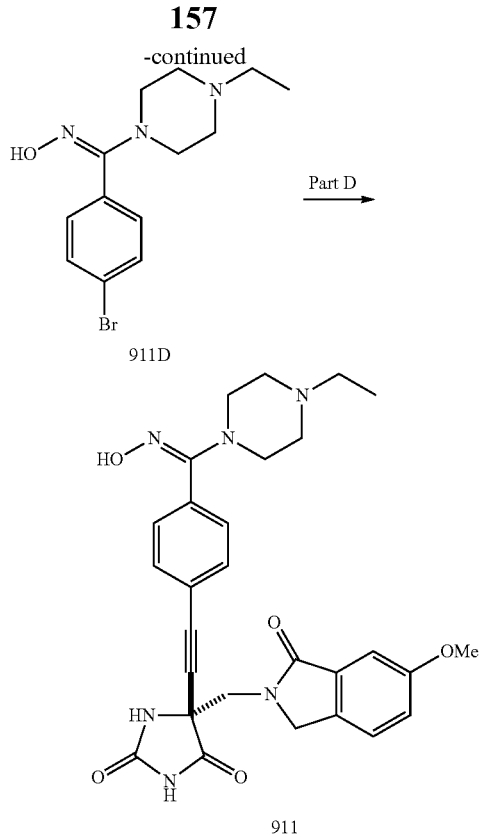

Part A

A mixture of p-bromobenzaldehyde (Compound 911A; 5.00 g, 27.0 mmol), hydroxylamine hydrochloride (3.73 g, 54.1 mmol) and anhydrous sodium acetate (4.43 g, 54.1 mmol) in absolute ethanol (100 mL) was stirred at reflux (80° C. external oil bath temperature) in a pressure vessel for 24 h. The solvent was removed under reduced pressure. The remaining solid was dissolved in $Et_2O$ (~250 mL) and the resulting solution was washed sequentially with water (2×~100 mL) and brine (~100 mL). The organic layer was dried over anhydrous $MgSO_4$, filtered and concentrated under reduced pressure to afford Compound 911B as a white solid (5.23 g, 97% yield).

Part B

Solid N-chlorosuccinimide (0.722 g, 5.39 mmol) was added to a stirred solution of oxime (Compound 9116; 1.072 g, 5.39 mmol) in dry DMF (15 mL). The reaction mixture was stirred at rt for 18 h. The reaction mixture was diluted with $Et_2O$ (150 mL) and was washed sequentially with water (3×50 mL) and brine (~50 mL). The organic layer was dried over anhydrous $MgSO_4$, filtered and concentrated under reduced pressure to give a pale yellow solid. Purification of the solid by sgc (40 g silica gel cartridge; 5-25% EtOAc-hexanes gradient) gave 973 mg (77% yield) of the desired product, Compound 911C, as a white solid.

Part C

N-Ethylpiperazine (97 mg, 0.86 mmol) was added to a solution of oximyl chloride (Compound 911C, 100 mg, 0.43 mmol) in $CH_2Cl_2$ (4 mL) and the resulting mixture was stirred overnight at rt. Evaporation of the solvent gave a residue that was purified by sgc (1-10% $MeOH/NH_3$ in $CH_2Cl_2$ gradient) to afford 112 mg (84% yield) of the desired product, Compound 911D, as an off-white solid.

Part D

Aryl bromide 911D was converted into Compound 911 by following the procedures given in Lavey, B. J. et al. PCT Appl. WO2007084451 (A1), p. 144 for Example 410, Part B.

The following compounds were prepared in a manner analogous to that described in this Example: 911, 912, 913, 914, 915, 916, 922, 923, 924, 925, 926, 927, 928, 931, 941, 942, 943, 945, 946, and 1309

Compound 911. HPLC-MS $t_R$=2.05 min ($UV_{254\,nm}$); mass calculated for formula $C_{28}H_{30}N_6O_5$ 530.2, observed LCMS m/z 531.3 $[M+H]^+$.

Compound 912. HPLC-MS $t_R$=2.36 min ($UV_{254\,nm}$); mass calculated for formula $C_{26}H_{25}N_5O_5S$ 519.2, observed LCMS m/z 520.3 $[M+H]^+$.

Compound 913. HPLC-MS $t_R$=1.88 min ($UV_{254\,nm}$); mass calculated for formula $C_{28}H_{30}N_6O_5$ 530.2, observed LCMS m/z 531.3 $[M+H]^+$.

Compound 914. HPLC-MS $t_R$=2.24 min ($UV_{254\,nm}$); mass calculated for formula $C_{25}H_{23}N_5O_5$ 473.2, observed LCMS m/z 474.3 $[M+H]^+$.

Compound 915. HPLC-MS $t_R$=2.02 min ($UV_{254\,nm}$); mass calculated for formula $C_{27}H_{28}N_6O_5$ 516.2, observed LCMS m/z 517.3 $[M+H]^+$.

Compound 916. HPLC-MS $t_R$=2.20 min ($UV_{254\,nm}$); mass calculated for formula $C_{26}H_{25}N_5O_6$ 503.2, observed LCMS m/z 504.3 $[M+H]^+$.

Compound 922. HPLC-MS $t_R$=2.07 min ($UV_{254\,nm}$); mass calculated for formula $C_{29}H_{30}N_6O_5$ 542.2, observed LCMS m/z 543.3 $[M+H]^+$.

Compound 923. HPLC-MS $t_R$=1.89 min ($UV_{254\,nm}$); mass calculated for formula $C_{27}H_{29}N_7O_5$ 531.2, observed LCMS m/z 532.3 $[M+H]^+$.

Compound 924. HPLC-MS $t_R$=1.77 min ($UV_{254\,nm}$); mass calculated for formula $C_{27}H_{29}N_7O_5$ 531.2, observed LCMS m/z 532.3 $[M+H]^+$.

Compound 925. HPLC-MS $t_R$=2.29 min ($UV_{254\,nm}$); mass calculated for formula $C_{30}H_{34}N_6O_5$ 558.2, observed LCMS m/z 559.3 $[M+H]^+$.

Compound 926. HPLC-MS $t_R$=2.29 min ($UV_{254\,nm}$); mass calculated for formula $C_{32}H_{36}N_6O_5$ 584.2, observed LCMS m/z 585.3 $[M+H]^+$.

Compound 927. HPLC-MS $t_R$=2.44 min ($UV_{254\,nm}$); mass calculated for formula $C_{33}H_{38}N_6O_5$ 598.3, observed LCMS m/z 599.3 $[M+H]^+$.

Compound 928. HPLC-MS $t_R$=2.82 min ($UV_{254\,nm}$); mass calculated for formula $C_{32}H_{30}N_6O_5$ 578.2, observed LCMS m/z 579.3 $[M+H]^+$.

Compound 931. HPLC-MS $t_R$=1.90 min ($UV_{254\,nm}$); mass calculated for formula $C_{30}H_{34}N_6O_5$ 558.2, observed LCMS m/z 559.3 $[M+H]^+$.

Compound 941. HPLC-MS $t_R$=2.22 min ($UV_{254\,nm}$); mass calculated for formula $C_{26}H_{25}N_5O_6$ 503.2, observed LCMS m/z 504.3 $[M+H]^+$.

Compound 942. HPLC-MS $t_R$=2.36 min ($UV_{254\,nm}$); mass calculated for formula $C_{26}H_{25}N_5O_5$ 487.2, observed LCMS m/z 488.3 $[M+H]^+$.

Compound 943. HPLC-MS $t_R$=2.01 min ($UV_{254\,nm}$); mass calculated for formula $C_{27}H_{28}N_6O_5$ 516.2, observed LCMS m/z 517.3 $[M+H]^+$.

Compound 945. HPLC-MS $t_R$=2.20 min ($UV_{254\,nm}$); mass calculated for formula $C_{27}H_{25}N_5O_6$ 515.2, observed LCMS m/z 516.3 $[M+H]^+$.

Compound 946. HPLC-MS $t_R$=2.42 min ($UV_{254\,nm}$); mass calculated for formula $C_{27}H_{27}N_5O_5$ 501.2, observed LCMS m/z 502.3 $[M+H]^+$.

Compounds 2293 and 2294 were prepared using methods similar to those described in Example 27 and Example 6, Part B.

Example 28

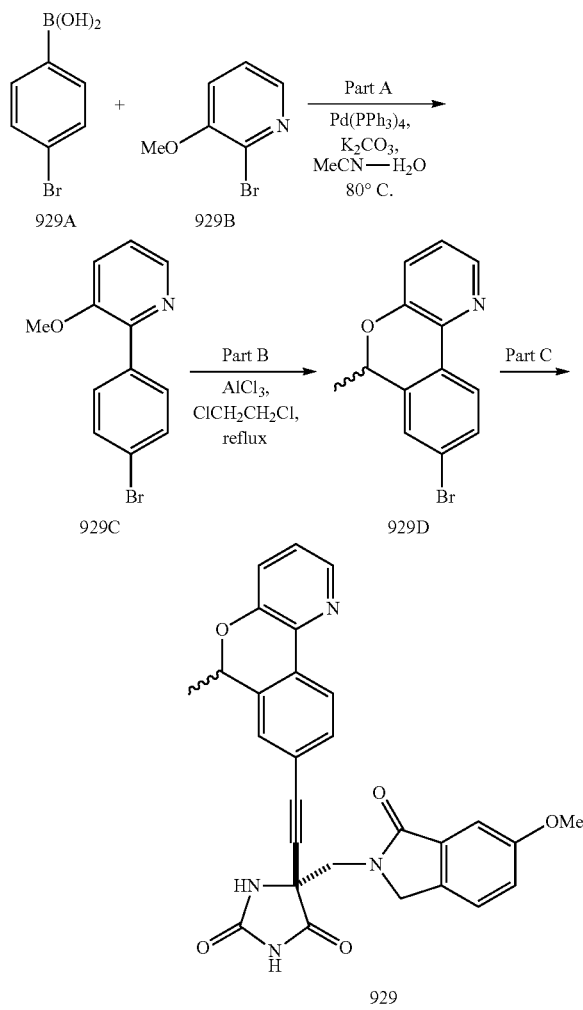

Part A

To a sealed tube containing boronic acid 929A (427 mg, 2.12 mmol), bromopyridine 929B (200 mg, 1.06 mmol) and Pd(PPh$_3$)$_4$ (12.3 mg, 0.0106 mmol) was added dry acetonitrile (5 mL) and 1 M aq. K$_2$CO$_3$ solution (5 mL). The reaction was allowed to proceed at 80° C. for 3 d. The reaction mixture was filtered through a Celite® pad. The aqueous layer was separated and extracted with EtOAc (20 mL). The combined organic phases were washed with brine (~10 mL), dried over anhydrous MgSO$_4$, filtered and concentrated under reduced pressure. The residue was purified by sgc (0-50% EtOAc-hexanes gradient) to afford 70 mg (25% yield) of desired product 929C.

Part B

A solution of 929C (70 mg, 0.27 mmol) in 1,2-dichloroethane (5 mL) was treated with anhydrous aluminum chloride (88 mg, 0.66 mmol) and the resulting solution was heated overnight at reflux. The solvent was removed under reduced pressure. The residue was partitioned between EtOAc (25 mL) and water (25 mL). The aqueous layer was extracted further with EtOAc (3×~25 mL). The combined organic extracts were washed with brine (~25 mL), dried over anhydrous MgSO$_4$, filtered, and concentrated under reduced pressure. The resulting crude product was purified by sgc (0-50% EtOAc-hexanes gradient) to give a 47 mg of a product that was identified to be 929D (64% yield).

Part C

Aryl bromide 929D was converted into Compound 929 by following the procedures given in Lavey, B. J. et al. PCT Appl. WO2007084451 (A1), p. 144 for Example 410, Part B.

Compound 1010 was prepared from compound 929C using procedures similar to Example 6, Part B.

Compound 934 was prepared using procedures similar to those described in Example 28 and Example 6, Part B.

Example 29

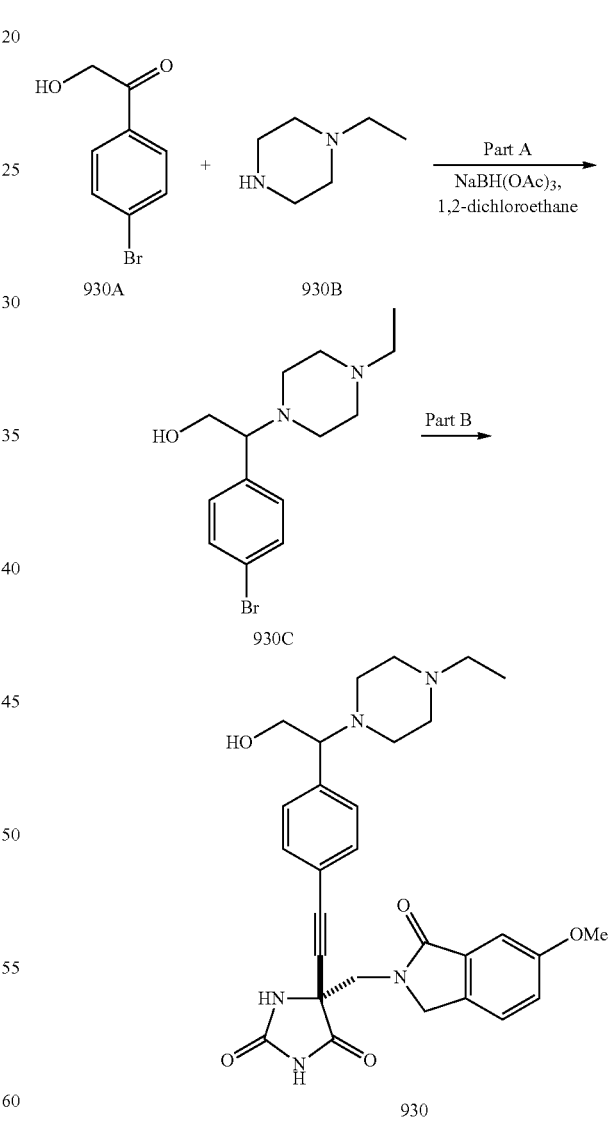

Part A

The ketone 930A (500 mg, 2.33 mmol) and amine 930B (398 mg, 3.48 mmol) was stirred in 1,2-dichloroethane solvent (25 mL) at rt for 4 h. Solid NaBH(OAc)$_3$ (1.97 g, 3.30 mmol) was added and the reaction was allowed to proceed at rt for 3 d. Upon completion of the reaction, the reaction mixture was diluted with DCM (50 mL) and washed sequentially with 10% aq NaOH (~25 mL), water (~25 mL) and brine (~25 mL). The organic layer was dried over anhydrous MgSO$_4$, filtered, and concentrated under reduced pressure. The resulting crude product was purified by sgc (1-10% MeOH/NH$_3$ in CH$_2$Cl$_2$) to give 345 mg (58% yield) of Compound 930C as an oil.

Part B

Aryl bromide 930C was converted into Compound 930 by following the procedures given in Lavey, B. J. et al. PCT Appl. WO2007084451 (A1), p. 144 for Example 410, Part B.

Example 30

(0.017 mL, 39.3 mg, 0.28 mmol) was added. The reaction mixture was allowed to warm to rt and was stirred overnight at rt. The reaction mixture was diluted with EtOAc (50 mL) and was washed sequentially with water (3×25 mL) and brine (25 mL). The organic layer was dried over anhydrous MgSO$_4$, filtered, and concentrated under reduced pressure. The resulting crude product was purified by PTLC (40% EtOAc-hexanes) to afford 66 mg (80% yield) of Compound 932B as a colorless oil.

Part B

Aryl bromide 932B was converted into Compound 932 by following the procedures given in Lavey, B. J. et al. PCT Appl. WO2007084451 (A1), O. 144 for Example 410, Part B.

Example 31

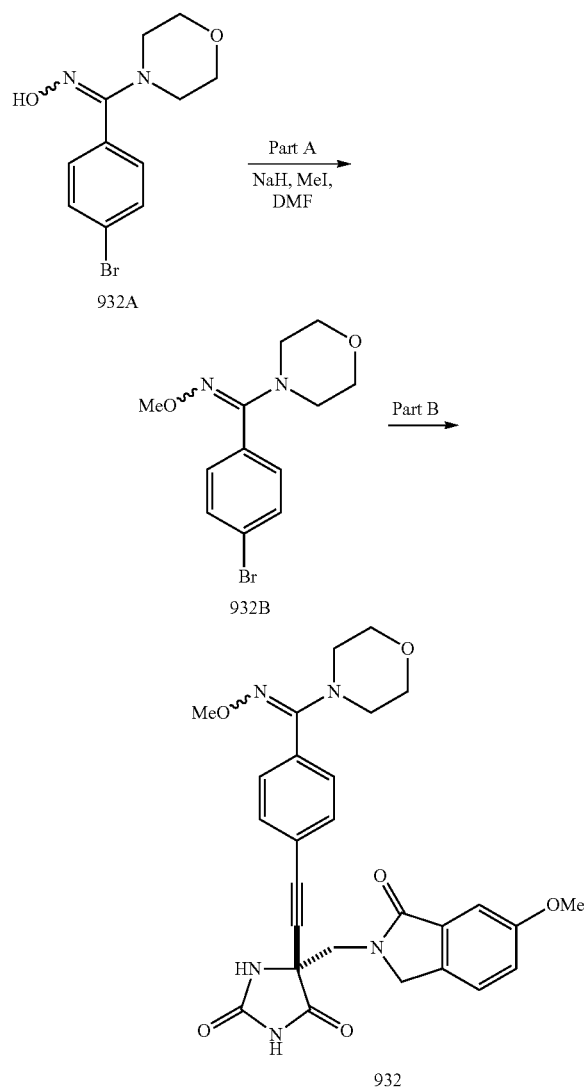

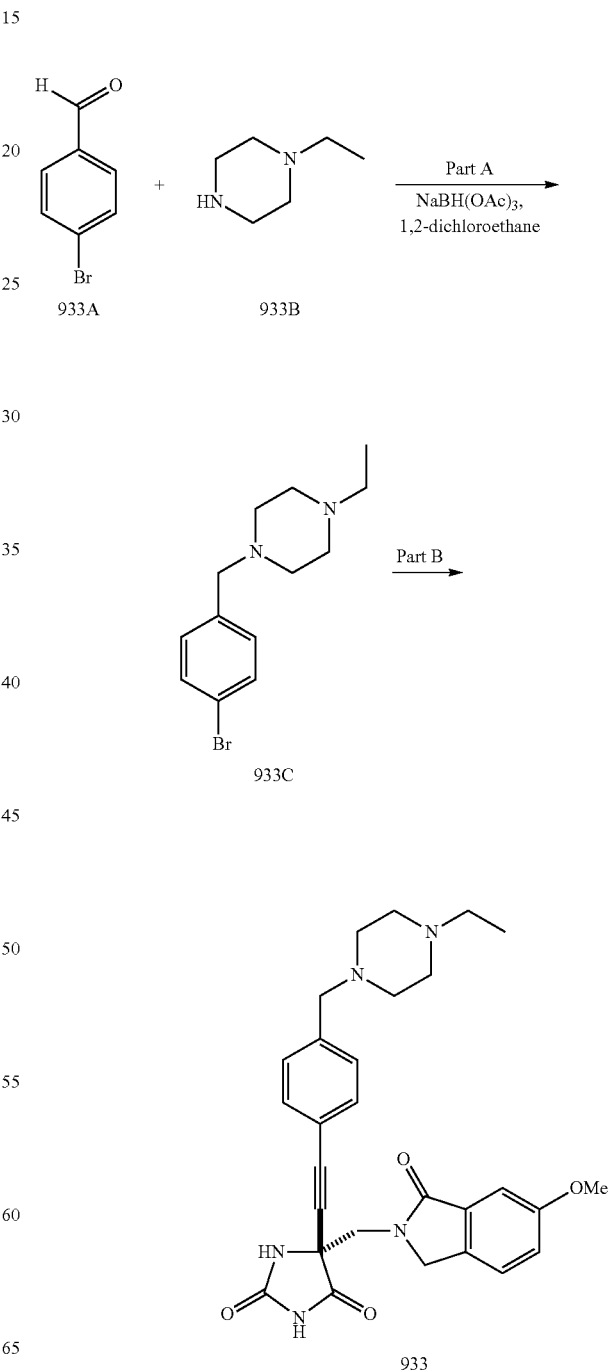

Part A

The oxime (Compound 932A) was prepared via the procedure outlined for the preparation of Compound 911D, given in Example 27. A solution of Compound 932A (79 mg, 0.28 mmol) in dry DMF (0.55 mL) was cooled to 0° C. and NaH (13.3 mg, 60% dispersion in oil; 0.33 mmol) was added. After the reaction was stirred at 0° C. for 30 min, iodomethane

Part A

Compound 933C was prepared via the procedure outlined for the preparation of Compound 930C, given in Example 29.

Part B

Aryl bromide 933C was converted into Compound 933 by following the procedures given in Lavey, B. J. et al. PCT Appl. WO2007084451 (A1), p. 144 for Example 410, Part B.

Example 32

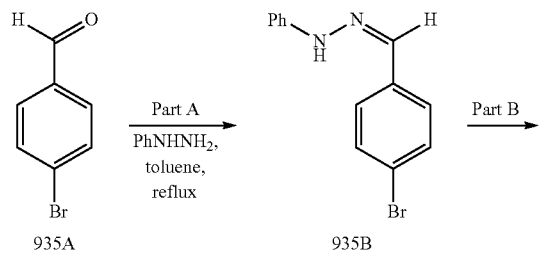

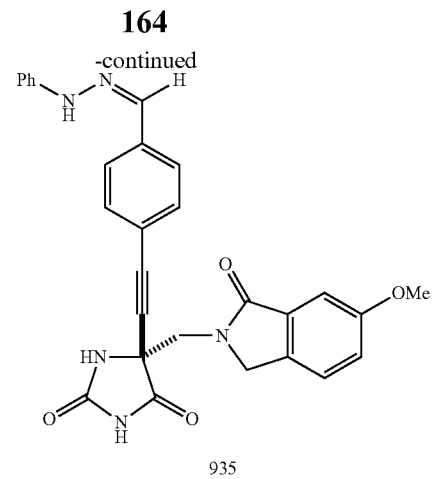

Part A

A solution of phenylhydrazine (4.0 mL, 4.4 g, 41 mmol) in toluene (13 mL) was added to a stirred solution of Compound 935A (5.0 g, 27 mmol) in toluene (27 mL). The reaction mixture was heated at reflux for 3 h, during which azeotropic removal of water was accomplished using a Dean-Stark apparatus. The reaction mixture was allowed to cool to rt and was concentrated under reduced pressure to afford a crude residue. Purification of the residue by sgc (Isco, 0-30% EtOAc-hexanes gradient) gave 3.15 g of Compound 935B (36% yield).

Part B

Aryl bromide 935B was converted into Compound 935 by following the procedures given in Lavey, B. J. et al. PCT Appl. WO2007084451 (A1), p. 144 for Example 410, Part B.

Example 33

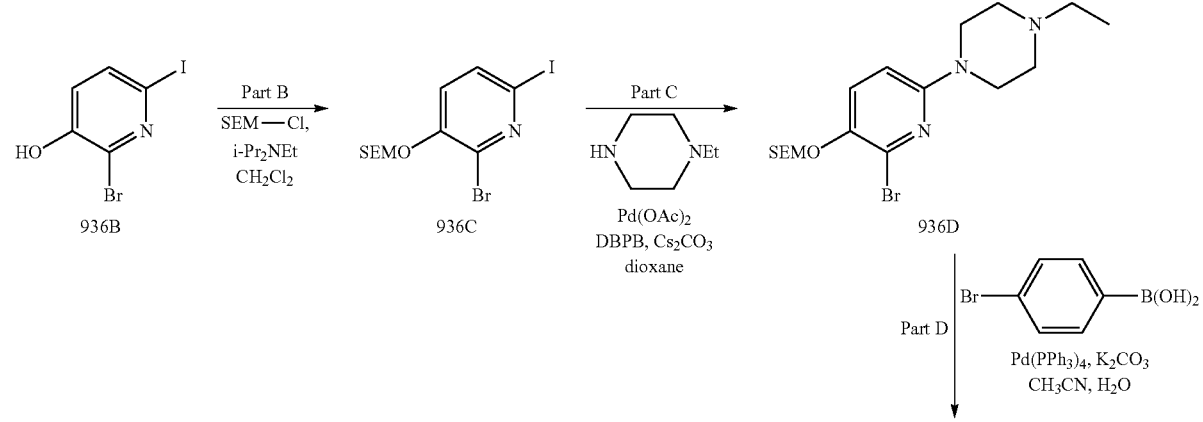

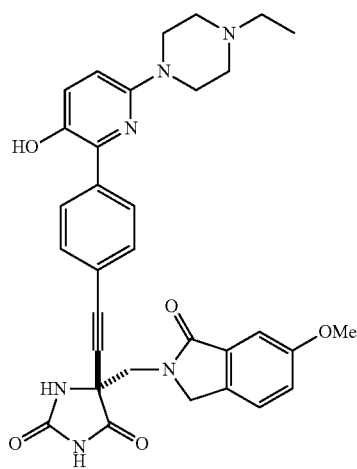

936

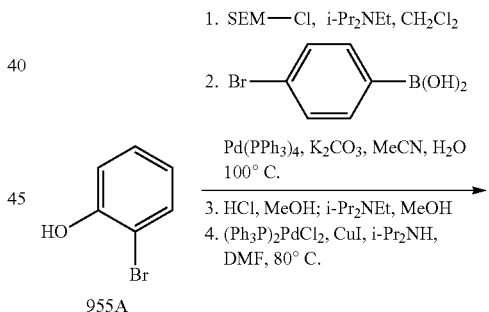

936F ← Part E, HCl, MeOH; i-Pr₂NEt, MeOH — 936E

Part A

Compound 936A (5.00 g, 28.7 mmol) and potassium carbonate (7.90 g, 57.5 mmol) were dissolved in water (66 mL) and iodine (7.51 g, 29.6 mmol) was added. The reaction was allowed to proceed at rt for 3 d. Excess iodine was quenched by addition of solid sodium bisulfite. The pH of the solution was adjusted to ~5-6 using glacial acetic acid. A solid formed during the process and was collected by filtration and dried in vacuo. The desired product, Compound 936B, was obtained as a light gray solid (8.25 g, 96% yield).

Part B

SEM-Cl (5.8 mL, 5.5 g, 33 mmol) was added to a stirred solution of Compound 936B (8.25 g, 28 mmol) and diisopropylethylamine (7.2 mL, 5.3 g, 41 mmol) in $CH_2Cl_2$ at 0° C. The solution was allowed to warm to rt and was stirred overnight at it Volatile components were removed by rotary evaporation under reduced pressure, and the resulting oily residue was purified by sgc (0-50% EtOAc-hexanes gradient). The desired product, Compound 936C, was obtained as a pale yellow oil (9.25 g, 78% yield).

Part C

A Schlenk flask containing an admixture of Compound 936C (2.1 g, 4.9 mmol), N-ethylpiperazine (0.62 mL, 560 mg, 4.9 mmol), $Pd(OAc)_2$ (240 mg, 0.36 mmol), 2-(di-t-butylphosphino)biphenyl (106 mg, 0.36 mmol), and $Cs_2CO_3$ (318 mg, 10 mmol) was sealed, evacuated and placed under nitrogen atmosphere. Dry, degassed dioxane (12.5 mL) was added and the reaction vessel was lowered into a preheated 80° C. oil bath. The reaction was allowed to proceed at 80° C. for 3 d. The reaction mixture was filtered through a pad of Celite® and the filtrate was concentrated under reduced pressure. The resulting solid was redissolved in EtOAc (400 mL), and the solution was washed sequentially with water (2×100 mL) and brine (~100 mL), dried over anhydrous $MgSO_4$, filtered, and concentrated under reduced pressure. The resulting crude product was purified by sgc (0-10% $MeOH/NH_3$—$CH_2Cl_2$ gradient). The desired product, Compound 936D, was obtained as an oil (218 mg, 10% yield).

Part D

Compound 936E was prepared from Compound 936D following the procedure described in Example 28, Part A.

Part E

HCl solution (1.6 mL, 4 M in dioxane; 6.4 mmol) was added to a solution of Compound 936E (105 mg, 0.21 mmol) in methanol (4 mL) in a sealed tube. The reaction mixture was stirred at 90° C. (external oil bath temperature) for 5 h. Volatile components were removed by rotary evaporation under reduced pressure. The residue was redissolved in methanol (4 mL). Diisopropylethylamine (2 mL, 1.5 g, 11 mmol) was added and the reaction mixture was stirred overnight at rt. The solvent was evaporated and the residue was purified by sgc (0-10% $MeOH/NH_3$—$CH_2Cl_2$ gradient). The desired product, Compound 936F, was obtained as a brown oil (77 mg, 100% yield).

Part B

Compound 936F was converted into Compound 936 by following the procedures given in Lavey, B. J. et al. PCT Appl. WO2007084451 (A1), p. 144 for Example 410, Part B.

Example 34

1. SEM—Cl, i-Pr₂NEt, CH₂Cl₂

2. Br—⟨phenyl⟩—B(OH)₂

Pd(PPh₃)₄, K₂CO₃, MeCN, H₂O
   100° C.

3. HCl, MeOH; i-Pr₂NEt, MeOH
4. (Ph₃P)₂PdCl₂, CuI, i-Pr₂NH, DMF, 80° C.

955A

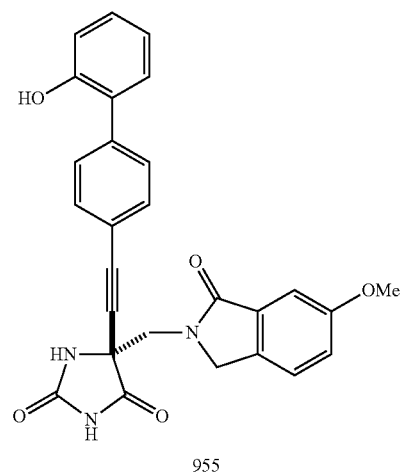

955

Compound 955 was prepared by a combination of procedures given in Example 33, Parts B, D, E and F.

Example 35

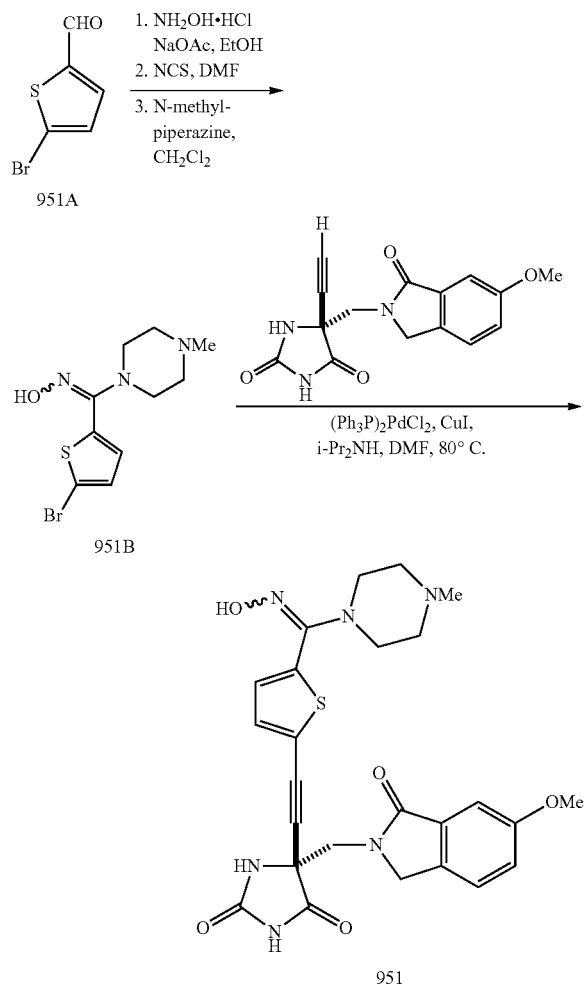

Compound 951 was prepared from commercially available Compound 951A by a multistep procedure analogous to that given in Example 27.

Example 36

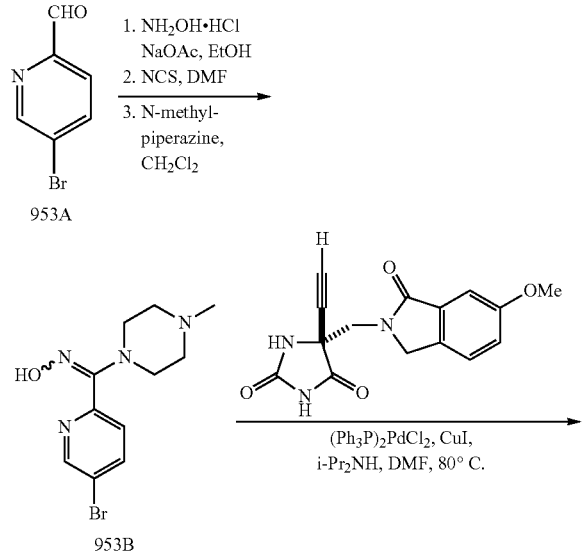

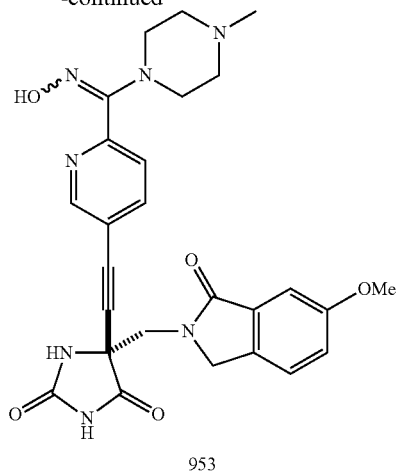

Compound 953 was prepared from commercially available Compound 953A by a multistep sequence analogous to those described in Examples 27 and 35.

Compounds 952 and 954 were prepared from Compound 951A and 953A, respectively, following procedures analogous to those in Examples 27, 35 and 36.

Compound 951. HPLC-MS $t_R$=2.14 min (UV$_{254\,nm}$); mass calculated for formula $C_{25}H_{26}N_6O_5S$ 522.2, observed LCMS m/z 523.3 $[M+H]^+$.

Compound 952. HPLC-MS $t_R$=2.84 min (UV$_{254\,nm}$); mass calculated for formula $C_{24}H_{23}N_5O_6S$ 509.1, observed LCMS m/z 510.3 $[M+H]^+$.

Compound 953. HPLC-MS $t_R$=1.83 min (UV$_{254\,nm}$); mass calculated for formula $C_{26}H_{27}N_7O_5$ 517.2, observed LCMS m/z 518.3 $[M+H]^+$.

Compound 954. HPLC-MS $t_R$=1.91 min (UV$_{254\,nm}$); mass calculated for formula $C_{27}H_{29}N_7O_5$ 531.2, observed LCMS m/z 532.3 $[M+H]^+$.

Example 37

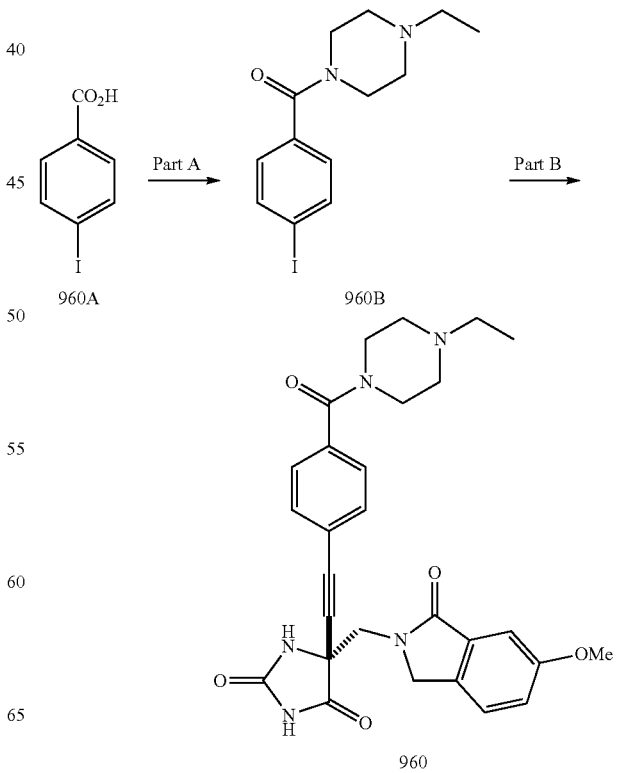

Part A:

N-Ethylpiperazine hydrochloride (0.234 mL, 211 mg, 1.85 mmol) and triethylamine (0.256 mL, 187 mg, 1.85 mmol) were added sequentially to a stirred solution of 4-iodobenzoic acid (382 mg, 1.54 mmol) and HATU (702 mg, 1.85 mmol) in dry DMF (3.0 mL). The reaction mixture was stirred at rt for 18 h. The reaction mixture was diluted with EtOAc (50 mL) and washed sequentially with water (50 mL) and brine (50 mL). The organic layer was dried over anhydrous MgSO$_4$, filtered, and concentrated to give an orange oil. Excess DMF was removed by co-evaporation with toluene (2×20 mL). The crude product was purified by sgc (0.5-9% MeOH/CH$_2$Cl$_2$) to afford 370 mg of the desired product 960B as a beige solid (70% yield). Mass calcd for formula $C_{13}H_{17}IN_2O$ 344.0, observed m/z 344.9 [M+H]$^+$.

Part B:

Compound 960B was converted to Compound 960 following the procedure of Example 6. HPLC-MS $t_R$=2.05 min (UV$_{254\ nm}$); mass calculated for formula $C_{31}H_{23}N_5O_5$ 515.2, observed LCMS m/z 516.3 [M+H]$^+$.

Example 38

Part B:

Compound 961A was converted to Compound 961 following the procedure of Example 6. HPLC-MS $t_R$=2.07 min (UV$_{254\ nm}$), mass calculated for formula $C_{29}H_{29}N_5O_5$ 527.2, observed LCMS m/z 528.3 [M+H]$^+$.

Example 39

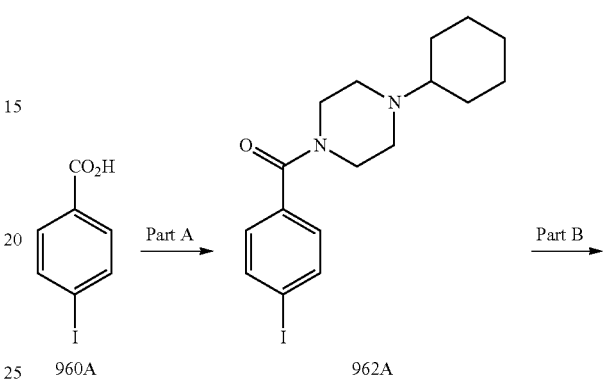

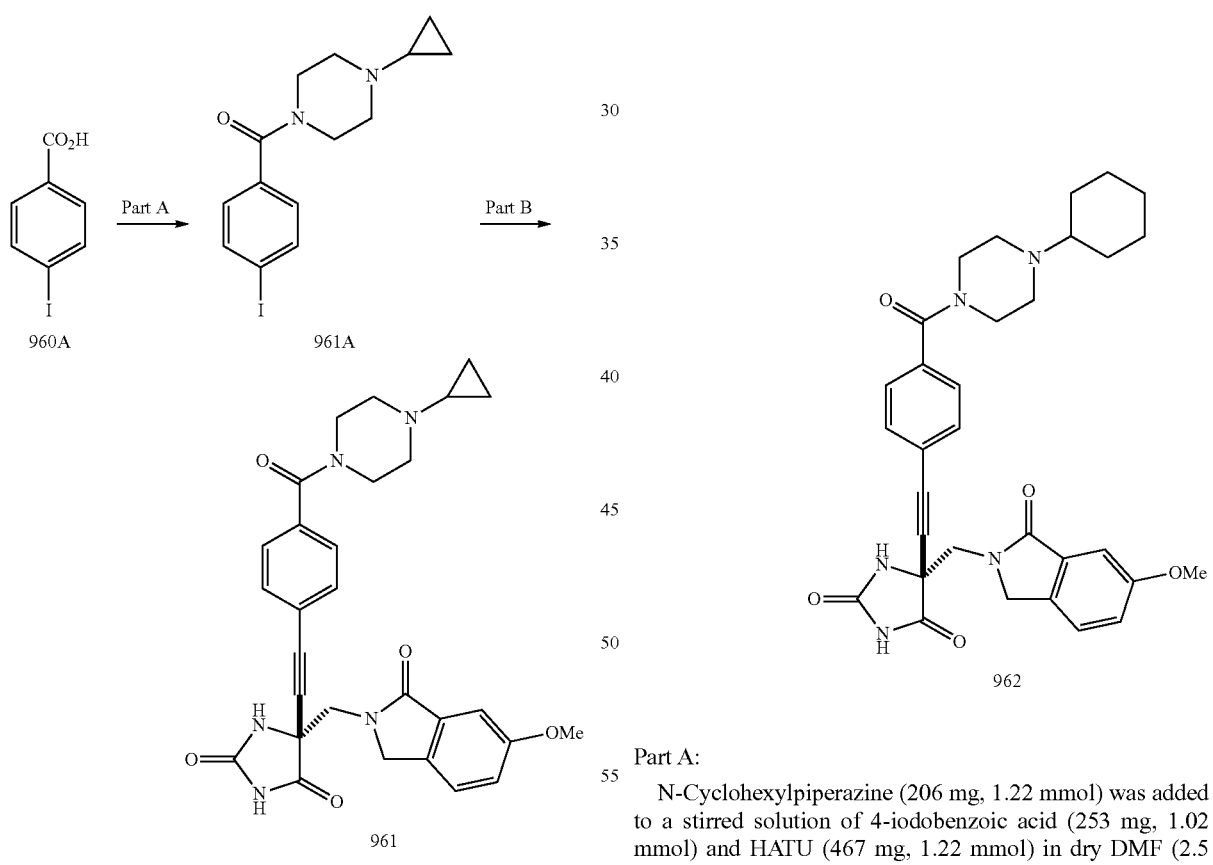

Part A:

N-Cyclohexylpiperazine (206 mg, 1.22 mmol) was added to a stirred solution of 4-iodobenzoic acid (253 mg, 1.02 mmol) and HATU (467 mg, 1.22 mmol) in dry DMF (2.5 mL). The reaction mixture was stirred at rt for 18 h. Work-up and purification was carried out following the procedure described in Example 37, Part A. The desired product 962A was obtained in 184 mg, 45% yield. $^1$H NMR (500 MHz, CDCl$_3$) δ=7.79 (d, J=8.5 Hz, 2H), 7.18 (d, J=8.5 Hz, 2H), 3.80-3.96 (bs, 2H), 3.46-3.64 (bs, 2H), 2.65-2.91 (m, 4H), 2.52-2.62 (m, 1H), 1.79-1.96 (m, 4H), 1.63-1.71 (m, 1H), 1.20-1.33 (m, 4H), 1.05-1.18 (m, 1H). Mass calcd for formula $C_{17}H_{23}IN_2O$ 398.1, observed m/z 399.3 [M+H]$^+$.

Part A:

The iodobenzamide 961A was prepared from 4-iodobenzoic acid 960A following the procedure given in Example 960, Part A. $^1$H NMR (500 MHz, CDCl$_3$) δ=7.73 (d, J=8.5 Hz, 2H), 7.12 (d, J=8.5 Hz, 2H), 3.70 (bs, 2H), 3.34 (bs, 2H), 2.66 (bs, 2H), 2.52 (bs, 2H), 0.43-0.48 (m, 2H), 0.38-0.43 (m, 2H). Mass calcd for formula $C_{14}H_{17}IN_2O$ 356.04, observed m/z 357.00 [M+H]$^+$.

Part B:

Compound 962A was converted to Compound 962 following the procedure of Example 6. HPLC-MS $t_R$=2.41 min ($U_{254\ nm}$); mass calculated for formula $C_{32}H_{35}N_5O_5$ 569.3, observed LCMS m/z 570.3 [M+H]+·

Example 40

Part A:

Compound 963A was prepared from 4-iodobenzoic acid 960A following the procedure given in Example 39. Mass calcd for formula $C_{17}H_{23}IN_2O$ 398.1, observed m/z 399.3 [M+H]+·

Part B:

Compound 963A was converted to Compound 963 following the procedure of Example 6. HPLC-MS $t_R$=2.15 min ($UV_{254\ nm}$); mass calculated for formula $C_{32}H_{35}N_5O_5$ 569.3, observed LCMS m/z 570.3 [M+H]+·

Example 41

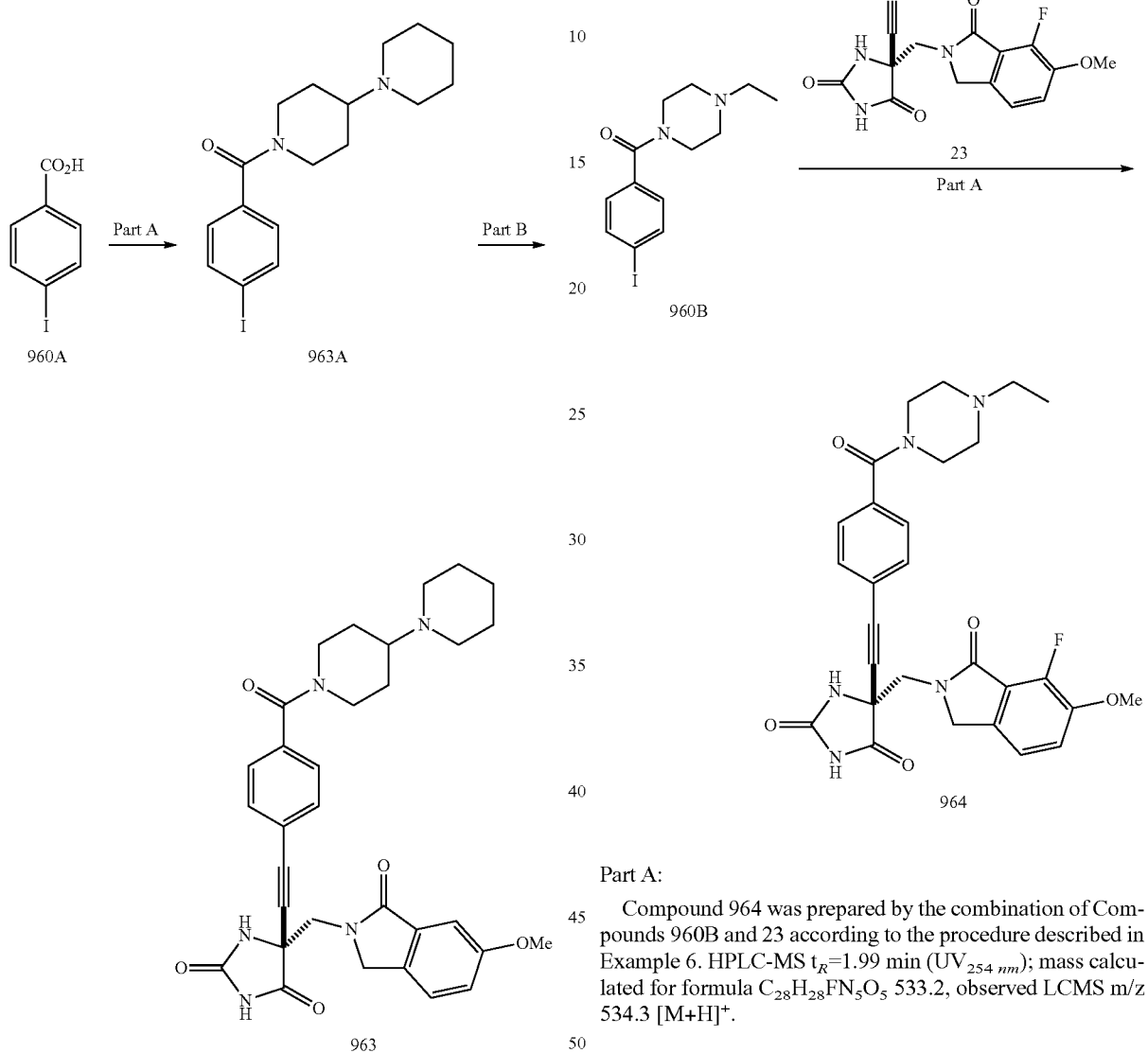

Part A:

Compound 964 was prepared by the combination of Compounds 960B and 23 according to the procedure described in Example 6. HPLC-MS $t_R$=1.99 min ($UV_{254\ nm}$); mass calculated for formula $C_{28}H_{28}FN_5O_5$ 533.2, observed LCMS m/z 534.3 [M+H]+.

Example 42

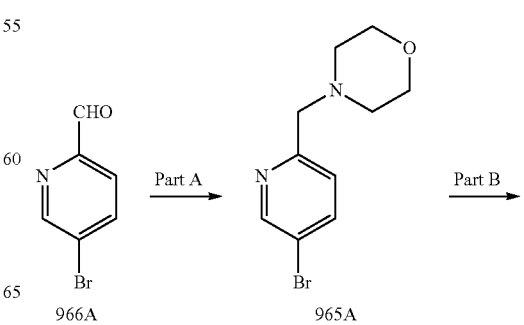

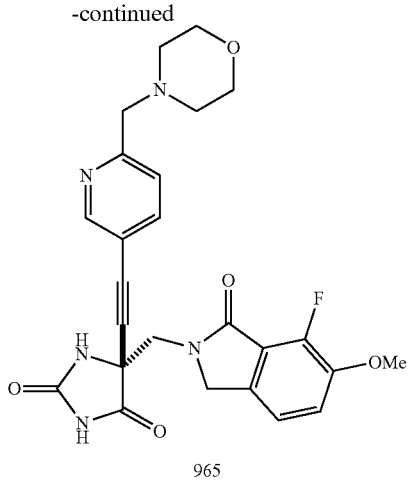

965

Part A:

Compound 965A was prepared from aldehyde 966A following the procedure described in Example 943. $^1$H NMR (500 MHz, CDCl$_3$) δ=8.59 (d, J=2.5 Hz, 1H), 7.75 (dd, J=8.5, 2.5 Hz, 1H), 7.31 (d, J=8.5 Hz, 1H), 3.68-3.74 (m, 4H), 2.43-2.51 (m, 4H). Mass calcd for formula C$_{10}$H$_{13}$$^{79}$BrN$_2$O 256.0, observed m/z 257.1 [M+H]$^+$.

Part B:

Compound 965A was converted to Compound 965 following the procedure of Example 6. HPLC-MS t$_R$=2.08 min (UV$_{254\ nm}$); mass calculated for formula C$_{25}$H$_{24}$FN$_5$O$_5$ 493.2, observed LCMS m/z 494.3 [M+H]$^+$.

Example 43

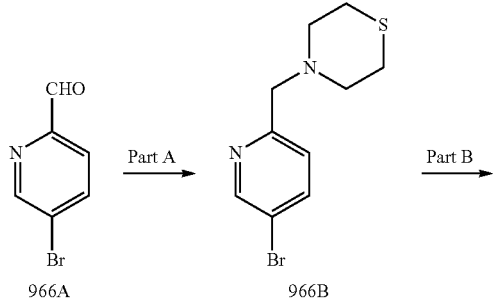

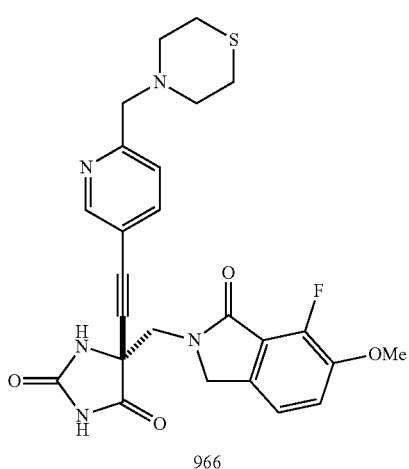

966

Part A:

Thiomorpholine (0.161 mL, 166 mg, 1.61 mmol) was added to a stirred solution of aldehyde 966A (200 mg, 1.08 mmol) in 1,2-dichloroethane (5.5 mL). The resulting solution was stirred at rt for 2 h. Solid sodium triacetoxyborohydride (342 mg, 1.61 mmol) was added in portions. The reaction was allowed to proceed at rt for 24 h. The reaction mixture was diluted with DCM (~50 mL) and was washed sequentially with water (~50 mL) and brine (~50 mL). The organic layer was dried over anhydrous MgSO$_4$, filtered and concentrated under reduced pressure to afford an orange oil. Purification by flash sgc (12 g Teledyne-ISCO RediSep® cartridge; 1-6% MeOH-DCM gradient) gave 160 mg (55% yield) of the desired product 966B. $^1$H NMR (500 MHz, CDCl$_3$) δ=8.58 (d, J=2.5 Hz, 1H), 7.75 (dd, J=8.5, 2.5 Hz, 1H), 7.29 (d, J=8.5 Hz, 1H), 3.59 (s, 2H), 2.72-2.74 (m, 4H), 2.67-2.68 (m, 4H). Mass calcd for formula C$_{10}$H$_{13}$$^{79}$BrN$_2$S 272.00, observed m/z 273.02 [M+H]$^+$.

Part B:

Compound 966B was converted to Compound 966 following the procedure of Example 6. HPLC-MS t$_R$=2.23 min (UV$_{254\ nm}$); mass calculated for formula C$_{25}$H$_{24}$FN$_5$O$_4$S 509.2, observed LCMS m/z 510.3 [M+H]$^+$.

Example 44

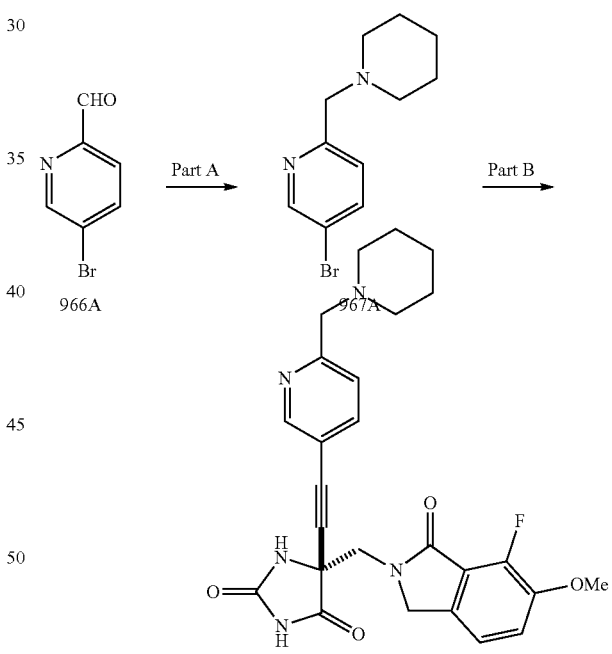

967

Part A:

The aryl bromide 967A was prepared from aldehyde 966A following the procedure of Example 43. $^1$H NMR (500 MHz, CDCl$_3$) δ=8.58 (d, J=2.5 Hz, 1H), 7.73 (dd, J=8.2, 2.5 Hz, 1H), 7.32 (d, J=8.2 Hz, 1H), 3.54 (s, 2H), 2.40 (bs, 4H), 1.53-1.64 (m, 4H), 1.37-1.48 (m, 2H). Mass calcd for formula C$_{11}$H$_{15}$$^{79}$BrN$_2$ 254.04, observed m/z 255.05 [M+H]$^+$.

Part B:

Compound 967A was converted to Compound 967 following the procedure of Example 6. HPLC-MS t$_R$=2.13 min (UV$_{254\ nm}$); mass calculated for formula C$_{26}$H$_{26}$FN$_5$O$_4$ 491.2, observed LCMS m/z 492.3 [M+H]$^+$

Example 45

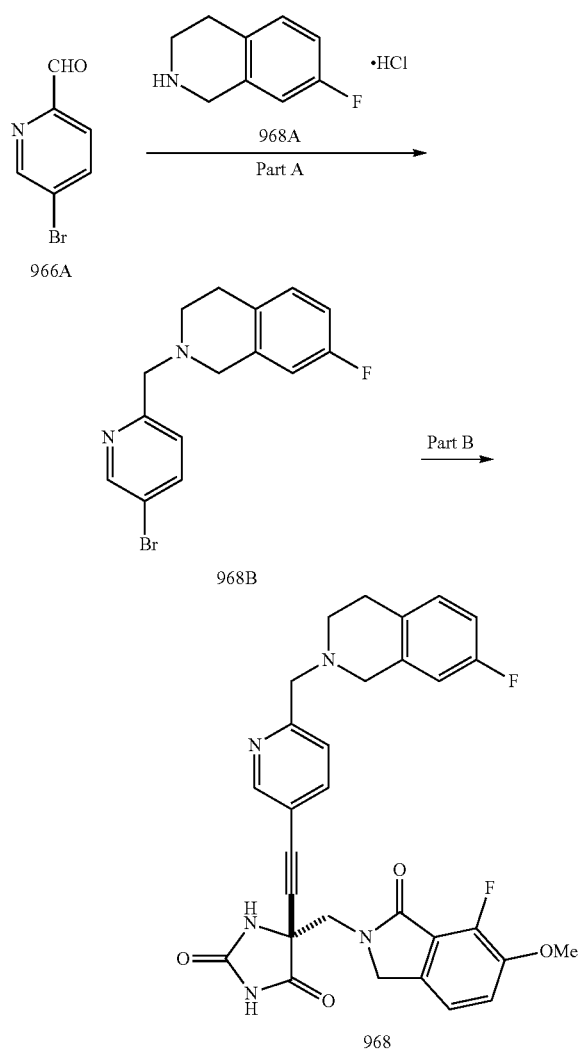

Part A:

A solid admixture of aldehyde 966A (200 mg, 1.08 mmol) and amine hydrochloride salt 968A (302 mg, 1.61 mmol) was suspended in 1,2-dichloroethane (5.5 mL). Triethylamine (0.149 mL, 109 mg, 1.61 mmol) was added. The resulting solution was stirred at rt for 2 h. Solid sodium triacetoxyborohydride (342 mg, 1.61 mmol) was added in portions. The reaction was allowed to proceed at rt for 24 h. The reaction mixture was diluted with DCM (~50 mL) and was washed sequentially with water (~50 mL) and brine (~50 mL). The organic layer was dried over anhydrous MgSO$_4$, filtered and concentrated under reduced pressure to afford an orange oil. Purification by flash sgc (12 g Teledyne-ISCO RediSep® cartridge; 1-6% MeOH-DCM gradient) gave 228 mg (66% yield) of the desired product 968B. $^1$H NMR (500 MHz, CDCl$_3$) δ=8.58 (d, J=2.5 Hz, 1H), 7.75 (dd, J=8.5, 2.5 Hz, 1H), 7.29 (d, J=8.5 Hz, 1H), 3.59 (s, 2H), 2.72-2.74 (m, 4H), 2.67-2.68 (m, 4H). Mass calcd for formula C$_{10}$H$_{13}$$^{79}$BrN$_2$S 272.00, observed m/z 273.02 [M+H]$^+$.

Part B:

Compound 968B was converted to Compound 968 following the procedure of Example 6. HPLC-MS t$_R$=2.53 min (UV$_{254\ nm}$); mass calculated for formula C$_{30}$H$_{25}$F$_2$N$_5$O$_4$ 557.2, observed LCMS m/z 558.3 [M+H]$^+$

Example 46

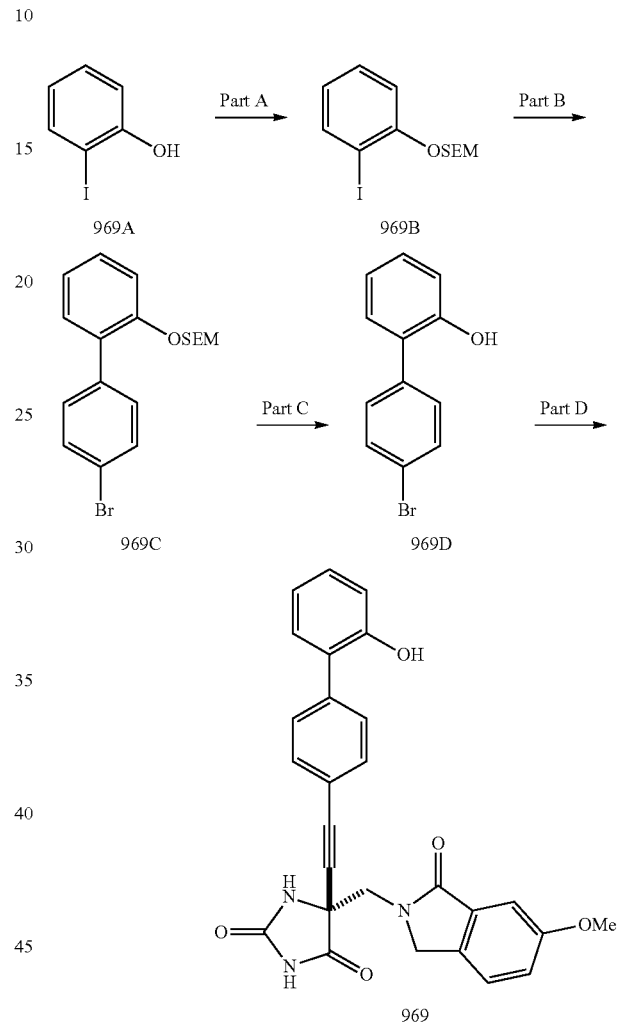

Part A:

SEM-Cl (0.97 mL, 0.91 g, 5.5 mmol) was added to a stirred, ice-cooled solution of 2-iodophenol 969A (1.0 g, 4.6 mmol) and DIPEA (1.2 mL, 0.88 g, 6.8 mmol) in dichloromethane (23 mL). The solution was allowed to warm to rt and was stirred overnight at rt. The solvent was evaporated and the crude residue was purified directly by sgc (0-50% EtOAc-hexanes gradient) to give 1.59 g of the desired product 969B as a clear colorless oil (100% yield).

Part B:

Compound 969B (443 mg, 1.26 mmol), 4-bromobenzeneboronic acid (242 mg, 1.20 mmol) and (Ph$_3$P)$_4$Pd (140 mg, 0.12 mmol) were admixed in a microwave tube. The tube was stoppered, evacuated and refilled with nitrogen. Acetonitrile (2.4 mL) and 1 M aq. K$_2$CO$_3$ solution (2.4 mL) were added sequentially and the reaction tube was lowered into a preheated 80° C. oil bath. The reaction was allowed to proceed with stirring at 80° C. for 18 h. The reaction mixture was then allowed to cool. The aqueous layer was separated and extracted with EtOAc (2x~20 mL). The combined organic layers were washed with brine (~20 mL), dried over anhydrous $MgSO_4$. Evaporation of solvent gave a brown residue that was purified by sgc (0-20% EtOAc-hexanes gradient) to give 210 mg of the desired compound 969C as a clear, colorless oil (46% yield).

Part C:

In a pressure vessel, a solution of Compound 969C (126 mg, 0.33 mmol) in MeOH (5 mL) was treated with hydrogen chloride solution (1.6 mL, 4 M in dioxane). The vessel was stoppered and the reaction mixture was heated with stirring in a 90° C. oil bath for 24 h. The solvents were evaporated and the residue was re-dissolved in MeOH (5 mL). DIPEA (12 mL, 859 mg, 6.6 mmol) was added and the reaction mixture was stirred for 3 h. The solvent was removed by rotary evaporation and the residue was purified by sgc (0-30% EtOAc-hexanes gradient) to afford 75 mg of the desired alcohol 969D as a clear, colorless oil (90% yield).

Part D:

Compound 969D was converted to Compound 969 following the procedure of Example 6. HPLC-MS $t_R$=3.82 min ($UV_{254\,nm}$); mass calculated for formula $C_{27}H_{21}N_3O_5$ 467.2, observed LCMS m/z 468.3 $[M+H]^+$.

Example 47

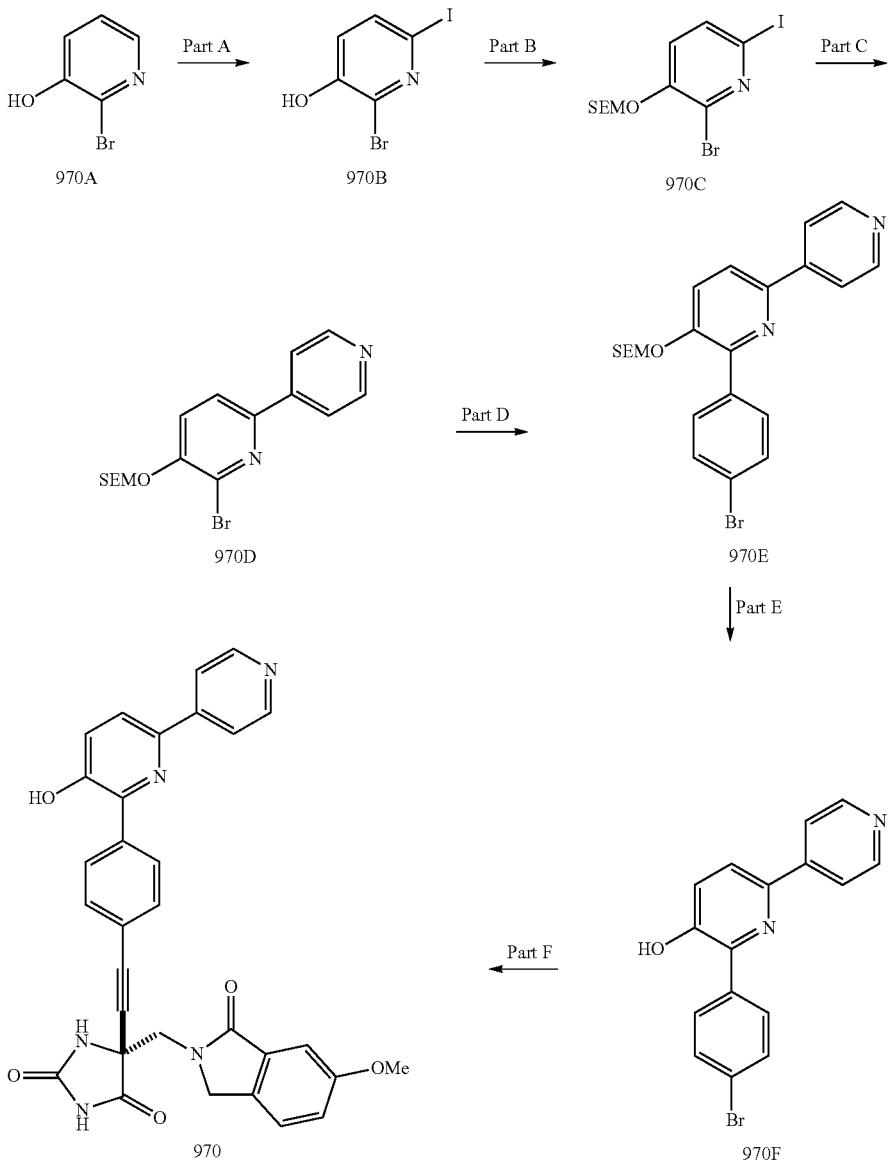

Part A:

Iodine (7.51 g, 29.6 mmol) was added portionwise to a stirred solution of 2-bromo-3-hydroxypyridine 970A (5.00 g, 28.7 mmol) and potassium carbonate (7.9 g, 58 mmol) in water (66 mL). The reaction mixture was stirred overnight at rt. Solid sodium bisulfite was added to quench excess iodine.

Acetic acid was added until pH 5-6 was attained. The precipitated solid was collected by filtration and was dried in vacuo. The desired product 970B was obtained in 8.25 g, 96% yield.

Part B:

Compound 970B was converted to Compound 970C following the procedure of Example 46, Part A.

Part C:

Compound 970C was converted to Compound 970D following the procedure of Example 46, Part B, but using pyridine-4-boronic acid in place of 4-bromobenzeneboronic acid.

Part D:

Compound 970D was converted to Compound 970E following the procedure of Example 46, Part B.

Part E:

Compound 970E was converted to Compound 970F following the procedure of Example 46, Part C.

Part F:

Compound 970F was converted to Compound 970 following the procedure of Example 6. HPLC-MS $t_R$=3.05 min (UV$_{254\,nm}$); mass calculated for formula $C_{31}H_{23}N_5O_5$ 545.2, observed LCMS m/z 546.3 [M+H]$^{+\cdot}$ Example 48

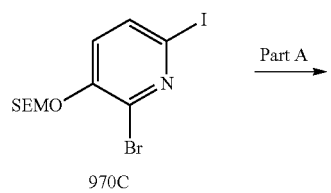

970C

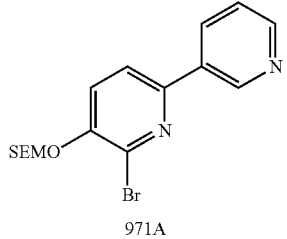

971A

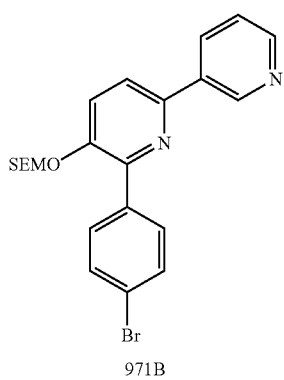

971B

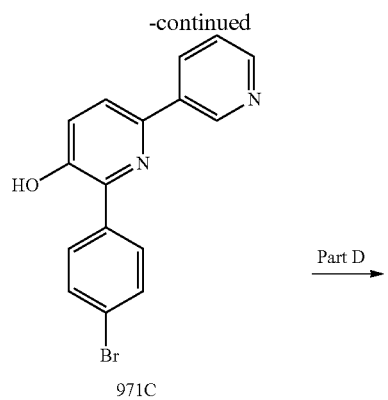

971C

971

Compound 971 was prepared from Compound 970C following a procedure analogous to that of Example 47, Parts C-F.

Compound 971C: mass calculated for formula $C_{16}H_{11}BrN_2O$ 326.0, observed LCMS m/z 327.2 [M+H]$^+$ Compound 971: HPLC-MS $t_R$=2.31 min (UV$_{254\,nm}$); mass calculated for formula $C_{31}H_{23}N_5O_5$ 545.2, observed LCMS m/z 546.3 [M+H]$^{+\cdot}$ Example 49

972A

-continued

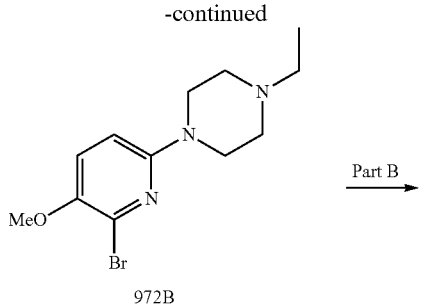
972B

| Part B |

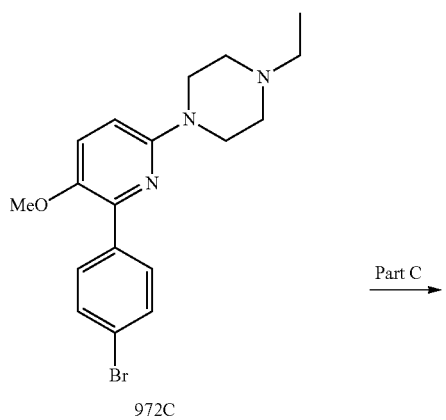
972C

| Part C |

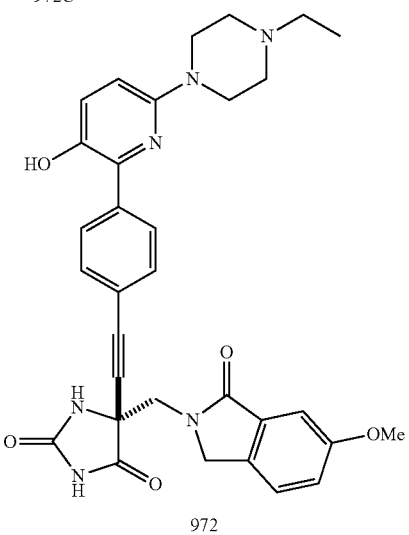
972

Part A:

Compound 972A was prepared according to the method described in Chapman, G. M.; Stanforth, S. P; Tarbit, B.; Watson, M. D. *J. Chem. Soc., Perkin Trans.* 1 2002, 581-582. Under nitrogen, a pressure vessel was charged with Compound 972A (2.0 g, 6.4 mmol), N-ethylpiperazine (0.81 mL, 0.73 g, 6.4 mmol), Pd(OAc)$_2$ (104 mg, 0.47 mmol), 2-(di-t-butylphosphino)biphenyl (139 mg, 0.47 mmol) and cesium carbonate (4.15 g, 12.8 mmol). The vessel was stoppered. Dry dioxane (6 mL) was added, and the resulting reaction mixture was stirred at 80° C. for 24 h. The reaction mixture was filtered through a Celite® pad. The filtrate was concentrated to dryness and the residue was taken up in EtOAc (50 mL) and washed with water (2×~25 mL) and brine (~25 mL). The organic layer was dried over MgSO$_4$, filtered, and concentrated. The crude product was purified by sgc (6% MeOH/DCM) to afford 508 mg of the desired product 972B (25% yield).

Part B:

Compound 972B was converted to Compound 972C following the procedure of Example 46, Part B. Compound 972C: mass calculated for formula $C_{18}H_{22}{}^{79}BrN_3O$ 375.1, observed LCMS m/z 376.3 [M+H]$^+$.

Part C:

Compound 972C was converted to Compound 972 following the procedure of Example 6. HPLC-MS $t_R$=2.51 min (UV$_{254\,nm}$); mass calculated for formula $C_{33}H_{34}N_6O_5$ 594.3, observed LCMS m/z 595.3 [M+H].

Example 973

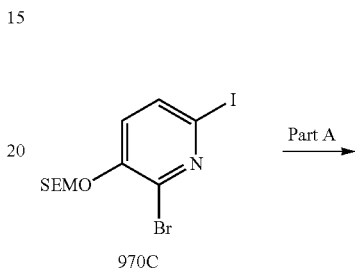
970C

| Part A |

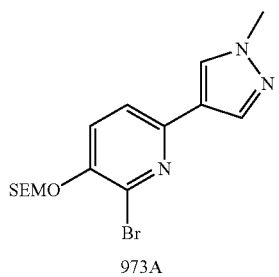
973A

| Part B |

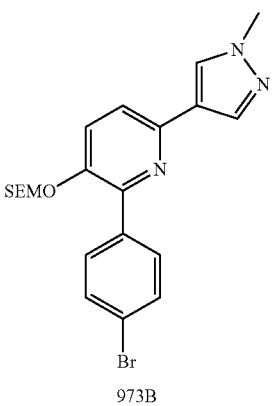
973B

| Part C |

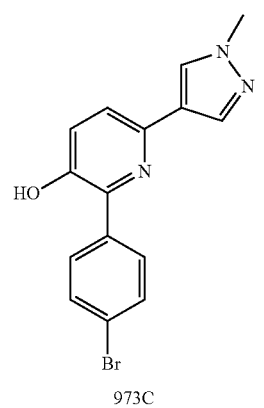
973C

| Part D |

-continued

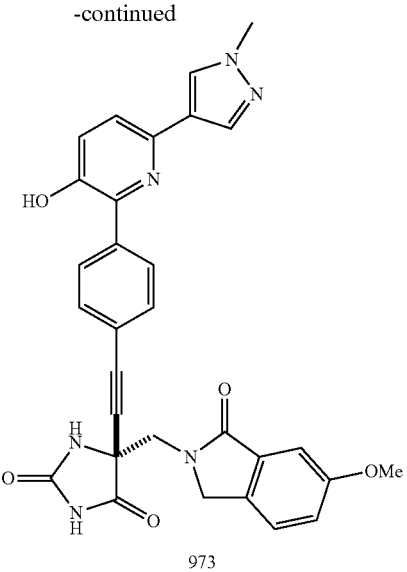

973

Compound 970C was converted to Compound 973 by following a procedure analogous to that to Example 47, Parts C-F.

Compound 973C: mass calculated for formula $C_{15}H_{12}{}^{79}BrN_3O$ 329.0, observed LCMS m/z 330.2 [M+H]$^{+.}$ Compound 973: HPLC-MS $t_R$=2.40 min ($U_{254\ nm}$); mass calculated for formula $C_{30}H_{24}N_6O_5$ 548.2, observed LCMS m/z 549.3 [M+H]$^+$.

Example 51

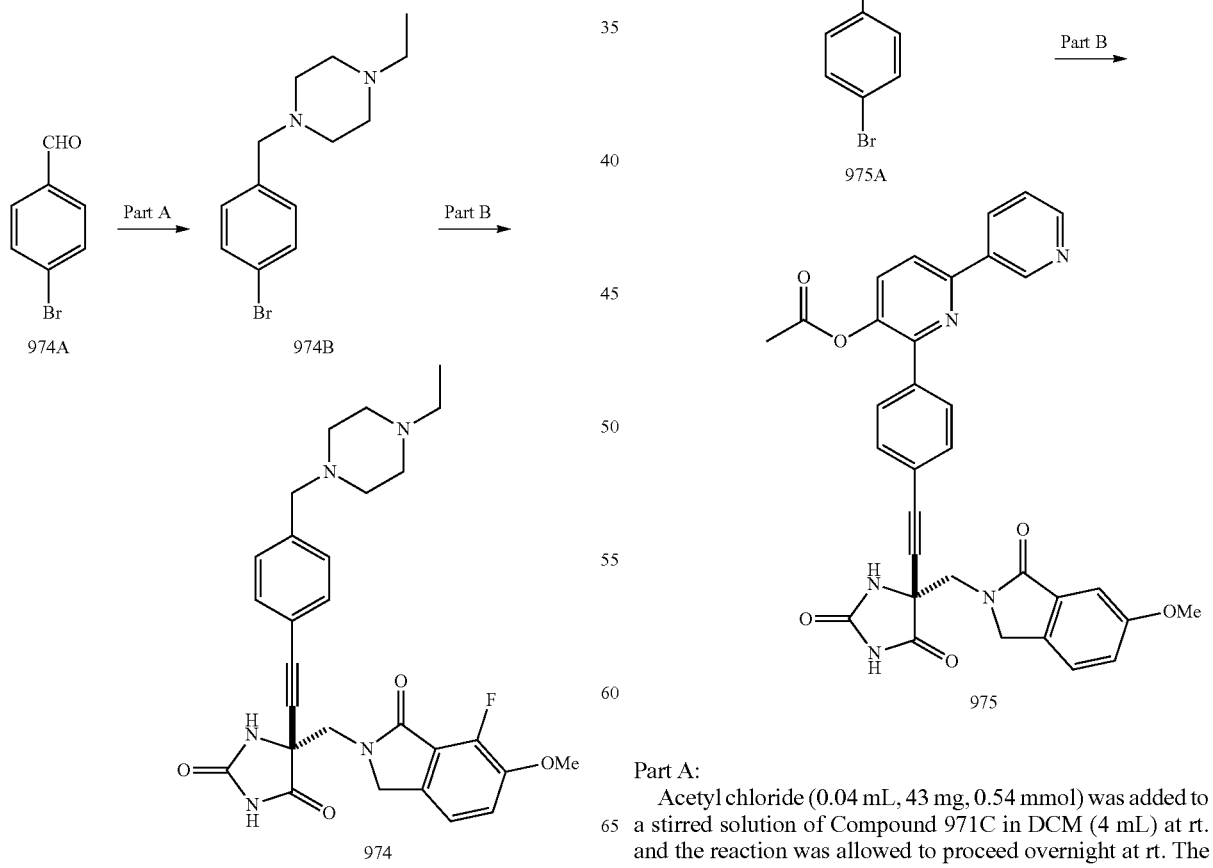

974A → 974B → 974

4-Bromobenzaldehyde 974A was converted to Compound 974 via a procedure analogous to that described in Example 43.

Compound 974B: mass calculated for formula $C_{13}H_{19}{}^{79}BrN_2$ 282.1, observed LCMS m/z 283.2 [M+H]$^{+.}$ Compound 974: HPLC-MS $t_R$=1.74 min (UV$_{254\ nm}$); mass calculated for formula $C_{28}H_{30}FN_5O_4$ 519.2, observed LCMS m/z 520.3 [M+H]$^{+.}$ Example 52

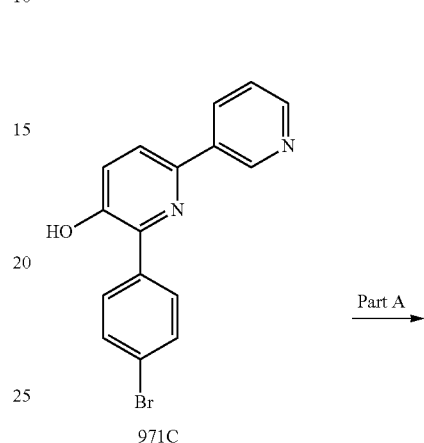

971C

975A

975

Part A:

Acetyl chloride (0.04 mL, 43 mg, 0.54 mmol) was added to a stirred solution of Compound 971C in DCM (4 mL) at rt. and the reaction was allowed to proceed overnight at rt. The reaction mixture was diluted with DCM (~25 mL) and washed sequentially with water (~25 mL) and brine (~25 mL). The organic layer was dried over MgSO$_4$, filtered, and concentrated to dryness. The crude product was purified by sgc (0-60% EtOAc/hexanes gradient) to afford 74 mg of the desired product 975A (44% yield). Mass calculated for formula C$_{18}$H$_{13}$$^{79}$BrN$_2$O$_2$ 368.0, observed LCMS m/z 369.2 [M+H]$^{+}$ Part B:

Compound 975A was converted to Compound 975 following the procedure of Example 6. HPLC-MS t$_R$=2.59 min (UV$_{254\ nm}$); mass calculated for formula C$_{33}$H$_{25}$N$_5$O$_6$ 5872, observed LCMS m/z 588.3 [M+H]$^{+}$ Example 53

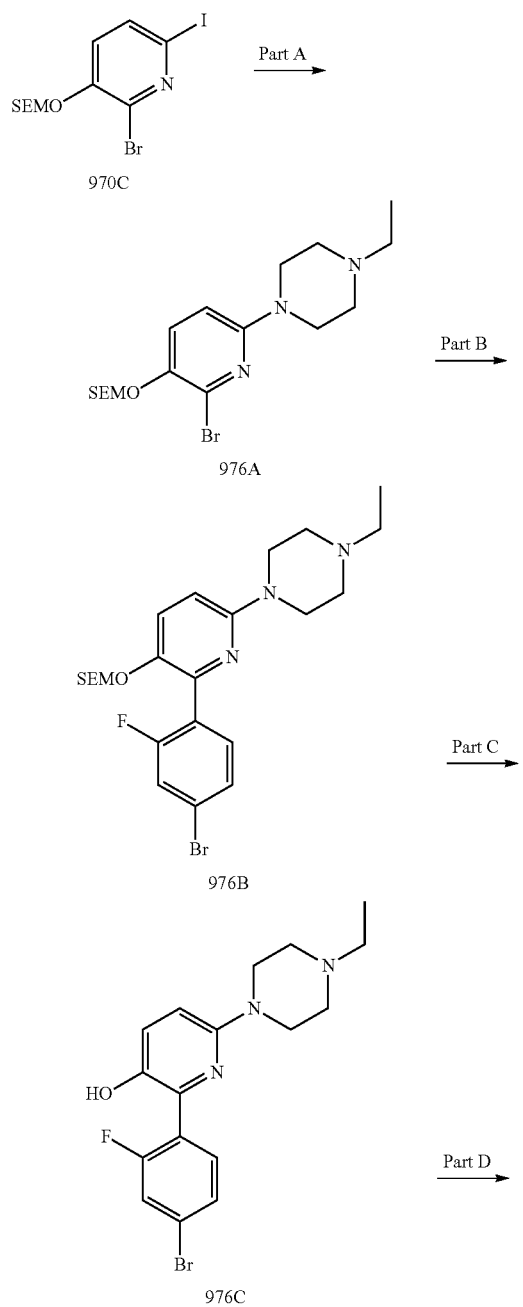

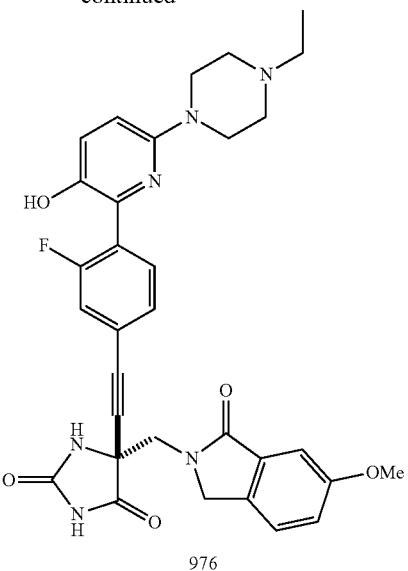

Part A:

Compound 976A was prepared from Compound 970C following the procedure for Example 49, Part A.

Part B:

Compound 976A was converted to Compound 976B following the procedure given in Example 49, Part B, using commercially available 4-bromo-2-fluorobenzeneboronic acid in place of 4-bromobenzeneboronic acid.

Part C:

The conversion of Compound 976B to Compound 976C was carried out in accordance to the procedure in Example 49, Part C. Mass calculated for formula C$_{17}$H$_{19}$$^{79}$BrFN$_3$O 379.1, observed LCMS m/z 380.2 [M+H]$^{+}$ Part D:

Compound 976C was converted to Compound 976 following the procedure of Example 6. HPLC-MS t$_R$=2.35 min (UV$_{254\ nm}$); mass calculated for formula C$_{32}$H$_{31}$FN$_6$O$_5$ 598.2, observed LCMS m/z 599.3 [M+H]$^{+}$ Example 54

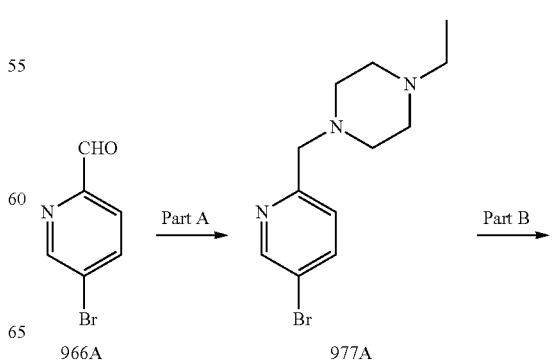

-continued

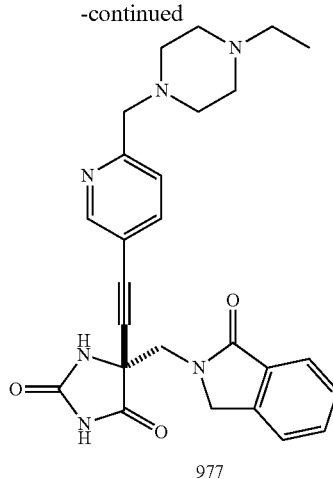

977

Compound 977 was prepared from aldehyde 966A following an analogous procedure to that given in Example 43.

Compound 977A: mass calculated for formula $C_{12}H_{18}{}^{79}BrN_3$ 283.1, observed m/z 284.2 $[M+H]^{+}$.

Compound 977: HPLC-MS $t_R$=1.67 min ($UV_{254\ nm}$); mass calculated for formula $C_{27}H_{30}N_6O_4$ 502.2, observed LCMS m/z 503.3 $[M+H]^{+}$.

Example 55

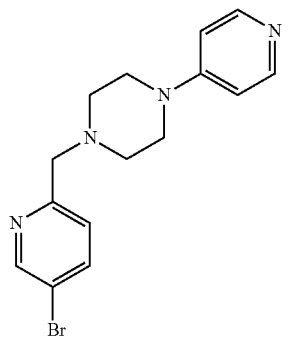

978

Compound 978 was prepared from aldehyde 966A following an analogous procedure to that given in Examples 43 and 44. Compound 978: HPLC-MS $t_R$=1.62 min ($UV_{254\ nm}$); mass calculated for formula $C_{27}H_{29}FN_6O_4$ 520.2, observed LCMS m/z 521.3 $[M+H]^{+}$.

Example 56

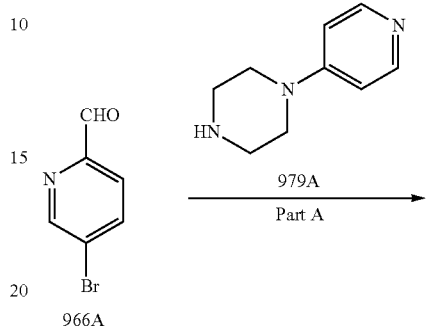

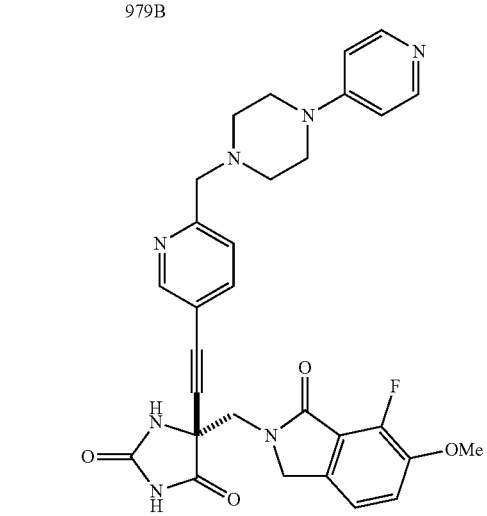

979B

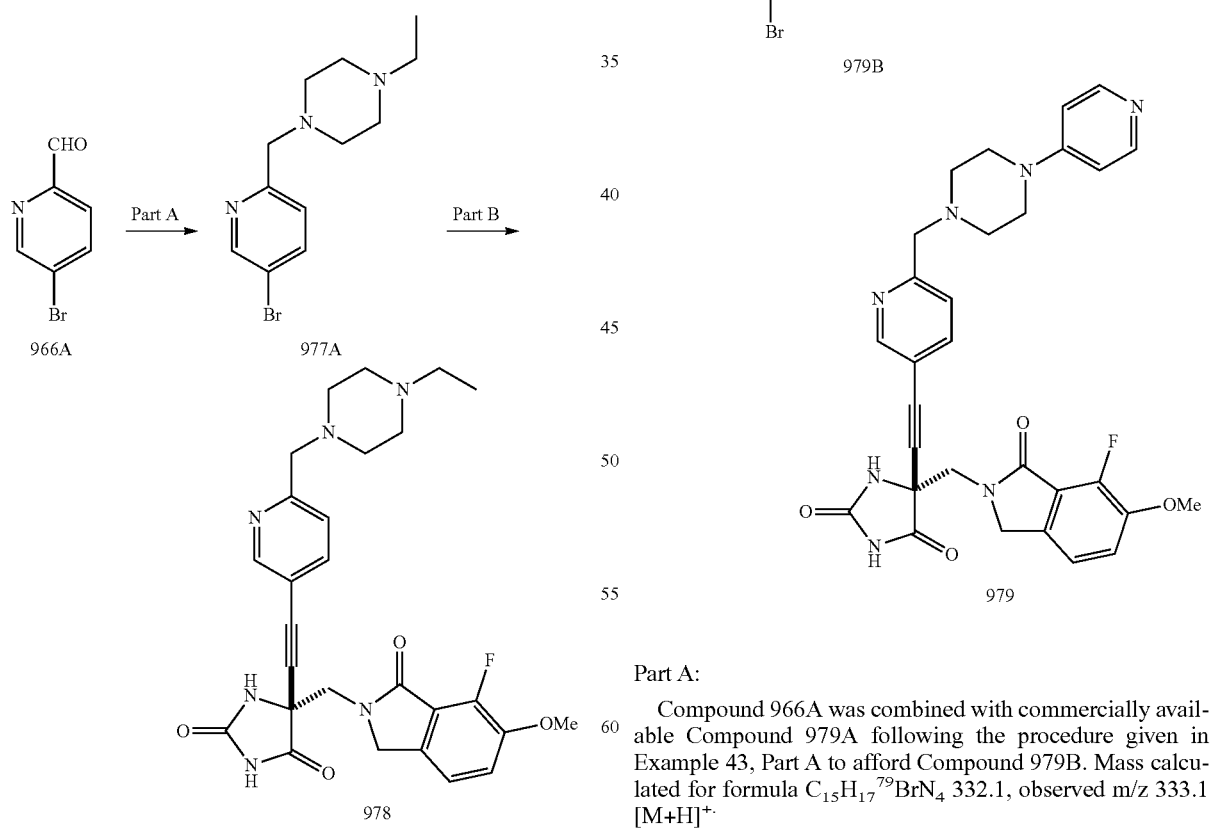

979

Part A:

Compound 966A was combined with commercially available Compound 979A following the procedure given in Example 43, Part A to afford Compound 979B. Mass calculated for formula $C_{15}H_{17}{}^{79}BrN_4$ 332.1, observed m/z 333.1 $[M+H]^{+}$.

Part B:

Compound 979B was converted to Compound 979 following the procedure of Example 6. HPLC-MS $t_R$=1.54 min (UV$_{254 nm}$); mass calculated for formula C$_{30}$H$_{28}$FN$_{7}$O$_{4}$ 569.2, observed LCMS m/z 570.3 [M+H]$^{+}$.

Example 57

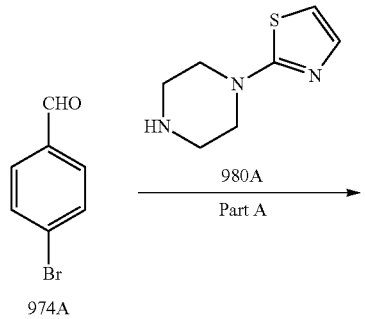

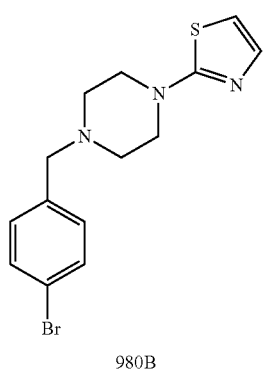

Compound 980 was prepared from Compound 974A via a sequence analogous to that described in Example 43.

Compound 980B: Mass calculated for formula C$_{14}$H$_{16}$$^{79}$BrN$_{3}$S 337.0, observed m/z 338.3 [M+H]$^{+}$ Compound 980: HPLC-MS t$_R$=2.20 min (UV$_{254 nm}$); mass calculated for formula C$_{29}$H$_{28}$N$_{6}$O$_{4}$S 556.2, observed LCMS m/z 557.3 [M+H]$^{+}$ Example 58

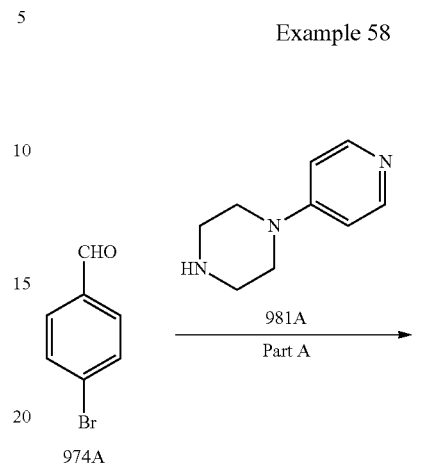

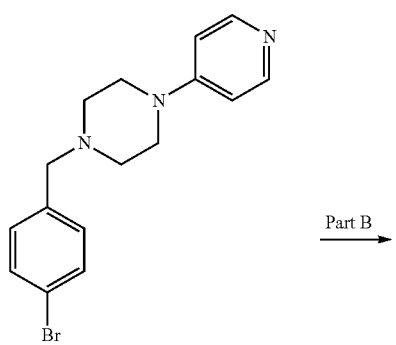

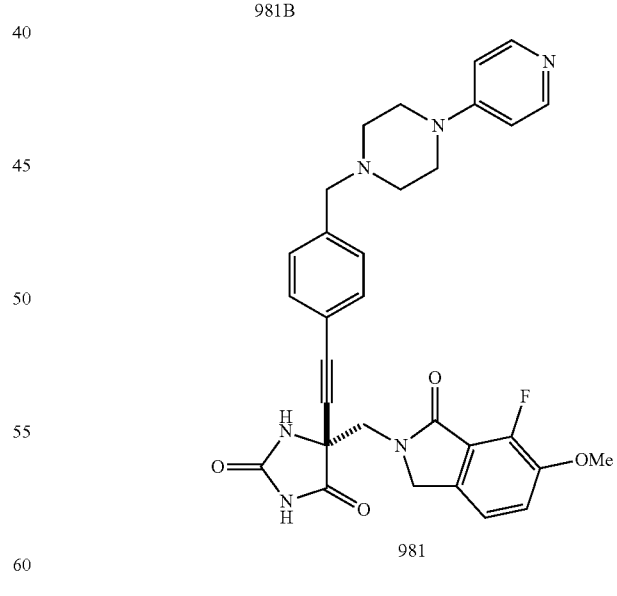

Compound 974A was converted to Compound 981 following a procedure analogous to that given in Examples 43 and 56.

Compound 981B: Mass calculated for formula C$_{16}$H$_{18}$$^{79}$BrN$_{3}$ 331.1, observed m/z 332.2 [M+H]$^{+}$ Compound 981: HPLC-MS $t_R$=1.64 min (UV$_{254\,nm}$); mass calculated for formula $O_{31}H_{29}FN_6O_4$ 568.2, observed LCMS m/z 569.3 [M+H]$^+$.

Example 59

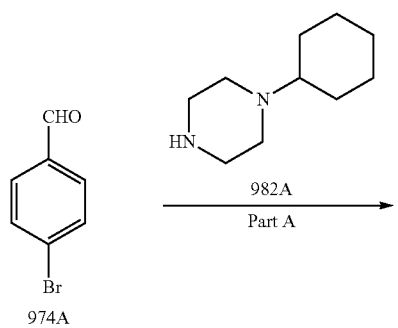

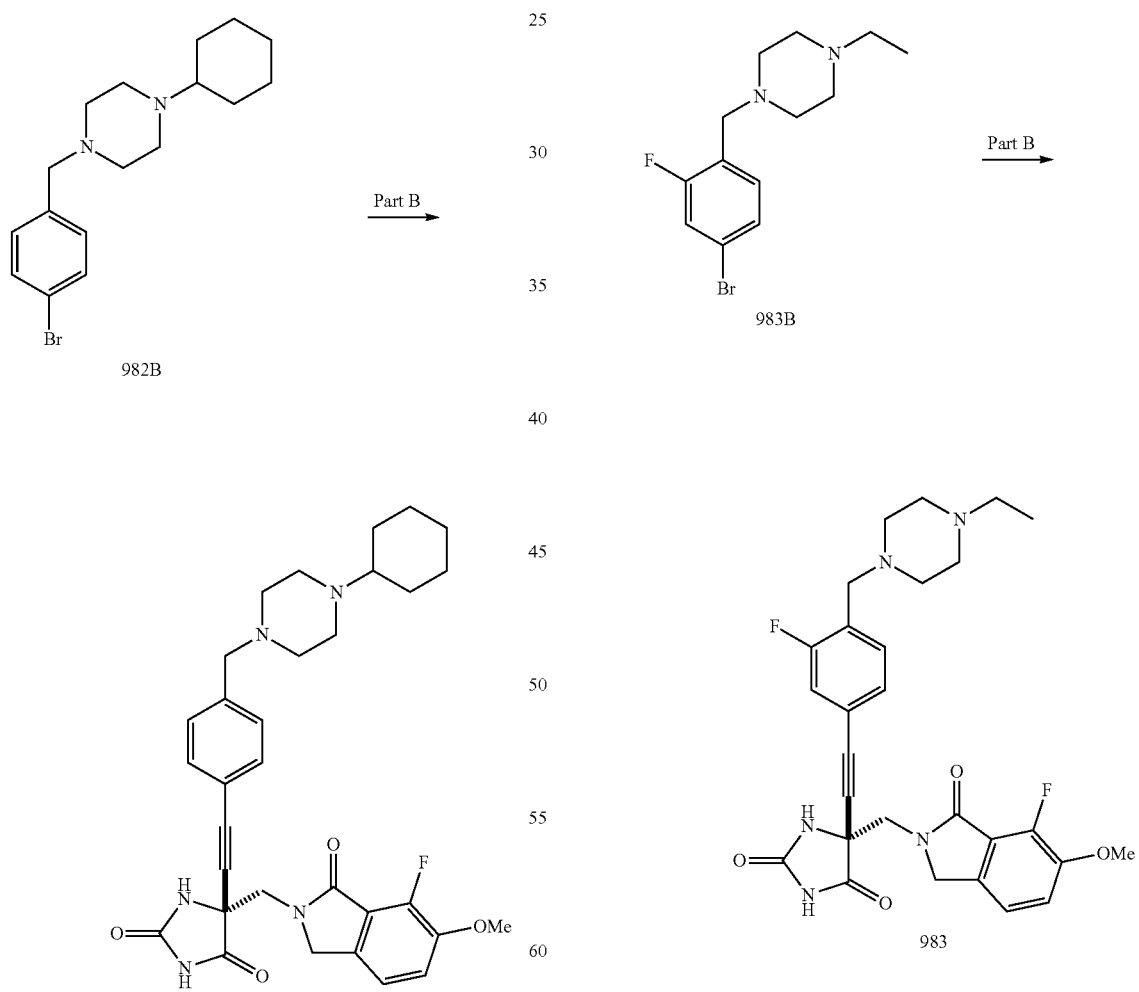

Compound 982 was prepared via a procedure analogous to that presented in Example 43.

Compound 982B: Mass calculated for formula $C_{17}H_{25}{}^{79}BrN_2$ 336.1, observed m/z 337.2 [M+H]$^+$.

Compound 982: HPLC-MS $t_R$=2.12 min (UV$_{254\,nm}$); mass calculated for formula $C_{32}H_{36}FN_5O_4$ 573.3, observed LCMS m/z 574.3 [M+H]$^+$.

Example 60

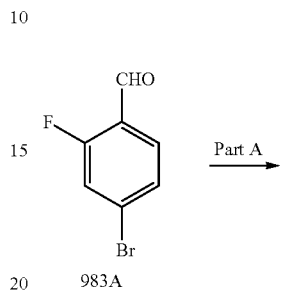

Compound 983 was prepared via a procedure analogous to that presented in Example 43.

Compound 983B: Mass calculated for formula $C_{13}H_{18}{}^{79}BrFN_2$ 300.1, observed m/z 301.2 [M+H]$^+$.

Compound 983: HPLC-MS $t_R$=2.03 min (UV$_{254\ nm}$); mass calculated for formula $C_{28}H_{29}F_2N_5O_4$ 537.2, observed LCMS m/z 538.3 [M+H]$^+$ Example 61

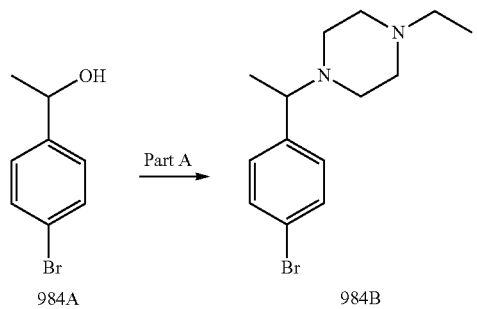

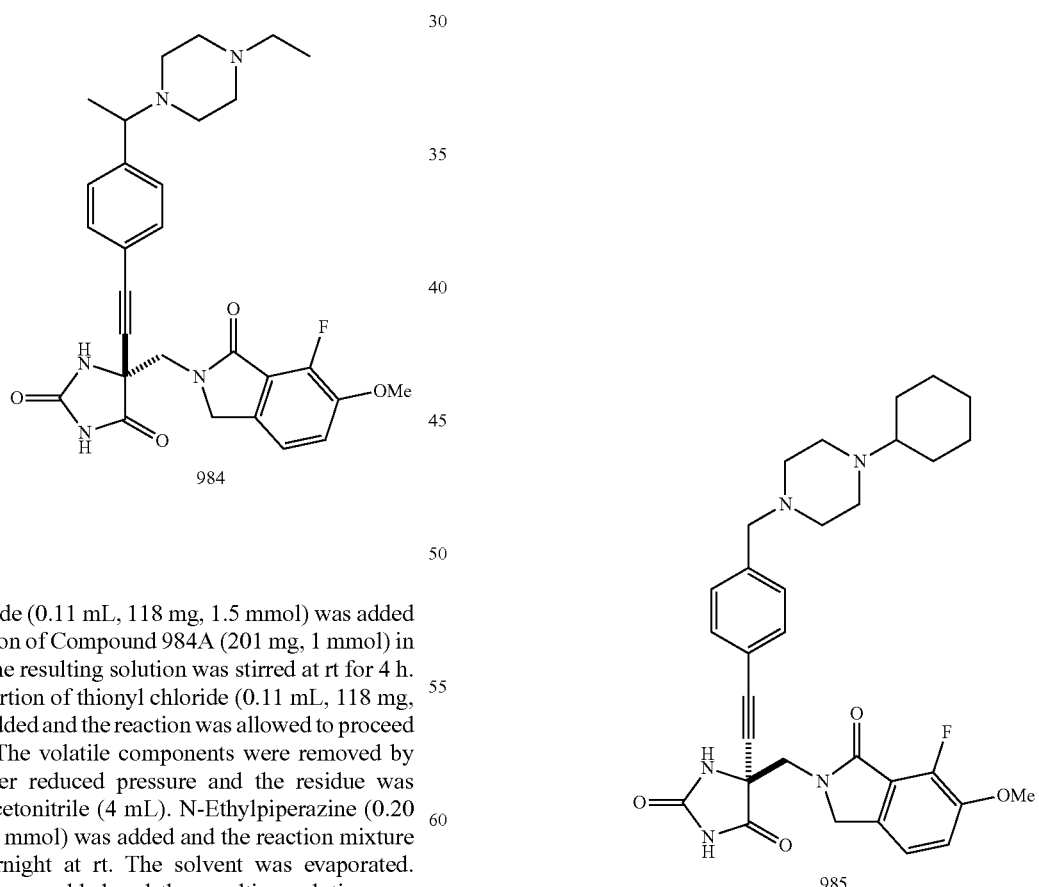

Part A:

Thionyl chloride (0.11 mL, 118 mg, 1.5 mmol) was added to a stirred solution of Compound 984A (201 mg, 1 mmol) in DCM (4 mL). The resulting solution was stirred at rt for 4 h. An additional portion of thionyl chloride (0.11 mL, 118 mg, 1.5 mmol) was added and the reaction was allowed to proceed overnight at rt. The volatile components were removed by evaporation under reduced pressure and the residue was redissolved in acetonitrile (4 mL). N-Ethylpiperazine (0.20 mL, 171 mg, 1.5 mmol) was added and the reaction mixture was stirred overnight at rt. The solvent was evaporated. EtOAc (25 mL) was added and the resulting solution was washed sequentially with water (2x~20 mL) and brine (~20 mL). The organic layer was dried over MgSO$_4$, filtered, and the resulting crude product was purified by sgc (1-10% MeOH/DCM containing 1% NH$_4$OH). The desired product 984B was obtained in 94 mg, 31% yield. Mass calculated for formula $C_{14}H_{21}BrN_2$ 296.1, observed m/z 297.2 [M+H]$^+$ Part B:

Compound 984B was converted to Compound 984 following the procedure of Example 6. HPLC-MS $t_R$=1.90 min (UV$_{254\ nm}$); mass calculated for formula $C_{29}H_{32}FN_5O_4$ 533.2, observed LCMS m/z 534.3 [M+H]$^+$ Example 62

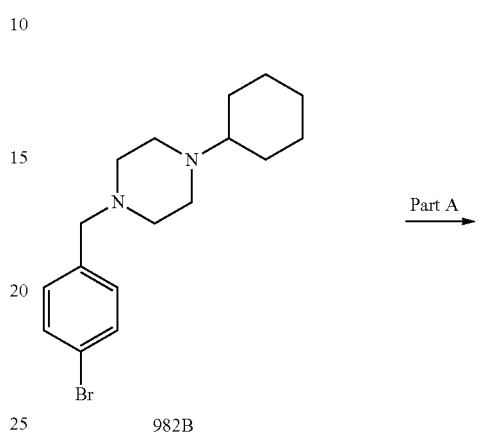

Compound 982B was converted to Compound 985 following the procedure of Example 6, but using the enantiomer of Compound 23, obtained from the resolution described in Example 4, Part F. HPLC-MS $t_R$=2.24 min (UV$_{254\ nm}$); mass calculated for formula $C_{32}H_{36}FN_5O_4$ 573.3, observed LCMS m/z 574.3 [M+H]$^+$.

Example 63

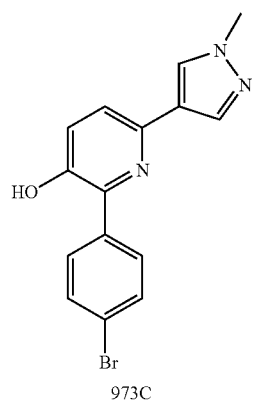

973C

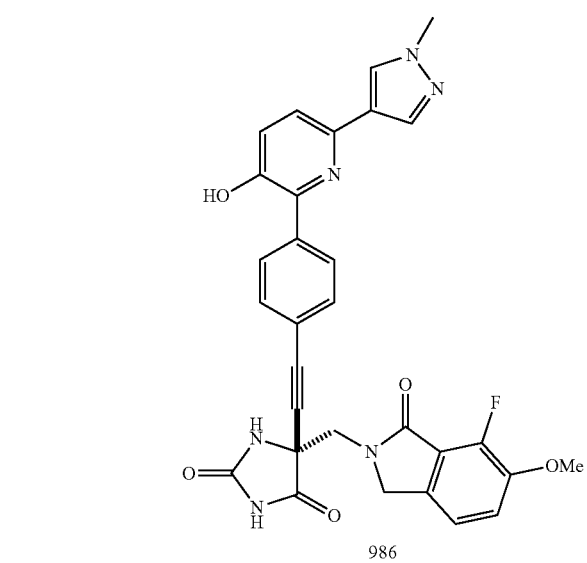

986

Compound 986 was prepared from Compound 973C following the procedure of Example 6. HPLC-MS $t_R$=2.36 min (UV$_{254\ nm}$); mass calculated for formula $C_{30}H_{23}FN_6O_5$ 566.2, observed LCMS m/z 567.3 [M+H]$^+$.

Example 64

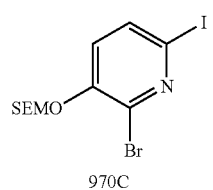

970C

-continued

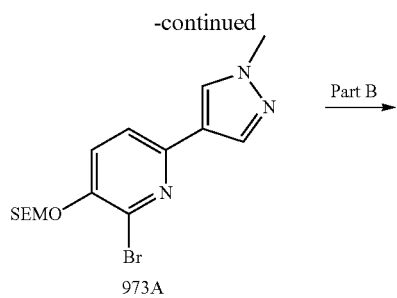

973A

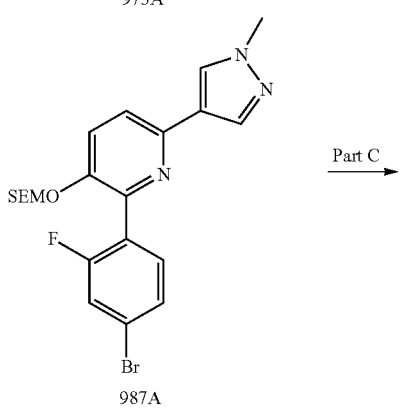

987A

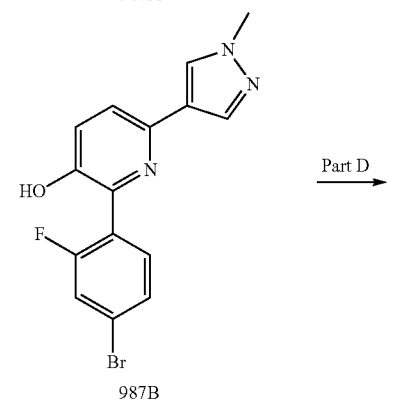

987B

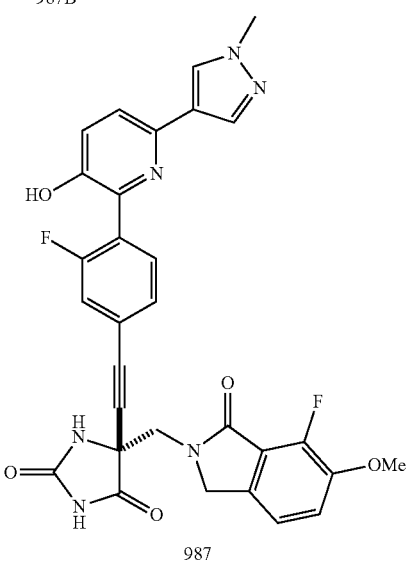

987

Compound 987 was prepared via a sequence analogous to that described in Example 973, using procedures given in Examples 50 and 53.

Compound 987B: Mass calculated for formula $C_{15}H_{11}{}^{79}BrFN_3O$ 347.0, observed m/z 348.2 [M+H]+.

Compound 987: HPLC-MS $t_R$=2.43 min (UV$_{254\ nm}$); mass calculated for formula $C_{30}H_{22}F_2N_6O_5$ 584.2, observed LCMS m/z 585.3 [M+H]+.

Example 65

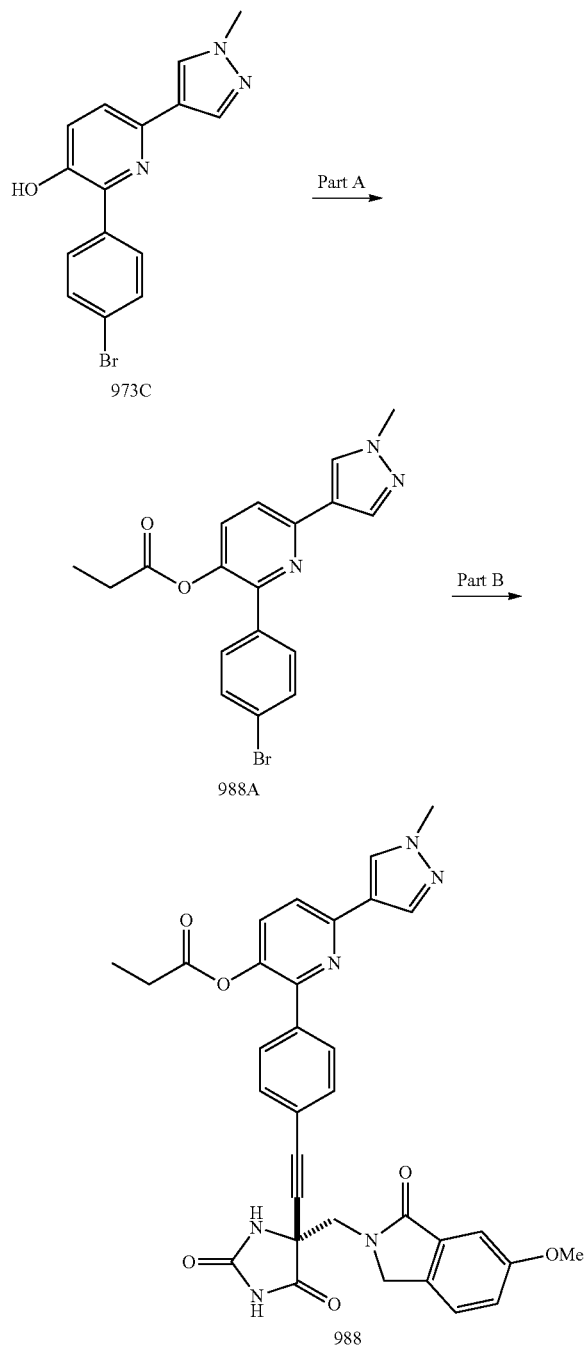

Part B:
Compound 988A was converted to Compound 988 following the procedure of Example 6. HPLC-MS $t_R$=3.66 min (UV$_{254\ nm}$); mass calculated for formula $C_{33}H_{28}N_6O_6$ 604.2, observed LCMS m/z 605.3 [M+H]+.

Example 66

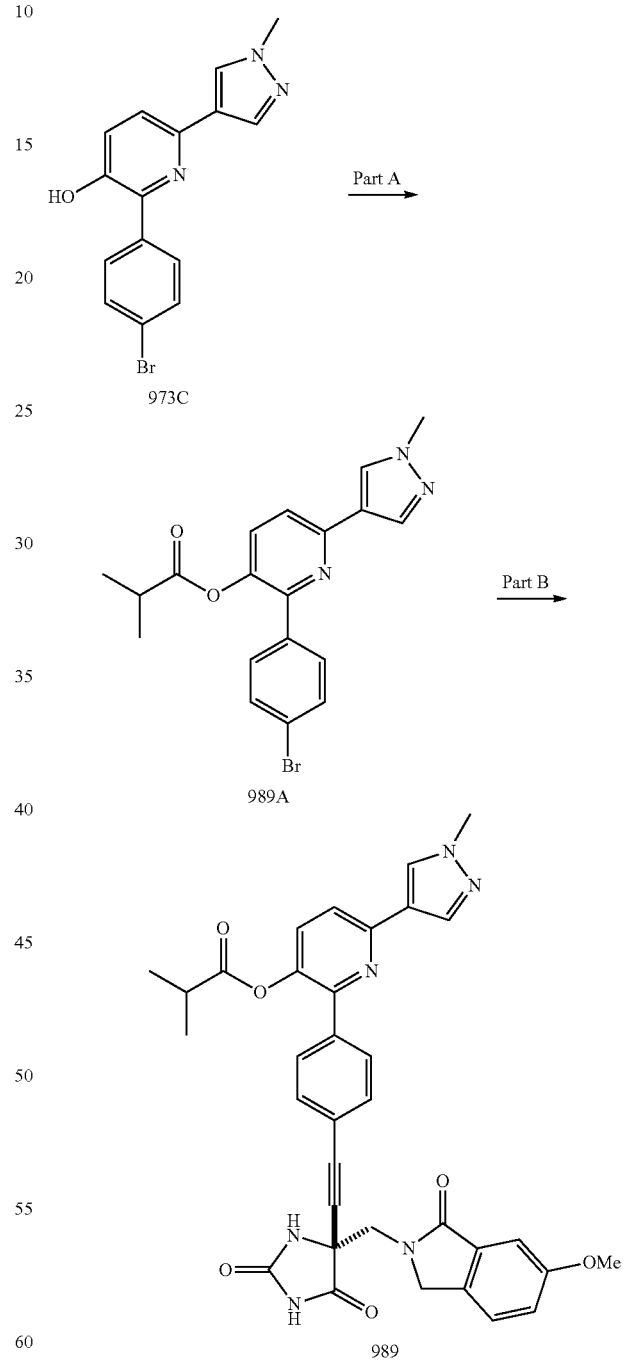

Part A:
Compound 973C was converted to Compound 988A by analogy to the procedure given in Example 52, Part A. Mass calculated for formula $C_{18}H_{16}{}^{79}BrN_3O_2$ 385.0, observed m/z 386.0 [M+H]+.

Part A:
Compound 973C was converted to Compound 989A by analogy to the procedure given in Example 52, Part A. Mass calculated for formula $C_{19}H_{18}{}^{79}BrN_3O_2$ 399.1, observed m/z 400.2 [M+H]+.

Part B:
Compound 989A was converted to Compound 989 following the procedure of Example 6. HPLC-MS $t_R$=3.82 min (UV$_{254\,nm}$); mass calculated for formula $C_{34}H_{30}N_6O_6$ 618.2, observed LCMS m/z 619.3 [M+H]$^+$.

Example 67

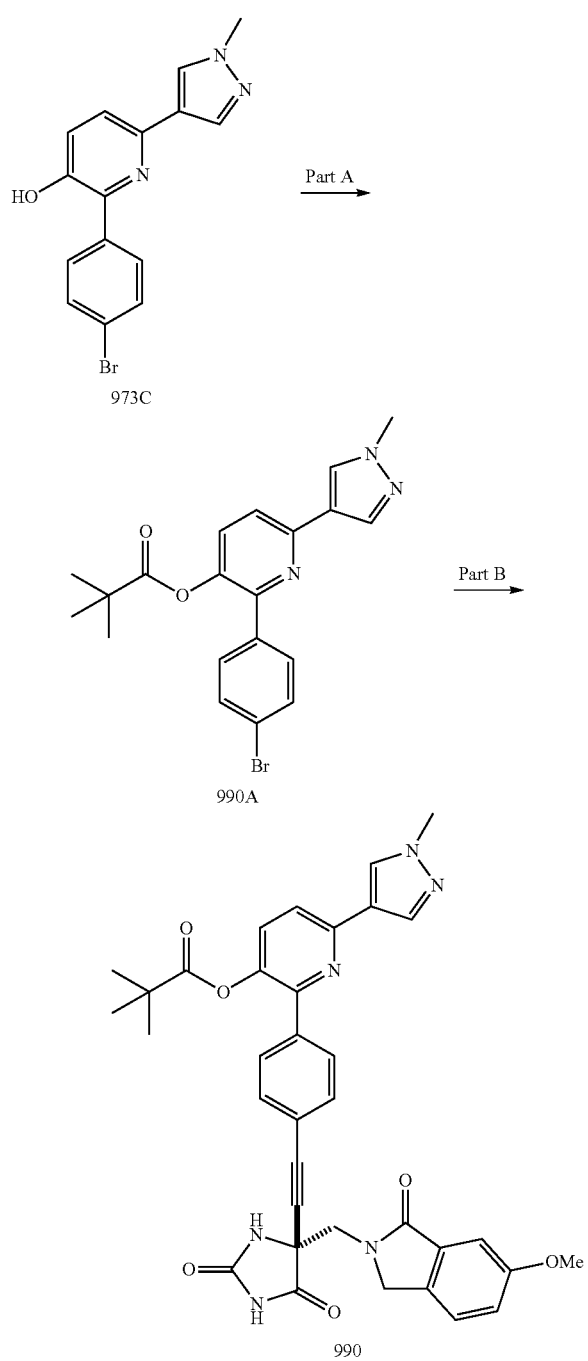

Part A:
Compound 973C was converted to Compound 990A by analogy to the procedure given in Example 52, Part A. Mass calculated for formula $C_{20}H_{20}{}^{79}BrN_3O_2$ 413.1, observed m/z 414.3 [M+H]$^+$.

Part B:
Compound 990A was converted to Compound 990 following the procedure of Example 6. HPLC-MS $t_R$=3.97 min (UV$_{254\,nm}$); mass calculated for formula $C_{35}H_{32}N_6O_6$ 632.2, observed LCMS m/z 633.3 [M+H]$^+$.

Example 68

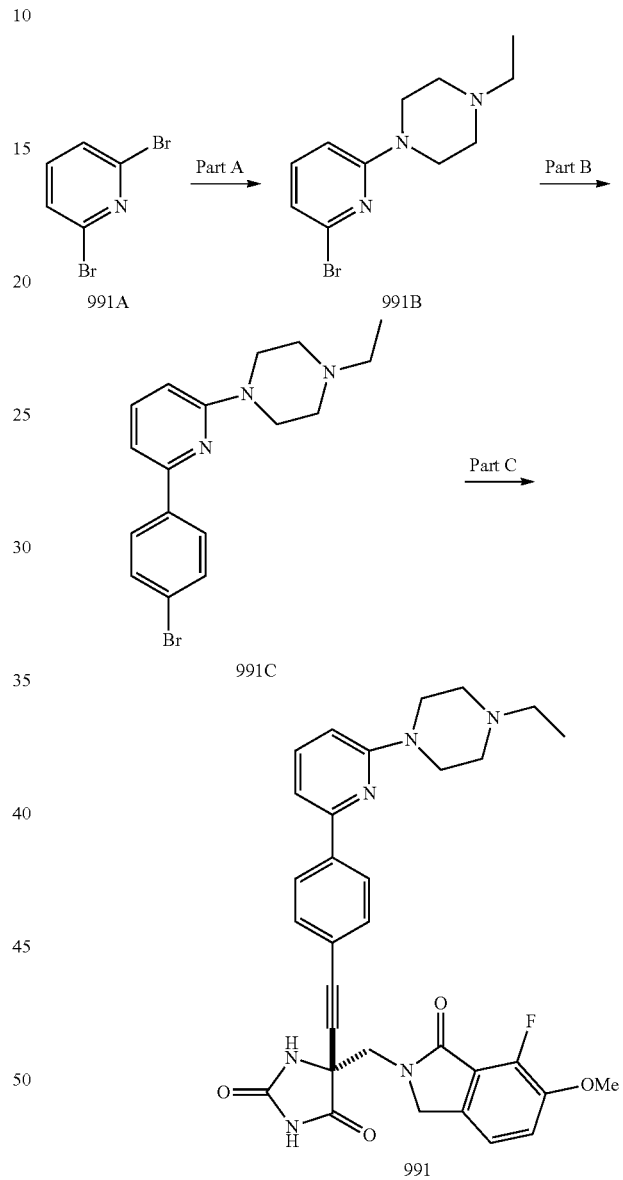

Part A:
A flame-dried Schlenk flask was charged with Compound 991A (5.0 g, 21 mmol), N-ethylpiperazine (2.2 g, 19 mmol), copper (I) iodide (402 mg, 2.1 mmol), L-proline (486 mg, 4.2 mmol), and potassium carbonate (5.8 g, 42 mmol). The flask was stoppered, evacuated, and refilled with nitrogen. Dry, degassed DMSO (52 mL) was added and the reaction mixture was stirred at 60° C. for 24 h. The reaction mixture was allowed to cool to rt, and was then diluted with EtOAc (100 mL). The organic solution was washed sequentially with water (3×100 mL) and brine (100 mL), dried over anhydrous MgSO$_4$, filtered, and concentrated under reduced pressure.

The crude residue was purified by sgc employing a solvent gradient of 1-10% MeOH—CH$_2$Cl$_2$ (containing 1% NH$_4$OH). The desired product 991B was obtained in 223 g, 43% yield.

Part B:
Compound 991B was converted to Compound 991C employing the procedure given in Example 46, Part B. Mass calculated for formula C$_{17}$H$_{20}$$^{79}$BrN$_3$ 345.1, observed m/z 346.3 [M+H]$^+$.

Part C:
Compound 991C was converted to Compound 991 following the procedure of Example 6. HPLC-MS t$_R$=2.83 min (UV$_{254\ nm}$); mass calculated for formula C$_{32}$H$_{31}$FN$_6$O$_4$ 582.2, observed LCMS m/z 583.3 [M+H]$^+$.

Part A:
The conversion of Compound 991B to Compound 992A was performed by analogy to the procedure given in Example 68, Part B. Mass calculated for formula C$_{17}$H$_{19}$$^{79}$BrN$_3$ 363.1, observed m/z 364.3 [M+H]$^+$.

Part B:
Compound 992A was converted to Compound 992 following the procedure of Example 6. HPLC-MS t$_R$=2.86 min (UV$_{254\ nm}$); mass calculated for formula C$_{32}$H$_{30}$F$_2$N$_6$O$_4$ 600.2, observed LCMS m/z 601.3 [M+H]$^+$.

Example 70

Example 69

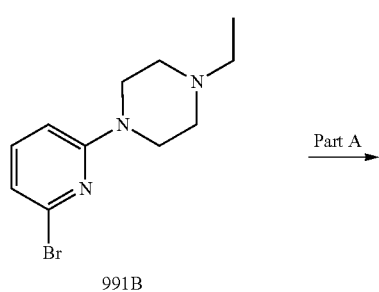

991B

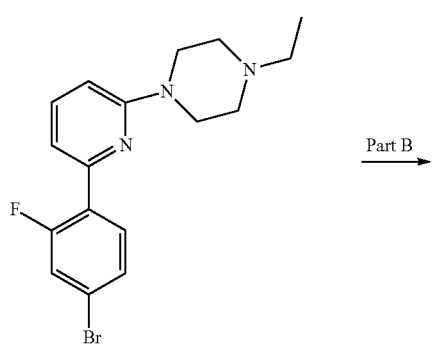

992A

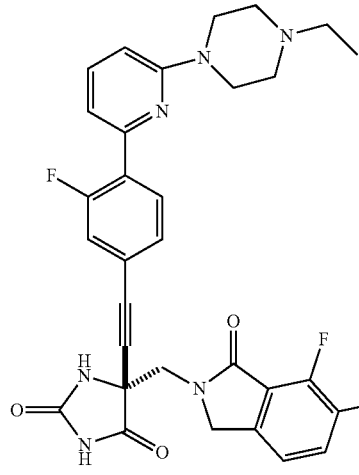

992

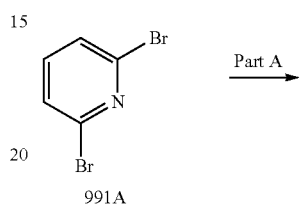

991A

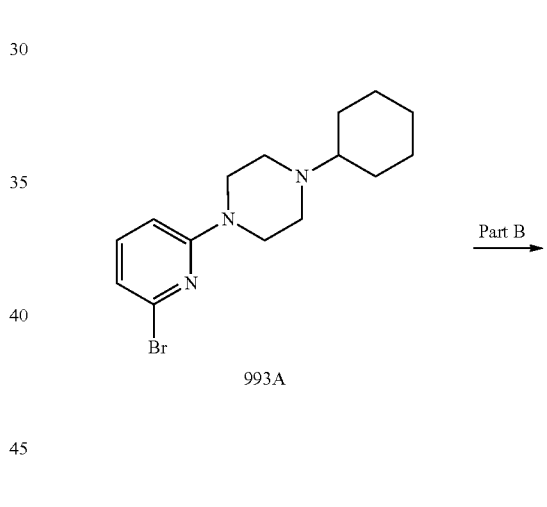

993A

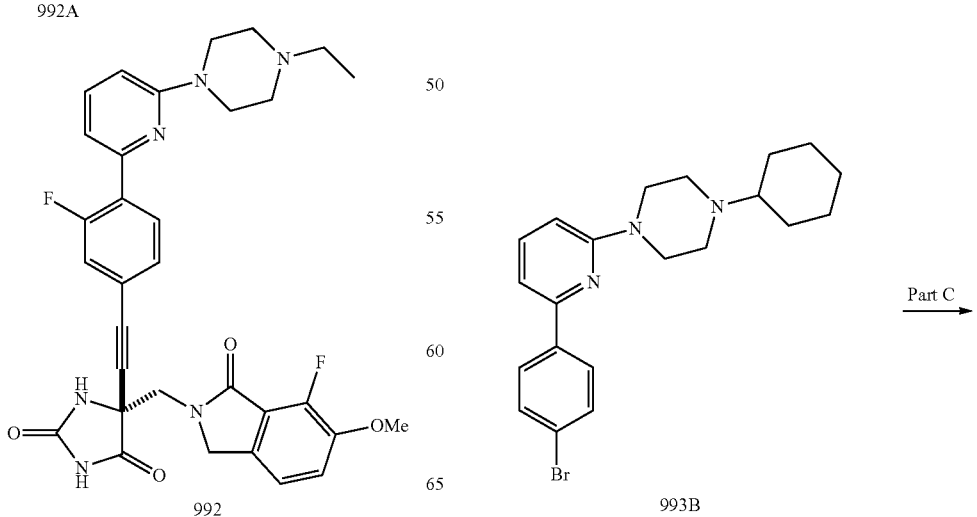

993B

-continued

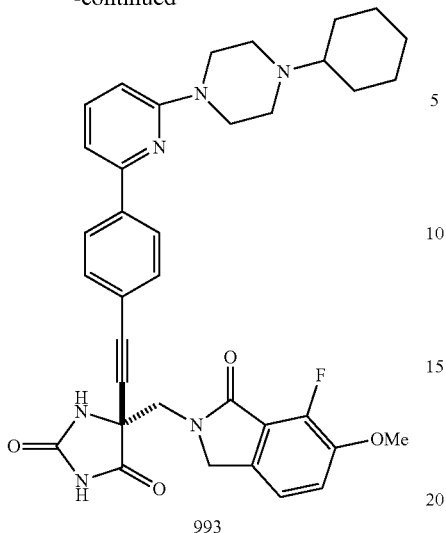

993

The preparation of Compound 993 from Compound 991A was accomplished by adapting the procedure given in Example 68.

Compound 993B: Mass calculated for formula $C_{21}H_{26}{}^{79}BrN_3$ 399.1, observed m/z 400.4 [M+H]+·

Compound 993: HPLC-MS $t_R$=2.80 min (UV$_{254\ nm}$); mass calculated for formula $C_{36}H_{37}FN_6O_4$ 636.3, observed LCMS m/z 637.4 [M+H]+·

Example 71

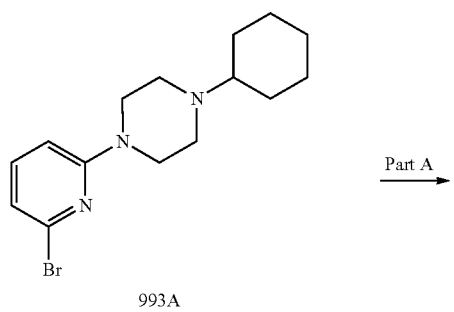

993A

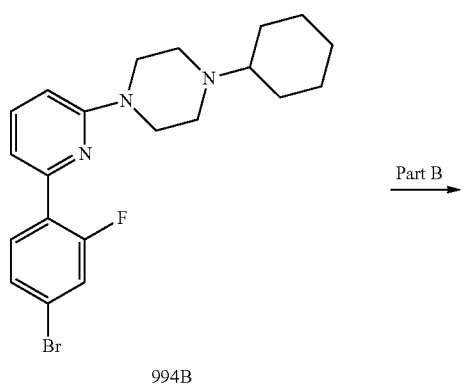

994B

-continued

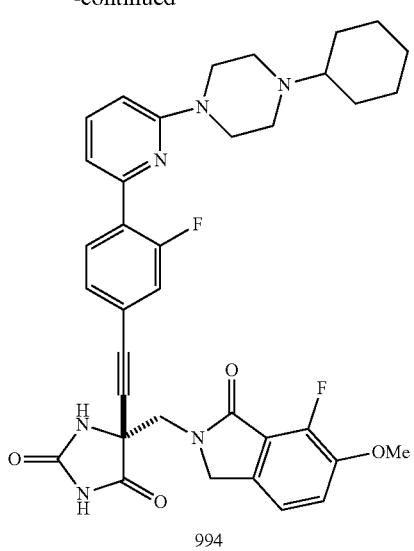

994

Part A:

Compound 993A was converted to Compound 994A by analogy to the procedure in Example 46, Part B. Mass calculated for formula $C_{21}H_{25}{}^{79}BrFN_3$ 417.1, observed m/z 418.4 [M+H]+·

Part B:

Compound 994A was converted to Compound 994 following the procedure of Example 6. HPLC-MS $t_R$=2.85 min (UV$_{254\ nm}$); mass calculated for formula $C_{36}H_{36}F_2N_6O_4$ 654.3, observed LCMS m/z 655.4 [M+H]+·

Examples 72, 73, 74, and 75

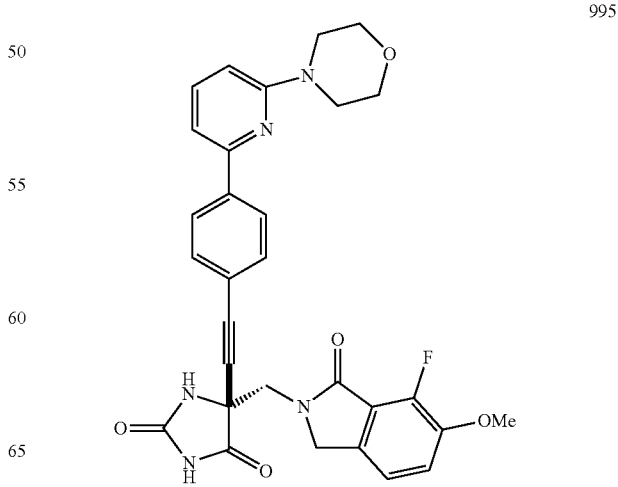

995

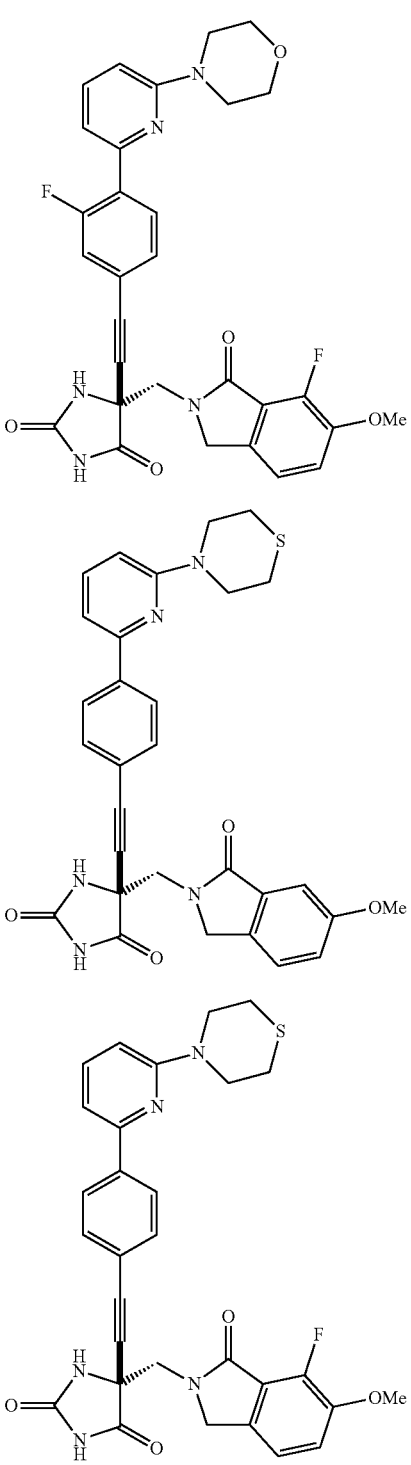

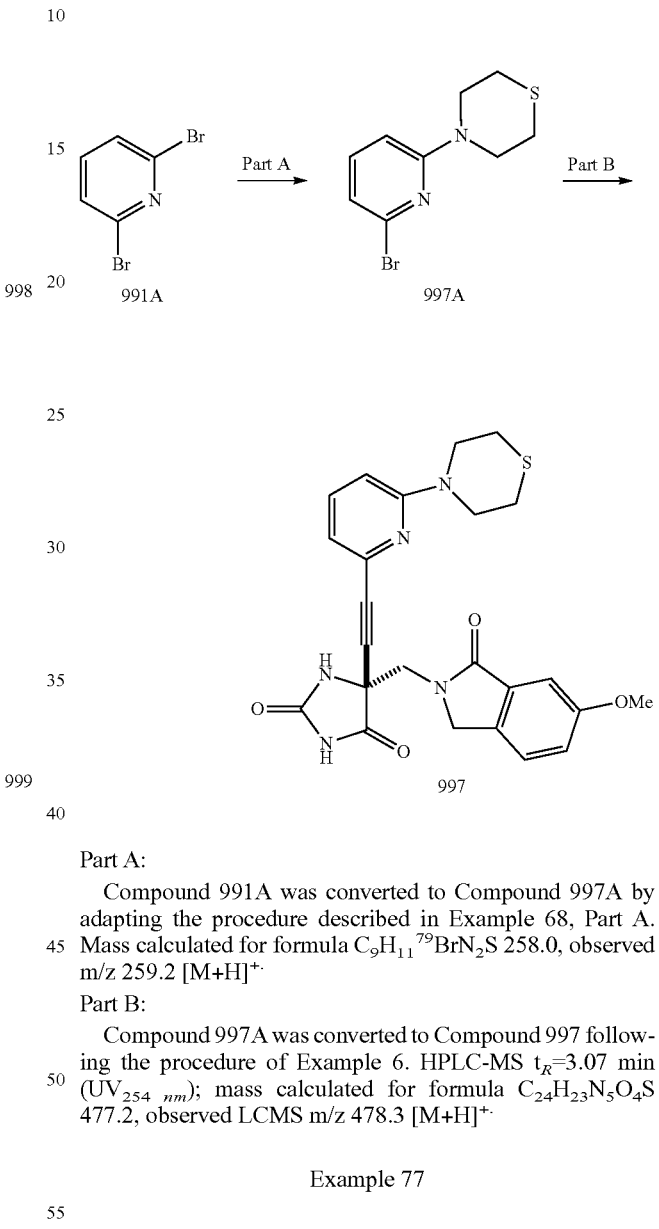

Compounds 995, 996, 998 and 999 were prepared by following procedures analogous to those given in Example 70 or 71.

Compound 995: HPLC-MS $t_R$=3.28 min (UV$_{254\,nm}$); mass calculated for formula $C_{30}H_{26}FN_5O_5$ 555.2, observed LCMS m/z 556.3 [M+H]$^+$.

Compound 996: HPLC-MS $t_R$=3.39 min (UV$_{254\,nm}$); mass calculated for formula $C_{30}H_{25}F_2N_5O_5$ 573.2, observed LCMS m/z 574.3 [M+H]$^+$.

Compound 998: HPLC-MS $t_R$=3.73 min (UV$_{254\,nm}$); mass calculated for formula $C_{30}H_{27}N_5O_4S$ 553.2, observed LCMS m/z 554.3 [M+H]$^+$.

Compound 999: HPLC-MS $t_R$=3.95 min (UV$_{254\,nm}$); mass calculated for formula $C_{30}H_{26}FN_5O_4S$ 571.2, observed LCMS m/z 572.3 [M+H]$^+$.

Example 76

Part A:

Compound 991A was converted to Compound 997A by adapting the procedure described in Example 68, Part A. Mass calculated for formula $C_9H_{11}{}^{79}BrN_2S$ 258.0, observed m/z 259.2 [M+H]$^+$.

Part B:

Compound 997A was converted to Compound 997 following the procedure of Example 6. HPLC-MS $t_R$=3.07 min (UV$_{254\,nm}$); mass calculated for formula $C_{24}H_{23}N_5O_4S$ 477.2, observed LCMS m/z 478.3 [M+H]$^+$.

Example 77

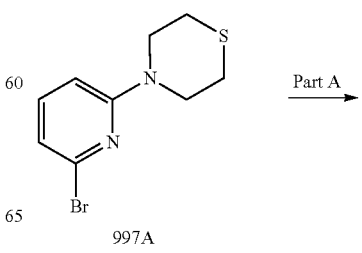

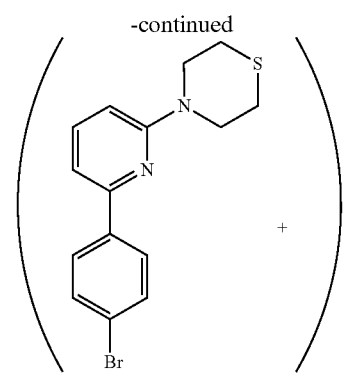

999A

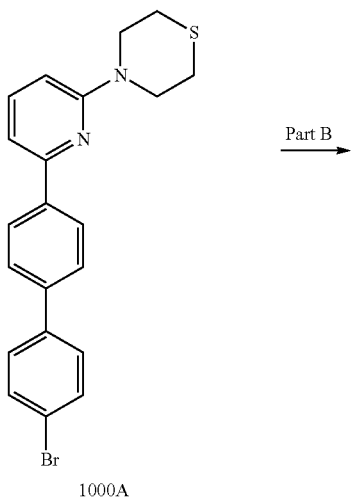

1000A reaction mixture was stirred at 80° C. for 18 h. The aqueous layer was separated and extracted with EtOAc (25 mL). The combined organic layers were washed with brine (~25 mL), dried over anhydrous $MgSO_4$, filtered, and concentrated. The crude product was purified first by sgc (0-10% EtOAc/hexanes gradient), then by PTLC (10% $Et_2O$/hexanes, developed twice). Compound 999A (46 mg) was isolated as the major product, while Compound 1000A (25 mg) was isolated as a minor product.

Compound 999A: Mass calculated for formula $C_{15}H_{15}BrN_2S$ 334.0, observed m/z 335.3 $[M+H]^+$.

Compound 1000A: Mass calculated for formula $C_{21}H_{19}BrN_2S$ 410.0, observed m/z 411.4 $[M+H]^+$.

Part B:

Compound 1000A was converted to Compound 1000 following the procedure of Example 6. HPLC-MS $t_R$=4.35 min ($UV_{254\ nm}$); mass calculated for formula $C_{36}H_{31}N_5O_4S$ 629.2, observed LCMS m/z 630.3 $[M+H]^+$.

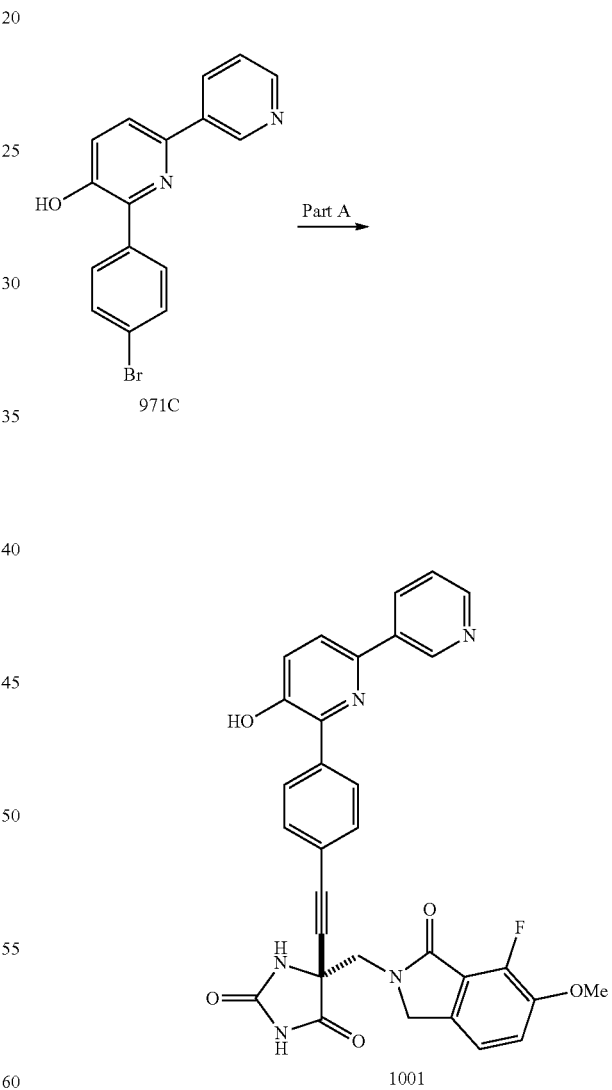

1000

Part A:

A flame-dried microwave tube containing Compound 997A (95.1 mg, 0.366 mmol), 4-bromobenzeneboronic acid (111 mg, 0.55 mmol), $(Ph_3P)_4Pd$ (42.4 mg, 0.037 mmol) and a magnetic stir bar was sealed, evacuated and refilled with nitrogen. Acetonitrile (1.1 mL) and 1 M aq. potassium carbonate solution (1.1 mL) were added sequentially and the Example 78

Compound 971C and Compound 23 were combined according to the procedure in Example 6 to afford Compound 1001. HPLC-MS $t_R$=2.69 min (UV$_{254\ nm}$); mass calculated for formula C$_{31}$H$_{22}$FN$_5$O$_5$ 563.2, observed LCMS m/z 564.3 [M+H]$^+$.

Example 79

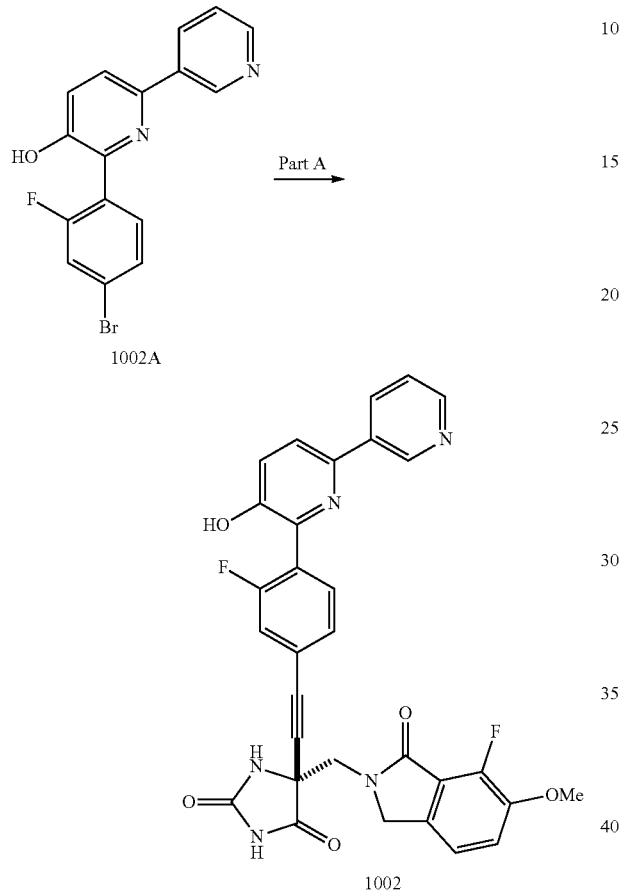

Compound 1002A, which was prepared via a procedure analogous to that for Compound 987B (Example 64), was converted to Compound 1002 by reaction with Compound 23 according to the method described in Example 6.

Compound 1002A: Mass calculated for formula C$_{16}$H$_{10}$$^{79}$BrFN$_2$O 344.0, observed m/z 345.2 [M+H]$^+$.

Compound 1002: HPLC-MS $t_R$=2.67 min (UV$_{254\ nm}$); mass calculated for formula C$_{31}$H$_{21}$F$_2$N$_5$O$_5$ 581.2, observed LCMS m/z 582.3 [M+H]$^+$.

Example 80

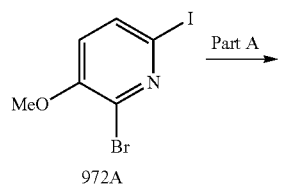

972A

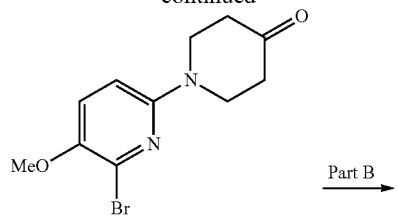

1003A

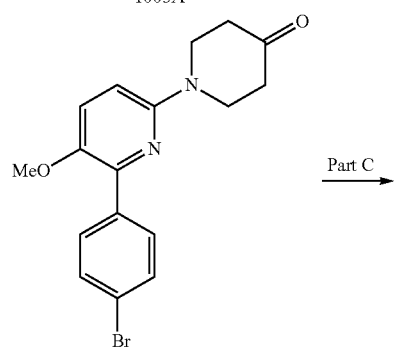

1003B

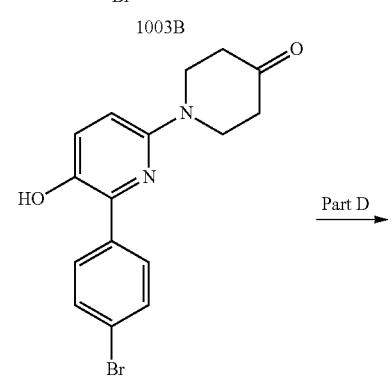

1003C

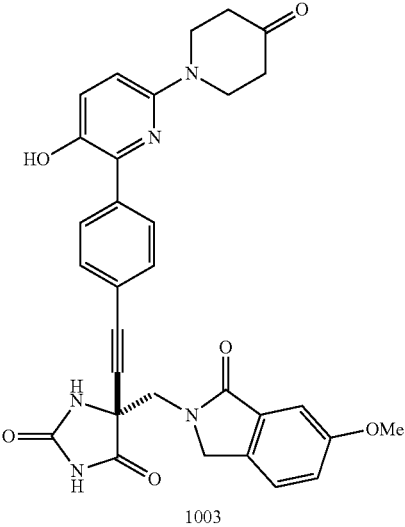

1003

Part A:
Compound 972A was allowed to react with piperidone hydrate hydrochloride according to conditions described in Example 49, Part A to afford Compound 1003A.
Part B:
Compound 1003A was converted to Compound 1003B following the procedure of Example 46, Part B.

Part C:

Solid anhydrous aluminum chloride (167 mg, 1.26 mmol) was added to a stirred solution of Compound 1003B (151 mg, 0.42 mmol) in 1,2-dichloroethane (4 mL). The reaction mixture was heated with stirring at reflux overnight, then allowed to cool, and was diluted with $CH_2Cl_2$ (~50 mL). The solution was washed sequentially with water (2×~25 mL) and brine (~25 mL). The organic layer was dried over $MgSO_4$, filtered, and concentrated under reduced pressure. The residue was purified by sgc (0-70% EtOAc-hexanes) to afford 22 mg of pure Compound 1003C as a yellow oil. Mass calculated for formula $C_{16}H_{15}{}^{79}BrN_2O_2$ 346.0, observed m/z 347.2 $[M+H]^+$.

Part D:

Compound 1003C was converted to Compound 1003 following the procedure of Example 6. HPLC-MS $t_R$=2.93 min ($UV_{254\ nm}$); mass calculated for formula $C_{31}H_{26}FN_5O_6$ 583.2, observed LCMS m/z 584.3 $[M+H]^+$.

Example 81

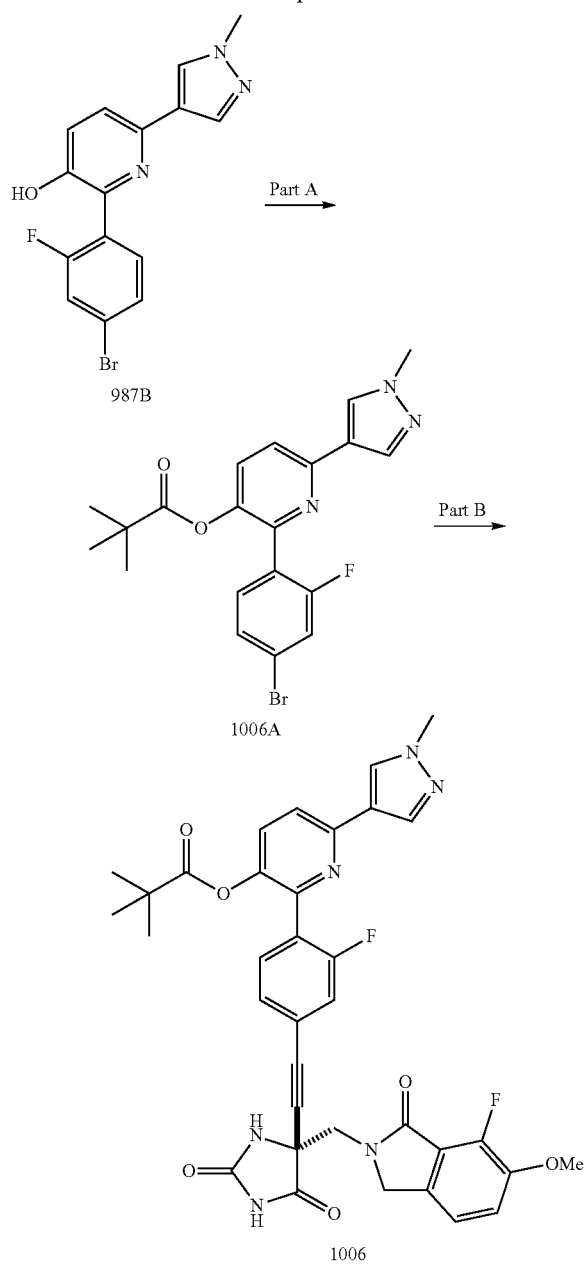

Part A:

Lithium hydride (6.8 mg, 0.86 mmol) was added to a stirred solution of Compound 987B (200 mg, 0.57 mmol) in DMF (5 mL). To this solution was added a solution of chloromethyl pivalate (95 mg, 0.63 mmol) in DMF (1.3 mL). The reaction was allowed to proceed overnight with stirring at rt. The reaction was quenched by addition of 1 N HCl (0.3 mL). The reaction mixture was diluted with EtOAc (~50 mL) and was then washed sequentially with water (3×~25 mL) and brine (~25 mL). The organic layer was dried over $MgSO_4$, filtered, and concentrated. The residue was purified by sgc (10-75% EtOAc-hexanes gradient) to give 238 mg of Compound 1006A as a pale yellow oil. Mass calculated for formula $C_{20}H_{19}{}^{79}BrFN_3O_2$ 431.1, observed m/z 432.3 $[M+H]^+$.

Part B:

Compound 1006A was converted to Compound 1006 following the procedure of Example 6. HPLC-MS $t_R$=3.86 min ($UV_{254\ nm}$); mass calculated for formula $C_{35}H_{30}F_2N_6O_6$ 668.2, observed LCMS m/z 669.4 $[M+H]^+$.

Example 82

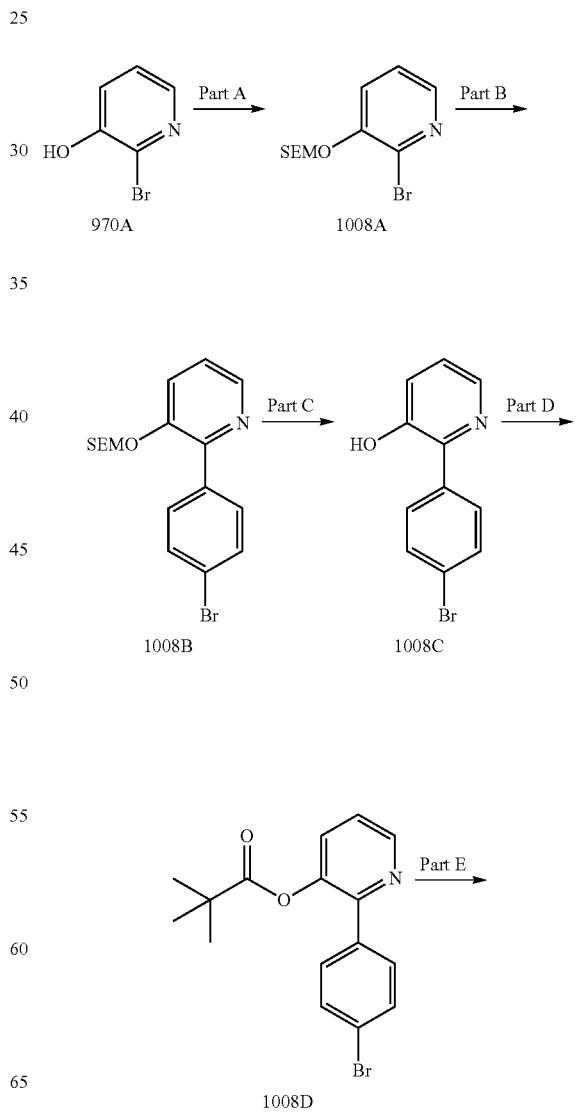

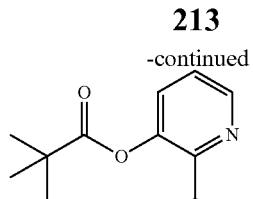

1008

Part A:

Compound 970A was converted to Compound 1008A using the procedure in Example 46, Part A.

Part B:

Compound 1008A was converted to Compound 1008B using the procedure in Example 46, Part B.

Part C:

Compound 1008B was converted to Compound 1008C using the procedure in Example 46, Part C.

Part D:

Pivaloyl chloride (0.060 mL, 63 mg, 0.52 mmol) was added to a stirred solution of Compound 1008C (108 mg, 0.43 mmol) and triethylamine (0.15 mL, 109 mg, 1.08 mmol) in $CH_2Cl_2$ (4 mL) at rt. The reaction was allowed to proceed overnight at rt. The reaction mixture was diluted with $CH_2Cl_2$ (~25 mL) and was washed sequentially with water (~25 mL) and brine (~25 mL). The organic layer was dried over anhydrous $MgSO_4$, filtered, and concentrated under reduced pressure. The residue obtained was purified by sgc (0-75% EtOAc-hexanes gradient) to give 100 mg of the desired Compound 1008D as a pale yellow oil (69% yield). Mass calculated for formula $C_{16}H_{16}{}^{79}BrNO_2$ 333.0, observed m/z 334.2 $[M+H]^+$.

Part E:

Compound 1008D was converted to Compound 1008 following the procedure of Example 6. HPLC-MS $t_R$=3.74 min ($UV_{254\,nm}$); mass calculated for formula $C_{31}H_{28}N_4O_6$ 552.2, observed LCMS m/z 553.3 $[M+H]^+$.

Example 83

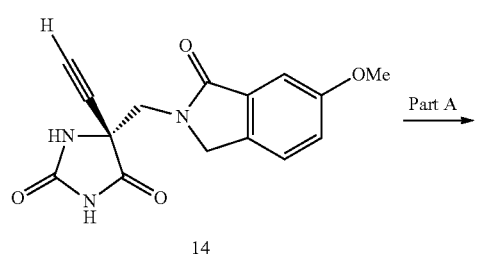

14

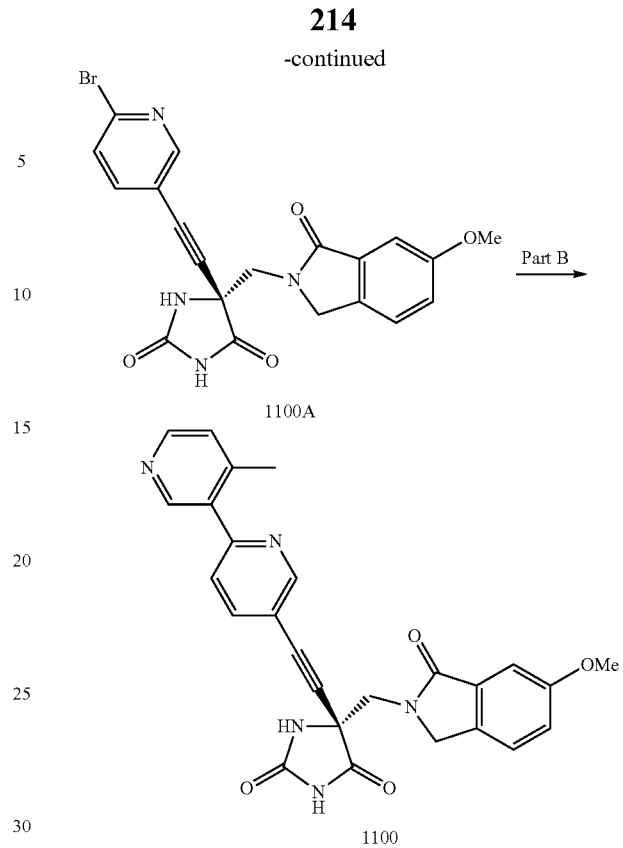

1100A

1100

Part A

Compound 14 (304 mg, 1.02 mmol), 2-bromo-5-iodopyridine (338 mg, 1.19 mmol), copper (I) iodide (7.6 mg, 0.04 mmol), and $PdCl_2(PPh_3)_2$ (38 mg, 0.05 mmol) were added to a Schlenck tube equipped with a stir bar. The tube was capped with a septum and cycled between vacuum and $N_2$ five times. DMF (3 mL) was added via syringe and the flask was cycled between vacuum and $N_2$ four times. Triethylamine (0.4 mL) was added via syringe and the flask was placed in a 80° C. oil bath. The reaction mixture was stirred overnight at 80° C. under $N_2$. The solution was partially concentrated and acetic acid (0.8 mL) was added. The resulting crude reaction mixture was injected directly onto an Isco C-18 cartridge and eluted with a 20%-85% $CH_3CN$—$H_2O$ gradient with 0.1% (by volume) formic acid added to each component of the mobile phase. The major peak was collected as impure 1100A. The impure product was dissolved in 10% absolute $EtOH/CH_2Cl_2$ and adsorbed onto 15 g of silica gel which was dried down and added to the top of a $SiO_2$ column. The product was purified via flash sgc using a 1%-5% EtOH/$CH_2Cl_2$ gradient as the mobile phase. Compound 1100A was obtained as a white solid (0.23 g). LRMS calcd. 454.03 obsd 454.99, 456.99—(bromine isotope pattern).

Part B

Potassium phosphate (196 mg, 0.923 mmol), bis(tri-tert-butylphosphine) palladium (0) (18 mg, 0.13 mmol), and 4-methylpyridine-3-boronic acid (124 mg, 0.905 mmol) were added to a microwave tube equipped with a stir bar. The vial was capped and connected to a vacuum manifold via syringe needle and tubing. The microwave tube was cycled between vacuum and $N_2$ three times. Compound 1100A (123 mg, 0.27 mmol) was dissolved in DMF (2.0 mL) and water (0.4 mL). The resulting solution was added to the microwave vial via syringe. The vial was cycled between vacuum and $N_2$ four times. The reaction mixture was placed in the microwave and heated at 150° C. for 1 h. The crude product was diluted with acetic acid (0.25 mL) and injected directly onto an Isco C-18 cartridge. The cartridge was eluted with a 20%-80% CH$_3$CN—H$_2$O gradient with 0.1% (by volume) formic acid added to each component of the mobile phase. The major peak was collected as impure 1100. The impure product was purified via prep TLC using 7% absolute EtOH/CH$_2$Cl$_2$ as the mobile phase to give 14 mg of 1100 as a white solid. LRMS calcd. 467.16 obsd 468.3.

Example 84

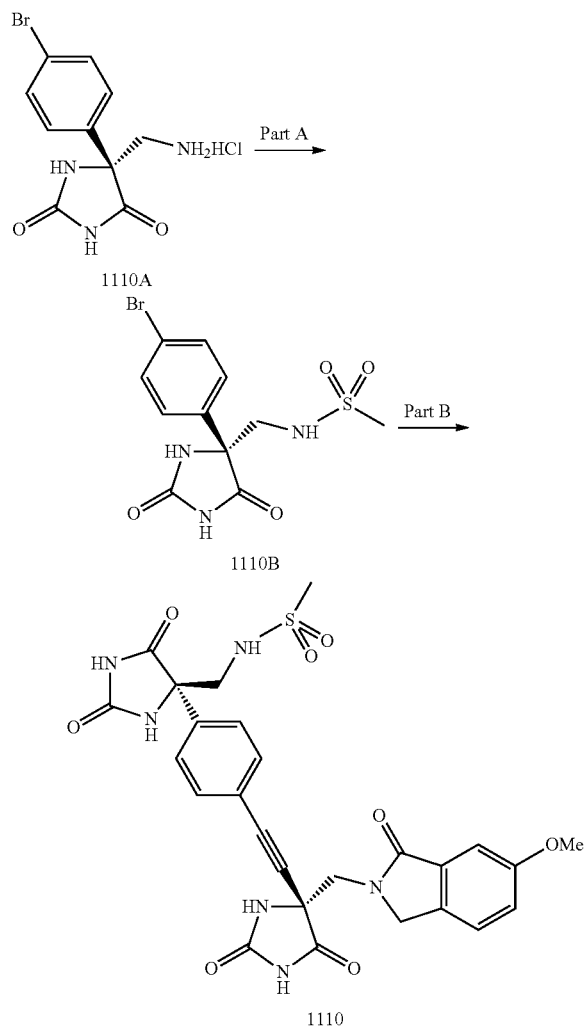

Part A

Compound 1110A was obtained using procedures described in Yu, W.; Tong, L. et al Compounds for the treatment of inflammatory disorders US 2007/0219218 and/or Yu, W.; Tong, L. et at PCT Int. Appl. (2006), WO2006019768.

Compound 1110A (301 mg, 0.94 mmol), DMF (10 mL), and N-methyl morpholine (0.220 mL, 2.0 mmol) were added to a flask equipped with a stir bar. Methane sulfonyl chloride was added (0.075 mL, 0.97 mmol) and the flask was left stirring at rt over the weekend. The reaction mixture was partially concentrated on the rotovap and water (1.5 mL) was added. The resulting solution (about 6 mL) was injected directly onto an Isco 130 g C-18 cartridge. The cartridge was eluted using a 15%-85% CH$_3$CN/H$_2$O gradient with 0.1% formic acid added to each component of the mobile phase. Compound 1110B was obtained (0.28 g/82% yield) as a white solid. LCMS calcd. 361.0 obsd 364.2.

Part B

Compound 1110B was converted to 1110 using a Sonogashira procedure similar to that described in Example 83 Part A. LCMS calcd 580.1 obsd 581.3.

Compounds 2215 and 2218 were prepared using procedures similar to those described in Example 84 and Example 6, Part B.

Compounds 2216 and 2218 were prepared using procedures similar to those described in Example 1, Example 84 and Example 6, Part B.

Example 85

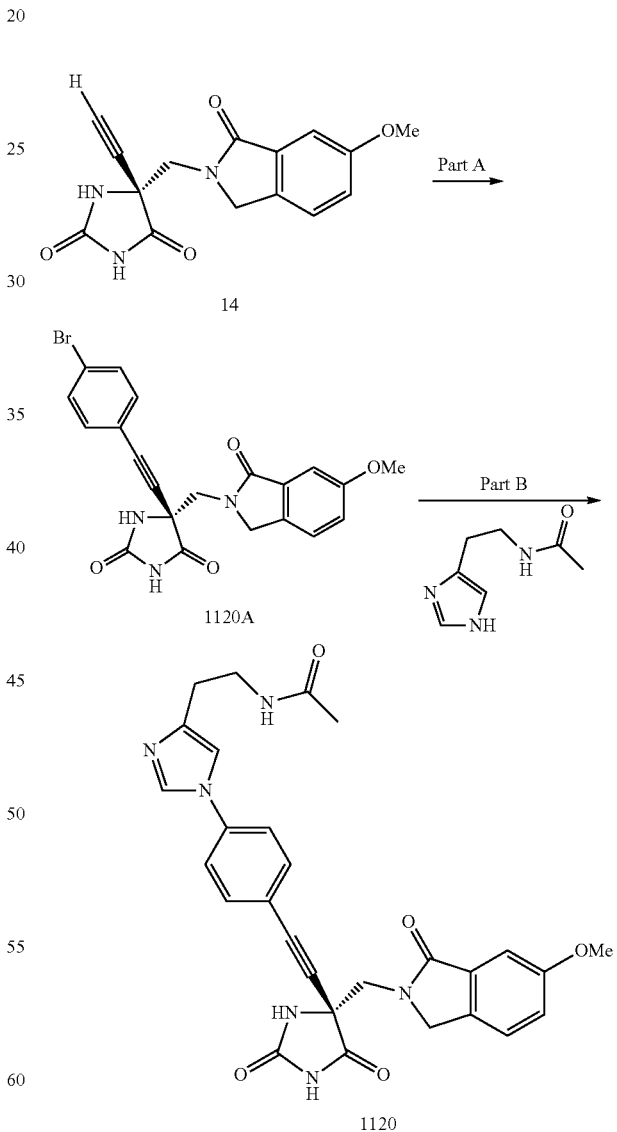

Part A.

Compound 14 and para-bromo-iodobenzene were converted to 1120A using a Sonogashira procedure similar to that described in Example 83 Part A. ¹HNMR (CD₃OD) δ 7.55-7.48 (m, 2H), 7.47-7.40 (m, 1H), 7.37-7.31 (m, 1H), 7.30-7.23 (m, 1H), 7.21-7.13 (m, 1H), 4.71-4.49 (m, 2H), 4.28-4.19 (m, 2H), 3.84 (s, 3H).

Part B

Compound 1120A (0.10 g, 0.21 mmol), N-acetylhistamine (39 mg, 0.25 mmol), CuI (10 mg, 0.052 mmol), 8-hydroxyquinoline (8 mg, 0.55 mmol), and cesium carbonate (68 mg, 0.20 mmol) were added to a rb flask and placed under N₂. DMF (1.5 mL, Aldrich anhydrous) was added via syringe and the flask was heated overnight at 125° C. The reaction mixture was partially concentrated in vacuo, then purified via reverse phase chromatography using a 5%-95% CH₃CN—H₂O gradient with 0.1% (by volume) formic acid added to each component of the mobile phase. The major peak was collected as impure 1120. The impure product was dissolved in MeOH. Methanolic ammonia was added until the pH was >7. The solution was concentrated to dryness. The impure product was purified via prep scg using CH₂Cl₂/MeOH/NH₄OH 100/10/1 as the mobile phase to give 17 mg of 1120 as a white solid. LCMS calcd. 526.19 obsd 527.3.

Compound 2228 was prepared using procedures similar to those described in Example 85 and Example 6, Part B.

Example 86

Compound 1100A was converted to 1130 using a procedure similar to that described in Example 85. LCMS calcd. 527.19 obsd 528.3.

Compound 2226 was prepared using procedures similar to the ones described in Example 86 and Example 6, Part B.

Example 87

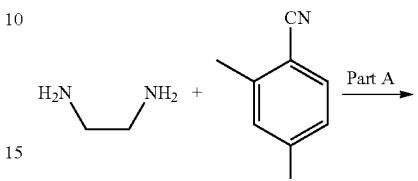

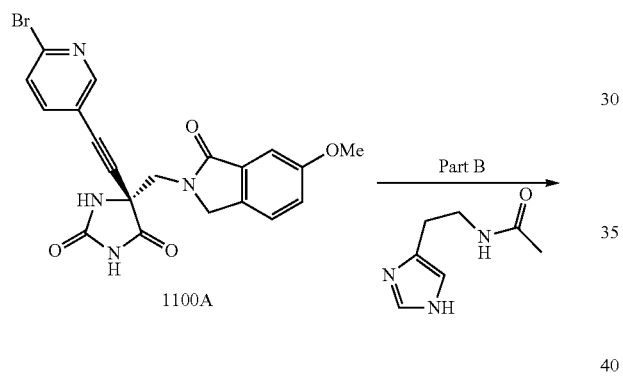

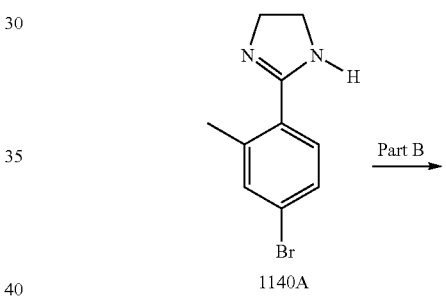

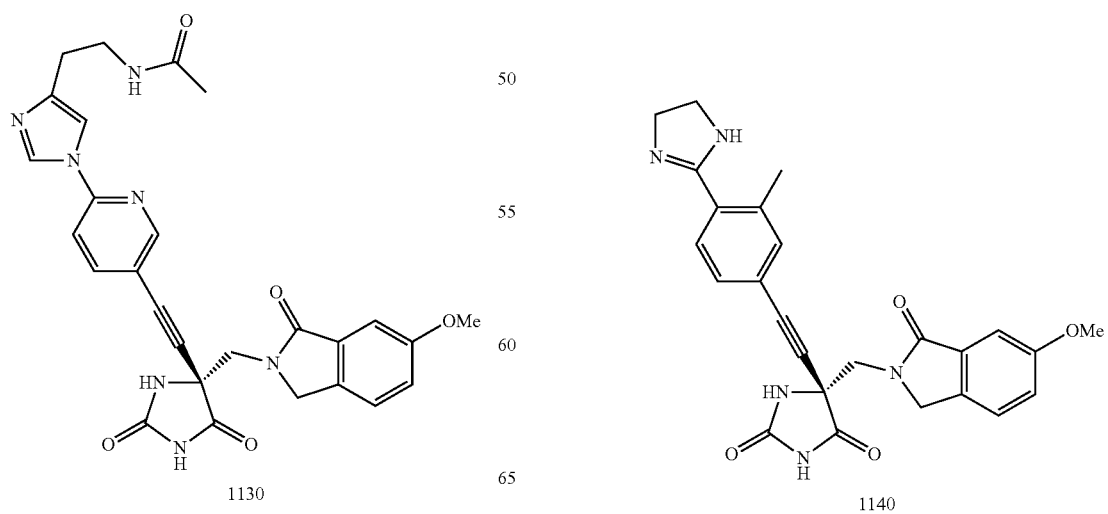

Part A

1-Bromo-3-methyl-4-cyanobenzene (0.50 g, 2.55 mmol) and ethylene diamine (0.61 g) were added to a microwave tube equipped with a stir bar. The tube was heated in a microwave at 170° C. for 30 min. The crude reaction mixture was purified via sgc using a 5%-100% gradient of (CH$_2$Cl$_2$/MeOH/NH$_4$OH 100/10/1) in CH$_2$Cl$_2$ as the mobile phase to give 66 mg of 1140A. LRMS calcd. 238.01 obsd 239.05.

Compound 2222 was prepared using procedures similar to those described in Example 87 and Example 6, Part B.

Example 88

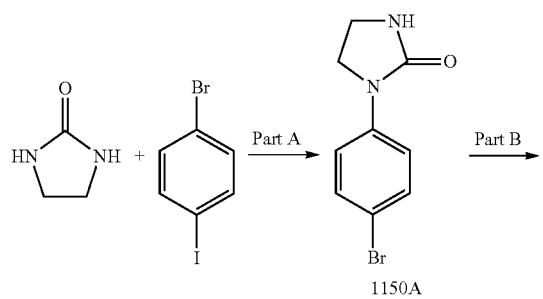

1150A

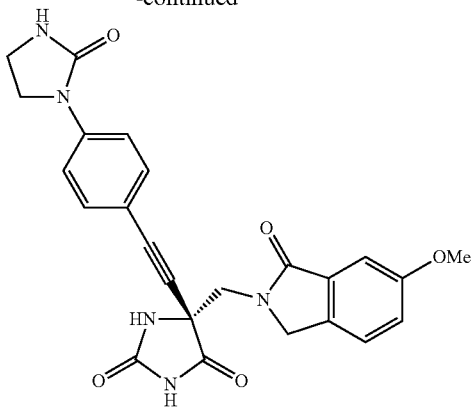

1150

Part A

2-Imidazolidone (0.30 g, 3.48 mmol), 1-bromo-4-iodobenzene (0.50 g, 1.77 mmol), CuI (34 mg, 0.18 mmol), 1,10-phenanthroline (64 mg, 0.36 mmol), cesium carbonate (1.15 g, 3.53 mmol) and dimethylacetamide (5 mL) were added to a rb flask equipped with a stir bar. The flask was placed under N$_2$ and heated to 80° C. The reaction mixture was stirred at 80° C. for 4 h. The reaction mixture was diluted with EtOAc and washed with water. The organic layer was concentrated to dryness. The crude product was purified via sgc using a 50%-100% EtOAc/Hexanes gradient as the mobile phase to give 62 mg of 1150A as the product.

Part B

Compound 1150A was converted to 1150 using Sonogashira conditions similar to those described in Example 83 Part A.

Compound 1160 and 1170 were prepared using procedures similar to those described in Example 88.

Example 89

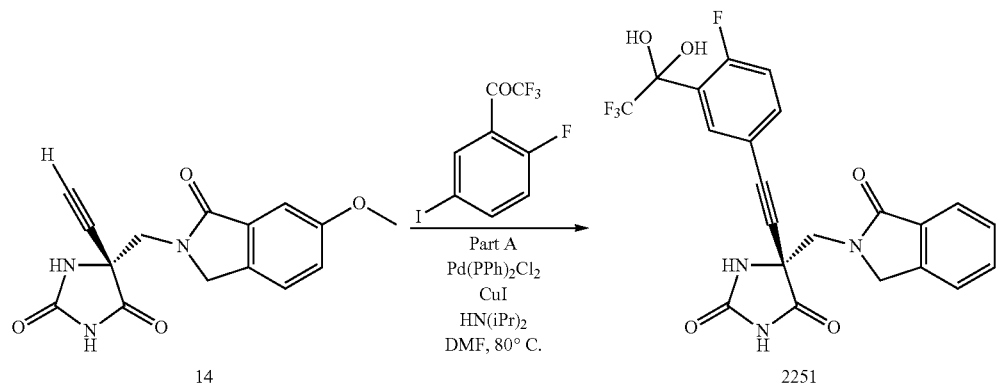

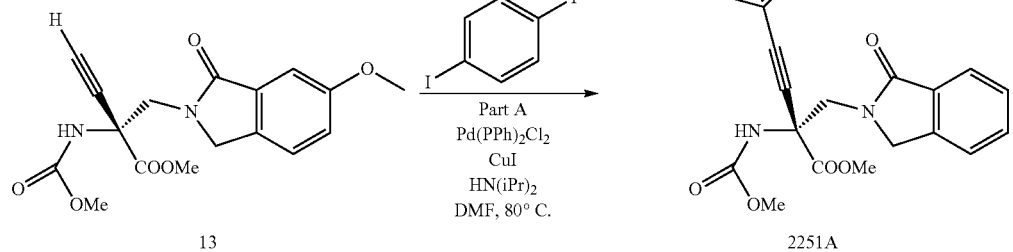

Part A:

A mixture of 14 (0.05 g, 0.16 mmol), 5'-iodo-2',2,2,2-tetrafluoroacetophenone (0.08 g, 0.25 mmol), copper iodide (0.005 g, 0.026 mmol), Pd(PPh₃)₂Cl₂ (0.008 g, 0.0113 mmol) and diisopropylethylamine (0.047 mL, 0.33 mmol) in DMF (1 mL) was charged into a sealed tube and purged with nitrogen (3×). The mixture was heated at 80° C. for 12 h. The reaction mixture was filtered and the filtrate was concentrated and purified by reverse phase chromatography using a 0.1% formic acid in the aqueous mobile phase (100% water to 50% acetonitrile/water) to provide 0.028 g (33%) of pure product 2251.

Alternate Part A:

Alternatively, compound 13 is subjected in Part A conditions to provide 2251A.

Part B:

Compound 2251A is dissolved in 7N ammonia/methanol and the solution is charged into a sealed tube. The mixture is heated to 90° C. for 24 h. After cooling, the solvent is removed and the crude is purified by reverse phase chromatography as described above to provide 2251.

The following compounds were made using the procedures described in Example 89, using corresponding appropriate iodo/bromo derivative (commercially available) in step Part A and compound 14 or 23. In alternate Part A compound 13 or 22 is used instead of 14/23.

| ID | STRUCTURE | (M + 1)⁺ | LC MS* $t_R$ |
|---|---|---|---|
| 2247 | 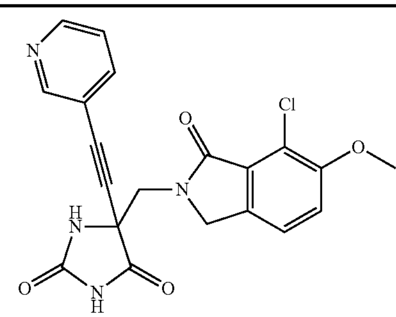 | 411.2 | 2.34 |
| 2248 | 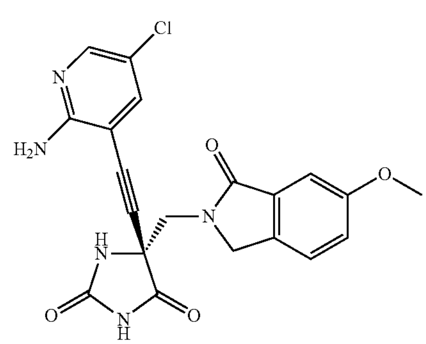 [SMILES: COc1ccc2c(c1)C(=O)N(C[C@@]1(C#Cc3cc(Cl)cnc3N)NC(=O)NC1=O)C2] | 426.2 | 2.81 |

| ID | STRUCTURE | (M + 1)⁺ | LC MS* t_R |
|---|---|---|---|
| 2249 | 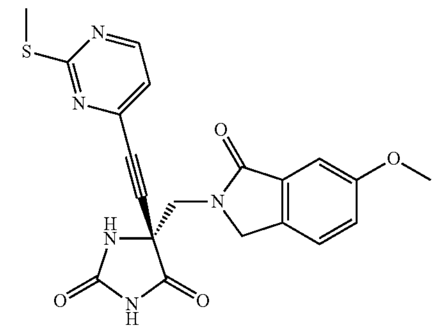 [SMILES: COc1ccc2c(c1)C(=O)N(C[C@@]1(C#Cc3ccnc(SC)n3)NC(=O)NC1=O)C2] | 424.2 | 2.91 |
| 2250 | 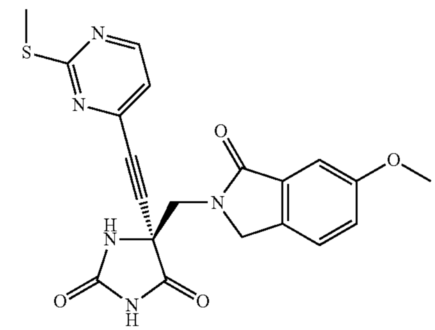 [SMILES: COc1ccc2c(c1)C(=O)N(C[C@]1(C#Cc3ccnc(SC)n3)NC(=O)NC1=O)C2] | 424.2 | 3.11 |
| 2251 | 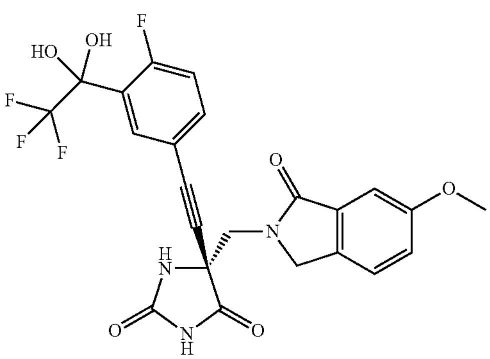 [SMILES: COc1ccc2c(c1)C(=O)N(C[C@@]1(C#Cc3ccc(F)c(C(O)(O)C(F)(F)F)c3)NC(=O)NC1=O)C2] | 508.3 | 3.15 |
| 2252 | 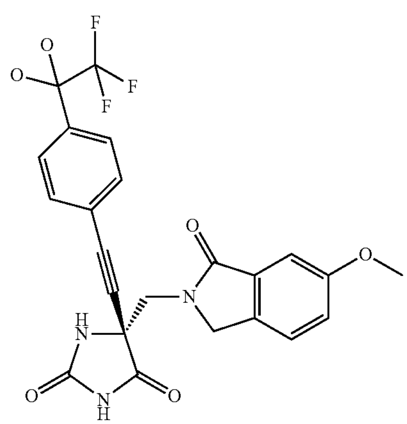 [SMILES: COc1ccc2c(c1)C(=O)N(C[C@@]1(C#Cc3ccc(C(O)(O)C(F)(F)F)cc3)NC(=O)NC1=O)C2] | 490 | 3.10 |

-continued
| ID | STRUCTURE | (M + 1)+ | LC MS* t$_R$ |
|---|---|---|---|
| 2253 | 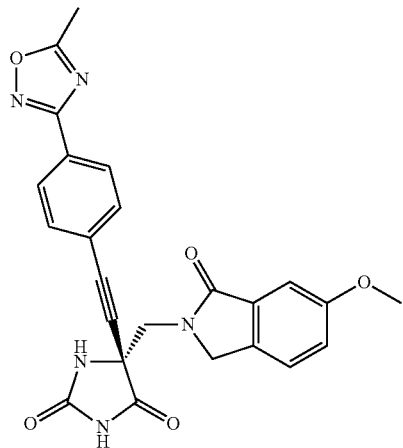 [SMILES: COc1ccc2c(c1)C(=O)N(C[C@@]1(C#Cc3ccc(-c4noc(C)n4)cc3)NC(=O)NC1=O)C2] | 458.3 | 3.23 |
| 2254 | 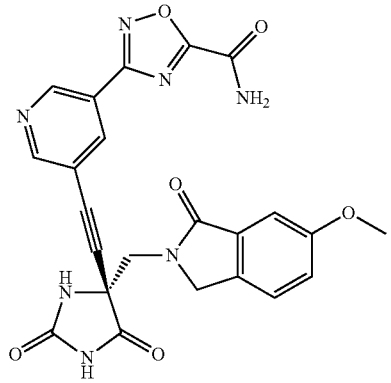 [SMILES: COc1ccc2c(c1)C(=O)N(C[C@@]1(C#Cc3cncc(-c4noc(C(N)=O)n4)c3)NC(=O)NC1=O)C2] | 488.3 | 2.61 |
| 2255 | 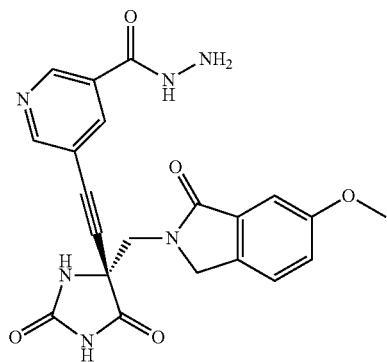 [SMILES: COc1ccc2c(c1)C(=O)N(C[C@@]1(C#Cc3cncc(C(=O)NN)c3)NC(=O)NC1=O)C2] | 435.2 | 1.95 |
| 2256 | 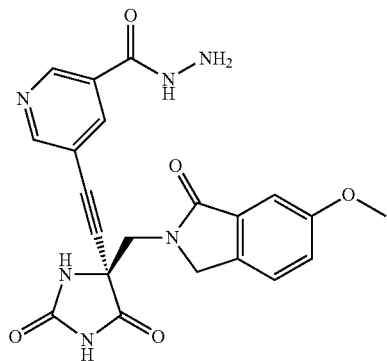 [SMILES: COc1ccc2c(c1)C(=O)N(C[C@]1(C#Cc3cncc(C(=O)NN)c3)NC(=O)NC1=O)C2] | 435.2 | 1.96 |

-continued
| ID | STRUCTURE | (M + 1)⁺ | LC MS* $t_R$ |
|---|---|---|---|
| 1505 | 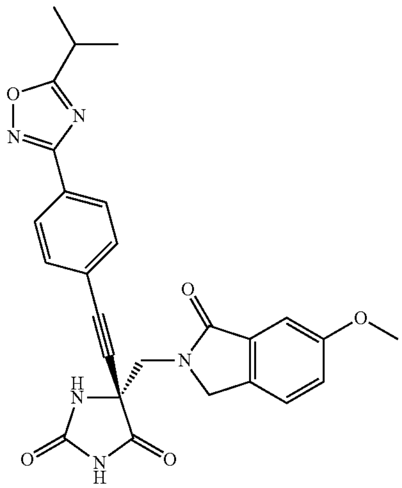 [SMILES: COc1ccc2c(c1)C(=O)N(C[C@@]1(C#Cc3ccc(-c4noc(C(C)C)n4)cc3)NC(=O)NC1=O)C2] | 486.3 | 4.05 |
| 1509 | 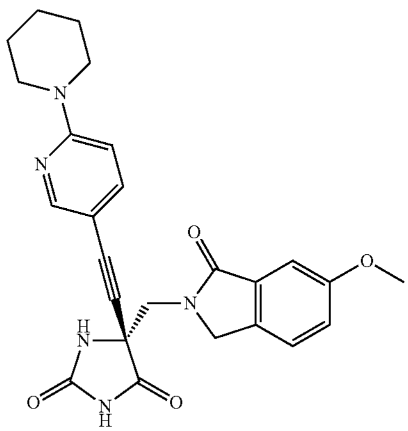 [SMILES: COc1ccc2c(c1)C(=O)N(C[C@@]1(C#Cc3ccc(N4CCCCC4)nc3)NC(=O)NC1=O)C2] | 460.3 | 2.35 |
Example 90
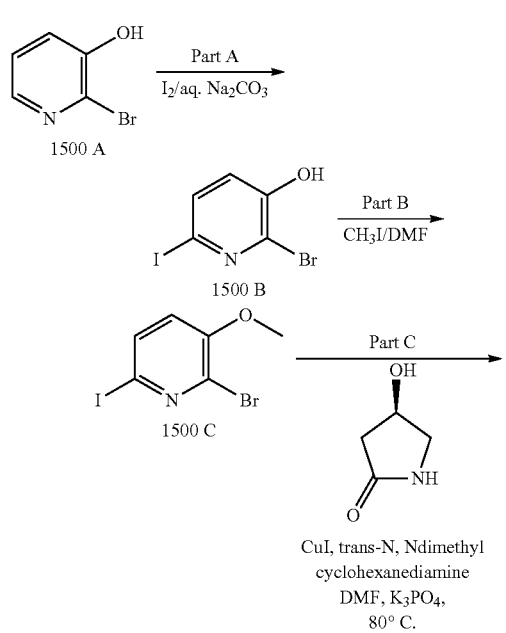
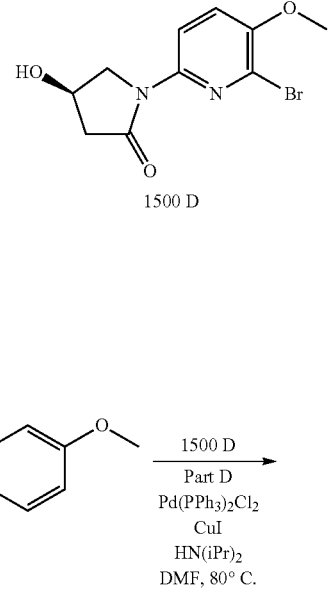

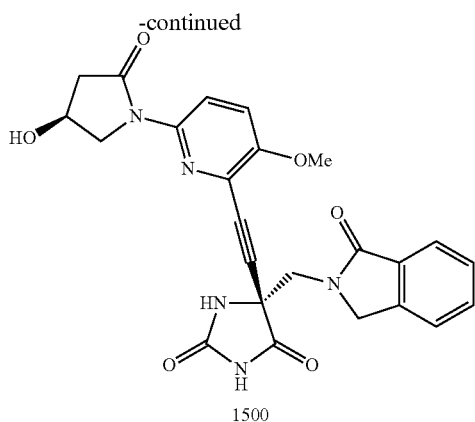

1500

Part A and Part B:

Intermediate 1500 C was prepared following the literature procedures. See Koch, V.; Schnatterer, S. *Synthesis*, 497, 1990.2 and Chapman, G. M.; Stanforth, S. P.; Tarbit, B; Watson, M. D. *Journal of the Chemical Society, Perkin Transactions* 1, 581, 2002.

Part C:

A mixture of 2-Bromo-5-iodo-3-methoxy pyridine 1500 C (0.5 g, 1.59 mmol), (S)-(−)-4-hydroxy-2-pyrrolidinone (commercially available, 0.16 g, 1.59 mmoles), Potassium phosphate, 0.68 g, 3.2 mmol), CuI (0.015 g, 0.079 mmol) and DMF (4 ml) was charged into a sealed tube and purged with nitrogen (3×). trans-N,N-Dimethyl-1,2-cyclohexanediamine (0.01 g, 0.07 mmol) was added under $N_2$ through the seal. The reaction was heated at 80° C. for 16 h. After cooling to room temperature the reaction was diluted with EtOAc (20 ml), washed with water (3×20 ml), dried ($Na_2SO_4$), filtered, concentrated to give a crude which was purified by flash column chromatography (ISCO CombiFlash Rf, $SiO_2$, 12 g cartridge (Hexanes to 50% EtOAc/hexanes) to yield compound 1500D (0.16 g, 35%).

Part D:

A mixture of 14 (0.04 g, 0.14 mmol), 1500 D (0.04 g, 0.14 mmol), copper iodide (0.004 g, 0.023 mmol), $Pd(PPh_3)_2Cl_2$ (0.005 g, 0.008 mmol) and diisopropylethylamine (0.1 mL, 0.86 mmol) in DMF (3 mL) was charged into a sealed tube and purged with nitrogen (3×). The mixture was heated at 80° C. for 12 h. The reaction mixture was filtered and the filtrate was concentrated and purified by reverse phase chromatography using a 0.1% formic acid in the aqueous mobile phase (100% water to 50% acetonitrile/water) to provide 0.045 g (67%) of pure product 1500.

The following compounds were made using the procedure described in Example 90, using corresponding appropriate amine in step Part C and compound 14 or 23 in step Part D.

| ID | STRUCTURE | (M + 1)+ | LC MS* $t_R$ |
|---|---|---|---|
| 1500 | 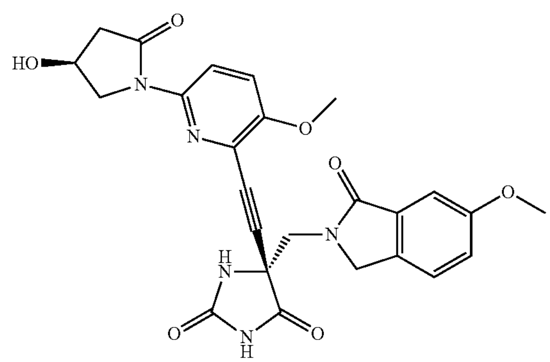 [SMILES: COc1ccc2c(c1)C(=O)N(C[C@@]1(C#Cc3nc(N4C[C@@H](O)CC4=O)ccc3OC)NC(=O)NC1=O)C2] | 506.3 | 2.62 |
| 1501 | 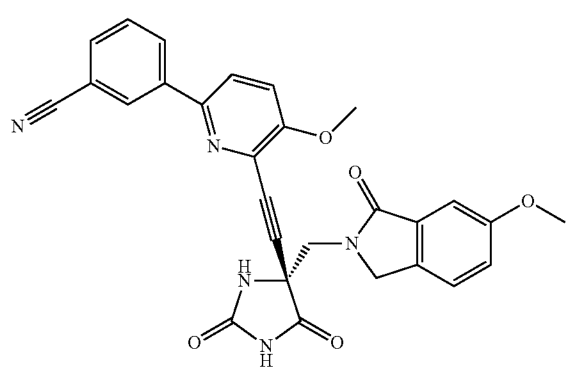 [SMILES: COc1ccc2c(c1)C(=O)N(C[C@@]1(C#Cc3nc(-c4cccc(C#N)c4)ccc3OC)NC(=O)NC1=O)C2] | 508.3 | 3.65 |

-continued

| ID | STRUCTURE | (M + 1)+ | LC MS* $t_R$ |
|---|---|---|---|
| 1502 | 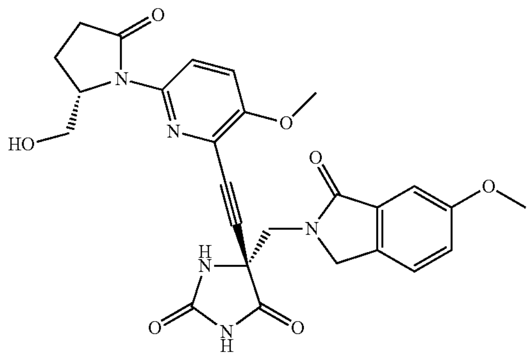 [SMILES: COc1ccc2c(c1)C(=O)N(C[C@@]1(C#Cc3nc(N4C(=O)CC[C@H]4CO)ccc3OC)NC(=O)NC1=O)C2] | 520.3 | 2.60 |
| 1503 | 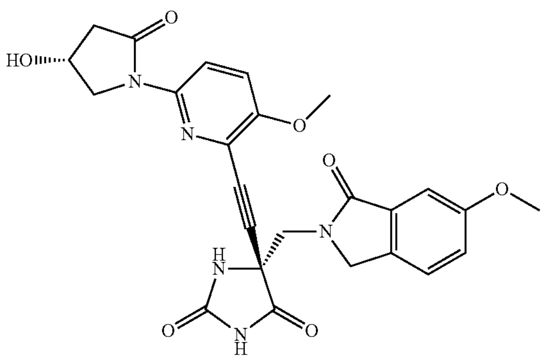 [SMILES: COc1ccc2c(c1)C(=O)N(C[C@@]1(C#Cc3nc(N4C[C@H](O)CC4=O)ccc3OC)NC(=O)NC1=O)C2] | 506.3 | 2.48 |
| 1504 | 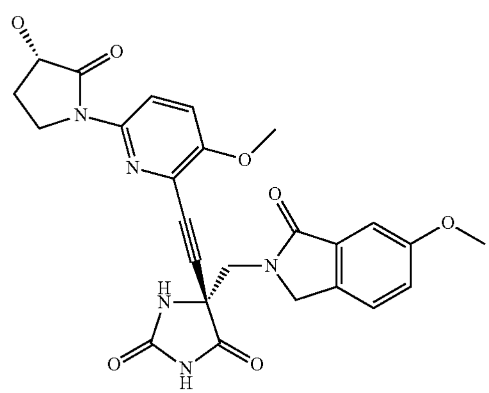 [SMILES: COc1ccc2c(c1)C(=O)N(C[C@@]1(C#Cc3nc(N4CC[C@H](O)C4=O)ccc3OC)NC(=O)NC1=O)C2] | 506.3 | 2.73 |
| 1506 | 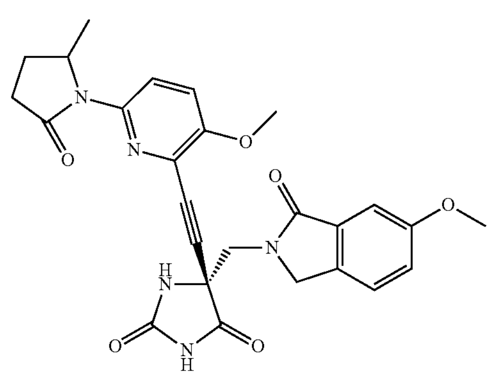 [SMILES: COc1ccc2c(c1)C(=O)N(C[C@@]1(C#Cc3nc(N4C(=O)CCC4C)ccc3OC)NC(=O)NC1=O)C2] | 504.3 | 2.88 |

-continued

| ID | STRUCTURE | (M + 1)+ | LC MS* $t_R$ |
|---|---|---|---|
| 1507 | 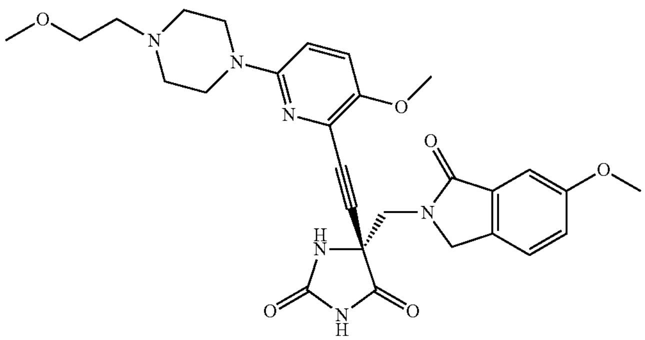 | 549.3 | 2.21 |
| 1508 | 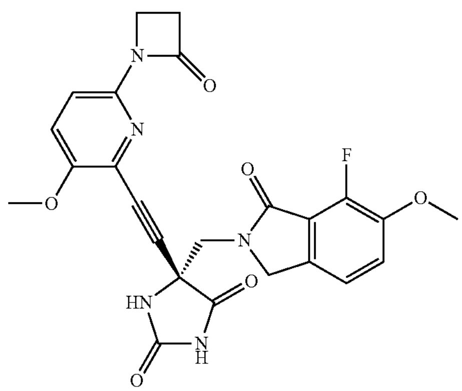 | 494.3 | 2.76 |
| 1510 | 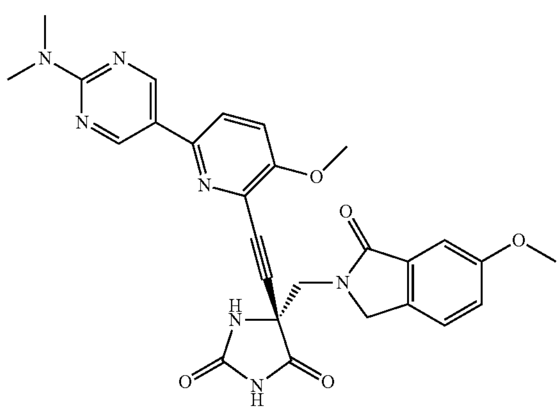 | 528.3 | 2.83 |
| 1511 | 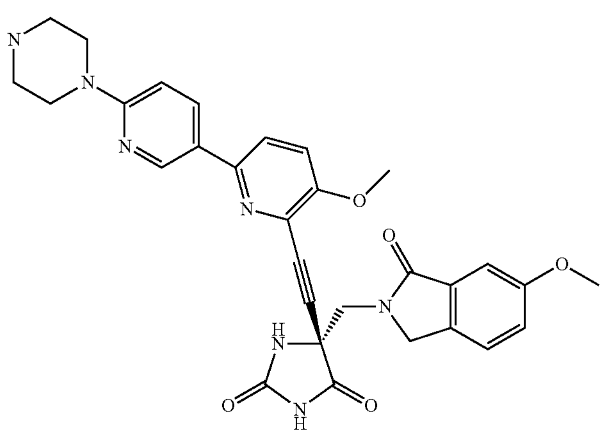 [SMILES: COc1ccc2c(c1)C(=O)N(C[C@@]1(C#Cc3nc(-c4ccc(N5CCNCC5)nc4)ccc3OC)NC(=O)NC1=O)C2] | 568.3 | 1.94 |

-continued
| ID | STRUCTURE | (M + 1)+ | LC MS* t$_R$ |
|---|---|---|---|
| 1512 | 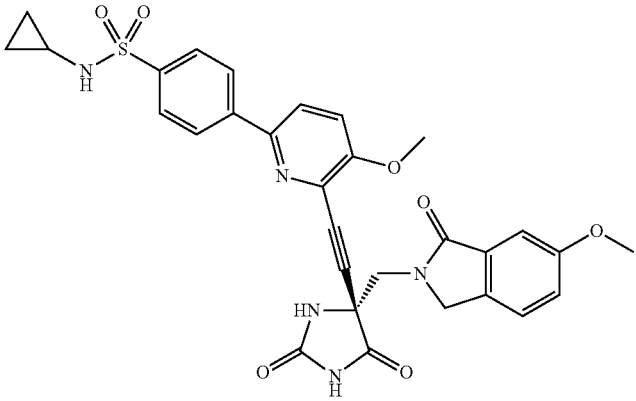 [SMILES: COc1ccc2c(c1)C(=O)N(C[C@@]1(C#Cc3nc(-c4ccc(S(=O)(=O)NC5CC5)cc4)ccc3OC)NC(=O)NC1=O)C2] | 602.3 | 3.54 |
| 1513 | 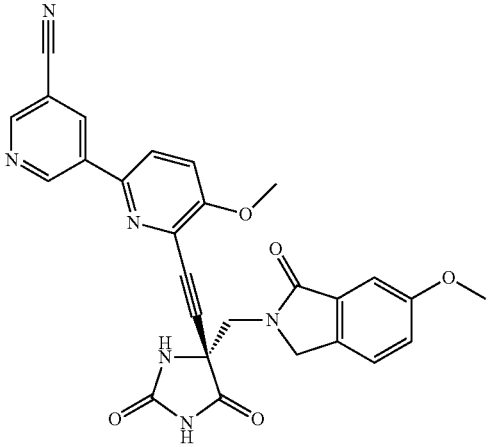 [SMILES: COc1ccc2c(c1)C(=O)N(C[C@@]1(C#Cc3nc(-c4cncc(C#N)c4)ccc3OC)NC(=O)NC1=O)C2] | 509.3 | 3.16 |
| 1514 | 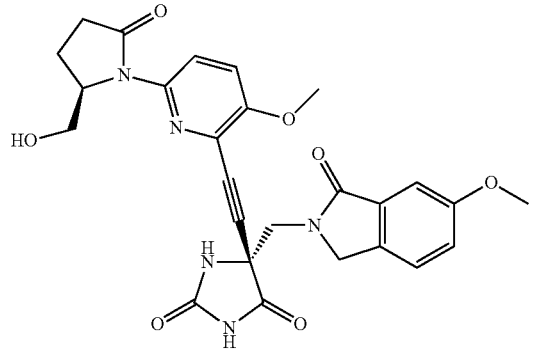 [SMILES: COc1ccc2c(c1)C(=O)N(C[C@@]1(C#Cc3nc(N4C(=O)CC[C@@H]4CO)ccc3OC)NC(=O)NC1=O)C2] | 509.3 | 3.38 |
| 1515 | 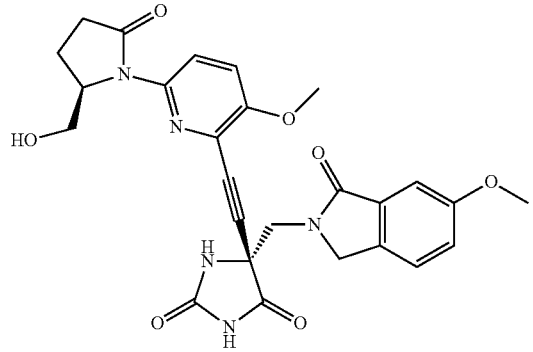 [SMILES: COc1ccc2c(c1)C(=O)N(C[C@@]1(C#Cc3nc(N4C(=O)CC[C@@H]4CO)ccc3OC)NC(=O)NC1=O)C2] | 520.3 | 2.6 |

Example 91

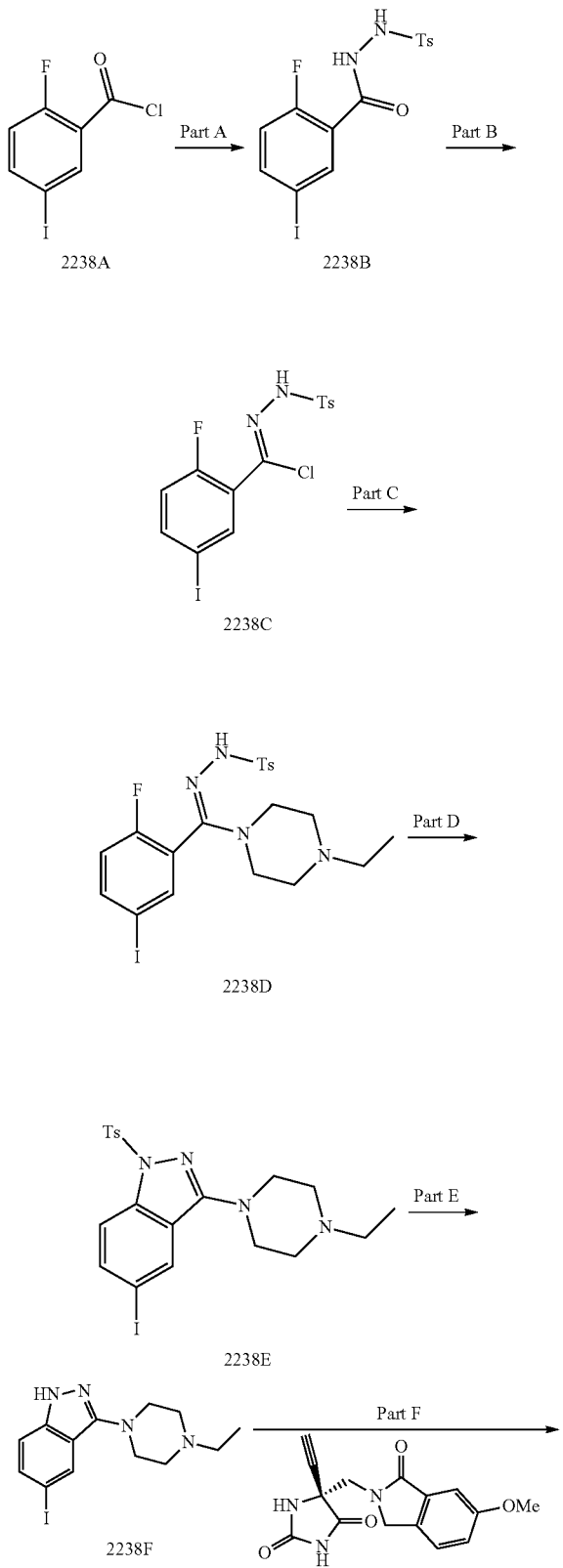

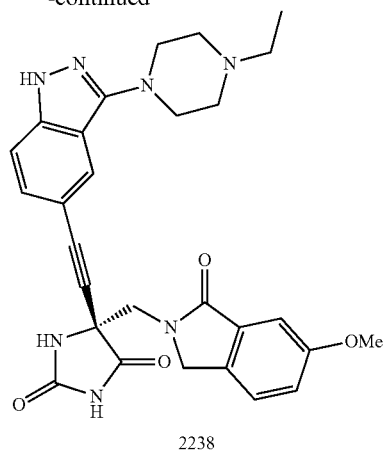

2238

Part A:

Compound 2238A (1.0 g, 4.2 mmol) and tosyl hydrazide (860 mg, 4.62 mmol) were dissolved in NMP (5 mL) and stirred at 150° C. for 15 minutes in a microwave. The reaction was diluted with ethyl acetate and water. The organic layer was dried over sodium sulfate and concentrated to provide compound 2238B that was used without purification (1.8 g).

Part B:

Compound 2238B (500 mg, 1.15 mmol) was dissolved in thionyl chloride (5 mL) and refluxed for 2 hours. The thionyl chloride was removed under reduced pressure and the resulting solids were triturated with hexanes to provide compound 2238C (420 mg). $^1$H NMR (400 MHz, CDCl$_3$): δ 8.2 (bs, 1H), 7.8 (m, 2H), 7.6 (m, 1H), 7.7 (m, 1H), 7.35 (m, 2H), 6.8 (m, 1H), 2.45 (m, 3H).

Part C:

Compound 2238C (420 mg, 0.927 mmol) and 1-ethylpiperazine (213 mg, 1.85 mmol) were dissolved in THF and stirred at room temperature for 30 minutes. The solvent was removed under reduced pressure and the crude product 2238D was used without purification.

Part D:

The crude product 2238D from Part C was dissolved in NMP (10 mL) and treated with potassium carbonate (1.0 g). The mixture was stirred at 125° C. for 1 hour and then diluted with ethyl acetate and water. The organic layer was dried over sodium sulfate and concentrated to provide 2238E (250 mg). HPLC-MS $t_R$=1.38 min (UV$_{254\,nm}$); mass calculated for formula C$_{20}$H$_{23}$N$_4$IO$_2$S 510.0, observed LCMS m/z 511.0 (M+H).

Part E:

Compound 2238E (250 mg, 0.47 mmol) was dissolved in ethanol (5 mL) and water (1 mL) and treated with potassium hydroxide (0.5 g). The mixture was stirred at 150° C. for 20 minutes in a microwave. After the reaction mixture was acidified to pH 2, the aqueous layer was extracted with ethyl acetate. The aqueous layer was then made basic (pH 12) with 1 M NaOH solution and extracted with chloroform. The chloroform layers were dried over sodium sulfate and concentrated to provide compound 2238F (130 mg).

Part F:

The reaction was performed in a similar manner to Example 6, Part F. HPLC-MS $t_R$=0.92 min (UV$_{254\,nm}$); mass calculated for formula C$_{28}$H$_{29}$N$_7$O$_4$ 527.2, observed LCMS m/z 528.2 (M+H). $^1$H NMR (400 MHz, DMSO): δ 11.2 (s, 1H), 10.0 (s, 1H), 8.8 (s, 1H), 7.9 (s, 1H), 7.5 (m, 1H), 7.4-7.3

(m, 2H), 7.2 (m, 2H), 4.5 (m, 4H), 4.05 (m, 2H), 3.9 (m, 1H), 3.8 (s, 3 H), 3.5 (m, 2H), 3.25 (m, 2H), 3.1 (m, 6H), 1.2 (m, 3H).

Compound 2239 was prepared using procedures similar to those described in Example 91 and Example 6, Part B.

Example 92

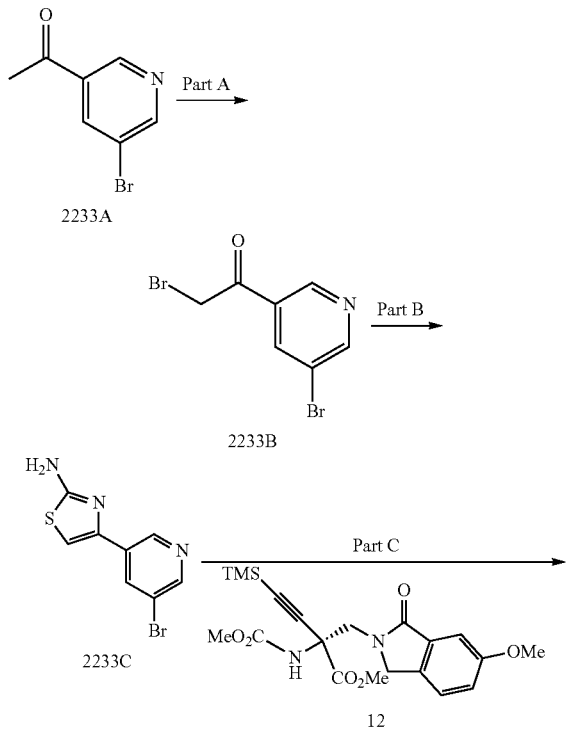

Part A:

Compound 2233A (525 mg, 2.66 mmol) was dissolved in 30% HBr/AcOH (2 mL) and treated with bromine (0.15 mL, 2.93 mmol). The solution was stirred overnight and then treated with diethyl ether. The solids were filtered to provide compound 2233B as an HBr salt (500 mg).

Part B:

Compound 2233B (500 mg, 1.4 mmol), thiourea (114 mg, 1.5 mmol), and triethylamine (2 mL) were dissolved in DMF (10 mL) and stirred at 70° C. for 2 hours. The reaction was quenched with water and extracted with ethyl acetate. The combined organic layers were dried over sodium sulfate and concentrated to provide compound 2233C (300 mg).

Part C:

Compound 2233C (64 mg, 0.25 mmol), compound 12 (80 mg, 0.23 mmol), Pd(PPh$_3$)$_2$Cl$_2$ (20 mg), CuI (10 mg), and triethylamine (1 mL) were dissolved in DMF (4 mL) and stirred at 80° C. overnight. The reaction mixture was concentrated under reduced pressure and then purified by column chromatography (3% MeOH/ethyl acetate) to provide compound 2233D (40 mg). HPLC-MS $t_R$=1.326 min (UV$_{254\ nm}$); mass calculated for formula C$_{25}$H$_{23}$N$_5$O$_6$ 521.1, observed LCMS m/z 522.1 (M+H).

Part D:

Compound 2233D (60 mg, 0.114 mmol) was dissolved in 7 M ammonia in MeOH (5 mL) and stirred at 80° C. overnight in a pressure bottle. After cooling to room temperature the solvent was removed under reduced pressure. The residue was purified by reverse phase chromatography to provide compound 2233 (24 mg). HPLC-MS $t_R$=1.06 min (UV$_{254\ nm}$); mass calculated for formula C$_{23}$H$_{18}$N$_6$O$_4$S 474.1, observed LCMS m/z 475.1 (M+H). $^1$H NMR (400 MHz, DMSO): δ 11.2 (s, 1H), 8.9 (s, 2H), 8.5 (m, 1H), 8.2 (m, 1H), 7.5 (m, 2H), 7.4-7.3 (m, 1H), 7.2 (m, 2H), 4.5 (m, 4H), 4.05 (m, 2H), 3.8 (s, 3 H).

Example 93

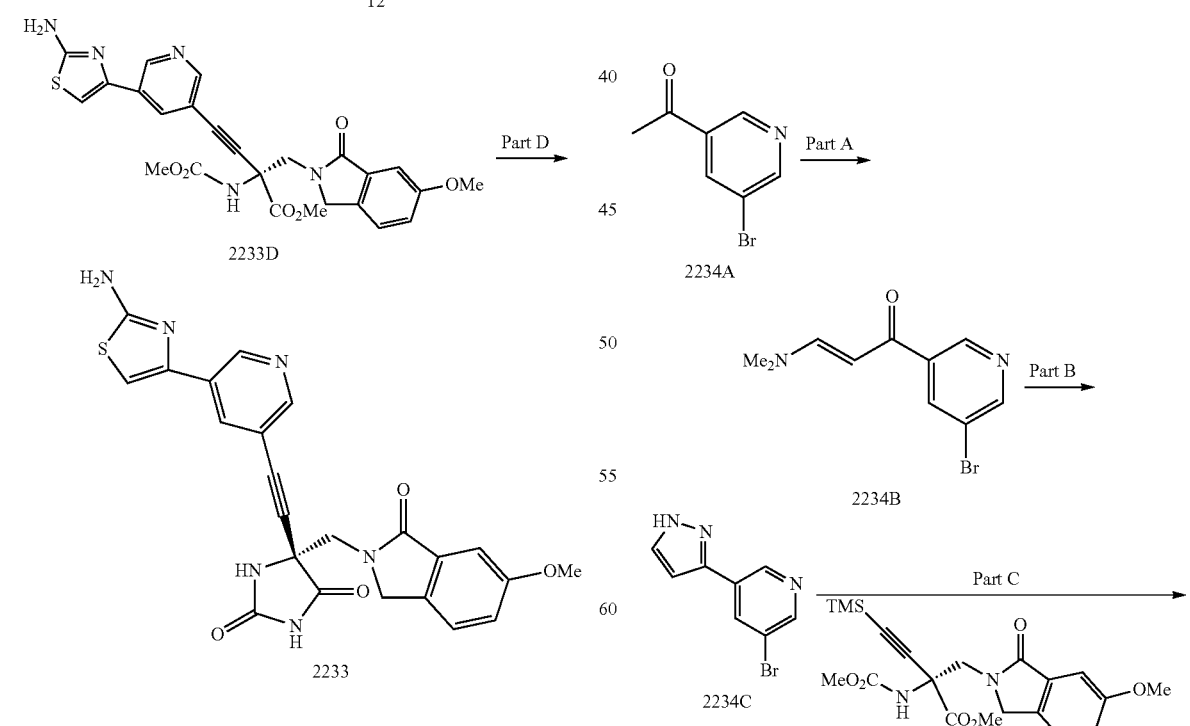

-continued

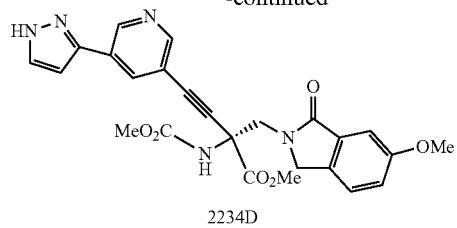

2234D

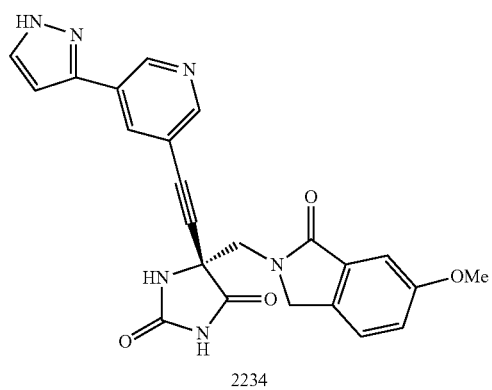

2234

Part A:

Compound 2234A (654 mg, 3.31 mmol) was dissolved in 1,2-dimethoxyethane (10 mL) and treated with 1-tert-butoxy-N,N,N',N'-tetramethylmethanediamine (2 mL). After stirring overnight the solvent was removed to provide compound 2234B that was used without purification.

Part B:

Compound 2234B from Part A was dissolved in ethanol (15 mL) and treated with sodium carbonate (700 mg, 6.62 mmol) and hydrazine monohydrate (248 mg, 4.96 mmol). The mixture was stirred at 70° C. for 2 hours and then diluted with water and extracted with ethyl acetate. The combined organic layers were dried over sodium sulfate and concentrated. The residue was triturated with diethyl ether to provide compound 2234C (500 mg).

Part C:

Compound 2234C (57 mg, 0.25 mmol), compound 12 (80 mg, 0.23 mmol), Pd(PPh$_3$)$_2$Cl$_2$ (20 mg), CuI (10 mg), and triethylamine (1 mL) were dissolved in DMF (4 mL) and stirred at 80° C. overnight. The reaction mixture was concentrated under reduced pressure and then purified by column chromatography (3% MeOH/ethyl acetate) to provide compound 2234D (50 mg). HPLC-MS $t_R$=1.349 min (UV$_{254\,nm}$), mass calculated for formula C$_{25}$H$_{23}$N$_5$O$_6$ 489.1, observed LCMS m/z 490.1 (M+H).

Part D:

Compound 2234D (70 mg, 0.142 mmol) was dissolved in 7 M ammonia in MeOH (5 mL) and stirred at 80° C. overnight in a pressure bottle. After cooling to room temperature the solvent was removed under reduced pressure. The residue was purified by reverse phase chromatography to provide compound 2234 (24 mg). HPLC-MS $t_R$=1.11 min (UV$_{254\,nm}$); mass calculated for formula C$_{23}$H$_{18}$N$_6$O$_4$ 442.1, observed LCMS m/z 443.1 (M+H). $^1$H NMR (400 MHz, DMSO): δ 11.2 (s, 1H), 8.8 (m, 2H), 8.5 (m, 1H), 8.2 (m, 1H), 7.8 (m, 1H), 7.5 (m, 1H), 7.2-7.1 (m, 2H), 6.9 (m, 1H), 4.5 (m, 4H), 4.05 (m, 2H), 3.8 (s, 3 H).

Example 94

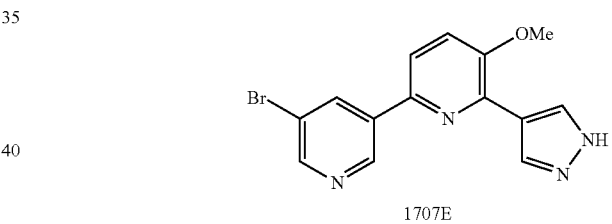

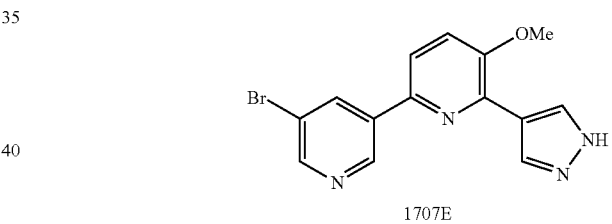

Part A:

To a pressure bottle was added compound 1707A (700 mg, 3.47 mmol), compound 1707B (1.1 g, 3.50 mmol), Pd(PPh$_3$)$_4$ (380 mg, 0.33 mmol), acetonitrile (5 mL) and potassium carbonate (3 mL, 1 N aq.). The reaction mixture was vacuumed and purged with nitrogen for three times and stirred at 85° C. overnight. The reaction mixture was diluted with water (30 mL) and extracted with EtOAc (20 mL×3). The organic layers were combined and washed with brine, dried over sodium sulfate concentrated to dryness. The residue was purified by silica gel chromatography (Hexane/EtOAc:1:3) to afford 1707C (475 mg, 40%).

Part B:

To a pressure bottle was added compound 1707C (475 mg, 1.38 mmol), compound 1707D (406 mg, 1.38 mmol), Pd(PPh$_3$)$_4$ (160 mg, 0.138 mmol), DMF (3 mL) and potassium carbonate (3 mL, 1 N aq.). The reaction mixture was vacuumed and purged with nitrogen for three times and stirred at 85° C. overnight. Yellow precipitate occurred. The solid was collected by suction filtration to afford 1707E (270 mg, 57%).

Example 95

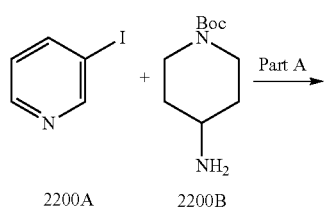

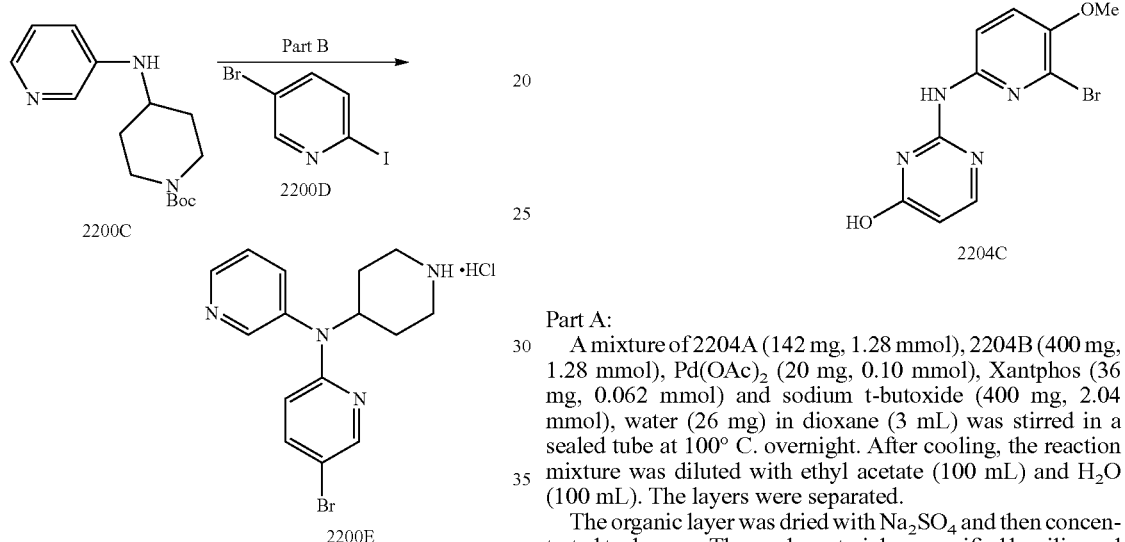

Part A:

A mixture of 2200A (500 mg, 2.44 mmol), 2200B (488 mg, 2.44 mmol), copper iodide (46 mg, 0.24 mmol), L-proline (56 mg, 0.48 mmol) and $K_2CO_3$ (674 mg, 4.9 mmol) in DMSO (3 mL) was stirred at 90° C. overnight. After cooling, the reaction mixture was diluted with ethyl acetate (20 mL) and Brine (20 mL). The layers were separated. The organic layer was dried with $Na_2SO_4$ and then concentrated to dryness. The crude material was purified by silica gel chromatography (Hexane/EtOAc:1:1) to afford compound 2200C (650 mg, 96%).

Part B:

A mixture of 2200C (100 mg, 0.36 mmol), 2200D (102 mg, 0.36 mmol), Pd(OAc)$_2$ (8 mg, 0.012 mmol), Xantphos (16 mg, 0.028 mmol) and sodium t-butoxide (56 mg, 0.58 mmol) in dioxane (3 mL) was stirred in a sealed tube at 100° C. overnight. After cooling, the reaction mixture was diluted with ethyl acetate (100 mL) and $H_2O$ (100 mL). The layers were separated. The organic layer was dried with $Na_2SO_4$ and then concentrated to dryness. The crude material was purified by silica gel chromatography (Hexane/EtOAc: 1:1) to afford product (19 mg). This material was then dissolved in methanol (2 mL) and HCl (2 mL, 4N in dioxane) was added. The reaction was stirred at room temperature for 2 hours. Solvent was removed and the material was dried under vacuum to afford 2200E (14 mg, 12%).

Compound 2200 was prepared from 2200E using a procedure similar to the one described in Example 6, Part B.

Example 96

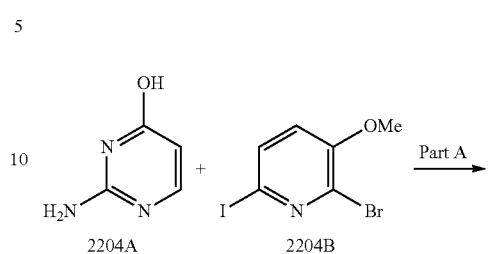

Part A:

A mixture of 2204A (142 mg, 1.28 mmol), 2204B (400 mg, 1.28 mmol), Pd(OAc)$_2$ (20 mg, 0.10 mmol), Xantphos (36 mg, 0.062 mmol) and sodium t-butoxide (400 mg, 2.04 mmol), water (26 mg) in dioxane (3 mL) was stirred in a sealed tube at 100° C. overnight. After cooling, the reaction mixture was diluted with ethyl acetate (100 mL) and $H_2O$ (100 mL). The layers were separated.

The organic layer was dried with $Na_2SO_4$ and then concentrated to dryness. The crude material was purified by silica gel chromatography (5%-10% 7N Ammonia MeOH solution in $CH_2Cl_2$) to afford compound 2204C (170 mg, 45%).

Compound 2204 was prepared from 2204C using a procedure similar to the one described in Example 6, Part B.

Example 97

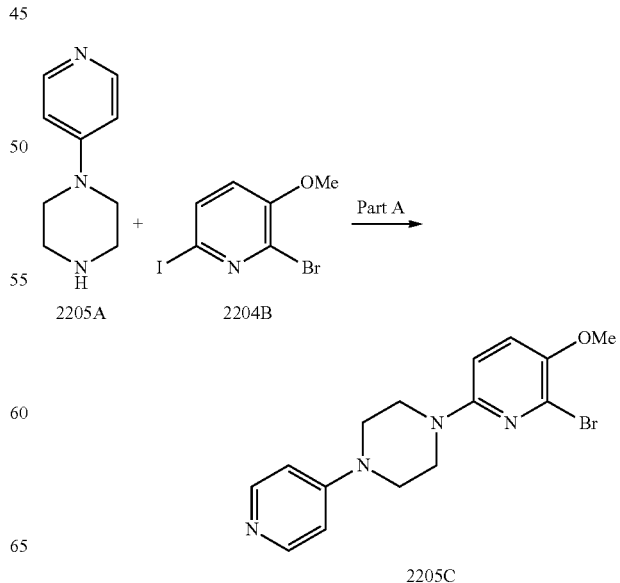

Part A:

A mixture of 2205A (208 mg, 1.27 mmol), 2204B (400 mg, 1.27 mmol), copper iodide (24 mg, 0.12 mmol), L-proline (29 mg, 0.25 mmol) and $K_2CO_3$ (352 mg, 2.54 mmol) in DMSO (3 mL) was stirred at 90° C. overnight. After cooling, the reaction mixture was diluted with ethyl acetate (20 mL) and Brine (20 mL). The layers were separated. The organic layer was dried with $Na_2SO_4$ and then concentrated to dryness. The crude material was purified by silica gel chromatography (5% 7N Ammonia MeOH solution in $CH_2Cl_2$) to afford compound 2205C (154 mg, 35%).

Compound 2205 was prepared from 2205C using a procedure similar to the one described in Example 6, Part B.

Example 98

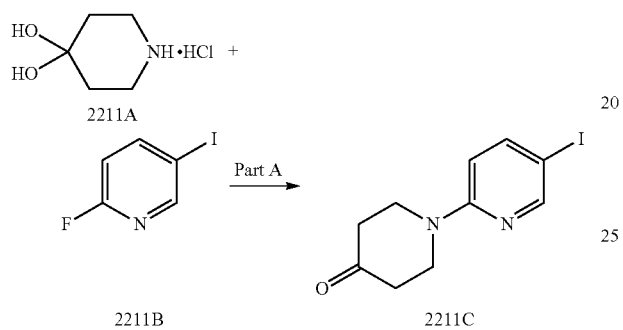

Part A:

To a microwave tube charged with stirring bar was added 2211A (750 mg, 5 mmol), 2211B (1.1 g, 1.0 mmol), Diisopropylethylamine (2 mL), the mixture was then dissolved in 5 mL DMF. The reaction mixture was vacuumed and purged with nitrogen for three times and heated at 100° C. overnight. The mixture was then cooled down to room temperature and 20 mL $CH_2Cl_2$ was added. The solvent was evaporated and the residue was purified by preparative TLC (Hex:EtOAc=5:1) to give 2211C (180 mg, 12%).

Compound 2211 was prepared from 2211C using a procedure similar to the one described in Example 6, Part B.

Compound 2210 was prepared using procedures similar to the those described in Example 98 and Example 6, Part B.

Example 99

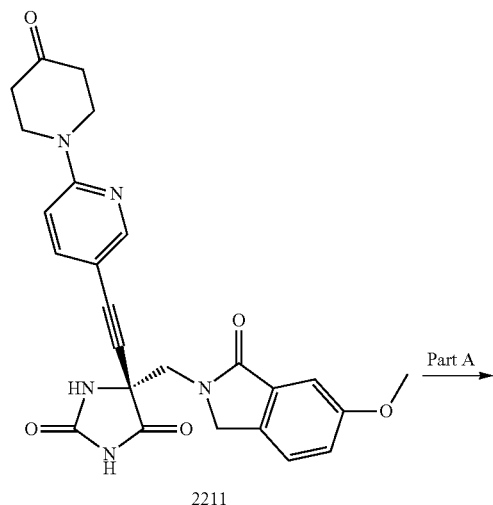

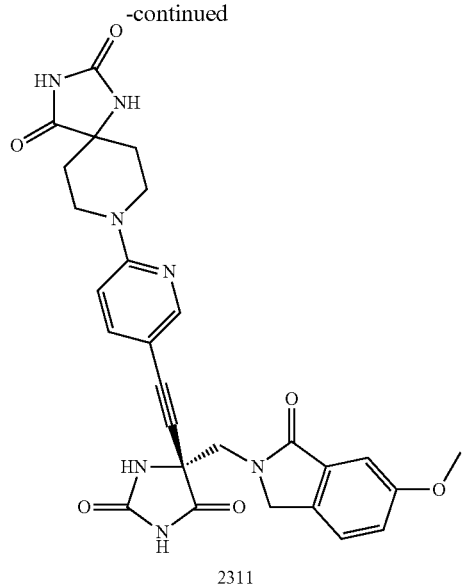

Part A:

To a microwave tube charged with stirring bar was added 2211 (40 mg, 0.084 mmol), KCN (8.3 mg, 0.1267 mmol), $(NH_4)_2CO_3$ (24.4 mg, 0.253 mmol), and 1 mL 7N ammonia in methanol. The reaction was heated at 90° C. overnight. The crude material was purified by preparative TLC (10% 7N Ammonia MeOH solution in $CH_2Cl_2$) to give 2311 (6.7 mg, 15%).

Compound 2310 was made by a similar procedure as the one described in Example 99.

Example 100

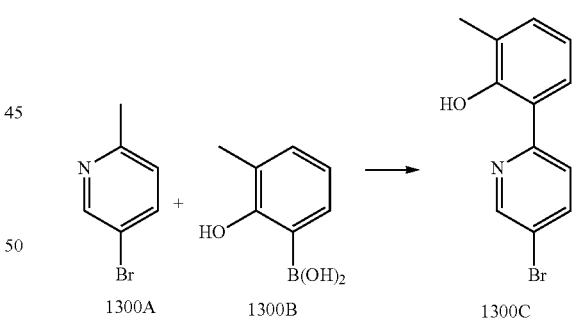

To a 25 mL flask was added compound 1300A (500 mg, 1.77 mmol), compound 1300B (224 mg, 1.47 mmol), and $Pd(dppf)_2Cl_2$. The flask was vacuumed and flushed with $N_2$ for three times. $K_2CO_3$ (1M, 2.5 mL, 2.5 mmol) and $CH_3CN$ were added. The solution was stirred at 65° C. for 3 h. After cooling down, water and EtOAc were added. The organic layer was separated, washed with brine, dried over $Na_2SO_4$, and concentrated. The product was purified by $SiO_2$ chromatography (EtOAc/Hexane: 10%) to give compound 1300C (180 mg, 46.6%).

Compounds 1300, 1301, 1303, 1305, 1315, 1316, 2206, 2207, 2208, 2213, 2263, 2264, 2266, 2268, 2269, 2270, 2277, 2290, 2291, 2292, and 2296 were prepared by the methods described in Example 100 and Example 6.

Example 101

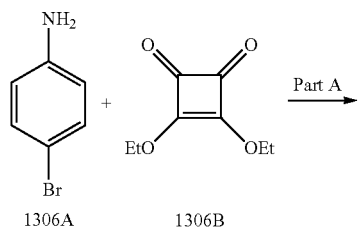

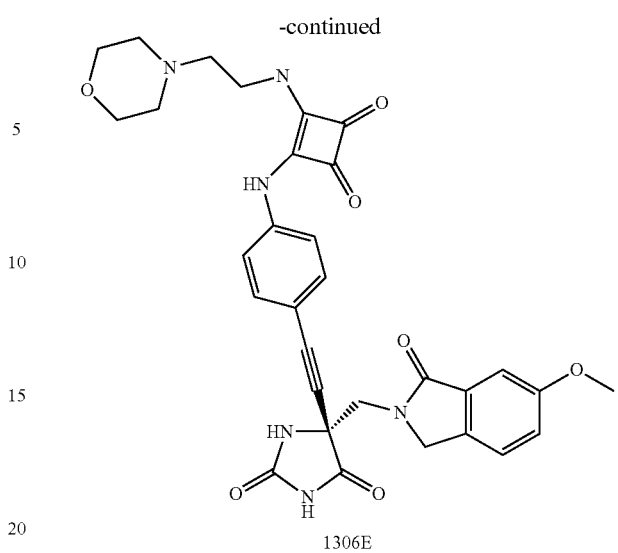

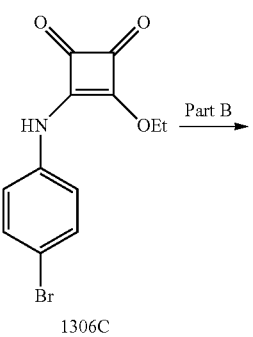

Part A:
Compound 1306A (1.0 g, 5.85 mmol) and compound 1306B (974 mg, 5.85 mmol) were dissolved in EtOH (10 mL). The solution was stirred at 25° C. for 3 h. The solvent was removed and the product was purified by sgc (20% EtOAc/Hexane) to give compound 1306C (515 mg, 29.8%).

Part B
Compound 1306D was prepared by the same method as described in Example 6.

Part C
Compound 1306D (50 mg, 0.097 mmol) was dissolved in EtOH (3 mL). 4-(2-aminoethyl) morpholine (0.014 mL, 0.10 mmol) and DIPEA (0.051 mL, 0.29 mmol) were added. The solution was stirred at RT for 2 h. The solvent was removed and the product was purified by sgc (5% MeOH/DCM) to give compound 1306E (4.7 mg, 8.1%)

Compounds 1306, 1307, and 1308 were prepared by the methods described in Example 101 and Example 6.

Example 102

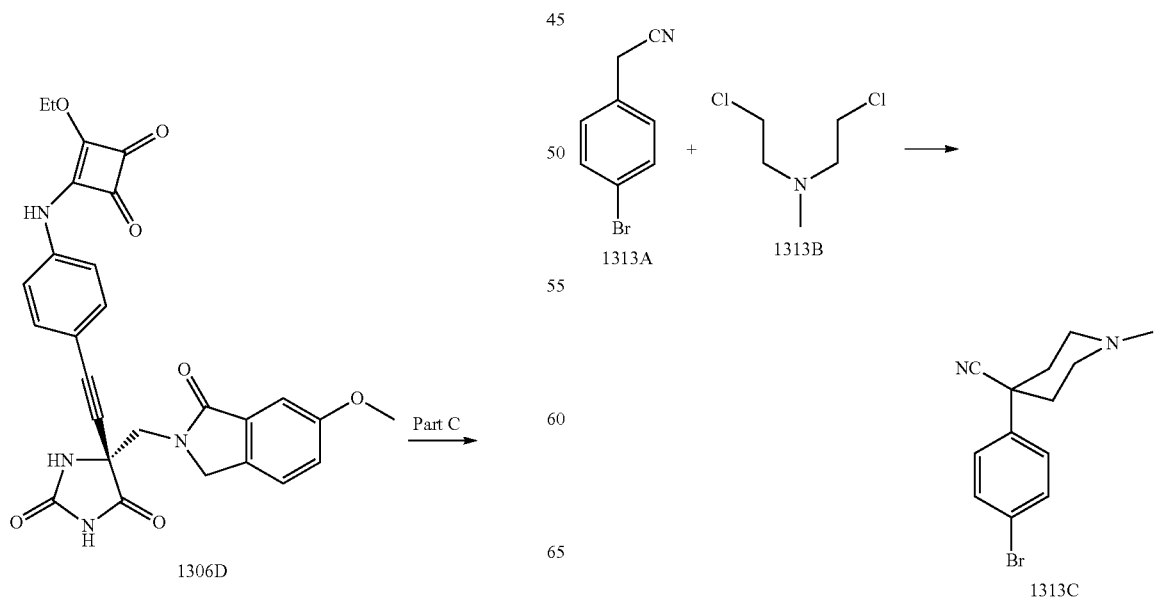

Compound 1313A (5.0 g, 51.3 mmol), compound 1313B (HCl salt, 8.3 g, 102.5 mmol), and tetrabutyl ammonium bromide (860 mg, 5.13 mmol) were suspended in toluene (21 mL). NaOH (50% w/w, 18.7 g) was added slowly. The solution was stirred at 120° C. for 18 h. After cooling down, water and more toluene were added. The organic layer was separated, washed with brine, dried over $Na_2SO_4$, and concentrated. The product was purified by C18 chromatography ($CH_3CN/H_2O$, 5% to 90%) to give compound 1313C (2.25 g, 15.8%)

Compound 1313 were prepared by the methods described in Example 102 and Example 6.

Example 103

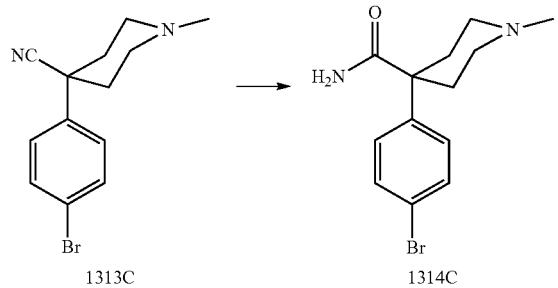 [SMILES: CN1CCC(C#N)(c2ccc(Br)cc2)CC1 ; CN1CCC(C(N)=O)(c2ccc(Br)cc2)CC1]

Compound 1313C (1.85 g, 6.65 mmol) and KOH (3.87 g, 69.2 mmol) were dissolved in $EtOH/H_2O$ (6:1, 14 mL). The solution was stirred at reflux temperature for 18 h. After cooling down, solvent was removed and water was added. The solid was collected by filtration, washed with water, and dried under vacuum to give compound 1314C which was used without further purification.

Compound 1314 were prepared by the methods described in Example 103 and Example 6.

Example 104

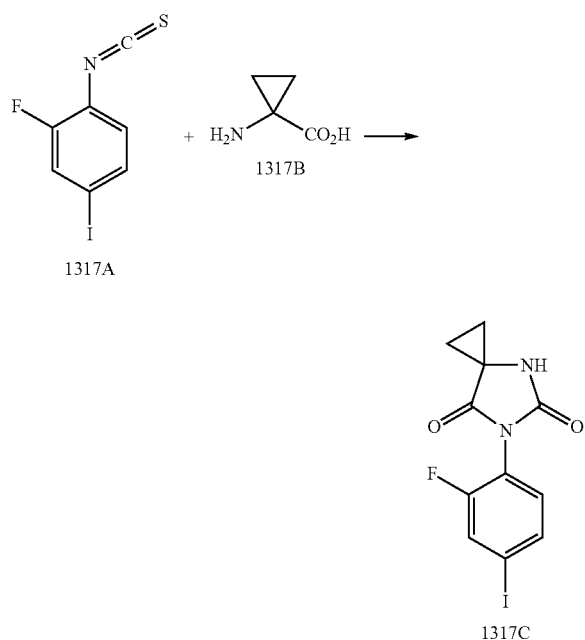

A DCM (8 mL) solution of compound 1317A (1.0 g, 3.40 mmol), compound 1317B (344 mg, 3.40 mmol), and triethylamine (0.48 mL, 3.40 mmol) were stirred at RT for overnight. The product was purified by C18 chromatography ($CH_3CN/H_2O$, 5% to 90%) to give compound 1317C (1.17 g, 99%)

Compound 1317 were prepared by the methods described in Example 104 and Example 6.

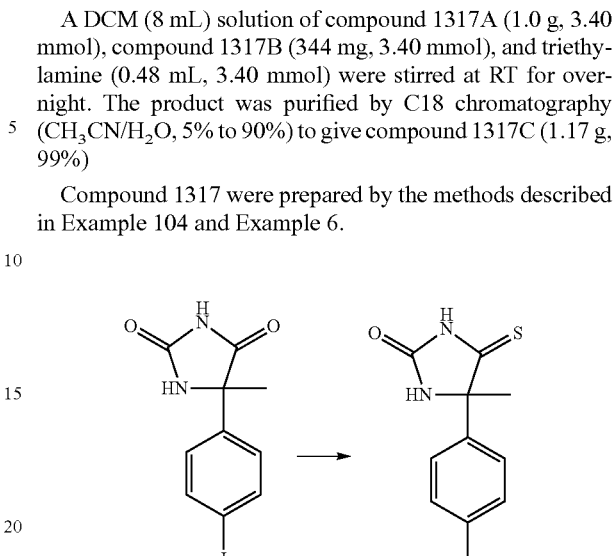

Example 105

Compound 2258A (800 mg, 2.53 mmol) and Lawesson's Reagent (717 mg, 1.77 mmol) were dissolved in toluene (925 ml). The solution was stirred at reflux temperature for 3 h. After cooling down, the solid was removed by filtration, and the solvent was removed. The product was purified by sgc ($DCM/MeOH/NH_3$—$H_2O$ 40; 1:0.1 to 20:1:0.1) to give compound 2258B (365 mg, 43.5%).

Compound 2258 were prepared by the methods described in Example 105 and Example 6.

Example 106

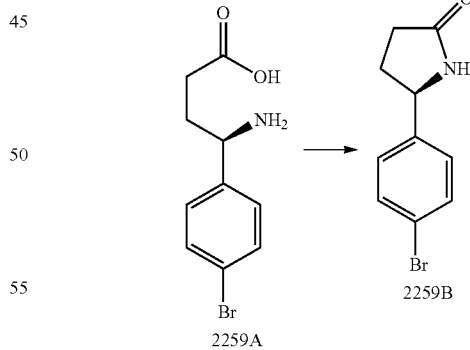

Compound 2259A (300 mg, 1.02 mmol), HATU (503 mg, 1.32 mmol), and DIPEA (0.53 mL, 3.06 mmol) were stirred in DMF (20 mL) for overnight. Water and EtOAc were added. The organic layer was washed with water three times, dried over $Na_2SO_4$, concentrated, and dried under vacuum to give compound 2259B which was used without further purification.

Compound 2259 were prepared by the methods described in Example 106 and Example 6.

Example 107

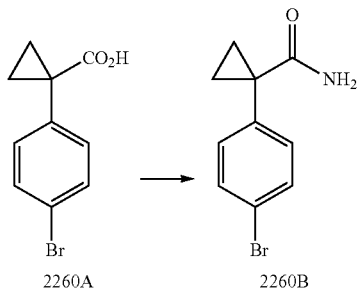 [SMILES: O=C(O)C1(c2ccc(Br)cc2)CC1 ; NC(=O)C1(c2ccc(Br)cc2)CC1]

2260A → 2260B

Compound 2260A (220 mg) was stirred with SOCl$_2$ 1.5 mL) at reflux condition for two hours. After cooling down, SOCl$_2$ was removed under vacuum and the residue was dissolved in DCM and it was added into a cold solution of NH$_3$—H$_2$O (37%, 10 ml). Then the solution was stirred at RT for 30 min, the aqueous layer was extracted with EtOAc. The organic layer was washed with HCl (2N) twice, brine, dried over Na$_2$SO$_4$, and concentrated to give compound 2260B which was used without further purification.

Compounds 2260, 2261, 2262, and 2283 were prepared by the methods described in Example 107 and Example 6.

Example 108

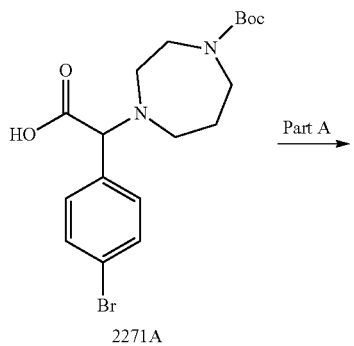

2271A

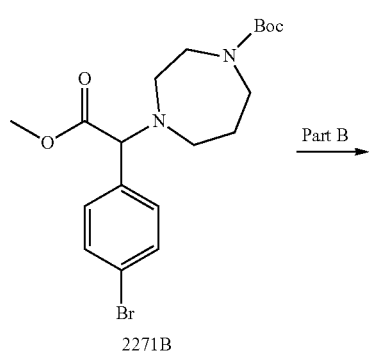

2271B

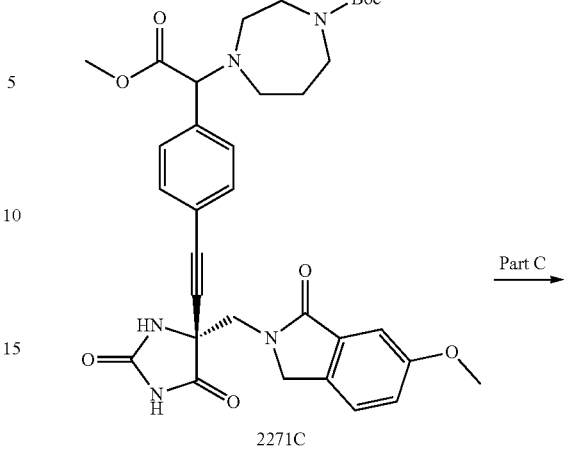

2271C

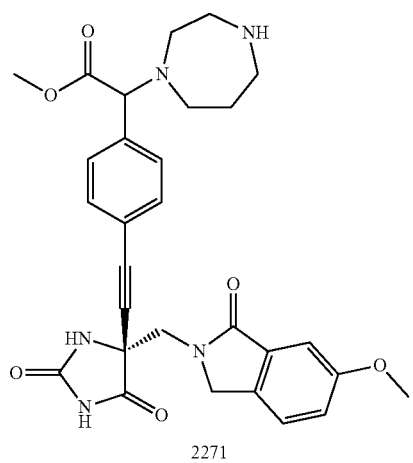

2271

Part A

Compound 2271A (300 mg, 0.73 mmol) was dissolved in DMF (5 ml). Cs$_2$CO$_3$ (476 mg, 1.45 mmol) and MeI (0.5 mL) were added. The solution was stirred at RT for overnight. Water and EtOAc were added. The organic layer was separated, washed with brine, dried over Na$_2$SO$_4$, and concentrated. The product was purified by SiO$_2$ chromatography (Hexane/EtOAc 1:0 to 1:1) to give compound 2271B (295 mg, 95.1%).

Part B

Compound 2271C was prepared by the same method as described in Example 6.

Part C

Compound 2271C (35 mg) was stirred with HCl (4M in dioxane, 1 mL) in MeOH (3 mL) at RT for overnight. The solvent was removed and the product was dried under vacuum to give compound 2271 (25.7 mg).

Compound 2284 were prepared by the methods described in Part A of Example 108 and Example 6.

Example 109

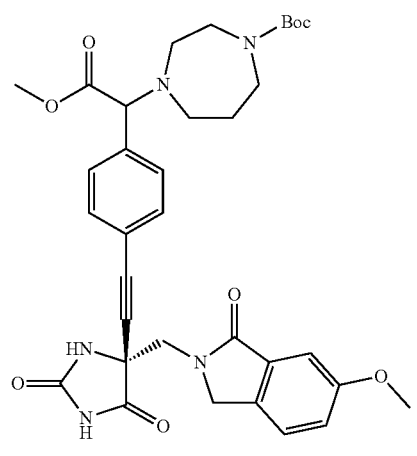

2271C

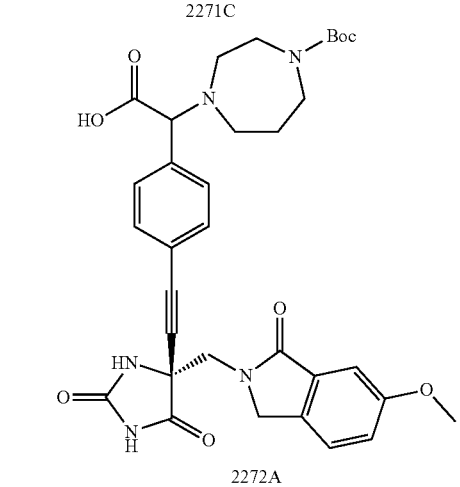

2272A

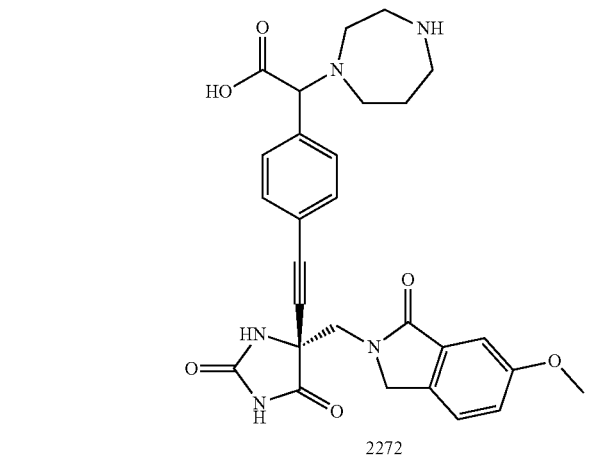

2272

Part A

Compound 2271C (76 mg, 0.118 mmol) and LiOH (11.3 mg, 0.47 mmol) were stirred in THF (1 mL) and water (0.5 mL) solution at 70° C. for overnight. The product was purified by C18 chromatography (CH₃CN/H₂O, 5% to 90%, with 0.1% HCO₂H) to give compound 2272A (56 mg, 87%).

Part B

Compound 2272 was prepared by the same method as described in part B of Example 108 Part C.

Example 110

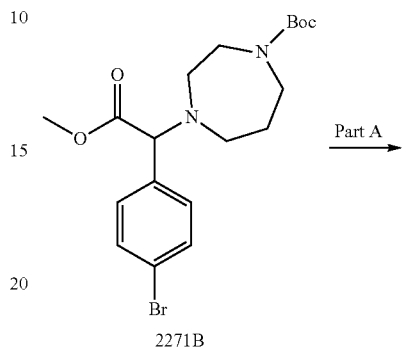

2271B

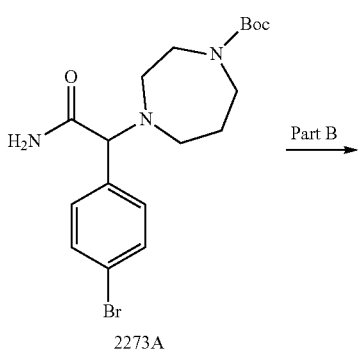

2273A

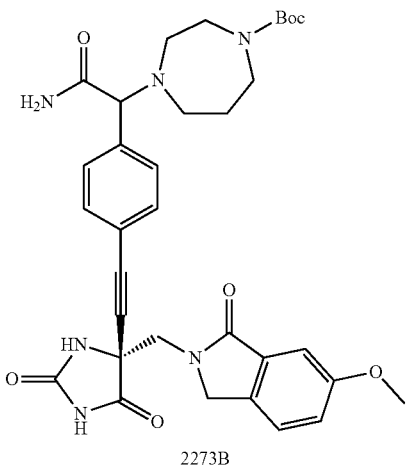

2273B

-continued

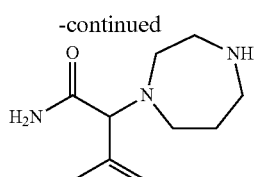

2273

Part A

Compound 2271B (140 mg, 0.33 mmol) was stirred with NH$_3$/MeOH (7N, 3 mL) in a pressure tube at 110° C. for three days. After cooling down, the solvent was removed by rotary evaporator and the product was purified by sgc (DCM/MeOH/NH$_3$—H$_2$O: 20:1:0.1 to 10:1:0.1) to give compound 2273A (67 mg, 49%).

Part B:

Compound 2273B was prepared by the same method as described in Example 6.

Part C

Compound 2273 was prepared by the same method as described in part C of Example 108.

Example 2275

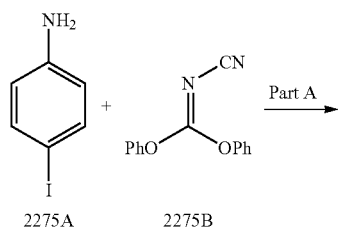

2275A        2275B

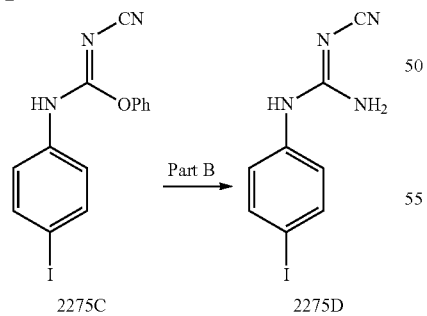

2275C        2275D

Part A

Compound 2275A (1.0 g, 4.56 mmol) and compound 2275B (1.09 g, 4.56 mmol) were stirred together in dioxane (15 ml) at RT for three days. The solid was collected by filtration, washed with dioxane, and dried under vacuum to give compound 2275C (1.3 g, 99.7%).

Part B

Compound 2275C (150 mg) was stirred in NH$_3$/MeOH (7N, 3 ml) in a pressure tube at 80° C. for overnight. After cooling down, the solvent was removed and the product was dried under vacuum to give compound 2275D which was used without further purification.

Compound 2275, 2297, and 2298 were prepared by the method described in Example 111 and Example 6.

Example 112

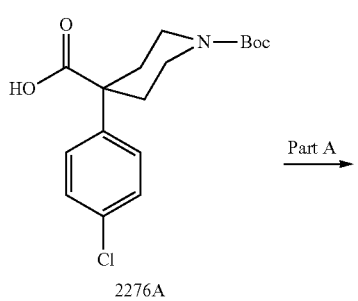

2276A

Part A

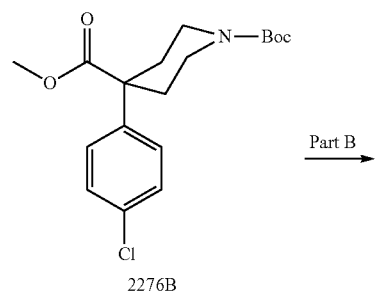

2276B

Part B

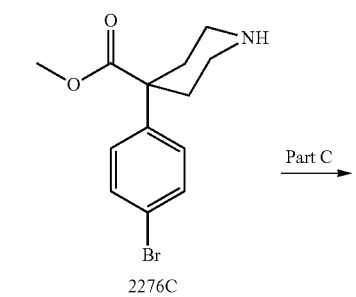

2276C

Part C

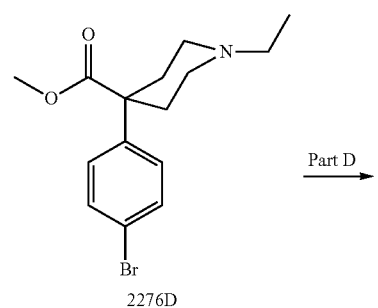

2276D

Part D

-continued

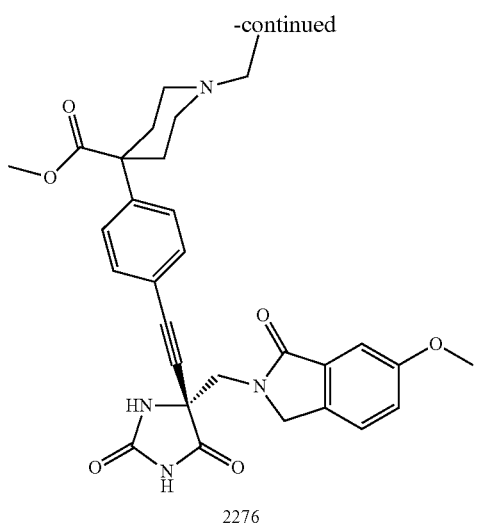

2276

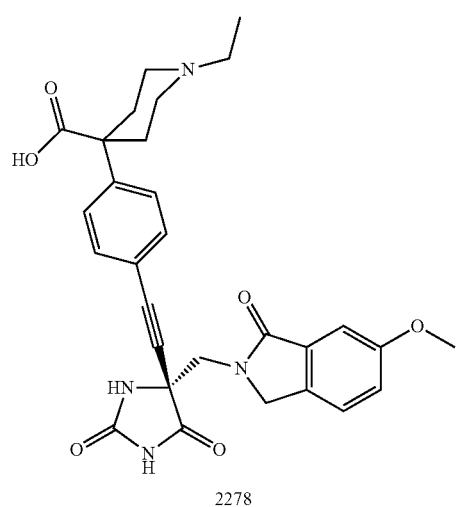 [SMILES: CCN1CCC(C(=O)O)(c2ccc(C#C[C@]3(CN4Cc5ccc(OC)cc5C4=O)NC(=O)NC3=O)cc2)CC1]

2278

Part A

Compound 22768 was prepared by the same method as described in Part A of Example 108.

Part B

Compound 2276B (350 mg, 1.03 mmol), NiBr$_2$ (450 mg, 2.06 mmol), and DMF (0.7 mL) were placed in a microwave reactor tube and heated to 170° C. in a microwave reactor for 10 min. Water and EtOAc were added. The pH was adjusted to around 12 by adding NaOH (1N). The aqueous layer was extracted with water five times. The organic layers were combined, washed with brine, dried over Na$_2$SO$_4$, concentrated, and dried under vacuum to give compound 2276C (320 mg) which still contained about 50% compound 22768. 2276C was used without further purification.

Part C

Compound 2276C (~50% pure, 300 mg, 1.0 mmol) was dissolved in DCM. Ethyl bromide (0.082 mL, 1.10 mmol) and triethyl amine (0.42 mL, 3.00 mmol) were added. The solution was stirred at RT for two days. More ethyl bromide (0.082 mL, 1.10 mmol) was added after one day. The solvent was removed and the product was purified by sgc (DCM/MeOH/NH$_3$—H$_2$O: 20:1:0.1) to give compound 2276D (212 mg, ~50% purity).

Part D

Compound 2276 was prepared by the same method as described in Example 6.

Part C

Compound 2278 was prepared by the same method as described in Part A of Example 109.

Example 113

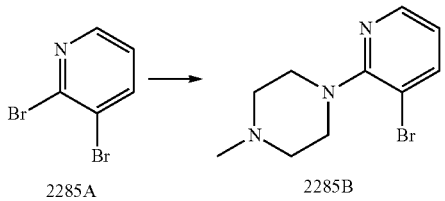

2214A → 2214B

Compound 2214A (2.0 g, 9.48 mmol) was dissolved in a solution of H$_2$O (10 mL) and NH$_3$/MeOH (7N, 10 mL) in a 150 mL pressure bottle. KCN (617 mg, 9.48 mmol), (NH$_4$)$_2$CO$_3$ (3.64 g, 37.9 mmol) were added. The pressure bottle was capped and stirred at 80° C. for 16 h. After cooling down, the solution was concentrated to one fourth of its original volume, adjusting the pH to 6-7 with HCl (2N). The solid was collected, washed with water, dried under vacuum to give compound 2214B (1.89 g, 70.9%)

Compound 2214 was prepared from 2214B using a procedure similar to the one described in Example 6, Part B.

Compounds 1302, 1304, 2214, 2257, 2279, 2280, 2281, and 2282 were prepared by the methods described in Example 113 and Example 6.

Example 114

2285A → 2285B

Compound 2285A (500 mg, 2.12 mmol), N-methylpiperazine (0.21 mL, 1.91 mmol), K$_3$PO$_4$, 899 mg, 4.24 mmol), CuI (40 mg, 0.21 mmol) and L-proline (49 mg, 0.424 mmol) were dissolved in DMSO (2 mL). The solution was stirred at 90° C. for 40 h. Water and EtOAc were added. The organic layer was separated, washed with brine, dried over Na$_2$SO$_4$, and concentrated. The product was purified by sgc (MeOH/DCM: 10%) to give compound 2285B (336 mg, 69.0%).

Compounds 2285, 2286, 2287, and 2289 were prepared by the methods described in Example 114 and Example 6.

Compound 2295 were prepared by the methods described in Example 115 and Example 6.

Example 115

Example 116

Part A

Compound 2295B (1.0 g. 7.35 mmol) was stirred in reflux SOCl$_2$ for two hours. After cooling down, SOCl$_2$ was removed and DCM was added. Compound 2295A (1.26 g, 7.35 mmol) was added. The solution was stirred at RT for 10 min, the solid was collected and washed with DCM to give compound 2295C which was used without further purification.

Part B

Compound 2295C (300 mg, 1.04 mmol) was dissolved in CH$_3$CN (5 mL). NaH (30 mg, 1.24 mmol) was added at 0° C. The solution was then stirred at RT for 18 h. More NaH (78.8 mg, 3.12 mmol) was added and the solution was stirred at RT for three more days. The solution was quenched with water. More water and EtOAc were added. The organic layer was separated, washed with brine, dried over Na$_2$SO$_4$, and concentrated. The product was purified by sgc to give compound 2295D (206.5 mg, 78.5%).

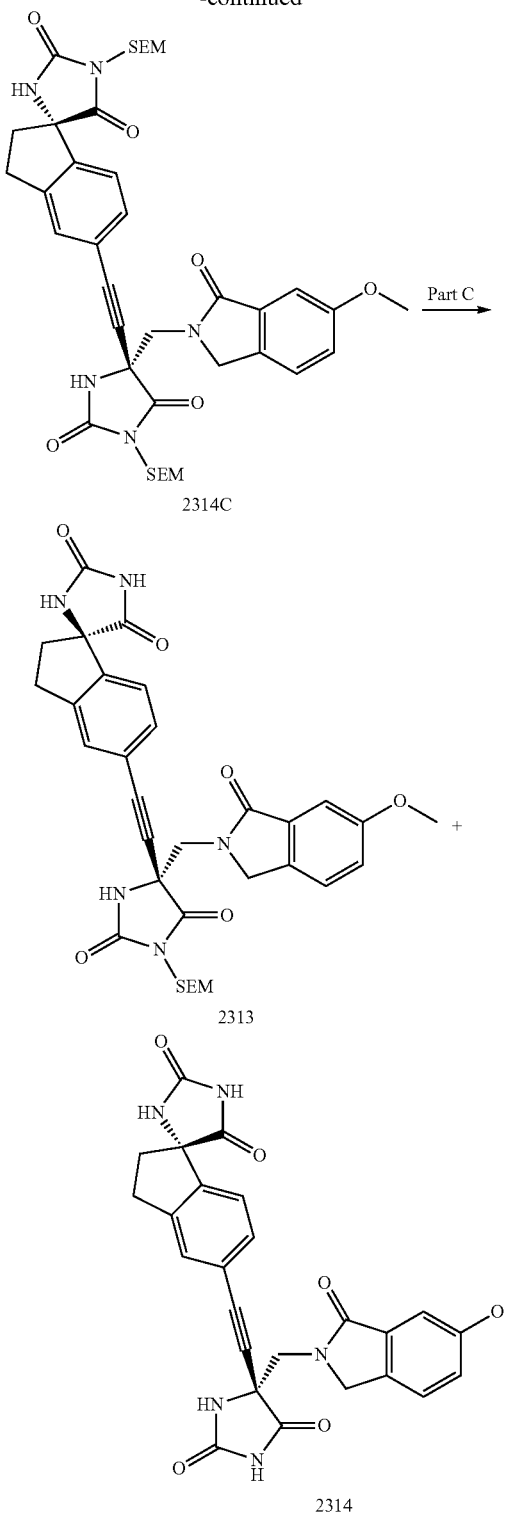

(0.058 mL, 0.22 mmol) were added. It was stirred at RT for overnight. DMF was removed under vacuum and the product was purified by sgc (DCM/MeOH/NH$_3$—H$_2$O: 20:1:0.1) to give compound 2313B (105 mg).

Part B

Compound 2313B (105 mg) was dissolved in MeOH (5 ml) and it was injected into a AD chiral column eluted by Hexane/i-PrOH (3:1, flow rate 20 mL/min). The first peak was collected and concentrated to give compound 2313C. The second peak was collected and concentrated to give compound 2314C (93 mg).

Part C

Compound 2313C was dissolved in CH$_3$CN (1 ml) and cooled to 0° C. BF$_3$.Et$_2$O (0.035 mL, 0.28 mmol) was added. The solution was stirred at RT for three hours. DIPEA (0.52 mL) and MeOH (1 mL) was added. The solution was stirred at RT for overnight. The solvent was removed and the product was purified by C18 chromatography (CH$_3$CN/H$_2$O, 5% to 90%, with 0.1% HCO$_2$H) to give compound 2313 (43 mg).

Compound 2314 and 2315 were prepared by the same methods.

Example 117

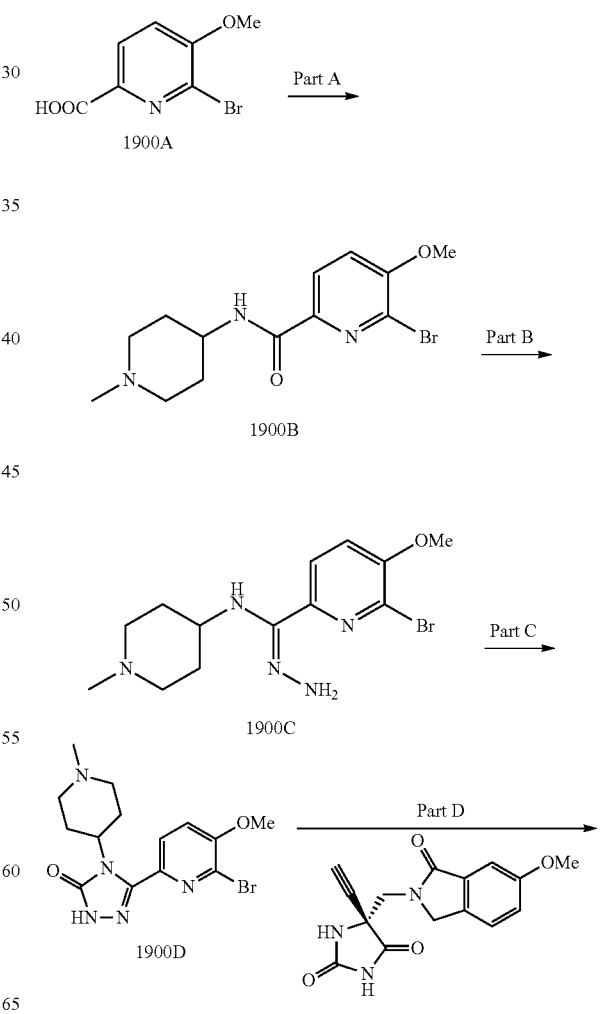

Part A

Intermediate 2214B was SEM protected using the procedure described in Example 116. Part B and coupled to compound 14 using the procedures described in Example 6 to afford compound 2313A.

Compound 2313A (110 mg, 0.163 mmol) was dissolved in DMF (1 mL). SEMCI (0.051 mL, 0.20 mmol) and DIPEA -continued

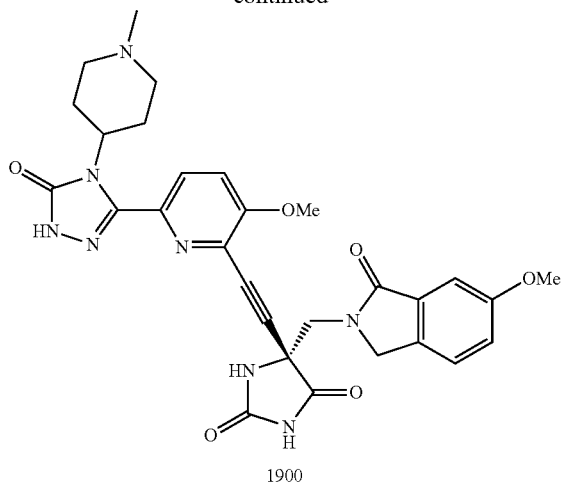

1900

Part A:

Compound 1900A (500 mg, 2.17 mmol, prepared by a procedure similar to that described by T. Ross Kelly and F. Lang, *J. Org. Chem.* 1996, 61, 4623-4633), N-methyl-4-aminopiperidine (297 mg, 2.60 mmol), PyBop (1.35 g, 2.60 mmol), and N,N-diisopropylethylamine (0.46 mL, 2.60 mmol) were dissolved in $CH_2Cl_2$ (50 mL). The solution was stirred at 25° C. for 18 h and added to aq. $NaHCO_3$ solution. The organic layers were extracted with $CH_2Cl_2$ and the combined organic solution was washed with brine solution, dried ($Na_2SO_4$), and concentrated in vacuo. The residue was purified by silica gel column ($MeOH/CH_2Cl_2$, gradient from 0% to 10% MeOH) to provide the desired product 1900B (602 mg, 85%).

Part B:

A solution of compound 1900B (246 mg, 0.75 mmol) in thionyl chloride (3 mL) was stirred at 100° C. for 2 h. After concentrated in vacuo, the residue was dissolved in $CH_2Cl_2$ (5 mL) and treated with excess hydrazine (0.5 mL) at 0° C. The mixture was stirred for 10 min. and N,N-diisopropylethylamine (0.20 mL, 1.12 mmol) was added at 25° C. After stirred for 1 h, the mixture was added to cold water and the organic layers were extracted with $CH_2Cl_2$. The combined organic solution was washed with brine solution, dried ($Na_2SO_4$), and concentrated in vacuo. The residue was purified by $SiO_2$ column ($MeOH/CH_2Cl_2$ gradient from 0% to 5% MeOH) to provide desired product 1900C (60 mg, 24%).

Part C:

A mixture of Compound 1900C (60 mg, 0.17 mmol) and carbonyl diimidazole (53 mg, 0.32 mmol) was stirred at 25° C. for 2 h. The mixture was concentrated in vacuo and the residue was purified by $SiO_2$ column ($MeOH/CH_2Cl_2$ gradient from 0% to 12% MeOH) to provide desired product 1900D (28 mg, 46%).

Part D:

Compound 14 (23 mg, 0.08 mmol), compound 1900D (28 mg, 0.08 mmol), $Pd(PPh_3)_2Cl_2$ (2.1 mg, 0.003 mmol), CuI (0.6 mg, 0.003 mmol), and N,N-diisopropylethylamine (26 μL, 0.15 mmol) in DMF (1 mL) was stirred at 80° C. for 18 h. After cooled to 25° C., the solid was removed by filtration and the filtrate was purified by HPLC (water-acetonitrile) to provide the desired product 1900 (10 mg, 23%).

Example 118

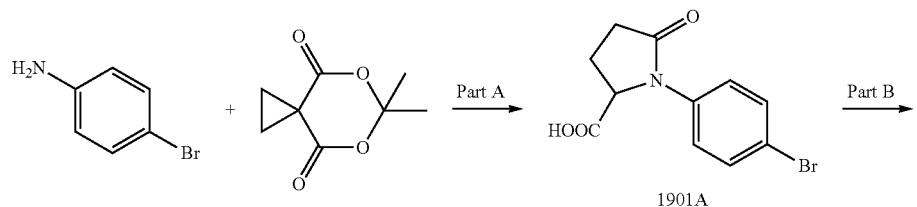

1901A

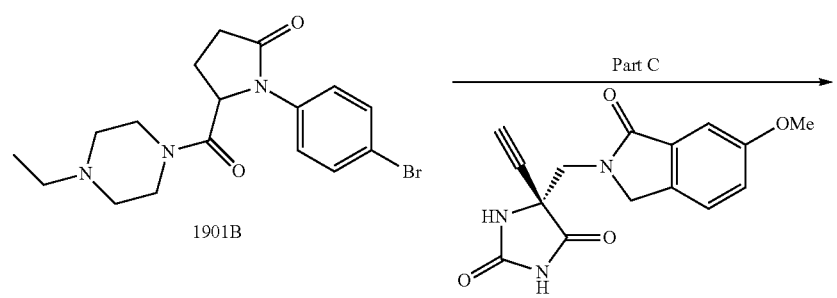

1901B

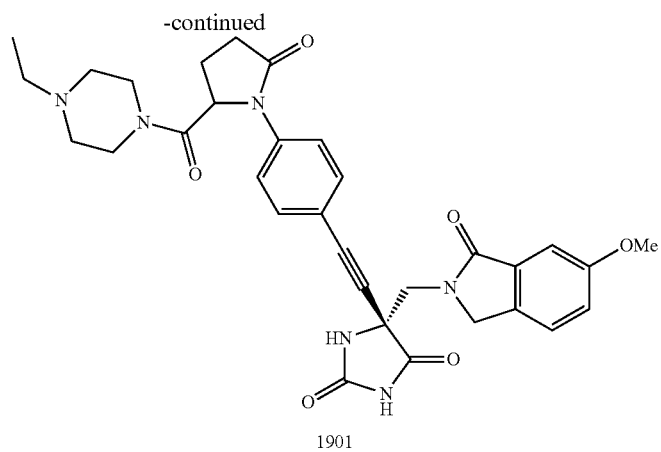

1901

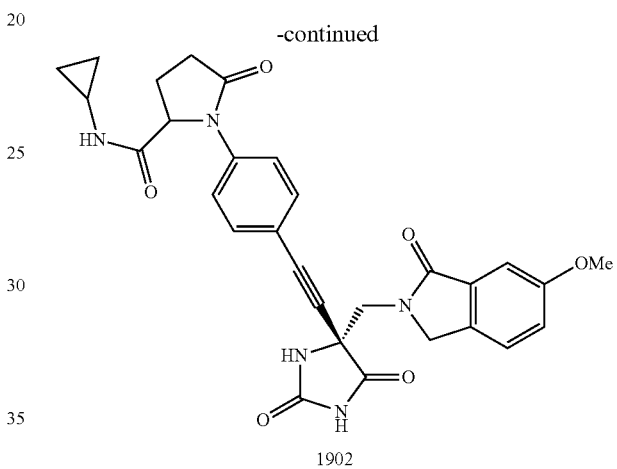

1902

Part A:

To a solution of 4-bromoaniline (1.0 g, 5.814 mmol) in toluene (12 mL) was added 6,6-dimethyl-5,7-dioxaspiro[2,5]octane-4,8-dione (1.08 g, 6.395 mmol). The reaction was stirred for 3 days at 60° C. The reaction mixture was cooled in an ice bath and the precipitate was collected by filtration to afford white solid 1901A (930 mg, 56%) which was used without further purification.

Part B:

To a flamed dried flask was added compound 1901A (150 mg, 0.5282 mmol), methyl piperazine (0.06 mL, 0.5809 mmol), HATU (301 mg, 0.7923 mmol), DIPEA (0.27 mL, 1.584 mmol) and anhydrous DMF (3 mL). The reaction mixture was stirred at room temperature for 48 hours. DMF was removed, and reaction mixture was diluted with EtOAc and washed with aq. sodium bicarbonate solution. The organic layers were combined, dried over sodium sulfate, and concentrated in vacuo. The product was purified by silica gel column (5% MeOH in $CH_2Cl_2$) to afford compound 1901B (152 mg, 78%).

Part C:

Compound 1901 was prepared from compounds 14 and 1901B by using a procedure described in Part D of Example 117.

Compound 1319 was prepared using procedures similar to those described in Example 118 and Example 6, Part B.

Example 119

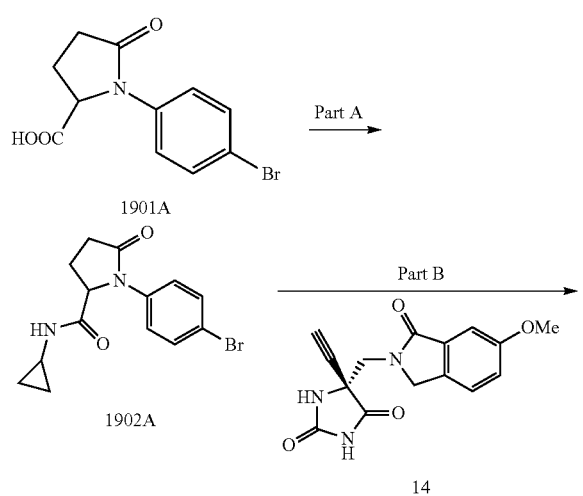

Part A:

Compound 1902A was prepared from compound 1901A by using a procedure described in Part B of Example 118.

Part B:

Compound 1902 was prepared from compounds 14 and 1902A by using a procedure described in Part D of Example 117.

Example 120

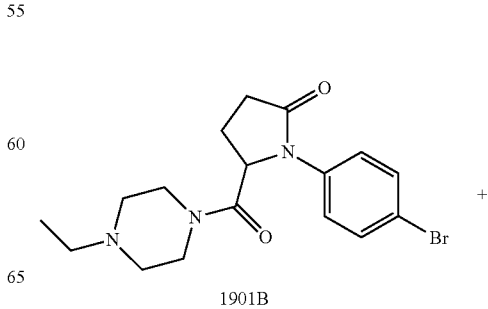

1901B

267
-continued
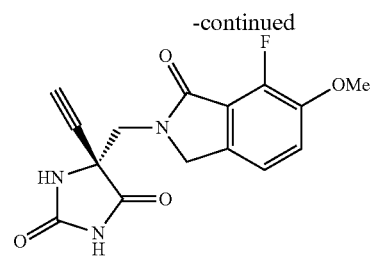
23
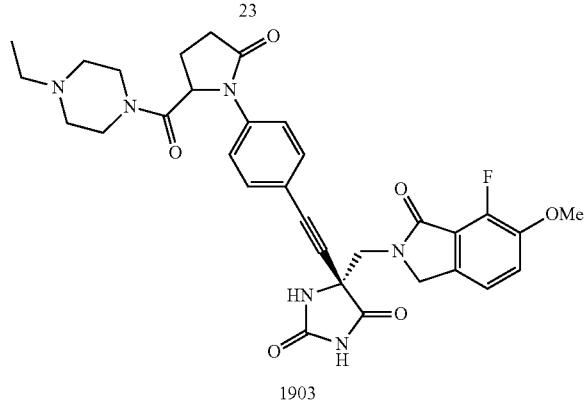
1903
Part A:
Compound 1903 was prepared from compounds 23 and 1901B by using a procedure described in Part D of Example 117.
Example 121
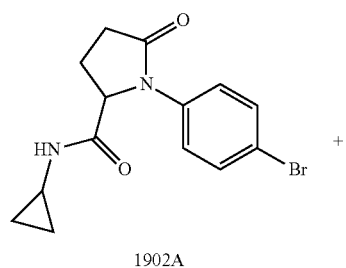
1902A
268
-continued
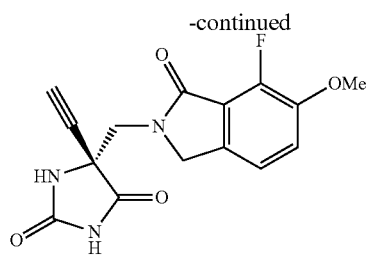
23
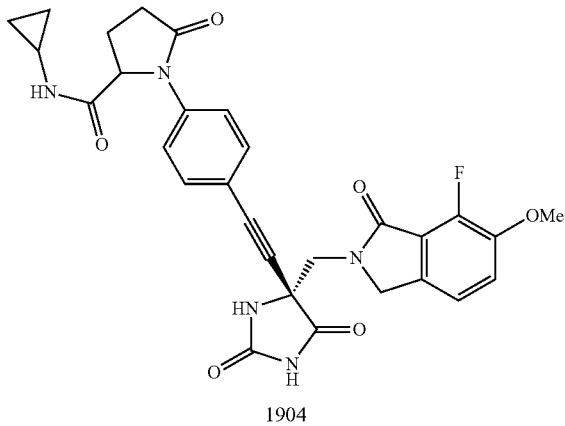
1904
Part A:
Compound 1904 was prepared from compounds 23 and 1902A by using a procedure described in Part D of Example 117.
Example 122
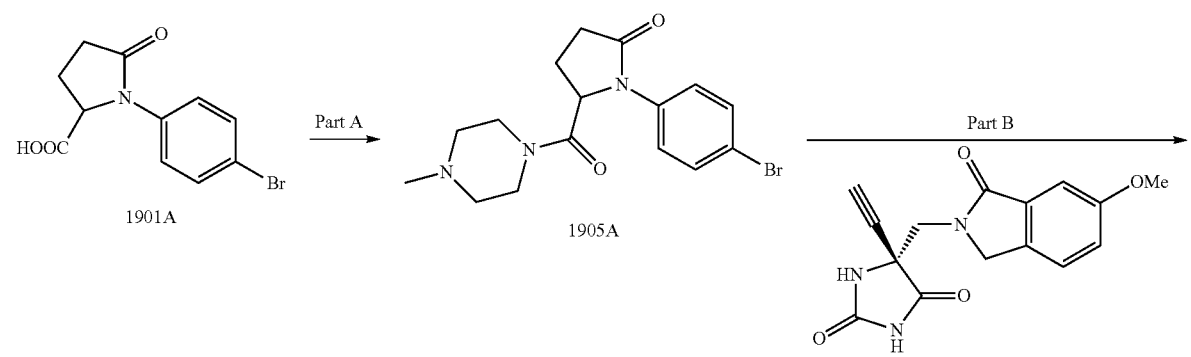

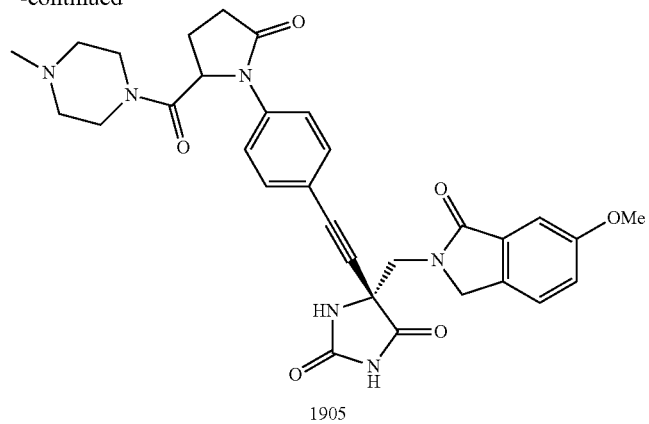

1905

Part A:
Compound 1905A was prepared from compound 1901A by using a procedure described in Part B of Example 118.
Part B:
Compound 1905 was prepared from compounds 14 and 1905A by using a procedure described in Part D of Example 117.

Example 123

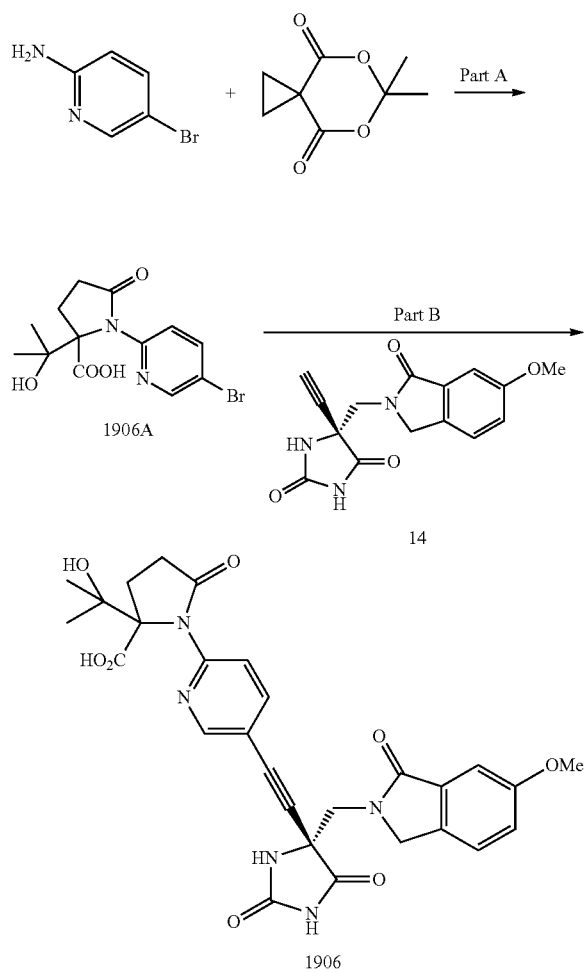

Part A:
To a solution of 2-amino-5-bromopyridine (1.0 g, 5.814 mmol) in toluene (12 mL) was added 6,6-dimethyl-5,7-dioxaspiro[2,5]octane-4,8-dione (1.09 g, 6.395 mmol). The reaction was stirred for 20 h at 60° C. The reaction mixture was cooled in an ice bath and the precipitate was collected by filtration to afford the product 1906A (800 mg, 40%) which was used without further purification.
Part B:
Compound 1906 was prepared from compounds 14 and 1906A by using a procedure described in Part D of Example 117.

Example 124

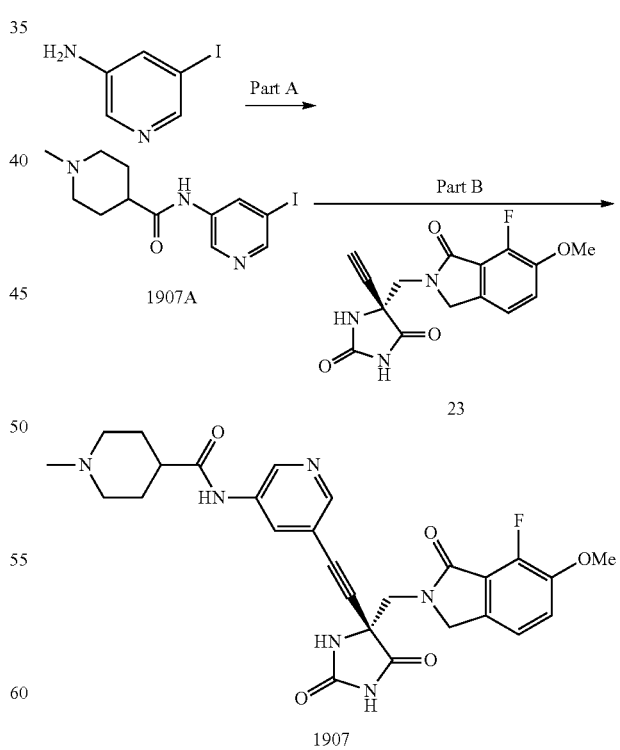

Part A:
Compound 1907A was prepared from 3-amino-5-iodopyridine and M-methylisonipecotic acid by using a procedure described in Part B of Example 118.

Part B:
Compound 1907 was prepared from compounds 23 and 1907A by using a procedure found in Part D of Example 117.
Example 125
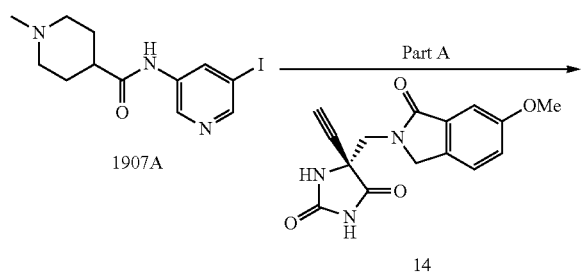
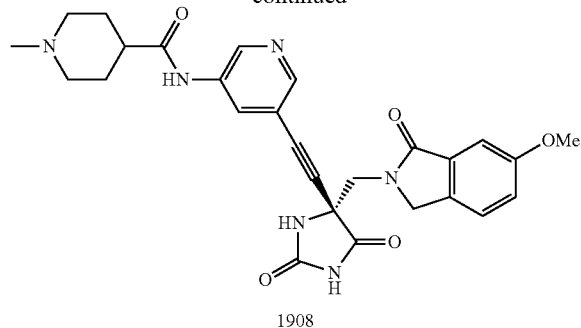
1908
Part A:
Compound 1908 was prepared from compounds 14 and 1907A by using a procedure found in Part D of Example 117.
Example 126
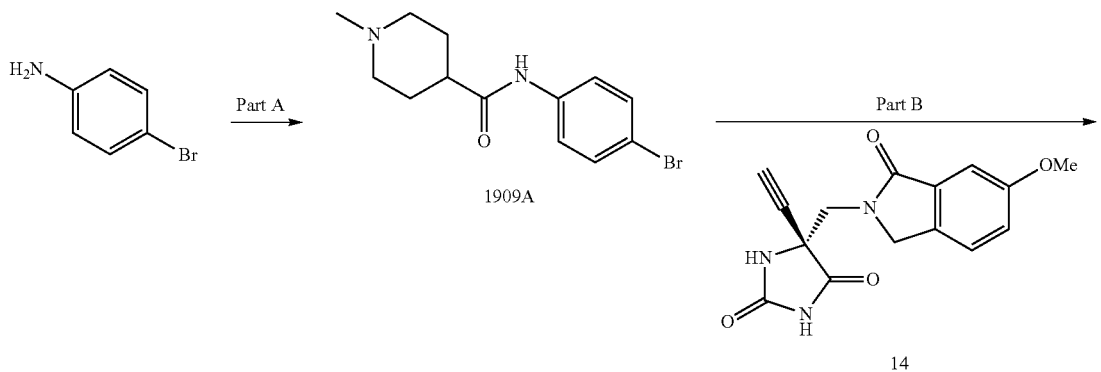
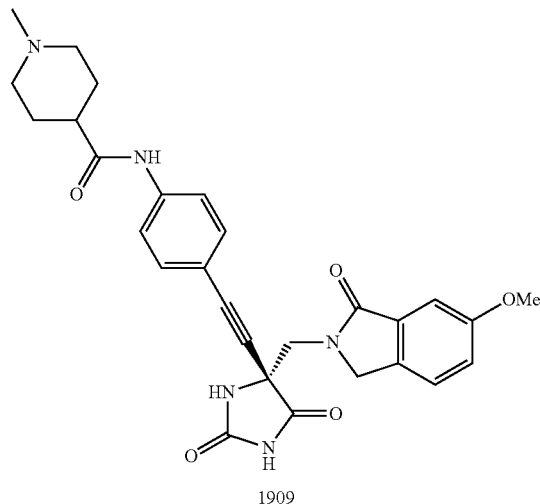
1909

Part A:
Compound 1909A was prepared from 4-bromoaniline and N-methylisonipecotic acid by using a procedure described in Part B of Example 118.

Part B:
Compound 1909 was prepared from compounds 14 and 1909A by using a procedure found in Part D of Example 117.

Example 127

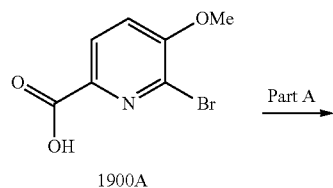

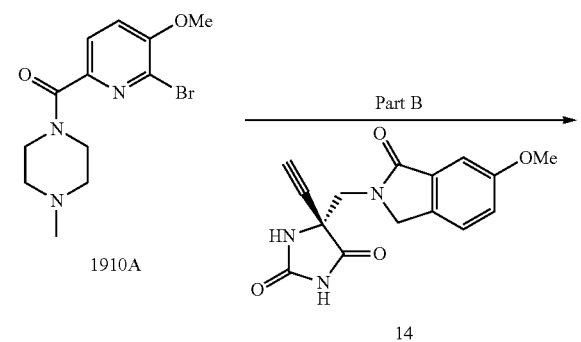

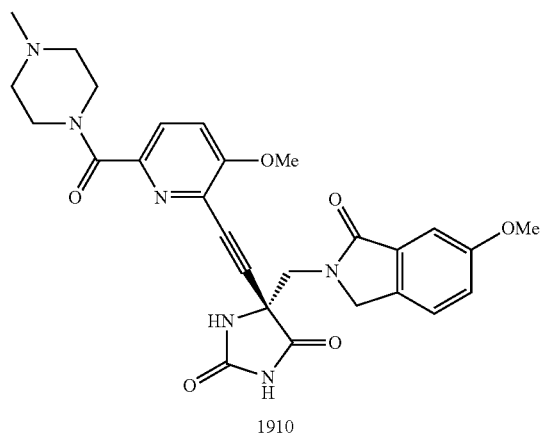

Part A:
Compound 1910A was prepared from compound 1900A and methylpiperazine by using a procedure described in Part B of Example 118.

Part B:
Compound 1910 was prepared from compounds 14 and 1910A by using a procedure found in Part D of Example 117.

Example 128

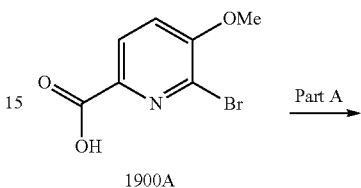

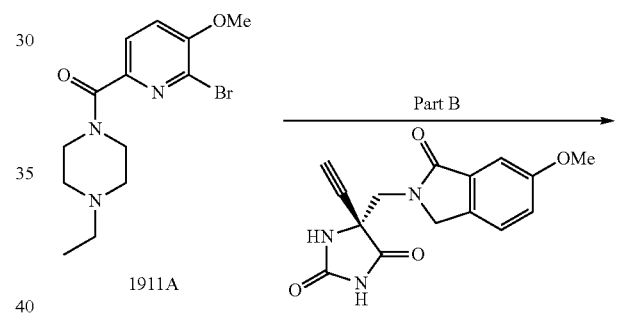

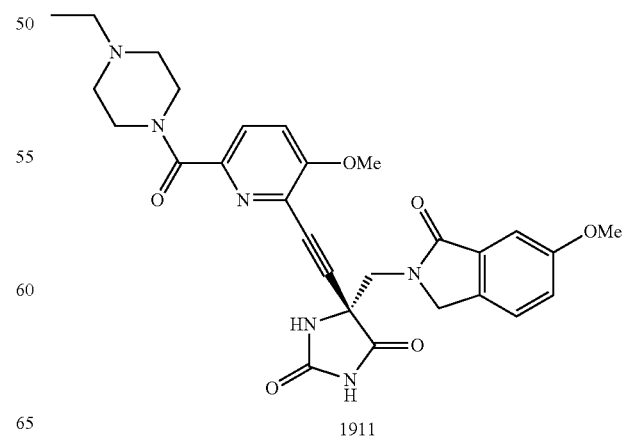

Part A:
Compound 1911A was prepared from compound 1900A and ethylpiperazine by using a procedure described in Part B of Example 118.

Part B:
Compound 1911 was prepared from compounds 14 and 1911A by using a procedure found in Part D of Example 117.

Example 129

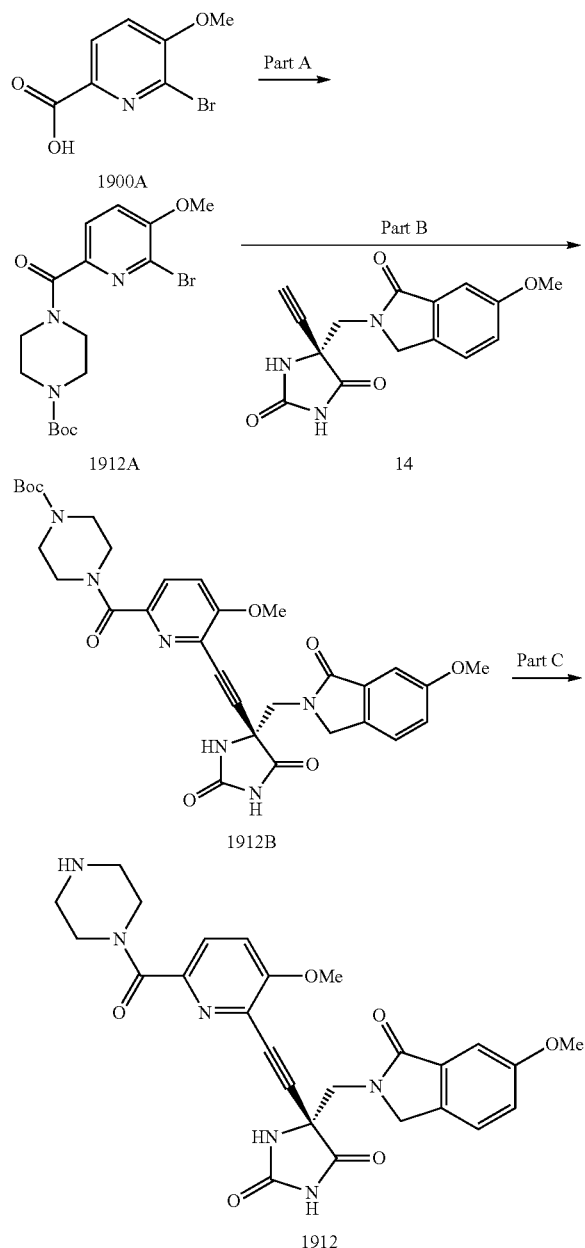

Part A:
Compound 1912A was prepared from compound 1900A and N-Boc-piperazine by using a procedure described in Part B of Example 118.

Part B:
Compound 1912B was prepared from compounds 14 and 1912A by using a procedure found in Part D of Example 117.

Part C:
Compound 1912B (40 mg, 0.07 mmol) was dissolved in $CH_2Cl_2$ (2.0 mL)-MeOH (1.0 mL) and HCl (4 N in dioxane, 0.4 mL) was added to the solution. After stirred for 3 h at 25° C., the mixture was concentrated in vacuo and the residue was purified by silica gel column (5% MeOH in $CH_2Cl_2$) to provide the product 1912 (10 mg, 30%).

Example 130

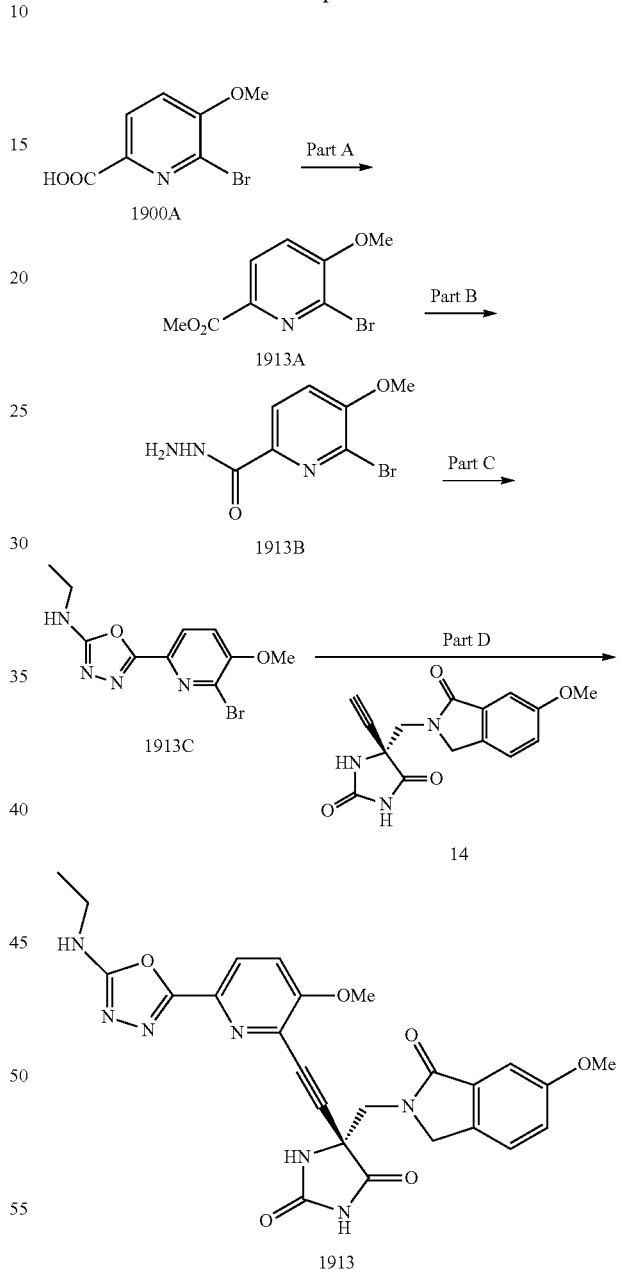

Part A:
Compound 1900A (450 mg, 1.94 mmol) was suspended in $CH_2Cl_2$-MeOH and cooled to 0° C. The mixture was stirred for 15 min and treated with TMS-diazomethane (2 M in hexane, 1.95 mL, 3.9 mmol). After stirred for 3 h at 25° C., the reaction mixture was flushed with $N_2$ stream for 20 min. Filtration through silica gel provided the desired product 1913A (380 mg, 80%).

Part B:

Compound 1913A (380 mg, 1.55 mmol) and hydrazine (0.15 mL, 4.6 mmol) were dissolved in EtOH (30 mL). The reaction mixture was stirred at 100° C. for 19 h. The mixture was cooled to 25° C. and the precipitates were filtered and washed with cold EtOH to provide the desired product 1913B (380 mg, quant.).

Part C:

Compound 1913B (400 mg, 1.62 mmol) and ethyl isocyanate (0.13 mL, 1.62 mmol) was dissolved in acetonitrile (3 mL). The mixture was stirred at 25° C. for 1 h followed by addition of p-toluenesulfonyl chloride (618 mg, 3.25 mmol) and triethylamine (0.65 mL, 4.88 mmol). The mixture was stirred at 25° C. for 20 h and concentrated in vacuo. The residue was purified by silica gel column (MeOH/$CH_2Cl_2$, gradient from 0% to 10% MeOH) to provide the desired product 1913C (260 mg, 54%).

Part D:

Compound 1913 was prepared from compounds 14 and 1913C by using a procedure found in Part D of Example 117.

Example 131

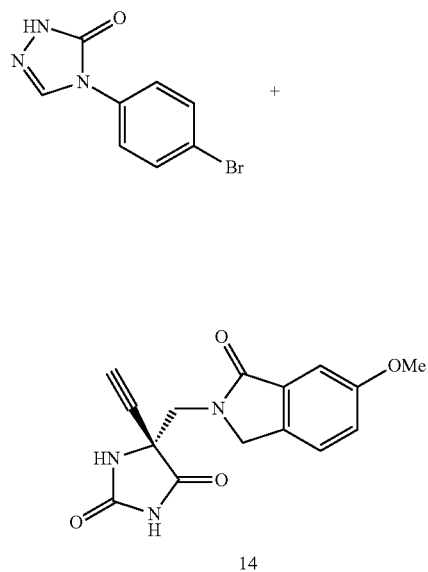

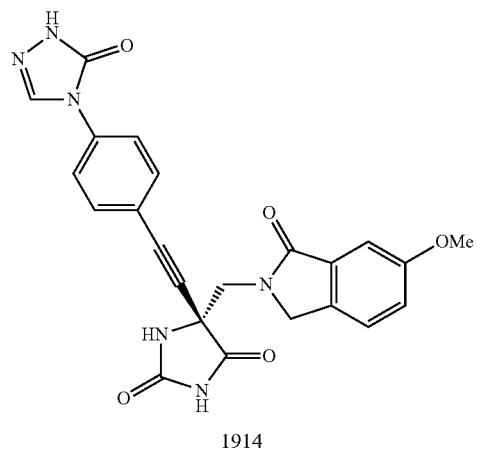

1914

Part A:

Compound 1914 was prepared from compounds 14 and 4-(4-bromophenyl)-2,4-dihydro-3H-1,2,4-triazol-3-one by using a procedure found in Part D of Example 117.

Example 132

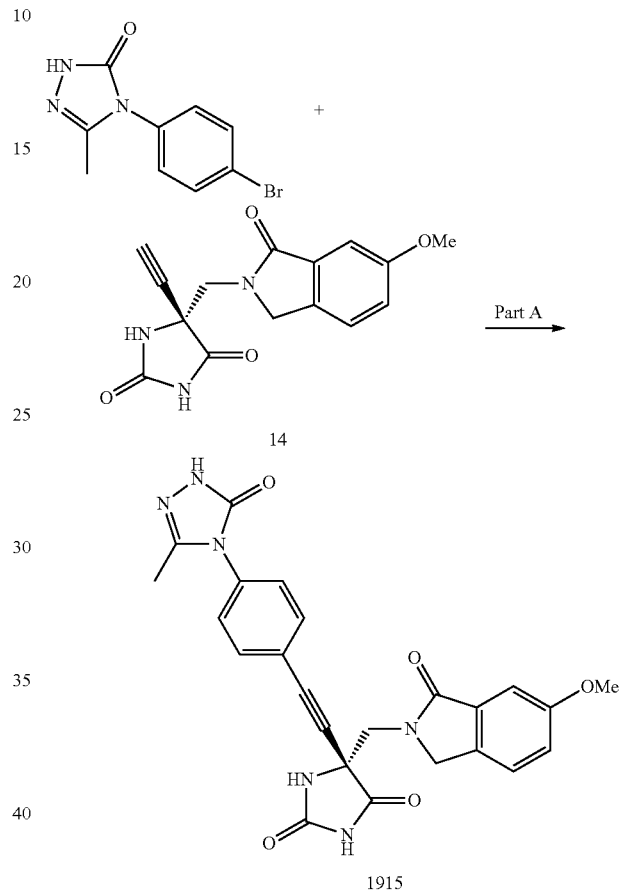

1915

Part A:

Compound 1915 was prepared from compounds 14 and 4-(4-bromophenyl)-5-methyl-2,4-dihydro-3H-1,2,4-triazol-3-one by using a procedure found in Part D of Example 117.

Example 133

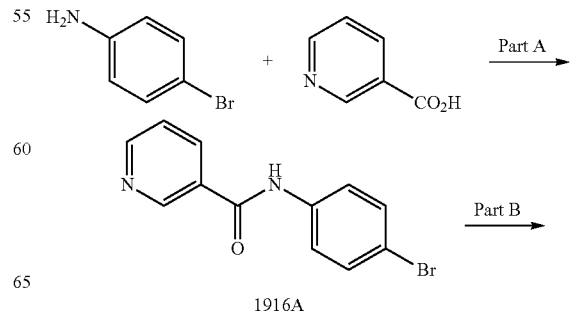

1916A

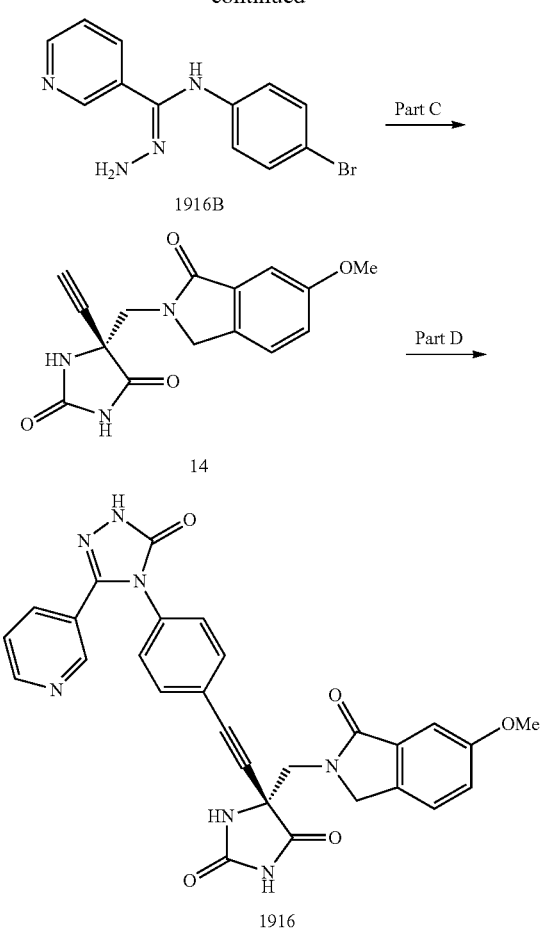

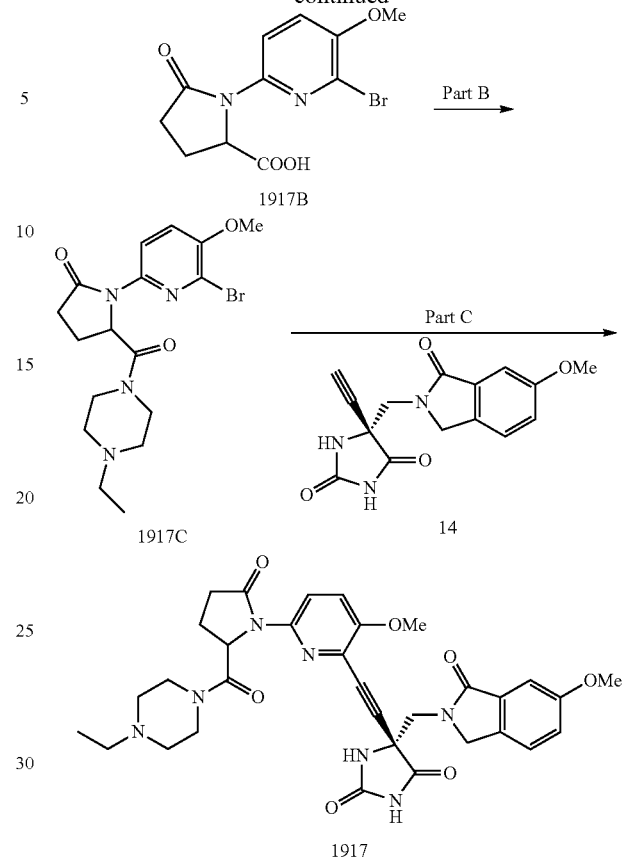

Part A:

Compound 1916A was prepared from compounds 4-bromoaniline and nicotinic acid by using a procedure found in Part A of Example 117.

Part B:

Compound 1916B was prepared from compound 1916A by using a procedure found in Part B of Example 117.

Part C:

Compound 1916C was prepared from compound 1916B by using a procedure found in Part C of Example 117.

Part D:

Compound 1916 was prepared from compounds 14 and 1916C by using a procedure found in Part D of Example 117.

Example 134

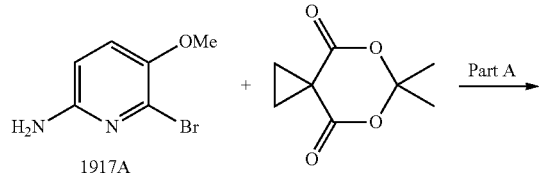

Part A:

Compound 1917B was prepared from compounds 1917A (prepared by a procedure similar to that described by Gary J. Clark and Leslie W. Deady, *Australian Journal of Chemistry* 1981, 34, 927-32) and 6,6-dimethyl-5,7-dioxaspiro[2,5]octane-4,8-dione by using a procedure found in Part A of Example 118.

Part B:

Compound 1917C was prepared from compounds 1917B and ethylpiperazine by using a procedure found in Part B of Example 117.

Part C:

Compound 1917 was prepared from compounds 14 and 1917C by using a procedure found in Part D of Example 117.

Example 135

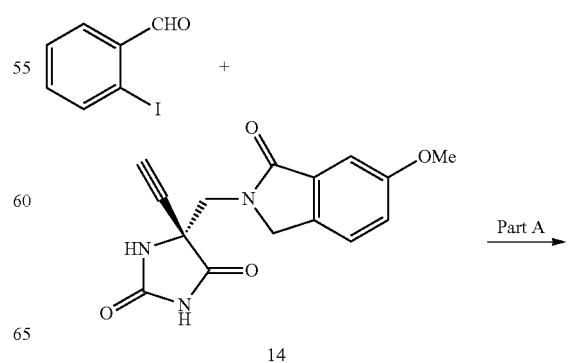

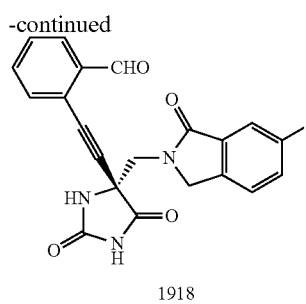

1918

Part A:

Compound 1918 was prepared from compounds 14 and 2-iodobenzaldehyde by using a procedure found in Part D of Example 117.

Example 136

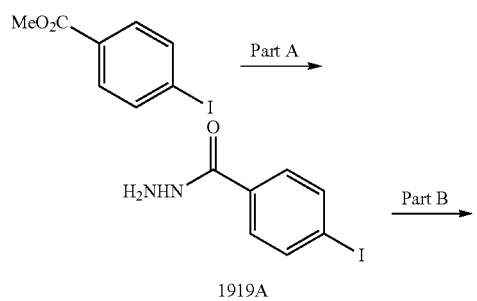

Part A:

Compound 1919A was prepared from methyl 4-iodobenzoate by using a procedure described in Part B of Example 130.

Part B:

A solution of compound 1919A (220 mg, 0.84 mmol) in MeOH (6 mL) and 1,4-dioxane (3 mL) was treated with BrCN and the mixture was stirred at 25° C. for 1 h. After addition of NaHCO$_3$ (150 mg), the mixture was stirred for 19 h. The solid was filtered and washed with water to provide the product 1919B (205 mg, 85%).

Part C:

Compound 1919 was prepared from compounds 14 and 1919B by using a procedure found in Part D of Example 117.

Example 137

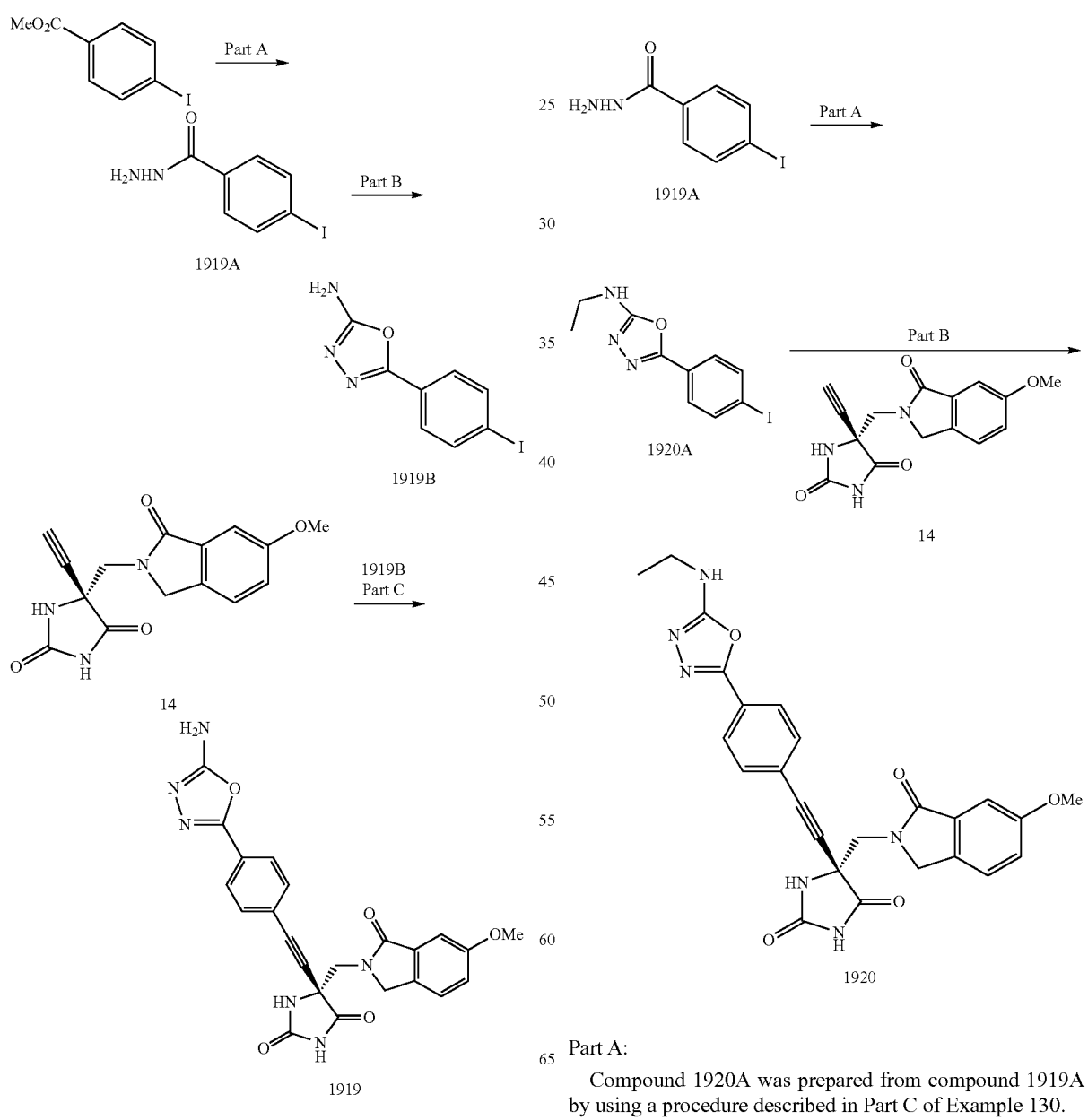

Part A:

Compound 1920A was prepared from compound 1919A by using a procedure described in Part C of Example 130.

Part B:

Compound 1920 was prepared from compounds 14 and 1920A by using a procedure found in Part D of Example 117.

Example 138

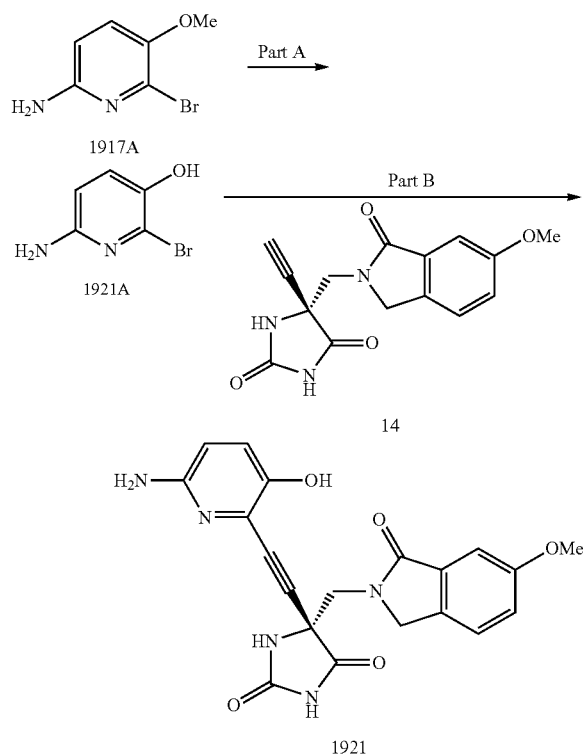

Part A:

Compound 1917A (41 mg, 0.20 mmol) was dissolved in 1,2-dichloroethane (2 mL) and aluminum chloride (54 mg, 0.40 mmol) was added. The reaction mixture was stirred at 40° C. for 18 h. After cooling, the mixture was added to aq. Na$_2$CO$_3$ solution and the organic layers were extracted with EtOAc. The combined organic layers were washed with brine solution, dried (Na$_2$SO$_4$), and concentrated in vacuo to provide the crude product 1921A (37 mg, 99%).

Part B:

Compound 1921 was prepared from compounds 14 and 1921A by using a procedure found in Part D of Example 117.

Example 139

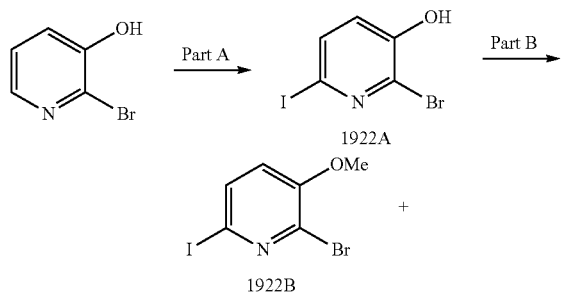

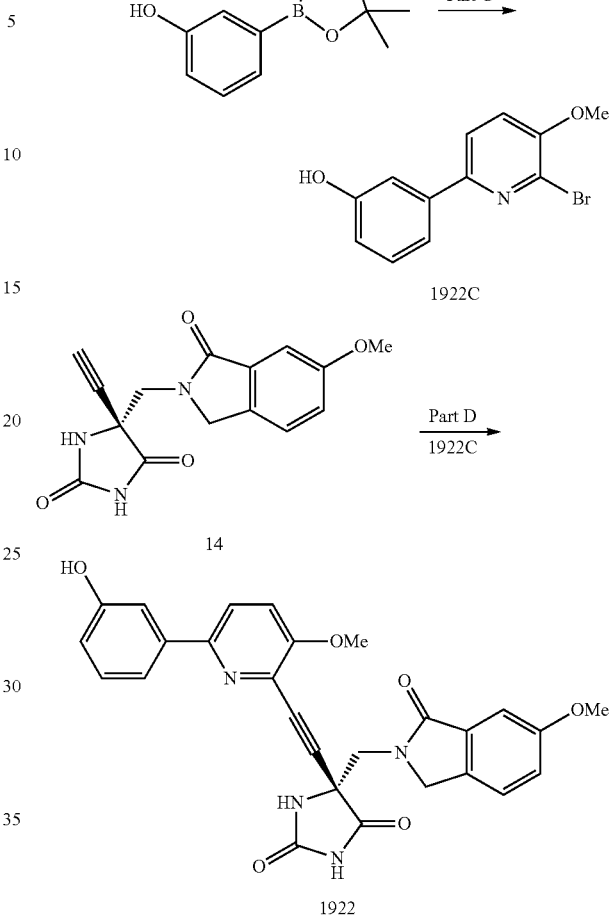

Part A:

A suspension of 2-bromo-3-hydroxypyridine (6 g, 34.4 mmol) in water (140 mL) was treated with potassium carbonate (9.52 g, 69.0 mmol) and iodine (9.6 g, 38.0 mmol) at 25° C. The mixture was stirred for 3 h and the solid was filtered and washed with water to provide the desired product 1922A (6.5 g, 63%).

Part B:

A solution of compound 1922A (6.5 g, 21.7 mmol) in DMF was treated with potassium carbonate (8.9 g, 65.0 mmol) and iodomethane (5.4 mL, 86.7 mmol) at 25° C. The mixture was stirred for 3 h and added to water. The solid was filtered and washed with water to provide the desired product 1922B (6.7 g, 99%).

Part C:

Compound 1922B (550 mg, 1.75 mmol), 2-(3-Hydroxyphenyl)-4,4,5,5-tetramethyl-1,3,2-dioxaborolane (425 mg, 1.93 mmol), Pd(PPh$_3$)$_4$ (100 mg, 0.087 mmol), and potassium carbonate (1M aq. solution, 10 mL, 10 mmol) were dissolved in acetonitrile (70 mL). The mixture was degassed and heated to 90° C. for 29 h. After cooling to 25° C., the mixture was concentrated and the residue was purified by SiO$_2$ column chromatography (MeOH/CH$_2$Cl$_2$ gradient from 0% to 10% MeOH) to provide 1922C (430 mg, 88%).

Part D:

Compound 1922 was prepared from compounds 14 and 1922C by using a procedure found in Part D of Example 117.

Example 140

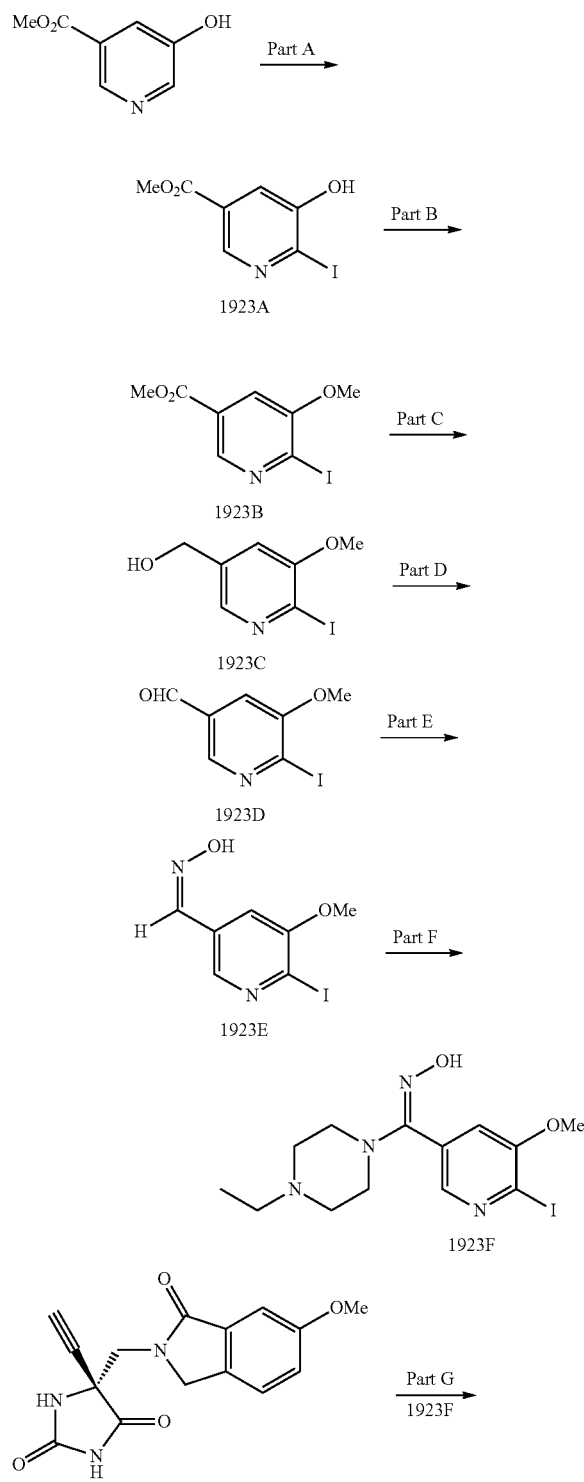

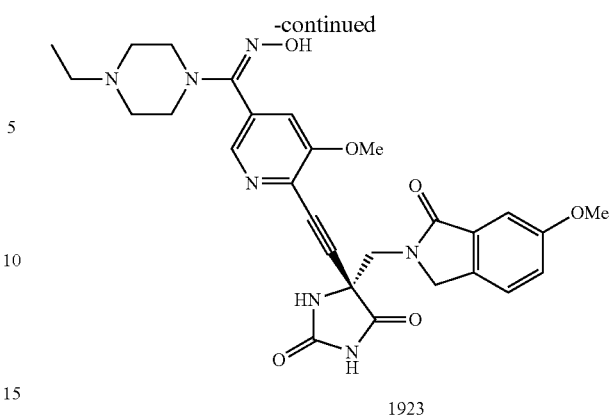

Part A:

Methyl 5-hydroxynicotinate (1 g, 6.54 mmol), sodium carbonate (1.39 g, 13.1 mmol), and iodine (1.6 g, 6.54 mmol) were suspended in water (100 mL) and stirred at 25° C. for 1.5 h. The mixture was acidified with aq. 1 N HCl and the resulting solid was filtered to provide the desired product 1923A (1.62 g, 89%).

Part B:

A solution of compound 1923A (5.5 g, 19.7 mmol) in DMF (20 mL) was treated with iodomethane (3.7 mL, 59.1 mmol) and sodium hydride (60% dispersion in oil, 867 mg, 21.7 mmol) at 0° C. After stirred for 2 h, the mixture was added to cold water and the organic layers were extracted with EtOAc. Combined organic solution was washed with brine solution, dried ($Na_2SO_4$), and concentrated in vacuo. The residue was purified by silica gel column ($CH_2Cl_2$) to provide the desired product 1923B (4.5 g, 78%).

Part C:

Compound 1923B (2.15 g, 7.33 mmol) was suspended in $CH_2Cl_2$ (50 mL) and cooled in dry ice-acetone bath. Diisopropylaluminum hydride (1M in THF, 17.0 mL, 17.0 mmol) was added slowly and the temperature was allowed to warm to 0° C. for 2 h. The reaction was quenched by 10% aq. citric acid and the mixture was stirred at 25° C. for 1 h. The organic layers were extracted with $CH_2Cl_2$ and the combined organic solution was washed with brine solution, dried ($Na_2SO_4$), and concentrated in vacuo to provide crude product 1923C (1.39 g, 72%).

Part D:

Compound 1923C (1.03 g, 3.90 mmol) was dissolved in $CHCl_3$ (20 mL) and $MnO_2$ (1.2 g, 11.7 mmol) was added at 25° C. After stirring for 1 days at 40° C., the solid was removed by filtration and the filtrate was concentrated in vacuo to provide the desired product 1923D (860 mg, 83%).

Part E:

A mixture of compound 1923D (200 mg, 0.76 mmol), hydroxylamine hydrochloride (63 mg, 0.91 mmol), and sodium acetate (75 mg, 0.91 mmol) in EtOH (7 mL) was stirred at 80° C. for 20 h in a pressure vessel. After cooled to 25° C., the mixture was added to water and the organic layers were extracted with $CH_2Cl_2$. Combined organic solution was washed with brine solution, dried ($Na_2SO_4$), and concentrated in vacuo. The residue was purified by silica gel column (MeOH/$CH_2Cl_2$, gradient from 0% to 3% MeOH) to provide the desired product 1923E (137 mg, 65%).

Part F:

A solution of compound 1923E (137 mg, 0.49 mmol) in DMF (1 mL) was treated with N-chlorosuccinimide (72 mg, 0.54 mmol) at 25° C. After stirred for 3 h, the mixture was treated with ethylpiperazine (0.13 mL, 0.99 mmol) and stirred for 2 h. The mixture was added to water and the organic layers were extracted with EtOAc. Combined organic solution was washed with brine solution, dried (Na$_2$SO$_4$), and concentrated in vacuo. The residue was purified by silica gel column (MeOH/CH$_2$Cl$_2$, gradient from 0% to 4% MeOH) to provide the desired product 1923F (133 mg, 70%).

Part G:

Compound 1923 was prepared from compounds 14 and 1923F by using a procedure found in Part D of Example 117.

Example 141

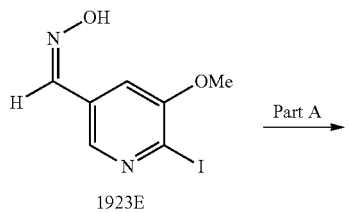

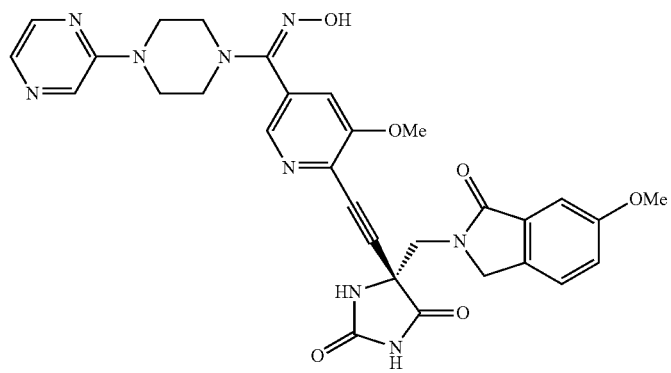

Part A:
Compound 1924A was prepared from compounds 1923E and N-(2-pyrazine)-piperazine by using a procedure described in Part F of Example 140.

Part B:
Compound 1924 was prepared from compounds 14 and 1924A by using a procedure found in Part D of Example 117.

Example 142

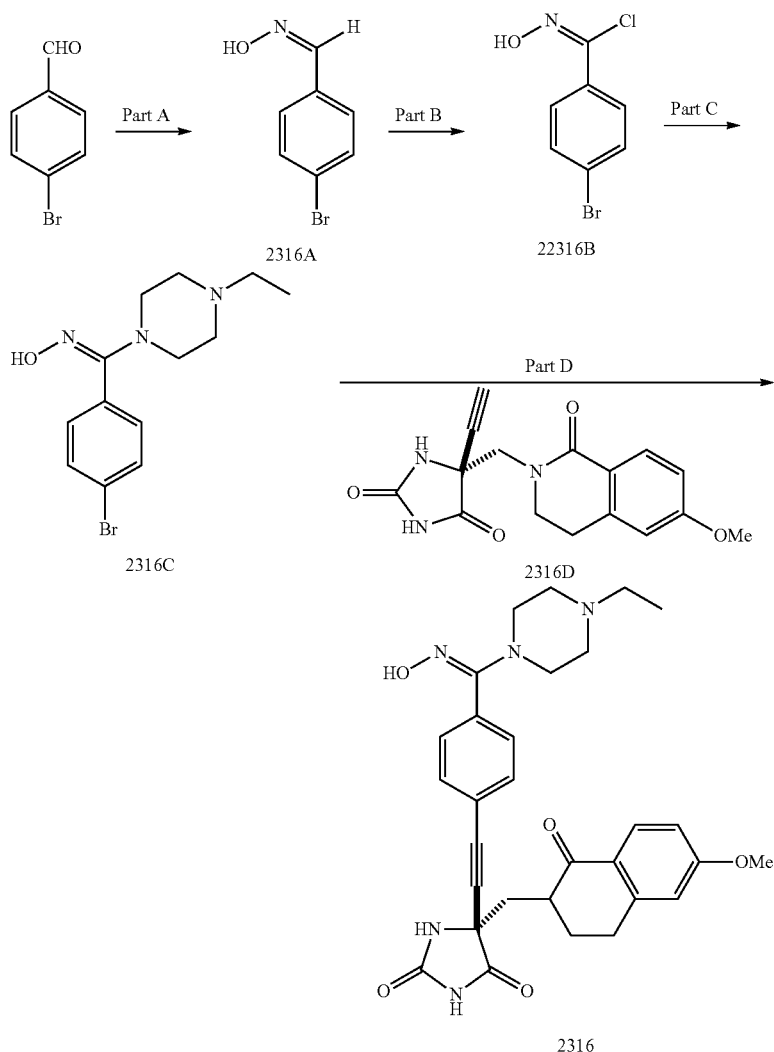

Part B
Solid N-chlorosuccinimide (0.722 g, 5.39 mmol) was added to a stirred solution of oxime (Compound 2316A; 1.072 g, 5.39 mmol) in dry DMF (15 mL). The reaction mixture was stirred at rt for 18 h. The reaction mixture was diluted with Et₂O (150 mL) and was washed sequentially with water (3×50 mL) and brine (~50 mL). The organic layer was dried over anhydrous MgSO₄, filtered and concentrated under reduced pressure to give a pale yellow solid. Purification of the solid by sgc (40 g silica gel cartridge; 5-25% EtOAc-hexanes gradient) gave 973 mg (77% yield) of the desired product, Compound 2316B, as a white solid.

Part C
N-Ethylpiperazine (97 mg, 0.86 mmol) was added to a solution of oximyl chloride (Compound 2316B, 100 mg, 0.43 mmol) in CH₂Cl₂ (4 mL) and the resulting mixture was stirred overnight at rt. Evaporation of the solvent gave a residue that was purified by sgc (1-10% MeOH/NH₃ in CH₂Cl₂ gradient) to afford 112 mg (84% yield) of the desired product, Compound 2316C, as an off-white solid.

Part D
Aryl bromide 2316C was combined with Compound 2316D according to the procedure of Example 6 to give Part A
A mixture of p-bromobenzaldehyde (5.00 g, 27.0 mmol), hydroxylamine hydrochloride (3.73 g, 54.1 mmol) and anhydrous sodium acetate (4.43 g, 54.1 mmol) in absolute ethanol (100 mL) was stirred at reflux (80° C. external oil bath temperature) in a pressure vessel for 24 h. The solvent was removed under reduced pressure. The remaining solid was dissolved in Et₂O (~250 mL) and the resulting solution was washed sequentially with water (2×~100 mL) and brine (~100 mL). The organic layer was dried over anhydrous MgSO₄, filtered and concentrated under reduced pressure to afford Compound 2316A as a white solid (5.23 g, 97% yield).

Compound 2316. The preparation of Compound 2316D was described previously in Lavey, B. J. WO 2007/084451, Example 1087.

Compound 2316: HPLC-MS $t_R$=2.13 min (UV$_{254\ nm}$); mass calculated for formula $C_{29}H_{32}N_6O_5$ 544.2, observed LCMS m/z 545.3 [M+H]$^+$.

Compounds 2317, 2319 and 2320 were prepared in an analogous manner as 2316.

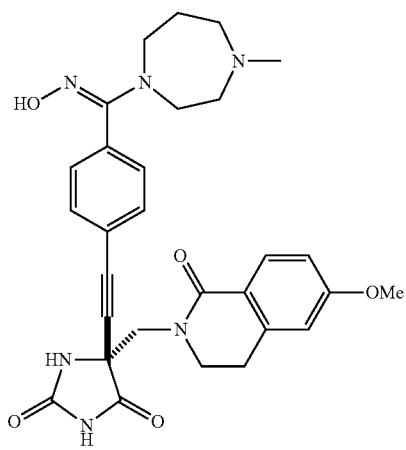

2317

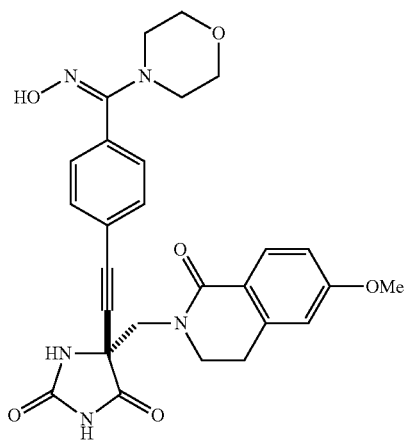

2319

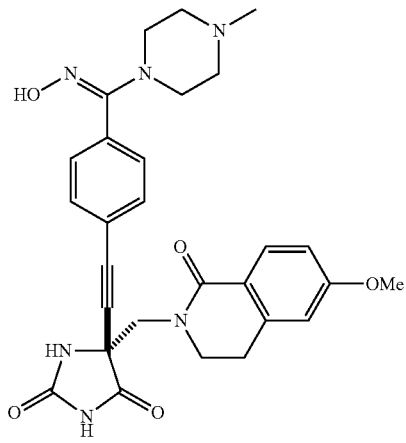

2320

Compound 2317: HPLC-MS $t_R$=1.85 min (UV$_{254\ nm}$); mass calculated for formula $C_{29}H_{32}N_6O_5$ 544.2, observed LCMS m/z 545.3 [M+H]$^+$.

Compound 2319: HPLC-MS $t_R$=2.37 min (UV$_{254\ nm}$); mass calculated for formula $C_{27}H_{27}N_5O_6$ 515.2, observed LCMS m/z 518.3 [M+H]$^+$.

Compound 2320: HPLC-MS $t_R$=2.07 min (UV$_{254\ nm}$); mass calculated for formula $C_{28}H_{30}N_6O_5$ 530.2, observed LCMS m/z 531.3 [M+H]$^+$.

Example 143

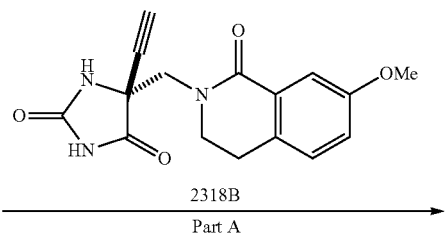

2318A

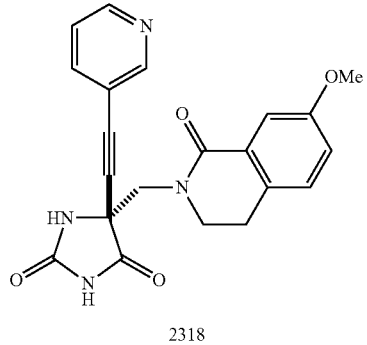

2318

Compound 2318 was prepared via a route analogous to that described in Lavey, B. J. WO 2007/084451, Example 1087.
Compound 2318: HPLC-MS $t_R$=2.47 min (UV$_{254\ nm}$); mass calculated for formula $C_{21}H_{18}N_4O_4$ 390.1, observed LCMS m/z 391.3 [M+H]$^+$.

Example 144

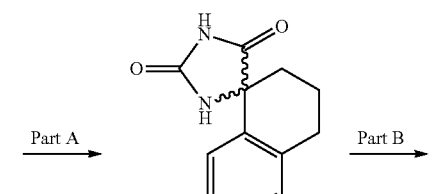

2321A   2321B

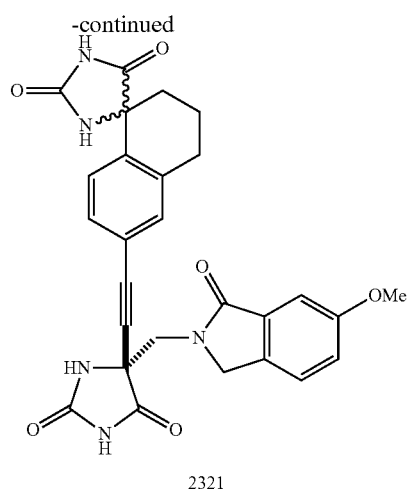

2321

Part A

To a solution of Compound 2321A (238 mg, 1.06 mmol) in absolute EtOH (1 mL) in a pressure vessel were sequentially added potassium cyanide (103 mg, 1.59 mmol), ammonium carbonate (355 mg, 3.70 mmol) and conc. ammonium hydroxide (1.0 mL). The vessel was capped and the reaction was allowed to proceed for 18 h at 60° C. The reaction mixture was allowed to cool to rt and was extracted with $CH_2Cl_2$ (2×25 mL). The combined extracts were washed with brine (25 mL), dried over anhydrous $MgSO_4$ and filtered. Evaporation of solvent yielded a crude product that could be purified by reverse-phase C18 chromatography (20-80% MeCN—$H_2O$ gradient) to afford Compound 2321B as a white solid (102 mg, 33% yield).

Part B

Compound 2321B was converted into Compound 2321 by following the procedure given in Example 6. HPLC-MS $t_R$=2.94 min ($UV_{254\ nm}$); mass calculated for formula $C_{28}H_{25}N_5O_6$ 527.2, observed LCMS m/z 528.3 $[M+H]^+$.

The present invention provides compounds which are selected from the group consisting of compounds listed in Table A below, or a pharmaceutically acceptable salt, solvate, ester or isomer thereof. Table A also lists the mass spectroscopy data.

Example 144.1

Preparation of Deuterium in Benzyl Lactam Moiety of Compounds

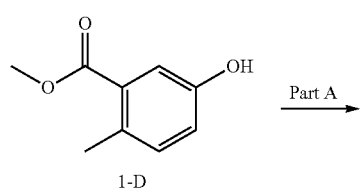

1-D

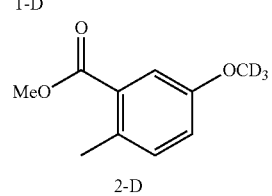

2-D

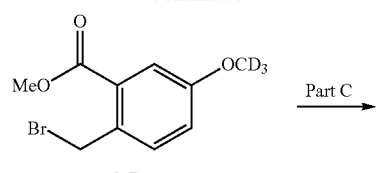

3-D

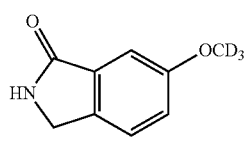

4-D

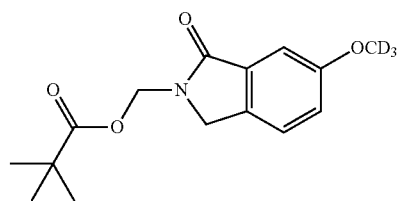

5-D

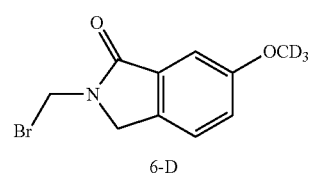

6-D

Incorporation of deuterium in to the benzyl lactam moiety can be accomplished by the treatment of compound 1-D with cesium carbonate and iodomethane-$D_3$ in DMF to afford compound 2-D upon work up. Compound 2-D can be converted to compound 6-D using the procedures described in Example 1. Using the procedures described in Examples 2, 3 and 6 compound 6-D, the benzyl lactam moiety can be incorporated into the compounds of the invention, such as compound 976, as shown in the scheme below.

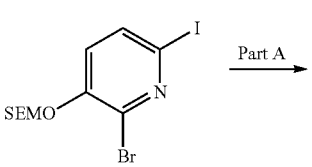

970C

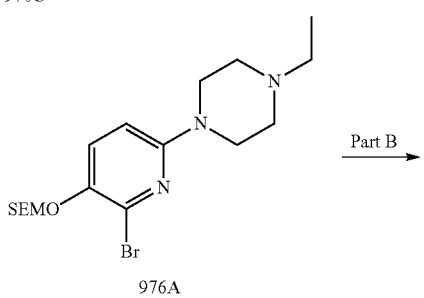

976A

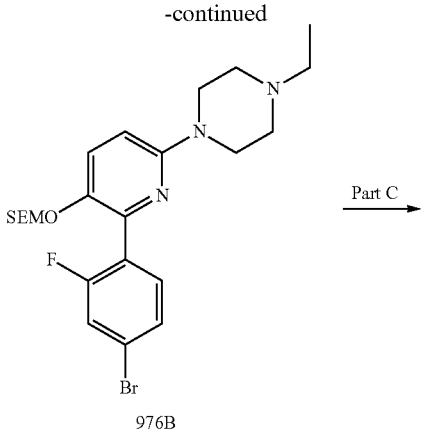

976B

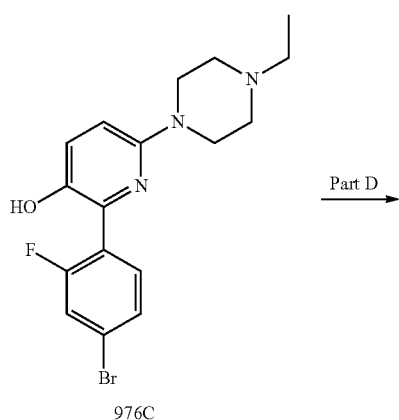

976C

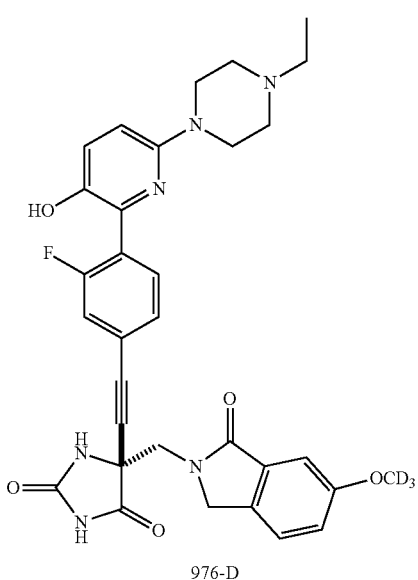

976-D

Example 145

Assay for Inhibition of TNF-α Production from Human Whole Blood (hWBA)

Human whole blood was diluted 1:1 with serum free medium (RPMI, L-glutamine, Pen-Strep, HEPES) and incubated with a test compound in a final volume of 360 μL for 1 h at 37° C. Forty microliters of LPS (10 μg/mL) was then added. Supernatant was collected after 3.5 h incubation and the concentration of TNF-α was determined by ELISA (R&D Systems). The concentration of the test compound which inhibits 50% of the amount of TNF-α from the untreated control was determined. The $IC_{50}$ values for representative compounds of the invention are shown below in Table A.

Example 146

Area under the Curve Determinations of Plasma Levels in Rats (rrAUC)

To gain insight into the pharmacokinetic properties of the compounds of the invention, plasma levels of the compounds in rats were determined according to the protocol described in Korfmacher, W. A.; Cox, K. A.; Ng, K. J.; Veals, J.; Hsieh, Y.; Wainhaus, S.; Broske, L.; Prelusky, D.; Nomeir, A.; White, R. E. *Rapid Commun. Mass Spectrom.* 2001, 15, 335. Briefly, rats, after an overnight fast, were dosed orally with the test compound at a dose of 10 mg/kg in a 5 mL/kg dose volume. Blood was collected at 0.5, 1, 2, 3, 4, and 6 h post-dosing. Mass spectrometry using high performance liquid chromatography was used to identify and measure the concentrations of the test compounds in the plasma at the various time points. The parent ion of each test compound was used to identify and quantitate the compounds in plasma. The area under the curve (AUC) data for representative compounds of the invention is shown below in Table A.

TABLE A

| ID | Structure | Exact Mass | Mass Obsvd | Ki (nM) | hWBA (nM) | RR AUC (nM·h)[1] |
|---|---|---|---|---|---|---|
| 300 | 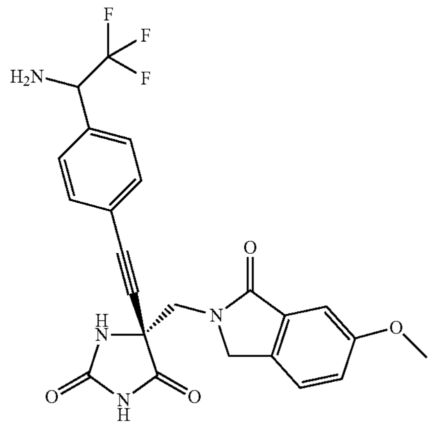 [SMILES: COc1ccc2c(c1)C(=O)N(C[C@@]1(C#Cc3ccc(C(N)C(F)(F)F)cc3)NC(=O)NC1=O)C2] | 472.14 | 473.2 | 0.306 | 1086 | 2597 |
| 301 | 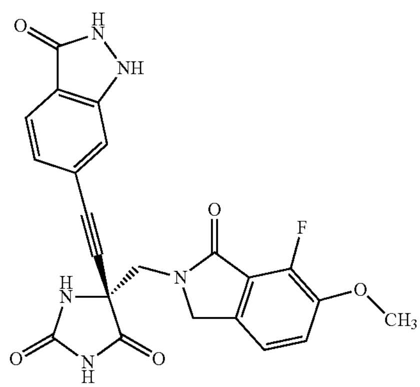 [SMILES: COc1ccc2c(c1F)C(=O)N(C[C@@]1(C#Cc3ccc4c(=O)[nH][nH]c4c3)NC(=O)NC1=O)C2] | 449.11 | 450.1 | 0.349 | 226.45 | |
| 302 | 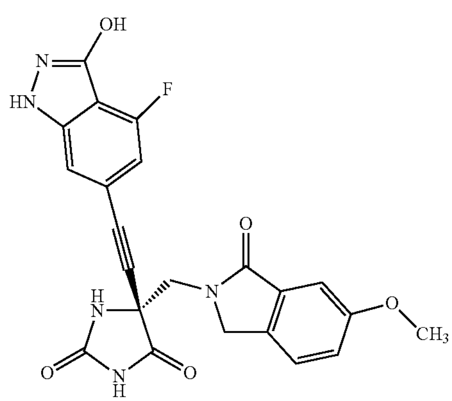 [SMILES: COc1ccc2c(c1)C(=O)N(C[C@@]1(C#Cc3cc(F)c4c(O)n[nH]c4c3)NC(=O)NC1=O)C2] | 449.11 | 450.1 | 0.0521 | 723 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 303 | 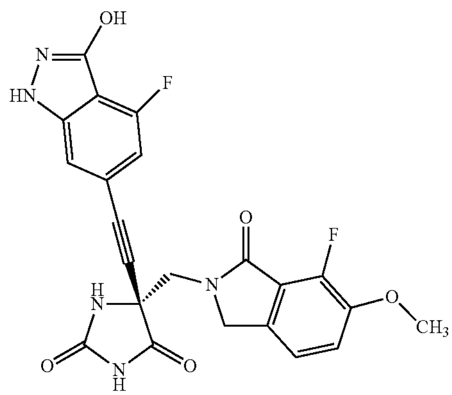 [SMILES: COc1ccc2c(c1F)C(=O)N(C[C@@]1(C#Cc3cc(F)c4c(O)n[nH]c4c3)NC(=O)NC1=O)C2] | 467.10 | 468.1 | 0.03 | 383.45 | 0 |
| 306 | 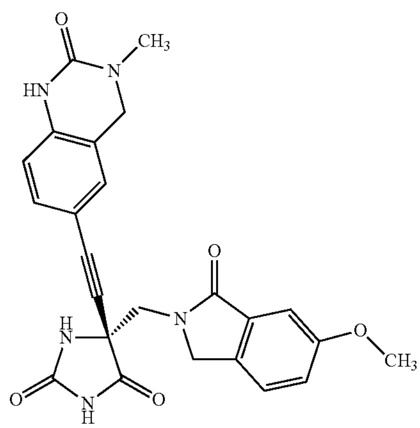 [SMILES: COc1ccc2c(c1)C(=O)N(C[C@@]1(C#Cc3ccc4c(c3)CN(C)C(=O)N4)NC(=O)NC1=O)C2] | 459.15 | 460.1 | 0.351 | 507.15 | 12 |
| 307 | 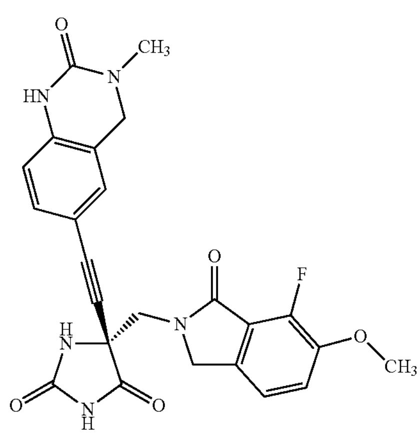 [SMILES: COc1ccc2c(c1F)C(=O)N(C[C@@]1(C#Cc3ccc4c(c3)CN(C)C(=O)N4)NC(=O)NC1=O)C2] | 477.14 | 478.1 | 0.31 | 281.3 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 308 | 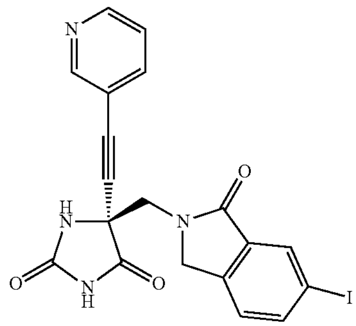 [SMILES: O=C1NC(=O)[C@](C#Cc2cccnc2)(CN2Cc3ccc(I)cc3C2=O)N1] | 472.00 | 473.0 | 146 | 100001 | |
| 309 | 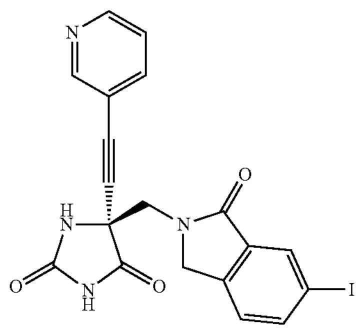 [SMILES: O=C1NC(=O)[C@](C#Cc2cccnc2)(CN2Cc3ccc(I)cc3C2=O)N1] | 472.00 | 473.0 | 0.324 | 976.7 | |
| 310 | 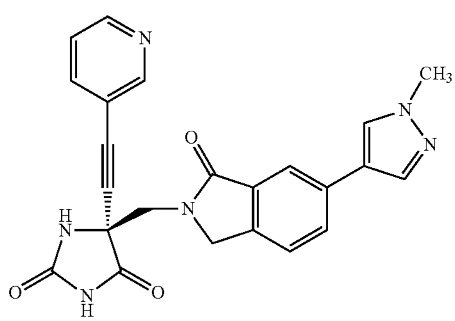 [SMILES: Cn1cc(-c2ccc3c(c2)C(=O)N(C[C@]2(C#Cc4cccnc4)NC(=O)NC2=O)C3)cn1] | 426.14 | 427.1 | 501 | 10000001 | |
| 311 | 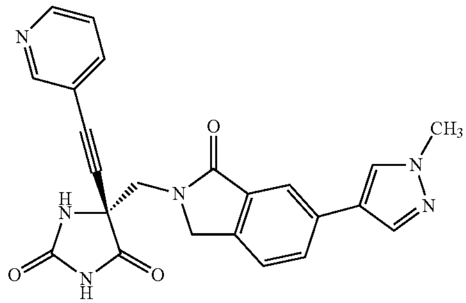 [SMILES: Cn1cc(-c2ccc3c(c2)C(=O)N(C[C@@]2(C#Cc4cccnc4)NC(=O)NC2=O)C3)cn1] | 426.14 | 427.1 | 501 | 1000001 | |

TABLE A-continued
| ID | Structure | Exact Mass | Mass Obsvd | Ki (nM) | hWBA (nM) | RR AUC (nM · h)[1] |
|---|---|---|---|---|---|---|
| 312 | 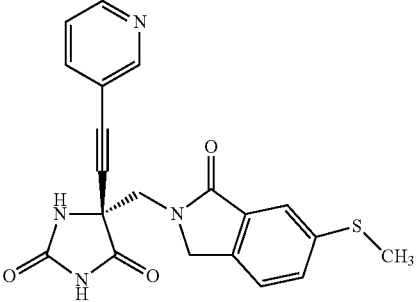 [SMILES: CSc1ccc2c(c1)C(=O)N(C[C@@]1(C#Cc3cccnc3)NC(=O)NC1=O)C2] | 392.09 | 393.1 | 0.391 | 651.1 | |
| 500 | 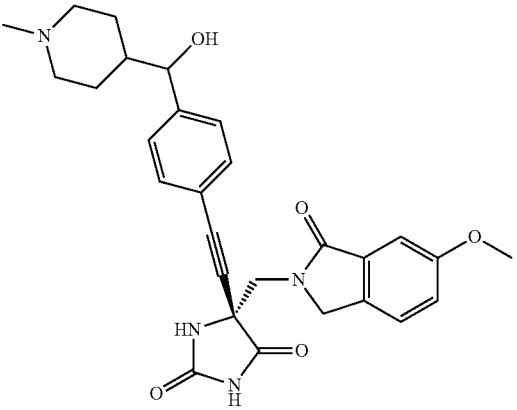 | 502.22 | 503.2 | 0.408 | 244.5 | 11 |
| 705 | 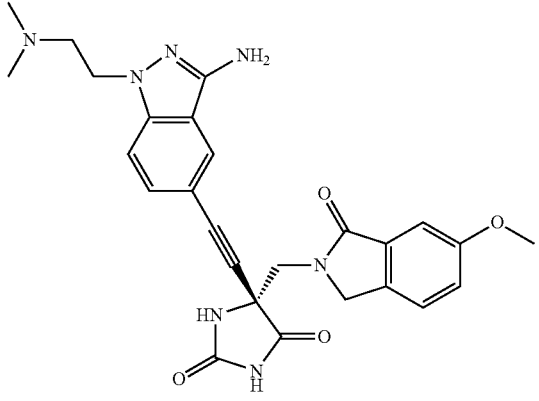 | 501.2 | 502.3 | 0.521 | 101 | 0 |
| 746 | 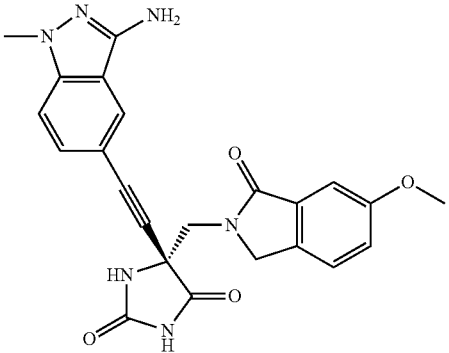 | 444.1 | 445.1 | 0.477 | 2903.5 | 82 |

TABLE A-continued
| ID | Structure | Exact Mass | Mass Obsvd | Ki (nM) | hWBA (nM) | RR AUC (nM·h)[1] |
|---|---|---|---|---|---|---|
| 709 | 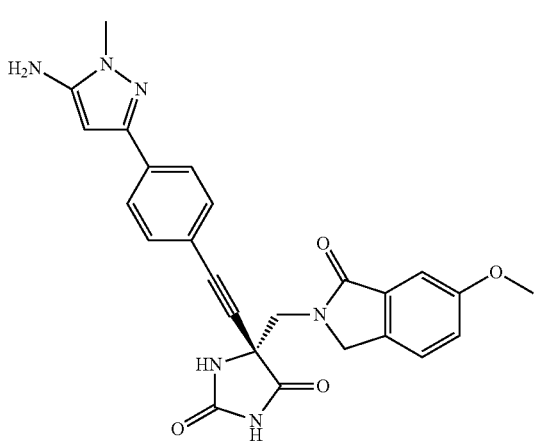 [SMILES: COc1ccc2c(c1)C(=O)N(C[C@@]1(C#Cc3ccc(-c4cc(N)n(C)n4)cc3)NC(=O)NC1=O)C2] | 470.1 | 471.1 | 0.271 | 223 | 357 |
| 747 | 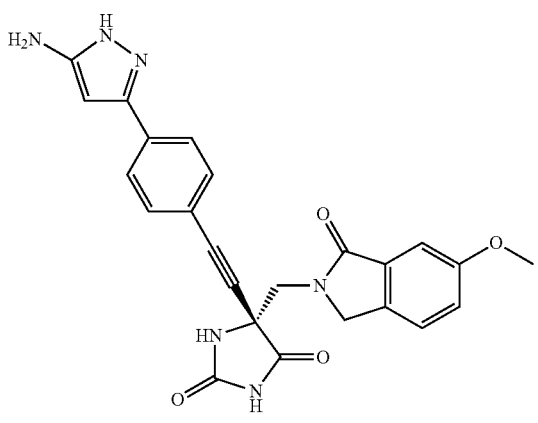 [SMILES: COc1ccc2c(c1)C(=O)N(C[C@@]1(C#Cc3ccc(-c4cc(N)[nH]n4)cc3)NC(=O)NC1=O)C2] | 456.1 | 457.1 | 0.419 | 128 | 0 |
| 712 | 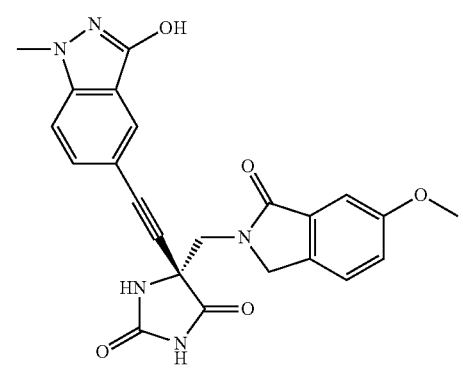 | 445.1 | 446.0 | 0.253 | 1527 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 715 | 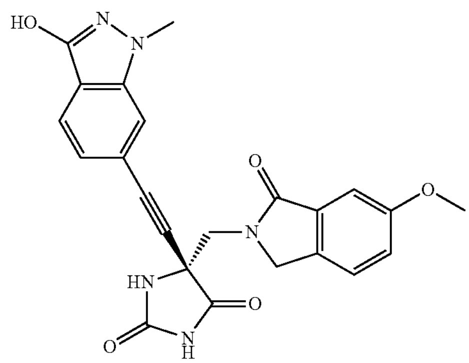 [SMILES: COc1ccc2c(c1)C(=O)N(C[C@@]1(C#Cc3ccc4c(O)nn(C)c4c3)NC(=O)NC1=O)C2] | 445.1 | 446.0 | 0.259 | 456 | 0 |
| 748 | 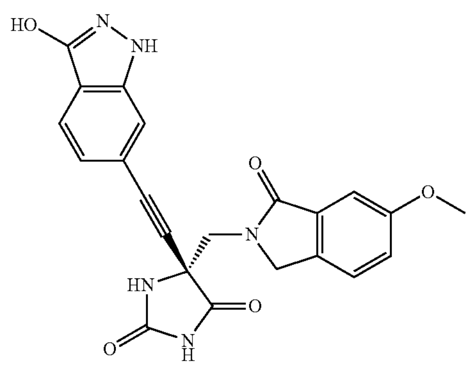 [SMILES: COc1ccc2c(c1)C(=O)N(C[C@@]1(C#Cc3ccc4c(O)n[nH]c4c3)NC(=O)NC1=O)C2] | 431.1 | 432.1 | 0.237 | 156 | 0 |
| 718 | 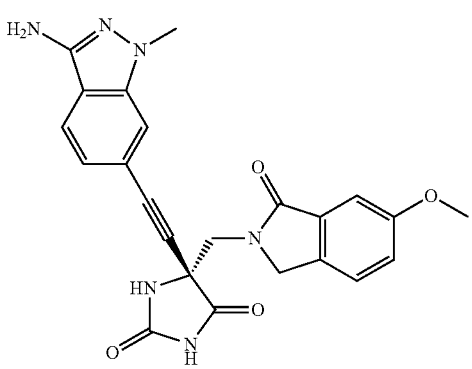 [SMILES: COc1ccc2c(c1)C(=O)N(C[C@@]1(C#Cc3ccc4c(N)nn(C)c4c3)NC(=O)NC1=O)C2] | 444.1 | 445.1 | 0.487 | 1114.5 | 12 |
| 723 | 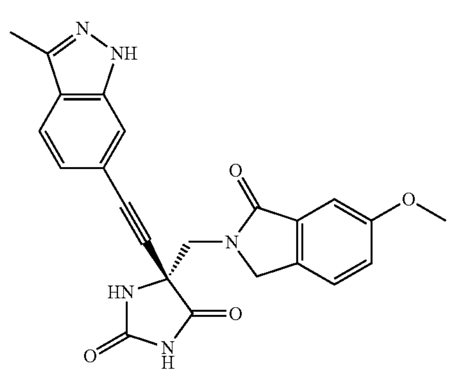 | 429.1 | 430.1 | 0.337 | 2948 | 7593 |

TABLE A-continued

| ID | Structure | Exact Mass | Mass Obsvd | Ki (nM) | hWBA (nM) | RR AUC (nM·h)[1] |
|---|---|---|---|---|---|---|
| 728 | 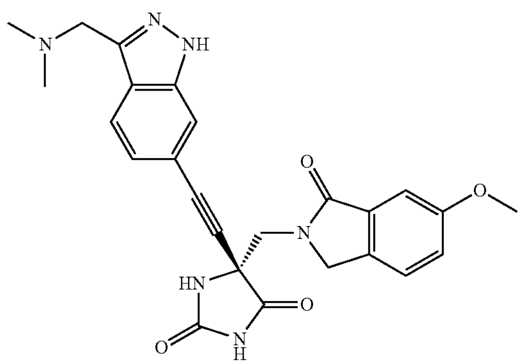 | 472.1 | 473.2 | 0.325 | 163 | 0 |
| 734 | 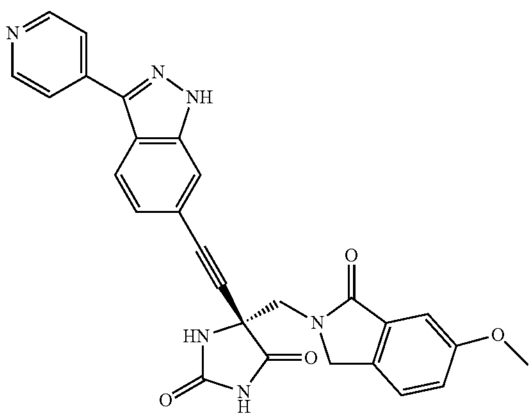 [SMILES: COc1ccc2c(c1)C(=O)N(C[C@@]1(C#Cc3ccc4c(-c5ccncc5)n[nH]c4c3)NC(=O)NC1=O)C2] | 492.1 | 493.1 | 0.444 | 1005.4 | 0 |
| 739 | 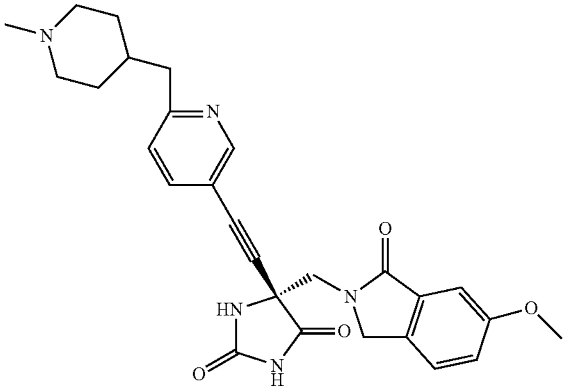 | 487.2 | 488.2 | 0.47 | 194.9 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 745 | 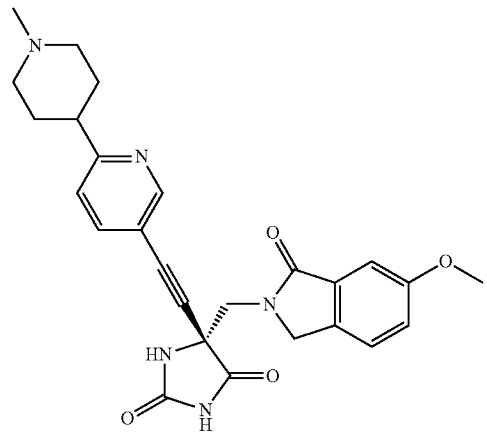 [SMILES: COc1ccc2c(c1)C(=O)N(C[C@@]1(C#Cc3ccc(C4CCN(C)CC4)nc3)NC(=O)NC1=O)C2] | 473.2 | 474.1 | 0.349 | 244.9 | 0 |
| 1700 | 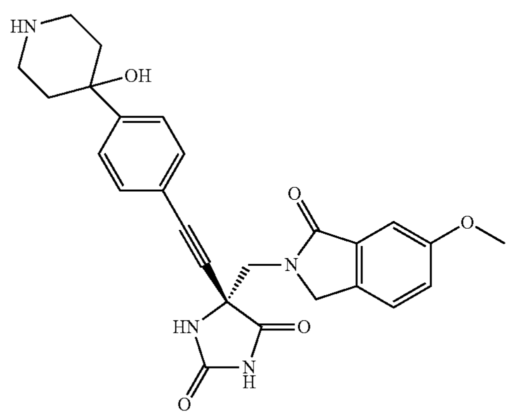 [SMILES: COc1ccc2c(c1)C(=O)N(C[C@@]1(C#Cc3ccc(C4(O)CCNCC4)cc3)NC(=O)NC1=O)C2] | 474.19 | 475.3 | 0.79 | 2390 | 0 |
| 1701 | 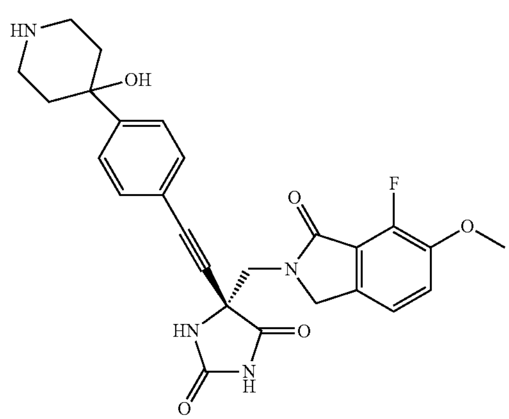 [SMILES: COc1ccc2c(c1F)C(=O)N(C[C@@]1(C#Cc3ccc(C4(O)CCNCC4)cc3)NC(=O)NC1=O)C2] | 492.18 | 493.3 | 0.57 | 137 | 41 |

TABLE A-continued

| ID | Structure | Exact Mass | Mass Obsvd | Ki (nM) | hWBA (nM) | RR AUC (nM·h)[1] |
|---|---|---|---|---|---|---|
| 1702 | 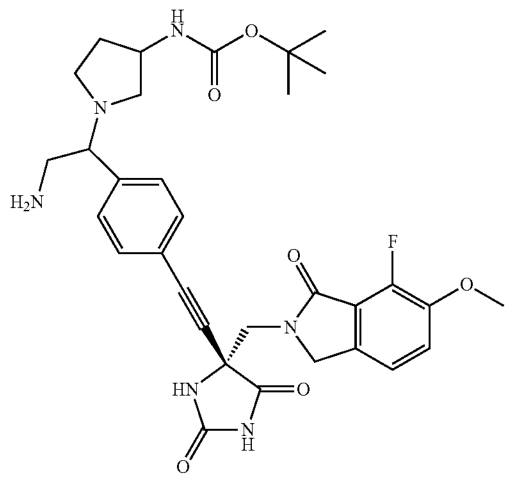 [SMILES: COc1ccc2c(c1F)C(=O)N(C[C@@]1(C#Cc3ccc(C(CN)N4CCC(NC(=O)OC(C)(C)C)C4)cc3)NC(=O)NC1=O)C2] | 620.28 | 621.3 | 0.82 | 303 | |
| 1703 | 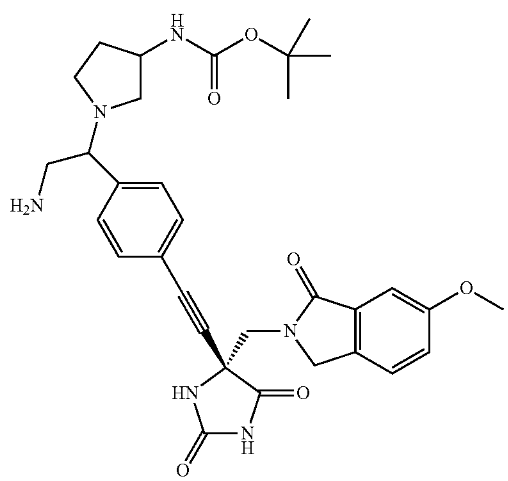 [SMILES: COc1ccc2c(c1)C(=O)N(C[C@@]1(C#Cc3ccc(C(CN)N4CCC(NC(=O)OC(C)(C)C)C4)cc3)NC(=O)NC1=O)C2] | 602.29 | 603.3 | 0.52 | 316 | |
| 1704 | 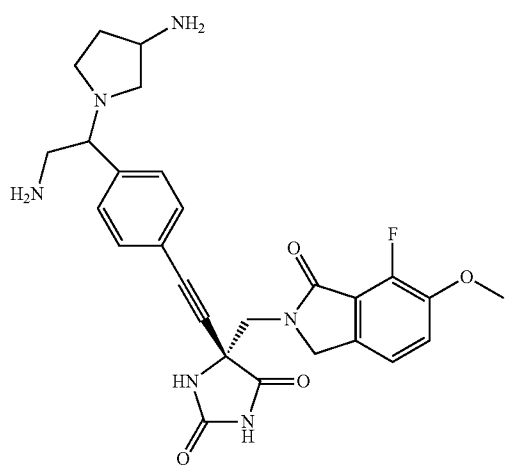 [SMILES: COc1ccc2c(c1F)C(=O)N(C[C@@]1(C#Cc3ccc(C(CN)N4CCC(N)C4)cc3)NC(=O)NC1=O)C2] | 520.22 | 521.3 | 0.41 | 109 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 1705 | 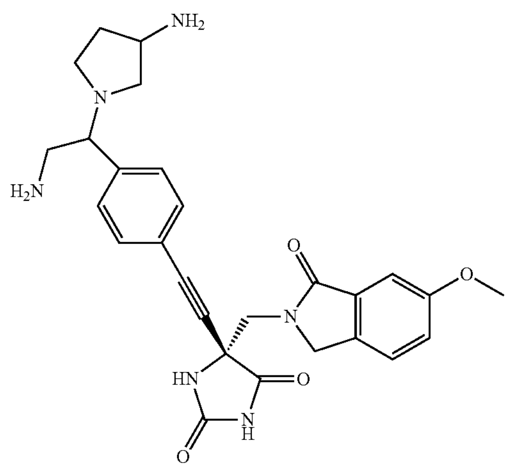 [SMILES: COc1ccc2c(c1)C(=O)N(C[C@@]1(C#Cc3ccc(C(CN)N4CCC(N)C4)cc3)NC(=O)NC1=O)C2] | 502.23 | 503.3 | 0.56 | 233 | 0 |
| 1706 | 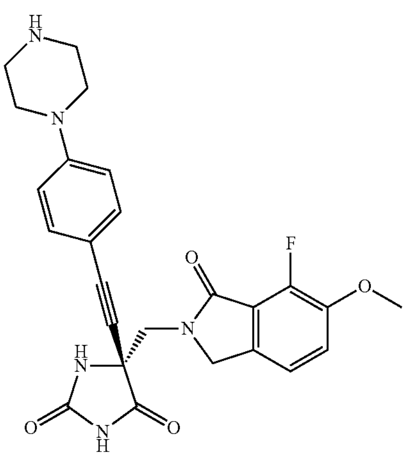 [SMILES: COc1ccc2c(c1F)C(=O)N(C[C@@]1(C#Cc3ccc(N4CCNCC4)cc3)NC(=O)NC1=O)C2] | 477.2 | 478.3 | 0.38 | 118 | 0 |
| 1707 | 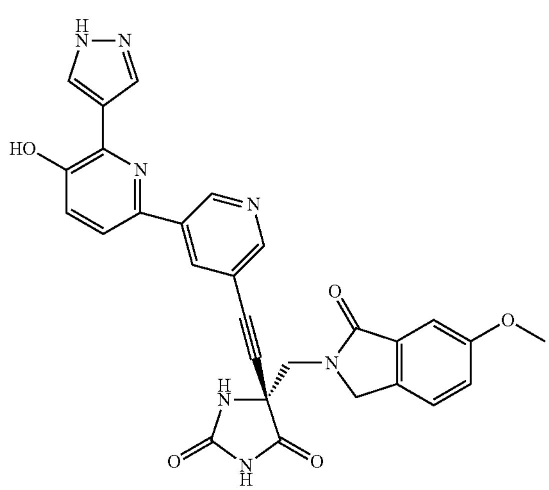 [SMILES: COc1ccc2c(c1)C(=O)N(C[C@@]1(C#Cc3cncc(-c4ccc(O)c(-c5cn[nH]c5)n4)c3)NC(=O)NC1=O)C2] | 535.2 | 536.3 | 0.32 | 374 | |

TABLE A-continued
| ID | Structure | Exact Mass | Mass Obsvd | Ki (nM) | hWBA (nM) | RR AUC (nM·h)[1] |
|---|---|---|---|---|---|---|
| 960 | 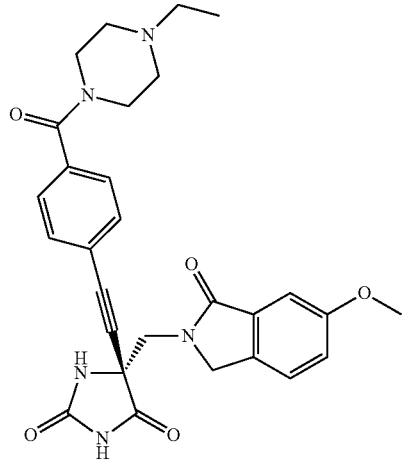 [SMILES: CCN1CCN(C(=O)c2ccc(C#C[C@]3(CN4Cc5ccc(OC)cc5C4=O)NC(=O)NC3=O)cc2)CC1] | 515.2 | 516.3 | 0.364 | 446 | |
| 961 | 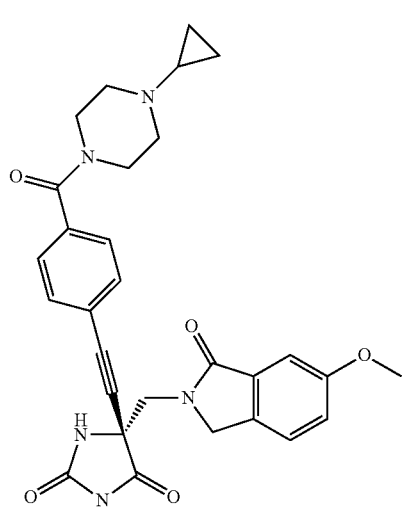 | 527.2 | 528.3 | 0.382 | 1158 | |
| 962 | 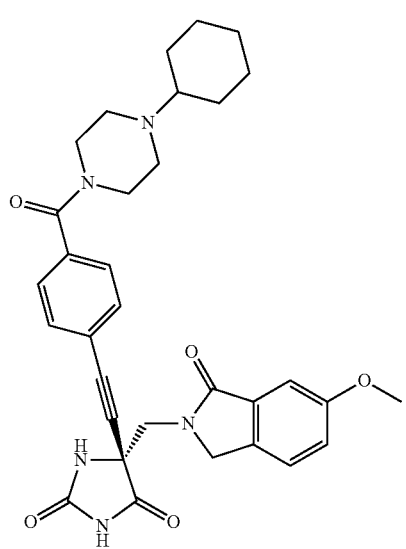 [SMILES: COc1ccc2c(c1)C(=O)N(C[C@@]1(C#Cc3ccc(C(=O)N4CCN(C5CCCCC5)CC4)cc3)NC(=O)NC1=O)C2] | 569.3 | 570.3 | 0.452 | 578 | |

TABLE A-continued

| ID | Structure | Exact Mass | Mass Obsvd | Ki (nM) | hWBA (nM) | RR AUC (nM · h)[1] |
|---|---|---|---|---|---|---|
| 963 | 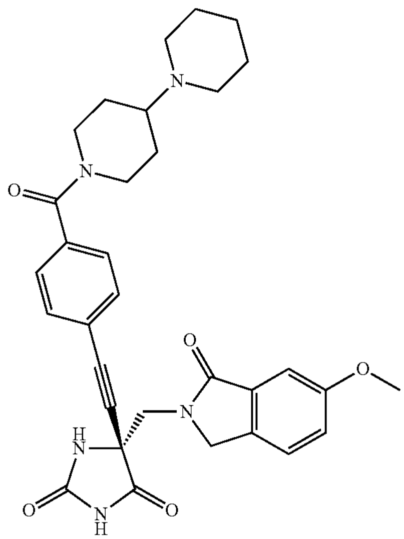 [SMILES: COc1ccc2c(c1)C(=O)N(C[C@@]1(C#Cc3ccc(C(=O)N4CCC(N5CCCCC5)CC4)cc3)NC(=O)NC1=O)C2] | 569.3 | 570.3 | 0.523 | 400.6 | |
| 964 | 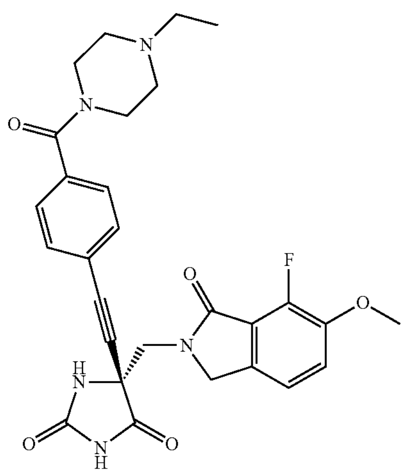 [SMILES: CCN1CCN(C(=O)c2ccc(C#C[C@]3(CN4Cc5ccc(OC)c(F)c5C4=O)NC(=O)NC3=O)cc2)CC1] | 533.2 | 534.3 | 0.288 | 307.85 | |
| 965 | 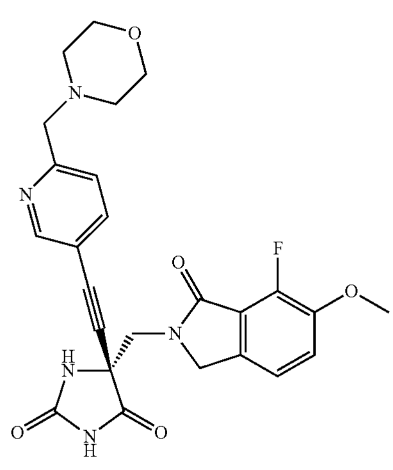 [SMILES: COc1ccc2c(c1F)C(=O)N(C[C@@]1(C#Cc3ccc(CN4CCOCC4)nc3)NC(=O)NC1=O)C2] | 493.2 | 494.3 | 0.437 | 698.1 | |

TABLE A-continued

| ID | Structure | Exact Mass | Mass Obsvd | Ki (nM) | hWBA (nM) | RR AUC (nM·h)[1] |
|---|---|---|---|---|---|---|
| 966 | 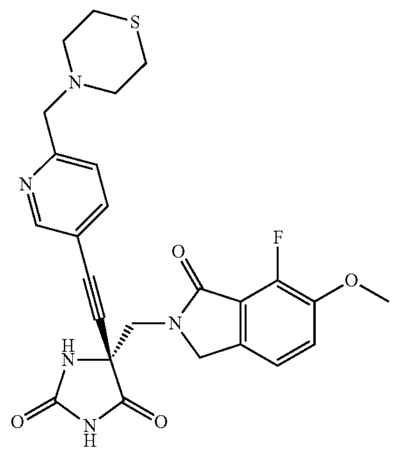 [SMILES: COc1ccc2c(c1F)C(=O)N(C[C@@]1(C#Cc3ccc(CN4CCSCC4)nc3)NC(=O)NC1=O)C2] | 509.2 | 510.3 | 0.527 | 587.5 | |
| 967 | 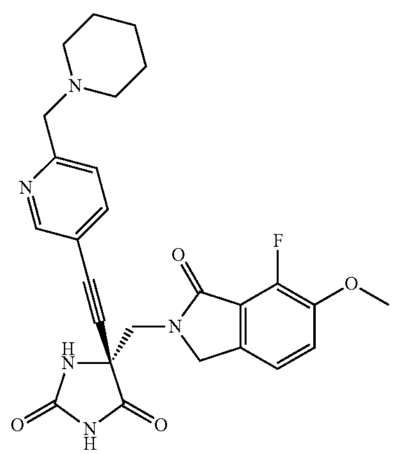 [SMILES: COc1ccc2c(c1F)C(=O)N(C[C@@]1(C#Cc3ccc(CN4CCCCC4)nc3)NC(=O)NC1=O)C2] | 491.2 | 492.3 | 1.21 | 785.1 | |
| 968 | 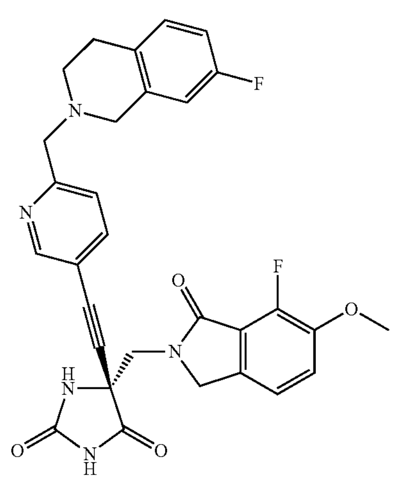 [SMILES: COc1ccc2c(c1F)C(=O)N(C[C@@]1(C#Cc3ccc(CN4CCc5ccc(F)cc5C4)nc3)NC(=O)NC1=O)C2] | 557.2 | 558.3 | 0.73 | 4980 | |

TABLE A-continued

| ID | Structure | Exact Mass | Mass Obsvd | Ki (nM) | hWBA (nM) | RR AUC (nM·h)[1] |
|---|---|---|---|---|---|---|
| 969 | 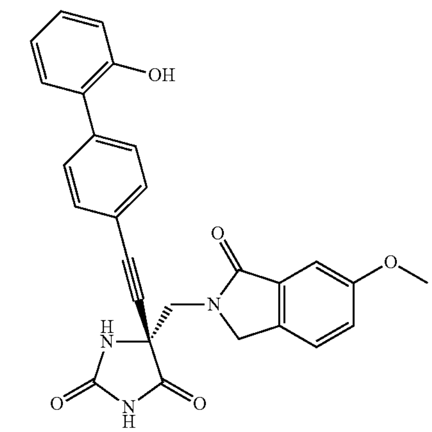 [SMILES: COc1ccc2c(c1)C(=O)N(C[C@@]1(C#Cc3ccc(-c4ccccc4O)cc3)NC(=O)NC1=O)C2] | 467.2 | 468.3 | 0.313 | 652.1 | |
| 970 | 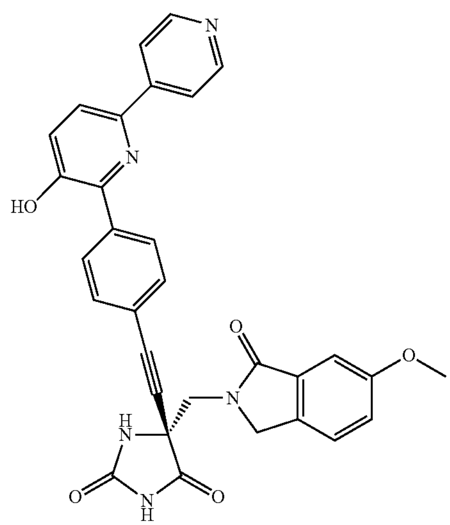 [SMILES: COc1ccc2c(c1)C(=O)N(C[C@@]1(C#Cc3ccc(-c4nc(-c5ccncc5)ccc4O)cc3)NC(=O)NC1=O)C2] | 545.2 | 546.3 | 0.0556 | 65 | 0 |
| 971 | 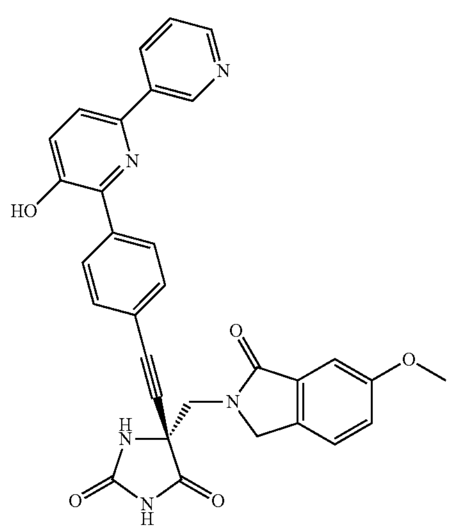 [SMILES: COc1ccc2c(c1)C(=O)N(C[C@@]1(C#Cc3ccc(-c4nc(-c5cccnc5)ccc4O)cc3)NC(=O)NC1=O)C2] | 545.2 | 546.3 | 0.0651 | 80.25 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 972 | 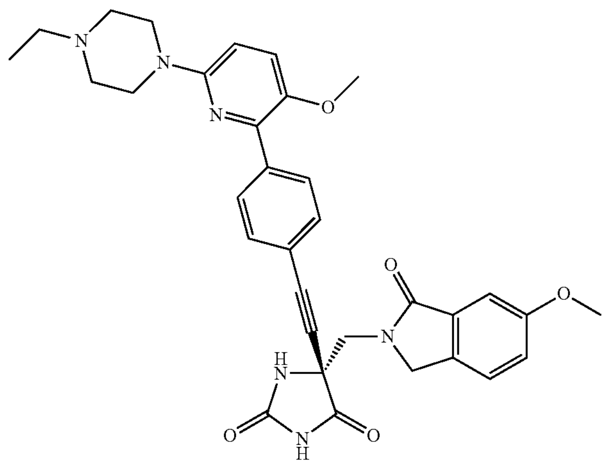 [SMILES: CCN1CCN(c2ccc(OC)c(-c3ccc(C#C[C@]4(CN5Cc6ccc(OC)cc6C5=O)NC(=O)NC4=O)cc3)n2)CC1] | 594.3 | 595.3 | 0.46 | 573.3 | |
| 973 | 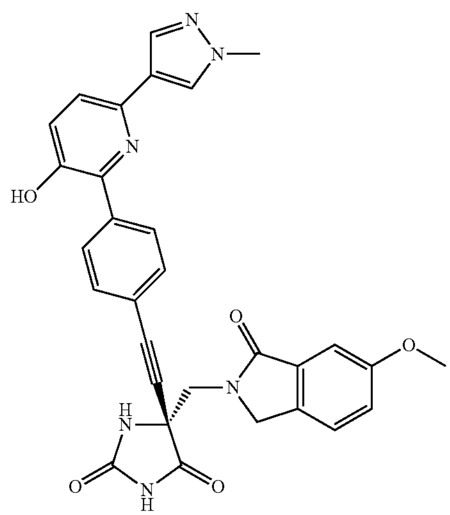 [SMILES: COc1ccc2c(c1)C(=O)N(C[C@@]1(C#Cc3ccc(-c4nc(-c5cnn(C)c5)ccc4O)cc3)NC(=O)NC1=O)C2] | 548.2 | 549.3 | 0.0524 | 61 | 0 |
| 974 | 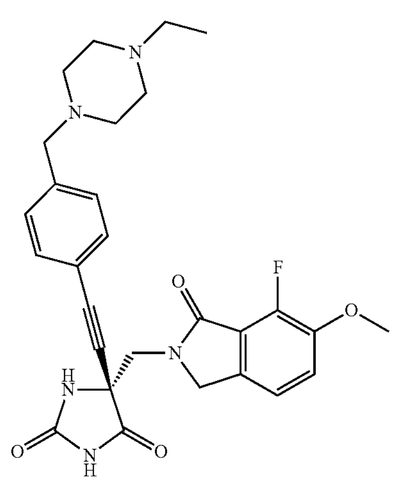 [SMILES: CCN1CCN(Cc2ccc(C#C[C@]3(CN4Cc5ccc(OC)c(F)c5C4=O)NC(=O)NC3=O)cc2)CC1] | 519.2 | 520.3 | 0.259 | 124.6 | 34 |

TABLE A-continued

| ID | Structure | Exact Mass | Mass Obsvd | Ki (nM) | hWBA (nM) | RR AUC (nM·h)[1] |
|---|---|---|---|---|---|---|
| 975 | 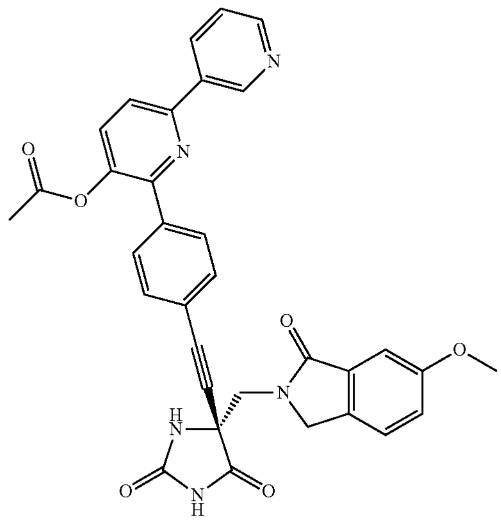 [SMILES: COc1ccc2c(c1)C(=O)N(C[C@@]1(C#Cc3ccc(-c4nc(-c5cccnc5)ccc4OC(C)=O)cc3)NC(=O)NC1=O)C2] | 587.2 | 588.3 | 0.195 | 61.65 | 0 |
| 976 | 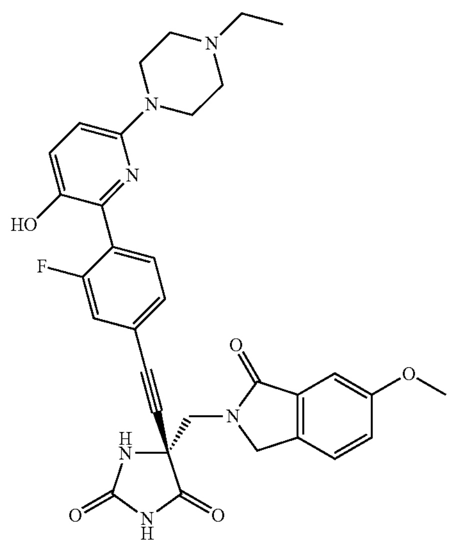 [SMILES: CCN1CCN(c2ccc(O)c(-c3ccc(C#C[C@]4(CN5Cc6ccc(OC)cc6C5=O)NC(=O)NC4=O)cc3F)n2)CC1] | 598.2 | 599.3 | 0.0988 | 39.75 | 0 |
| 977 | 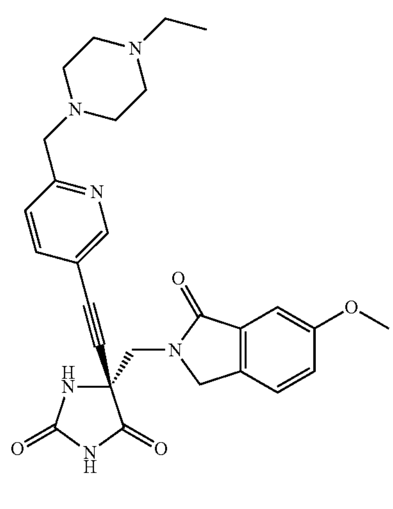 [SMILES: CCN1CCN(Cc2ccc(C#C[C@]3(CN4Cc5ccc(OC)cc5C4=O)NC(=O)NC3=O)cn2)CC1] | 502.2 | 503.3 | 0.55 | 782.3 | |

TABLE A-continued
| ID | Structure | Exact Mass | Mass Obsvd | Ki (nM) | hWBA (nM) | RR AUC (nM·h)[1] |
|---|---|---|---|---|---|---|
| 978 | 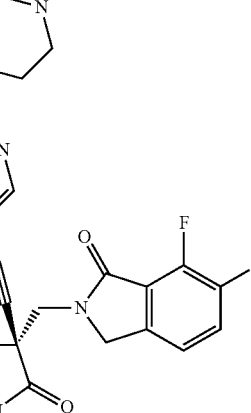 | 520.2 | 521.3 | 0.379 | 156 | |
| 979 | 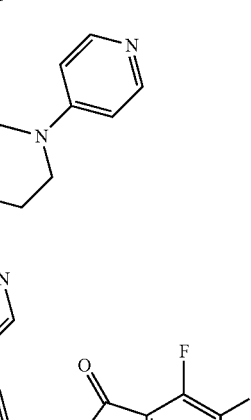 | 569.2 | 570.3 | 0.77 | 228 | |
| 980 | 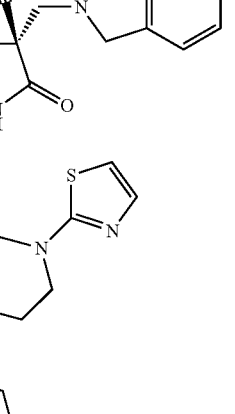 | 556.2 | 557.3 | 0.49 | 3127 | |

TABLE A-continued
| ID | Structure | Exact Mass | Mass Obsvd | Ki (nM) | hWBA (nM) | RR AUC (nM · h)[1] |
|---|---|---|---|---|---|---|
| 981 | 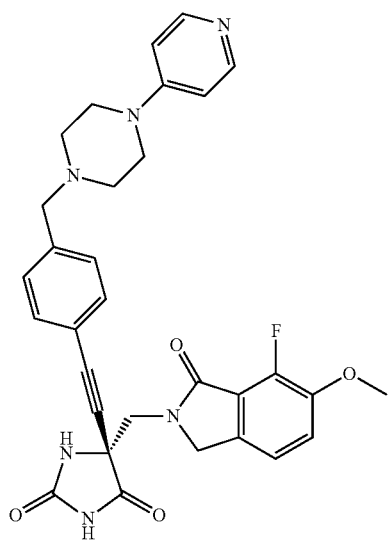 [SMILES: COc1ccc2c(c1F)C(=O)N(C[C@@]1(C#Cc3ccc(CN4CCN(c5ccncc5)CC4)cc3)NC(=O)NC1=O)C2] | 568.2 | 569.3 | 0.388 | 289.6 | |
| 982 | 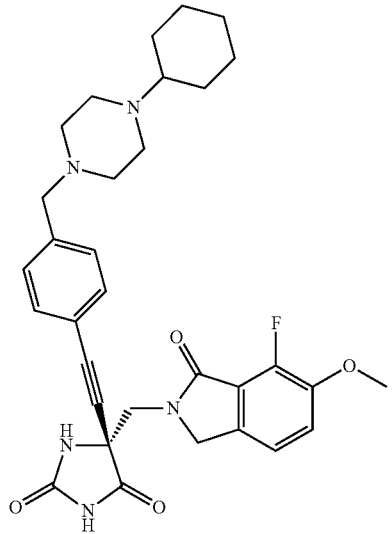 [SMILES: COc1ccc2c(c1F)C(=O)N(C[C@@]1(C#Cc3ccc(CN4CCN(C5CCCCC5)CC4)cc3)NC(=O)NC1=O)C2] | 573.3 | 574.3 | 0.36 | 255.4 | |
| 983 | 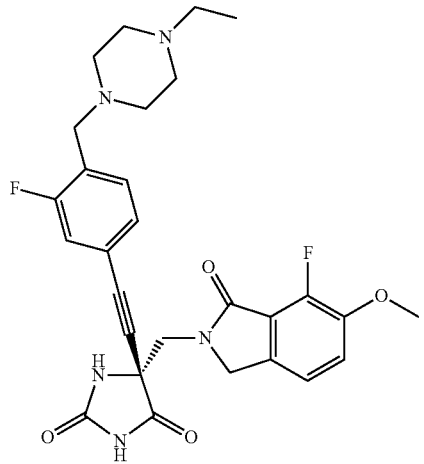 [SMILES: CCN1CCN(Cc2ccc(C#C[C@]3(CN4Cc5ccc(OC)c(F)c5C4=O)NC(=O)NC3=O)cc2F)CC1] | 537.2 | 538.3 | 0.652 | 249.8 | |

TABLE A-continued
| ID | Structure | Exact Mass | Mass Obsvd | Ki (nM) | hWBA (nM) | RR AUC (nM · h)[1] |
|---|---|---|---|---|---|---|
| 984 | 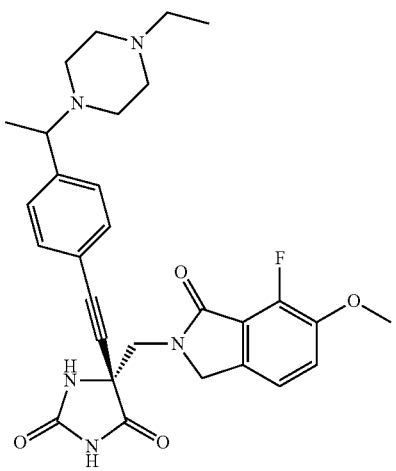 [SMILES: CCN1CCN(C(C)c2ccc(C#C[C@]3(CN4Cc5ccc(OC)c(F)c5C4=O)NC(=O)NC3=O)cc2)CC1] | 533.2 | 534.3 | 0.509 | 695.1 | |
| 985 | 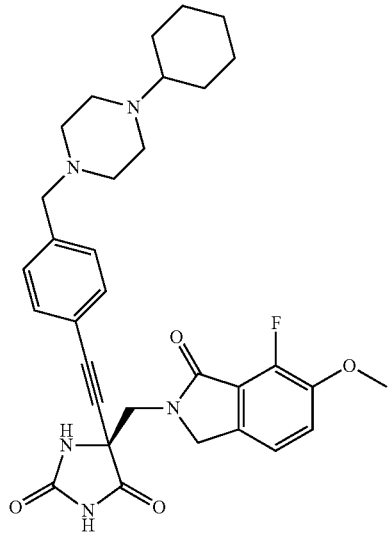 [SMILES: COc1ccc2c(c1F)C(=O)N(C[C@]1(C#Cc3ccc(CN4CCN(C5CCCCC5)CC4)cc3)NC(=O)NC1=O)C2] | 573.3 | 574.3 | 46300 | 100001 | |
| 986 | 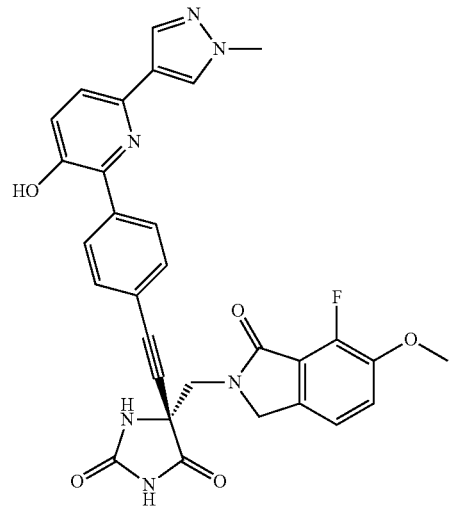 [SMILES: COc1ccc2c(c1F)C(=O)N(C[C@@]1(C#Cc3ccc(-c4nc(-c5cnn(C)c5)ccc4O)cc3)NC(=O)NC1=O)C2] | 566.2 | 567.3 | 0.0973 | 87 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 987 | 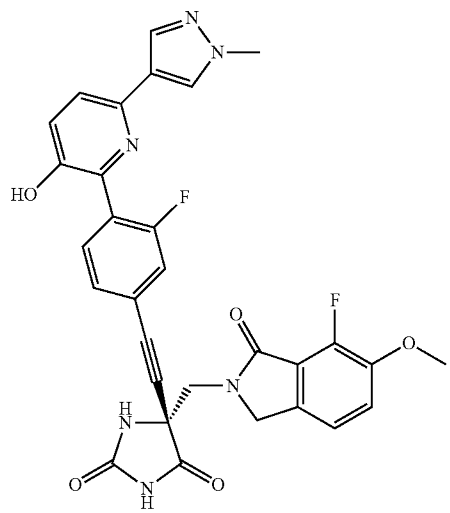 [SMILES: COc1ccc2c(c1F)C(=O)N(C[C@@]1(C#Cc3ccc(-c4nc(-c5cnn(C)c5)ccc4O)c(F)c3)NC(=O)NC1=O)C2] | 584.2 | 585.3 | 0.0627 | 75.4 | 0 |
| 988 | 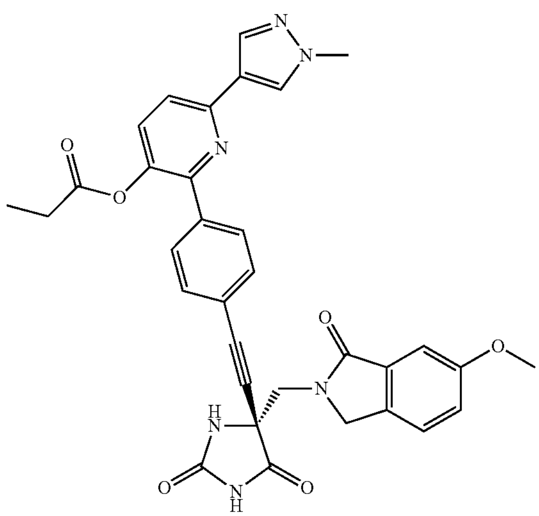 [SMILES: CCC(=O)Oc1ccc(-c2cnn(C)c2)nc1-c1ccc(C#C[C@]2(CN3Cc4ccc(OC)cc4C3=O)NC(=O)NC2=O)cc1] | 604.2 | 605.3 | 0.115 | 55.9 | 0 |
| 989 | 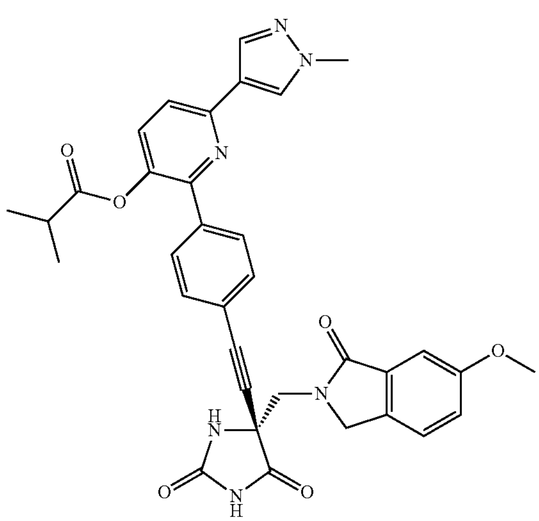 [SMILES: COc1ccc2c(c1)C(=O)N(C[C@@]1(C#Cc3ccc(-c4nc(-c5cnn(C)c5)ccc4OC(=O)C(C)C)cc3)NC(=O)NC1=O)C2] | 618.2 | 619.3 | 0.673 | 47.97 | 0 |

TABLE A-continued

| ID | Structure | Exact Mass | Mass Obsvd | Ki (nM) | hWBA (nM) | RR AUC (nM · h)[1] |
|----|-----------|-----------|------------|---------|-----------|--------------------|
| 990 | 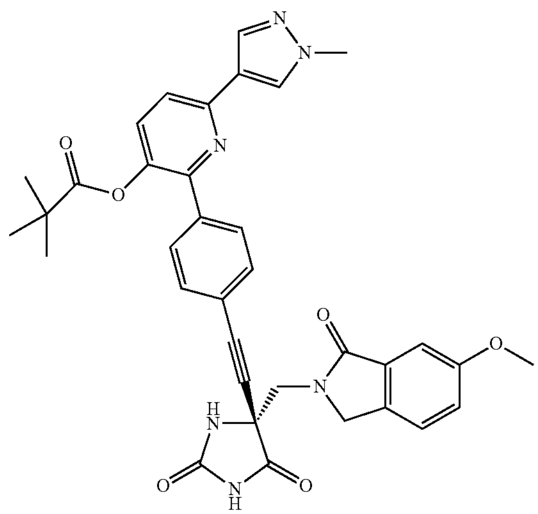 [SMILES: COc1ccc2c(c1)C(=O)N(C[C@@]1(C#Cc3ccc(-c4nc(-c5cnn(C)c5)ccc4OC(=O)C(C)(C)C)cc3)NC(=O)NC1=O)C2] | 632.2 | 633.3 | 0.699 | 42.75 | 0 |
| 991 | 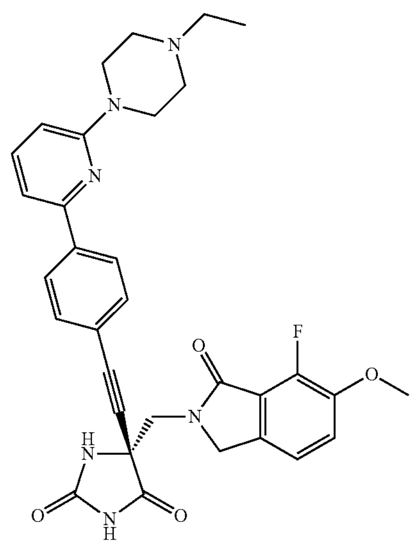 [SMILES: CCN1CCN(c2cccc(-c3ccc(C#C[C@]4(CN5Cc6ccc(OC)c(F)c6C5=O)NC(=O)NC4=O)cc3)n2)CC1] | 582.2 | 583.3 | 0.28 | 605.65 | |

TABLE A-continued

| ID | Structure | Exact Mass | Mass Obsvd | Ki (nM) | hWBA (nM) | RR AUC (nM · h)[1] |
|---|---|---|---|---|---|---|
| 992 | 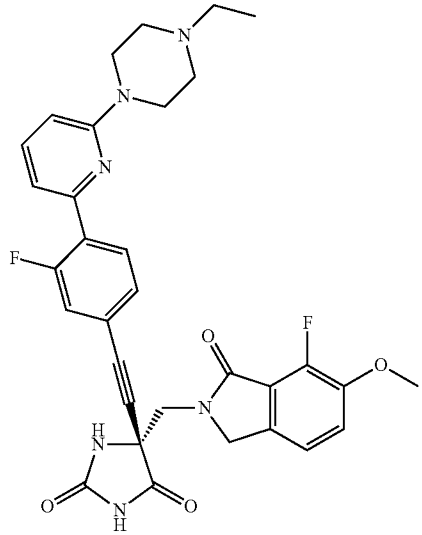 [SMILES: CCN1CCN(c2cccc(-c3ccc(C#C[C@]4(CN5Cc6ccc(OC)c(F)c6C5=O)NC(=O)NC4=O)cc3F)n2)CC1] | 600.2 | 601.3 | 0.35 | 808.3 | |
| 993 | 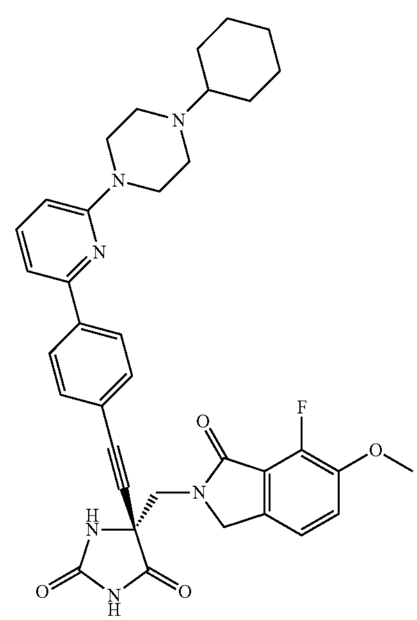 [SMILES: COc1ccc2c(c1F)C(=O)N(C[C@@]1(C#Cc3ccc(-c4cccc(N5CCN(C6CCCCC6)CC5)n4)cc3)NC(=O)NC1=O)C2] | 636.3 | 637.4 | 0.835 | 855.6 | |

TABLE A-continued

| ID | Structure | Exact Mass | Mass Obsvd | Ki (nM) | hWBA (nM) | RR AUC (nM·h)[1] |
|---|---|---|---|---|---|---|
| 994 | 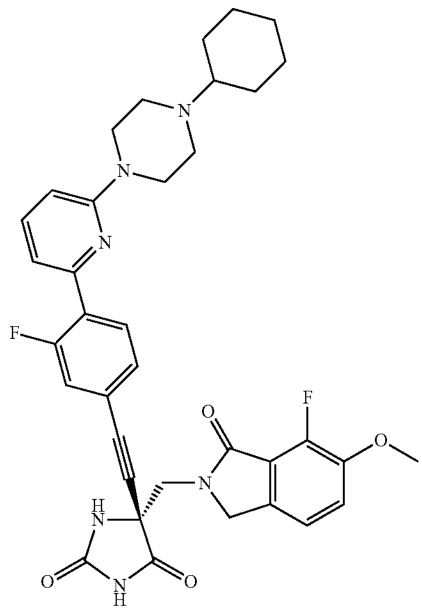 [SMILES: COc1ccc2c(c1F)C(=O)N(C[C@@]1(C#Cc3ccc(-c4cccc(N5CCN(C6CCCCC6)CC5)n4)c(F)c3)NC(=O)NC1=O)C2] | 654.3 | 655.4 | 1.49 | 2431 | |
| 995 | 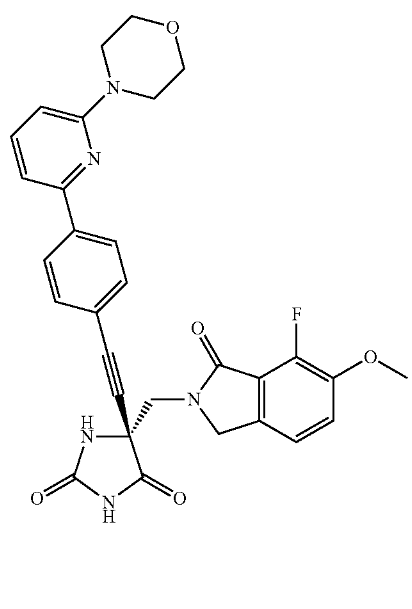 [SMILES: COc1ccc2c(c1F)C(=O)N(C[C@@]1(C#Cc3ccc(-c4cccc(N5CCOCC5)n4)cc3)NC(=O)NC1=O)C2] | 555.2 | 556.3 | 0.512 | 1635 | |

TABLE A-continued

| ID | Structure | Exact Mass | Mass Obsvd | Ki (nM) | hWBA (nM) | RR AUC (nM · h)[1] |
|---|---|---|---|---|---|---|
| 996 | 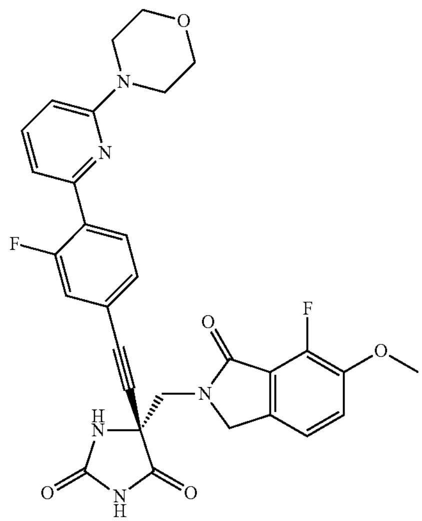 [SMILES: COc1ccc2c(c1F)C(=O)N(C[C@@]1(C#Cc3ccc(-c4cccc(N5CCOCC5)n4)c(F)c3)NC(=O)NC1=O)C2] | 573.2 | 574.3 | 0.429 | 2557 | |
| 997 | 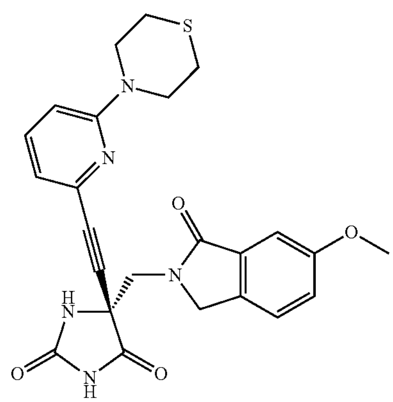 [SMILES: COc1ccc2c(c1)C(=O)N(C[C@@]1(C#Cc3cccc(N4CCSCC4)n3)NC(=O)NC1=O)C2] | 477.2 | 478.3 | 0.5 | 4316 | |
| 998 | 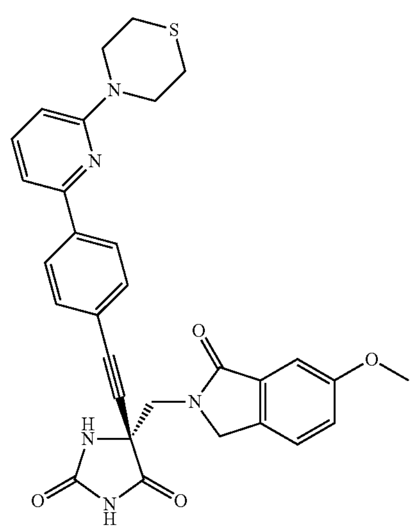 [SMILES: COc1ccc2c(c1)C(=O)N(C[C@@]1(C#Cc3ccc(-c4cccc(N5CCSCC5)n4)cc3)NC(=O)NC1=O)C2] | 553.2 | 554.3 | 3.45 | 1000001 | |

TABLE A-continued

| ID | Structure | Exact Mass | Mass Obsvd | Ki (nM) | hWBA (nM) | RR AUC (nM · h)[1] |
|---|---|---|---|---|---|---|
| 999 | 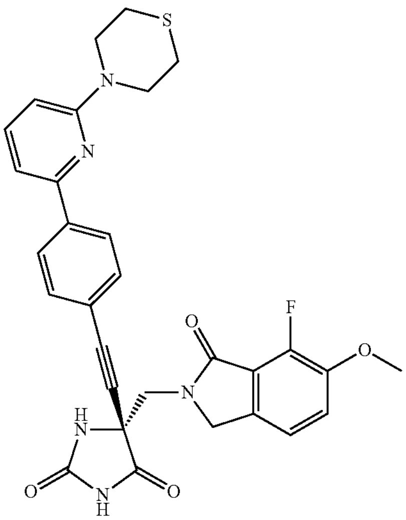 | 571.2 | 572.3 | 1.89 | 4154 | |
| 1000 | 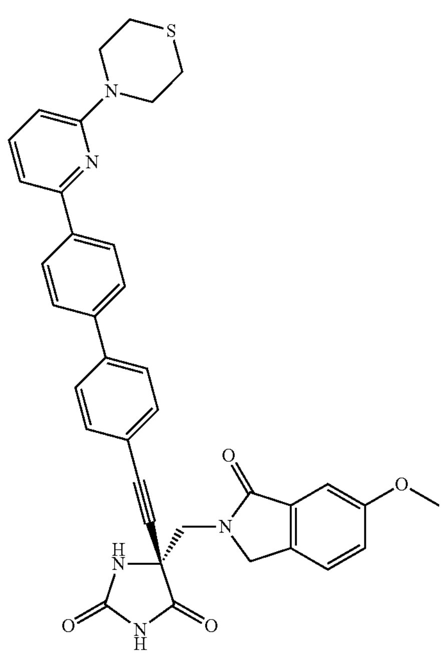 [SMILES: COc1ccc2c(c1)C(=O)N(C[C@@]1(C#Cc3ccc(-c4ccc(-c5cccc(N6CCSCC6)n5)cc4)cc3)NC(=O)NC1=O)C2] | 629.2 | 630.3 | 10.3 | 1000001 | |

TABLE A-continued

| ID | Structure | Exact Mass | Mass Obsvd | Ki (nM) | hWBA (nM) | RR AUC (nM·h)[1] |
|---|---|---|---|---|---|---|
| 1001 | 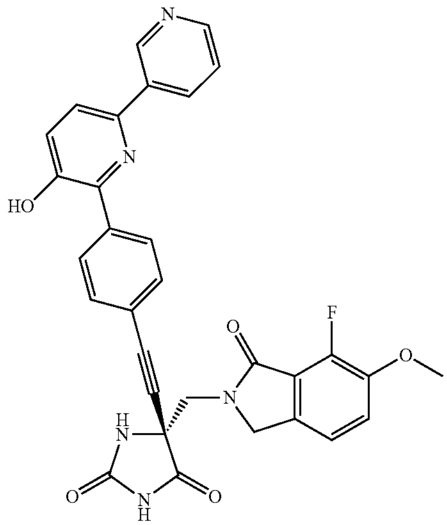 [SMILES: COc1ccc2c(c1F)C(=O)N(C[C@@]1(C#Cc3ccc(-c4nc(-c5cccnc5)ccc4O)cc3)NC(=O)NC1=O)C2] | 563.2 | 564.3 | 0.0781 | 105.65 | |
| 1002 | 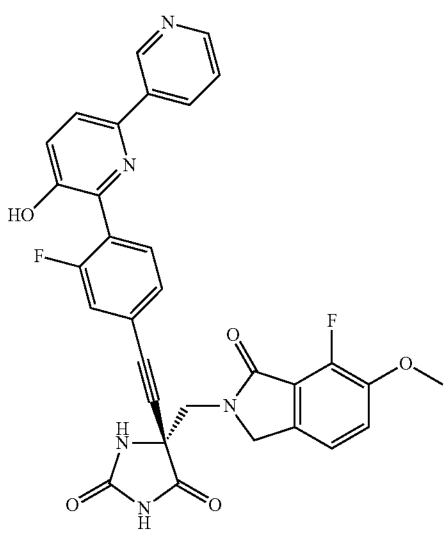 [SMILES: COc1ccc2c(c1F)C(=O)N(C[C@@]1(C#Cc3ccc(-c4nc(-c5cccnc5)ccc4O)c(F)c3)NC(=O)NC1=O)C2] | 581.2 | 582.3 | 0.077 | 118.7 | |

TABLE A-continued
| ID | Structure | Exact Mass | Mass Obsvd | Ki (nM) | hWBA (nM) | RR AUC (nM·h)[1] |
|---|---|---|---|---|---|---|
| 1003 | 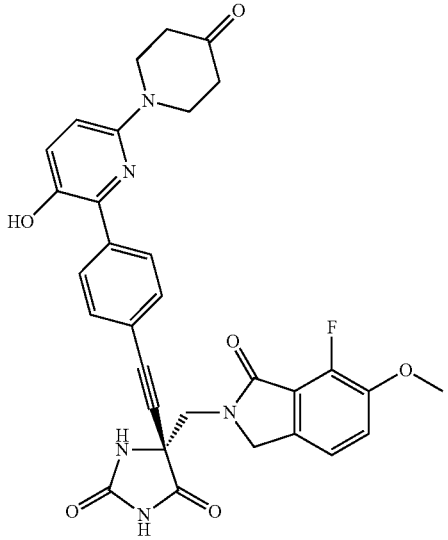 [SMILES: COc1ccc2c(c1F)C(=O)N(C[C@@]1(C#Cc3ccc(-c4nc(N5CCC(=O)CC5)ccc4O)cc3)NC(=O)NC1=O)C2] | 583.2 | 584.3 | 0.0826 | 123.85 | |
| 1006 | 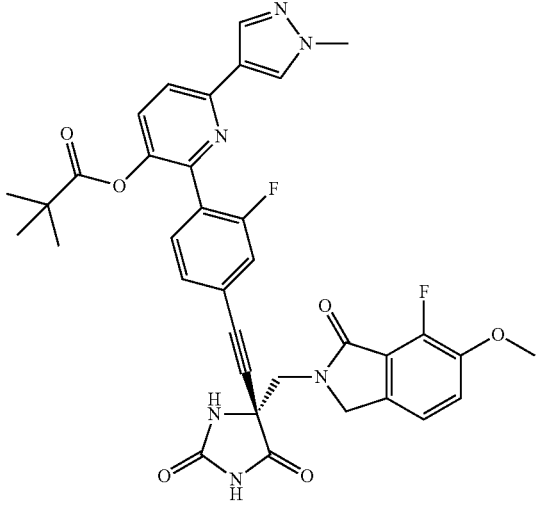 [SMILES: COc1ccc2c(c1F)C(=O)N(C[C@@]1(C#Cc3ccc(-c4nc(-c5cnn(C)c5)ccc4OC(=O)C(C)(C)C)c(F)c3)NC(=O)NC1=O)C2] | 668.2 | 669.4 | 1.09 | 68.45 | |
| 1008 | 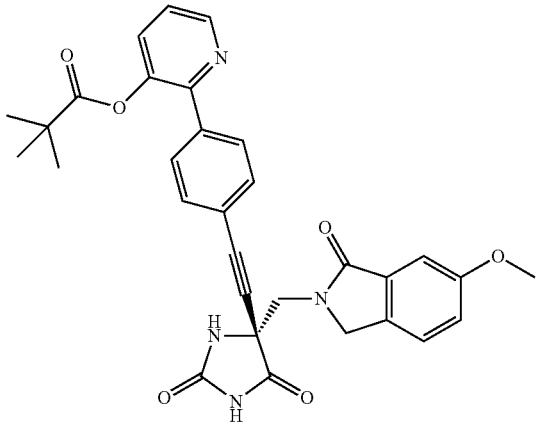 [SMILES: COc1ccc2c(c1)C(=O)N(C[C@@]1(C#Cc3ccc(-c4ncccc4OC(=O)C(C)(C)C)cc3)NC(=O)NC1=O)C2] | 552.2 | 553.3 | 0.0762 | 341.55 | |

TABLE A-continued

| ID | Structure | Exact Mass | Mass Obsvd | Ki (nM) | hWBA (nM) | RR AUC (nM · h)[1] |
|---|---|---|---|---|---|---|
| 1010 | 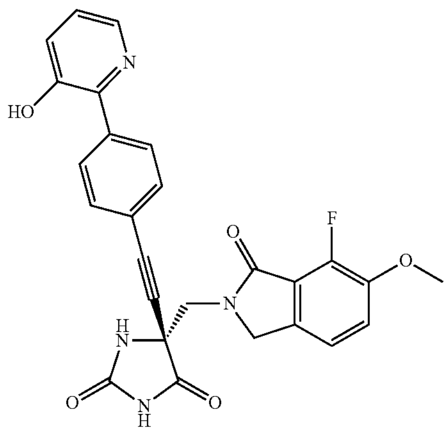 [SMILES: COc1ccc2c(c1F)C(=O)N(C[C@@]1(C#Cc3ccc(-c4ncccc4O)cc3)NC(=O)NC1=O)C2] | | 4 | 487.3 | | 96 |
| 1100 | 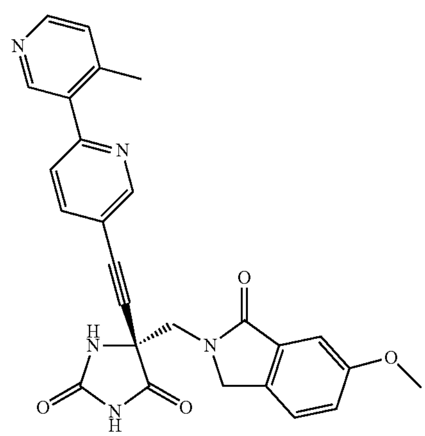 [SMILES: COc1ccc2c(c1)C(=O)N(C[C@@]1(C#Cc3ccc(-c4cnccc4C)nc3)NC(=O)NC1=O)C2] | 467.16 | 468.3 | 0.52 | | 2392 |
| 1105 | 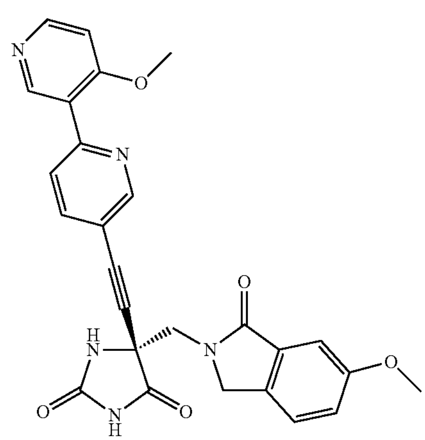 [SMILES: COc1ccc2c(c1)C(=O)N(C[C@@]1(C#Cc3ccc(-c4cnccc4OC)nc3)NC(=O)NC1=O)C2] | 483.15 | 484.3 | 0.92 | | 5377 |

TABLE A-continued

| ID | Structure | Exact Mass | Mass Obsvd | Ki (nM) | hWBA (nM) | RR AUC (nM · h)[1] |
|---|---|---|---|---|---|---|
| 1110 | 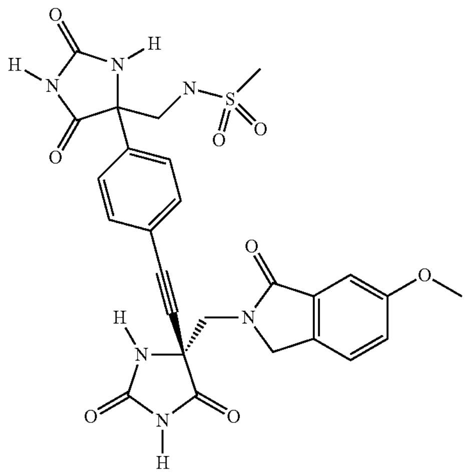 [SMILES: COc1ccc2c(c1)C(=O)N(C[C@@]1(C#Cc3ccc(C4(CNS(C)(=O)=O)NC(=O)NC4=O)cc3)NC(=O)NC1=O)C2] | 580.1 | 581.3 | 0.338 | 176 | |
| 1120 | 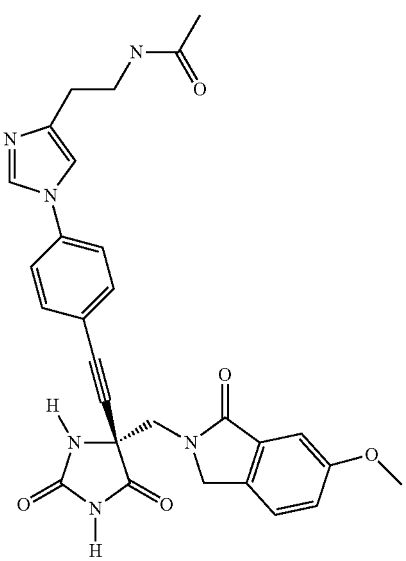 [SMILES: COc1ccc2c(c1)C(=O)N(C[C@@]1(C#Cc3ccc(-n4cnc(CCNC(C)=O)c4)cc3)NC(=O)NC1=O)C2] | 526.19 | 527.3 | 0.52 | 453 | |

TABLE A-continued

| ID | Structure | Exact Mass | Mass Obsvd | Ki (nM) | hWBA (nM) | RR AUC (nM · h)[1] |
|---|---|---|---|---|---|---|
| 1130 | 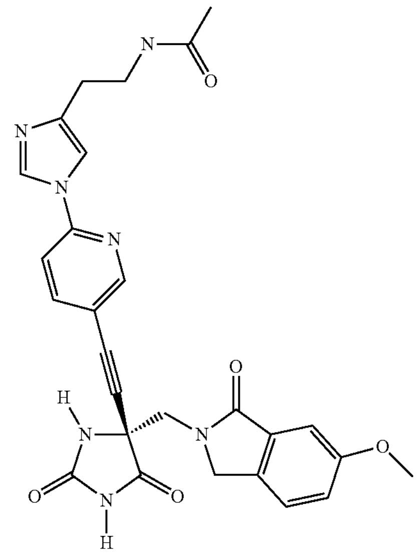 [SMILES: COc1ccc2c(c1)C(=O)N(C[C@@]1(C#Cc3ccc(-n4cnc(CCNC(C)=O)c4)nc3)NC(=O)NC1=O)C2] | 527.19 | 528.3 | 0.60 | 524 | |
| 1140 | 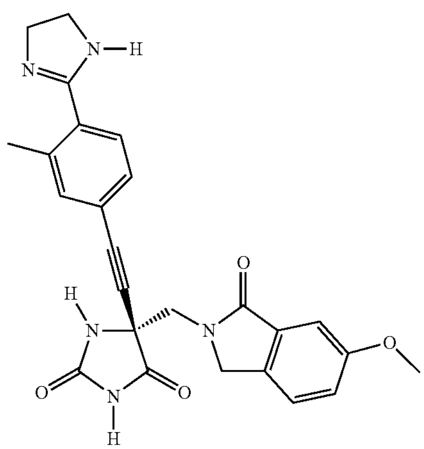 | 457.17 | 458.3 | 0.75 | 504 | |
| 1150 | 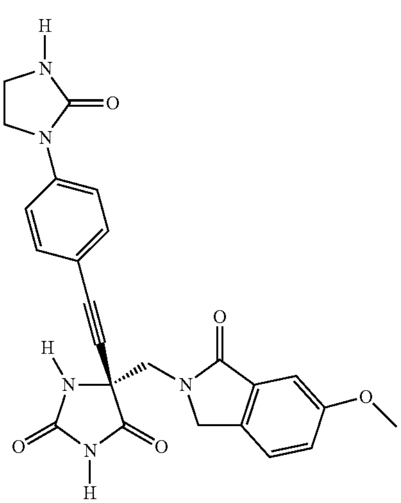 [SMILES: COc1ccc2c(c1)C(=O)N(C[C@@]1(C#Cc3ccc(N4CCNC4=O)cc3)NC(=O)NC1=O)C2] | 459.15 | 460.3 | 0.33 | 1618 | |

TABLE A-continued

| ID | Structure | Exact Mass | Mass Obsvd | Ki (nM) | hWBA (nM) | RR AUC (nM · h)[1] |
|---|---|---|---|---|---|---|
| 1160 | 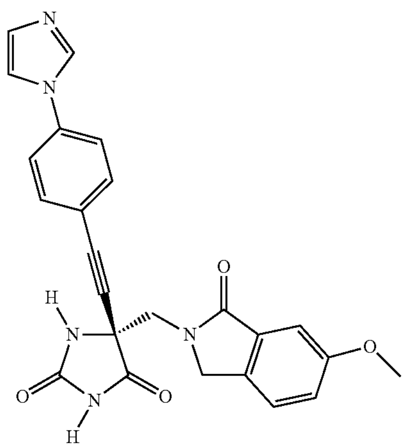 [SMILES: COc1ccc2c(c1)C(=O)N(C[C@@]1(C#Cc3ccc(-n4ccnc4)cc3)NC(=O)NC1=O)C2] | 441.14 | 442.2 | 0.44 | 786 | |
| 1170 | 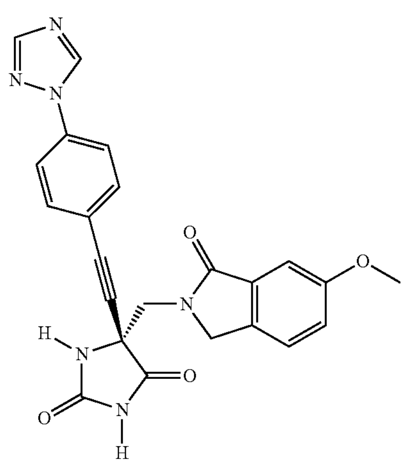 [SMILES: COc1ccc2c(c1)C(=O)N(C[C@@]1(C#Cc3ccc(-n4cncn4)cc3)NC(=O)NC1=O)C2] | 442.14 | 443.2 | 0.51 | 1140 | |
| 1300 | 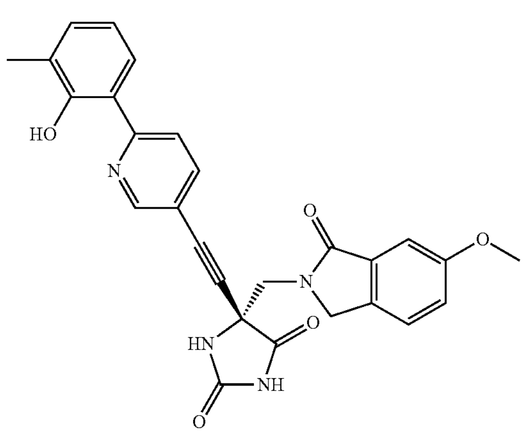 | 482.16 | 483.3 | 3.54 | 3505 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 1301 | 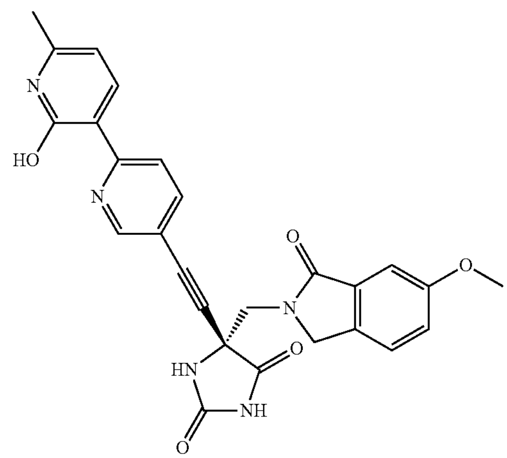 [SMILES: COc1ccc2c(c1)C(=O)N(C[C@@]1(C#Cc3ccc(-c4ccc(C)nc4O)nc3)NC(=O)NC1=O)C2] | 483.15 | 484.3 | 0.27 | 766 | |
| 1302 | 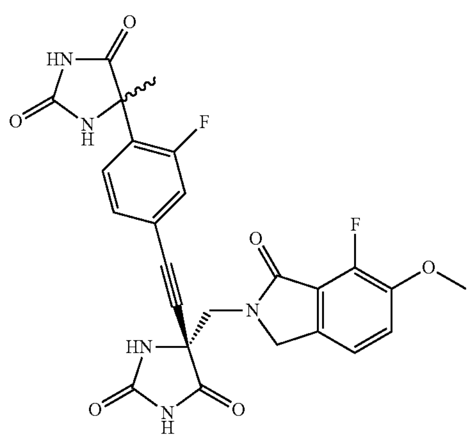 [SMILES: COc1ccc2c(c1F)C(=O)N(C[C@@]1(C#Cc3ccc(C4(C)NC(=O)NC4=O)c(F)c3)NC(=O)NC1=O)C2] | 523.15 | 524.3 | 0.28 | 148 | 5641 |
| 1303 | 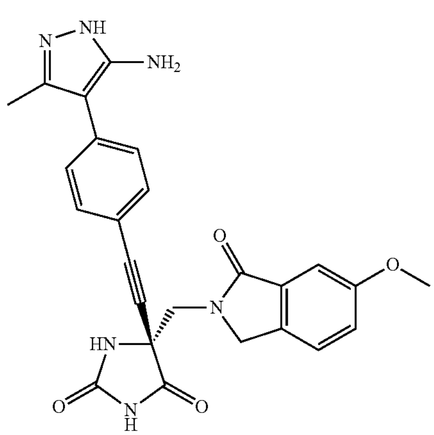 | 470.17 | 471.3 | 0.36 | 488 | |

TABLE A-continued
| ID | Structure | Exact Mass | Mass Obsvd | Ki (nM) | hWBA (nM) | RR AUC (nM · h)[1] |
|---|---|---|---|---|---|---|
| 1304 | 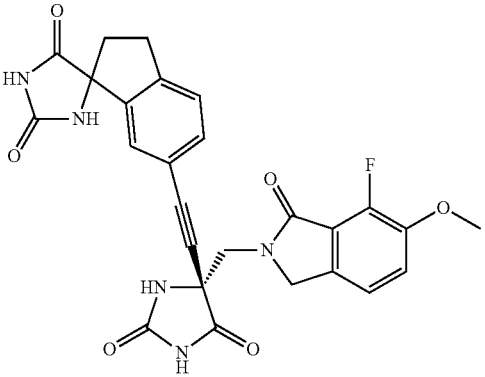 [SMILES: COc1ccc2c(c1F)C(=O)N(C[C@@]1(C#Cc3ccc4c(c3)C3(CC4)NC(=O)NC3=O)NC(=O)NC1=O)C2] | 517.14 | 518.3 | 0.68 | 367 | 0 |
| 1305 | 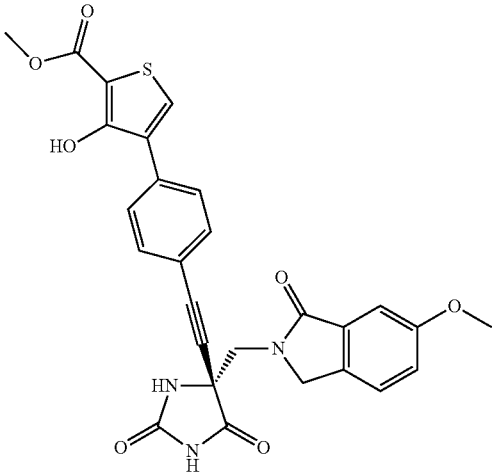 | 531.11 | 532.3 | 1.71 | inactive | |
| 1306 | 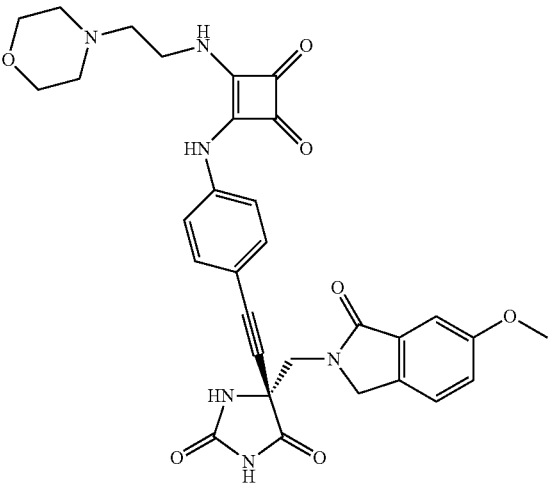 [SMILES: COc1ccc2c(c1)C(=O)N(C[C@@]1(C#Cc3ccc(Nc4c(NCCN5CCOCC5)c(=O)c4=O)cc3)NC(=O)NC1=O)C2] | 598.22 | 600.3 | 0.19 | 169 | |

TABLE A-continued
| ID | Structure | Exact Mass | Mass Obsvd | Ki (nM) | hWBA (nM) | RR AUC (nM · h)[1] |
|---|---|---|---|---|---|---|
| 1307 | 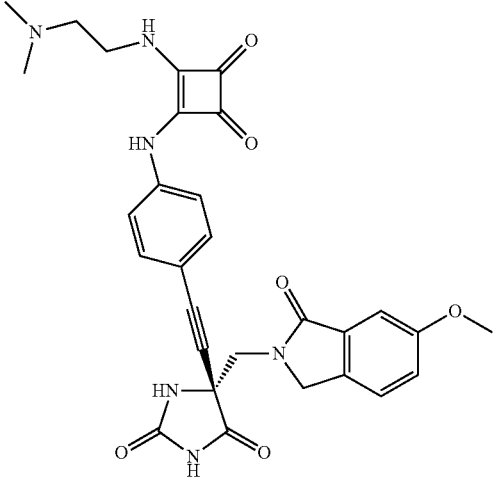 | 556.21 | 557.3 | 0.22 | 161 | 0 |
| 1308 | 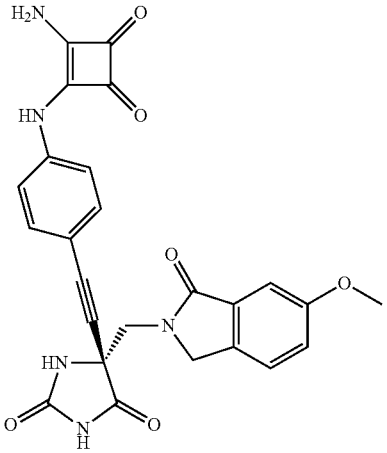 [SMILES: COc1ccc2c(c1)C(=O)N(C[C@@]1(C#Cc3ccc(Nc4c(N)c(=O)c4=O)cc3)NC(=O)NC1=O)C2] | 485.13 | 486.3 | 0.19 | 306 | |
| 1309 | 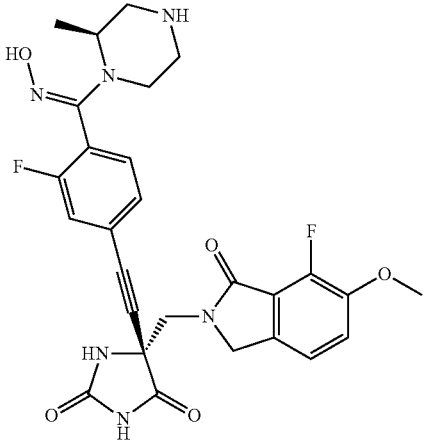 [SMILES: COc1ccc2c(c1F)C(=O)N(C[C@@]1(C#Cc3ccc(/C(=N/O)N4CCNC[C@@H]4C)c(F)c3)NC(=O)NC1=O)C2] | 552.19 | 553.3 | 0.19 | 42 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 1310 | 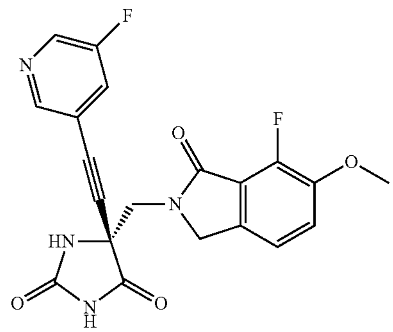 [SMILES: COc1ccc2c(c1F)C(=O)N(C[C@@]1(C#Cc3cncc(F)c3)NC(=O)NC1=O)C2] | 412.10 | 413.2 | 0.39 | 305 | 1767 |
| 1311 | 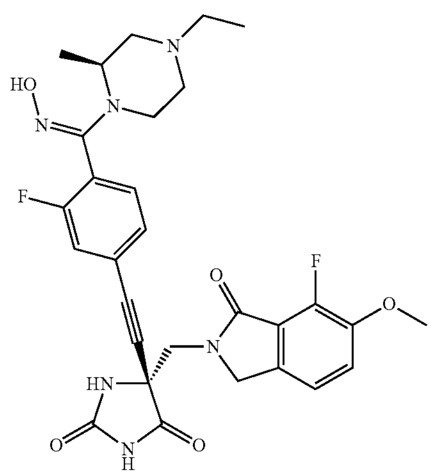 [SMILES: CCN1CCN(/C(=N\O)c2ccc(C#C[C@]3(CN4Cc5ccc(OC)c(F)c5C4=O)NC(=O)NC3=O)cc2F)[C@@H](C)C1] | 580.22 | 581.3 | 0.18 | 69 | 0 |
| 1312 | 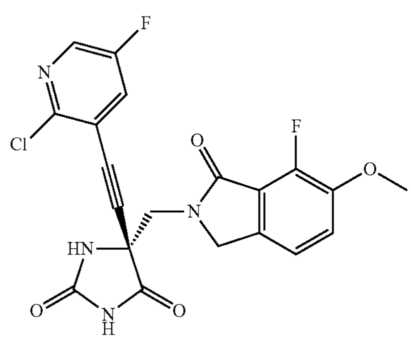 [SMILES: COc1ccc2c(c1F)C(=O)N(C[C@@]1(C#Cc3cc(F)cnc3Cl)NC(=O)NC1=O)C2] | 446.06 | 447.2 | 0.20 | 935 | |

TABLE A-continued

| ID | Structure | Exact Mass | Mass Obsvd | Ki (nM) | hWBA (nM) | RR AUC (nM · h)[1] |
|---|---|---|---|---|---|---|
| 1313 | 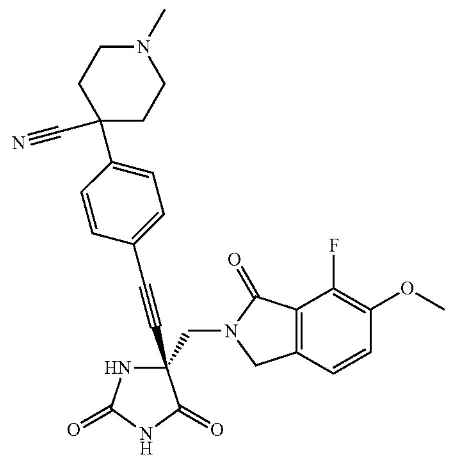 [SMILES: COc1ccc2c(c1F)C(=O)N(C[C@@]1(C#Cc3ccc(C4(C#N)CCN(C)CC4)cc3)NC(=O)NC1=O)C2] | 515.20 | 516.3 | 0.28 | 669 | |
| 1314 | 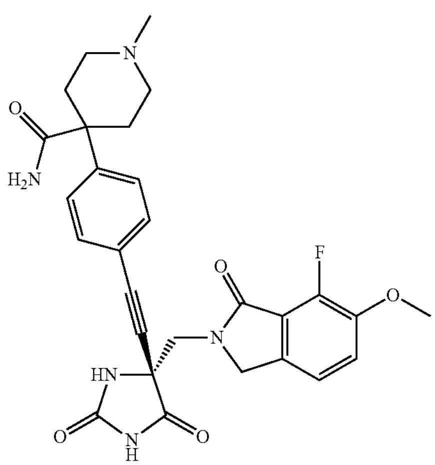 [SMILES: COc1ccc2c(c1F)C(=O)N(C[C@@]1(C#Cc3ccc(C4(C(N)=O)CCN(C)CC4)cc3)NC(=O)NC1=O)C2] | 533.21 | 534.3 | 0.45 | 152 | 16 |
| 1315 | 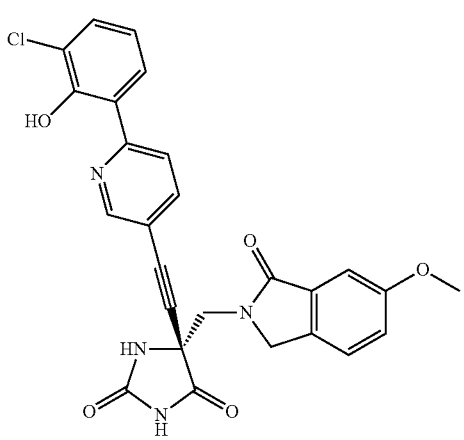 [SMILES: COc1ccc2c(c1)C(=O)N(C[C@@]1(C#Cc3ccc(-c4cccc(Cl)c4O)nc3)NC(=O)NC1=O)C2] | 502.10 | 503.3 | 3.53 | Inactive | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 1316 | 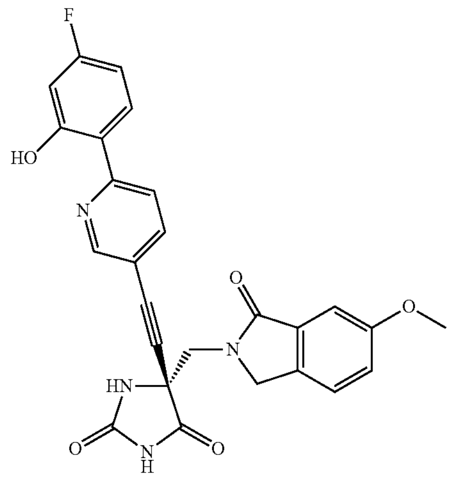 [SMILES: COc1ccc2c(c1)C(=O)N(C[C@@]1(C#Cc3ccc(-c4ccc(F)cc4O)nc3)NC(=O)NC1=O)C2] | 486.13 | 487.3 | 1.28 | 9459 | |
| 1317 | 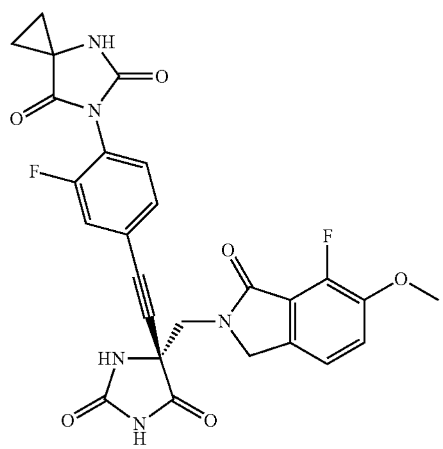 [SMILES: COc1ccc2c(c1F)C(=O)N(C[C@@]1(C#Cc3ccc(N4C(=O)NC5(CC5)C4=O)c(F)c3)NC(=O)NC1=O)C2] | 535.13 | 536.3 | 0.34 | 148 | 0 |
| 1318 | 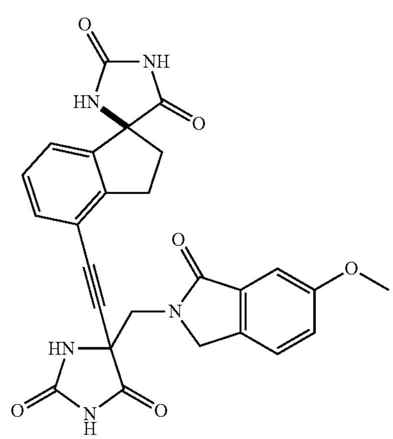 | 499.15 | 500.3 | 0.53 | >1000 | |

TABLE A-continued

| ID | Structure | Exact Mass | Mass Obsvd | Ki (nM) | hWBA (nM) | RR AUC (nM · h)[1] |
|---|---|---|---|---|---|---|
| 1319 | 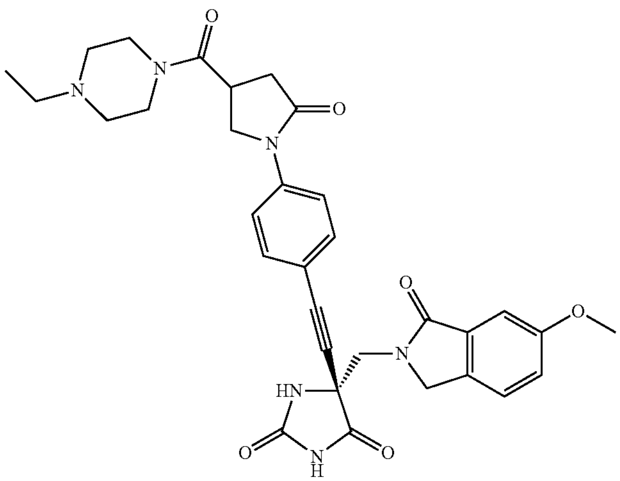 [SMILES: CCN1CCN(C(=O)C2CC(=O)N(c3ccc(C#C[C@]4(CN5Cc6ccc(OC)cc6C5=O)NC(=O)NC4=O)cc3)C2)CC1] | 598.25 | 599.3 | 1.20 | 940 | |
| 1900 | 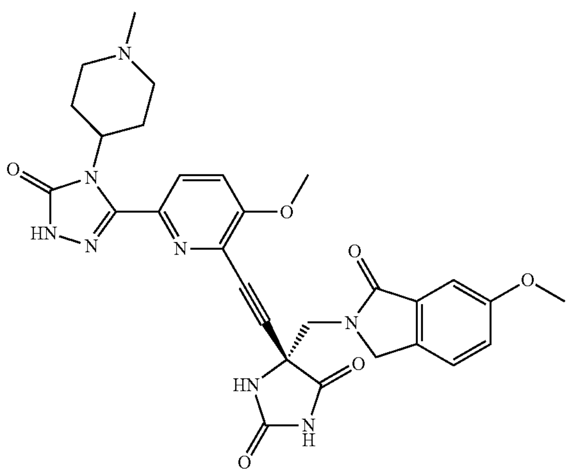 [SMILES: COc1ccc2c(c1)C(=O)N(C[C@@]1(C#Cc3nc(-c4n[nH]c(=O)n4C4CCN(C)CC4)ccc3OC)NC(=O)NC1=O)C2] | 586.2 | 587.3 | 3.71 | 2189 | |
| 1901 | 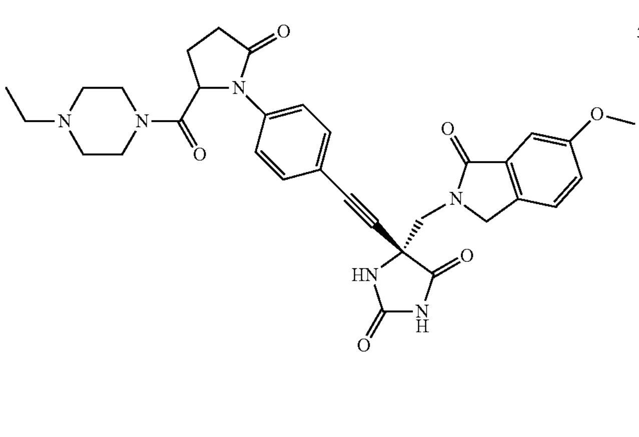 | 598.3 | 599.2 | 0.13 | 113 | 0 |

TABLE A-continued
| ID | Structure | Exact Mass | Mass Obsvd | Ki (nM) | hWBA (nM) | RR AUC (nM·h)[1] |
|---|---|---|---|---|---|---|
| 1902 | 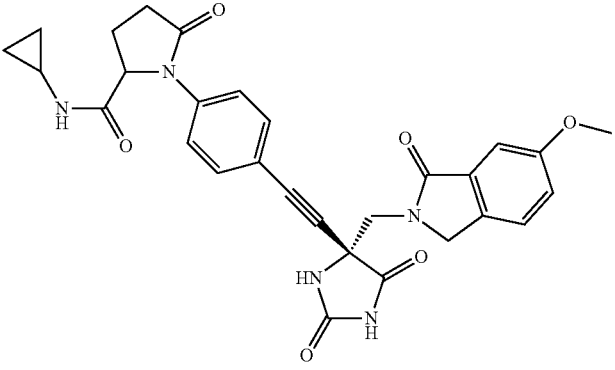 [SMILES: COc1ccc2c(c1)C(=O)N(C[C@@]1(C#Cc3ccc(N4C(=O)CCC4C(=O)NC4CC4)cc3)NC(=O)NC1=O)C2] | 541.2 | 542.3 | 0.12 | 127 | 25 |
| 1903 | 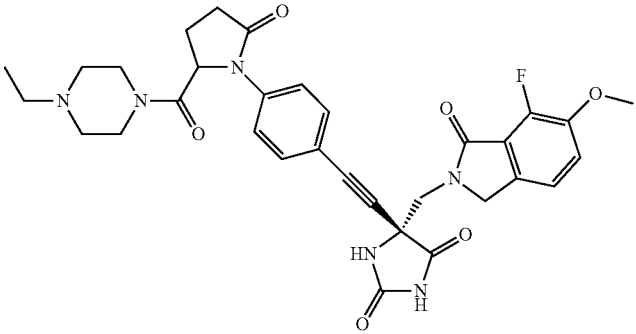 [SMILES: CCN1CCN(C(=O)C2CCC(=O)N2c2ccc(C#C[C@]3(CN4Cc5ccc(OC)c(F)c5C4=O)NC(=O)NC3=O)cc2)CC1] | 616.2 | 617.3 | 0.23 | 152 | |
| 1904 | 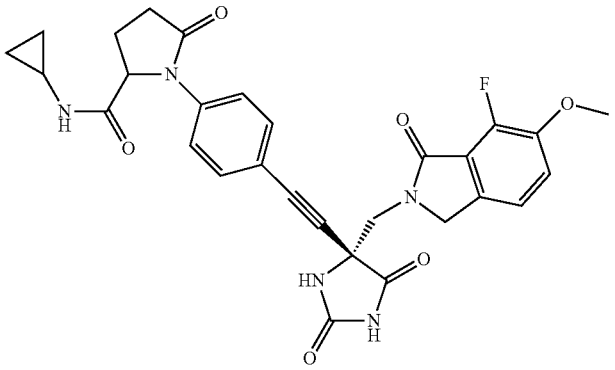 [SMILES: COc1ccc2c(c1F)C(=O)N(C[C@@]1(C#Cc3ccc(N4C(=O)CCC4C(=O)NC4CC4)cc3)NC(=O)NC1=O)C2] | 559.2 | 560.2 | 0.38 | 278 | 213 |
| 1905 | 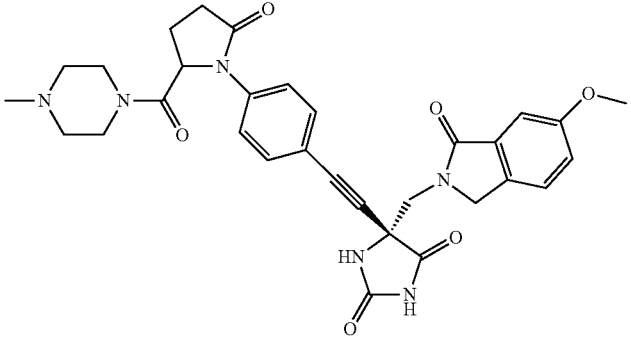 | 584.2 | 585.3 | 0.24 | 416 | |

TABLE A-continued

| ID | Structure | Exact Mass | Mass Obsvd | Ki (nM) | hWBA (nM) | RR AUC (nM · h)[1] |
|---|---|---|---|---|---|---|
| 1906 | 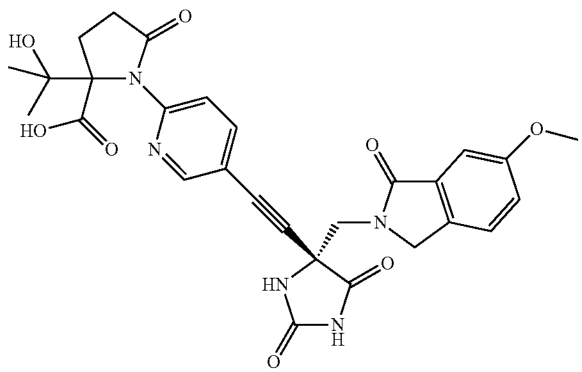 [SMILES: COc1ccc2c(c1)C(=O)N(C[C@@]1(C#Cc3ccc(N4C(=O)CCC4(C(=O)O)C(C)(C)O)nc3)NC(=O)NC1=O)C2] | 561.2 | 562.2 | 0.77 | 578 | |
| 1907 | 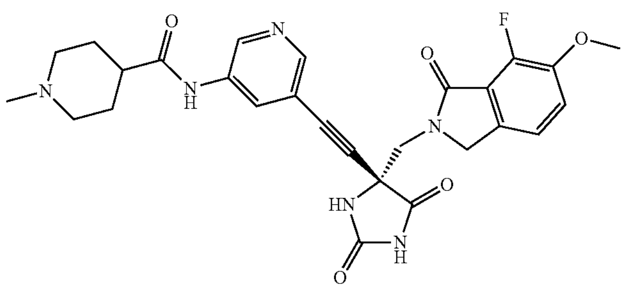 | 534.2 | 535.3 | 0.18 | 86 | 0 |
| 1908 | 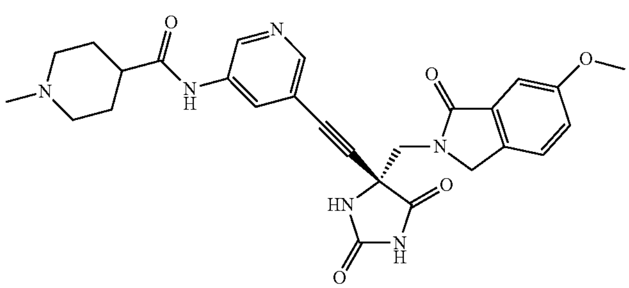 | 516.2 | 517.2 | 0.35 | 299 | 0 |
| 1909 | 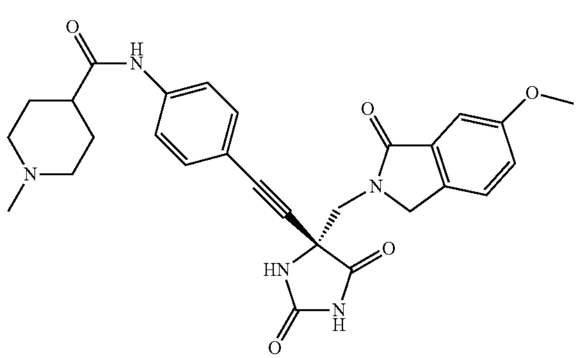 [SMILES: COc1ccc2c(c1)C(=O)N(C[C@@]1(C#Cc3ccc(NC(=O)C4CCN(C)CC4)cc3)NC(=O)NC1=O)C2] | 515.2 | 516.3 | 0.17 | 78 | |

TABLE A-continued

| ID | Structure | Exact Mass | Mass Obsvd | Ki (nM) | hWBA (nM) | RR AUC (nM · h)[1] |
|---|---|---|---|---|---|---|
| 1910 | 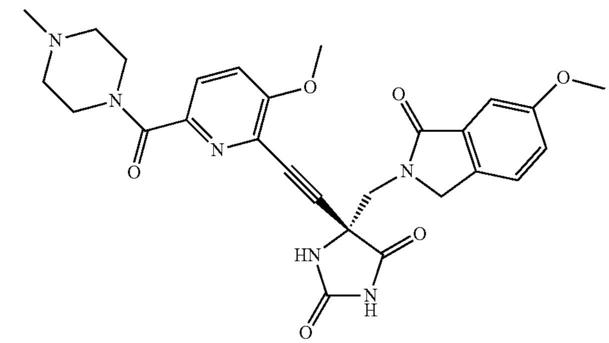 | 425.1 | 426.3 | 2.02 | 2961 | |
| 1911 | 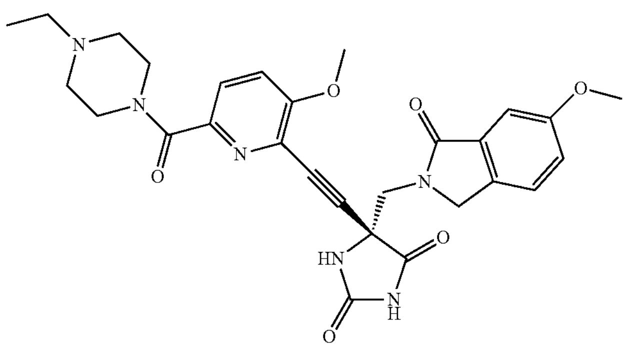 [SMILES: CCN1CCN(C(=O)c2ccc(OC)c(C#C[C@]3(CN4Cc5ccc(OC)cc5C4=O)NC(=O)NC3=O)n2)CC1] | 532.2 | 533.3 | 1.36 | 622 | |
| 1912 | 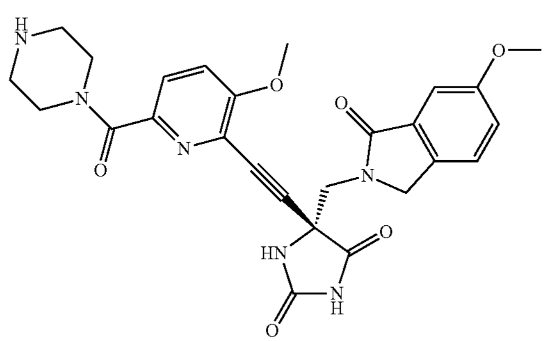 [SMILES: COc1ccc2c(c1)C(=O)N(C[C@@]1(C#Cc3nc(C(=O)N4CCNCC4)ccc3OC)NC(=O)NC1=O)C2] | 511.2 | 512.3 | 4.50 | | |
| 1913 | 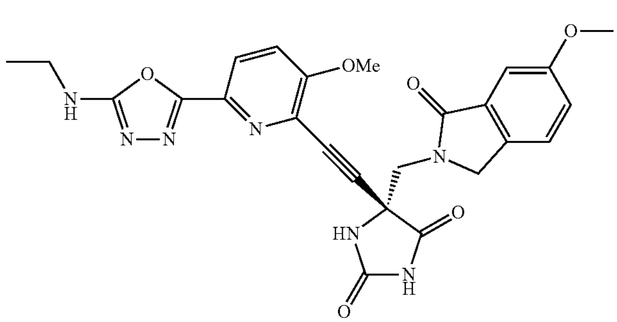 [SMILES: CCNc1nnc(-c2ccc(OC)c(C#C[C@]3(CN4Cc5ccc(OC)cc5C4=O)NC(=O)NC3=O)n2)o1] | 513.2 | 514.3 | 0.77 | 899 | |

TABLE A-continued
| ID | Structure | Exact Mass | Mass Obsvd | Ki (nM) | hWBA (nM) | RR AUC (nM·h)[1] |
|---|---|---|---|---|---|---|
| 1914 | 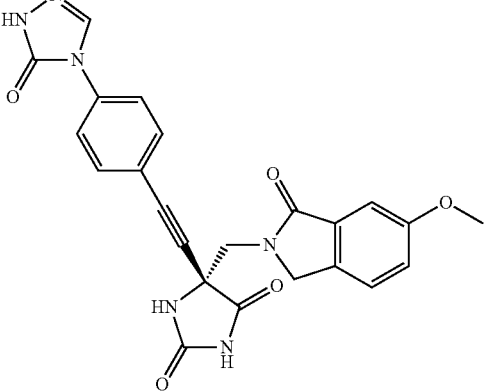 | 458.1 | 459.1 | 0.60 | 538 | |
| 1915 | 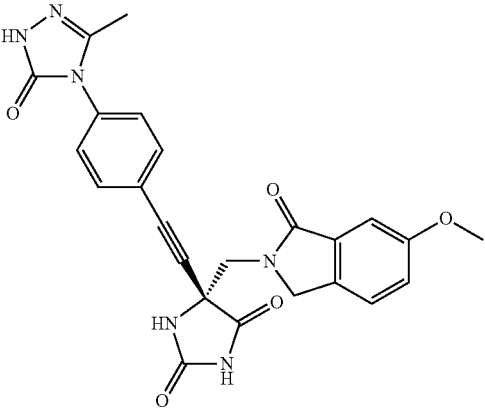 [SMILES: COc1ccc2c(c1)C(=O)N(C[C@@]1(C#Cc3ccc(-n4c(C)n[nH]c4=O)cc3)NC(=O)NC1=O)C2] | 472.1 | 473.1 | 0.30 | 243 | 0 |
| 1916 | 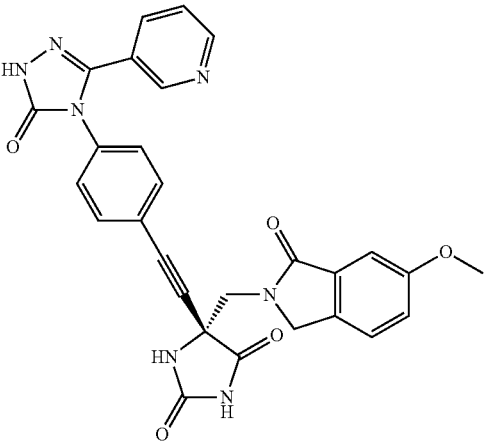 [SMILES: COc1ccc2c(c1)C(=O)N(C[C@@]1(C#Cc3ccc(-n4c(-c5cccnc5)n[nH]c4=O)cc3)NC(=O)NC1=O)C2] | 535.1 | 536.1 | 0.43 | 258 | |

TABLE A-continued

| ID | Structure | Exact Mass | Mass Obsvd | Ki (nM) | hWBA (nM) | RR AUC (nM·h)[1] |
|---|---|---|---|---|---|---|
| 1917 | 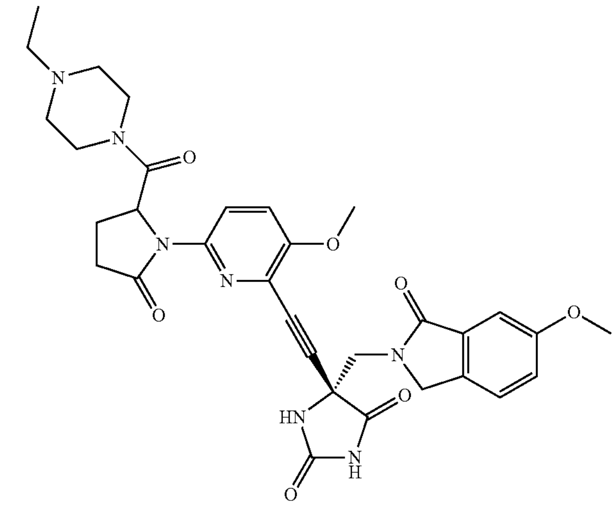 [SMILES: CCN1CCN(C(=O)C2CCC(=O)N2c2ccc(OC)c(C#C[C@]3(CN4Cc5ccc(OC)cc5C4=O)NC(=O)NC3=O)n2)CC1] | 629.2 | 630.2 | 1.15 | 3363 | |
| 1918 | 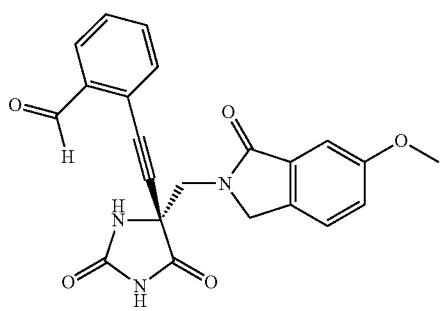 [SMILES: COc1ccc2c(c1)C(=O)N(C[C@@]1(C#Cc3ccccc3C=O)NC(=O)NC1=O)C2] | 403.1 | 404.1 | 0.11 | 936 | |
| 1919 | 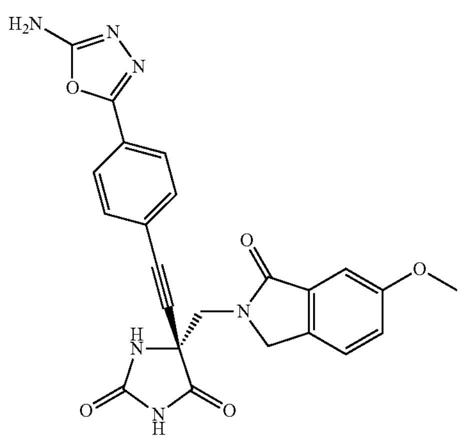 [SMILES: COc1ccc2c(c1)C(=O)N(C[C@@]1(C#Cc3ccc(-c4nnc(N)o4)cc3)NC(=O)NC1=O)C2] | 458.1 | 459.1 | 0.33 | 244 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 1920 | 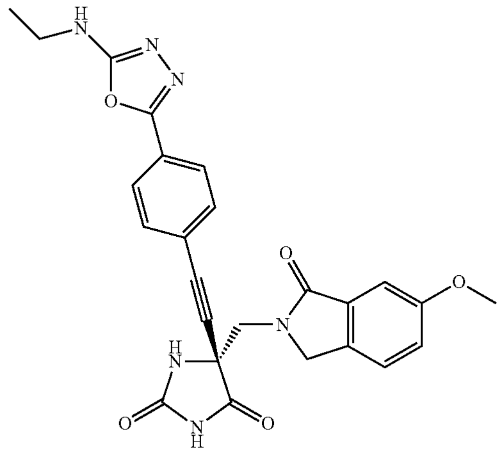 [SMILES: CCNc1nnc(-c2ccc(C#C[C@]3(CN4Cc5ccc(OC)cc5C4=O)NC(=O)NC3=O)cc2)o1] | 486.1 | 487.1 | 0.29 | 269 | 0 |
| 1921 | 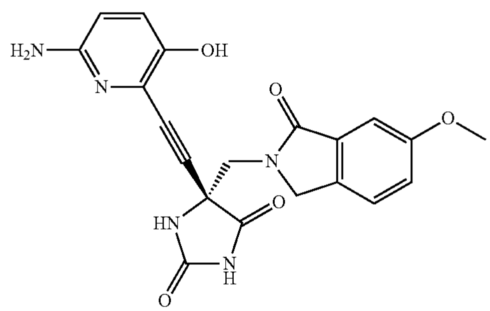 [SMILES: COc1ccc2c(c1)C(=O)N(C[C@@]1(C#Cc3nc(N)ccc3O)NC(=O)NC1=O)C2] | 407.1 | 408.1 | 0.47 | 808 | |
| 1922 | 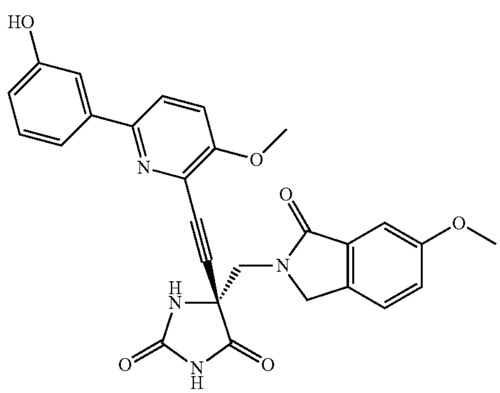 [SMILES: COc1ccc2c(c1)C(=O)N(C[C@@]1(C#Cc3nc(-c4cccc(O)c4)ccc3OC)NC(=O)NC1=O)C2] | 498.1 | 499.1 | 0.73 | 9906 | |
| 1923 | 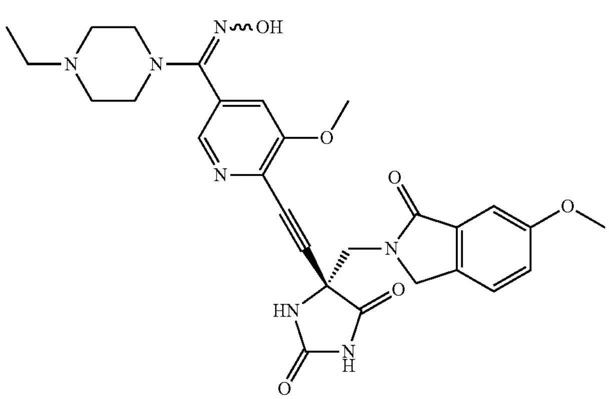 [SMILES: CCN1CCN(C(=NO)c2cnc(C#C[C@]3(CN4Cc5ccc(OC)cc5C4=O)NC(=O)NC3=O)c(OC)c2)CC1] | 561.2 | 562.2 | 0.27 | 204 | |

TABLE A-continued

| ID | Structure | Exact Mass | Mass Obsvd | Ki (nM) | hWBA (nM) | RR AUC (nM · h)[1] |
|---|---|---|---|---|---|---|
| 1924 | 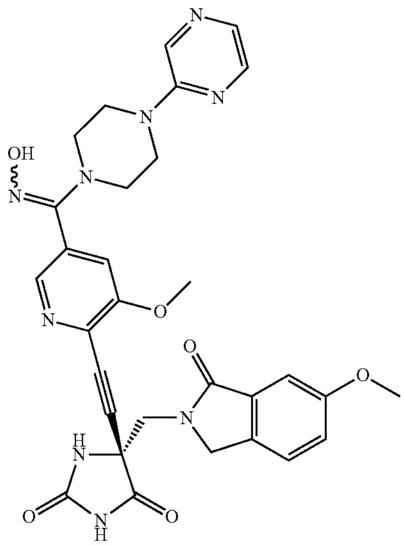 [SMILES: COc1ccc2c(c1)C(=O)N(C[C@@]1(C#Cc3ncc(C(=NO)N4CCN(c5cnccn5)CC4)cc3OC)NC(=O)NC1=O)C2] | 611.2 | 612.2 | 0.25 | 515 | |
| 1500 | 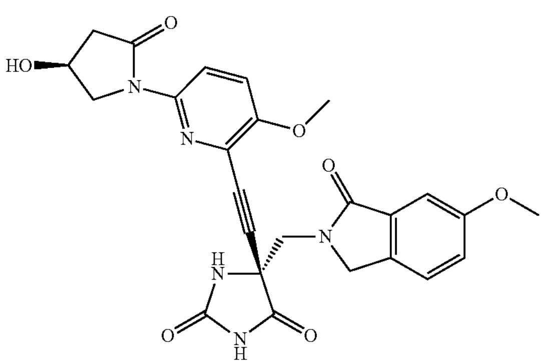 [SMILES: COc1ccc2c(c1)C(=O)N(C[C@@]1(C#Cc3nc(N4C[C@@H](O)CC4=O)ccc3OC)NC(=O)NC1=O)C2] | 505.5 | 506.3 | 0.688 | 837.1 | 0 |
| 1501 | 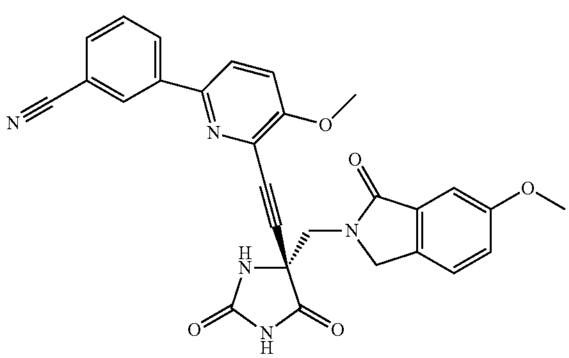 [SMILES: COc1ccc2c(c1)C(=O)N(C[C@@]1(C#Cc3nc(-c4cccc(C#N)c4)ccc3OC)NC(=O)NC1=O)C2] | 507.5 | 508.3 | 1.1 | 1000001 | |

TABLE A-continued

| ID | Structure | Exact Mass | Mass Obsvd | Ki (nM) | hWBA (nM) | RR AUC (nM · h)[1] |
|---|---|---|---|---|---|---|
| 1502 | 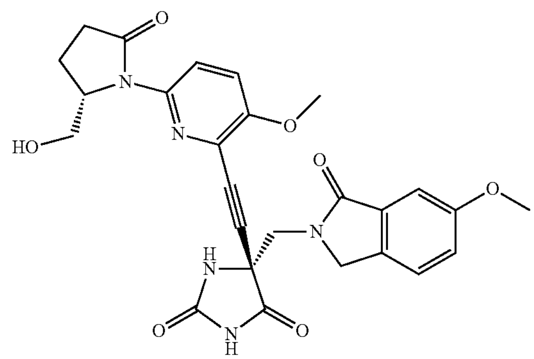 [SMILES: COc1ccc2c(c1)C(=O)N(C[C@@]1(C#Cc3nc(N4C(=O)CC[C@H]4CO)ccc3OC)NC(=O)NC1=O)C2] | 519.5 | 520.3 | 0.97 | 1542 | 0 |
| 1503 | 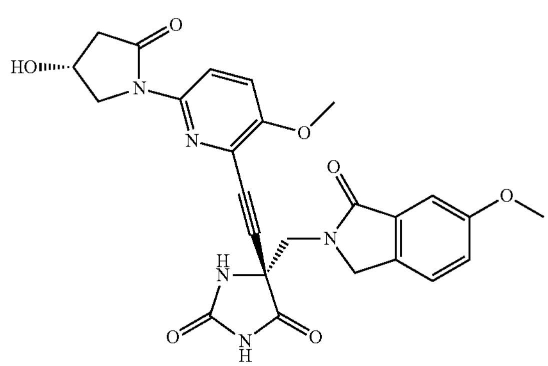 [SMILES: COc1ccc2c(c1)C(=O)N(C[C@@]1(C#Cc3nc(N4C[C@H](O)CC4=O)ccc3OC)NC(=O)NC1=O)C2] | 505.5 | 506.3 | 0.73 | 1132 | 35 |
| 1504 | 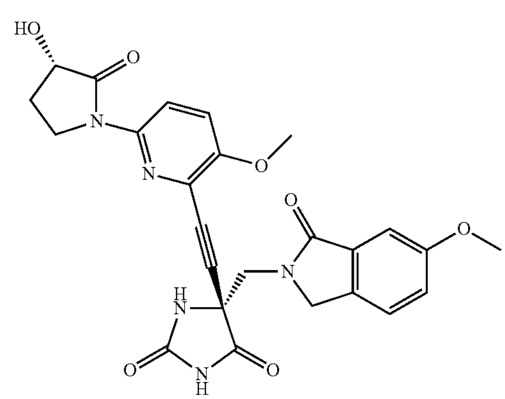 [SMILES: COc1ccc2c(c1)C(=O)N(C[C@@]1(C#Cc3nc(N4CC[C@H](O)C4=O)ccc3OC)NC(=O)NC1=O)C2] | 505.5 | 506.3 | 0.98 | 3588 | 0 |

TABLE A-continued
| ID | Structure | Exact Mass | Mass Obsvd | Ki (nM) | hWBA (nM) | RR AUC (nM · h)[1] |
|---|---|---|---|---|---|---|
| 1505 | 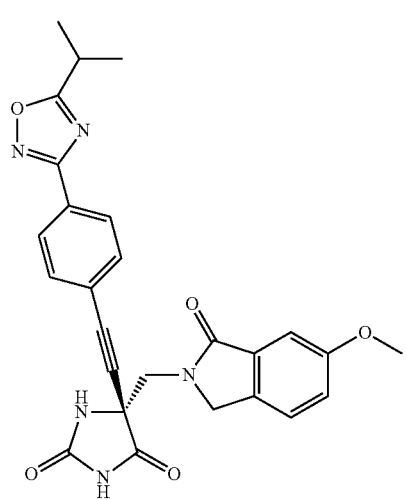 [SMILES: COc1ccc2c(c1)C(=O)N(C[C@@]1(C#Cc3ccc(-c4noc(C(C)C)n4)cc3)NC(=O)NC1=O)C2] | 485.5 | 486.3 | 0.92 | 1000001 | 243 |
| 1506 | 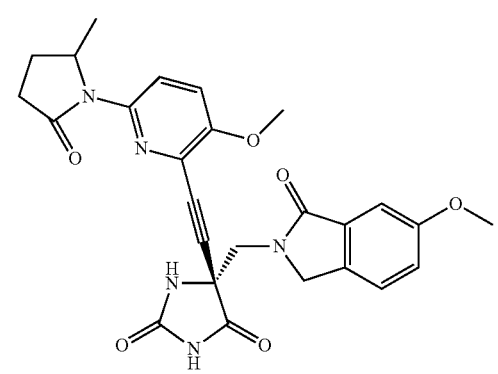 [SMILES: COc1ccc2c(c1)C(=O)N(C[C@@]1(C#Cc3nc(N4C(=O)CCC4C)ccc3OC)NC(=O)NC1=O)C2] | 503.5 | 504.3 | 1.53 | 9537.2 | 0 |
| 1507 | 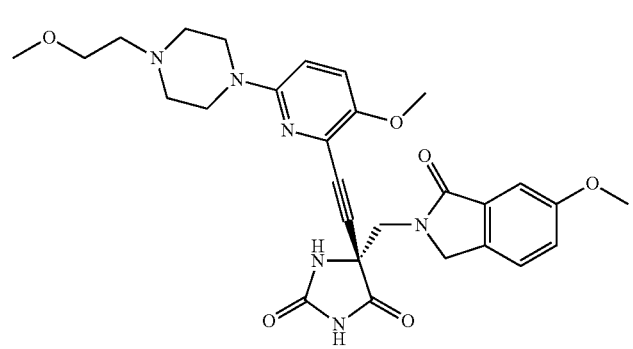 | 548.6 | 549.3 | 1.77 | 5710.4 | |

TABLE A-continued

| ID | Structure | Exact Mass | Mass Obsvd | Ki (nM) | hWBA (nM) | RR AUC (nM·h)[1] |
|---|---|---|---|---|---|---|
| 1508 | 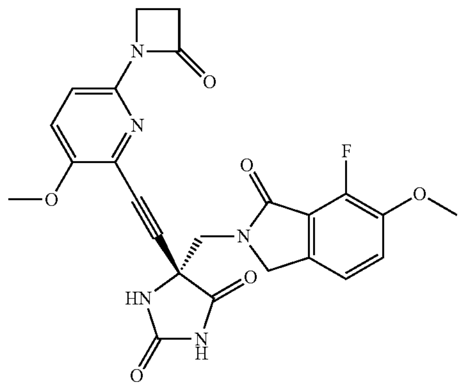 | 493.4 | 494.3 | 0.426 | 1171 | |
| 1509 | 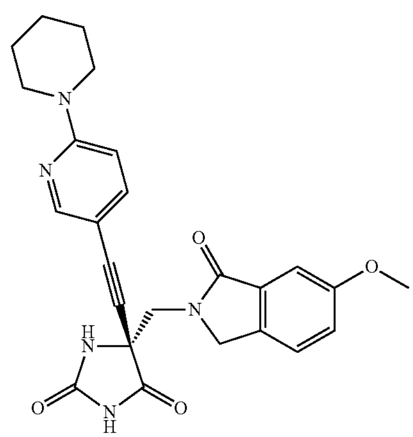 [SMILES: COc1ccc2c(c1)C(=O)N(C[C@@]1(C#Cc3ccc(N4CCCCC4)nc3)NC(=O)NC1=O)C2] | 459.5 | 460.3 | 0.19 | 514 | |
| 1510 | 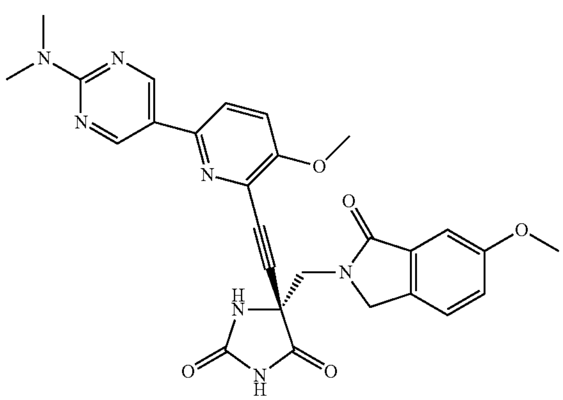 | 527.5 | 528.3 | 0.93 | 10001 | |

TABLE A-continued

| ID | Structure | Exact Mass | Mass Obsvd | Ki (nM) | hWBA (nM) | RR AUC (nM · h)[1] |
|---|---|---|---|---|---|---|
| 1511 | 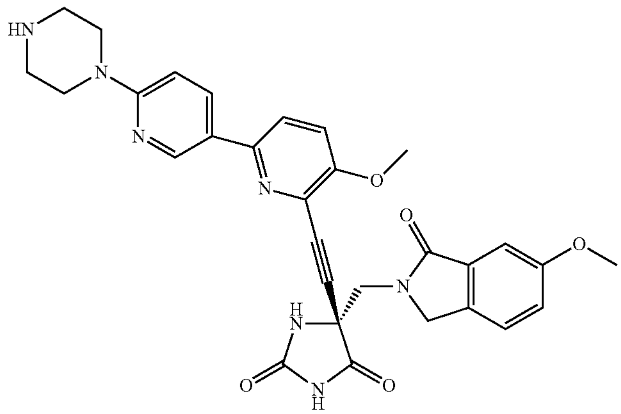 [SMILES: COc1ccc2c(c1)C(=O)N(C[C@@]1(C#Cc3nc(-c4ccc(N5CCNCC5)nc4)ccc3OC)NC(=O)NC1=O)C2] | 567.6 | 568.3 | 0.62 | 2049 | 0 |
| 1512 | 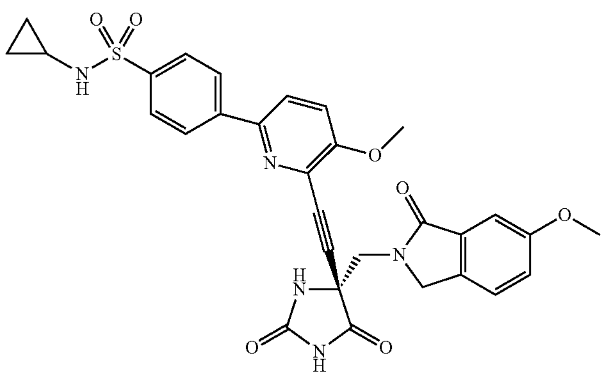 [SMILES: COc1ccc2c(c1)C(=O)N(C[C@@]1(C#Cc3nc(-c4ccc(S(=O)(=O)NC5CC5)cc4)ccc3OC)NC(=O)NC1=O)C2] | 601.6 | 602.3 | 0.9 | 7043 | |
| 1513 | 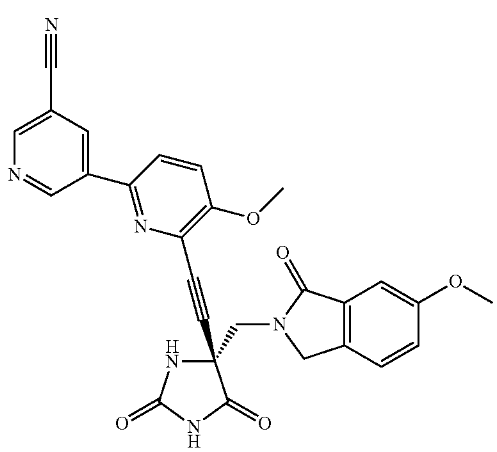 [SMILES: COc1ccc2c(c1)C(=O)N(C[C@@]1(C#Cc3nc(-c4cncc(C#N)c4)ccc3OC)NC(=O)NC1=O)C2] | 508.5 | 509.3 | 1.53 | 1790 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 1514 | 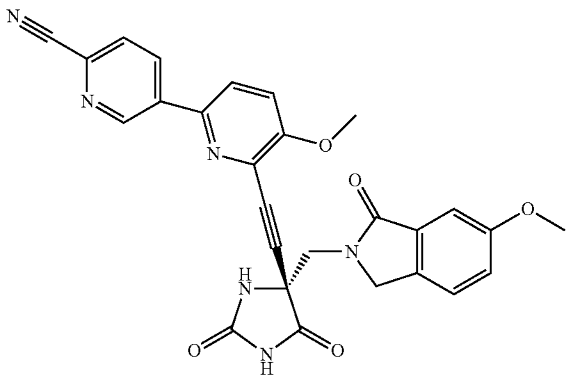 [SMILES: COc1ccc2c(c1)C(=O)N(C[C@@]1(C#Cc3nc(-c4ccc(C#N)nc4)ccc3OC)NC(=O)NC1=O)C2] | 508.5 | 509.3 | 1.02 | 10000001 | |
| 1515 | 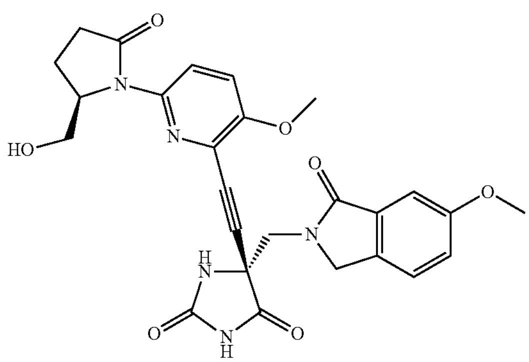 [SMILES: COc1ccc2c(c1)C(=O)N(C[C@@]1(C#Cc3nc(N4C(=O)CC[C@@H]4CO)ccc3OC)NC(=O)NC1=O)C2] | 519.5 | 520.3 | 1.55 | | 0 |
| 2200 | 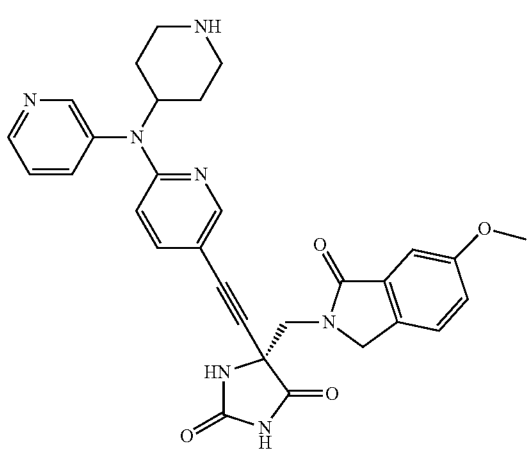 [SMILES: COc1ccc2c(c1)C(=O)N(C[C@@]1(C#Cc3ccc(N(c4cccnc4)C4CCNCC4)nc3)NC(=O)NC1=O)C2] | 551.23 | 552.3 | 1.02 | 430 | |

TABLE A-continued

| ID | Structure | Exact Mass | Mass Obsvd | Ki (nM) | hWBA (nM) | RR AUC (nM · h)[1] |
|---|---|---|---|---|---|---|
| 2201 | 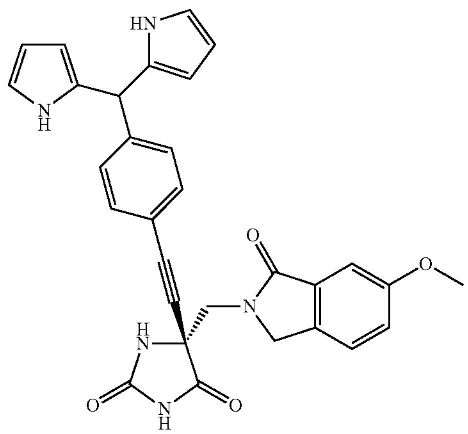 [SMILES: COc1ccc2c(c1)C(=O)N(C[C@@]1(C#Cc3ccc(C(c4ccc[nH]4)c4ccc[nH]4)cc3)NC(=O)NC1=O)C2] | 519.19 | | 0.58 | 1199 | |
| 2202 | 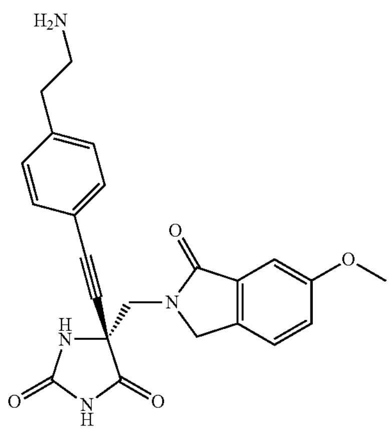 [SMILES: COc1ccc2c(c1)C(=O)N(C[C@@]1(C#Cc3ccc(CCN)cc3)NC(=O)NC1=O)C2] | 418.16 | 419.2 | 0.55 | 219 | |
| 2203 | 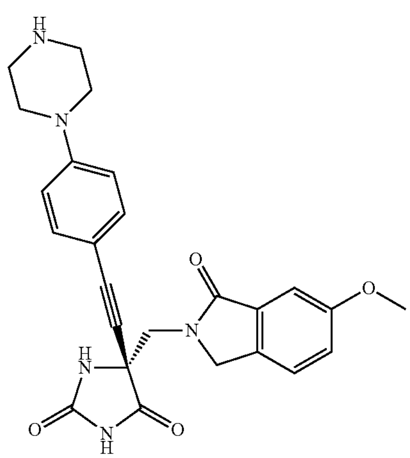 [SMILES: COc1ccc2c(c1)C(=O)N(C[C@@]1(C#Cc3ccc(N4CCNCC4)cc3)NC(=O)NC1=O)C2] | 459.19 | 460.3 | 0.61 | 205 | 0 |

TABLE A-continued
| ID | Structure | Exact Mass | Mass Obsvd | Ki (nM) | hWBA (nM) | RR AUC (nM · h)[1] |
|---|---|---|---|---|---|---|
| 2204 | 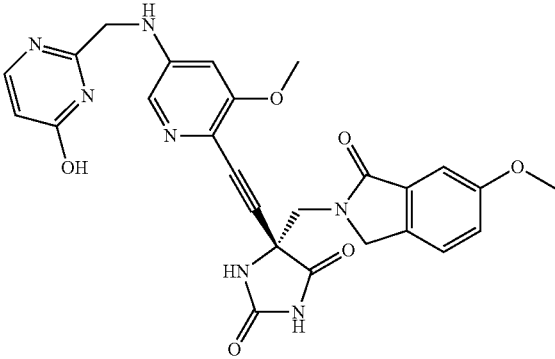 [SMILES: COc1ccc2c(c1)C(=O)N(C[C@@]1(C#Cc3ncc(NCc4nccc(O)n4)cc3OC)NC(=O)NC1=O)C2] | 515.16 | 516.3 | 0.98 | 632 | |
| 2205 | 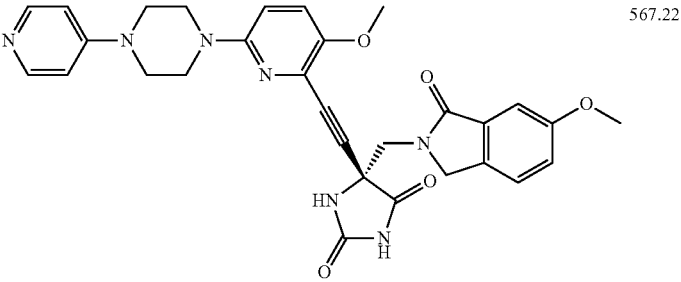 | 567.22 | 568.3 | 1.37 | 7271 | |
| 2206 | 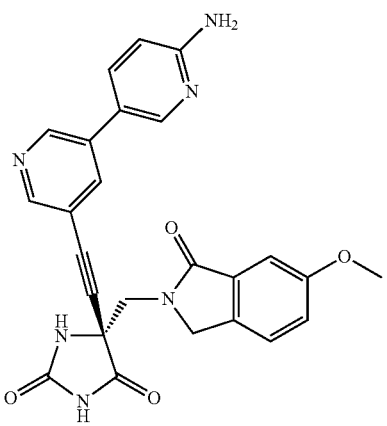 [SMILES: COc1ccc2c(c1)C(=O)N(C[C@@]1(C#Cc3cncc(-c4ccc(N)nc4)c3)NC(=O)NC1=O)C2] | 468.15 | 469.3 | 0.24 | 513.5 | 0 |
| 2207 | 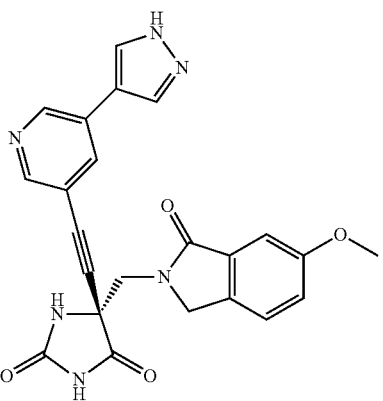 [SMILES: COc1ccc2c(c1)C(=O)N(C[C@@]1(C#Cc3cncc(-c4cn[nH]c4)c3)NC(=O)NC1=O)C2] | 442.14 | 443.2 | 0.03 | 260 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 2208 | 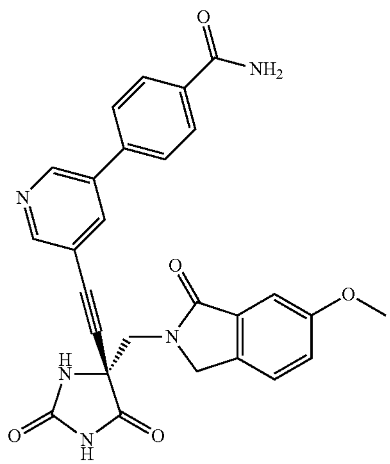 [SMILES: COc1ccc2c(c1)C(=O)N(C[C@@]1(C#Cc3cncc(-c4ccc(C(N)=O)cc4)c3)NC(=O)NC1=O)C2] | 495.15 | 496.3 | 0.94 | 361 | |
| 2209 | 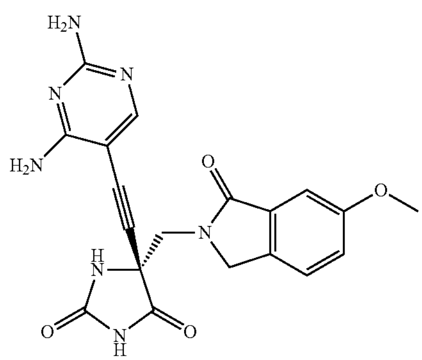 [SMILES: COc1ccc2c(c1)C(=O)N(C[C@@]1(C#Cc3cnc(N)nc3N)NC(=O)NC1=O)C2] | 407.13 | 408.2 | 0.22 | 1597 | |
| 2210 | 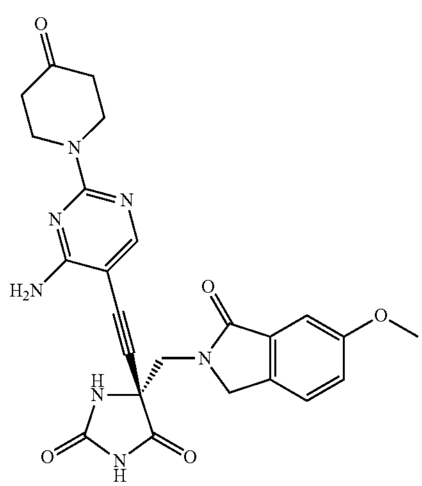 [SMILES: COc1ccc2c(c1)C(=O)N(C[C@@]1(C#Cc3cnc(N4CCC(=O)CC4)nc3N)NC(=O)NC1=O)C2] | 489.18 | 490.3 | 0.43 | 1008 | |

TABLE A-continued
| ID | Structure | Exact Mass | Mass Obsvd | Ki (nM) | hWBA (nM) | RR AUC (nM · h)[1] |
|---|---|---|---|---|---|---|
| 2211 | 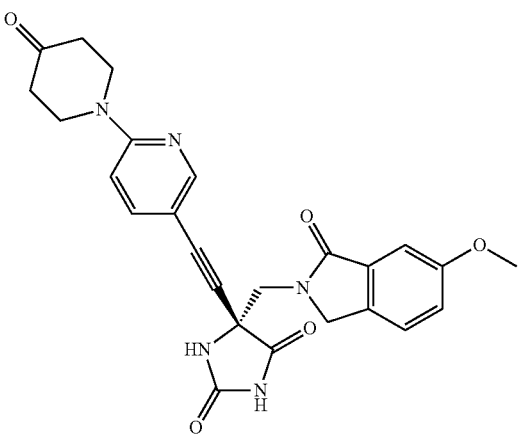 [SMILES: COc1ccc2c(c1)C(=O)N(C[C@@]1(C#Cc3ccc(N4CCC(=O)CC4)nc3)NC(=O)NC1=O)C2] | 473.17 | 474.3 | 0.50 | 1001 | |
| 2213 | 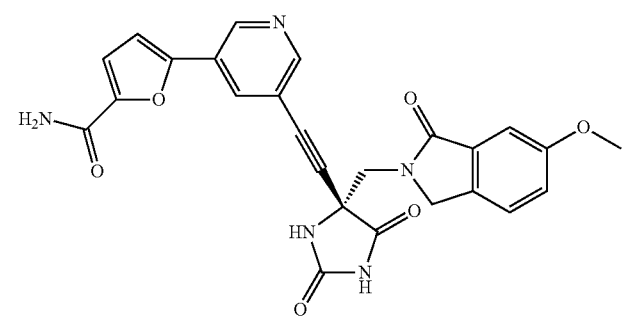 [SMILES: COc1ccc2c(c1)C(=O)N(C[C@@]1(C#Cc3cncc(-c4ccc(C(N)=O)o4)c3)NC(=O)NC1=O)C2] | 485.13 | 486.3 | 0.373 | 776.1 | |
| 2214 | 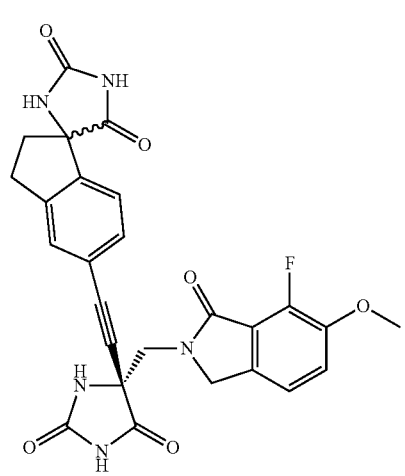 [SMILES: COc1ccc2c(c1F)C(=O)N(C[C@@]1(C#Cc3ccc4c(c3)CCC43NC(=O)NC3=O)NC(=O)NC1=O)C2] | 517.14 | 518.3 | 0.22 | 186 | 3465 |

TABLE A-continued

| ID | Structure | Exact Mass | Mass Obsvd | Ki (nM) | hWBA (nM) | RR AUC (nM · h)[1] |
|---|---|---|---|---|---|---|
| 2215 | 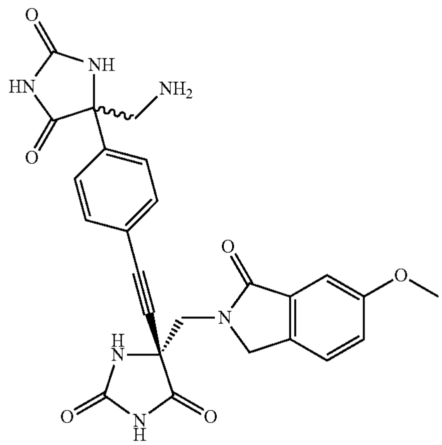 [SMILES: COc1ccc2c(c1)C(=O)N(C[C@@]1(C#Cc3ccc(C4(CN)NC(=O)NC4=O)cc3)NC(=O)NC1=O)C2] | 502.16 | 503.3 | 0.16 | 229 | 0 |
| 2216 | 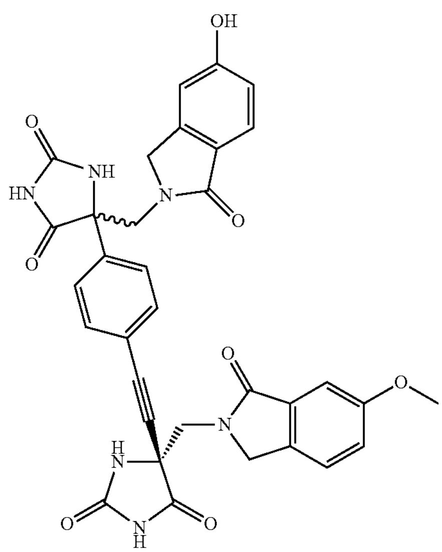 [SMILES: COc1ccc2c(c1)C(=O)N(C[C@@]1(C#Cc3ccc(C4(CN5Cc6cc(O)ccc6C5=O)NC(=O)NC4=O)cc3)NC(=O)NC1=O)C2] | 634.18 | 635.3 | 0.81 | 419 | |
| 2217 | 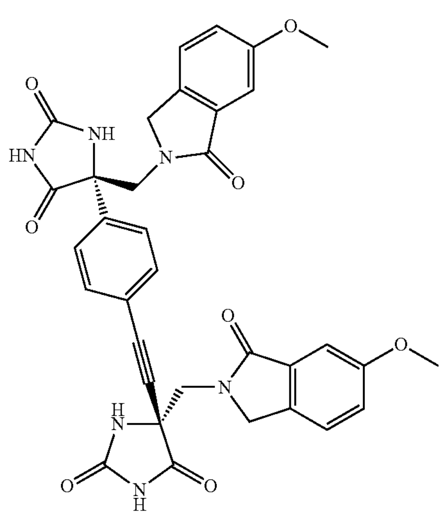 [SMILES: COc1ccc2c(c1)C(=O)N(C[C@@]1(C#Cc3ccc([C@@]4(CN5Cc6ccc(OC)cc6C5=O)NC(=O)NC4=O)cc3)NC(=O)NC1=O)C2] | 648.20 | 649.4 | 0.19 | 849 | |

TABLE A-continued
| ID | Structure | Exact Mass | Mass Obsvd | Ki (nM) | hWBA (nM) | RR AUC (nM·h)[1] |
|---|---|---|---|---|---|---|
| 2218 | 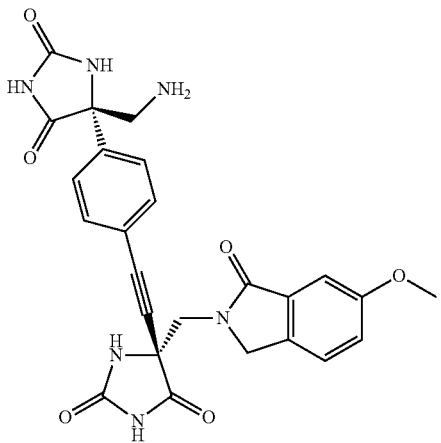 [SMILES: COc1ccc2c(c1)C(=O)N(C[C@@]1(C#Cc3ccc([C@@]4(CN)NC(=O)NC4=O)cc3)NC(=O)NC1=O)C2] | 502.16 | 503.3 | 5.6 | 122 | |
| 2219 | 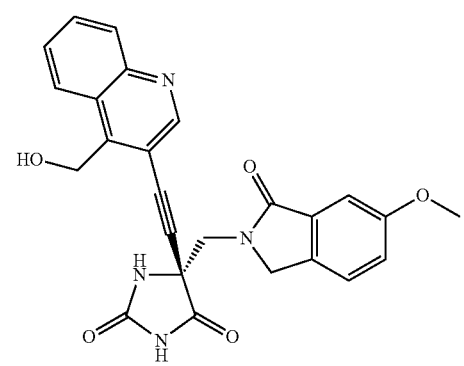 [SMILES: COc1ccc2c(c1)C(=O)N(C[C@@]1(C#Cc3cnc4ccccc4c3CO)NC(=O)NC1=O)C2] | 456.14 | 457.3 | 0.21 | 8897 | |
| 2220 | 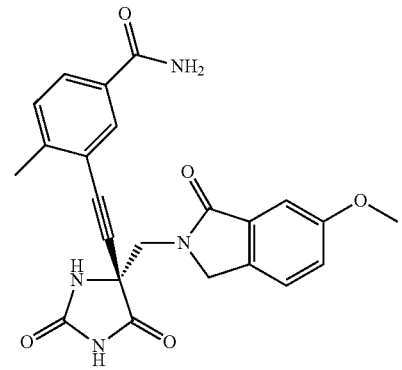 | 432.14 | 433.2 | 0.15 | 417 | |

TABLE A-continued

| ID | Structure | Exact Mass | Mass Obsvd | Ki (nM) | hWBA (nM) | RR AUC (nM · h)[1] |
|---|---|---|---|---|---|---|
| 2221 | 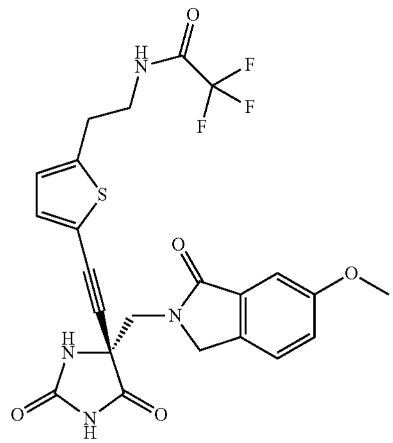 [SMILES: COc1ccc2c(c1)C(=O)N(C[C@@]1(C#Cc3ccc(CCNC(=O)C(F)(F)F)s3)NC(=O)NC1=O)C2] | 520.10 | 521.3 | 0.25 | 930 | |
| 2222 | 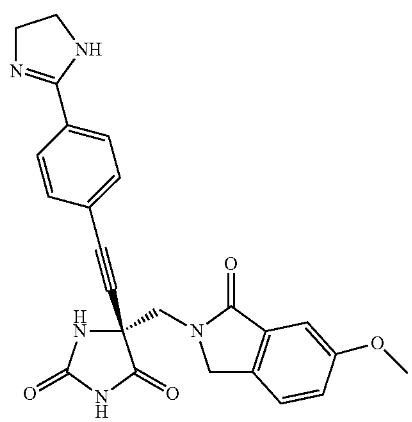 [SMILES: COc1ccc2c(c1)C(=O)N(C[C@@]1(C#Cc3ccc(C4=NCCN4)cc3)NC(=O)NC1=O)C2] | 443.16 | 444.2 | 0.63 | 227 | |
| 2223 | 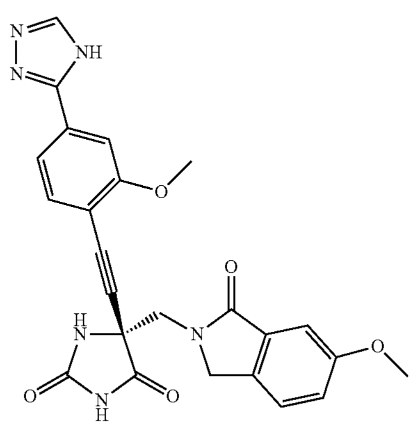 [SMILES: COc1ccc2c(c1)C(=O)N(C[C@@]1(C#Cc3ccc(-c4nnc[nH]4)cc3OC)NC(=O)NC1=O)C2] | 472.15 | 473.3 | 0.20 | 131 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 2224 | 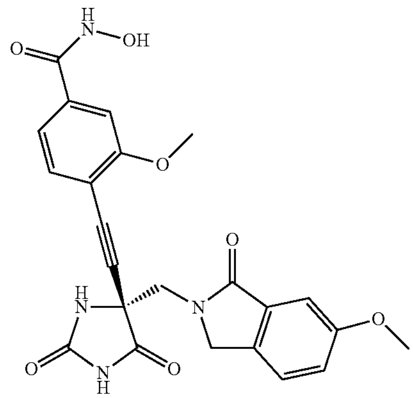 [SMILES: COc1ccc2c(c1)C(=O)N(C[C@@]1(C#Cc3ccc(C(=O)NO)cc3OC)NC(=O)NC1=O)C2] | 434.12 | 435.2 | 0.30 | 146 | |
| 2226 | 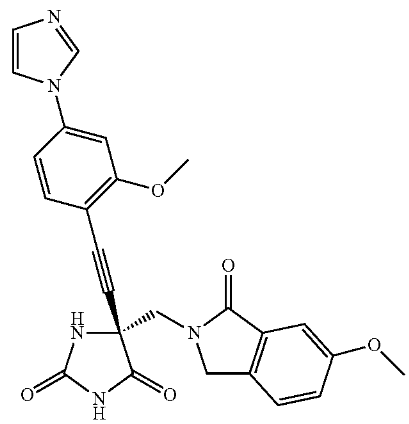 [SMILES: COc1ccc2c(c1)C(=O)N(C[C@@]1(C#Cc3ccc(-n4ccnc4)cc3OC)NC(=O)NC1=O)C2] | 441.14 | 442.2 | 0.44 | 786 | |
| 2228 | 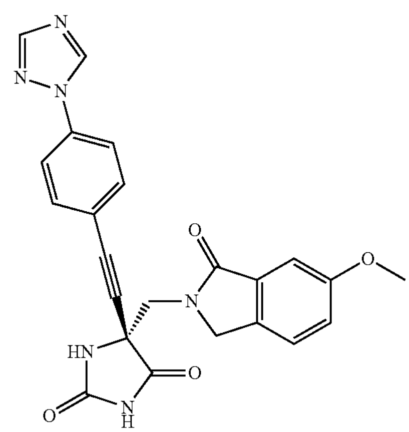 [SMILES: COc1ccc2c(c1)C(=O)N(C[C@@]1(C#Cc3ccc(-n4cncn4)cc3)NC(=O)NC1=O)C2] | 442.14 | 443.2 | 0.512 | 1140 | |
| 2229 | 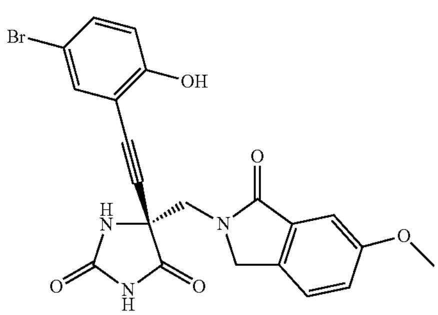 [SMILES: COc1ccc2c(c1)C(=O)N(C[C@@]1(C#Cc3cc(Br)ccc3O)NC(=O)NC1=O)C2] | 469.0 | 470, 472.3 | 0.43 | 10,001 | |

TABLE A-continued

| ID | Structure | Exact Mass | Mass Obsvd | Ki (nM) | hWBA (nM) | RR AUC (nM·h)[1] |
|---|---|---|---|---|---|---|
| 2230 | 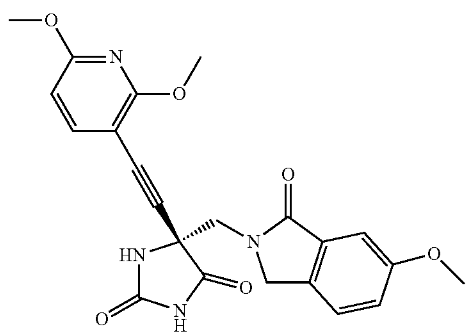 | 436.14 | 437.1 | 1.09 | 1001 | |
| 2231 | 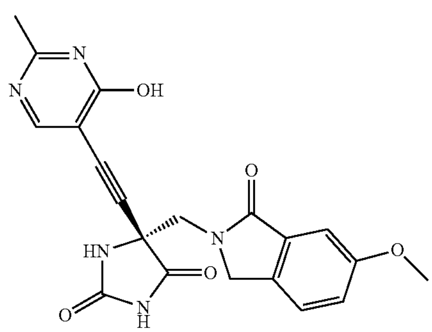 [SMILES: COc1ccc2c(c1)C(=O)N(C[C@@]1(C#Cc3cnc(C)nc3O)NC(=O)NC1=O)C2] | 407.12 | 408.2 | 0.52 | 1130 | |
| 2232 | 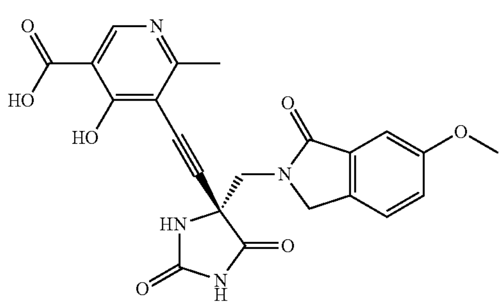 [SMILES: COc1ccc2c(c1)C(=O)N(C[C@@]1(C#Cc3c(C)ncc(C(=O)O)c3O)NC(=O)NC1=O)C2] | 450.12 | 451.2 | 0.91 | 699 | |
| 2233 | 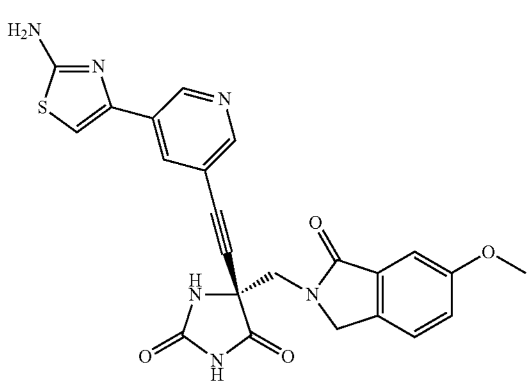 [SMILES: COc1ccc2c(c1)C(=O)N(C[C@@]1(C#Cc3cncc(-c4csc(N)n4)c3)NC(=O)NC1=O)C2] | 474.11 | 475.1 | 0.15 | 811 | |

TABLE A-continued

| ID | Structure | Exact Mass | Mass Obsvd | Ki (nM) | hWBA (nM) | RR AUC (nM·h)[1] |
|---|---|---|---|---|---|---|
| 2235 | 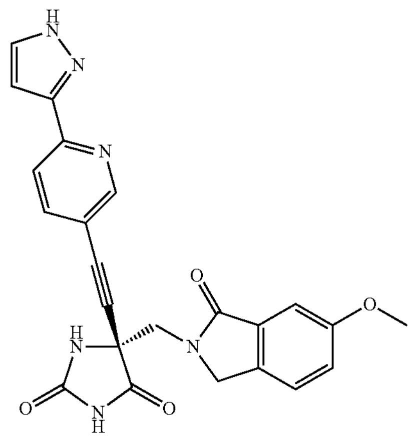 [SMILES: COc1ccc2c(c1)C(=O)N(C[C@@]1(C#Cc3ccc(-c4cc[nH]n4)nc3)NC(=O)NC1=O)C2] | 442.14 | 443.2 | 0.45 | 231 | 230 |
| 2234 | 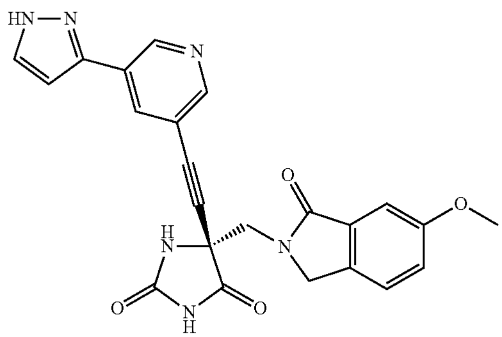 [SMILES: COc1ccc2c(c1)C(=O)N(C[C@@]1(C#Cc3cncc(-c4cc[nH]n4)c3)NC(=O)NC1=O)C2] | 442.14 | 443.2 | 0.06 | 678 | |
| 2236 | 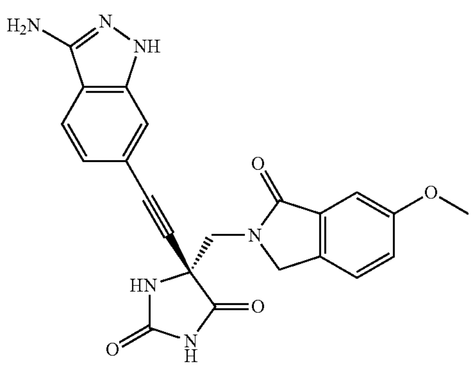 [SMILES: COc1ccc2c(c1)C(=O)N(C[C@@]1(C#Cc3ccc4c(N)n[nH]c4c3)NC(=O)NC1=O)C2] | 430.14 | 431.1 | 0.26 | 309.6 | 0 |
| 2237 | 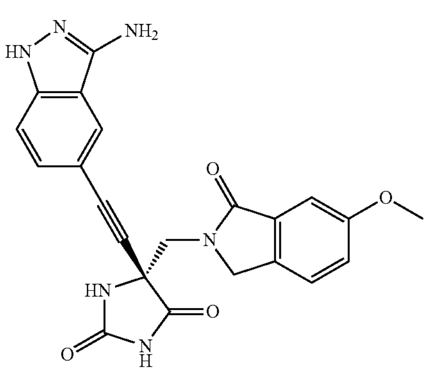 [SMILES: COc1ccc2c(c1)C(=O)N(C[C@@]1(C#Cc3ccc4[nH]nc(N)c4c3)NC(=O)NC1=O)C2] | 430.14 | 431.0 | 0.25 | 520.1 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 2238 | 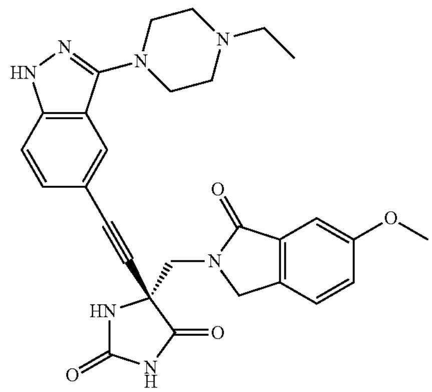 [SMILES: CCN1CCN(c2n[nH]c3ccc(C#C[C@]4(CN5Cc6ccc(OC)cc6C5=O)NC(=O)NC4=O)cc23)CC1] | 527.23 | 528.2 | 0.754 | 421.75 | |
| 2239 | 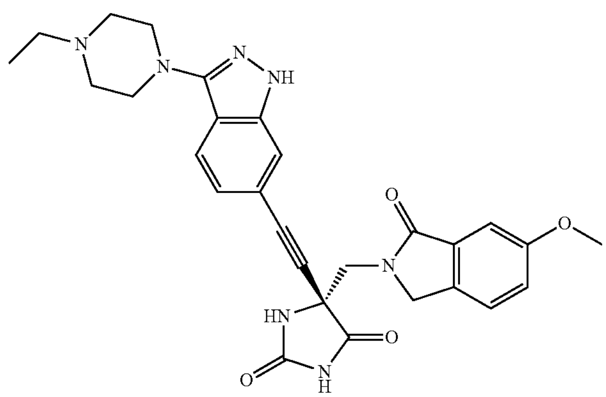 [SMILES: CCN1CCN(c2n[nH]c3cc(C#C[C@]4(CN5Cc6ccc(OC)cc6C5=O)NC(=O)NC4=O)ccc23)CC1] | 527.23 | 528.3 | 0.17 | 187.95 | 0 |
| 2240 | 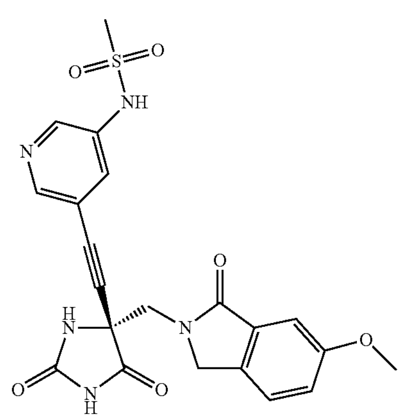 [SMILES: COc1ccc2c(c1)C(=O)N(C[C@@]1(C#Cc3cncc(NS(C)(=O)=O)c3)NC(=O)NC1=O)C2] | 469.10 | 470.0 | 0.33 | 386 | 0 |

TABLE A-continued
| ID | Structure | Exact Mass | Mass Obsvd | Ki (nM) | hWBA (nM) | RR AUC (nM·h)[1] |
|---|---|---|---|---|---|---|
| 2241 | 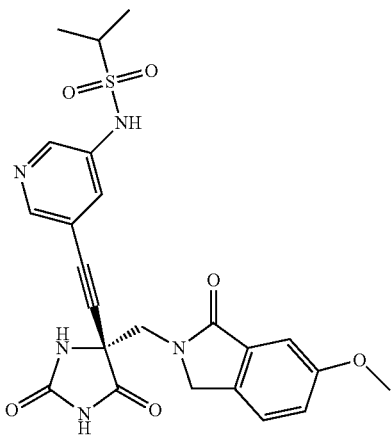 [SMILES: COc1ccc2c(c1)C(=O)N(C[C@@]1(C#Cc3cncc(NS(=O)(=O)C(C)C)c3)NC(=O)NC1=O)C2] | 497.14 | 498.1 | 0.95 | 1001 | 0 |
| 2242 | 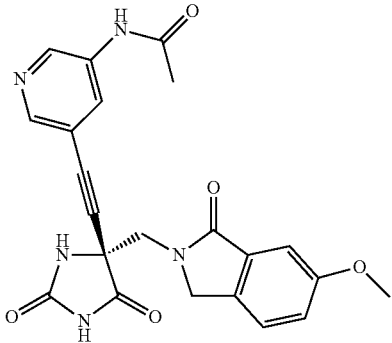 [SMILES: COc1ccc2c(c1)C(=O)N(C[C@@]1(C#Cc3cncc(NC(C)=O)c3)NC(=O)NC1=O)C2] | 433.14 | 434.2 | 1.71 | 444 | 0 |
| 2243 | 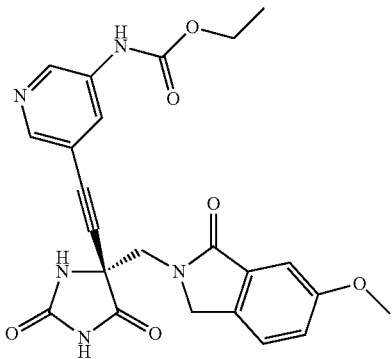 [SMILES: CCOC(=O)Nc1cncc(C#C[C@]2(CN3Cc4ccc(OC)cc4C3=O)NC(=O)NC2=O)c1] | 463.15 | 464.2 | 0.25 | 1230 | |
| 2244 | 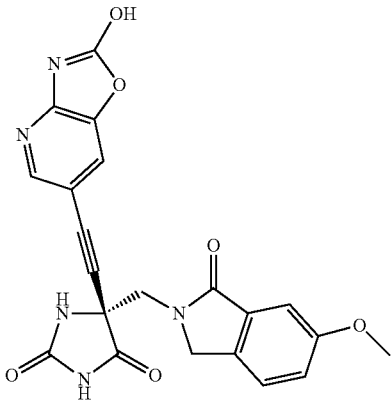 [SMILES: COc1ccc2c(c1)C(=O)N(C[C@@]1(C#Cc3cnc4nc(O)oc4c3)NC(=O)NC1=O)C2] | 433.10 | 434.0 | 0.56 | 574 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 2245 | 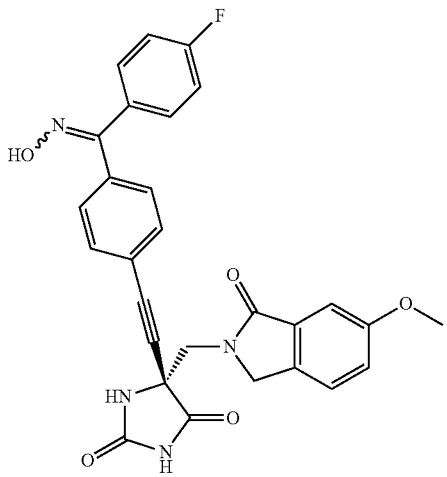 [SMILES: COc1ccc2c(c1)C(=O)N(C[C@@]1(C#Cc3ccc(C(=NO)c4ccc(F)cc4)cc3)NC(=O)NC1=O)C2] | 512.15 | 513.1 | 0.26 | 954 | 1068 |
| 2246 | 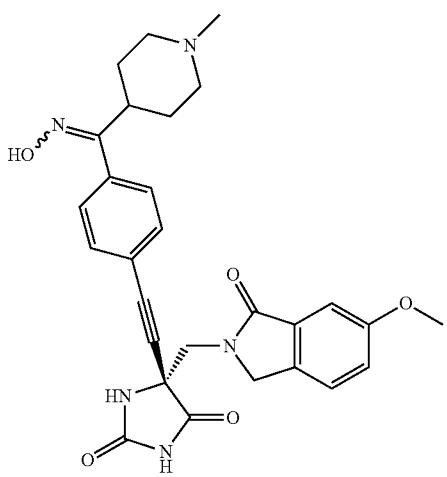 [SMILES: COc1ccc2c(c1)C(=O)N(C[C@@]1(C#Cc3ccc(C(=NO)C4CCN(C)CC4)cc3)NC(=O)NC1=O)C2] | 515.22 | 516.3 | 0.28 | 40 | 0 |
| 2247 | 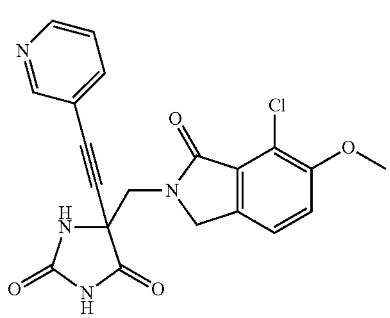 [SMILES: COc1ccc2c(c1Cl)C(=O)N(CC1(C#Cc3cccnc3)NC(=O)NC1=O)C2] | 410.8 | 411.2 | 2.35 | 1001 | 380 |

TABLE A-continued
| ID | Structure | Exact Mass | Mass Obsvd | Ki (nM) | hWBA (nM) | RR AUC (nM · h)[1] |
|---|---|---|---|---|---|---|
| 2248 | 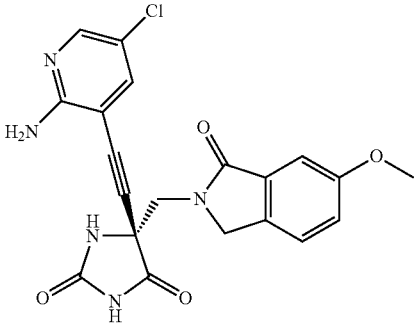 [SMILES: COc1ccc2c(c1)C(=O)N(C[C@@]1(C#Cc3cc(Cl)cnc3N)NC(=O)NC1=O)C2] | 425.8 | 411.2 | 26.2 | 10001 | 4035 |
| 2249 | 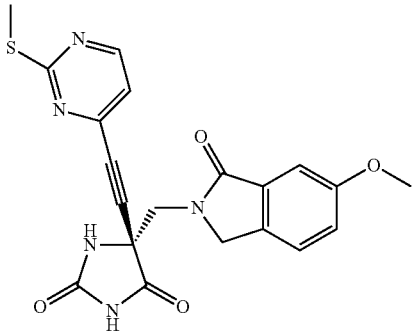 [SMILES: COc1ccc2c(c1)C(=O)N(C[C@@]1(C#Cc3ccnc(SC)n3)NC(=O)NC1=O)C2] | 423.44 | 424.2 | 0.467 | 3035 | 0 |
| 2250 | 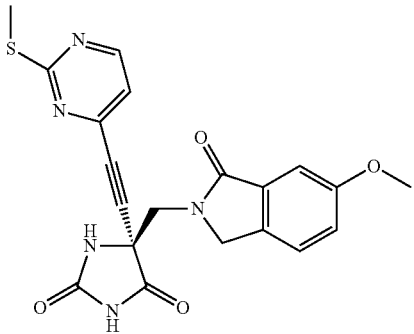 [SMILES: COc1ccc2c(c1)C(=O)N(C[C@]1(C#Cc3ccnc(SC)n3)NC(=O)NC1=O)C2] | 423.44 | 424.2 | 0.317 | 10001 | |
| 2251 | 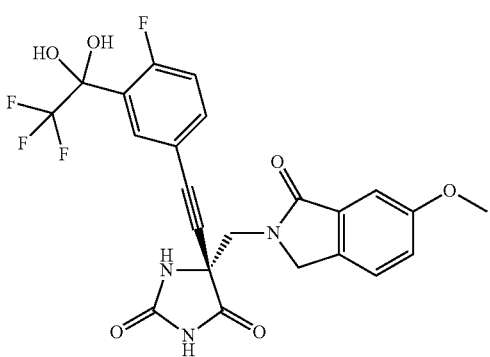 [SMILES: COc1ccc2c(c1)C(=O)N(C[C@@]1(C#Cc3ccc(F)c(C(O)(O)C(F)(F)F)c3)NC(=O)NC1=O)C2] | 507.39 | 508.3 | 0.371 | 1178 | 171 |

TABLE A-continued

| ID | Structure | Exact Mass | Mass Obsvd | Ki (nM) | hWBA (nM) | RR AUC (nM · h)[1] |
|---|---|---|---|---|---|---|
| 2252 | 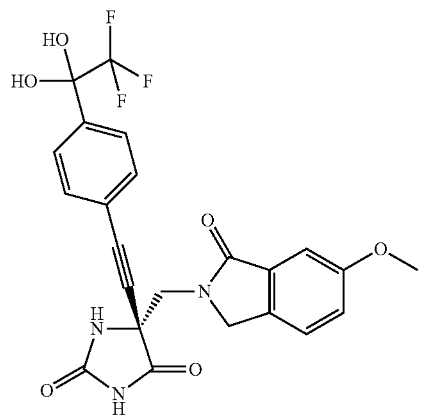 [SMILES: COc1ccc2c(c1)C(=O)N(C[C@@]1(C#Cc3ccc(C(O)(O)C(F)(F)F)cc3)NC(=O)NC1=O)C2] | 489.4 | 490.3 | 0.16 | 257.8 | 768 |
| 2253 | 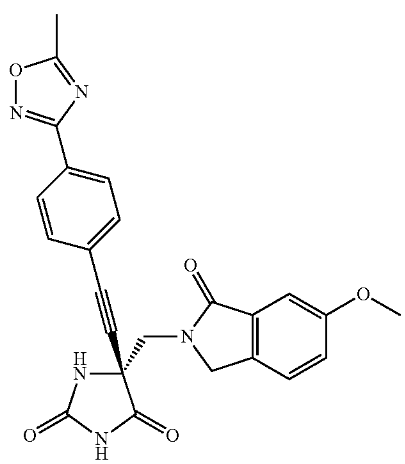 [SMILES: COc1ccc2c(c1)C(=O)N(C[C@@]1(C#Cc3ccc(-c4noc(C)n4)cc3)NC(=O)NC1=O)C2] | 457.43 | 458.3 | 0.27 | 2430 | 4140 |
| 2254 | 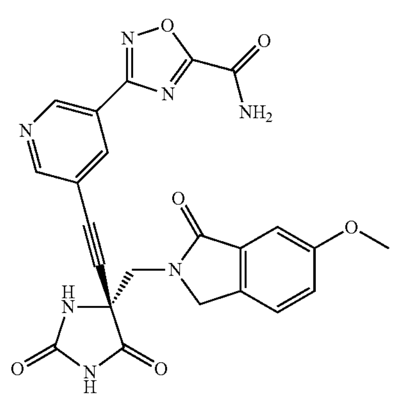 [SMILES: COc1ccc2c(c1)C(=O)N(C[C@@]1(C#Cc3cncc(-c4noc(C(N)=O)n4)c3)NC(=O)NC1=O)C2] | 487.42 | 488.3 | 0.314 | 712.9 | |

TABLE A-continued

| ID | Structure | Exact Mass | Mass Obsvd | Ki (nM) | hWBA (nM) | RR AUC (nM·h)[1] |
|---|---|---|---|---|---|---|
| 2255 | 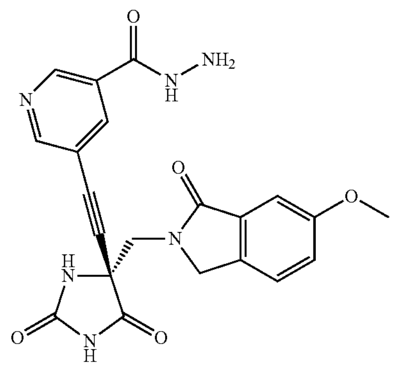 [SMILES: COc1ccc2c(c1)C(=O)N(C[C@@]1(C#Cc3cncc(C(=O)NN)c3)NC(=O)NC1=O)C2] | 434.4 | 435.2 | 0.534 | 432 | |
| 2256 | 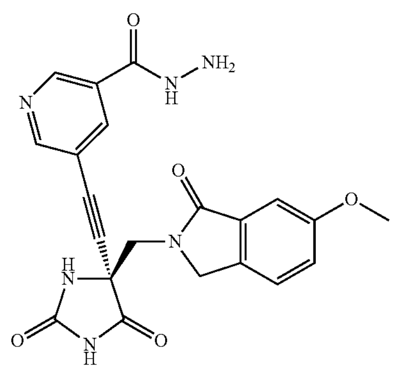 [SMILES: COc1ccc2c(c1)C(=O)N(C[C@]1(C#Cc3cncc(C(=O)NN)c3)NC(=O)NC1=O)C2] | 434.4 | 435.2 | 32.6 | 1001 | |
| 901 | 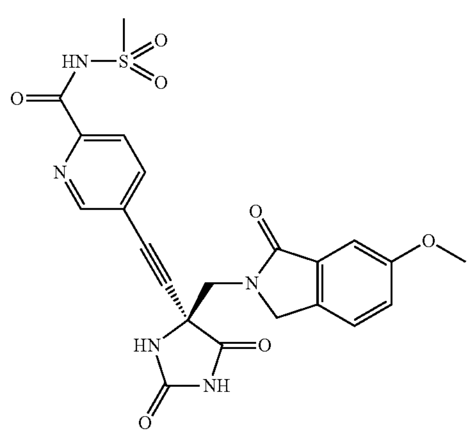 [SMILES: COc1ccc2c(c1)C(=O)N(C[C@]1(C#Cc3ccc(C(=O)NS(C)(=O)=O)nc3)NC(=O)NC1=O)C2] | 497.1 | 498.3 | 501 | 1001 | |

TABLE A-continued

| ID | Structure | Exact Mass | Mass Obsvd | Ki (nM) | hWBA (nM) | RR AUC (nM · h)[1] |
|---|---|---|---|---|---|---|
| 902 | 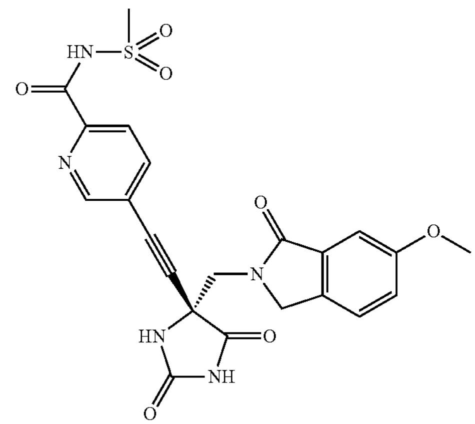 [SMILES: COc1ccc2c(c1)C(=O)N(C[C@@]1(C#Cc3ccc(C(=O)NS(C)(=O)=O)nc3)NC(=O)NC1=O)C2] | 497.1 | 498.3 | 1.67 | 1368 | |
| 903 | 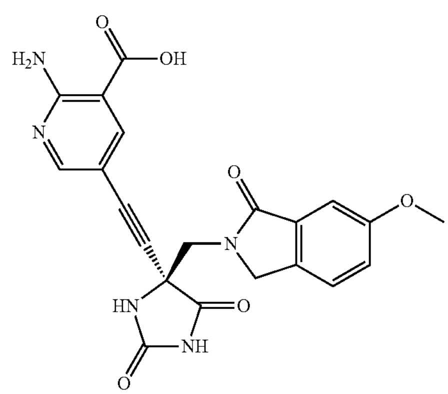 [SMILES: COc1ccc2c(c1)C(=O)N(C[C@]1(C#Cc3cnc(N)c(C(=O)O)c3)NC(=O)NC1=O)C2] | 435.1 | 436.2 | 501 | 1001 | |
| 904 | 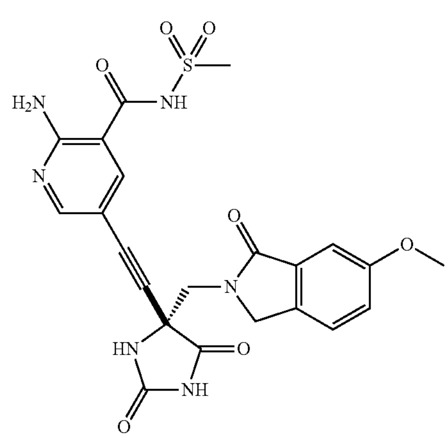 [SMILES: COc1ccc2c(c1)C(=O)N(C[C@@]1(C#Cc3cnc(N)c(C(=O)NS(C)(=O)=O)c3)NC(=O)NC1=O)C2] | 512.1 | 513.3 | 0.73 | 10001 | |

TABLE A-continued
| ID | Structure | Exact Mass | Mass Obsvd | Ki (nM) | hWBA (nM) | RR AUC (nM·h)[1] |
|---|---|---|---|---|---|---|
| 905 | 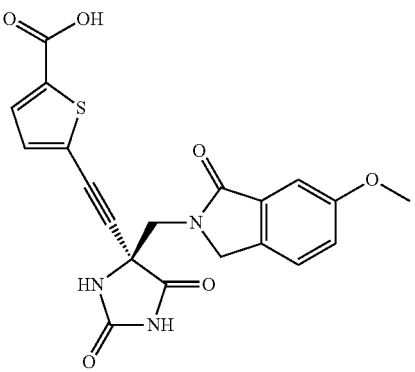 [SMILES: COc1ccc2c(c1)C(=O)N(C[C@]1(C#Cc3ccc(C(=O)O)s3)NC(=O)NC1=O)C2] | 425.1 | 426.2 | 501 | 10001 | |
| 906 | 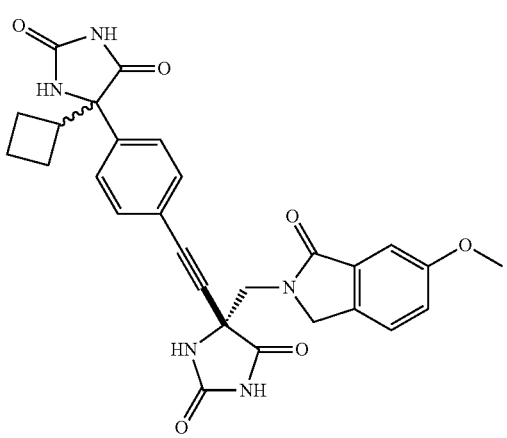 [SMILES: COc1ccc2c(c1)C(=O)N(C[C@@]1(C#Cc3ccc(C4(C5CCC5)NC(=O)NC4=O)cc3)NC(=O)NC1=O)C2] | 527.2 | 528.3 | 0.17 | 382 | |
| 907 | 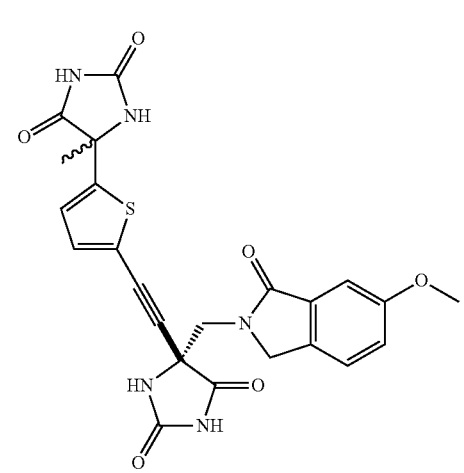 [SMILES: COc1ccc2c(c1)C(=O)N(C[C@@]1(C#Cc3ccc(C4(C)NC(=O)NC4=O)s3)NC(=O)NC1=O)C2] | 493.1 | 494.3 | 0.44 | 208 | |

TABLE A-continued

| ID | Structure | Exact Mass | Mass Obsvd | Ki (nM) | hWBA (nM) | RR AUC (nM·h)[1] |
|---|---|---|---|---|---|---|
| 908 | 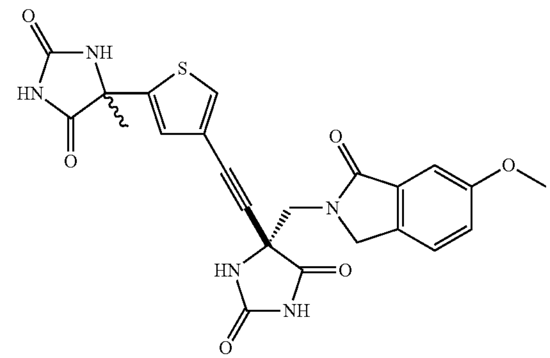 [SMILES: COc1ccc2c(c1)C(=O)N(C[C@@]1(C#Cc3csc(C4(C)NC(=O)NC4=O)c3)NC(=O)NC1=O)C2] | 493.1 | 494.3 | 0.42 | 531 | |
| 909 | 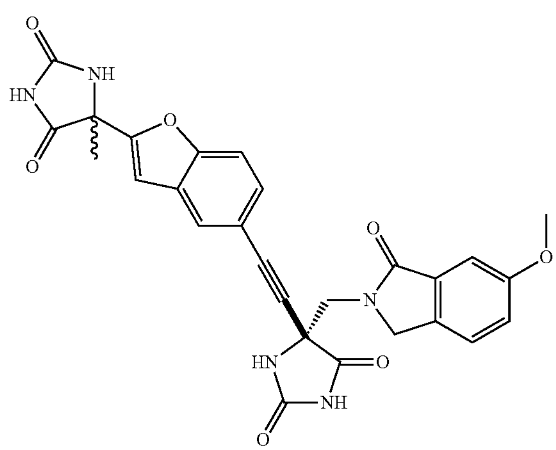 [SMILES: COc1ccc2c(c1)C(=O)N(C[C@@]1(C#Cc3ccc4oc(C5(C)NC(=O)NC5=O)cc4c3)NC(=O)NC1=O)C2] | 527.1 | 528.3 | 0.18 | 292 | |
| 910 | 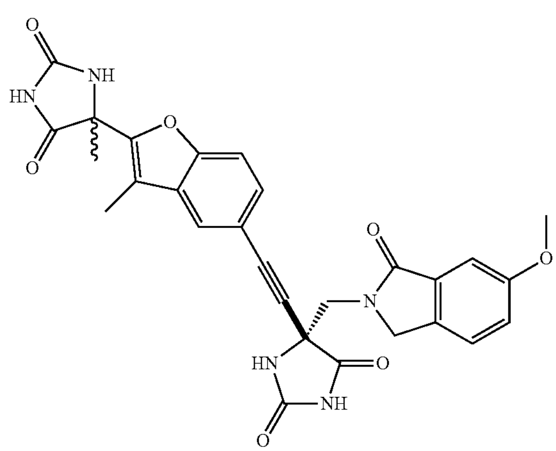 [SMILES: COc1ccc2c(c1)C(=O)N(C[C@@]1(C#Cc3ccc4oc(C5(C)NC(=O)NC5=O)c(C)c4c3)NC(=O)NC1=O)C2] | 541.2 | 542.3 | 0.22 | 545 | |

TABLE A-continued

| ID | Structure | Exact Mass | Mass Obsvd | Ki (nM) | hWBA (nM) | RR AUC (nM · h)[1] |
|---|---|---|---|---|---|---|
| 911 | 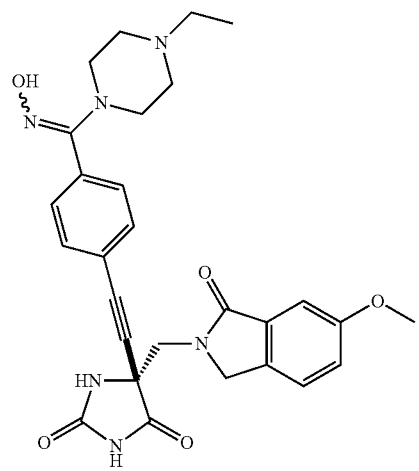 | 530.2 | 531.3 | 0.16 | 20 | 0 |
| 912 | 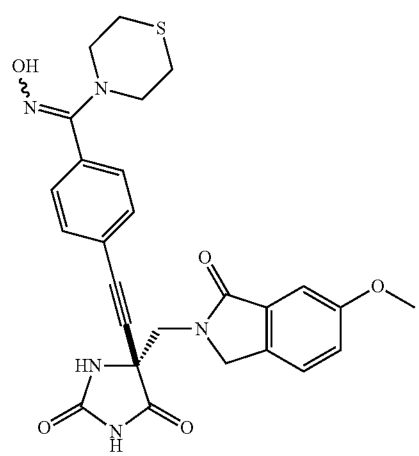 | 519.2 | 520.3 | 0.16 | 153 | 0 |
| 913 | 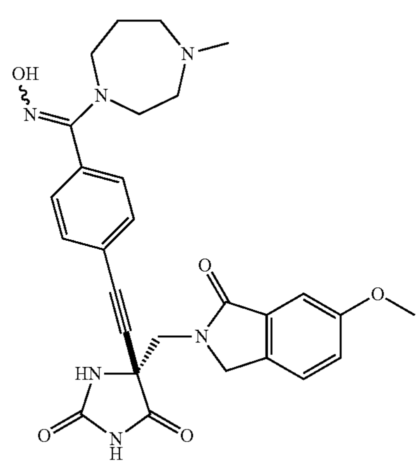 | 530.2 | 531.3 | 0.24 | 45 | 0 |

TABLE A-continued

| ID | Structure | Exact Mass | Mass Obsvd | Ki (nM) | hWBA (nM) | RR AUC (nM·h)[1] |
|---|---|---|---|---|---|---|
| 914 | 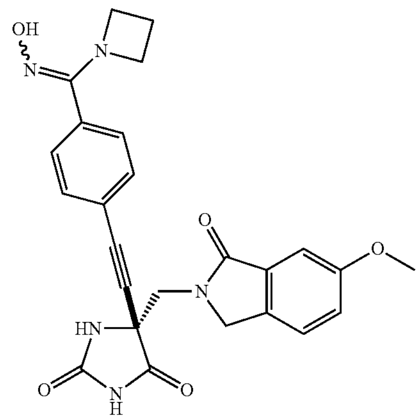 | 473.2 | 474.3 | 0.27 | 186 | 0 |
| 915 | 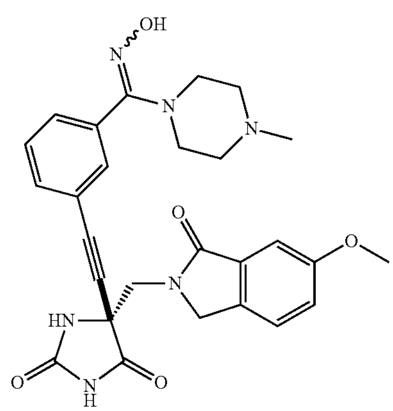 | 516.2 | 517.3 | 0.24 | 221 | 0 |
| 916 | 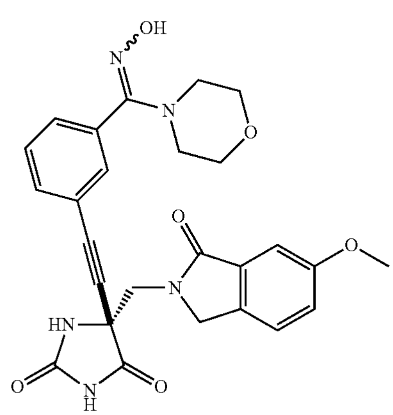 | 503.2 | 504.3 | 0.18 | 274 | |

TABLE A-continued

| ID | Structure | Exact Mass | Mass Obsvd | Ki (nM) | hWBA (nM) | RR AUC (nM · h)[1] |
|---|---|---|---|---|---|---|
| 922 | 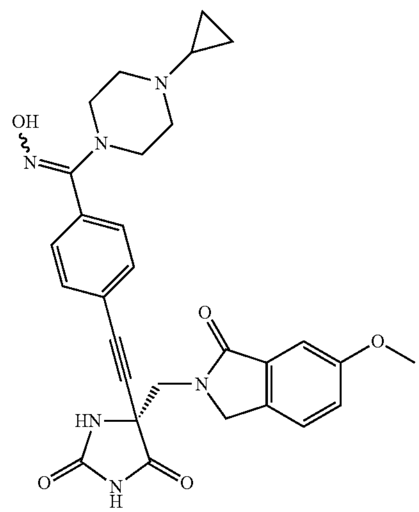 [SMILES: COc1ccc2c(c1)C(=O)N(C[C@@]1(C#Cc3ccc(C(=NO)N4CCN(C5CC5)CC4)cc3)NC(=O)NC1=O)C2] | 542.2 | 543.3 | 0.072 | 92 | |
| 923 | 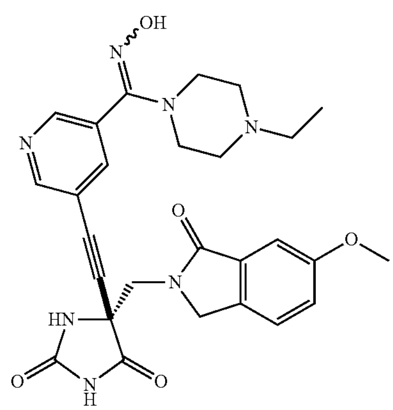 | 531.2 | 532.3 | 0.39 | 435 | |
| 924 | 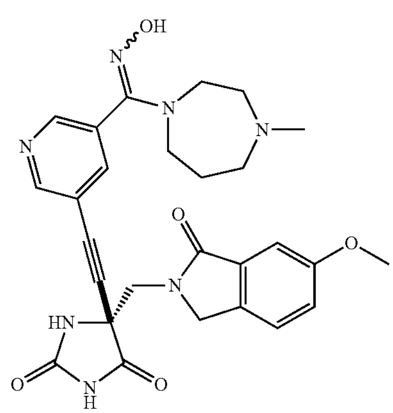 | 531.2 | 532.3 | 0.71 | 1322 | |

TABLE A-continued
| ID | Structure | Exact Mass | Mass Obsvd | Ki (nM) | hWBA (nM) | RR AUC (nM·h)[1] |
|---|---|---|---|---|---|---|
| 925 | 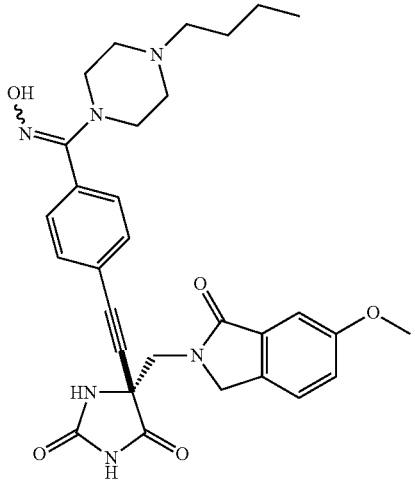 | 558.3 | 599.3 | 0.093 | 74 | |
| 926 | 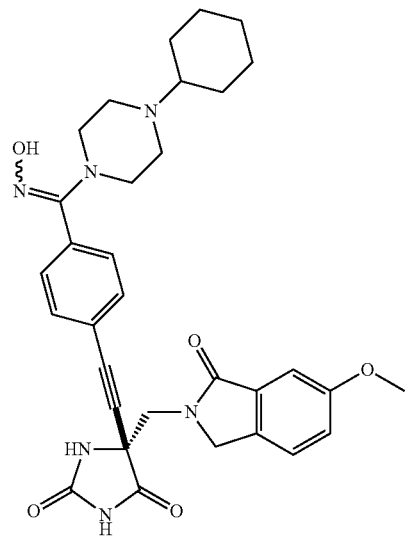 | 584.3 | 585.3 | 0.11 | 76 | 0 |
| 927 | 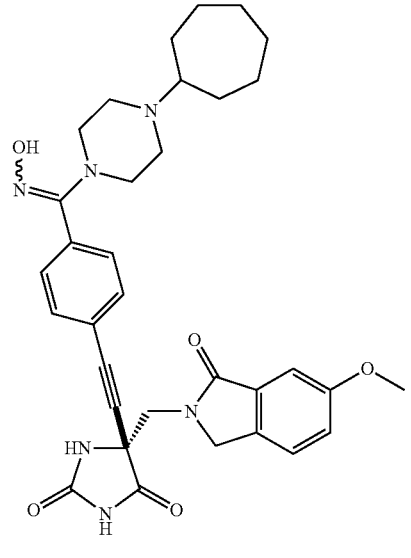 | 598.3 | 599.3 | 0.063 | 151 | |

TABLE A-continued

| ID | Structure | Exact Mass | Mass Obsvd | Ki (nM) | hWBA (nM) | RR AUC (nM · h)[1] |
|---|---|---|---|---|---|---|
| 928 | 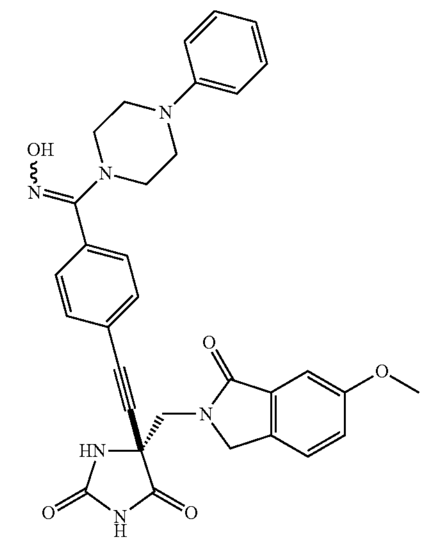 | 578.2 | 579.3 | 0.15 | 278 | |
| 929 | 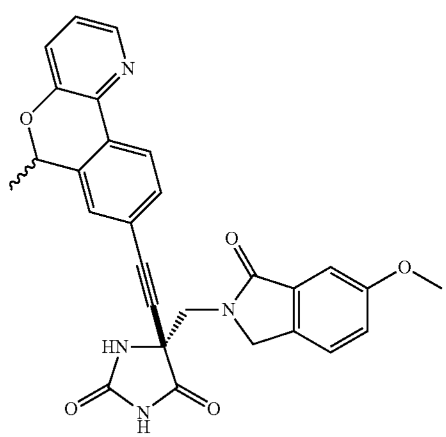 | 494.2 | 495.3 | 0.46 | 3546 | |
| 930 | 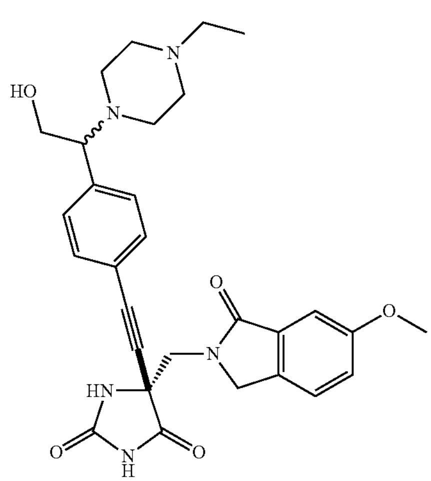 | 531.2 | 516.3 [M − CH₃] + H | 0.32 | 504 | |

TABLE A-continued

| ID | Structure | Exact Mass | Mass Obsvd | Ki (nM) | hWBA (nM) | RR AUC (nM · h)[1] |
|---|---|---|---|---|---|---|
| 931 | 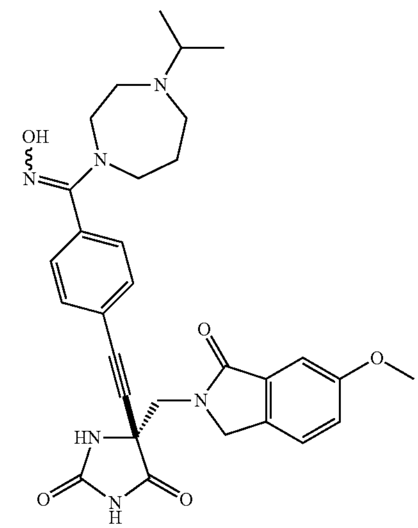 | 558.3 | 559.3 | 0.19 | 47 | |
| 932 | 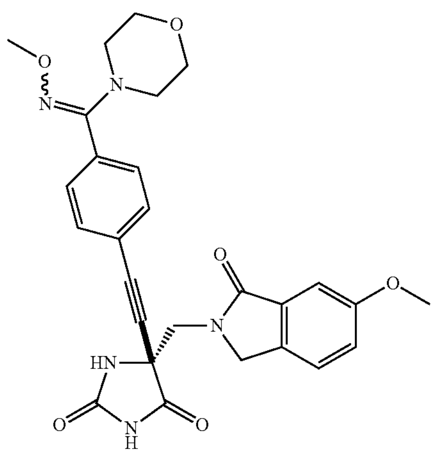 | 517.2 | 518.3 | 0.50 | 1237 | 3173 |
| 933 | 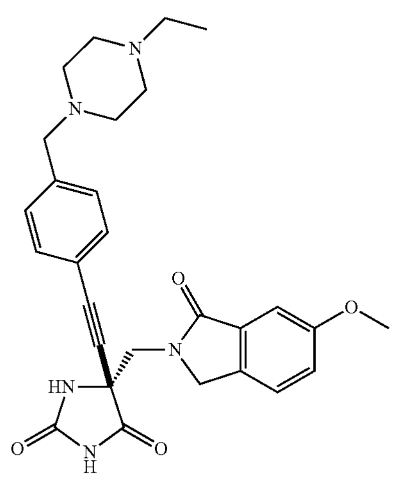 | 501.2 | 502.3 | 0.29 | 238 | 24 |

TABLE A-continued

| ID | Structure | Exact Mass | Mass Obsvd | Ki (nM) | hWBA (nM) | RR AUC (nM·h)[1] |
|---|---|---|---|---|---|---|
| 934 | 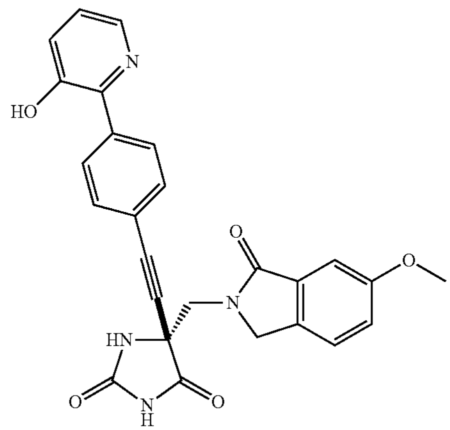 | 468.1 | 469.3 | 0.074 | 117 | 0 |
| 935 | 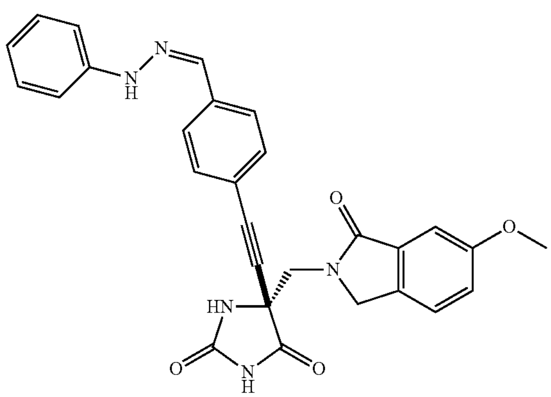 | 493.2 | 494.3 | 0.986 | 1224 | |
| 936 | 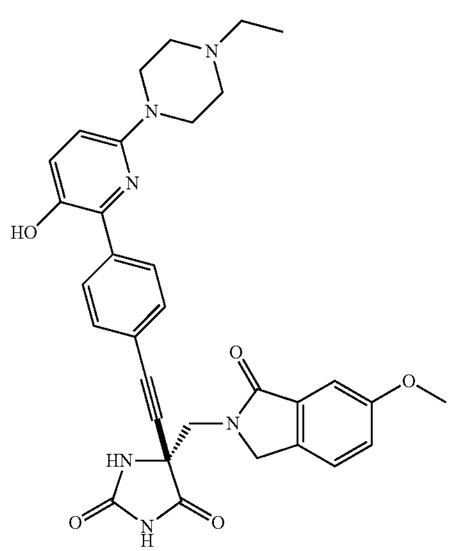 | 580.2 | 581.3 | 0.093 | 72.4 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 941 | 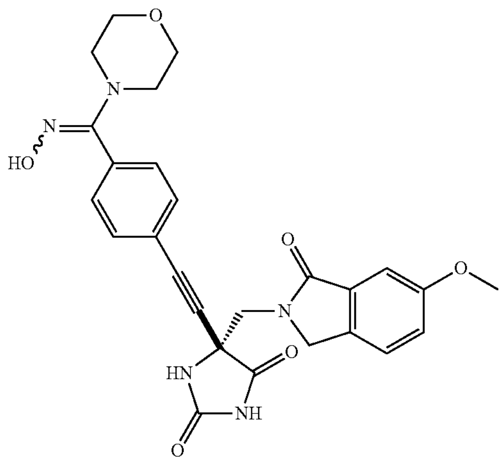 [SMILES: COc1ccc2c(c1)C(=O)N(C[C@@]1(C#Cc3ccc(C(=NO)N4CCOCC4)cc3)NC(=O)NC1=O)C2] | 503.2 | 504.3 | 0.13 | 100 | 58 |
| 942 | 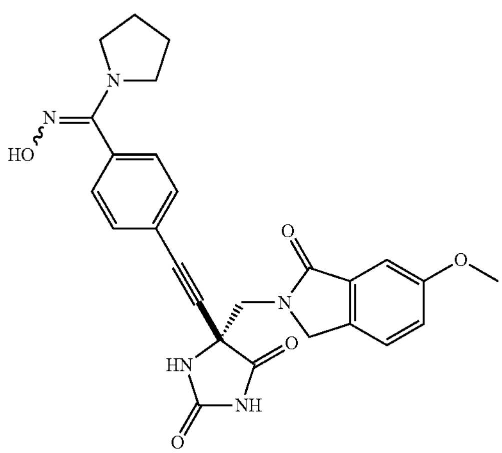 [SMILES: COc1ccc2c(c1)C(=O)N(C[C@@]1(C#Cc3ccc(C(=NO)N4CCCC4)cc3)NC(=O)NC1=O)C2] | 487.2 | 473.3 [M − CH₃] + H | 0.19 | 641 | |
| 943 | 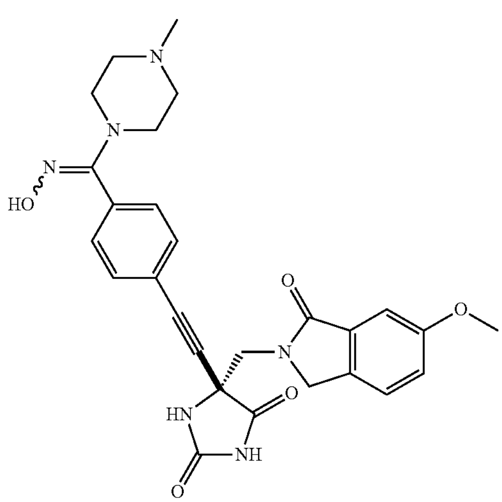 [SMILES: COc1ccc2c(c1)C(=O)N(C[C@@]1(C#Cc3ccc(C(=NO)N4CCN(C)CC4)cc3)NC(=O)NC1=O)C2] | 516.2 | 517.3 | 0.083 | 65 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 945 | 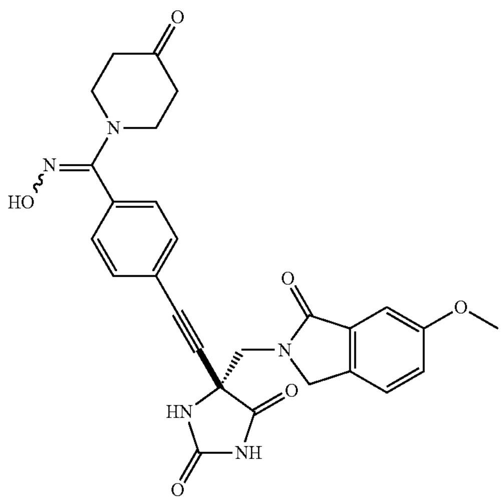 [SMILES: COc1ccc2c(c1)C(=O)N(C[C@@]1(C#Cc3ccc(C(=NO)N4CCC(=O)CC4)cc3)NC(=O)NC1=O)C2] | 515.2 | 516.3 | 0.17 | 86 | 0 |
| 946 | 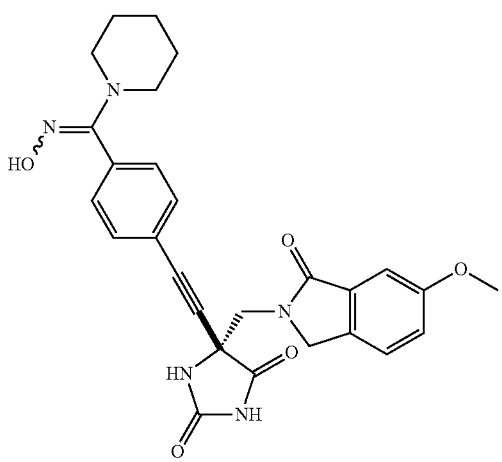 [SMILES: COc1ccc2c(c1)C(=O)N(C[C@@]1(C#Cc3ccc(C(=NO)N4CCCCC4)cc3)NC(=O)NC1=O)C2] | 501.2 | 502.3 | 0.12 | 154 | |
| 951 | 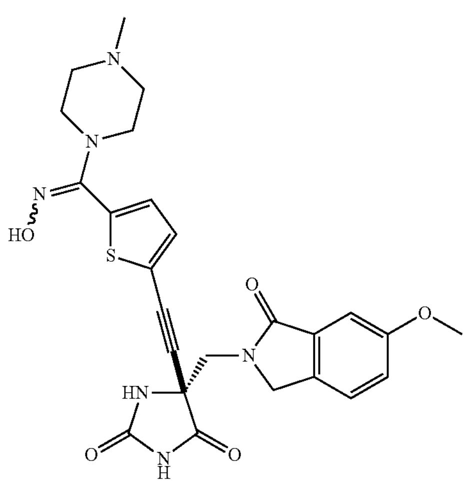 | 522.2 | 523.3 | 0.12 | 220 | |

TABLE A-continued

| ID | Structure | Exact Mass | Mass Obsvd | Ki (nM) | hWBA (nM) | RR AUC (nM · h)[1] |
|---|---|---|---|---|---|---|
| 952 | 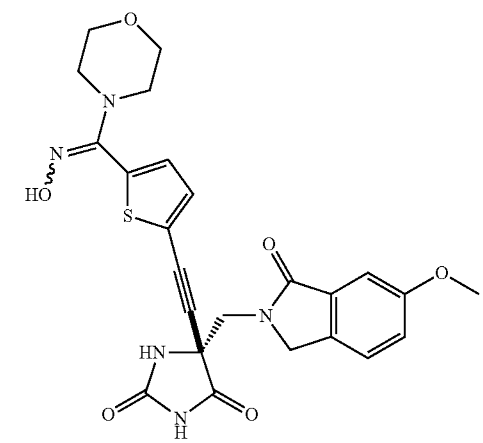 | 509.1 | 510.3 | 0.21 | 571 | |
| 953 | 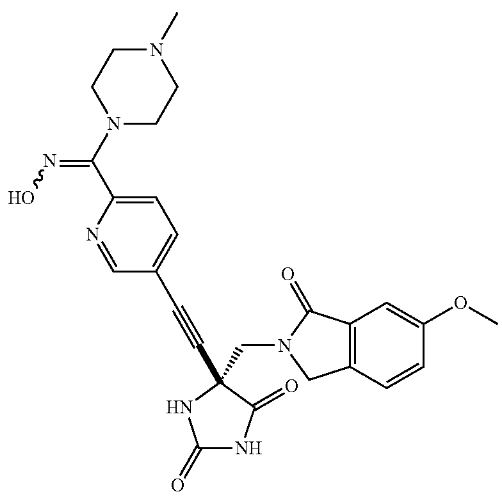 [SMILES: COc1ccc2c(c1)C(=O)N(C[C@@]1(C#Cc3ccc(C(=NO)N4CCN(C)CC4)nc3)NC(=O)NC1=O)C2] | 517.2 | 518.3 | 0.21 | 87 | |
| 954 | 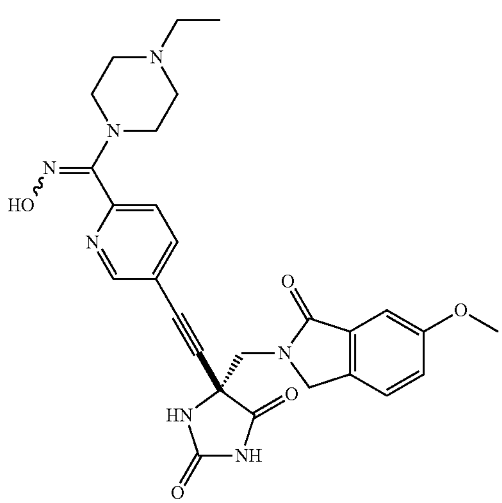 [SMILES: CCN1CCN(C(=NO)c2ccc(C#C[C@]3(CN4Cc5ccc(OC)cc5C4=O)NC(=O)NC3=O)cn2)CC1] | 531.2 | 532.3 | 0.18 | 87 | |

TABLE A-continued

| ID | Structure | Exact Mass | Mass Obsvd | Ki (nM) | hWBA (nM) | RR AUC (nM · h)[1] |
|---|---|---|---|---|---|---|
| 955 | 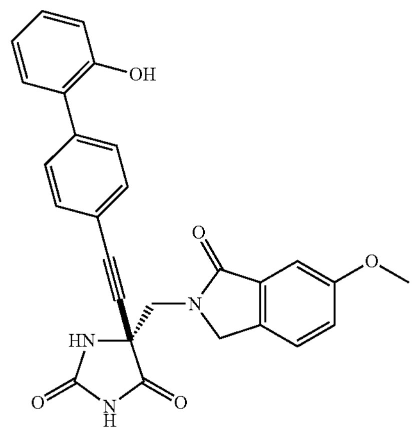 | 467.1 | 468.3 | 0.313 | 652.1 | |
| 2257 | 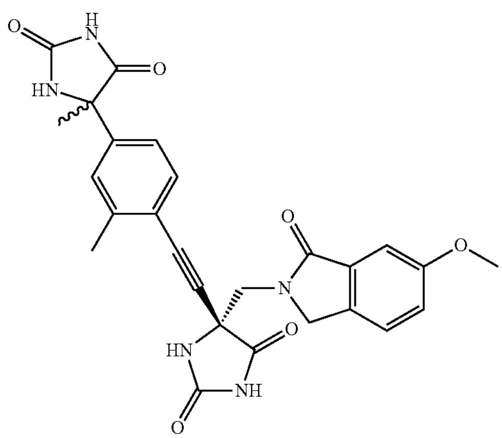 [SMILES: COc1ccc2c(c1)C(=O)N(C[C@@]1(C#Cc3ccc(C4(C)NC(=O)NC4=O)cc3C)NC(=O)NC1=O)C2] | 501.16 | 502.3 | 0.10 | 490 | |
| 2258 | 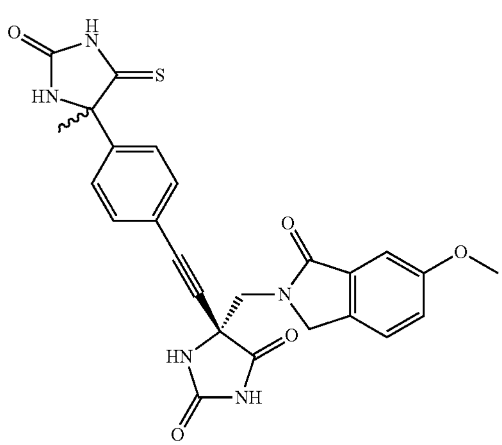 [SMILES: COc1ccc2c(c1)C(=O)N(C[C@@]1(C#Cc3ccc(C4(C)NC(=O)NC4=S)cc3)NC(=O)NC1=O)C2] | 503.13 | 504.3 | 0.21 | 398 | 438 |

TABLE A-continued
| ID | Structure | Exact Mass | Mass Obsvd | Ki (nM) | hWBA (nM) | RR AUC (nM · h)[1] |
|---|---|---|---|---|---|---|
| 2259 | 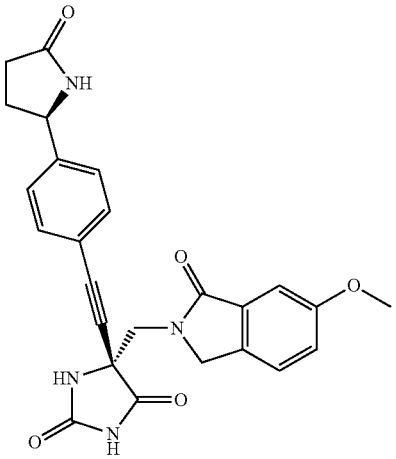 [SMILES: COc1ccc2c(c1)C(=O)N(C[C@@]1(C#Cc3ccc([C@H]4CCC(=O)N4)cc3)NC(=O)NC1=O)C2] | 458.16 | 459.3 | 0.39 | 736 | 126 |
| 2260 | 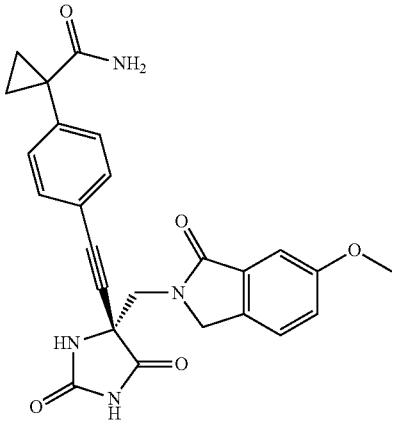 [SMILES: COc1ccc2c(c1)C(=O)N(C[C@@]1(C#Cc3ccc(C4(C(N)=O)CC4)cc3)NC(=O)NC1=O)C2] | 458.16 | 459.3 | 0.28 | 227 | 0 |
| 2261 | 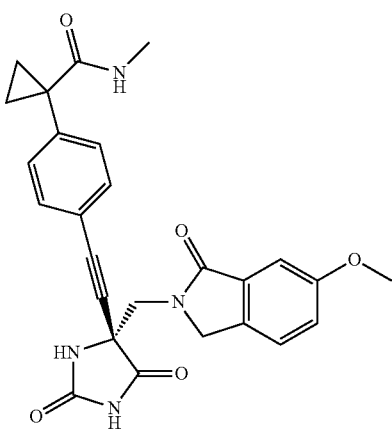 [SMILES: CNC(=O)C1(c2ccc(C#C[C@]3(CN4Cc5ccc(OC)cc5C4=O)NC(=O)NC3=O)cc2)CC1] | 472.17 | 473.3 | 0.30 | 443 | |

TABLE A-continued
| ID | Structure | Exact Mass | Mass Obsvd | Ki (nM) | hWBA (nM) | RR AUC (nM·h)[1] |
|---|---|---|---|---|---|---|
| 2262 | 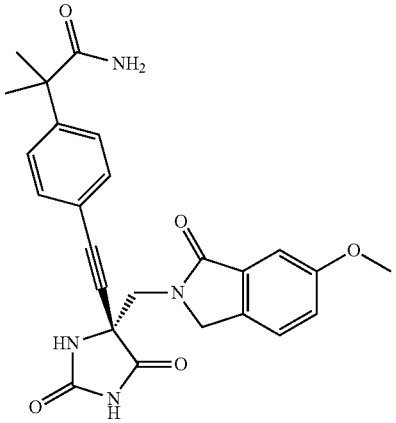 [SMILES: COc1ccc2c(c1)C(=O)N(C[C@@]1(C#Cc3ccc(C(C)(C)C(N)=O)cc3)NC(=O)NC1=O)C2] | 460.17 | 461.3 | 0.24 | 517 | |
| 2263 | 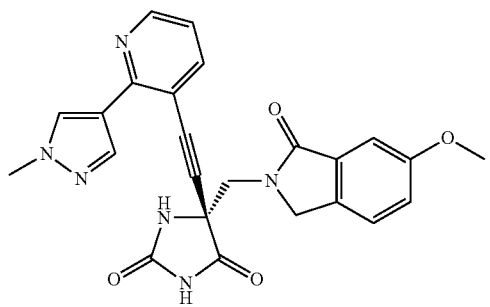 | 456.15 | 457.3 | 0.20 | 2223 | 187 |
| 2264 | 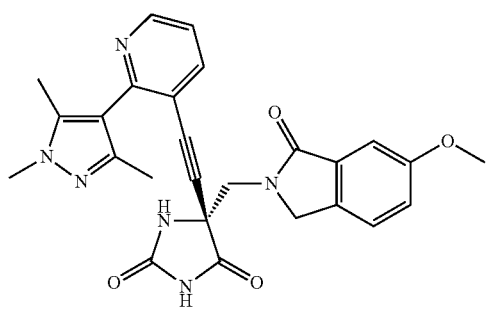 | 484.19 | 485.3 | 0.22 | 2535 | |
| 23 | 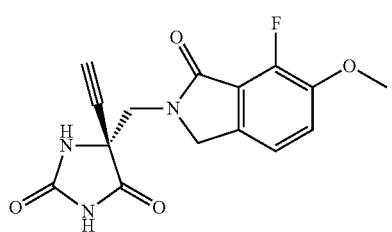 [SMILES: C#C[C@]1(CN2Cc3ccc(OC)c(F)c3C2=O)NC(=O)NC1=O] | 317.18 | 318.2 | 0.68 | 841 | |

TABLE A-continued

| ID | Structure | Exact Mass | Mass Obsvd | Ki (nM) | hWBA (nM) | RR AUC (nM·h)[1] |
|---|---|---|---|---|---|---|
| 2266 | 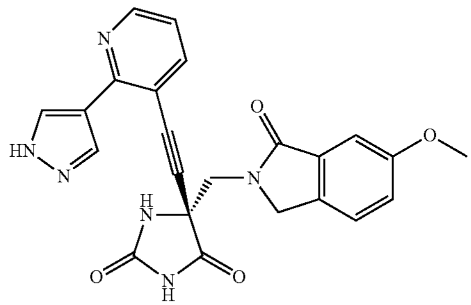 [SMILES: COc1ccc2c(c1)C(=O)N(C[C@@]1(C#Cc3cccnc3-c3cn[nH]c3)NC(=O)NC1=O)C2] | 442.14 | 443.2 | 0.12 | 927 | |
| 2267 | 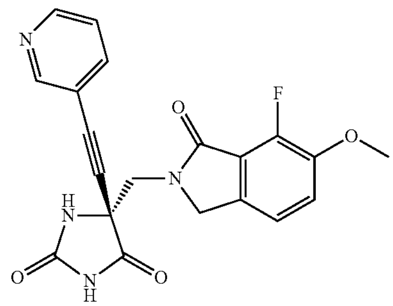 [SMILES: COc1ccc2c(c1F)C(=O)N(C[C@@]1(C#Cc3cccnc3)NC(=O)NC1=O)C2] | 394.11 | 395.2 | 0.11 | 134 | 2437 |
| 2268 | 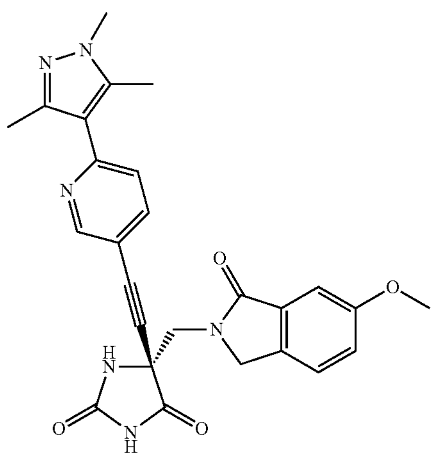 | 484.19 | 485.3 | 0.21 | 9028 | 1069 |
| 2269 | 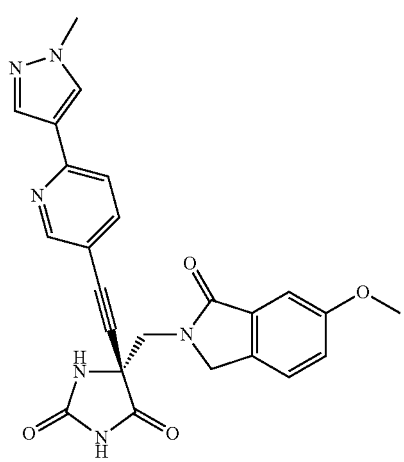 [SMILES: COc1ccc2c(c1)C(=O)N(C[C@@]1(C#Cc3ccc(-c4cnn(C)c4)nc3)NC(=O)NC1=O)C2] | 456.15 | 457.3 | 0.36 | 1026 | 924 |

TABLE A-continued

| ID | Structure | Exact Mass | Mass Obsvd | Ki (nM) | hWBA (nM) | RR AUC (nM·h)[1] |
|---|---|---|---|---|---|---|
| 2270 | 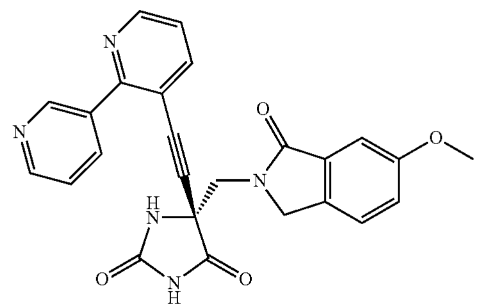 [SMILES: COc1ccc2c(c1)C(=O)N(C[C@@]1(C#Cc3cccnc3-c3cccnc3)NC(=O)NC1=O)C2] | 453.14 | 454.2 | 0.31 | 2113 | |
| 2271 | 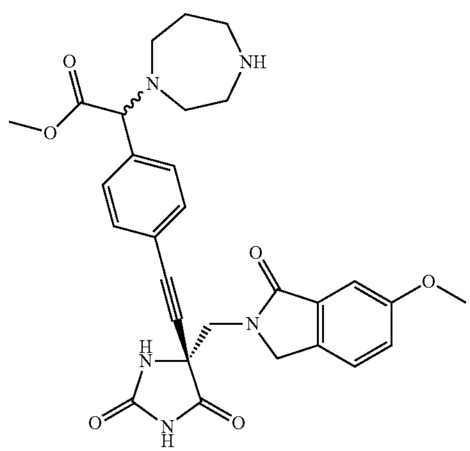 | 545.23 | 546.3 | 0.57 | 566 | |
| 2272 | 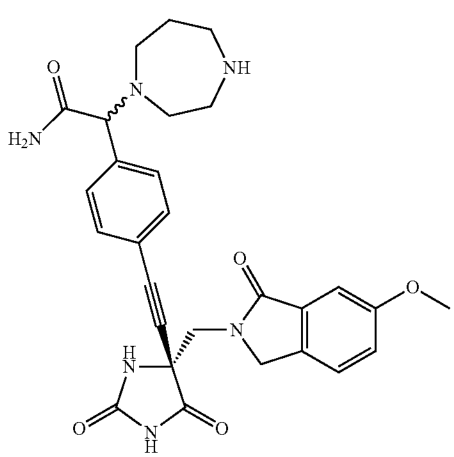 [SMILES: COc1ccc2c(c1)C(=O)N(C[C@@]1(C#Cc3ccc(C(C(N)=O)N4CCCNCC4)cc3)NC(=O)NC1=O)C2] | 530.23 | 531.3 | 0.25 | 302 | 17 |

TABLE A-continued

| ID | Structure | Exact Mass | Mass Obsvd | Ki (nM) | hWBA (nM) | RR AUC (nM·h)[1] |
|---|---|---|---|---|---|---|
| 2272 | 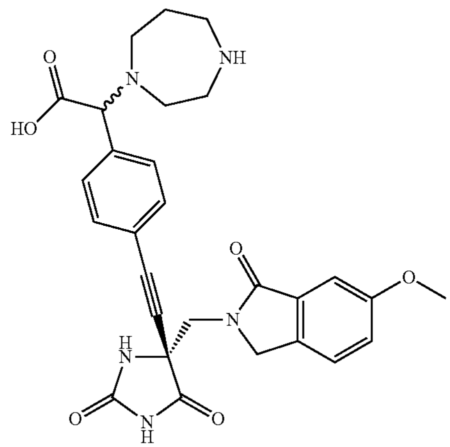 [SMILES: COc1ccc2c(c1)C(=O)N(C[C@@]1(C#Cc3ccc(C(C(=O)O)N4CCCNCC4)cc3)NC(=O)NC1=O)C2] | 531.21 | 532.3 | 0.34 | 588 | |
| 2273 | 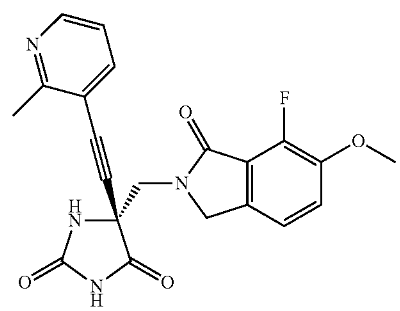 | 408.12 | 409.2 | 0.19 | 193 | 2894 |
| 2274 | 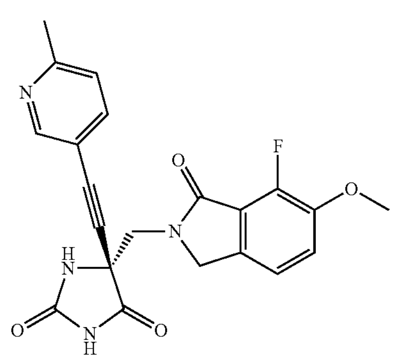 [SMILES: COc1ccc2c(c1F)C(=O)N(C[C@@]1(C#Cc3ccc(C)nc3)NC(=O)NC1=O)C2] | 408.12 | 409.2 | 0.38 | 396 | 16420 |

TABLE A-continued

| ID | Structure | Exact Mass | Mass Obsvd | Ki (nM) | hWBA (nM) | RR AUC (nM · h)[1] |
|---|---|---|---|---|---|---|
| 2275 | 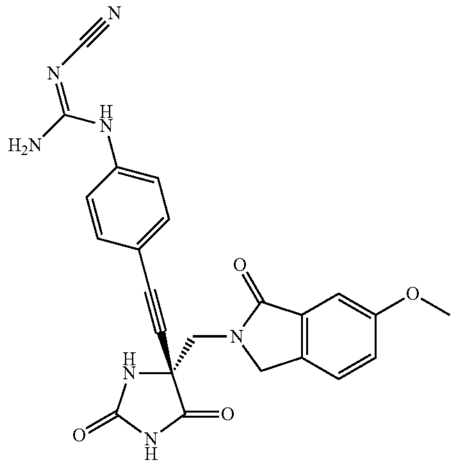 [SMILES: COc1ccc2c(c1)C(=O)N(C[C@@]1(C#Cc3ccc(N/C(N)=N\C#N)cc3)NC(=O)NC1=O)C2] | 457.15 | 458.3 | 0.21 | 150 | 0 |
| 2276 | 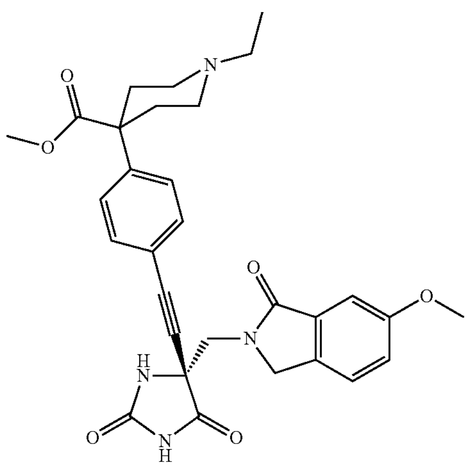 | 544.23 | 545.3 | 0.283 | 288 | 2316 |
| 2277 | 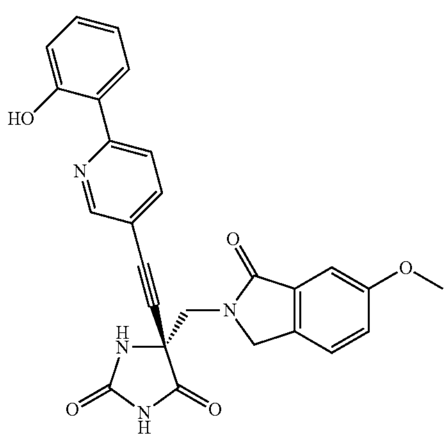 [SMILES: COc1ccc2c(c1)C(=O)N(C[C@@]1(C#Cc3ccc(-c4ccccc4O)nc3)NC(=O)NC1=O)C2] | 468.11 | 469.3 | 1.67 | 2090 | 271 |

TABLE A-continued

| ID | Structure | Exact Mass | Mass Obsvd | Ki (nM) | hWBA (nM) | RR AUC (nM·h)[1] |
|---|---|---|---|---|---|---|
| 2278 | 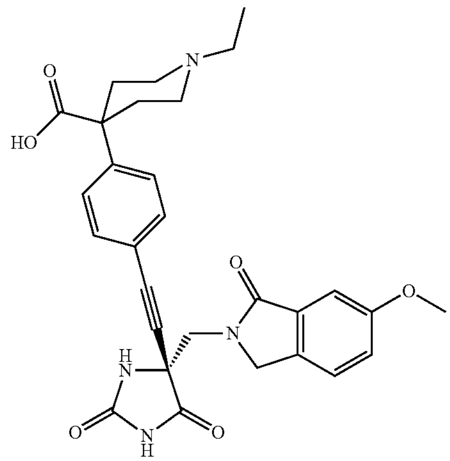 [SMILES: CCN1CCC(C(=O)O)(c2ccc(C#C[C@]3(CN4Cc5ccc(OC)cc5C4=O)NC(=O)NC3=O)cc2)CC1] | 530.22 | 531.3 | 0.644 | 239.8 | |
| 2279 | 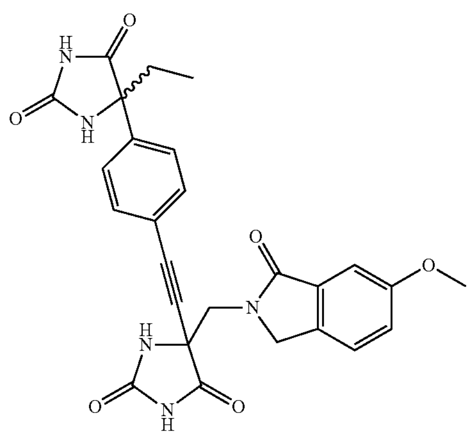 [SMILES: CCC1(c2ccc(C#CC3(CN4Cc5ccc(OC)cc5C4=O)NC(=O)NC3=O)cc2)NC(=O)NC1=O] | 501.16 | | 0.59 | 225 | 0 |
| 2280 | 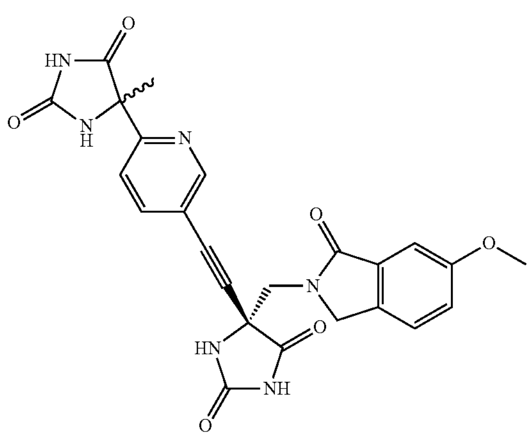 [SMILES: COc1ccc2c(c1)C(=O)N(C[C@@]1(C#Cc3ccc(C4(C)NC(=O)NC4=O)nc3)NC(=O)NC1=O)C2] | 488.14 | 489.3 | 1.40 | 544 | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 2281 | 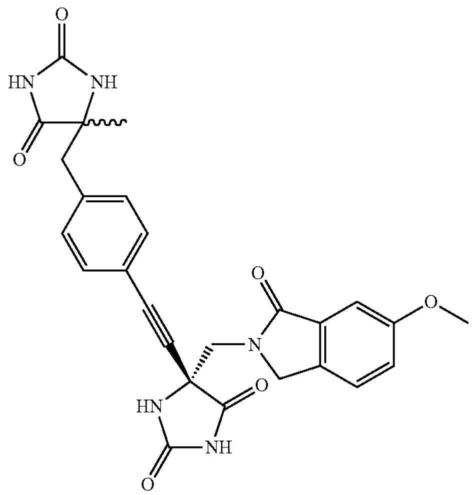 [SMILES: COc1ccc2c(c1)C(=O)N(C[C@@]1(C#Cc3ccc(CC4(C)NC(=O)NC4=O)cc3)NC(=O)NC1=O)C2] | 501.16 | 502.3 | 0.54 | 1001 | |
| 2282 | 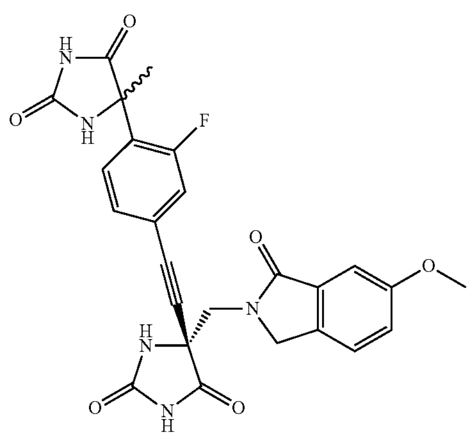 [SMILES: COc1ccc2c(c1)C(=O)N(C[C@@]1(C#Cc3ccc(C4(C)NC(=O)NC4=O)c(F)c3)NC(=O)NC1=O)C2] | 504.14 | 506.3 | 0.96 | 243 | 42 |
| 2283 | 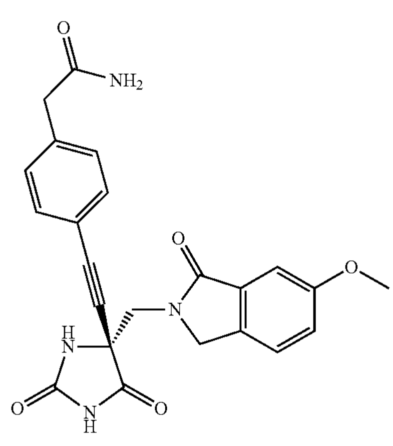 [SMILES: COc1ccc2c(c1)C(=O)N(C[C@@]1(C#Cc3ccc(CC(N)=O)cc3)NC(=O)NC1=O)C2] | 432.14 | 433.2 | 0.42 | 139 | |

TABLE A-continued

| ID | Structure | Exact Mass | Mass Obsvd | Ki (nM) | hWBA (nM) | RR AUC (nM · h)[1] |
|---|---|---|---|---|---|---|
| 2284 | 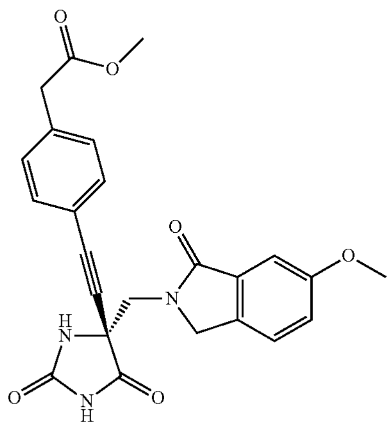 [SMILES: COC(=O)Cc1ccc(C#C[C@]2(CN3Cc4ccc(OC)cc4C3=O)NC(=O)NC2=O)cc1] | 447.14 | 448.2 | 0.74 | 379 | |
| 2285 | 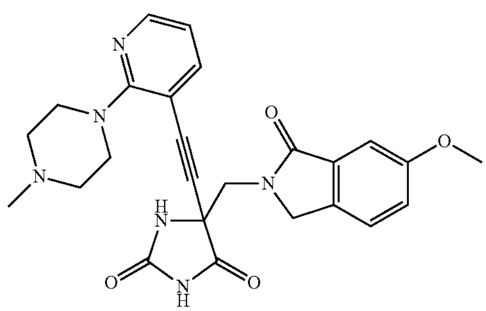 | 474.20 | 475.3 | 0.66 | 1231 | |
| 2286 | 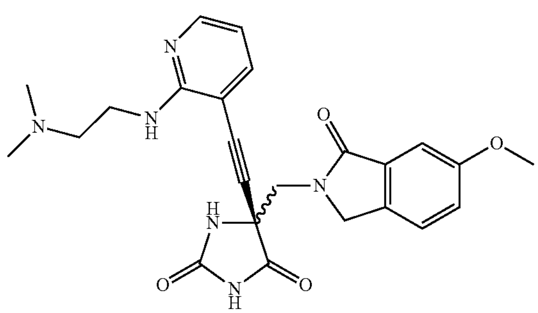 | 462.20 | 463.3 | 0.83 | 1996 | |
| 2287 | 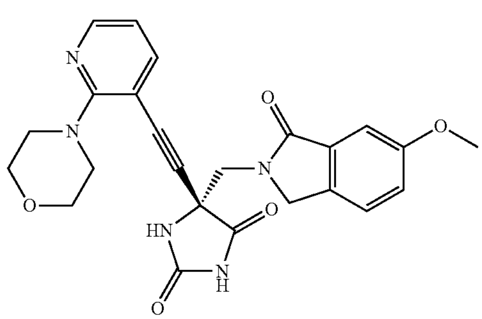 [SMILES: COc1ccc2c(c1)C(=O)N(C[C@@]1(C#Cc3cccnc3N3CCOCC3)NC(=O)NC1=O)C2] | 461.17 | 462.3 | 0.19 | 633 | |

TABLE A-continued

| ID | Structure | Exact Mass | Mass Obsvd | Ki (nM) | hWBA (nM) | RR AUC (nM·h)[1] |
|---|---|---|---|---|---|---|
| 2289 | 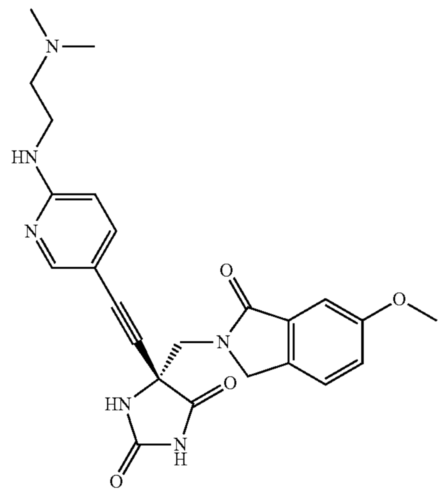 [SMILES: COc1ccc2c(c1)C(=O)N(C[C@@]1(C#Cc3ccc(NCCN(C)C)nc3)NC(=O)NC1=O)C2] | 462.20 | 463.3 | 0.43 | 419 | |
| 2290 | 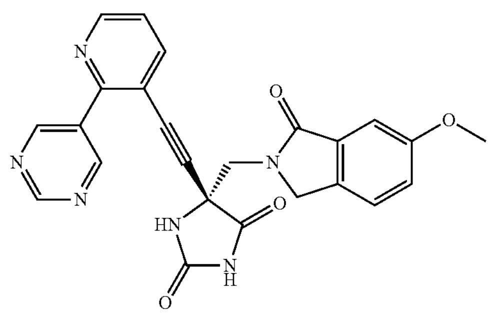 [SMILES: COc1ccc2c(c1)C(=O)N(C[C@@]1(C#Cc3cccnc3-c3cncnc3)NC(=O)NC1=O)C2] | 454.14 | 455.3 | | 1593 | |
| 2291 | 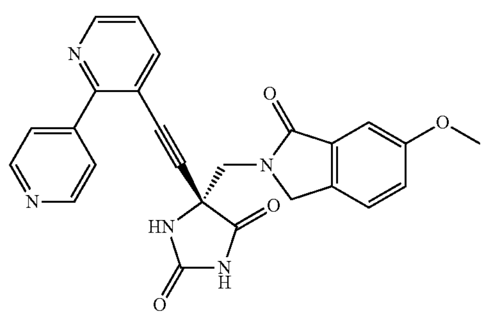 [SMILES: COc1ccc2c(c1)C(=O)N(C[C@@]1(C#Cc3cccnc3-c3ccncc3)NC(=O)NC1=O)C2] | 453.14 | 454.2 | | 2265 | |
| 2292 | 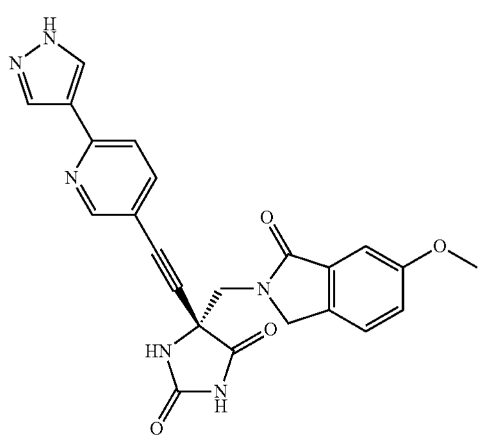 [SMILES: COc1ccc2c(c1)C(=O)N(C[C@@]1(C#Cc3ccc(-c4cn[nH]c4)nc3)NC(=O)NC1=O)C2] | 442.14 | 443.2 | 0.19 | 372 | |

TABLE A-continued

| ID | Structure | Exact Mass | Mass Obsvd | Ki (nM) | hWBA (nM) | RR AUC (nM·h)[1] |
|---|---|---|---|---|---|---|
| 2293 | 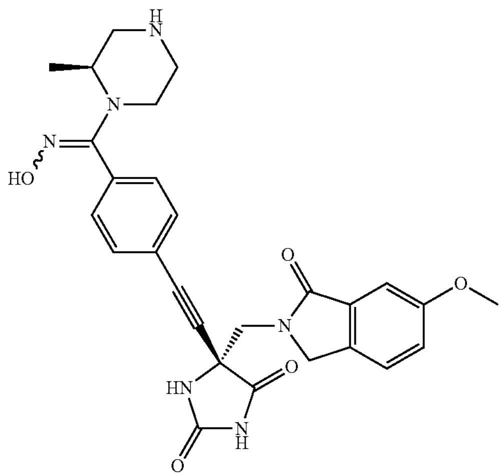 [SMILES: COc1ccc2c(c1)C(=O)N(C[C@@]1(C#Cc3ccc(C(=NO)N4CCNC[C@@H]4C)cc3)NC(=O)NC1=O)C2] | 516.21 | 517.3 | 0.43 | 84 | |
| 2294 | 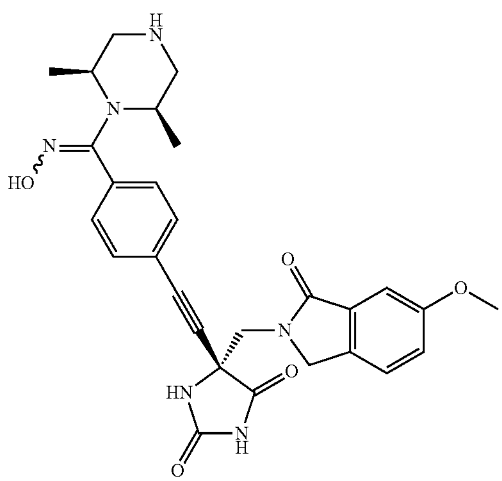 [SMILES: COc1ccc2c(c1)C(=O)N(C[C@@]1(C#Cc3ccc(C(=NO)N4[C@H](C)CNC[C@@H]4C)cc3)NC(=O)NC1=O)C2] | 530.23 | 529.3 | 0.68 | 327 | |
| 2295 | 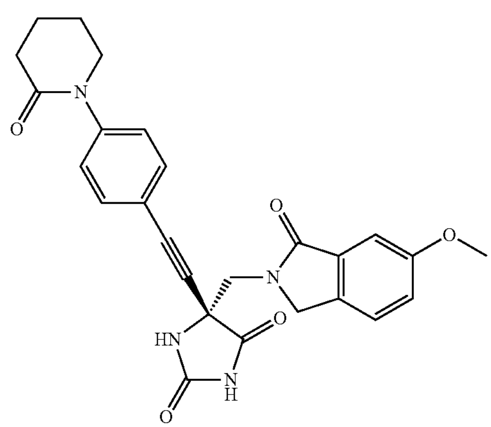 [SMILES: COc1ccc2c(c1)C(=O)N(C[C@@]1(C#Cc3ccc(N4CCCCC4=O)cc3)NC(=O)NC1=O)C2] | 472.17 | 473.3 | 0.68 | 1394 | |

TABLE A-continued

| ID | Structure | Exact Mass | Mass Obsvd | Ki (nM) | hWBA (nM) | RR AUC (nM · h)[1] |
|---|---|---|---|---|---|---|
| 2296 | 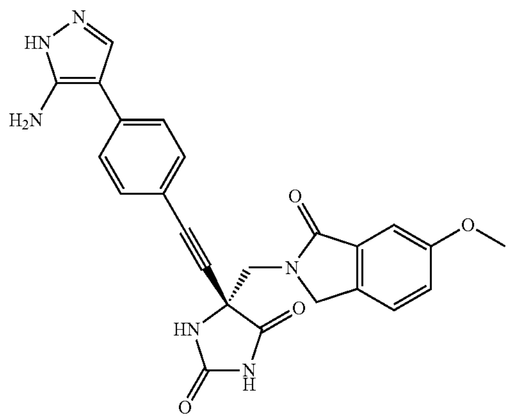 [SMILES: COc1ccc2c(c1)C(=O)N(C[C@@]1(C#Cc3ccc(-c4cn[nH]c4N)cc3)NC(=O)NC1=O)C2] | 456.15 | 457.3 | 0.62 | 236 | |
| 2297 | 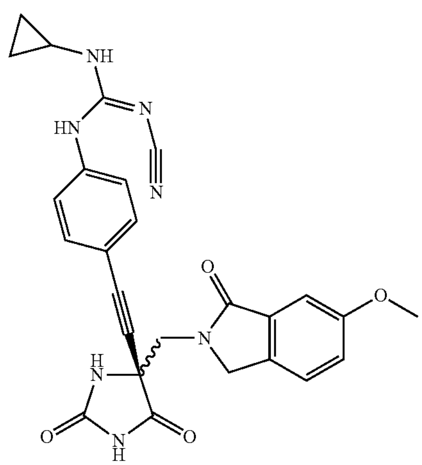 | 497.18 | 493.8 | | 268 | 0 |
| 2298 | 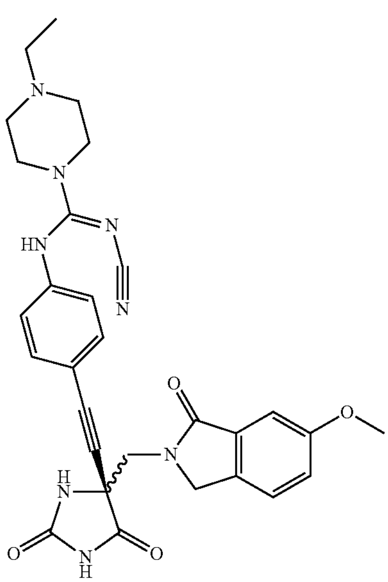 | 554.24 | 555.3 | | | 0 |

TABLE A-continued

| ID | Structure | Exact Mass | Mass Obsvd | Ki (nM) | hWBA (nM) | RR AUC (nM · h)[1] |
|---|---|---|---|---|---|---|
| 2310 | 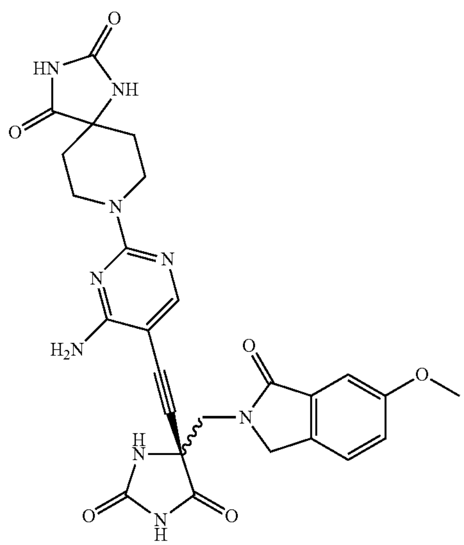 | 559.19 | 560.3 | 1.1 | 557 | |
| 2311 | 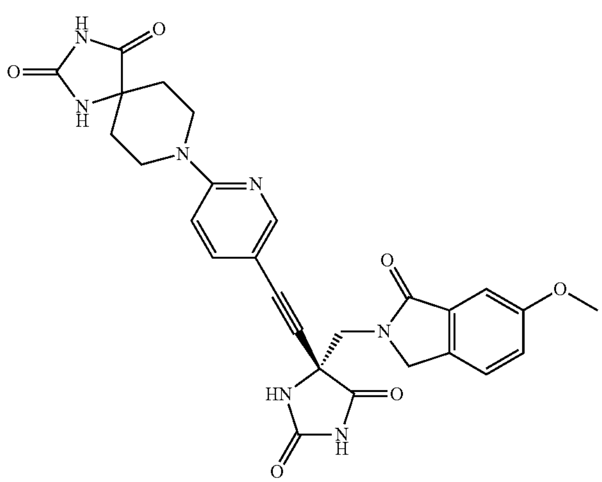 [SMILES: COc1ccc2c(c1)C(=O)N(C[C@@]1(C#Cc3ccc(N4CCC5(CC4)NC(=O)NC5=O)nc3)NC(=O)NC1=O)C2] | 543.19 | 544.3 | 0.26 | 347.7 | |
| 2312 | 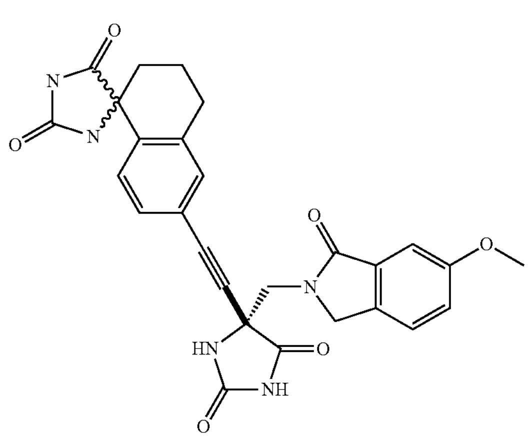 | 511.1 | 512.3 | 0.29 | 137 | 14 |

TABLE A-continued

| ID | Structure | Exact Mass | Mass Obsvd | Ki (nM) | hWBA (nM) | RR AUC (nM · h)[1] |
|---|---|---|---|---|---|---|
| 2313 | 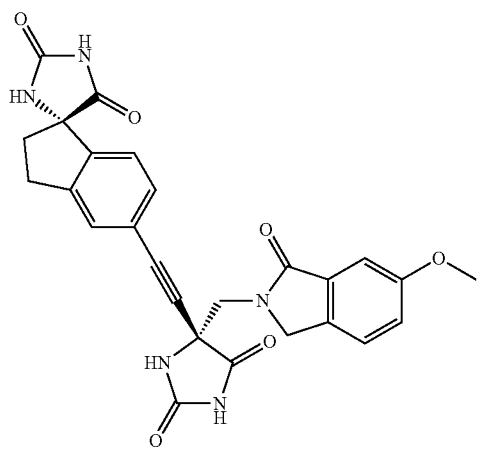 [SMILES: COc1ccc2c(c1)C(=O)N(C[C@@]1(C#Cc3ccc4c(c3)CC[C@]43NC(=O)NC3=O)NC(=O)NC1=O)C2] | 499.15 | 500.3 | 0.26 | 186 | 530 |
| 2314 | 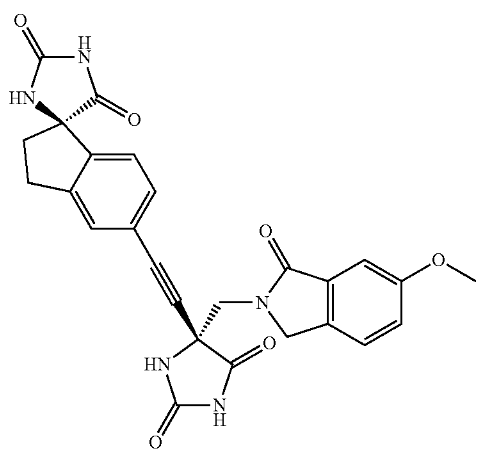 [SMILES: COc1ccc2c(c1)C(=O)N(C[C@@]1(C#Cc3ccc4c(c3)CC[C@@]43NC(=O)NC3=O)NC(=O)NC1=O)C2] | 499.15 | 500.3 | 0.24 | 281 | 218 |
| 2315 | 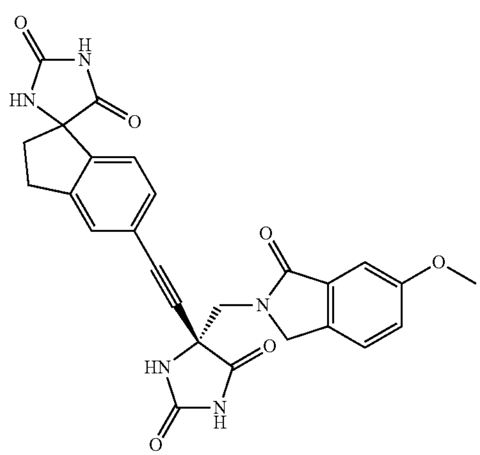 [SMILES: COc1ccc2c(c1)C(=O)N(C[C@@]1(C#Cc3ccc4c(c3)CCC43NC(=O)NC3=O)NC(=O)NC1=O)C2] | 499.15 | 500.3 | 0.27 | 151 | 673 |

TABLE A-continued

| ID | Structure | Exact Mass | Mass Obsvd | Ki (nM) | hWBA (nM) | RR AUC (nM·h)[1] |
|---|---|---|---|---|---|---|
| 2316 | 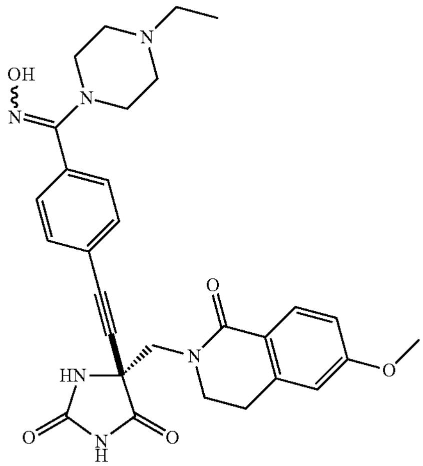 | 544.2 | 545.3 | 0.27 | 335 | |
| 2317 | 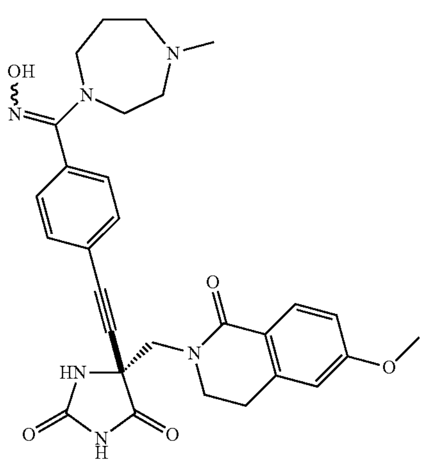 | 544.2 | 545.3 | 0.48 | 639 | |
| 2318 | 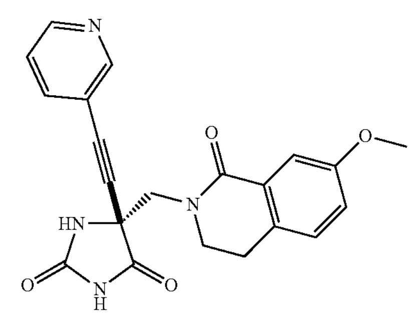 | 390.1 | 391.2 | 30.5 | 10001 | |

TABLE A-continued

| ID | Structure | Exact Mass | Mass Obsvd | Ki (nM) | hWBA (nM) | RR AUC (nM · h)[1] |
|---|---|---|---|---|---|---|
| 2319 | 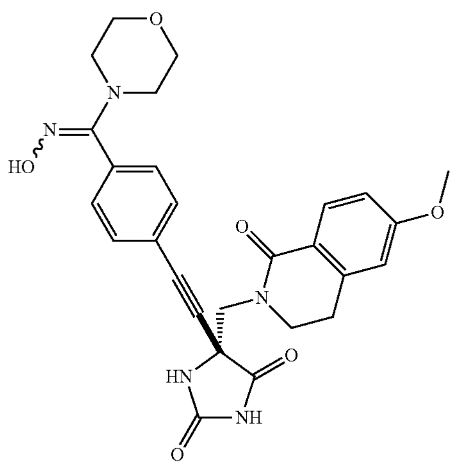 [SMILES: COc1ccc2c(c1)CCN(C[C@@]1(C#Cc3ccc(C(=NO)N4CCOCC4)cc3)NC(=O)NC1=O)C2=O] | 517.2 | 518.3 | n/a | 1055 | |
| 2320 | 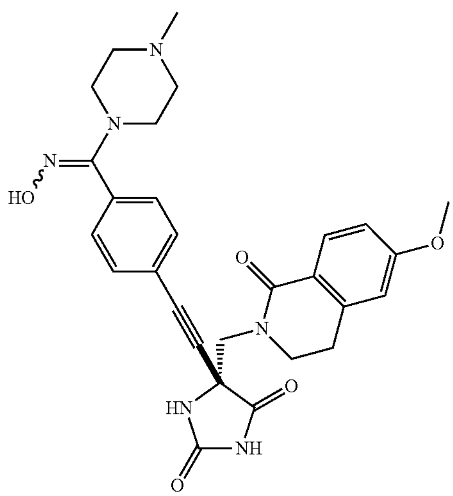 [SMILES: COc1ccc2c(c1)CCN(C[C@@]1(C#Cc3ccc(C(=NO)N4CCN(C)CC4)cc3)NC(=O)NC1=O)C2=O] | 530.2 | 531.3 | 0.24 | 261 | 0 |
| 2321 | 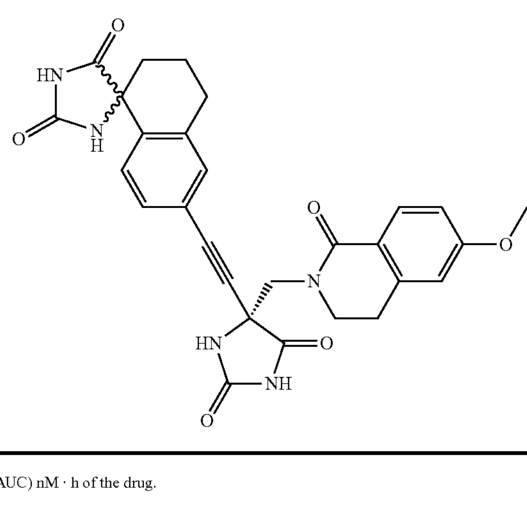 | 527.2 | 528.3 | 0.52 | 1103 | |

[1] rapid rat AUC (rrAUC) nM · h of the drug.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document referred to herein is incorporated by reference in its entirety for all purposes.

Therefore, we claim:

1. A compound selected from the group consisting of

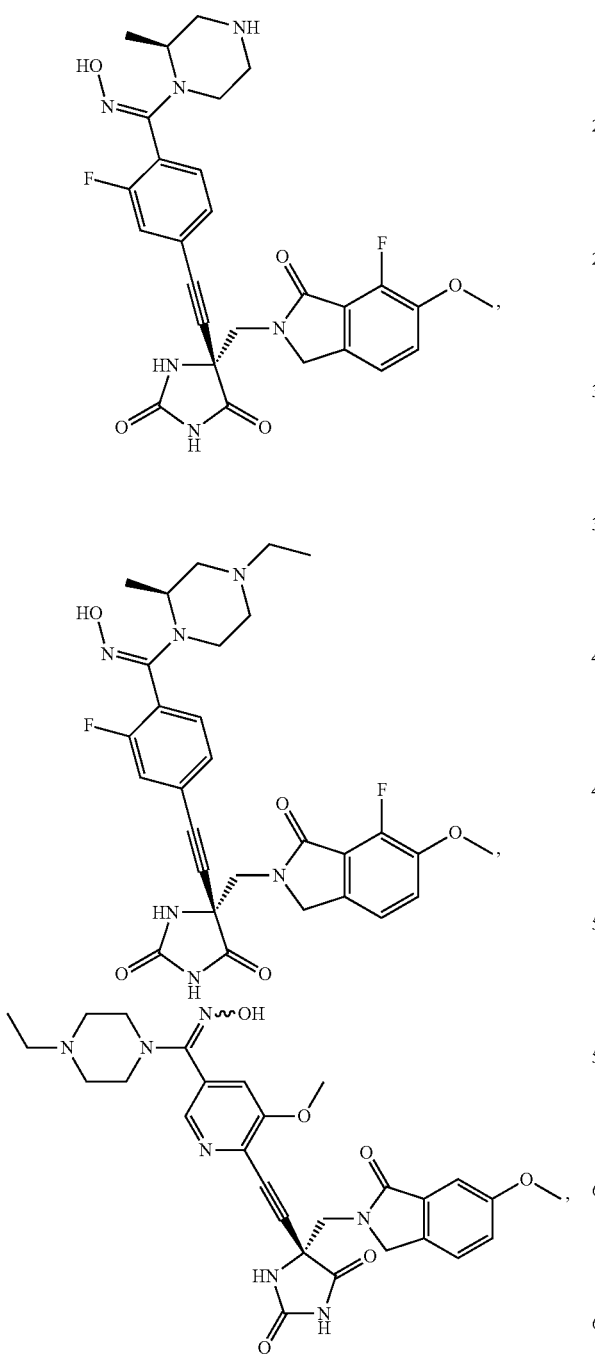

-continued

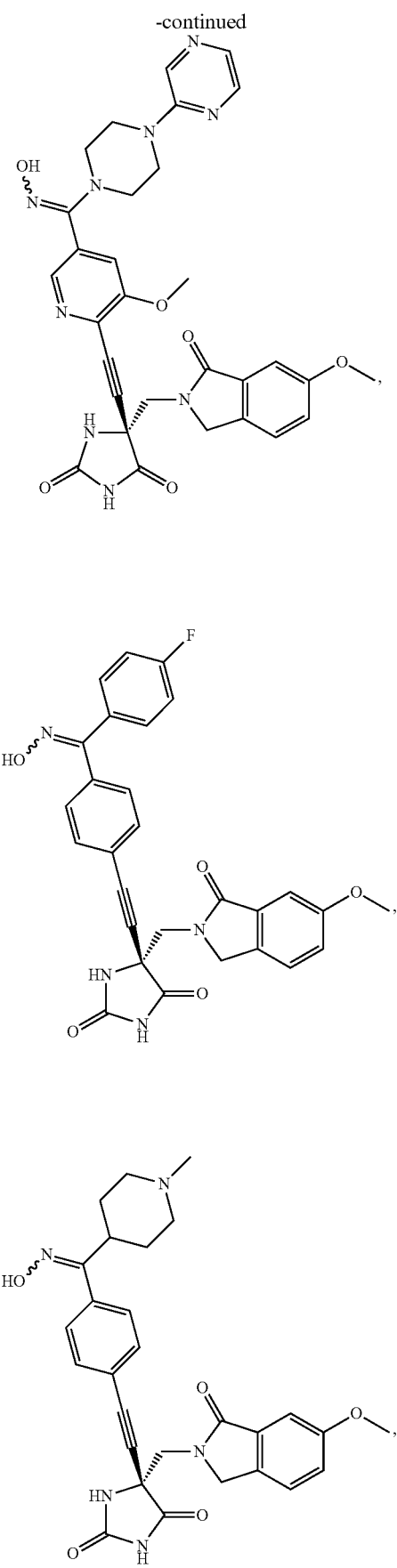

491
-continued
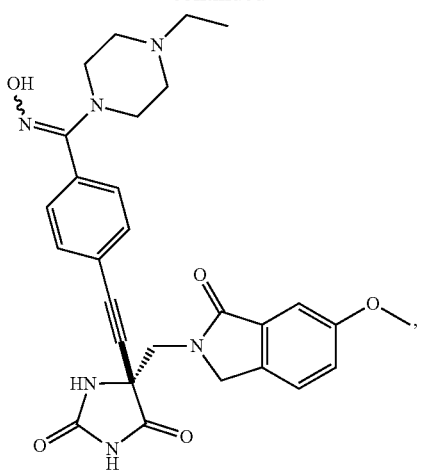
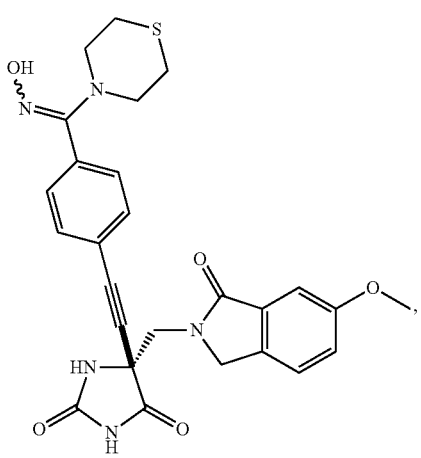
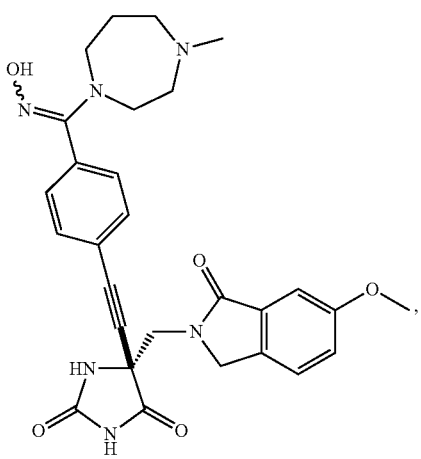
492
-continued
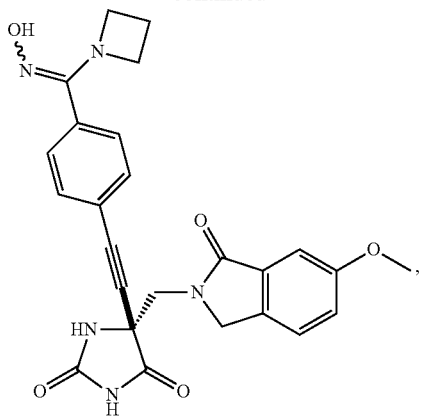
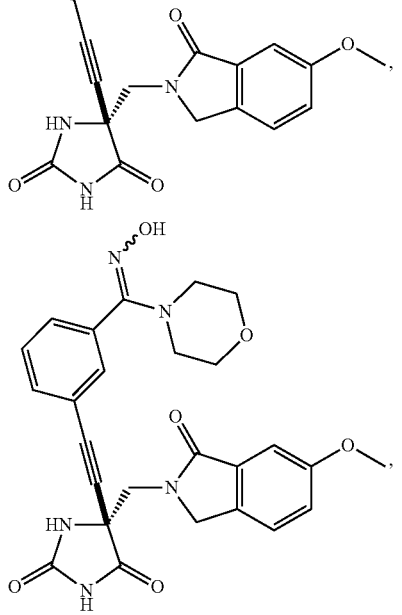
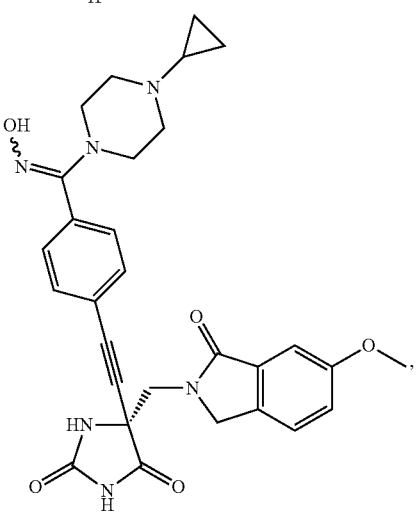

493
-continued
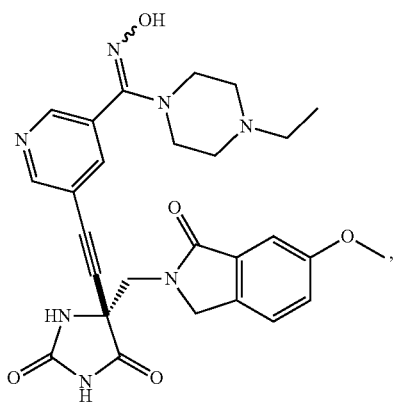
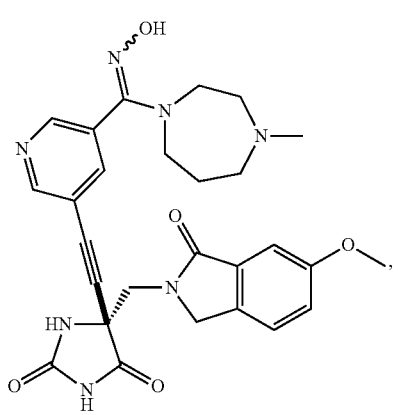
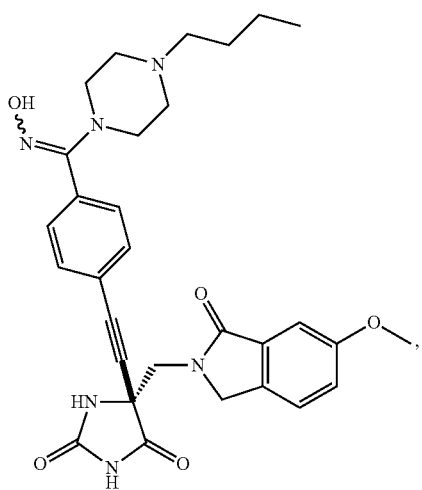
494
-continued
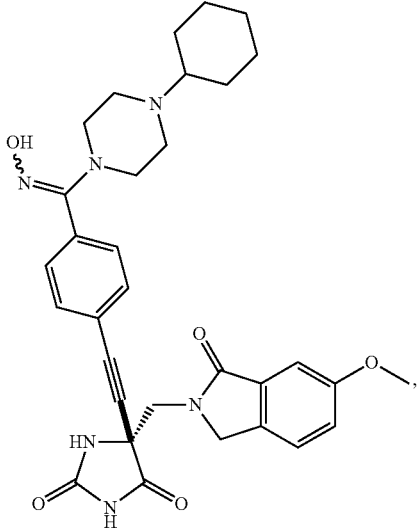
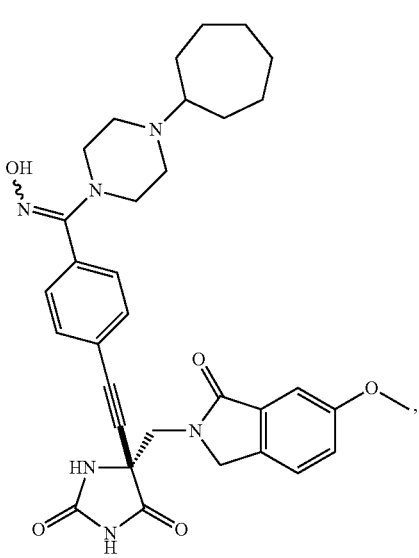
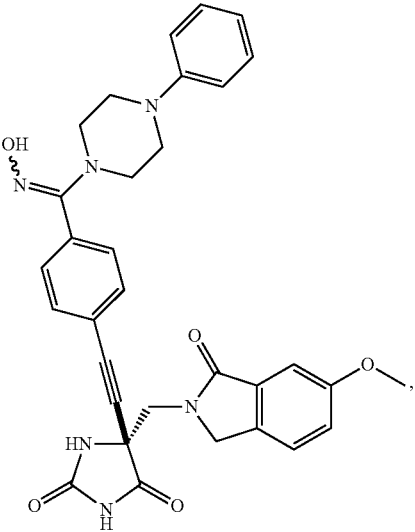

495
-continued
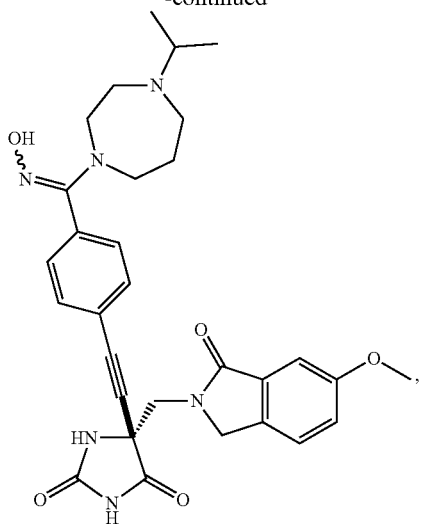
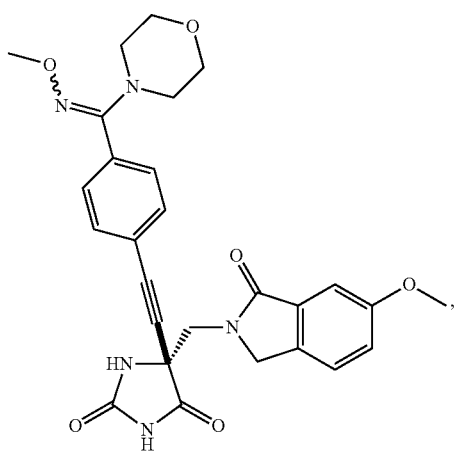
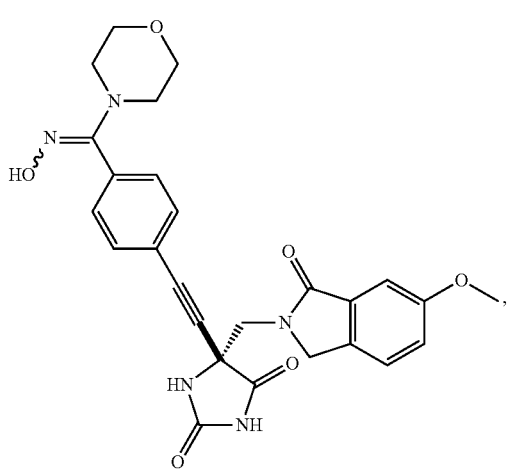
496
-continued
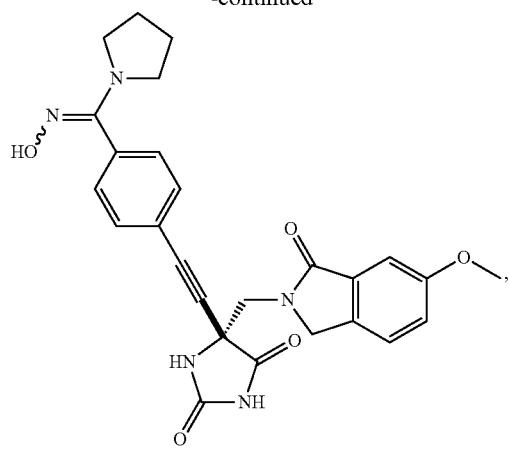
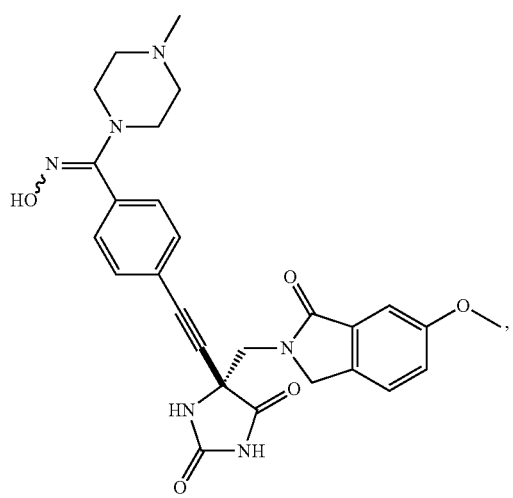
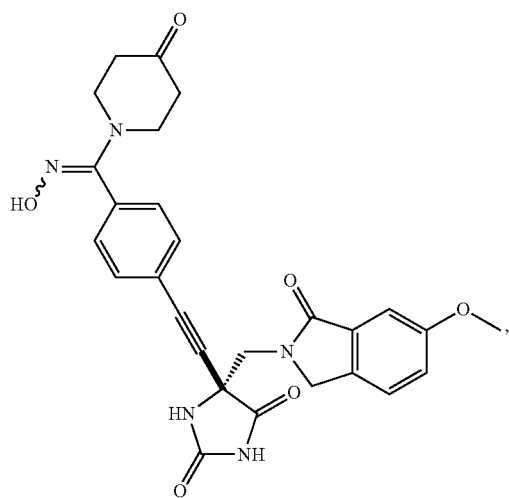

497         498
-continued  -continued
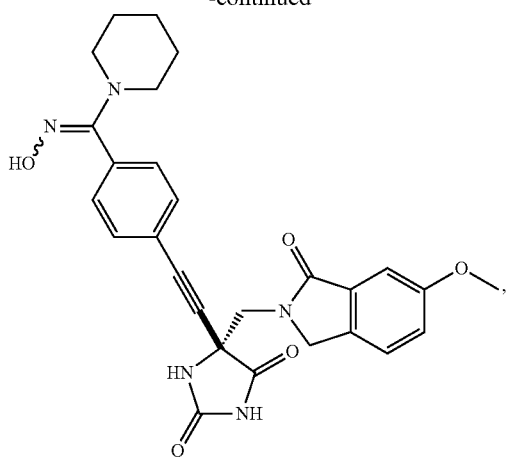
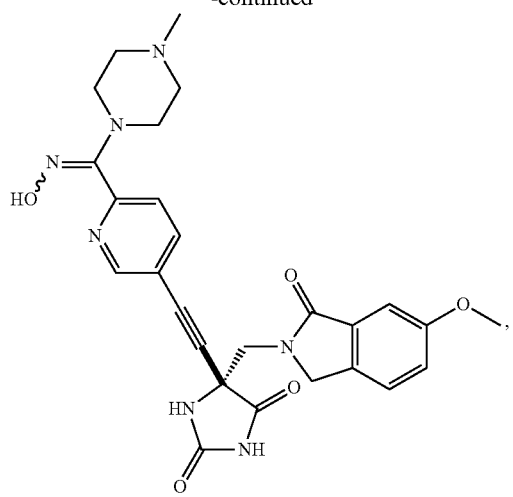
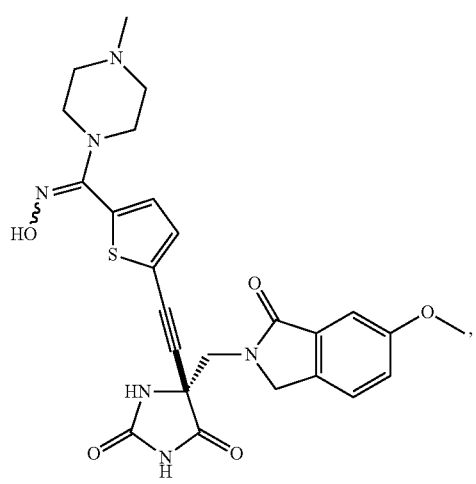
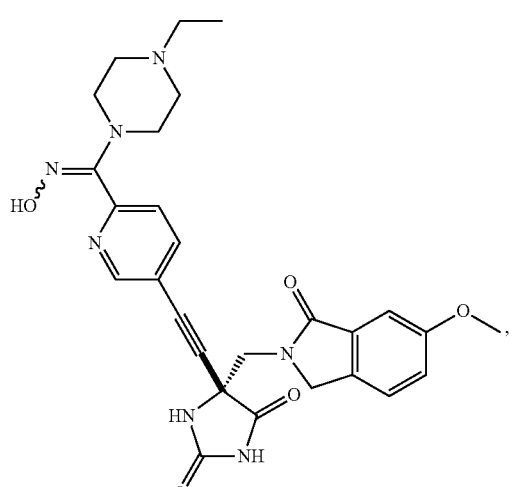
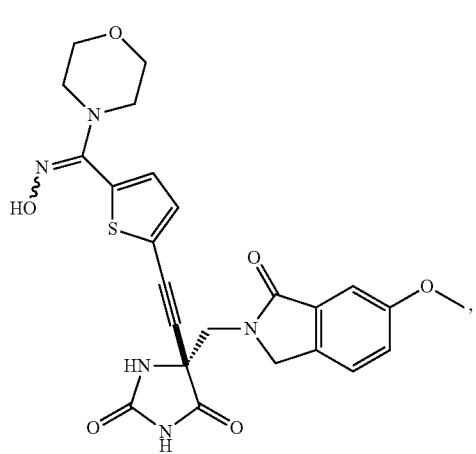
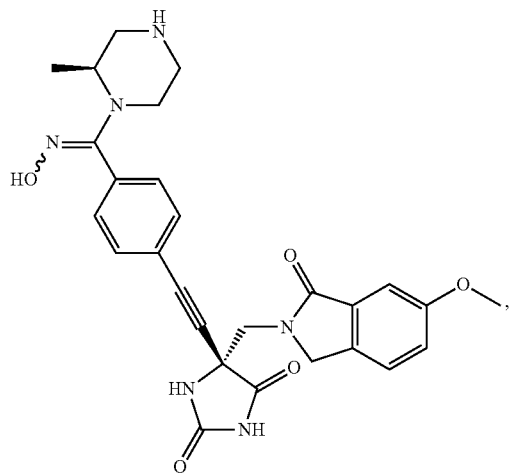

499
-continued
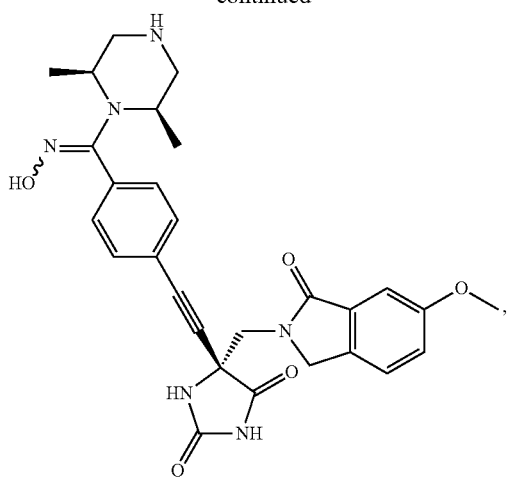
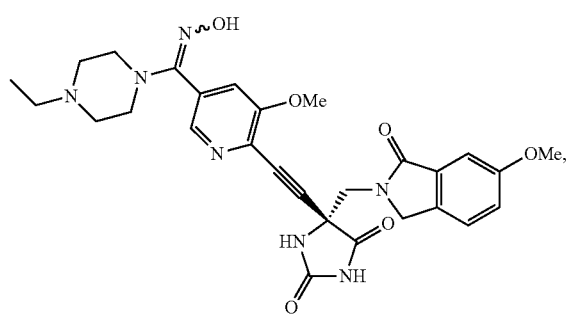
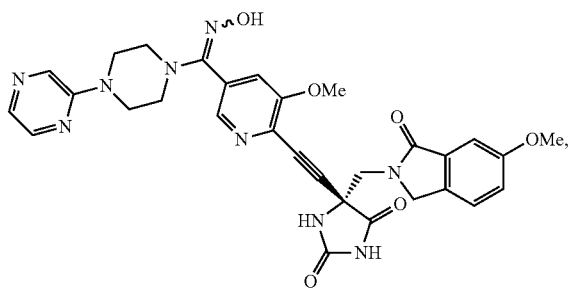
500
-continued
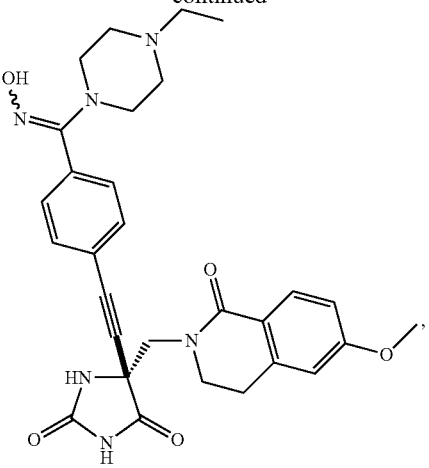
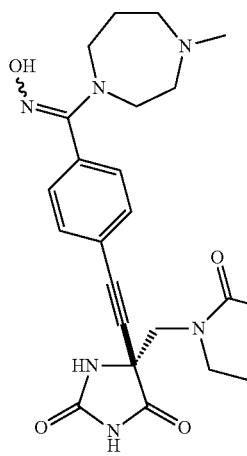
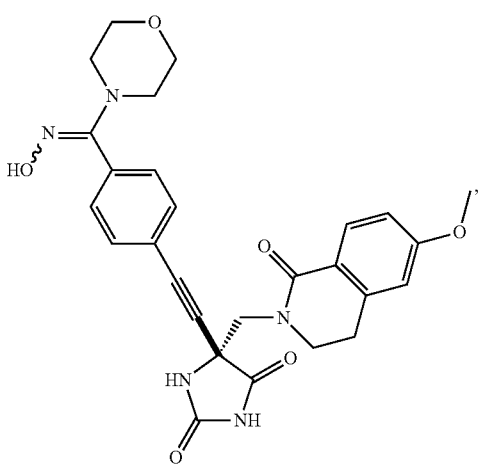

501
-continued
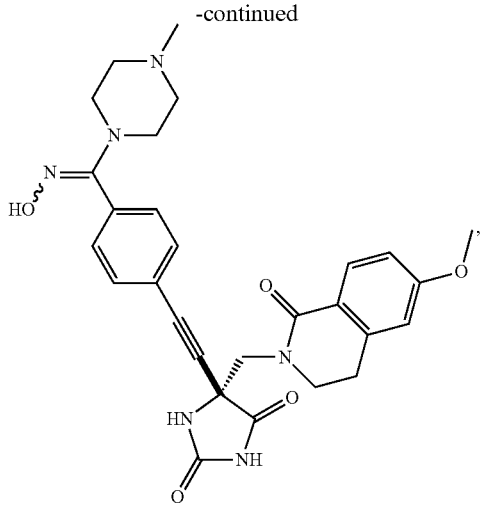
and a pharmaceutically acceptable salt thereof.
2. The compound of claim 1, selected from the group consisting of:
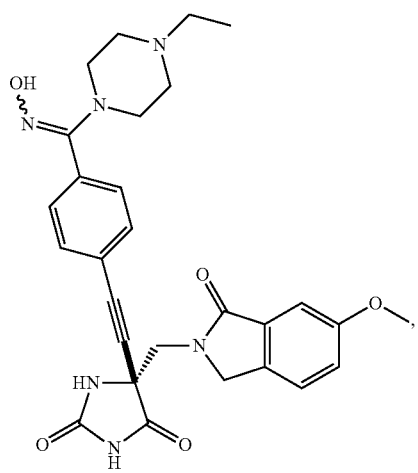
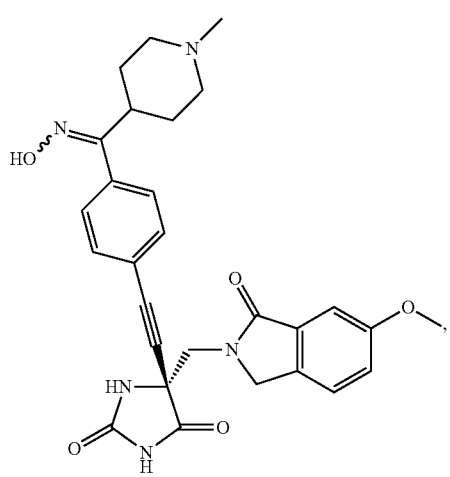
502
-continued
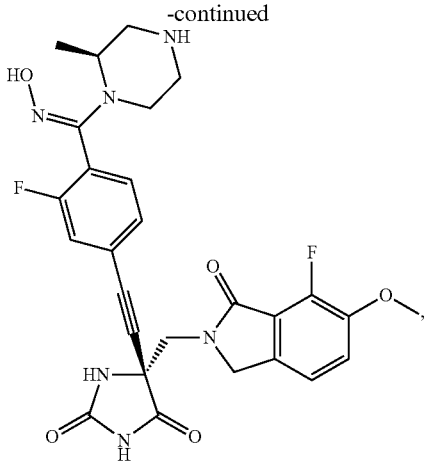
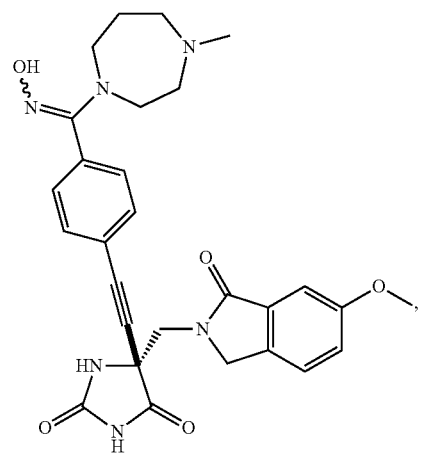
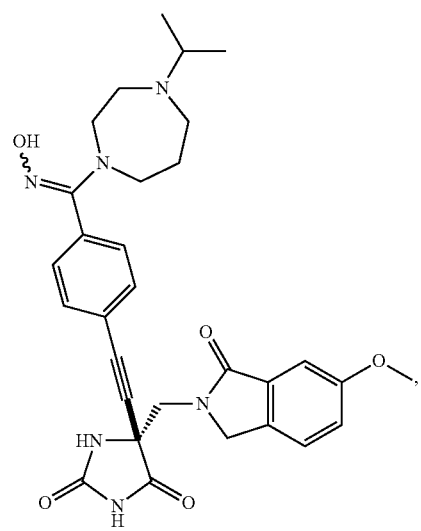

503
-continued
504
-continued
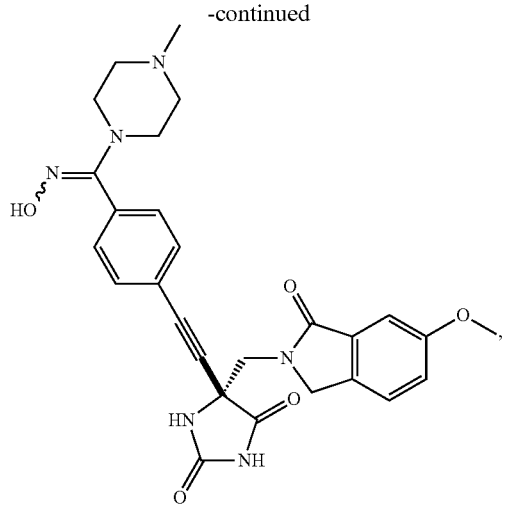
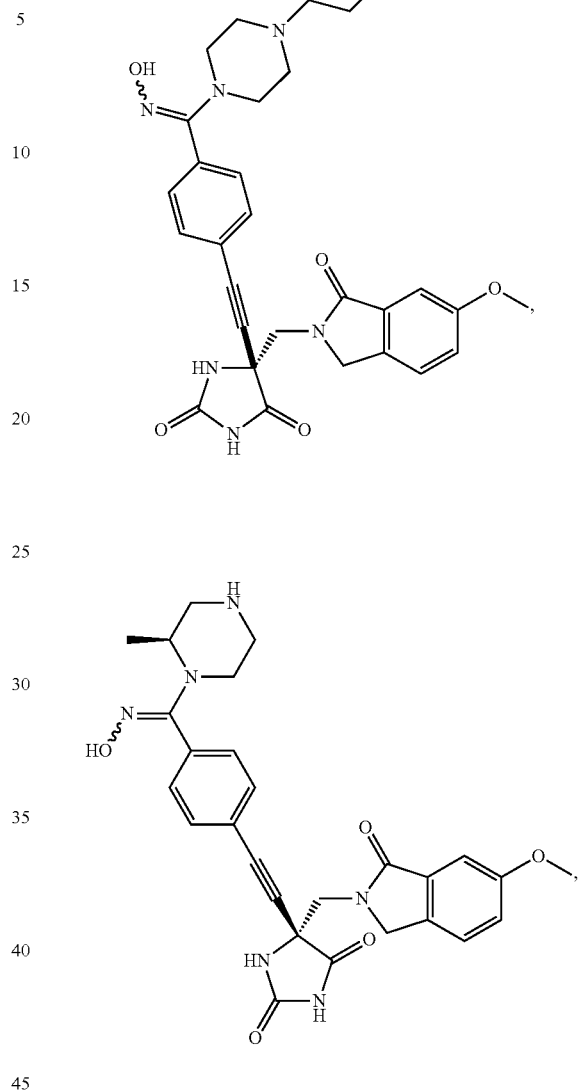
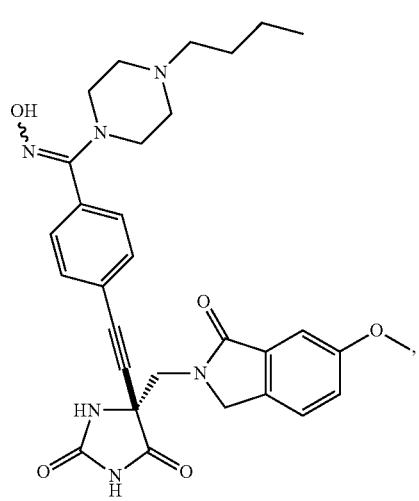
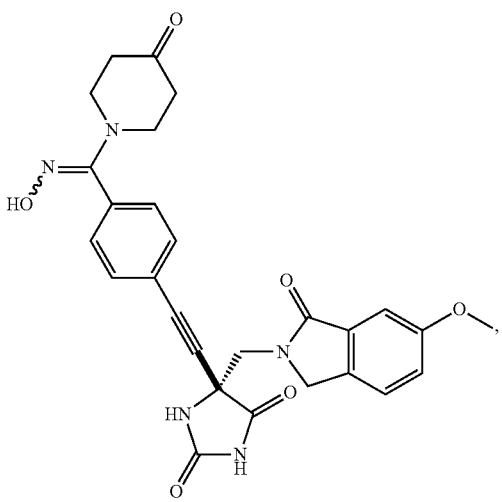

505
-continued
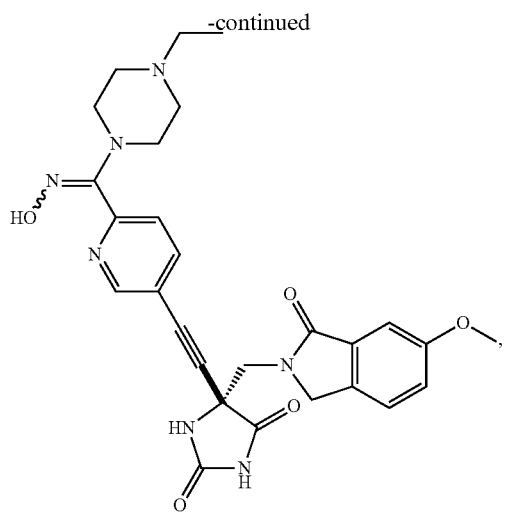
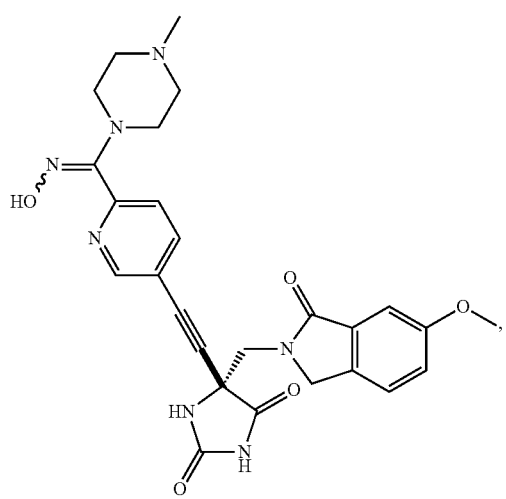
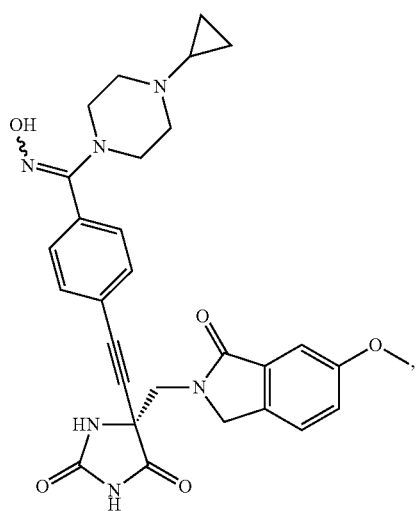
506
-continued
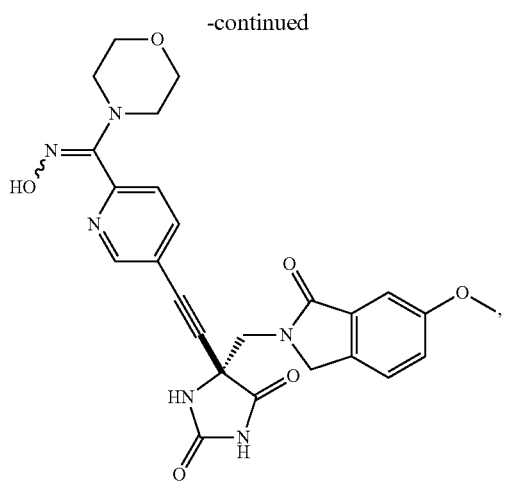
and a pharmaceutically acceptable salt thereof.
3. The compound of claim 2, selected from the group consisting of:
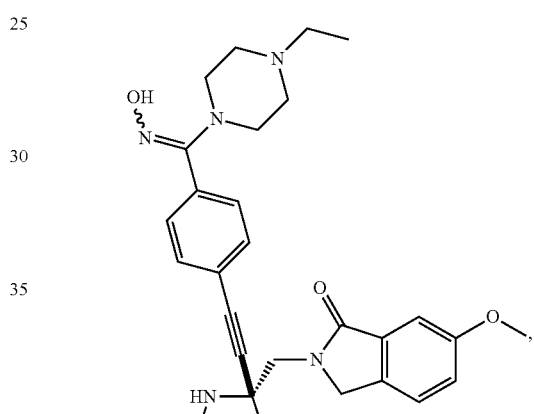
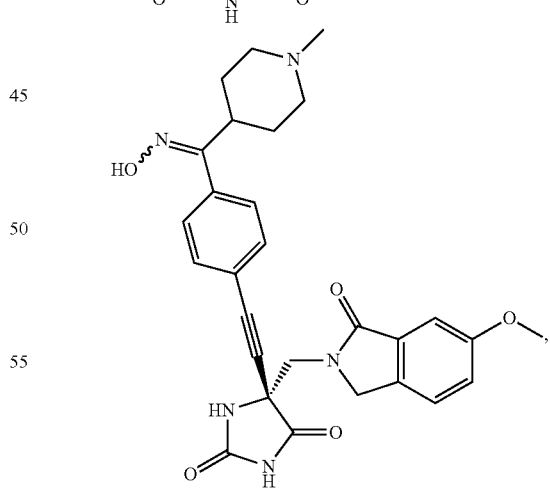
and a pharmaceutically acceptable salt thereof.
4. A pharmaceutical composition comprising the compound of claim 1 or a pharmaceutically acceptable salt thereof, and at least one pharmaceutically acceptable carrier.
* * * * *